US012767660B2

(12) United States Patent
Kamaura et al.

(10) Patent No.: US 12,767,660 B2
(45) Date of Patent: Oct. 20, 2026

(54) SUBSTITUTED PYRAZOLO[1,5-A]PYRIMIDINES AS SEPIAPTERIN REDUCTASE INHIBITORS

(71) Applicants: NISSAN CHEMICAL CORPORATION, Tokyo (JP); SHIONOGI & CO., LTD., Osaka (JP)

(72) Inventors: Masahiro Kamaura, Funabashi (JP); Yusuke Inaba, Funabashi (JP); Yusuke Shintani, Funabashi (JP); Yuki Kuwano, Funabashi (JP); Moemi Nakao, Funabashi (JP); Hiroshi Nagai, Funabashi (JP); Noriyuki Kurose, Toyonaka (JP); Kenji Takaya, Toyonaka (JP); Mado Nakajima, Toyonaka (JP)

(73) Assignees: NISSAN CHEMICAL CORPORATION;, Tokyo (JP); SHIONOGI & CO., LTD., Osaka (JP)

( * ) Notice: Subject to any disclaimer, the term of this patent is extended or adjusted under 35 U.S.C. 154(b) by 830 days.

(21) Appl. No.: 17/919,033

(22) PCT Filed: Apr. 13, 2021

(86) PCT No.: PCT/JP2021/015351
§ 371 (c)(1),
(2) Date: Oct. 14, 2022

(87) PCT Pub. No.: WO2021/210586
PCT Pub. Date: Oct. 21, 2021

(65) Prior Publication Data

US 2024/0092784 A1 Mar. 21, 2024

(30) Foreign Application Priority Data

Apr. 14, 2020 (JP) ................................ 2020-072341

(51) Int. Cl.
*A61K 31/519* (2006.01)
*C07D 487/04* (2006.01)
*C07D 487/14* (2006.01)
*C07D 519/00* (2006.01)

(52) U.S. Cl.
CPC ......... *C07D 487/04* (2013.01); *C07D 487/14* (2013.01); *C07D 519/00* (2013.01)

(58) Field of Classification Search
CPC ........................... A61K 31/519; C07D 487/04
USPC ....................................... 514/259.3; 544/282
See application file for complete search history.

(56) References Cited

U.S. PATENT DOCUMENTS

2005/0197341 A1 9/2005 Woolf et al.
2008/0171756 A1 7/2008 Shaw et al.
2011/0223131 A1 9/2011 Jin et al.
2013/0225596 A1 8/2013 Kai et al.
2017/0096435 A1 4/2017 Tebbe et al.

FOREIGN PATENT DOCUMENTS

EP 4219500 A1 * 8/2023 .......... C07D 487/04
JP 2007-511520 A 5/2007
JP WO2012/020742 A1 10/2013
JP 2018-529739 A 10/2018
WO 2005/077050 A2 8/2005
WO 2007/019098 A2 2/2007
WO 2007/019100 A2 2/2007
WO 2007/019101 A2 2/2007
WO 2007/103905 A2 9/2007
WO 2008/042240 A2 4/2008
WO 2008/076425 A1 6/2008
WO 2009/039321 A1 3/2009
WO 2009/039322 A1 3/2009
WO 2009/039323 A1 3/2009
WO 2010/011959 A1 1/2010
WO 2011/046946 A2 4/2011
WO 2011/047256 A1 4/2011
WO 2011/057942 A1 5/2011
(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Jun. 2, 2025 Office Action issued in European Patent Application No. 21789341.1.
Kurian et al, "The monoamine neurotransmitter disorders: an expanding range of neurological syndromes", Lancet Neurol, 2011, pp. 721-733.
Tegeder et al, "GTP cyclohydrolase and tetrahydrobiopterin regulate pain sensitivity and persistence", Nature Medicine, vol. 12 No. 11, Nov. 2006, pp. 1269-1277.
(Continued)

*Primary Examiner* — Douglas M Willis
(74) *Attorney, Agent, or Firm* — Oliff PLC

(57) ABSTRACT

A condensed heterocyclic compound has a sepiapterin reductase inhibitory action and is particularly useful for treatment of a pain. The condensed heterocyclic compound represented by Formula (I) below ($R^1$ represents a hydrocarbon group or the like; $R^2$ and $R^3$ represent a hydrogen atom or the like; $R^4$, X, and Y represent defined substituents), a tautomer or a pharmaceutically acceptable salt of the compound, or a solvate of any of these.

(I)

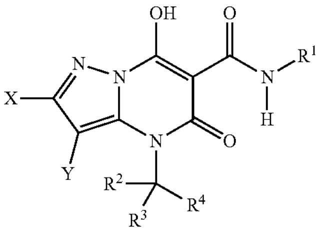

31 Claims, No Drawings

(56) References Cited

FOREIGN PATENT DOCUMENTS

| | | | |
|---|---|---|---|
| WO | 2011/071849 | A2 | 6/2011 |
| WO | 2011/117210 | A1 | 9/2011 |
| WO | 2012/051492 | A2 | 4/2012 |
| WO | 2012/068366 | A2 | 5/2012 |
| WO | 2013/162757 | A1 | 10/2013 |
| WO | 2017/059191 | A1 | 4/2017 |

OTHER PUBLICATIONS

Smith et al, "New Inhibitor of Sepiapterin Reductase: Lack of an Effect of Intracellular Tetrahydrobiopterin Depletion Upon in Vitro Proliferation of Two Human Cell Lines", The Journal of Biological Chemistry, vol. 267, No. 8, Mar. 15, 1992, pp. 5599-5607.

Wu et al, "Sepiapterin reductase: Characteristics and role in diseases", Wiley, Jun. 21, 2020, pp. 9495-9506.

Jun. 22, 2021 Written Opinion issued in International Patent Application No. PCT/JP2021/015351.

Jun. 22, 2021 Search Report issued in International Patent Application No. PCT/JP2021/015351.

Dec. 19, 2024 Office Action issued in Taiwanese Patent Application No. 110113273.

* cited by examiner

SUBSTITUTED PYRAZOLO[1,5-A]PYRIMIDINES AS SEPIAPTERIN REDUCTASE INHIBITORS

TECHNICAL FIELD

The present invention relates to a novel condensed heterocyclic compound having a sepiapterin reductase (hereinafter may be abbreviated as "SPR") inhibitory action.

BACKGROUND ART

Tetrahydrobiopterin (hereinafter may be abbreviated as "BH4") is known to serve as an important cofactor for various aromatic amino acid hydroxylases (including phenylalanine hydroxylase, tyrosine hydroxylase, and tryptophan hydroxylase) and other enzymes, such as nitric oxide synthases (inducible nitric oxide synthase (iNOS), endothelial nitric oxide synthase (eNOS), and neuronal nitric oxide synthase (nNOS)) and alkyl glycerol monooxygenase. Thus, BH4 is involved in controlling the synthesis of various neurotransmitters (e.g., serotonin, dopamine, and noradrenaline) and nitric oxide, etc., and depletion of BH4 causes depletion of neurotransmitters (including serotonin and dopamine) (Non-Patent Document 1). A decrease in BH4 production leads to lowered sensitivity to pain (Patent Document 1).

SPR is an enzyme that catalyzes the final step of the BH4 de novo pathway for converting 6-pyruvoyltetrahydropterin into BH4, and a decrease in BH4 production caused by SPR inhibition results in pain relief (Patent Document 2 and Non-Patent Document 2).

Reported SPR-inhibiting compounds include compounds having an indole ring and aromatic heterocyclic compounds (Patent Documents 1 and 2).

PRIOR ART DOCUMENTS

Patent Documents

Patent Document 1: WO 2011/047156
Patent Document 2: WO 2017/059191

Non-Patent Documents

Non-Patent Document 1: Lancet Neurol., 2011, Vol. 10: pp. 721-733
Non-Patent Document 2: Nature Medicine, 2006, Vol. 12, No. 11: pp. 1269-1277

SUMMARY OF THE INVENTION

Problems to be Solved by the Invention

An object of the present invention is to provide a novel pharmaceutical compound having excellent SPR inhibitory action.

Means for Solving the Problems

The present inventors have conducted extensive studies to find a compound having SPR inhibitory action, and as a result have found that the compound of the present invention exhibits excellent SPR inhibitory action. The present invention has been accomplished on the basis of this finding.

Accordingly, the present invention is characterized by the following.

(1)

A compound of the following Formula (I):

(I)

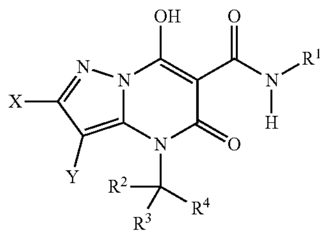

[wherein $R^1$ is a substitutable hydrocarbon group;

$R^2$ and $R^3$ are each independently a hydrogen atom or a substitutable $C_{1-6}$ alkyl group;

$R^4$ is a hydrogen atom, a substitutable hydrocarbon group, or a substitutable heterocyclic group;

X and Y are bonded with each other to form a substitutable 5- to 7-membered ring together with each carbon atom bonded to X and Y; or X is a hydrogen atom, a halogen atom, a hydroxy group, a cyano group, a substitutable amino group, a substitutable hydrocarbon group, a substitutable heterocyclic group, an acyl group, or a group of the formula $—CR^5═NR^6$;

Y is a hydrogen atom, a halogen atom, a cyano group, a substitutable hydrocarbon group, a substitutable heterocyclic group, an acyl group, or a group of the formula $—CR^7═NR^8$;

$R^5$ and $R^7$ are each independently a hydrogen atom or a $C_{1-6}$ alkyl group;

$R^6$ and $R^8$ are each independently a substitutable hydroxy group;

when X is a hydrogen atom, Y is not a hydrogen atom; and when Y is a hydrogen atom, X is not a hydrogen atom], a tautomer or pharmaceutically acceptable salt of the compound, or a solvate of any of these.

(2) The compound, tautomer or pharmaceutically acceptable salt of the compound, or solvate of any of these according to (1), wherein:

X is a hydrogen atom, a halogen atom, a substitutable amino group, a substitutable hydrocarbon group, a substitutable heterocyclic group, an acyl group, or a group of the formula $—CR^5═NR^6$;

Y is a hydrogen atom, a halogen atom, a substitutable hydrocarbon group, a substitutable heterocyclic group, an acyl group, or a group of the formula $—CR^7═NR^8$;

$R^5$, $R^6$, $R^7$, and $R^8$ have the same definition as (1) above;

when X is a hydrogen atom, Y is not a hydrogen atom; and when Y is a hydrogen atom, X is not a hydrogen atom.

(3)

The compound, tautomer or pharmaceutically acceptable salt of the compound, or solvate of any of these according to (1) or (2), wherein $R^2$ and $R^3$ are each a hydrogen atom.

(4)

The compound, tautomer or pharmaceutically acceptable salt of the compound, or solvate of any of these according to any one of (1) to (3), wherein $R^1$ is a substitutable $C_{3-10}$ cycloalkyl group.

(5)

The compound, tautomer or pharmaceutically acceptable salt of the compound, or solvate of any of these according to any one of (1) to (4), wherein $R^4$ is a $C_{1-6}$ alkyl group substitutable with one or more substituents independently selected from the group consisting of a hydroxy group, a halogen atom, and a $C_{1-6}$ alkoxy group.

(6)

The compound, tautomer or pharmaceutically acceptable salt of the compound, or solvate of any of these according to any one of (1) to (4), wherein $R^4$ is:

a $C_{3-10}$ cycloalkyl group, $C_{6-14}$ aryl group, or 3- to 14-membered non-aromatic heterocyclic group substitutable with one or more substituents independently selected from the group consisting of:

a $C_{1-6}$ alkyl group substitutable with one or more substituents independently selected from the group consisting of a halogen atom and a hydroxy group, a $C_{1-6}$ alkoxy group substitutable with one or more substituents independently selected from the group consisting of a halogen atom and a hydroxy group, a halogen atom, a hydroxy group, and a $C_{1-6}$ alkoxy-carbonyl group.

(7)

The compound, tautomer or pharmaceutically acceptable salt of the compound, or solvate of any of these according to any one of (2) to (6), wherein:

X is a substitutable amino group; and

Y is a hydrogen atom or a fluorine atom.

(8)

The compound, tautomer or pharmaceutically acceptable salt of the compound, or solvate of any of these according to any one of (2) to (6), wherein:

X is a substitutable heterocyclic group; and

Y is a hydrogen atom.

(9)

The compound, tautomer or pharmaceutically acceptable salt of the compound, or solvate of any of these according to any one of (2) to (6), wherein:

X is an acyl group; and

Y is a hydrogen atom or a fluorine atom.

(10)

The compound, tautomer or pharmaceutically acceptable salt of the compound, or solvate of any of these according to any one of (2) to (6), wherein:

X is a hydrogen atom; and

Y is a substitutable hydrocarbon group.

(11)

The compound, tautomer or pharmaceutically acceptable salt of the compound, or solvate of any of these according to any one of (2) to (6), wherein:

X is a hydrogen atom; and

Y is a substitutable heterocyclic group.

(12)

The compound, tautomer or pharmaceutically acceptable salt of the compound, or solvate of any of these according to any one of (2) to (6), wherein:

X is an amino group or a $C_{1-6}$ alkylamino group; and

Y is a substitutable hydrocarbon group.

(13)

The compound, tautomer or pharmaceutically acceptable salt of the compound, or solvate of any of these according to any one of (2) to (6), wherein:

X is a $C_{1-6}$ alkyl group; and

Y is a substitutable hydrocarbon group.

(14)

The compound, tautomer or pharmaceutically acceptable salt of the compound, or solvate of any of these according to (1), wherein:

X and Y are bonded with each other to form a substitutable 5- to 7-membered ring together with each carbon atom bonded to X and Y, and the ring is a group of the following Formula (i-a), (i-b), (i-c), (i-d), or (i-e):

(i-a)

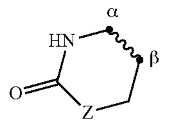

(i-b)

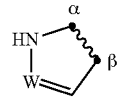

(i-c)

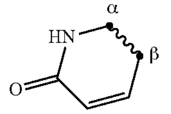

(i-d)

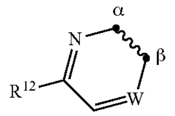

(i-e)

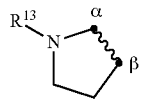

(wherein α is a carbon atom bonded to X, and β is a carbon atom bonded to Y;

Z is a single bond, $—CH_2—$, —O—, $—OCH_2—$ (wherein O is bonded to the carbonyl group, and $CH_2$ is bonded to the other carbon atom) or $—NR^{11}—$;

$R^{11}$ is a possibly halogenated $C_{1-6}$ alkyl group, a possibly halogenated $C_{3-6}$ cycloalkyl group, a 4- to 10-membered non-aromatic heterocyclic group, or a $C_{1-6}$ alkyl group substituted with a 4- to 10-membered non-aromatic heterocyclic group;

W is CH or a nitrogen atom;

$R^{12}$ is a hydrogen atom or a $C_{1-6}$ alkoxy group; and $R^{13}$ is a hydrogen atom, a possibly halogenated $C_{1-6}$ alkyl group, or a carbamoyl group).

(15)

2-Amino-N-cyclopropyl-7-hydroxy-4-neopentyl-5-oxo-4,5-dihydropyrazolo[1,5-a]pyrimidine-6-carboxamide hydrochloride, a tautomer or pharmaceutically acceptable salt of the compound, or a solvate of any of these.

(16)

(E)-N-Cyclopropyl-7-hydroxy-4-isobutyl-3-(3-morpholino-3-oxoprop-1-en-1-yl)-5-oxo-4,5-dihydropyrazolo[1,5-a]pyrimidine-6-carboxamide, a tautomer or pharmaceutically acceptable salt of the compound, or a solvate of any of these.

(17)

The compound, tautomer or pharmaceutically acceptable salt of the compound, or solvate of any of these according to (2), wherein:

$R^1$ is a cyclopropyl group;

$R^2$ and $R^3$ are each a hydrogen atom;

$R^4$ is a tert-butyl group;

X is a pyrimidin-4-ylamino group, a pyrazin-2-ylamino group, a 2-aminopyridin-3-yl group, a (5-(trifluoromethyl)pyrazin-2-yl)amino group, a (5-methoxypyrazin-2-yl)amino group, a (6-methoxypyrazin-2-yl)amino group, an amino group, a (5-carbamoylpyrazin-2-yl) amino group, a ureido group, or a carbamoyl group; and Y is a hydrogen atom.

(18)

N-Cyclopropyl-7-hydroxy-4-isobutyl-5-oxo-2-(pyrazin-2-ylamino)-4,5-dihydropyrazolo[1,5-a]pyrimidine-6-carboxamide, a tautomer or pharmaceutically acceptable salt of the compound, or a solvate of any of these.

(19)

(E)-2-Amino-N-cyclopropyl-7-hydroxy-4-neopentyl-5-oxo-3-(2-(tetrahydro-2H-pyran-4-yl) vinyl)-4,5-dihydropyrazolo[1,5-a]pyrimidine-6-carboxamide hydrochloride, a tautomer or pharmaceutically acceptable salt of the compound, or a solvate of any of these.

(20)

(E)-N-Cyclopropyl-3-(3-(3,3-difluoropyrrolidin-1-yl)-3-oxoprop-1-en-1-yl)-7-hydroxy-4-isobutyl-5-oxo-4,5-dihydropyrazolo[1,5-a]pyrimidine-6-carboxamide, a tautomer or pharmaceutically acceptable salt of the compound, or a solvate of any of these.

(21)

N-Cyclopropyl-3-((E)-3-((3S,5S)-3,5-dimethylmorpholino)-3-oxoprop-1-en-1-yl)-7-hydroxy-4-isobutyl-5-oxo-4,5-dihydropyrazolo[1,5-a]pyrimidine-6-carboxamide, a tautomer or pharmaceutically acceptable salt of the compound, or a solvate of any of these.

(22)

(S,E)-N-Cyclopropyl-3-(3-(3-fluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide, a tautomer or pharmaceutically acceptable salt of the compound, or a solvate of any of these.

(23)

N-Cyclopropyl-3-((E)-3-((3S,5S)-3,5-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide, a tautomer or pharmaceutically acceptable salt of the compound, or a solvate of any of these.

(24)

(S,E)-N-Cyclopropyl-7-hydroxy-4-isobutyl-2-methyl-3-(3-(3-methylmorpholino)-3-oxoprop-1-en-1-yl)-5-oxo-4,5-dihydropyrazolo[1,5-a]pyrimidine-6-carboxamide, a tautomer or pharmaceutically acceptable salt of the compound, or a solvate of any of these.

(25)

N-Cyclopropyl-3-((E)-3-((3R,5R)-3,5-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide, a tautomer or pharmaceutically acceptable salt of the compound, or a solvate of any of these.

(26)

(E)-N-Cyclopropyl-3-(3-(4,4-difluoropiperidin-1-yl)-3-oxoprop-1-en-1-yl)-7-hydroxy-4-isobutyl-2-methyl-5-oxo-4,5-dihydropyrazolo[1,5-a]pyrimidine-6-carboxamide, a tautomer or pharmaceutically acceptable salt of the compound, or a solvate of any of these.

(27)

(E)-N-Cyclopropyl-3-(3-(4-(3,3-difluorocyclobutyl) piperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide, a tautomer or pharmaceutically acceptable salt of the compound, or a solvate of any of these.

(28)

A sepiapterin reductase inhibitor comprising, as an active ingredient, the compound, tautomer or pharmaceutically acceptable salt of the compound, or solvate of any of these according to any one of (1) to (27).

(29)

A drug for preventing, treating, and/or ameliorating a disease for which a sepiapterin reductase inhibitory action is effective, the drug comprising, as an active ingredient, the compound, tautomer or pharmaceutically acceptable salt of the compound, or solvate of any of these according to any one of (1) to (27).

(30)

A pain relief drug comprising, as an active ingredient, the compound, tautomer or pharmaceutically acceptable salt of the compound, or solvate of any of these according to any one of (1) to (27).

(31)

A pharmaceutical comprising, as an active ingredient, the compound, tautomer or pharmaceutically acceptable salt of the compound, or solvate of any of these according to any one of (1) to (27).

Effects of the Invention

The present invention can provide a novel condensed heterocyclic compound having an excellent SPR inhibitory action and particularly useful for treatment and/or prevention of a pain.

MODES FOR CARRYING OUT THE INVENTION

The definitions of substituents used herein will next be described in detail. Unless otherwise specified, the respective substituents have the definitions described below.

As used herein, "n-" denotes normal; "s-" and "sec-," secondary; "t-" and "tert-," tertiary; "m-," meta; "p-," para; "cis-," cis form; "trans-," trans form; "Ph," phenyl; and "Bu," butyl.

The term "substitutable" refers to unsubstituted, or substituted with one or more substituents.

The term "possibly having a substituent" refers to unsubstituted, or substituted with one or more substituents.

The term "possibly halogenated" refers to unsubstituted, or substituted with one or more halogen atoms.

The "$C_{a-b}$" of $C_{a-b}$ alkyl, $C_{a-b}$ alkenyl, $C_{a-b}$ alkynyl, $C_{a-b}$ alkoxy, and $C_{a-b}$ aralkyl refers to the case where the number of carbon atoms forming the alkyl, alkenyl, alkynyl, alkoxy, and aralkyl is a to b. For example, the number of carbon atoms forming the $C_{a-b}$ alkyl of "$C_{a-b}$ alkyl-carbonyl group" is a to b, and the number of carbon atoms forming the entire "$C_{a-b}$ alkyl carbonyl group" is a +1 to b+1.

The "$C_{a-b}$" of $C_{a-b}$ aryl, $C_{a-b}$ cycloalkyl, and $C_{a-b}$ cycloalkenyl refers to the case where the number of carbon atoms forming the ring of each of the aryl, cycloalkyl, and cycloalkenyl is a to b.

The terms used herein for description of chemical structures will now be described.

The term "halogen atom" as used herein refers to a fluorine atom, a chlorine atom, a bromine atom, or an iodine atom.

The term "$C_{1-6}$ alkyl group" as used herein refers to a linear or branched alkyl group having a carbon atom number of 1 to 6. Examples of the $C_{1-6}$ alkyl group include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The term "possibly halogenated $C_{1-6}$ alkyl group" as used herein refers to an unsubstituted "$C_{1-6}$ alkyl group" or a "$C_{1-6}$ alkyl group" substituted with one or more "halogen atoms." Examples of the possibly halogenated $C_{1-6}$ alkyl group include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, and 6,6,6-trifluorohexyl. The number of halogens contained in the "possibly halogenated $C_{1-6}$ alkyl group" is preferably to 7, more preferably 0 to 5.

The term "$C_{2-6}$ alkenyl group" as used herein refers to a linear or branched alkenyl group having at least one double bond and a carbon atom number of 2 to 6. Examples of the $C_{2-6}$ alkenyl group include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

The term "$C_{2-6}$ alkynyl group" as used herein refers to a linear or branched alkynyl group having at least one triple bond and a carbon atom number of 2 to 6. Examples of the $C_{2-6}$ alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

The term "$C_{3-10}$ cycloalkyl group" as used herein refers to a group obtained by removal of one hydrogen atom at any position from a monocyclic, fused-cyclic, bridged-cyclic, or spiro-cyclic saturated-hydrocarbon ring ($C_{3-10}$ cycloalkane), wherein all the atoms forming the ring are carbon atoms, and the number of carbon atoms forming the ring is 3 to 10. Examples of the $C_{3-10}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl.

The term "$C_{3-6}$ cycloalkyl group" as used herein refers to a group among the aforementioned "$C_{3-10}$ cycloalkyl group," wherein the number of carbon atoms forming the ring is 3 to 6.

The term "$C_{3-10}$ cycloalkenyl group" as used herein refers to a group obtained by removal of one hydrogen atom at any position from a monocyclic-ring, fused-ring, bridged-ring, or spiro-ring ($C_{3-10}$ cycloalkene), wherein all the atoms forming the ring are carbon atoms, the number of carbon atoms forming the ring is 3 to 10, and at least one double bond is present in the ring. Examples of the $C_{3-10}$ cycloalkenyl group include cyclopropenyl, cyclobutenyl, cyclopentenyl, cyclohexenyl, cycloheptenyl, and cyclooctenyl.

The term "$C_{3-6}$ cycloalkenyl group" as used herein refers to a group among the aforementioned "$C_{3-10}$ cycloalkenyl group" wherein the number of carbon atoms forming the ring is 3 to 6.

The term "$C_{6-14}$ aryl group" as used herein refers to a monovalent substituent obtained by removal of one hydrogen atom at any position from a monocyclic or fused-cyclic aromatic hydrocarbon ring, wherein all the atoms forming the ring are carbon atoms, and the number of carbon atoms forming the ring is 6 to 14. Examples of the $C_{6-14}$ aryl group include phenyl, 1-naphthyl, 2-naphthyl, 1-anthryl, 2-anthryl, and 9-anthryl.

The term "$C_{7-16}$ aralkyl group" as used herein refers to a group obtained by bonding of the aforementioned "$C_{6-14}$ aryl group" to the aforementioned "$C_{1-6}$ alkyl group," wherein the number of carbon atoms is 7 to 16. Examples of the $C_{7-16}$ aralkyl group include benzyl, phenethyl, naphthylmethyl, and phenylpropyl.

The term "$C_{1-6}$ alkoxy group" as used herein refers to a group obtained by bonding of the aforementioned "$C_{1-6}$ alkyl group" to an oxy group. Examples of the $C_{1-6}$ alkoxy group include methoxy, ethoxy, propoxy, isopropoxy, butoxy, isobutoxy, sec-butoxy, tert-butoxy, pentyloxy, and hexyloxy.

The term "possibly halogenated $C_{1-6}$ alkoxy group" as used herein refers to an unsubstituted "$C_{1-6}$ alkoxy group" or a "$C_{1-6}$ alkoxy group" substituted with one or more of the aforementioned "halogen atoms." Specific examples of the possibly halogenated $C_{1-6}$ alkoxy group include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, and hexyloxy. The number of halogen atoms contained in the "possibly halogenated $C_{1-6}$ alkoxy group" is preferably 0 to 7, more preferably 0 to 5.

The term "$C_{3-10}$ cycloalkyloxy group" as used herein refers to a group obtained by bonding of the aforementioned "$C_{3-10}$ cycloalkyl group" to an oxy group. Example of the $C_{3-10}$ cycloalkyloxy group include cyclopropyloxy, cyclobutyloxy, cyclopentyloxy, cyclohexyloxy, cycloheptyloxy, and cyclooctyloxy.

The terms "$C_{2-6}$ alkenyloxy group," "$C_{6-14}$ aryloxy group," and "$C_{7-16}$ aralkyloxy group" refer to groups obtained by bonding, to an oxy group, of the aforementioned "$C_{2-6}$ alkenyl group," the aforementioned "$C_{6-14}$ aryl group," and the aforementioned "$C_{7-16}$ aralkyl group," respectively.

The term "$C_{1-6}$ alkylthio group" as used herein refers to a group obtained by bonding of the aforementioned "$C_{1-6}$ alkyl group" to a thio group. Examples of the $C_{1-6}$ alkylthio group include methylthio, ethylthio, propylthio, isopropylthio, butylthio, sec-butylthio, tert-butylthio, pentylthio, and hexylthio.

The term "$C_{1-6}$ alkyl-carbonyl group" as used herein refers to a group obtained by bonding of the aforementioned "$C_{1-6}$ alkyl group" to a carbonyl group. Examples of the $C_{1-6}$ alkyl-carbonyl group include acetyl, propanoyl, butanoyl, 2-methylpropanoyl, pentanoyl, 3-methylbutanoyl, 2-methylbutanoyl, 2,2-dimethylpropanoyl, hexanoyl, and heptanoyl.

The term "possibly halogenated $C_{1-6}$ alkyl-carbonyl group" as used herein refers to an unsubstituted "$C_{1-6}$ alkyl-carbonyl group" or a "$C_{1-6}$ alkyl-carbonyl group" substituted with one or more of the aforementioned "halogen atoms." Specific examples of the possibly halogenated $C_{1-6}$ alkyl-carbonyl group include acetyl, chloroacetyl, trifluoroacetyl, trichloroacetyl, propanoyl, butanoyl, pentanoyl, and hexanoyl. The number of halogens contained in the "possibly halogenated $C_{1-6}$ alkyl-carbonyl group" is preferably 0 to 7, more preferably 0 to 5.

The term "$C_{1-6}$ alkoxy-carbonyl group" as used herein refers to a group obtained by bonding of the aforementioned "$C_{1-6}$ alkoxy group" to a carbonyl group. Examples of the $C_{1-6}$ alkoxy-carbonyl group include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, and hexyloxycarbonyl.

The term "$C_{6-14}$ aryl-carbonyl group" as used herein refers to a group obtained by bonding of the aforementioned "$C_{6-14}$ aryl group" to a carbonyl group. Examples of the $C_{6-14}$ aryl-carbonyl group include benzoyl, 1-naphthoyl, and 2-naphthoyl.

The term "$C_{7-16}$ aralkyl-carbonyl group" as used herein refers to a group obtained by bonding of the aforementioned "$C_{7-16}$ aralkyl group" to a carbonyl group. Examples of the $C_{7-16}$ aralkyl-carbonyl group include phenylacetyl and phenylpropionyl.

The term "5- to 14-membered aromatic heterocyclic carbonyl group" refers to a group obtained by bonding of the below-described "5- to 14-membered aromatic heterocyclic group" to a carbonyl group. Examples of the 5- to 14-membered aromatic heterocyclic carbonyl group include nicotinoyl, isonicotinoyl, thenoyl, and furoyl.

The term "3- to 14-membered non-aromatic heterocyclic carbonyl group" refers to a group obtained by bonding of the below-described "3- to 14-membered non-aromatic heterocyclic group" to a carbonyl group. Examples of the 3- to 14-membered non-aromatic heterocyclic carbonyl group include morpholinylcarbonyl, piperidinylcarbonyl, and pyrrolidinylcarbonyl.

The terms "$C_{3-10}$ cycloalkylcarbonyl group" and "$C_{3-10}$ cycloalkenylcarbonyl group" as used herein refer to groups obtained by bonding, to a carbonyl group, of the aforementioned "$C_{3-10}$ cycloalkyl group" and the aforementioned "$C_{3-10}$ cycloalkenyl group," respectively.

The terms "$C_{6-14}$ aryloxy-carbonyl group" and "$C_{7-16}$ aralkyloxy-carbonyl group" refer to groups obtained by bonding, to the oxy group of an oxy-carbonyl group (—O—C(═O)—), of the aforementioned "$C_{6-14}$ aryl group" and the aforementioned "$C_{7-16}$ aralkyl group," respectively.

The terms "$C_{1-6}$ alkyl-carbonyloxy group," "$C_{6-14}$ aryl-carbonyloxy group," "$C_{1-6}$ alkoxy-carbonyloxy group," "5- to 14-membered aromatic heterocyclic carbonyloxy group," and "3- to 14-membered non-aromatic heterocyclic carbonyloxy group" refer to groups obtained by bonding, to the carbonyl group of a carbonyloxy group (—C(═O)O—), of the aforementioned "$C_{1-6}$ alkyl group," the aforementioned "$C_{6-14}$ aryl group," the aforementioned "$C_{1-6}$ alkoxy group," a "5- to 14-membered aromatic heterocyclic group," and a "3- to 14-membered non-aromatic heterocyclic group," respectively.

The term "mono- or di-$C_{1-6}$ alkyl-carbamoyl group" as used herein refers to a group obtained by bonding of the below-described "mono- or di-$C_{1-6}$ alkylamino group" to a carbonyl group. Examples of the mono- or di-$C_{1-6}$ alkyl-carbamoyl group include methylcarbamoyl, ethylcarbamoyl, dimethylcarbamoyl, diethylcarbamoyl, and N-ethyl-N-methylcarbamoyl.

The term "mono- or di-$C_{7-16}$ aralkyl-carbamoyl group" as used herein refers to a group obtained by bonding of the below-described "mono- or di-$C_{7-16}$ aralkylamino group" to a carbonyl group. Examples of the mono- or di-$C_{7-16}$ aralkyl-carbamoyl group include benzylcarbamoyl and phenethylcarbamoyl.

The terms "mono- or di-$C_{3-10}$ cycloalkyl-carbamoyl group" and "mono- or di-$C_{6-14}$ aryl-carbamoyl group" refer to groups obtained by bonding, to a carbonyl group, of a "mono- or di-$C_{3-10}$ cycloalkylamino group" and a "mono- or di-$C_{6-14}$ arylamino group," respectively.

The terms "$C_{1-6}$ alkyl-carbamoyl group," "$C_{3-10}$ cycloalkyl-carbamoyl group," "$C_{3-10}$ cycloalkenyl-carbamoyl group," "$C_{6-14}$ aryl-carbamoyl group," "5- to 14-membered aromatic heterocyclic carbamoyl group," and "3- to 14-membered non-aromatic heterocyclic carbamoyl group" refer to groups obtained by substitution of one hydrogen atom of a carbamoyl group with one "$C_{1-6}$ alkyl group," one "$C_{3-10}$ cycloalkyl group," one "$C_{3-10}$ cycloalkenyl group," one "$C_{6-14}$ aryl group," one "5- to 14-membered aromatic heterocyclic group," and one "3- to 14-membered non-aromatic heterocyclic group," respectively.

The term "(hydroxy)($C_{1-6}$ alkyl)-carbamoyl group" refers to a group obtained by substitution of two hydrogen atoms of a carbamoyl group with one hydroxy group and one $C_{1-6}$ alkyl group.

The term ($C_{1-6}$ alkoxy)($C_{1-6}$ alkyl)-carbamoyl group" refers to a group obtained by substitution of two hydrogen atoms of a carbamoyl group with one $C_{1-6}$ alkoxy group and one $C_{1-6}$ alkyl group.

The term "$C_{1-6}$ alkoxy-carbamoyl group" refers to a group obtained by substitution of one hydrogen atom of a carbamoyl group with one $C_{1-6}$ alkoxy group.

The term "mono- or di-$C_{1-6}$ alkyl-carbamoyloxy group" refers to a group obtained by bonding of the aforementioned "mono- or di-$C_{1-6}$ alkyl-carbamoyl group" to an oxy group. Specific examples of the mono- or di-$C_{1-6}$ alkylcarbamoyloxy group include methylcarbamoyloxy, ethylcarbamoyloxy, dimethylcarbamoyloxy, and diethylcarbamoyloxy.

The term "$C_{6-14}$ aryl-carbamoyloxy group" refers to a group obtained by bonding of the aforementioned "$C_{6-14}$ aryl group" to the nitrogen atom of a carbamoyloxy group (—NH—C(═O)—O—).

The terms "$C_{1-6}$ alkyl-carbamoyloxy group" and "$C_{7-16}$ aralkyl-carbamoyloxy group" refer to groups obtained by bonding, to the nitrogen atom of a carbamoyloxy group (—NH—C(═O)—O—), of one "$C_{1-6}$ alkyl group" and one "$C_{7-16}$ aralkyl group," respectively.

The terms "$C_{1-6}$ alkylsulfonyloxy group" and "$C_{6-14}$ arylsulfonyloxy group" refer to groups obtained by bonding, to the sulfonyl group of a sulfonyloxy group (—$SO_2$—O—), of one "$C_{1-6}$ alkyl group" and one "$C_{7-16}$ aralkyl group," respectively.

The term "mono- or di-$C_{1-6}$ alkylamino group" refers to a group obtained by substitution of one hydrogen atom of an amino group with one "$C_{1-6}$ alkyl group" or a group obtained by substitution of two hydrogen atoms of an amino group with the same or different two "$C_{1-6}$ alkyl groups." Examples of the mono- or di-$C_{1-6}$ alkylamino group include methylamino, ethylamino, propylamino, isopropylamino, butylamino, dimethylamino, diethylamino, dipropylamino, dibutylamino, and N-ethyl-N-methylamino.

The terms "mono- or di-$C_{6-14}$ arylamino group," "mono- or di-$C_{3-10}$ cycloalkylamino group," "mono- or di-$C_{7-16}$ aralkylamino group," "mono- or di-$C_{6-14}$ aryl-carbonylamino group," and "mono- or di-$C_{7-16}$ aralkyl-carbonyl amino group" are defined in the same manner as in the aforementioned "mono- or di-$C_{1-6}$ alkylamino group." When the nitrogen atom of each group has two substituents ($C_{6-14}$ aryl group, $C_{3-10}$ cycloalkyl group, $C_{7-16}$ aralkyl group, $C_{6-14}$ aryl-carbonyl group, and $C_{7-16}$ aralkyl-carbonyl group), the two substituents may be identical to or different from each other.

The term "(mono- or di-$C_{1-6}$ alkyl-carbamoyl)amino group" refers to a group obtained by bonding of one of the aforementioned "mono- or di-$C_{1-6}$ alkyl-carbamoyl groups" to an amino group.

The term "(mono- or di-$C_{7-16}$ aralkyl-carbamoyl)amino group" refers to a group obtained by bonding of one of the aforementioned "mono- or di-$C_{7-16}$ aralkyl-carbamoyl groups" to an amino group.

The term "$C_{1-6}$ alkylamino group" refers to a group obtained by bonding of one "$C_{1-6}$ alkyl group" to an amino group.

The terms "5- to 14-membered aromatic heterocyclic amino group," "5- to 10-membered aromatic heterocyclic amino group," "3- to 14-membered non-aromatic heterocyclic amino group," "4- to 10-membered non-aromatic heterocyclic amino group," "$C_{3-10}$ cycloalkylamino group," and "$C_{3-10}$ cycloalkenylamino group" refer to groups: obtained by bonding, to an amino group, of one "5- to 14-membered aromatic heterocyclic group," one "5- to 10-membered aromatic heterocyclic group," one "3- to 14-membered non-aromatic heterocyclic group," one "4- to 10-membered non-aromatic heterocyclic group," one "$C_{3-10}$ cycloalkyl group," and one "$C_{3-10}$ cycloalkenyl group," respectively.

The terms "5- to 14-membered aromatic heterocyclic oxy group," "3- to 14-membered non-aromatic heterocyclic oxy group," and "4- to 10-membered non-aromatic heterocyclic oxy group" refer to groups obtained by bonding, to an oxy group, of one "5- to 14-membered aromatic heterocyclic group," one "3- to 14-membered non-aromatic heterocyclic group," and one "4- to 10-membered non-aromatic heterocyclic group," respectively.

The terms "$C_{1-6}$ alkyl-carbonylamino group," "$C_{6-14}$ aryl-carbonylamino group," "$C_{1-6}$ alkoxy-carbonylamino group," and "$C_{7-16}$ aralkyloxy-carbonylamino group" refer to groups obtained by bonding, to the carbonyl group of a carbonylamino group (—C(═O)—NH—), of one "$C_{1-6}$ alkyl group," one "$C_{6-14}$ aryl group," one "$C_{1-6}$ alkoxy group," and one "$C_{7-16}$ aralkyl oxy group," respectively.

The term "($C_{1-6}$ alkyl)($C_{1-6}$ alkyl-carbonyl)amino group" refers to a group obtained by substitution of one hydrogen atom of an amino group with one "$C_{1-6}$ alkyl group," and substitution of one hydrogen atom of the amino group with one "$C_{1-6}$ alkyl-carbonyl group."

The term "$C_{1-6}$ alkylsulfonyl group" as used herein refers to a group obtained by bonding of the aforementioned "$C_{1-6}$ alkyl group" to a sulfonyl group. Examples of the $C_{1-6}$ alkylsulfonyl group include methylsulfonyl, ethylsulfonyl, propylsulfonyl, isopropylsulfonyl, butylsulfonyl, sec-butylsulfonyl, and tert-butylsulfonyl.

The term "possibly halogenated $C_{1-6}$ alkylsulfonyl group" as used herein refers to an unsubstituted "$C_{1-6}$ alkylsulfonyl group" or a "$C_{1-6}$ alkylsulfonyl group" substituted with one or more of the aforementioned "halogen atoms." Specific examples of the possibly halogenated $C_{1-6}$ alkylsulfonyl group include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, and hexylsulfonyl. The number of halogens contained in the "possibly halogenated $C_{1-6}$ alkylsulfonyl group" is preferably 0 to 7, more preferably 0 to 5.

The term "$C_{6-14}$ arylsulfonyl group" as used herein refers to a group obtained by bonding of the aforementioned "$C_{6-14}$ aryl group" to a sulfonyl group. Examples of the $C_{6-14}$ arylsulfonyl group include phenylsulfonyl, 1-naphthylsulfonyl, and 2-naphthylsulfonyl.

The term "hydrocarbon group" as used herein refers to a chain, branched, or cyclic saturated or unsaturated group composed of only carbon atoms and hydrogen atoms. Examples of the hydrocarbon group include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group, and a $C_{7-16}$ aralkyl group.

The term "substitutable hydrocarbon group" as used herein includes any of the aforementioned hydrocarbon groups possibly having one or more substituents independently selected from among, for example, the below-described substituent group A1. Among (1) to (67) described below, groups having a 5- to 14-membered aromatic heterocyclic ring, a 3- to 14-membered non-aromatic heterocyclic ring, a $C_{3-10}$ cycloalkane, and a $C_{3-10}$ cycloalkene may be substituted with one or more substituents independently selected from among the below-described substituent group D1.

[Substituent Group A1]

(1) halogen atom, (2) nitro group, (3) cyano group, (4) oxo group, (5) hydroxy group, (6) $C_{1-6}$ alkoxy group substitutable with one or more substituents independently selected from among the below-described substituent group C1, (7) $C_{6-14}$ aryloxy group (e.g., phenoxy or naphthoxy), (8) $C_{7-16}$ aralkyloxy group (e.g., benzyloxy), (9) 5- to 14-membered aromatic heterocyclic oxy group (e.g., pyridyloxy),

(10) 3- to 14-membered non-aromatic heterocyclic oxy group (e.g., morpholinyloxy or piperidinyloxy),

(11) $C_{1-6}$ alkyl-carbonyloxy group substitutable with one or more substituents independently selected from among the below-described substituent group C1 (e.g., acetoxy or propanoyloxy),

(12) $C_{6-14}$ aryl-carbonyloxy group (e.g., benzoyloxy, 1-naphthoyloxy, or 2-naphthoyloxy),

(13) $C_{1-6}$ alkoxy-carbonyloxy group substitutable with one or more substituents independently selected from among the below-described substituent group C1 (e.g., methoxycarbonyloxy, ethoxycarbonyloxy, propoxycarbonyloxy, or butoxycarbonyloxy),

(14) mono- or di-$C_{1-6}$ alkyl-carbamoyloxy group substitutable with one or more substituents independently selected from among the below-described substituent group C1 (e.g., methylcarbamoyloxy, ethylcarbamoyloxy, dimethylcarbamoyloxy, or diethylcarbamoyloxy),

(15) $C_{6-14}$ aryl-carbamoyloxy group (e.g., phenylcarbamoyloxy or naphthylcarbamoyloxy),

(16) 5- to 14-membered aromatic heterocyclic carbonyloxy group (e.g., nicotinoyloxy),

(17) 3- to 14-membered non-aromatic heterocyclic carbonyloxy group (e.g., morpholinylcarbonyloxy or piperidinylcarbonyloxy),

(18) $C_{1-6}$ alkylsulfonyloxy group substitutable with one or more substituents independently selected from among the below-described substituent group C1 (e.g., methylsulfonyloxy or trifluoromethylsulfonyloxy),

(19) $C_{6-14}$ arylsulfonyloxy group (e.g., phenylsulfonyloxy or toluenesulfonyloxy),

(20) $C_{1-6}$ alkylthio group substitutable with one or more substituents independently selected from among the below-described substituent group C1,

(21) 5- to 14-membered aromatic heterocyclic group,

(22) 3- to 14-membered non-aromatic heterocyclic group,

(23) formyl group,

(24) carboxy group,

(25) $C_{1-6}$ alkyl-carbonyl group substitutable with one or more substituents independently selected from among the below-described substituent group C1,

(26) $C_{6-14}$ aryl-carbonyl group,

(27) 5- to 14-membered aromatic heterocyclic carbonyl group,

(28) 3- to 14-membered non-aromatic heterocyclic carbonyl group,
(29) $C_{3-10}$ cycloalkylcarbonyl group,
(30) $C_{3-10}$ cycloalkenylcarbonyl group,
(31) $C_{1-6}$ alkoxy-carbonyl group substitutable with one or more substituents independently selected from among the below-described substituent group C1,
(32) $C_{6-14}$ aryloxy-carbonyl group (e.g., phenyloxycarbonyl, 1-naphthyloxycarbonyl, or 2-naphthyloxycarbonyl),
(33) $C_{7-16}$ aralkyloxy-carbonyl group (e.g., benzyloxycarbonyl or phenethyloxycarbonyl),
(34) carbamoyl group,
(35) thiocarbamoyl group,
(36) mono- or di-$C_{1-6}$ alkyl-carbamoyl group substitutable with one or more substituents independently selected from among the below-described substituent group C1,
(37) $C_{6-14}$ aryl-carbamoyl group (e.g., phenylcarbamoyl),
(38) 5- to 14-membered aromatic heterocyclic carbamoyl group (e.g., pyridylcarbamoyl or thienylcarbamoyl),
(39) 3- to 14-membered non-aromatic heterocyclic carbamoyl group (e.g., morpholinylcarbamoyl, piperidinylcarbamoyl, or tetrahydropyranylcarbamoyl),
(40) (hydroxy) ($C_{1-6}$ alkyl)-carbamoyl group (e.g., N-hydroxy-N-methyl-carbamoyl group),
(41) ($C_{1-6}$ alkoxy)($C_{1-6}$ alkyl)-carbamoyl group (e.g., N-methoxy-N-methyl-carbamoyl group),
(42) $C_{1-6}$ alkylsulfonyl group substitutable with one or more substituents independently selected from among the below-described substituent group C1,
(43) $C_{6-14}$ arylsulfonyl group,
(44) 5- to 14-membered aromatic heterocyclic sulfonyl group (e.g., pyridylsulfonyl or thienylsulfonyl),
(45) $C_{1-6}$ alkylsulfinyl group substitutable with one or more substituents independently selected from among the below-described substituent group C1,
(46) $C_{6-14}$ arylsulfinyl group (e.g., phenylsulfinyl, 1-naphthylsulfinyl, or 2-naphthylsulfinyl),
(47) 5- to 14-membered aromatic heterocyclic sulfinyl group (e.g., pyridylsulfinyl or thienylsulfinyl),
(48) amino group,
(49) mono- or di-$C_{1-6}$ alkylamino group substitutable with one or more substituents independently selected from among the below-described substituent group C1,
(50) mono- or di-$C_{6-14}$ arylamino group (e.g., phenylamino),
(51) 5- to 14-membered aromatic heterocyclic amino group (e.g., pyridylamino),
(52) $C_{7-16}$ aralkylamino group (e.g., benzylamino),
(53) formylamino group,
(54) $C_{1-6}$ alkyl-carbonylamino group substitutable with one or more substituents independently selected from among the below-described substituent group C1 (e.g., acetylamino, propanoylamino, or butanoylamino),
(55) ($C_{1-6}$ alkyl) ($C_{1-6}$ alkyl-carbonyl)amino group (e.g., N-acetyl-N-methylamino),
(56) $C_{6-14}$ aryl-carbonylamino group (e.g., phenylcarbonylamino or naphthylcarbonylamino),
(57) $C_{1-6}$ alkoxy-carbonylamino group substitutable with one or more substituents independently selected from among the below-described substituent group C1 (e.g., methoxycarbonylamino, ethoxycarbonylamino, propoxycarbonylamino, butoxycarbonylamino, or tert-butoxycarbonylamino),
(58) $C_{7-16}$ aralkyloxy-carbonylamino group (e.g., benzyloxycarbonylamino),
(59) $C_{1-6}$ alkylsulfonylamino group substitutable with one or more substituents independently selected from among the below-described substituent group C1 (e.g., methylsulfonylamino or ethylsulfonylamino),
(60) $C_{6-14}$ arylsulfonylamino group (e.g., phenylsulfonylamino or toluenesulfonylamino),
(61) carbamoylamino group,
(62) $C_{1-6}$ alkyl group substitutable with one or more substituents independently selected from among the below-described substituent group C1,
(63) $C_{2-6}$ alkenyl group substitutable with one or more substituents independently selected from among the below-described substituent group C1,
(64) $C_{2-6}$ alkynyl group,
(65) $C_{3-10}$ cycloalkyl group,
(66) $C_{3-10}$ cycloalkenyl group, and
(67) $C_{6-14}$ aryl group.

The term "substitutable hydrocarbon group" as used herein includes any of the aforementioned hydrocarbon groups possibly having one or more substituents independently selected from among the above-described substituent group A1 and, for example, the below-described substituent group A2. Among (1) to (75) described below, groups having a 5- to 14-membered aromatic heterocyclic ring, a 3- to 14-membered non-aromatic heterocyclic ring, a $C_{3-10}$ cycloalkane, and a $C_{3-10}$ cycloalkene may be substituted with one or more substituents independently selected from among the below-described substituent group D2.

[Substituent Group A2]

Substituents described in (1) to (67) of the substituent group A1,

(68) N—$C_{1-6}$ alkyl-N—$C_{3-10}$ cycloalkylcarbamoyl group (e.g., N-methyl-N-cyclopropylcarbamoyl),
(69) N—$C_{1-6}$ alkyl-N-3- to 14-membered non-aromatic heterocyclic carbamoyl group,
(70) N,N-di-$C_{3-10}$ cycloalkylcarbamoyl group,
(71) N,N-di-$C_{1-6}$ alkylcarbamoyl group substitutable with one or more substituents independently selected from among the below-described substituent group C2,
(72) N—$C_{1-6}$ alkylcarbamoyl group substitutable with one or more substituents independently selected from among the below-described substituent group C2,
(73) $C_{6-14}$ aryl-carbonyl group substituted with one or more substituents independently selected from among the below-described substituent group C2,
(74) 3- to 14-membered non-aromatic heterocyclic carbonyl amino group, and
(75) $C_{3-10}$ cycloalkylcarbonylamino group.

In the substituent group A2, among substituents described in (1) to (67) of the substituent group A1, groups having a 5- to 14-membered aromatic heterocyclic ring, a 3-to 14-membered non-aromatic heterocyclic ring, a $C_{3-10}$ cycloalkane, and a $C_{3-10}$ cycloalkene may be substituted with one or more substituents independently selected from among the below-described substituent group D2.

The substituent group B includes:
halogen atom,
nitro group,
cyano group,
hydroxy group,
formyl group,
carboxy group,
carbamoyl group,
thiocarbamoyl group,
amino group,
formylamino group, and
carbamoylamino group.

The substituent group C1 includes:

substituents constituting the aforementioned substituent group B, $C_{1-6}$ alkyl-carbonyloxy group $C_{1-6}$ alkoxy-carbonyloxy group, mono- or di-$C_{1-6}$ alkyl-carbamoyloxy group, possibly halogenated $C_{1-6}$ alkylsulfonyloxy group, possibly halogenated $C_{1-6}$ alkyl-carbonyl group, $C_{1-6}$ alkoxy-carbonyl group, possibly halogenated $C_{1-6}$ alkylsulfonyl group, mono- or di-$C_{1-6}$ alkylamino group, $C_{1-6}$ alkyl-carbonylamino group, ($C_{1-6}$ alkyl)($C_{1-6}$ alkyl-carbonyl)amino group, $C_{1-6}$ alkoxy-carbonylamino group, and $C_{1-6}$ alkylsulfonylamino group.

The substituent group C2 includes:

substituents constituting the aforementioned substituent group C1, $C_{7-16}$ aralkyloxy group, possibly halogenated $C_{1-6}$ alkoxy group, possibly halogenated $C_{3-10}$ cycloalkyl group, 4- to 10-membered non-aromatic heterocyclic group, 4- to 10-membered non-aromatic heterocyclic oxy group, $C_{6-14}$ aryl group, and 5- to 10-membered aromatic heterocyclic group substitutable with $C_{1-6}$ alkyl group.

The substituent group D1 includes:

substituents constituting the aforementioned substituent group C1, possibly halogenated $C_{1-6}$ alkyl group, and $C_{2-6}$ alkenyl group The substituent group D2 includes:

substituents constituting the aforementioned substituent group C2, possibly halogenated $C_{1-6}$ alkyl group, $C_{2-6}$ alkenyl group, $C_{1-6}$ alkyl group substituted with $C_{1-6}$ alkoxy group, $C_{1-6}$ alkyl group substituted with hydroxy group, N,N-di-$C_{1-6}$ alkylcarbamoyl group, and $C_{1-6}$ alkyl group substituted with possibly halogenated $C_{3-10}$ cycloalkyl group.

The number of substituents contained in "substitutable hydrocarbon group" is preferably 0 to 5, more preferably 0 to 3. When the number of substituents is 2 or more, the substituents may be identical to or different from one another.

The $C_{1-6}$ alkyl group substituted with a 3- to 14-membered non-aromatic heterocyclic group refers to a $C_{1-6}$ alkyl group substituted with one or more 3- to 14-membered non-aromatic heterocyclic groups, and includes a group wherein one carbon atom of a $C_{1-6}$ alkyl group forms a double bond (exoolefin structure) with a 3- to 14-membered non-aromatic heterocyclic ring.

Similarly, the $C_{1-6}$ alkyl group substituted with a $C_{3-10}$ cycloalkyl group and the $C_{1-6}$ alkyl group substituted with a $C_{3-10}$ cycloalkenyl group are respectively a $C_{1-6}$ alkyl group substituted with one or more $C_{3-10}$ cycloalkyl groups or $C_{3-10}$ cycloalkenyl groups, and include a group wherein one carbon atom of a $C_{1-6}$ alkyl group forms a double bond (exoolefin structure) with each of a $C_{3-10}$ cycloalkane and a $C_{3-10}$ cycloalkene.

The term "heterocyclic group" as used herein includes (i) a 5- to 14-membered aromatic heterocyclic group, and (ii) a 3- to 14-membered non-aromatic heterocyclic group, wherein each heterocyclic group contains, as ring-forming atoms, one or more carbon atoms and one to four heteroatoms independently selected from among a nitrogen atom, a sulfur atom, and an oxygen atom.

The term "5- to 14-membered aromatic heterocyclic group" as used herein refers to a group obtained by removal of one hydrogen atom at any position from a 5- to 14-membered monocyclic or fused-cyclic aromatic heterocyclic ring (5-to 14-membered aromatic heterocyclic ring) containing, as ring-forming atoms, one or more carbon atoms and one to four heteroatoms independently selected from among a nitrogen atom, a sulfur atom, and an oxygen atom.

Preferred examples of the aforementioned "5- to 14-membered aromatic heterocyclic group" include 5- or 6-membered monocyclic aromatic heterocyclic groups, such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, and triazinyl; and 8- to 14-membered condensed polycyclic (preferably bicyclic or tricyclic) aromatic heterocyclic groups, such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, and phenoxazinyl.

Among "5- to 14-membered aromatic heterocyclic groups," a "5- to 10-membered aromatic heterocyclic group" is preferably used, and a "5- or 6-membered aromatic heterocyclic group" is more preferably used.

The term "5- to 10-membered aromatic heterocyclic group" refers to a 5- to 10-membered aromatic heterocyclic group among the aforementioned "5- to 14-membered aromatic heterocyclic groups."

The term "5- or 6-membered aromatic heterocyclic group" refers to a 5- or 6-membered aromatic heterocyclic group among the aforementioned "5- to 14-membered aromatic heterocyclic groups."

The term "3- to 14-membered non-aromatic heterocyclic group" as used herein refers to a group obtained by removal of one hydrogen atom at any position from a 3- to 14-membered monocyclic, fused-cyclic (the fused-cyclic system may be formed by condensation between non-aromatic rings or condensation between one non-aromatic ring and an aromatic ring), bridged-cyclic, or spiro-cyclic non-aromatic heterocyclic ring (3- to 14-membered non-aromatic heterocyclic ring) containing, as ring-forming atoms, one or more carbon atoms and one to four heteroatoms independently selected from among a nitrogen atom, a sulfur atom, and an oxygen atom, and possibly containing a carbon-oxygen double bond (C=O) or a sulfur-oxygen double bond (S=O or $S(=O)_2$). No particular limitation is imposed on the bonding position, and the bonding may occur at any desired position. However, in the case of a fused-cyclic system formed by condensation between a non-aromatic ring and an aromatic ring, the substitution occurs on the non-aromatic ring side.

Preferred examples of the aforementioned "non-aromatic heterocyclic group" include 3- to 8-membered monocyclic non-aromatic heterocyclic groups, such as aziridinyl, oxiranyl, thiiranyl, azetidinyl, oxetanyl, thietanyl, tetrahydrothienyl, tetrahydrofuranyl, pyrrolinyl, pyrrolidinyl, oxopyrrolidinyl, imidazolinyl, oxoimidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydro-2H-pyranyl, tetrahydrothiopyranyl, morpholinyl, thiomorpholinyl, azepanyl, diazepanyl, azepinyl, oxepanyl, azocanyl, and diazocanyl; 9- to 14-membered condensed polycyclic (preferably bicyclic or tricyclic) non-aromatic heterocyclic groups, such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolidinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, and octahydroisoquinolyl; 7- to 10-membered heterocyclic bridged-ring groups, such as quinuclidinyl and 7-azabicyclo[2.2.1]heptanyl; and 7- to 11-membered heterocyclic spiro-ring groups, such as 1-oxa-8-azaspiro[4.5]decanyl, 1-oxa-8-azaspiro[4.5]dec-3-enyl, and 1,9-diazaspiro[5.5]undecanyl.

Among "3- to 14-membered non-aromatic heterocyclic groups," a "4- to 10-membered non-aromatic heterocyclic group" is preferably used, a "4- to 7-membered non-aromatic heterocyclic group" is more preferably used, and a "5- or 6-membered non-aromatic heterocyclic group" is still more preferably used.

The term "4- to 10-membered non-aromatic heterocyclic group" refers to a 4- to 10-membered non-aromatic heterocyclic group among the aforementioned "3- to 14-membered non-aromatic heterocyclic groups."

The term "4- to 7-membered non-aromatic heterocyclic group" refers to a 4- to 7-membered non-aromatic heterocyclic group among the aforementioned "3- to 14-membered non-aromatic heterocyclic groups."

The term "5- or 6-membered non-aromatic heterocyclic group" refers to a 5- or 6-membered non-aromatic heterocyclic group among the aforementioned "3- to 14-membered non-aromatic heterocyclic groups."

The term "nitrogen-containing heterocyclic group" as used herein refers to a group containing one or more nitrogen atoms as ring-forming atoms among "heterocyclic groups." Similarly, the terms "5- to 14-membered nitrogen-containing aromatic heterocyclic group," "5- to 10-membered nitrogen-containing aromatic heterocyclic group," and "5- or 6-membered nitrogen-containing aromatic heterocyclic group" refer to groups containing one or more nitrogen atoms among "5- to 14-membered aromatic heterocyclic groups," "5- to 10-membered aromatic heterocyclic groups," and "5- or 6-membered aromatic heterocyclic groups," respectively.

The term "substitutable heterocyclic group" as used herein includes heterocyclic groups possibly having substituents selected from among, for example, the aforementioned substituent group A (substituent group A1 or substituent group A2).

The number of substituents contained in the "substitutable heterocyclic group" is, for example, 0 to 3. When the number of substituents is 2 or more, the substituents may be identical to or different from one another.

The term "acyl group" as used herein refers to, for example, a group obtained by bonding of one substituent independently selected from the group (hereinafter referred to as "substituent group G") consisting of a $C_{1-6}$ alkyl group, $C_{2-6}$ alkenyl group, $C_{1-6}$ alkoxy group, $C_{3-10}$ cycloalkyl group, $C_{3-10}$ cycloalkenyl group, $C_{6-14}$ aryl group, $C_{7-16}$ aralkyl group, 5- to 14-membered aromatic heterocyclic group, and 3- to 14-membered non-aromatic heterocyclic group, which are possibly having one or more substituents independently selected from the substituent group A (substituent group A1 or substituent group A2); a hydroxy group; and an amino group to a carbonyl group, an oxygen atom of an oxycarbonyl group (—O—C(═O)—), a thiocarbonyl group, the oxygen atom of an oxy-thiocarbonyl group (—O—C(═S)—), a sulfonyl group, or a sulfinyl group, and a group obtained by bonding of one or two substituents independently selected from the substituent group G to the nitrogen atom of an amino-carbonyl group (—N—C(═O)—) or the nitrogen atom of an amino-thiocarbonyl group (—N—C(═S)—).

The term "acyl group" as used herein includes a group of the formula —C(═O)—NR$^a$R$^b$ (wherein R$^a$ and R$^b$ are each independently a hydrogen atom; a $C_{1-6}$ alkyl group, $C_{2-6}$ alkenyl group, $C_{1-6}$ alkoxy group, $C_{3-10}$ cycloalkyl group, $C_{3-10}$ cycloalkenyl group, $C_{6-14}$ aryl group, $C_{7-16}$ aralkyl group, 5- to 14-membered aromatic heterocyclic group, and 3- to 14-membered non-aromatic heterocyclic group, which are possibly having one or more substituents independently selected from the substituent group A (substituent group A1 or substituent group A2); hydroxy group; or amino group, or R$^a$ and R$^b$ form (together with the nitrogen atom bonded thereto) a 5- to 14-membered aromatic heterocyclic group or 3- to 14-membered non-aromatic heterocyclic group, which is each possibly having one or more substituents independently selected from the substituent group A (substituent group A1 or substituent group A2)).

Preferred examples of the "acyl group" include:

formyl group;

carboxy group;

carbamoyl group;

$C_{1-6}$ alkoxy-carbonyl group, $C_{1-6}$ alkyl-carbonyl group, or mono- or di-$C_{1-6}$ alkyl-carbamoyl group, which is each substitutable with 5- to 14-membered aromatic heterocyclic group, 3- to 14-membered non-aromatic heterocyclic group, $C_{6-14}$ aryl group, $C_{3-10}$ cycloalkyl group, and $C_{3-10}$ cycloalkenyl group, which are substitutable with one or more substituents independently selected from the below-described substituent group F, and one or more substituents independently selected from the group consisting of substituents constituting the below-described substituent group E;

(hydroxy) ($C_{1-6}$ alkyl)-carbamoyl group;

($C_{1-6}$ alkoxy)($C_{1-6}$ alkyl)-carbamoyl group;

$C_{1-6}$ alkoxy-carbamoyl group; and mono- or di-$C_{7-16}$ aralkyl-carbamoyl group, mono- or di-$C_{6-14}$ aryl-carbamoyl group, mono- or di-$C_{3-10}$ cycloalkyl-carbamoyl group, 5- to 14-membered aromatic heterocyclic carbamoyl group, 3- to 14-membered non-aromatic heterocyclic carbamoyl group, $C_{6-14}$ aryl-carbonyl group, $C_{3-10}$ cycloalkylcarbonyl group, $C_{3-10}$ cycloalkenylcarbonyl group, $C_{7-16}$ aralkyl-carbonyl group, 5- to 10-membered aromatic heterocyclic carbonyl group, and 3- to 10-membered non-aromatic heterocyclic carbonyl group, which are substitutable with one or more substituents independently selected from the below-described substituent group F.

The substituent group E includes halogen atom, possibly halogenated $C_{1-6}$ alkoxy group, carbamoyl group, carboxy group, hydroxy group, amino group, carbamoylamino group, $C_{1-6}$ alkyl-carbonyl group, $C_{1-6}$ alkoxy-carbonyl group, and $C_{7-16}$ aralkyloxy group.

The substituent group F includes substituents constituting the substituent group E, 4- to 7-membered non-aromatic heterocyclic group, and possibly halogenated $C_{1-6}$ alkyl group.

The term "substitutable amino group" as used herein is, for example, an amino group possibly having "one or two substituents independently selected from the group consisting of a $C_{1-6}$ alkyl group, $C_{2-6}$ alkenyl group, $C_{3-10}$ cycloalkyl group, $C_{6-14}$ aryl group, $C_{7-16}$ aralkyl group, 5- to 14-membered aromatic heterocyclic group, 3- to 14-membered non-aromatic heterocyclic group, $C_{1-6}$ alkyl-carbonyl group, $C_{6-14}$ aryl-carbonyl group, $C_{7-16}$ aralkyl-carbonyl group, 5- to 14-membered aromatic heterocyclic carbonyl group, 3- to 14-membered non-aromatic heterocyclic carbonyl group, $C_{1-6}$ alkoxy-carbonyl group, carbamoyl group, sulfamoyl group, mono- or di-$C_{1-6}$ alkyl-carbamoyl group, mono- or di-$C_{7-16}$ aralkyl-carbamoyl group, $C_{1-6}$ alkylsulfonyl group, $C_{6-14}$ arylsulfonyl group, and (di-$C_{1-6}$ alkylamino)methylene group, which are possibly having one or more substituents independently selected from the substituent group A (substituent group A1 or substituent group A2)."

The term "substitutable amino group" as used herein includes a group of the formula —N(H)—C(═O)—$Z^1$-$R^{d1}$ (wherein $Z^1$ is a methylene group substitutable with a $C_{1-6}$ alkyl group, —N—, or —O—;

when $Z^1$ is a methylene group substitutable with a $C_{1-6}$ alkyl group, $R^{d1}$ is a $C_{1-6}$ alkyl group, $C_{6-14}$ aryl group, $C_{7-16}$ aralkyl group, 5- to 14-membered aromatic heterocyclic group, or 3- to 14-membered non-aromatic heterocyclic group, which is each possibly having one or more substituents independently selected from the substituent group A (substituent group A1 or substituent group A2);

when $Z^1$ is —O—, $R^{d1}$ is a $C_{1-6}$ alkyl group possibly having one or more substituents independently selected from the substituent group A (substituent group A1 or substituent group A2); and when $Z^1$ is —N—, the combination of —$Z^1$-$R^{d1}$ is a carbamoyl group, (mono- or di-$C_{1-6}$ alkyl-carbamoyl) amino group, or (mono- or di-$C_{7-16}$ aralkyl-carbamoyl) amino group, which is each possibly having one or more substituents independently selected from the substituent group A (substituent group A1 or substituent group A2)).

The term "substitutable amino group" also includes a group of the formula —N(H)—S(═O)$_2$—$Z^2$—$R^{d2}$ (wherein $Z^2$ is a methylene group substitutable with a $C_{1-6}$ alkyl group, or an amino group;

when $Z^2$ is a methylene group substitutable with a $C_{1-6}$ alkyl group, $R^{d2}$ is a $C_{1-6}$ alkyl group or $C_{6-14}$ aryl group, which is each possibly having one or more substituents independently selected from the substituent group A (substituent group A1 or substituent group A2); and when $Z^2$ is an amino group, the combination of —$Z^2$—$R^{d2}$ is a sulfamoyl group possibly having one or more substituents independently selected from the substituent group A (substituent group A1 or substituent group A2)).

Preferred examples of the substitutable amino group include:

amino group;

carbamoylamino group;

sulfamoylamino group;

$C_{1-6}$ alkoxy-carbonylamino group;

$C_{1-6}$ alkyl-carbonylamino group;

$C_{6-14}$ aralkyl-carbonylamino group;

$C_{6-14}$ aralkyloxy-carbonylamino group;

$C_{1-6}$ alkylamino group substitutable with $C_{6-14}$ aryl group, $C_{3-10}$ cycloalkyl group, $C_{3-10}$ cycloalkenyl group, 3- to 14-membered non-aromatic heterocyclic group, or 5- to 14-membered aromatic heterocyclic group, which is each substitutable with one or more substituents independently selected from the substituent group F; and $C_{6-14}$ arylamino group, $C_{3-10}$ cycloalkylamino group, $C_{3-10}$ cycloalkenylamino group, 3- or 14-membered non-aromatic heterocyclic amino group, and 5- to 14-membered aromatic heterocyclic amino group, which are substitutable with one or more substituents independently selected from the substituent group F.

The term "substitutable hydroxy group" as used herein is, for example, a hydroxy group possibly having "a substituent selected from the group consisting of a $C_{1-6}$ alkyl group, $C_{2-6}$ alkenyl group, $C_{3-10}$ cycloalkyl group, $C_{3-10}$ cycloalkenyl group, $C_{6-14}$ aryl group, $C_{7-16}$ aralkyl group, 5- to 14-membered aromatic heterocyclic group, 3- to 14-membered non-aromatic heterocyclic group, $C_{1-6}$ alkyl-carbonyl group, $C_{6-14}$ aryl-carbonyl group, $C_{7-16}$ aralkyl-carbonyl group, 5- to 14-membered aromatic heterocyclic carbonyl group, 3- to 14-membered non-aromatic heterocyclic carbonyl group, $C_{1-6}$ alkoxy-carbonyl group, carbamoyl group, mono- or di-$C_{1-6}$ alkyl-carbamoyl group, mono- or di-$C_{7-16}$ aralkyl-carbamoyl group, $C_{1-6}$ alkylsulfonyl group, and $C_{6-14}$ arylsulfonyl group, which are possibly having one or more substituents independently selected from the substituent group A (substituent group A1 or substituent group A2)."

Preferred examples of the substitutable hydroxy group include:

hydroxy group; or $C_{1-6}$ alkoxy group and $C_{2-6}$ alkenyloxy group, which are substitutable with one or two substituents independently selected from the group consisting of halogen atom, $C_{1-6}$ alkoxy group, carboxy group, carbamoyl group, hydroxy group, amino group, 3- to 14-membered non-aromatic heterocyclic carbonyl group, 5- to 14-membered non-aromatic heterocyclic carbonyl group, $C_{6-14}$ aryl-carbonyl group, 3- to 14-membered non-aromatic heterocyclic group, 5- to 14-membered non-aromatic heterocyclic group, and $C_{6-14}$ aryl group.

More preferred examples of the substitutable hydroxy group include:

hydroxy group; or $C_{1-6}$ alkoxy group substitutable with one or two substituents independently selected from the group consisting of $C_{1-6}$ alkoxy group, carboxy group, carbamoyl group, 4- to 7-membered non-aromatic heterocyclic carbonyl group, and phenyl group.

The term "C1-3 alkylene group" as used herein refers to a methylene group, a 1,2-ethane-diyl group, a 1,1-ethane-diyl group, a 1,3-propane-diyl group, a 1,2-propane-diyl group, a 1,1-propane-diyl group, or a 2,2-propane-diyl group.

The term "$C_{1-6}$ alkylene group" as used herein refers to a divalent group obtained by removal of one hydrogen atom at any position from the aforementioned "$C_{1-6}$ alkyl group."

The term "$C_{2-6}$ alkenylene group" as used herein refers to a divalent group obtained by removal of one hydrogen atom at any position from the aforementioned "$C_{2-6}$ alkenyl group."

The term "$C_{2-6}$ alkynylene group" as used herein refers to a divalent group obtained by removal of one hydrogen atom at any position from the aforementioned "$C_{2-6}$ alkynyl group."

The term "$C_{6-14}$ arylene group" as used herein refers to a divalent group obtained by removal of one hydrogen atom at any position from the aforementioned "$C_{6-14}$ aryl group."

The term "heterocyclic-diyl group" as used herein refers to a divalent group obtained by removal of one hydrogen atom at any position from the aforementioned "heterocyclic group."

The compound having a moiety represented by the phrase "X and Y are bonded with each other to form a substitutable 5- to 7-membered ring together with each carbon atom bonded to X and Y" as used herein refers to a compound wherein X and Y are bonded with each other and bonded with each carbon atom bonded to X and Y, and then represented by the following Formula (I-A):

(I-A)

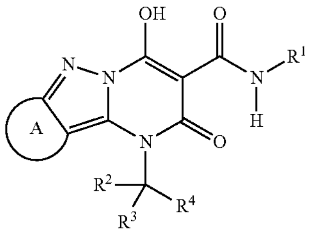

[wherein $R^1$, $R^2$, $R^3$, and $R^4$ have the same meanings as defined in Formula (I); and the ring A is a substitutable 5- to 7-membered non-aromatic heterocyclic ring, or a substitutable 5- or 6-membered nitrogen-containing aromatic heterocyclic ring], as a whole molecule.

The aforementioned "5- to 7-membered non-aromatic heterocyclic ring" of the ring A refers to a 5- to 7-membered monocyclic non-aromatic heterocyclic ring containing, as ring-forming atoms, one or more carbon atoms and one to four heteroatoms independently selected from among a nitrogen atom, a sulfur atom, and an oxygen atom, and possibly containing a carbon-oxygen double bond (C═O) or a sulfur-oxygen double bond (S═O or $S(═O)_2$). Preferred examples of the 5- to 7-membered non-aromatic heterocyclic ring include pyrrolidine, pyrrolidinone, piperidine, piperidinone, 1,3-oxazinan-2-one, 5,6-dihydropyridin-2(1H)-one, tetrahydropyrimidin-2(1H)-one, and 1,3-oxazepan-2-one.

Examples of the substituent of the aforementioned "substitutable 5- to 7-membered non-aromatic heterocyclic ring" include $C_{1-6}$ alkyl group, $C_{3-6}$ cycloalkyl group, and 4- to 10-membered non-aromatic heterocyclic group, which are substitutable with one or more substituents independently selected from the substituent group F.

The term "5- or 6-membered nitrogen-containing aromatic heterocyclic ring" refers to a 5- or 6-membered aromatic heterocyclic ring containing, as ring-forming atoms, one or more carbon atoms and one to four heteroatoms independently selected from among a nitrogen atom, a sulfur atom, and an oxygen atom, and containing at least one nitrogen atom. Preferred examples of the 5- or 6-membered nitrogen-containing aromatic heterocyclic ring include pyrrole, pyrazole, pyridine, pyrimidine, pyridazine, and pyrazine.

Examples of the substituent of the aforementioned "5- or 6-membered nitrogen-containing aromatic heterocyclic ring" include substituents constituting the substituent group E.

When X and Y are bonded with each other to form a substitutable 5- to 7-membered ring together with each carbon atom bonded to X and Y, X and Y are preferably a group of the following Formula (i-a), (i-b), (i-c), (i-d), or (i-e):

(i-a)

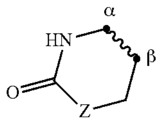

(i-b)

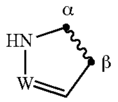

(i-c)

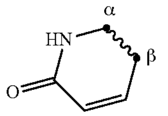

(i-d)

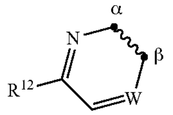

(i-e)

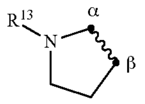

(wherein α is a carbon atom bonded to X, and β is a carbon atom bonded to Y;

Z is a single bond, —$CH_2$—, —O—, —$OCH_2$— (wherein O is bonded to the carbonyl group, and $CH_2$ is bonded to the other carbon atom) or —$NR^{11}$—;

$R^{11}$ is a $C_{1-6}$ alkyl group, $C_{3-6}$ cycloalkyl group, and a 4- to 10-membered non-aromatic heterocyclic group, which are substitutable with one or more substituents independently selected from the substituent group F;

W is CH or a nitrogen atom; and $R^{12}$ and $R^{13}$ are each a hydrogen atom or a substituent independently selected from the substituent group E).

When X and Y are a group of Formula (i-a), (i-b), (i-c), (i-d), or (i-e), the entire compound has a structure of the following Formula (I-a), (I-b), (I-c), (I-d), or (I-e):

(I-a)

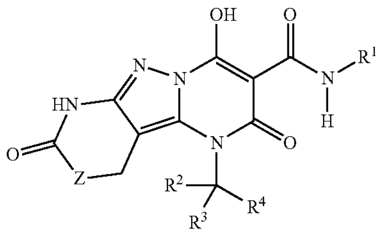

-continued (I-b)

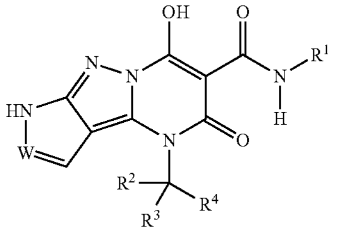

(I-c)

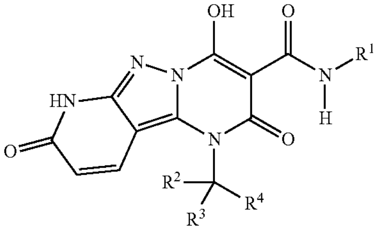

(I-d)

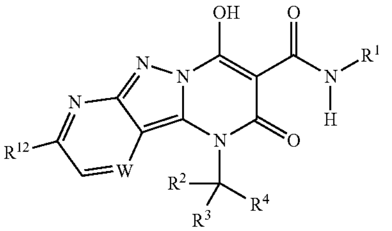

(I-e)

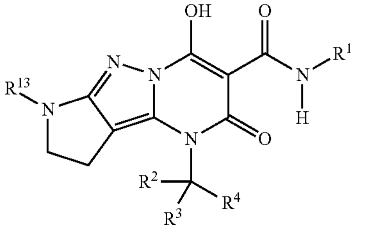

(wherein the respective symbols have the same meanings as defined above in Formula (i-a), (i-b), (i-c), (i-d), or (i-e)).

Preferred structures of the respective substituents in the present invention will next be described. Preferred examples of the respective substituents in the present invention include particularly, the substituents described below, those substituents being included in the above-defined substituents or being together with the above-defined substituents.

$R^2$ and $R^3$ are each preferably a hydrogen atom or a $C_{1-6}$ alkyl group, more preferably a hydrogen atom.

$R^1$ is preferably a $C_{3-10}$ cycloalkyl group substitutable with one or more substituents independently selected from the group consisting of a halogen atom and a possibly halogenated $C_{1-6}$ alkyl group.

$R^1$ is more preferably a $C_{3-6}$ cycloalkyl group.

$R^1$ is still more preferably a cyclopropyl group or a cyclobutyl group.

The substitutable hydrocarbon group of $R^4$ is preferably a $C_{1-6}$ alkyl group substitutable with one to three substituents independently selected from among the following (i) to (iii):

(i) halogen atom, (ii) hydroxy group, and (iii) $C_{1-6}$ alkoxy group.

The substitutable hydrocarbon group of $R^4$ is more preferably a $C_{1-6}$ alkyl group substitutable with a hydroxy group, still more preferably a tert-butyl group, an isopropyl group, or a tert-butyl group substituted with one hydroxy group, particularly preferably a tert-butyl group or an isopropyl group.

In another embodiment, the substitutable hydrocarbon group of $R^4$ is preferably a $C_{3-10}$ cycloalkyl group substitutable with one or more substituents independently selected from among the following (i), (ii), and (iv) to (vi):

(i) halogen atom, (ii) hydroxy group, (iv) $C_{1-6}$ alkyl group substitutable with one to three substituents selected from among halogen atoms and hydroxy group, (v) $C_{1-6}$ alkoxy group substitutable with one to three substituents selected from among halogen atoms and hydroxy group, and (vi) $C_{1-6}$ alkoxy-carbonyl group.

The substitutable hydrocarbon group of $R^4$ is more preferably a possibly halogenated $C_{3-6}$ cycloalkyl group, still more preferably a cyclohexyl group substitutable with one to three halogen atoms.

In another embodiment, the substitutable hydrocarbon group of $R^4$ is preferably a $C_{6-14}$ aryl group substitutable with one or more substituents independently selected from the group consisting of the aforementioned (i), (ii), and (iv) to (vi).

The substitutable hydrocarbon group of $R^4$ is more preferably a $C_{6-14}$ aryl group substitutable with one to three substituents independently selected from the group consisting of a $C_{1-6}$ alkyl group substitutable with a hydroxy group, and halogen atoms.

$R^4$ is more preferably a phenyl group substitutable with one to three substituents independently selected from the group consisting of a fluorine atom, a chlorine atom, and a hydroxymethyl group.

The substitutable heterocyclic group of $R^4$ is preferably a 4-to 10-membered non-aromatic heterocyclic group substitutable with one or more substituents independently selected from the group consisting of the aforementioned (i), (ii), and (iv) to (vi).

The substitutable heterocyclic group of $R^4$ is more preferably a 4- to 7-membered non-aromatic heterocyclic group substitutable with one to three substituents independently selected from the group consisting of halogen atoms and $C_{1-6}$ alkyl groups.

The substitutable heterocyclic group of $R^4$ is still more preferably a tetrahydropyran-4-yl group substitutable with one or two substituents independently selected from the group consisting of a fluorine atom and a methyl group.

The substitutable heterocyclic group of $R^4$ is particularly preferably a tetrahydropyran-4-yl group or a 4-methyltetrahydropyran-4-yl group.

When Y is a hydrogen atom, the substitutable amino group of X is preferably an amino group substituted with a heterocyclic group substitutable with one or more substituents independently selected from the substituent group F, a $C_{1-6}$ alkylamino group substituted with a heterocyclic group substitutable with one or more substituents independently selected from the substituent group F, an amino group, a carbamoylamino group, a sulfamoylamino group, a $C_{1-6}$ alkyl-carbonylamino group, or a $C_{1-6}$ alkoxy-carbonylamino group.

The substitutable amino group of X is more preferably an amino group substituted with a 5- to 10-membered aromatic heterocyclic group substitutable with one or two substituents independently selected from the group consisting of a $C_{1-6}$ alkoxy group, a carbamoyl group, a carboxy group, a possibly halogenated $C_{1-6}$ alkyl group, and a $C_{1-6}$ alkoxy-carbonyl group, a $C_{1-6}$ alkylamino group substituted with a 4- to 10-membered non-aromatic heterocyclic group, an amino group, or a carbamoylamino group.

The substitutable amino group of X is still more preferably an amino group substituted with a 5- or 6-membered nitrogen-containing aromatic heterocyclic group substitutable with one or two substituents independently selected from the group consisting of a $C_{1-6}$ alkoxy group, a carbamoyl group, a carboxy group, a possibly halogenated $C_{1-6}$ alkyl group, and a $C_{1-6}$ alkoxy-carbonyl group, an amino group, or a carbamoylamino group.

The substitutable amino group of X is much more preferably a pyrimidin-4-ylamino group or pyrazin-2-ylamino group, which is each substituted with one or more substituents independently selected from the group consisting of a methoxy group, a carbamoyl group, a carboxy group, a trifluoromethyl group, and a methoxycarbonyl group, an amino group, or a carbamoylamino group.

When Y is a hydrogen atom, the substitutable heterocyclic group of X is preferably a 5- to 14-membered aromatic heterocyclic group or 3- to 14-membered non-aromatic heterocyclic group, which is each substitutable with one or more substituents independently selected from the aforementioned substituent group F.

The substitutable heterocyclic group of X is more preferably a 5- to 14-membered nitrogen-containing aromatic heterocyclic group substitutable with one or more substituents independently selected from the group consisting of a halogen atom, a hydroxy group, a carbamoyl group, an amino group, a carbamoylamino group, a possibly halogenated $C_{1-6}$ alkyl group, a $C_{1-6}$ alkoxy group, a $C_{1-6}$ alkoxy-carbonyl group, and a 4-to 7-membered non-aromatic heterocyclic group.

The substitutable heterocyclic group of X is still more preferably a 5- or 6-membered nitrogen-containing aromatic heterocyclic group substituted with an amino group.

When Y is a hydrogen atom, the acyl group of X is preferably a carboxy group;

a carbamoyl group;

a sulfamoyl group;

a mono- or di-$C_{1-6}$ alkyl-carbamoyl group or $C_{1-6}$ alkoxy-carbonyl group substitutable with one or more substituents independently selected from the group consisting of a phenyl group, $C_{3-10}$ cycloalkyl group, 5- to 10-membered aromatic heterocyclic group, and 4- to 10-membered non-aromatic heterocyclic group, which are substitutable with one or more substituents independently selected from the substituent group F, and substituents constituting the substituent group E; or a benzoyl group, $C_{3-10}$ cycloalkylcarbonyl group, 5- to 10-membered aromatic heterocyclic carbonyl group, or 4- to 10-membered non-aromatic heterocyclic carbonyl group, which is each substitutable with one or more substituents independently selected from the substituent group F.

The acyl group of X is more preferably a carboxy group;

a carbamoyl group;

a sulfamoyl group;

a mono- or di-$C_{1-6}$ alkyl-carbamoyl group substitutable with one or two substituents independently selected from the group consisting of a possibly halogenated $C_{1-6}$ alkoxy group, a hydroxy group, a halogen atom, a 5- or 6-membered aromatic heterocyclic group, and a 4- to 7-membered non-aromatic heterocyclic group;

a $C_{1-6}$ alkoxy-carbonyl group;

a 5- or 6-membered aromatic heterocyclic carbonyl group;

a 4- to 7-membered non-aromatic heterocyclic carbonyl group; or a $C_{1-6}$ alkoxy-carbamoyl group.

The acyl group of X is still more preferably a carbamoyl group or a sulfamoyl group.

The acyl group of X is particularly preferably a carbamoyl group.

When Y is a hydrogen atom, the substitutable hydrocarbon group of X is preferably a $C_{1-6}$ alkyl group, $C_{2-6}$ alkenyl group, $C_{3-10}$ cycloalkyl group, or $C_{6-14}$ aryl group, which is each substitutable with one to three substituents independently selected from the group consisting of a possibly halogenated $C_{1-6}$ alkoxy group, a hydroxy group, a halogen atom, a $C_{1-6}$ alkoxy-carbonyl group, a carbamoyl group, an amino group, and a carboxy group.

The substitutable hydrocarbon group of X is more preferably a $C_{1-6}$ alkyl group, $C_{2-6}$ alkenyl group, $C_{3-6}$ cycloalkyl group, or phenyl group, which is each substitutable with one or two substituents independently selected from the group consisting of a $C_{1-6}$ alkoxy group, a hydroxy group, a $C_{1-6}$ alkoxy-carbonyl group, a carbamoyl group, and an amino group.

When X is a hydrogen atom, the acyl group of Y is preferably a carboxy group, a formyl group, a sulfamoyl group, a carbamoyl group, or a $C_{1-6}$ alkoxy-carbonyl group, or a mono- or di-$C_{1-6}$ alkyl-carbamoyl group substitutable with one to three substituents independently selected from the group consisting of halogen atoms and a hydroxy group, or a $C_{3-10}$ cycloalkyl-carbamoyl group, 5- to 10-membered aromatic heterocyclic carbonyl group, or 4- to 10-membered non-aromatic heterocyclic carbonyl group, which is each substitutable with one to three substituents independently selected from the group consisting of a $C_{1-6}$ alkyl group, halogen atoms, and a hydroxy group.

The acyl group of Y is more preferably a carboxy group, a formyl group, a $C_{1-6}$ alkoxy-carbonyl group, a mono- or di-$C_{1-6}$ alkyl-carbamoyl group, a possibly halogenated mono- or di-$C_{3-10}$ cycloalkyl-carbamoyl group, or a 4- to 7-membered non-aromatic heterocyclic carbonyl group substitutable with one to three $C_{1-6}$ alkyl groups.

When X is a hydrogen atom, the substitutable hydrocarbon group of Y is preferably a $C_{1-6}$ alkyl group, $C_{2-6}$ alkenyl group, $C_{6-14}$ aryl group, $C_{3-10}$ cycloalkyl group, or $C_{3-10}$ cycloalkenyl group, which is each substitutable with one or more substituents independently selected from the group consisting of a hydroxy group, a $C_{1-6}$ alkoxy group, a $C_{7-16}$ aralkyloxy group, a mono- or di-$C_{1-6}$ alkyl-carbamoyl group, and a $C_{1-6}$ alkoxy-carbonylamino group.

In another embodiment, when X is a hydrogen atom, the substitutable hydrocarbon group of Y is more preferably a $C_{1-6}$ alkyl group or $C_{2-6}$ alkenyl group, which is each substituted with one or more substituents selected from the group consisting of a 3- to 14-membered non-aromatic heterocyclic carbonyl group, 5- to 14-membered aromatic heterocyclic carbonyl group, $C_{6-14}$ aryl-carbonyl group, or $C_{3-10}$ cycloalkylcarbonyl group, which is each substitutable with one or more substituents independently selected from the substituent group F.

The substitutable hydrocarbon group of Y is still more preferably a $C_{2-6}$ alkenyl group substituted with a 4- to 10-membered non-aromatic heterocyclic carbonyl group substitutable with one or more substituents independently selected from the group consisting of a halogen atom, a hydroxy group, a carbamoyl group, an amino group, a possibly halogenated $C_{1-6}$ alkyl group, a $C_{1-6}$ alkoxy group, and a $C_{1-6}$ alkoxy-carbonyl group.

The substitutable hydrocarbon group of Y is much more preferably an ethenyl group substituted with a 4- to 7-membered non-aromatic heterocyclic carbonyl group substitutable with one or two substituents independently selected from the group consisting of a halogen atom, a possibly halogenated $C_{1-6}$ alkyl group, and a hydroxy group.

The ethenyl group is particularly preferably in a trans form.

When X is a hydrogen atom, the substitutable heterocyclic group of Y is preferably a 4- to 14-membered non-aromatic heterocyclic group or 5- to 14-membered aromatic heterocyclic group, which is each substitutable with one or more substituents independently selected from the group consisting of a halogen atom, a hydroxy group, a carbamoyl group, an amino group, a carbamoylamino group, a possibly halogenated $C_{1-6}$ alkyl group, a $C_{1-6}$ alkoxy group, and a $C_{1-6}$ alkoxy-carbonyl group.

The substitutable heterocyclic group of Y is more preferably an oxygen-atom-containing 4- to 7-membered non-aromatic heterocyclic group substitutable with one to four substituents independently selected from the group consisting of halogen atoms and a $C_{1-6}$ alkyl group.

The substitutable heterocyclic group of Y is still more preferably a dihydropyranyl group.

When Y is a halogen atom,

X is preferably a hydrogen atom, an amino group, a carbamoylamino group, a carbamoyl group, or a $C_{1-6}$ alkoxy-carbonyl group.

When X is a halogen atom,

Y is preferably a hydrogen atom, an amino group, a carbamoylamino group, a carbamoyl group, or a $C_{1-6}$ alkoxy-carbonyl group, more preferably a hydrogen atom.

When X is an amino group,

Y is preferably a hydrogen atom; a halogen atom; a $C_{2-6}$ alkenyl group substituted with a $C_{1-6}$ alkoxy-carbonyl group; or a 4- to 7-membered non-aromatic heterocyclic group substitutable with a $C_{1-6}$ alkyl group or a $C_{1-6}$ alkoxy-carbonyl group.

In another embodiment, when X is an amino group, the substitutable hydrocarbon group of Y is preferably an ethenyl group substituted with a 4- to 10-membered non-aromatic heterocyclic carbonyl group substitutable with one or two substituents independently selected from the group consisting of a halogen atom and a possibly halogenated $C_{1-6}$ alkyl group.

The substitutable hydrocarbon group of Y is more preferably an ethenyl group substituted with a 5- or 6-membered non-aromatic heterocyclic carbonyl group substitutable with one or two substituents independently selected from the group consisting of a halogen atom and a $C_{1-6}$ alkyl group.

The ethenyl group is particularly preferably in a trans form.

In another embodiment, when X is an amino group, the substitutable hydrocarbon group of Y is preferably an ethenyl group substituted with a $C_{1-6}$ alkyl group, a $C_{2-6}$ alkenyl group, or a 5- or 6-membered non-aromatic heterocyclic group.

The ethenyl group is particularly preferably in a trans form.

When X is a methylamino group, the substitutable hydrocarbon group of Y is preferably an ethenyl group substituted with a 4- to 10-membered non-aromatic heterocyclic carbonyl group substitutable with one or two substituents independently selected the group consisting of a halogen atom and a possibly halogenated $C_{1-6}$ alkyl group.

The substitutable hydrocarbon group of Y is more preferably an ethenyl group substituted with a 5- or 6-membered non-aromatic heterocyclic carbonyl group substitutable with one or two substituents independently selected from the group consisting of a halogen atom and a $C_{1-6}$ alkyl group.

The ethenyl group is particularly preferably in a trans form.

When X is a $C_{1-6}$ alkyl group, the substitutable hydrocarbon group of Y is preferably an ethenyl group substituted with a 4- to 10-membered non-aromatic heterocyclic carbonyl group substitutable with one or two substituents independently selected from the group consisting of a halogen atom, a possibly halogenated $C_{1-6}$ alkyl group, a possibly halogenated $C_{3-6}$ cycloalkyl group, and a $C_{1-6}$ alkoxy group.

The substitutable hydrocarbon group of Y is more preferably an ethenyl group substituted with a 5- or 6-membered non-aromatic heterocyclic carbonyl group substitutable with one or two substituents independently selected from the group consisting of a halogen atom and a $C_{1-6}$ alkyl group.

X is preferably a methyl group or an ethyl group, particularly preferably a methyl group. The ethenyl group is particularly preferably in a trans form.

When X and Y are bonded with each other to form a substitutable 5-to 7-membered ring together with each carbon atom bonded to X and Y, X and Y are preferably a group of the following Formula (i-a) or (i-b):

(i-a)

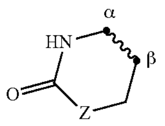

(i-b)

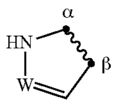

(wherein α is a carbon atom bonded to X, and β is a carbon atom bonded to Y;

Z is —$CH_2$—, —O—, or —$NR^{11}$—;

$R^{11}$ is a methyl group, a cyclopropyl group, a tetrahydropyran-4-yl group, a 3,3-difluorocyclobutyl group, or a tetrahydropyran-4-ylmethyl group; and W is CH).

X and Y are more preferably a group of Formula (i-a) wherein Z is $—CH_2—$.

Preferred compounds in the present invention will next be described.

(1)

A compound of the following Formula (I):

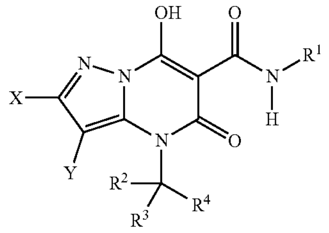

(I)

[wherein $R^1$ is a $C_{3-6}$ cycloalkyl group;

$R^2$ and $R^3$ are each a hydrogen atom;

$R^4$ is a $C_{1-6}$ alkyl group substitutable with one or more substituents independently selected from the group consisting of a hydroxy group, a halogen atom, and a $C_{1-6}$ alkoxy group; or a $C_{3-6}$ cycloalkyl group, phenyl group, or 4- to 7-membered non-aromatic heterocyclic group, which is each substitutable with one or more substituents independently selected from the group consisting of:

a $C_{1-6}$ alkyl group substitutable with one or more substituents independently selected from the group consisting of a halogen atom and a hydroxy group, a $C_{1-6}$ alkoxy group substitutable with one or more substituents independently selected from the group consisting of a halogen atom and a hydroxy group, a halogen atom, a hydroxy group, and a $C_{1-6}$ alkoxy-carbonyl group;

X is a hydrogen atom, a halogen atom, a substitutable amino group, a substitutable hydrocarbon group, a substitutable heterocyclic group, an acyl group, or a group of the formula $—CR^5═NR^6$;

the substitutable amino group is a phenylamino group, $C_{3-10}$ cycloalkylamino group, 5- to 10-membered aromatic heterocyclic amino group, or 4- to 10-membered non-aromatic heterocyclic amino group, which is each substitutable with one or more substituents independently selected from the substituent group F, a mono- or di-$C_{1-6}$ alkylamino group substitutable with a phenyl group, $C_{3-10}$ cycloalkyl group, 5- to 10-membered aromatic heterocyclic group, or 4- to 10-membered non-aromatic heterocyclic group, which is each substitutable with one or more substituents independently selected from the substituent group F, an amino group, a carbamoylamino group, a sulfamoylamino group, a $C_{1-6}$ alkyl-carbonylamino group, or a $C_{1-6}$ alkoxy-carbonylamino group, the substitutable hydrocarbon group of X is a $C_{1-6}$ alkyl group, $C_{2-6}$ alkenyl group, $C_{3-10}$ cycloalkyl group, or phenyl group, which is each substitutable with one to three substituents independently selected from the group consisting of a possibly halogenated $C_{1-6}$ alkoxy group, a hydroxy group, a halogen atom, a $C_{1-6}$ alkoxy-carbonyl group, a carbamoyl group, an amino group, and a carboxy group;

the substitutable heterocyclic group of X is a 5- to 10-membered aromatic heterocyclic group or 4- to 10-membered non-aromatic heterocyclic group, which is each substitutable with one or more substituents independently selected from the substituent group F;

the acyl group of X is a carboxy group, a carbamoyl group, a sulfamoyl group, or a mono- or di-$C_{1-6}$ alkyl-carbamoyl group or $C_{1-6}$ alkoxy-carbonyl group, which is each substitutable with one or more substituents independently selected from the group consisting of a phenyl group, $C_{3-10}$ cycloalkyl group, 5- to 10-membered aromatic heterocyclic group, and 4- to 10-membered non-aromatic heterocyclic group, which are substitutable with one or more substituents independently selected from the substituent group F, and substituents constituting the substituent group E, or a benzoyl group, $C_{3-10}$ cycloalkylcarbonyl group, 5- or 6-membered aromatic heterocyclic carbonyl group, or 4- to 7-membered non-aromatic heterocyclic carbonyl group, which is each substitutable with one or more substituents independently selected from the substituent group F, or a $C_{1-6}$ alkoxy-carbamoyl group;

Y is a hydrogen atom, a halogen atom, a substitutable hydrocarbon group, a substitutable heterocyclic group, an acyl group, or a group of the formula $—CR^7═NR^8$;

the substitutable hydrocarbon group of Y is a $C_{1-6}$ alkyl group or $C_{2-6}$ alkenyl group, which is each substituted with one substituent selected from the group consisting of a 3- to 10-membered non-aromatic heterocyclic carbonyl group, 5- to 10-membered aromatic heterocyclic carbonyl group, phenylcarbonyl group, or $C_{3-10}$ cycloalkylcarbonyl group, which is each substitutable with one or more substituents independently selected from the group consisting of substituents constituting the substituent group F, a possibly halogenated $C_{3-6}$ cycloalkyl group, a 4- to 10-membered non-aromatic heterocyclic group, a $C_{6-14}$ aryl group, a $C_{1-6}$ alkyl group substituted with a hydroxy group, and a $C_{1-6}$ alkyl group substituted with a $C_{1-6}$ alkoxy group, or a $C_{1-6}$ alkyl group, $C_{2-6}$ alkenyl group, $C_{6-14}$ aryl group, $C_{3-10}$ cycloalkyl group, or $C_{3-10}$ cycloalkenyl group, which is each substitutable with one or more substituents independently selected from the group consisting of a hydroxy group, a $C_{1-6}$ alkoxy group, a $C_{7-16}$ aralkyloxy group, a mono- or di-$C_{1-6}$ alkyl-carbamoyl group, and a $C_{1-6}$ alkoxy-carbonylamino group;

the substitutable heterocyclic group of Y is a 4- to 10-membered non-aromatic heterocyclic group or 5- to 10-membered aromatic heterocyclic group, which is each substitutable with one or more substituents independently selected from the group consisting of a halogen atom, a hydroxy group, a carbamoyl group, an amino group, a carbamoylamino group, a possibly halogenated $C_{1-6}$ alkyl group, a $C_{1-6}$ alkoxy group, and a $C_{1-6}$ alkoxy-carbonyl group;

the acyl group of Y is a carboxy group, a carbamoyl group, a sulfamoyl group, a mono- or di-$C_{1-6}$ alkyl-carbamoyl group or $C_{1-6}$ alkoxy-carbonyl group, which is each substitutable with one or more substituents independently selected from the substituent group E, a benzoyl group, $C_{3-10}$ cycloalkylcarbonyl group, $C_{3-10}$ cycloalkenylcarbonyl group, 5-to 10-membered aromatic heterocyclic carbonyl group, or 4- to 10-membered non-aromatic heterocyclic carbonyl group, which is each substitutable with one or more substituents independently selected from the substituent group F, or a phenylcarbamoyl group, $C_{3-10}$ cycloalkyl-carbamoyl group, $C_{3-10}$ cycloalkenyl-carbamoyl group, 4- to 10-membered non-aromatic heterocyclic carbamoyl group, or 5- to 10-membered aromatic heterocyclic carbamoyl group, which is each substitutable with one or more substituents independently selected from the substituent group F, or a $C_{1-6}$ alkoxy-carbamoyl group;

$R^5$ and $R^7$ are each independently a hydrogen atom or a $C_{1-6}$ alkyl group;

$R^6$ and $R^8$ are each independently a hydroxy group, or a $C_{1-6}$ alkoxy group substitutable with one substituent selected from the group consisting of a $C_{1-6}$ alkoxy group, a carboxy group, a carbamoyl group, a 4- to 7-membered non-aromatic heterocyclic carbonyl group, and a phenyl group;

when X is a hydrogen atom, Y is not a hydrogen atom; and when Y is a hydrogen atom, X is not a hydrogen atom], a tautomer or pharmaceutically acceptable salt of the compound, or a solvate of any of these.

(2) A compound of the following Formula (I):

(I)

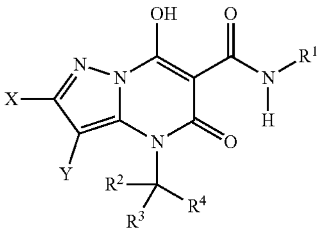

[wherein $R^1$ is a $C_{3-6}$ cycloalkyl group;

$R^2$ and $R^3$ are each a hydrogen atom;

$R^4$ is a $C_{1-6}$ alkyl group substitutable with one or more substituents independently selected from the group consisting of a hydroxy group, a halogen atom, and a $C_{1-6}$ alkoxy group; or a $C_{3-6}$ cycloalkyl group, phenyl group, or 4- to 7-membered non-aromatic heterocyclic group, which is each substitutable with one or more substituents independently selected from the group consisting of:

a $C_{1-6}$ alkyl group substitutable with one or more substituents independently selected from the group consisting of a halogen atom and a hydroxy group, a $C_{1-6}$ alkoxy group substitutable with one or more substituents independently selected from the group consisting of a halogen atom and a hydroxy group, a halogen atom, a hydroxy group, and a $C_{1-6}$ alkoxy-carbonyl group;

X is a hydrogen atom, a halogen atom, a substitutable amino group, a substitutable hydrocarbon group, a substitutable heterocyclic group, an acyl group, or a group of the formula —$CR^5$═$NR^6$;

the substitutable amino group is a phenyl group, $C_{3-10}$ cycloalkyl group, 5- to 10-membered aromatic heterocyclic amino group, or 4- to 10-membered non-aromatic heterocyclic amino group, which is each substitutable with one or more substituents independently selected from the substituent group F, a mono- or di-$C_{1-6}$ alkylamino group substitutable with a phenyl group, $C_{3-10}$ cycloalkyl group, 5- to 10-membered aromatic heterocyclic group, or 4- to 10-membered non-aromatic heterocyclic group, which is each substitutable with one or more substituents independently selected from the substituent group F, an amino group, a carbamoylamino group, a sulfamoylamino group, a $C_{1-6}$ alkyl-carbonylamino group, or a $C_{1-6}$ alkoxy-carbonylamino group, the substitutable hydrocarbon group of X is a $C_{1-6}$ alkyl group, $C_{2-6}$ alkenyl group, $C_{3-10}$ cycloalkyl group, or phenyl group, which is each substitutable with one to three substituents independently selected from the group consisting of a possibly halogenated $C_{1-6}$ alkoxy group, a hydroxy group, a halogen atom, a $C_{1-6}$ alkoxy-carbonyl group, a carbamoyl group, an amino group, and a carboxy group;

the substitutable heterocyclic group of X is a 5- to 10-membered aromatic heterocyclic group or 4- to 10-membered non-aromatic heterocyclic group, which is each substitutable with one or more substituents independently selected from the substituent group F;

the acyl group of X is a carboxy group, a carbamoyl group, a sulfamoyl group, or a mono- or di-$C_{1-6}$ alkyl-carbamoyl group or $C_{1-6}$ alkoxy-carbonyl group, which is each substitutable with one or more substituents independently selected from the group consisting of a phenyl group, $C_{3-10}$ cycloalkyl group, 5- to 10-membered aromatic heterocyclic group, and 4- to 10-membered non-aromatic heterocyclic group, which are substitutable with one or more substituents independently selected from the substituent group F, and substituents constituting the substituent group E, or a phenyl group, $C_{3-10}$ cycloalkyl group, 5- or 6-membered aromatic heterocyclic carbonyl group, or 4- to 7-membered non-aromatic heterocyclic carbonyl group, which is each substitutable with one or more substituents independently selected from the substituent group F, or a $C_{1-6}$ alkoxy-carbamoyl group;

Y is a hydrogen atom, a halogen atom, a substitutable hydrocarbon group, a substitutable heterocyclic group, an acyl group, or a group of the formula —$CR^7$═$NR^8$;

the substitutable hydrocarbon group of Y is a $C_{1-6}$ alkyl group or $C_{2-6}$ alkenyl group, which is each substituted with one substituent selected from the group consisting of a 3- to 10-membered non-aromatic heterocyclic carbonyl group, 5- to 10-membered aromatic heterocyclic carbonyl group, phenylcarbonyl group, or $C_{3-10}$ cycloalkylcarbonyl group substitutable with one or more substituents independently selected from the substituent group F, or a $C_{1-6}$ alkyl group, $C_{2-6}$ alkenyl group, $C_{6-14}$ aryl group, $C_{3-10}$ cycloalkyl group, or $C_{3-10}$ cycloalkenyl group, which is each substitutable with one or more substituents independently selected from the group consisting of a hydroxy group, a $C_{1-6}$ alkoxy group, a $C_{7-16}$ aralkyloxy group, a mono- or di-$C_{1-6}$ alkyl-carbamoyl group, and a $C_{1-6}$ alkoxy-carbonylamino group;

the substitutable heterocyclic group of Y is a 4- to 10-membered non-aromatic heterocyclic group or 5- to 10-membered aromatic heterocyclic group, which is each substitutable with one or more substituents independently selected from the group consisting of a halogen atom, a hydroxy group, a carbamoyl group, an amino group, a carbamoylamino group, a possibly halogenated $C_{1-6}$ alkyl group, a $C_{1-6}$ alkoxy group, and a $C_{1-6}$ alkoxy-carbonyl group;

the acyl group of Y is a carboxy group, a carbamoyl group, a sulfamoyl group, a mono- or di-$C_{1-6}$ alkyl-carbamoyl group or $C_{1-6}$ alkoxy-carbonyl group, which is each substitutable with one or more substituents independently selected from the substituent group E, a benzoyl group, $C_{3-10}$ cycloalkylcarbonyl group, $C_{3-10}$ cycloalkenylcarbonyl group, 5- to 10-membered aromatic heterocyclic carbonyl group, or 4- to 10-membered non-aromatic heterocyclic carbonyl group, which is each substitutable with one or more substituents independently selected from the substituent group F, or a phenylcarbamoyl group, $C_{3-10}$ cycloalkyl-carbamoyl group, $C_{3-10}$ cycloalkenyl-carbamoyl group, 4- to 10-membered non-aromatic heterocyclic carbamoyl group, or 5- to 10-membered aromatic heterocyclic carbamoyl group, which is each substitutable with one or more substituents independently selected from the substituent group F, or a $C_{1-6}$ alkoxy-carbamoyl group;

$R^5$ and $R^7$ are each independently a hydrogen atom or a $C_{1-6}$ alkyl group;

$R^6$ and $R^8$ are each independently a hydroxy group, or a $C_{1-6}$ alkoxy group substitutable with one substituent selected from the group consisting of a $C_{1-6}$ alkoxy group, a carboxy group, a carbamoyl group, a 4- to 7-membered non-aromatic heterocyclic carbonyl group, and a phenyl group;

when X is a hydrogen atom, Y is not a hydrogen atom; and when Y is a hydrogen atom, X is not a hydrogen atom], a tautomer or pharmaceutically acceptable salt of the compound, or a solvate of any of these.

(3)

The compound, tautomer or pharmaceutically acceptable salt of the compound, or solvate of any of these according to (1) or (2), wherein $R^1$ is a cyclopropyl group or a cyclobutyl group.

(4)

The compound, tautomer or pharmaceutically acceptable salt of the compound, or solvate of any of these according to (1), (2), or (3), wherein $R^4$ is a tert-butyl group, an isopropyl group, a 3-pentyl group, a 2,2-dimethylpropan-1-yl group, or a tert-butyl group substituted with one hydroxy group.

(5)

The compound, tautomer or pharmaceutically acceptable salt of the compound, or solvate of any of these according to (1), (2), or (3), wherein $R^4$ is a cyclohexyl group, phenyl group, or tetrahydropyranyl group, which is each substitutable with one to three substituents independently selected from the group consisting of:

a halogen atom, a $C_{1-6}$ alkyl group substitutable with a hydroxy group, and a $C_{1-6}$ alkoxy-carbonyl group.

(6)

The compound, tautomer or pharmaceutically acceptable salt of the compound, or solvate of any of these according to any one of (1) to (5), wherein either of X and Y is a hydrogen atom.

(7)

The compound, tautomer or pharmaceutically acceptable salt of the compound, or solvate of any of these according to any one of (1) to (6), wherein X is a group of the formula $-L^X-R^X$ (wherein $R^X$ is a phenyl group, $C_{3-10}$ cycloalkyl group, 4- to 10-membered non-aromatic heterocyclic group, or 5- to 10-membered aromatic heterocyclic group, which is each substitutable with one or more substituents independently selected from the substituent group F;

$L^X$ is a single bond, —N(H)—, a carbonyl group, —$N(R^9)$—$R^{10}$—*, or —C(═O)—$N(R^9)$—$R^{10}$—*;

$R^9$ is a hydrogen atom or a possibly halogenated $C_{1-6}$ alkyl group;

$R^{10}$ is a $C_{1-6}$ alkylene group; and

* is a bonding position to $R^X$).

(8)

The compound, tautomer or pharmaceutically acceptable salt of the compound, or solvate of any of these according to (7), wherein $R^9$ is a hydrogen atom.

(9)

The compound, tautomer or pharmaceutically acceptable salt of the compound, or solvate of any of these according to (7) or (8), wherein $R^X$ is a phenyl group, $C_{3-6}$ cycloalkyl group, 4- to 7-membered non-aromatic heterocyclic group, or 5- to 10-membered aromatic heterocyclic group, which is each substitutable with one to three substituents independently selected from the group consisting of a halogen atom, a carboxy group, a carbamoyl group, a hydroxy group, an amino group, a carbamoylamino group, a possibly halogenated $C_{1-6}$ alkyl group, a $C_{1-6}$ alkoxy group, a $C_{1-6}$ alkoxy-carbonyl group, and a 4- to 7-membered non-aromatic heterocyclic group.

(10)

The compound, tautomer or pharmaceutically acceptable salt of the compound, or solvate of any of these according to any one of (1) to (6), wherein X is a phenyl group, $C_{3-6}$ cycloalkyl group, 4- to 7-membered non-aromatic heterocyclic group, or 5- to 10-membered aromatic heterocyclic group, which is each substitutable with one or two substituents independently selected from the group consisting of a halogen atom, a carbamoyl group, a hydroxy group, an amino group, a carbamoylamino group, a $C_{1-6}$ alkyl group, a $C_{1-6}$ alkoxy group, a $C_{1-6}$ alkoxy-carbonyl group, and a 4- to 7-membered non-aromatic heterocyclic group.

(11)

The compound, tautomer or pharmaceutically acceptable salt of the compound, or solvate of any of these according to any one of (1) to (6), wherein X is a 4- to 7-membered non-aromatic heterocyclic group or 5- to 10-membered aromatic heterocyclic group, which is each substitutable with one or two substituents independently selected from the group consisting of a halogen atom, a carbamoyl group, a hydroxy group, an amino group, a carbamoylamino group, a $C_{1-6}$ alkoxy group, a $C_{1-6}$ alkoxy-carbonyl group, and a 4- to 7-membered non-aromatic heterocyclic group.

(12)

The compound, tautomer or pharmaceutically acceptable salt of the compound, or solvate of any of these according to any one of (1) to (6), wherein X is a 5- to 10-membered aromatic heterocyclic group substitutable with one or two substituents independently selected from the group consisting of a carbamoyl group, a carbamoylamino group, a hydroxy group, an amino group, a $C_{1-6}$ alkoxy group, and a 4-to 7-membered non-aromatic heterocyclic group.

(13)

The compound, tautomer or pharmaceutically acceptable salt of the compound, or solvate of any of these according to any one of (1) to (6), wherein X is a 5- to 10-membered aromatic heterocyclic group substituted with an amino group.

(14)

The compound, tautomer or pharmaceutically acceptable salt of the compound, or solvate of any of these according to any one of (1) to (6), wherein X is a pyridyl group, pyrimidyl group, pyrazolyl group, pyrazyl group, or benzimidazolyl group, which is each substituted with an amino group.

(15)

The compound, tautomer or pharmaceutically acceptable salt of the compound, or solvate of any of these according to (7) or (8), wherein $R^X$ is a 4- to 10-membered non-aromatic heterocyclic group or 5- to 10-membered aromatic heterocyclic group, which is each substitutable with one or more substituents independently selected from the substituent group F;

$L^X$ is —N(H)—, a carbonyl group, —N(H)—$R^{10}$—*, or —C(=O)—N(H)—$R^{10}$—*;

$R^{10}$ is a $C_{1-6}$ alkylene group; and

* is a bonding position to $R^X$.

(16)

The compound, tautomer or pharmaceutically acceptable salt of the compound, or solvate of any of these according to (7), (8), or (15), wherein $R^X$ is a 4- to 7-membered non-aromatic heterocyclic group or 5- or 6-membered aromatic heterocyclic group, which is each substitutable with one or two substituents independently selected from the group consisting of a possibly halogenated $C_{1-6}$ alkyl group, a possibly halogenated $C_{1-6}$ alkoxy group, a $C_{1-6}$ alkoxy-carbonyl group, a carboxy group, and a carbamoyl group.

(17)

The compound, tautomer or pharmaceutically acceptable salt of the compound, or solvate of any of these according to any one of (7), (8), (15), and (16) wherein $R^{10}$ is a $C_{1-3}$ alkylene group.

(18)

The compound, tautomer or pharmaceutically acceptable salt of the compound, or solvate of any of these according to any one of (7), (8), and (15) to (17) wherein $R^X$ is a 5- or 6-membered aromatic heterocyclic group substitutable with one substituent selected from the group consisting of a possibly halogenated $C_{1-6}$ alkyl group, a $C_{1-6}$ alkoxy group, a $C_{1-6}$ alkoxy-carbonyl group, a carboxy group, and a carbamoyl group; and $L^X$ is —N(H)—.

(19)

The compound, tautomer or pharmaceutically acceptable salt of the compound, or solvate of any of these according to any one of (7), (8), and (15) to (18) wherein $R^X$ is a pyrimidinyl group or pyrazinyl group, which is each substitutable with one substituent selected from the group consisting of a trifluoromethyl group, a methoxy group, a methoxy-carbonyl group, a carboxy group, and a carbamoyl group.

(20)

The compound, tautomer or pharmaceutically acceptable salt of the compound, or solvate of any of these according to (1) to (6), wherein X is an amino group, a carbamoylamino group, a sulfamoylamino group, a $C_{1-6}$ alkyl-carbonylamino group, a $C_{1-6}$ alkoxy-carbonylamino group, a $C_{1-6}$ alkoxy-carbamoyl group, a carbamoyl group, a carboxy group, a $C_{1-6}$ alkoxy-carbonyl group, a mono- or di-$C_{1-6}$ alkyl-carbamoyl group substitutable with one to three substituents independently selected from the group consisting of a possibly halogenated $C_{1-6}$ alkoxy group, a hydroxy group, and a halogen atom, a $C_{1-6}$ alkyl group or $C_{2-6}$ alkenyl group, which is each substitutable with one to three substituents independently selected from the group consisting of a $C_{1-6}$ alkoxy-carbonyl group, a carbamoyl group, and a hydroxy group, or a group of the formula —$CR^5$=$NR^6$;

$R^5$ is a hydrogen atom or a $C_{1-6}$ alkyl group; and $R^6$ is a hydroxy group, or a $C_{1-6}$ alkoxy group substitutable with one substituent independently selected from the group consisting of a $C_{1-6}$ alkoxy group, a carboxy group, a carbamoyl group, and a phenyl group.

(21)

The compound, tautomer or pharmaceutically acceptable salt of the compound, or solvate of any of these according to (1) to (6), wherein X is an amino group, a carbamoylamino group, or a carbamoyl group.

(22)

The compound, tautomer or pharmaceutically acceptable salt of the compound, or solvate of any of these according to (1) to (6), wherein X is a $C_{1-6}$ alkylamino group or a $C_{1-6}$ alkyl group.

(23)

The compound, tautomer or pharmaceutically acceptable salt of the compound, or solvate of any of these according to any one of (2) to (22), wherein Y is a group of the formula $-L^Y-L^{Yy}-R^Y$ (wherein $R^Y$ is a phenyl group, $C_{3-10}$ cycloalkyl group, $C_{3-10}$ cycloalkenyl group, 4- to 10-membered non-aromatic heterocyclic group, 5- to 10-membered aromatic heterocyclic group, phenylamino group, $C_{3-10}$ cycloalkylamino group, 4- to 10-membered non-aromatic heterocyclic amino group, or 5- to 10-membered aromatic heterocyclic amino group, which is each substitutable with one or more substituents independently selected from the substituent group F, or a mono- or di-$C_{1-6}$ alkylamino group, a $C_{1-6}$ alkoxy group, a hydroxy group, an amino group, or a hydrogen atom;

$L^Y$ is a single bond, a $C_{1-6}$ alkylene group, or a $C_{2-6}$ alkenylene group;

$L^{Yy}$ is a single bond or a carbonyl group; and when $L^Y$ and $L^{Yy}$ are each a single bond, $R^Y$ is not a hydrogen atom).

(24)

The compound, tautomer or pharmaceutically acceptable salt of the compound, or solvate of any of these according to any one of (2) to (23), wherein Y is a phenyl group, $C_{3-6}$ cycloalkyl group, $C_{3-6}$ cycloalkenyl group, 4- to 7-membered non-aromatic heterocyclic group, or 5- or 6-membered aromatic heterocyclic group, which is each substitutable with one or more substituents independently selected from the substituent group F.

(25)

The compound, tautomer or pharmaceutically acceptable salt of the compound, or solvate of any of these according to any one of (2) to (24), wherein Y is a phenyl group, $C_{3-6}$ cycloalkyl group, $C_{3-6}$ cycloalkenyl group, 4- to 7-membered non-aromatic heterocyclic group, or 5- or 6-membered aromatic heterocyclic group, which is each substitutable with one to four substituents independently selected from the group consisting of a possibly halogenated $C_{1-6}$ alkyl group, a $C_{1-6}$ alkoxy-carbonyl group, a $C_{1-6}$ alkoxy-carbonylamino group, a $C_{7-14}$ aralkyloxy group, and an amino group.

(26)

The compound, tautomer or pharmaceutically acceptable salt of the compound, or solvate of any of these according to any one of (2) to (25), wherein Y is a 4- to 7-membered non-aromatic heterocyclic group or 5- or 6-membered aromatic heterocyclic group, which is each substitutable with one to four substituents independently selected from the group consisting of a possibly halogenated $C_{1-6}$ alkyl group and a $C_{1-6}$ alkoxy-carbonyl group.

(27)

The compound, tautomer or pharmaceutically acceptable salt of the compound, or solvate of any of these according to any one of (2) to (26), wherein Y is a tetrahydropyranyl group substitutable with one to four methyl groups.

(28)

The compound, tautomer or pharmaceutically acceptable salt of the compound, or solvate of any of these according to (1) to (22), wherein Y is a group of the formula $$-L^Y-L^{Yy}-R^Y$$

(wherein $R^Y$ is a $C_{3-6}$ cycloalkyl group, 4- to 10-membered non-aromatic heterocyclic group, $C_{3-6}$ cycloalkylamino group, or 4- to 7-membered non-aromatic heterocyclic amino group, which is each substitutable with one to three substituents independently selected from the group consisting of a possibly halogenated $C_{1-6}$ alkyl group, a possibly halogenated $C_{3-6}$ cycloalkyl group, a $C_{1-6}$ alkoxy-carbonyl group, a hydroxy group, a 4- to 10-membered non-aromatic heterocyclic group, a $C_{6-14}$ aryl group, a $C_{1-6}$ alkyl group substituted with a hydroxy group, a $C_{1-6}$ alkyl group substituted with a $C_{1-6}$ alkoxy group, and a halogen atom, or a mono- or di-$C_{1-6}$ alkylamino group, a $C_{1-6}$ alkoxy group, a hydroxy group, or an amino group;

$L^Y$ is a $C_{1-6}$ alkylene group or a $C_{2-6}$ alkenylene group; and $L^{Yy}$ is a carbonyl group).

(29)

The compound, tautomer or pharmaceutically acceptable salt of the compound, or solvate of any of these according to (28), wherein $L^Y$ is a 1,2-ethane-diyl group or a 1,2-ethene-diyl group; and $R^Y$ is a 4- to 7-membered non-aromatic heterocyclic group, $C_{3-6}$ cycloalkylamino group, or 4- to 7-membered non-aromatic heterocyclic amino group, which is each substitutable with one to three substituents independently selected from among a possibly halogenated $C_{1-6}$ alkyl group, a possibly halogenated $C_{3-6}$ cycloalkyl group, a $C_{1-6}$ alkoxy-carbonyl group, a hydroxy group, and a halogen atom, or a mono- or di-$C_{1-6}$ alkylamino group, a $C_{1-6}$ alkoxy group, a hydroxy group, or an amino group.

(30)

The compound, tautomer or pharmaceutically acceptable salt of the compound, or solvate of any of these according to (29), wherein $R^Y$ is a morpholino group, pyrrolidin-1-yl group, piperazinyl group, piperidino group, tetrahydropyranylamino group, or cyclobutylamino group, which is each substitutable with one or two substituents independently selected from among a possibly halogenated $C_{1-6}$ alkyl group, a possibly halogenated $C_{3-6}$ cycloalkyl group, a $C_{1-6}$ alkoxy-carbonyl group, a hydroxy group, and a halogen atom.

(31)

The compound, tautomer or pharmaceutically acceptable salt of the compound, or solvate of any of these according to (23), wherein $R^Y$ is a $C_{3-6}$ cycloalkyl group, 4- to 7-membered non-aromatic heterocyclic group, $C_{3-6}$ cycloalkylamino group, or 4- to 7-membered non-aromatic heterocyclic amino group, which is each substitutable with one to three substituents independently selected from among a possibly halogenated $C_{1-6}$ alkyl group, a $C_{1-6}$ alkoxy-carbonyl group, a hydroxy group, and a halogen atom, or a mono- or di-$C_{1-6}$ alkylamino group, a $C_{1-6}$ alkoxy group, a hydroxy group, or an amino group;

$L^Y$ is a $C_{1-6}$ alkylene group or a $C_{2-6}$ alkenylene group; and $L^{Yy}$ is a carbonyl group.

(32)

The compound, tautomer or pharmaceutically acceptable salt of the compound, or solvate of any of these according to (31), wherein $L^Y$ is a 1,2-ethane-diyl group or a 1,2-ethene-diyl group; and $R^Y$ is a 4- to 7-membered non-aromatic heterocyclic group, $C_{3-6}$ cycloalkylamino group, or 4- to 7-membered non-aromatic heterocyclic amino group, which is each substitutable with one to three substituents independently selected from among a possibly halogenated $C_{1-6}$ alkyl group, a $C_{1-6}$ alkoxy-carbonyl group, a hydroxy group, and a halogen atom, or a mono- or di-$C_{1-6}$ alkylamino group, a $C_{1-6}$ alkoxy group, a hydroxy group, or an amino group.

(33)

The compound, tautomer or pharmaceutically acceptable salt of the compound, or solvate of any of these according to (32), wherein $R^Y$ is a morpholino group, piperazinyl group, piperidino group, tetrahydropyranylamino group, or cyclobutylamino group, which is each substitutable with one or two substituents independently selected from among a possibly halogenated $C_{1-6}$ alkyl group, a $C_{1-6}$ alkoxy-carbonyl group, a hydroxy group, and a halogen atom.

(34)

The compound, tautomer or pharmaceutically acceptable salt of the compound, or solvate of any of these according to (2), wherein $R^4$ is a tert-butyl group, an isopropyl group, a tetrahydropyran-4-yl group, or a 4-methyl-tetrahydropyran-4-yl group;

X is an amino group, a carbamoylamino group, a carbamoyl group, or a pyrazinylamino group or pyrimidinylamino group, which is each substituted with a possibly halogenated $C_{1-6}$ alkyl group, a $C_{1-6}$ alkoxy group, or a carbamoyl group, or a pyridyl group substituted with an amino group; and Y is a hydrogen atom.

(35)

The compound, tautomer or pharmaceutically acceptable salt of the compound, or solvate of any of these according to (2), wherein $R^4$ is a tert-butyl group, an isopropyl group, or a 4-methyl-tetrahydropyran-4-yl group;

X is a hydrogen atom; and

Y is a dihydro-2H-pyran-4-yl group, or an ethenyl group substituted with a morpholinocarbonyl group.

(36)

The compound, tautomer or pharmaceutically acceptable salt of the compound, or solvate of any of these according to (2), wherein $R^4$ is a tetrahydropyran-4-yl group or a 4-methyl-tetrahydropyran-4-yl group;

X is a hydrogen atom; and

Y is a dihydro-2H-pyran-4-yl group.

(37)

The compound, tautomer or pharmaceutically acceptable salt of the compound, or solvate of any of these according to (1), wherein $R^1$ is a cyclopropyl group;

$R^4$ is a tert-butyl group or an isopropyl group;

X is an amino group, a methylamino group, an ethyl group, or a methyl group; and Y is a group of the formula $-L^Y-L^{Yy}-R^Y$ (wherein $R^Y$ is a morpholino group, pyrrolidin-1-yl group, piperazin-1-yl group, piperidin-1-yl group, or dihydro-2H-pyran-4-yl group, which is each substitutable with one or two substituents independently selected from among a possibly halogenated $C_{1-6}$ alkyl group, a possibly halogenated $C_{3-6}$ cycloalkyl group, a $C_{1-6}$ alkoxy group, and a halogen atom;

$L^Y$ is a 1,2-ethene-diyl group; and $L^{Yy}$ is a single bond or a carbonyl group).

(38)

A compound wherein X and Y are bonded with each other to form a substitutable 5-to 7-membered ring together with each carbon atom bonded to X and Y in Formula (I), represented by the following Formula (I-a), (I-b), (I-c), (I-d), or (I-e):

(I-a)

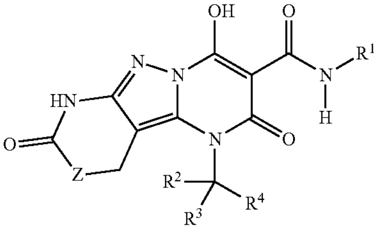

-continued (I-b)

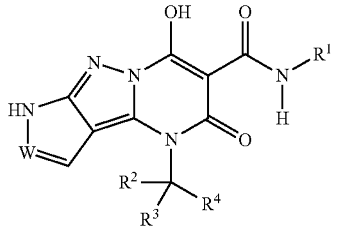

(I-c)

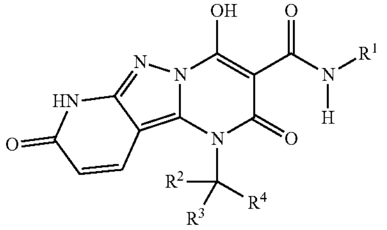

(I-d)

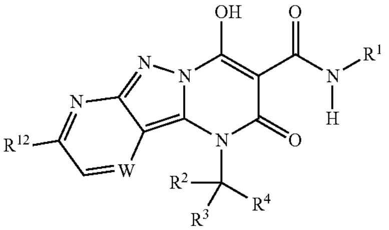

(I-e)

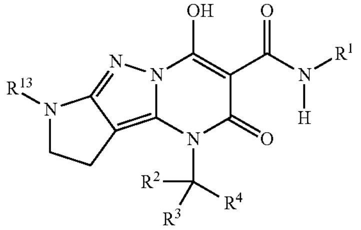

[wherein $R^1$ is a $C_{3-6}$ cycloalkyl group;

$R^2$ and $R^3$ are each a hydrogen atom;

$R^4$ is a $C_{1-6}$ alkyl group substitutable with one or more substituents independently selected from the group consisting of:

a hydroxy group, a halogen atom, and a $C_{1-6}$ alkoxy group; or a $C_{3-6}$ cycloalkyl group, phenyl group, or 4- to 7-membered non-aromatic heterocyclic group, which is each substitutable with one or more substituents independently selected from the group consisting of:

a $C_{1-6}$ alkyl group substitutable with one or more substituents independently selected from the group consisting of a halogen atom and a hydroxy group, a $C_{1-6}$ alkoxy group substitutable with one or more substituents independently selected from the group consisting of a halogen atom and a hydroxy group, a halogen atom, a hydroxy group, and a $C_{1-6}$ alkoxy-carbonyl group;

Z is a single bond, $—CH_2—$, —O—, $—OCH_2—$ (wherein O is bonded to the carbonyl group, and $CH_2$ is bonded to the other carbon atom) or $—NR^{11}—$;

$R^{11}$ is a $C_{1-6}$ alkyl group, $C_{3-6}$ cycloalkyl group, and 4- to 10-membered non-aromatic heterocyclic group, which are substitutable with one or more substituents independently selected from the substituent group F;

W is CH or a nitrogen atom; and $R^{12}$ and $R^{13}$ are each a hydrogen atom or a substituent independently selected from the substituent group E], a tautomer or pharmaceutically acceptable salt of the compound, or a solvate of any of these.

(39)

The compound, tautomer or pharmaceutically acceptable salt of the compound, or solvate of any of these according to (38), wherein $R^1$ is a cyclopropyl group or a cyclobutyl group.

(40)

The compound, tautomer or pharmaceutically acceptable salt of the compound, or solvate of any of these according to (38) or (39), wherein $R^4$ is a tert-butyl group, an isopropyl group, a tetrahydro-2H-pyran-4-yl group, or a 4-methyltetrahydro-2H-pyran-4-yl group.

(41)

The compound, tautomer or pharmaceutically acceptable salt of the compound, or solvate of any of these according to (38), (39), or (40), wherein X and wherein X and Y are bonded with each other to form a substitutable 5- to 7-membered ring together with each carbon atom bonded to X and Y in Formula (I), and wherein the compound is represented by the following formula (I-a) or (I-b):

(I-a)

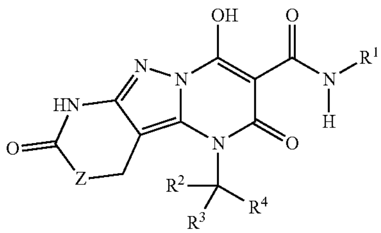

(I-b)

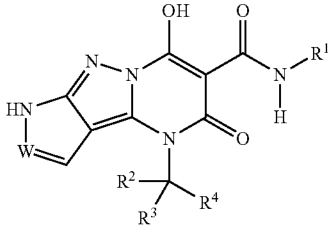

(wherein

Z is —$CH_2$—, —O—, or —$NR^{11}$—;

$R^{11}$ is a methyl group, a cyclopropyl group, a tetrahydropyran-4-yl group, a 3,3-difluorocyclobutyl group, or a tetrahydropyran-4-ylmethyl group; and W is CH).

(42)

A sepiapterin reductase inhibitor containing, as an active ingredient, the compound, tautomer or pharmaceutically acceptable salt of the compound, or solvate of any of these according to any one of (1) to (41).

(43)

A drug for preventing, treating, and/or ameliorating a disease for which a sepiapterin reductase inhibitory action is effective, the drug containing, as an active ingredient, the compound, tautomer or pharmaceutically acceptable salt of the compound, or solvate of any of these according to any one of (1) to (41).

(44)

A pain relief drug containing, as an active ingredient, the compound, tautomer or pharmaceutically acceptable salt of the compound, or solvate of any of these according to any one of (1) to (41).

(45)

A pharmaceutical containing, as an active ingredient, the compound, tautomer or pharmaceutically acceptable salt of the compound, or solvate of any of these according to any one of (1) to (41).

(46)

A pharmaceutical having a sepiapterin reductase inhibitory action, the pharmaceutical containing, as an active ingredient, the compound, tautomer or pharmaceutically acceptable salt of the compound, or solvate of any of these according to any one of (1) to (41).

(47)

A drug having a sepiapterin reductase inhibitory action for preventing, treating, and/or ameliorating a disease, the drug containing, as an active ingredient, the compound, tautomer or pharmaceutically acceptable salt of the compound, or solvate of any of these according to any one of (1) to (41).

Specific examples of the compound of Formula (I) include compounds of Synthesis Examples 1 to 40 described below, more preferably compounds of Synthesis Examples 4 and 10 to 33, particularly preferably compounds of Synthesis Examples 4, 10, 12, 18, 21, 23, 32, and 33.

Specific examples of the compound of Formula (I) include compounds of Synthesis Examples 215 to 756 described below, more preferably compounds of Synthesis Examples 390, 403, 433, 452 to 458, 511, 534, 544, 551, 563 to 586, 602 to 635, 639 to 642, 644 to 659, 662 to 669, 671 to 677, 679 to 694, 697 to 698, 701 to 723, 741, and 749 to 756, particularly preferably compounds of Synthesis Examples 433, 453, 457, 511, 534, 544, 551, 563, 564, 565, 566, 567, 568, 569, 570, 574, 576, 579, 582, 586, 602, 603, 606, 615, 628, 641, 644, 645, 646, 647, 648, 656, 657, 658, 659, 671, 681, 682, 683, 685, 697, 701, 702, 706, 708, 713, 716, 717, 718, 722, 723, 741, 749, 750, 751, 753, 754, 755, and 756.

In the present invention, the compounds of Formula (I) of the present invention may be present, for example, through tautomerization or geometric isomerization regardless of whether they are endocyclic or exocyclic, as well as may be present in the form of mixtures thereof or mixtures of their respective isomers. When an asymmetric center exists or when an asymmetric center is generated as a result of isomerization, the compounds may be present in the form of optical isomers and mixtures thereof in any proportions. When the compounds have two or more asymmetric centers, diastereomers due to their optical isomerism are also present. The compounds of the present invention also include those containing all these forms in any proportion. For example, diastereomers can be separated by a method well known to those skilled in the art, such as fractional crystallization, and optically active substances can be obtained by any organic chemical technique well known for this purpose.

The compound of Formula (I) of the present invention or a pharmaceutically acceptable salt thereof may be present in the form of any crystal or any hydrate depending on the production conditions. Such crystalline forms, hydrates, and mixtures thereof are also included within the scope of the present invention. The compound may be present in the form of a solvate containing an organic solvent such as acetone, ethanol, 1-propanol, or 2-propanol. Such a form is also included within the scope of the present invention.

The present invention also encompasses a pharmaceutically acceptable salt of the compound of Formula (I) of the present invention.

If necessary, the compound of Formula (I) of the present invention may be converted into a pharmaceutically acceptable salt, or may be released from the produced salt. Examples of the pharmaceutically acceptable salt of the present invention include salts of alkali metals (e.g., lithium, sodium, and potassium), alkaline earth metals (e.g., magnesium and calcium), ammonium, organic bases, amino acids, inorganic acids (e.g., hydrochloric acid, hydrobromic acid, phosphoric acid, and sulfuric acid), or organic acids (e.g., acetic acid, citric acid, maleic acid, fumaric acid, tartaric acid, benzenesulfonic acid, methanesulfonic acid, and p-toluenesulfonic acid).

The present invention also encompasses a prodrug of the compound of Formula (I) of the present invention.

A prodrug is a derivative of a pharmaceutical compound having a chemically or metabolically degradable group, and is degraded by solvolysis or in vivo under physiological conditions into a pharmacologically active pharmaceutical compound. Methods for selecting and producing appropriate prodrug derivatives are described in, for example, Design of Prodrugs (Elsevier, Amsterdam 1985). In the present invention, exemplified are prodrugs such as acyloxy derivatives produced by reacting a compound having a hydroxy group with an appropriate acyl halide, an appropriate acid anhydride, or an appropriate haloalkoxycarbonyl compound. Structures particularly preferred for the prodrug include $-O-COC_2H_5$, $-O-CO(t\text{-}Bu)$, $-O-COC_{15}H_{31}$, $-O-CO(m\text{-}CO_2Na\text{-}Ph)$, $-O-COCH_2CH_2CO_2Na$, $-OCOCH(NH_2)CH_3$, $-O-COCH_2N(CH_3)_2$, or $-O-CH_2OC(=O)CH_3$. When the compound of the present invention has a —NH— group, examples of the prodrug include those produced by reacting the compound having a —NH— group with an appropriate acid halide, an appropriate mixed acid anhydride, or an appropriate haloalkoxycarbonyl compound. Structures particularly preferred for the prodrug include $-N-CO(CH_2)_{20}OCH_3$, $-N-COCH(NH_2)CH_3$, and $-N-CH_2O(C=O)CH_3$.

Specific examples of the administration method of a pharmaceutical containing the compound of the present invention as an active ingredient include oral administration, rectal administration, percutaneous absorption, and injection.

Specific examples of the dosage form of a pharmaceutical containing the compound of the present invention as an active ingredient include a tablet, a capsule, a powder, a granule, a pill, and a syrup.

The pharmaceutical may be administered as a single therapeutic agent or a mixture with another therapeutic agent.

The pharmaceutical may be administered alone, but is generally administered in the form of a pharmaceutical composition. The formulation can be produced by a customary method through addition of pharmacologically and pharmaceutically acceptable additives. Specifically, an oral formulation can be produced by using additives such as an excipient, a lubricant, a binder, a disintegrant, a humectant, a plasticizer, and a coating agent.

An oral solution may be in the form of an aqueous or oily suspension, a solution, an emulsion, a syrup, an elixir, etc., or may be provided in the form of a dry syrup that is reconstituted with water or another appropriate solvent before use. The aforementioned solution may contain any common additive such as a suspending agent, a flavor, a diluent, or an emulsifier.

For rectal administration, the pharmaceutical may be administered as a suppository. The suppository can be produced by using an appropriate base, such as cacao butter, laurin butter, macrogol, glycerogelatin, witepsol, sodium stearate, or a mixture thereof, and if necessary, addition of an emulsifier, a suspending agent, a preservative, etc.

The injection is produced by using formulation ingredients, such as distilled water for injection capable of forming an aqueous or dissolution type dosage form, saline, 5% glucose solution, a solubilizer or solubilization aid (e.g., propylene glycol), a pH adjuster, an isotonic agent, and a stabilizer.

When the drug of the present invention is administered to a human, the dose thereof is determined depending on the age and condition of the patient. Generally, in the case of an adult, the drug is orally or rectally administered at a dose of about 0.1 mg to 1,000 mg/human/day, or administered in the form of injection at a dose of about 0.05 mg to 500 mg/human/day. Such a value is merely an example, and the dose is determined depending on the patient's symptoms.

The method of the present invention can be used for treatment of primates such as human, as well as a variety of other mammals. The method cam be used for treatment of mammals including, but are not limited to, cow, sheep, goat, horse, dog, cat, wild cavy, or bovine, ovine, equine, canine, feline, and rodents such as mouse. The method of the present invention can be used for treatment of other species such as avian species (e.g., chicken).

The present invention provides a novel method for the prevention and treatment of sepiapterin reductase (SPR)-related diseases. In the present invention, SPR-related diseases include pain. Specific examples of the aforementioned pain include inflammatory pain, nociceptive pain, functional pain, and neuropathic pain, whether acute or chronic.

More specific examples of the aforementioned pain include (1) musculoskeletal pain (after trauma, infection, and exercise), (2) neuropathic pain due to spinal cord injury, tumor, compression, inflammation, toothache, or episiotomy pain, (3) deep and visceral pain (e.g., heart pain, bladder pain, or pelvic organ pain), (4) muscle pain, (5) eye pain, (6) orofacial pain (e.g., toothache, trigeminal neuralgia, glossopharyngeal neuralgia), (7) abdominal pain, (8) gynecological pain (e.g., dysmenorrhea and labor pain), (9) neurological pain due to trauma, compression, inflammation, toxic chemicals, metabolic disorder, genetic conditions, infection, vasculitis, or autoimmune disease, (10) pain associated with nerve root injury, (11) central nervous system pain, such as pain due to spinal cord injury, brain stem injury, cerebrovascular accidents, tumor, infection, or demyelinating diseases (including multiple sclerosis), (12) low back pain, (13) sciatica, and (14) postoperative pain.

In the present invention, other examples of the SPR-related disease include (15) pain due to disease or injury in soft tissues or joints (e.g., acute trauma, osteoarthritis, or rheumatoid arthritis), (16) facial muscle pain syndrome (fibromuscular pain), (17) headache (including cluster headache, migraine, and tension-type headache), (18) myocardial infarction, angina, ischemic cardiovascular disease, post-stroke pain, (19) sickle cell anemia, peripheral vascular occlusive disease, cancer, skin or joint inflammatory conditions, and (20) diabetic neuropathy, and acute tissue injury due to surgery or traumatic injury (e.g., burn, laceration, or bone fracture).

The present invention is used for the prevention, treatment, and diagnosis of the aforementioned sepiapterin reductase (SPR)-related diseases. The concept of the treatment includes relief of symptoms. Among the above, the present invention is more preferably used for the prevention or treatment of the diseases, still more preferably for the treatment of the diseases.

Examples of the application of the present invention include, but are not limited to, the aforementioned ones.

(Combination Therapy)

The compound of the present invention, a tautomer, salt, solvate, or prodrug of the compound, or a pharmaceutical composition containing the compound may be administered alone or in combination with one or more additional therapeutic drugs (e.g., an analgesic) used for the treatment of nociceptive, inflammatory, functional, or neuropathic pain. In the present invention, such a second therapeutic drug may or may not provide a therapeutic effect when administered independently. However, the second therapeutic drug provides a therapeutic effect (e.g., pain relief) when administered with the composition of the present invention.

The compound of the present invention may be used alone or in combination with one or more of the drugs described below.

Examples of the drug that may be used in combination include, but are not limited to, non-steroidal anti-inflammatory drugs (NSAID) (e.g., rofecoxib, celecoxib, valdecoxib, parecoxib, salicylic acid, acetaminophen, diclofenac, piroxicam, indomethacin, ibuprofen, and naproxen), opioid analgesics (e.g., propoxyphene, meperidine, hydromorphone, hydrocodone, oxycodone, morphine, codeine, and tramadol), NMDA antagonist analgesics (e.g., 2-piperidino-1-alkanol derivatives, ketamine, dextromethorphan, eliprodil, or ifenprodil), anesthetics (e.g., nitrous oxide, halothane, and fluothane), local anesthetics (lidocaine, etidocaine, ropivacaine, chloroprocaine, thoroughpin, and bupivacaine), benzodiazepines (diazepam, chlordiazepoxide, alprazolam, and lorazepam), capsaicin, tricyclic antidepressants (e.g., amitriptyline, perphenazine, protriptyline, tranylcypromine, imipramine, desipramine, and clomipramine), skeletal muscle relaxant analgesics (flexeril, carisoprodol, robaxisal, norgesic, and dantrium), migraine therapeutic drugs (e.g., eletriptan, sumatriptan, rizatriptan, zolmitriptan, and naratriptan), anticonvulsants (e.g., phenytoin, lamotrigine, pregabalin, carbamazepine, oxcarbazepine, topiramate, valproic acid, and gabapentin), baclofen, clonidine, mexilitene, diphenhydramine, hydroxyzine, caffeine, prednisone, methylprednisone, decadrone, paroxetine, sertraline, fluoxetine, tramadol, ziconotide, and levodopa.

The compound of the present invention can be synthesized by the method described below, but the production method is not limited to the below-described method, which is an example of a common production method.

The raw materials and reagents used in the respective steps of the below-described production method and the resultant compounds may each form a salt. Examples of such a salt include those similar to the aforementioned salts of the compound of the present invention.

When the compound obtained in each step is a free form, the compound may be converted into a target salt by a method known per se. Conversely, when the compound obtained in each step is in a salt form, the compound may be converted into a free form or another target salt by a method known per se.

The compound obtained in each step may be used in the subsequent reaction in the form of a reaction solution or as a crude product. Alternatively, the compound obtained in each step may be isolated and/or purified from the reaction mixture according to a customary method by separation means, such as concentration, crystallization, recrystallization, distillation, solvent extraction, fractionation, or chromatography.

Generally, the compound of the present invention may be purified by column chromatography, thin layer chromatography, high performance liquid chromatography (HPLC), high performance liquid chromatography/mass spectrometry (LC/MS) system, supercritical fluid chromatography (SFC), etc. If necessary, a compound of high purity may be obtained by recrystallization or washing with a solvent.

When raw materials or reagent compounds for each step are commercially available, the commercially available products may be used as is.

In the reaction in each step, the reaction time may vary depending on the reagents and solvents used. Unless otherwise specified, the reaction time is generally one minute to 48 hours, preferably 10 minutes to eight hours.

In the reaction in each step, the reaction temperature may vary depending on the reagents and solvents used. Unless otherwise specified, the reaction temperature is generally −78° C. to 300° C., preferably −78° C. to 150° C.

In the reaction in each step, the pressure may vary depending on the reagents and solvents used. Unless otherwise specified, the pressure is generally 1 atm to 20 atm, preferably 1 atm to 3 atm.

The reaction in each step may be performed with a microwave synthesizer such as Initiator available from Biotage. Unless otherwise specified, the reaction temperature, which may vary depending on the reagents and solvents used, is generally room temperature to 300° C., preferably 50° C. to 250° C. Unless otherwise specified, the reaction time, which may vary depending on the reagents and solvents used, is generally one minute to 48 hours, preferably one minute to eight hours.

Unless otherwise specified, the amount of the reagent used in the reaction of each step is 0.5 equivalents to 20 equivalents, preferably 0.8 equivalents to 5 equivalents, relative to the amount of the substrate. When the reagent is used as a catalyst, the amount of the reagent used is 0.001 equivalents to 1 equivalent, preferably 0.01 equivalents to 0.2 equivalents, relative to the amount of the substrate. When the reagent also serves as a reaction solvent, the reagent is used in a solvent amount.

Unless otherwise specified, the reaction in each step is performed without a solvent or through dissolution or suspension in an appropriate solvent. Specific examples of the solvent include the solvents described in Examples or the following solvents.

Alcohols: methanol, ethanol, tert-butyl alcohol, 1-propanol, 2-propanol, 2-methoxyethanol, ethylene glycol, etc.;

Ethers: diethyl ether, diphenyl ether, tetrahydrofuran, 1,2-dimethoxyethane, 1,4-dioxane, cyclopentyl methyl ether, etc.;

Aromatic hydrocarbons: benzene, chlorobenzene, toluene, xylene, etc.;

Saturated hydrocarbons: cyclohexane, hexane, heptane, etc.;

Amides: N,N-dimethylformamide, N-methylpyrrolidone, N,N-dimethylacetamide, etc.;

Halogenated hydrocarbons: dichloromethane, chloroform, 1,2-dichloroethane, carbon tetrachloride, etc.;

Nitriles: acetonitrile, propionitrile, etc.;

Sulfoxides: dimethyl sulfoxide, etc.;

Aromatic organic bases: pyridine, etc.;

Acid anhydrides: acetic anhydride, etc.;

Organic acids: formic acid, acetic acid, trifluoroacetic acid, etc.;

Inorganic acids: hydrochloric acid, sulfuric acid, etc.;

Esters: ethyl acetate, etc.;

Ketones: acetone, methyl ethyl ketone, etc.; and

Water.

The reaction may be performed under conditions where the aforementioned solvents are mixed in any proportion or without a solvent.

When a base is used in the reaction of each step, the base used is selected from, for example, the below-described bases or the bases described in Examples.

Inorganic bases: sodium hydroxide, potassium hydroxide, magnesium hydroxide, etc.;

Basic salts: sodium carbonate, calcium carbonate, sodium hydrogen carbonate, potassium carbonate, tripotassium phosphate, cesium carbonate, etc.;

Organic bases: triethylamine, N,N-diisopropylethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, etc.;

Metal alkoxides: sodium ethoxide, sodium methoxide, potassium tert-butoxide, sodium tert-butoxide, etc.;

Alkali metal hydrides: sodium hydride, etc.;

Metal amides: sodium amide, lithium diisopropylamide, lithium hexamethyldisilazide, etc.; and Organolithiums: n-butyllithium, s-butyllithium, lithium diisopropylamide, isopropylmagnesium bromide, etc.

When an acid or an acidic catalyst is used in the reaction of each step, the acid or acidic catalyst used is selected from, for example, the below-described acids and acidic catalysts, or the acids and acidic catalysts described in Examples.

Inorganic acids: hydrochloric acid, sulfuric acid, nitric acid, hydrobromic acid, phosphoric acid, etc.;

Organic acids: acetic acid, trifluoroacetic acid, citric acid, p-toluenesulfonic acid, 10-camphorsulfonic acid, etc.; and Lewis acids: boron trifluoride-diethyl ether complex, zinc iodide, anhydrous aluminum chloride, anhydrous zinc chloride, anhydrous iron chloride, etc.

Unless otherwise specified, the reaction in each step is performed by a method known per se, for example, any of methods described in 5th Edition Jikken Kagaku Koza (Experimental Chemistry Course), Vols. 13-19 (edited by The Chemical Society of Japan); Shin-Jikken Kagaku Koza (New Experimental Chemistry Course), Vols. 14-15 (edited by The Chemical Society of Japan); Fine Organic Chemistry Revised 2nd Edition (L. F. Tietze, Th. Eicher, Nankodo Co., Ltd.); Revised Organic Name Reactions, Mechanism and Essence (authored by Hideo Togo, Kodansha Ltd.); ORGANIC SYNTHESES Collective Volume I-VII (John Wiley & Sons Inc.); Modern Organic Synthesis in the Laboratory, A Collection of Standard Experimental Procedures (authored by Jie Jack Li, published by OXFORD UNIVERSITY PRESS); Comprehensive Heterocyclic Chemistry III, Vol. 1 to Vol. 14 (Elsevier Japan Co., Ltd.); Strategic Applications of Named Reactions in Organic Synthesis (translated by Kiyoshi Tomioka, published by Kagaku-Doujin Publishing Co, Inc.); and Comprehensive Organic Transformations (VCH Publishers Inc.), 1989. Alternatively, the reaction is performed according to the method described in Examples.

General formulae of intermediates and final products in each step are shown in the below-described common methods for producing the compound of the present invention. The concept of the general formula of the intermediates and final products also includes derivatives protected with protective groups. The term "derivative protected with a protective group" as used herein refers to a compound that can be converted into a target product by hydrolysis, reduction, oxidation, alkylation, etc., if necessary. The derivative includes, for example, a compound protected with a protective group acceptable for organic synthetic chemistry.

The protection or deprotection reaction of a functional group in each step is performed by a method known per se, for example, any of methods described in "Protective Groups in Organic Synthesis, 4th Ed." (authored by Theodora W. Greene, Peter G. M. Wuts, Wiley-Interscience Inc.), 2007; and "Protecting Groups 3rd Ed." (authored by P. J. Kocienski, Thieme Publishers), 2004. Alternatively, the reaction is performed according to the method described in Examples.

Examples of the protective group of a hydroxy group of an alcohol or a phenolic hydroxy group include ether-type protective groups, such as methoxymethyl ether, benzyl ether, tert-butyl dimethylsilyl ether, and tetrahydropyranyl ether; carboxylate ester-type protective groups, such as acetate esters; sulfonate ester-type protective groups, such as methanesulfonate esters; and carbonate ester-type protective groups, such as tert-butyl carbonate.

Examples of the protective group of a carbonyl group of an aldehyde include acetal-type protective groups, such as dimethylacetal; and cyclic acetal-type protective groups, such as cyclic 1,3-dioxane.

Examples of the protective group of a carbonyl group of a ketone include ketal-type protective groups, such as dimethyl ketal; cyclic ketal-type protective groups, such as cyclic 1,3-dioxane; oxime-type protective groups, such as O-methyloxime; and hydrazone-type protective groups, such as N,N-dimethylhydrazone.

Examples of the protective group of a carboxyl group include ester-type protective groups, such as methyl ester; and amide-type protective groups, such as N,N-dimethylamide.

Examples of the protective group of a thiol include ether-type protective groups, such as benzylthioether; and ester-type protective groups, such as thioacetate, thiocarbonate, and thiocarbamate.

Examples of the protective group of an amino group or an aromatic heterocyclic ring (e.g., imidazole, pyrrole, or indole) include carbamate-type protective groups, such as benzyl carbamate; amide-type protective groups, such as acetamide; alkylamine-type protective groups, such as N-triphenylmethylamine; and sulfonamide-type protective groups, such as methanesulfonamide.

The removal of a protective group can be performed by a method known per se, for example, a method using an acid, a base, ultraviolet light, hydrazine, phenylhydrazine, sodium N-methyldithiocarbamate, tetrabutylammonium fluoride, palladium acetate, or trialkylsilyl halide (e.g., trimethylsilyl iodide or trimethylsilyl bromide) or a reduction method.

When a reduction reaction is performed in each step, the reductant used is, for example, a metal hydride such as lithium aluminum hydride, sodium triacetoxyborohydride, sodium cyanoborohydride, diisobutylaluminum hydride (DIBAL-H), sodium borohydride, or tetramethylammonium triacetoxyborohydride; a borane such as borane-tetrahydrofuran complex; Raney nickel; Raney cobalt; hydrogen; formic acid; or triethylsilane. When a carbon-carbon double bond or triple bond is reduced, a catalyst such as palladium-carbon or Lindlar's catalyst is used for the reduction.

When an oxidation reaction is performed in each step, the oxidant used is, for example, a peracid such as m-chloroperbenzoic acid (mCPBA), hydrogen peroxide, or tert-butyl hydroperoxide; a perchlorate such as tetrabutylammonium perchlorate; a chlorate such as sodium chlorate; a chlorite such as sodium chlorite; a periodic acid such as sodium periodate; a high-valent iodine reagent such as iodosylbenzene; a manganese-containing reagent such as manganese dioxide or potassium permanganate; a lead compound such as lead tetraacetate; a chromium-containing reagent such as pyridinium chlorochromate (PCC), pyridinium dichromate (PDC), or Jones reagent; a halogen compound such as N-bromosuccinimide (NBS); oxygen; ozone; sulfur trioxide-pyridine complex; osmium tetroxide; selenium dioxide; or 2,3-dichloro-5,6-dicyano-1,4-benzoquinone (DDQ).

When a radical cyclization reaction is performed in each step, the radical initiator used is, for example, an azo compound such as azobisisobutyronitrile (AIBN); a water-soluble radical initiator such as 4-4-azobis-4-cyanopentanoic acid (ACPA); triethylboron in the presence of air or oxygen; or benzoyl peroxide. Examples of the radical reaction reagent used include tributylstannane, tristrimethylsilylsilane, 1,1,2,2-tetraphenyldisilane, diphenylsilane, and samarium iodide.

When the Wittig reaction is performed in each step, the Wittig reagent used is, for example, an alkylidenephosphorane. The alkylidenephosphorane can be prepared by a method known per se, for example, by reacting a phosphonium salt with a strong base.

When the Horner-Emmons reaction is performed in each step, the reagent used is, for example, a phosphonoacetic acid ester such as methyl dimethylphosphonoacetate and ethyl diethylphosphonoacetate; or a base such as an alkali metal hydride or an organic lithium.

When the Friedel-Crafts reaction is performed in each step, the reagent used is, for example, a combination of a Lewis acid and an acid chloride, or a combination of a Lewis acid and an alkylating agent (e.g., an alkyl halide, an alcohol, or olefins). Alternatively, a Lewis acid may be replaced with an organic acid or an inorganic acid, or an acid chloride may be replaced with an acid anhydride such as acetic anhydride.

When an aromatic nucleophilic substitution reaction is performed in each step, the reagents used are a nucleophilic agent (e.g., an amine or imidazole) and a base (e.g., a basic salt or an organic base).

When a nucleophilic addition reaction with a carbanion, a nucleophilic 1,4-addition reaction (Michael addition reaction) with a carbanion, or a nucleophilic substitution reaction with a carbanion is performed in each step, the base used for generating a carbanion is, for example, an organic lithium, a metal alkoxide, an inorganic base, or an organic base.

When the Grignard reaction is performed in each step, the Grignard reagent used is, for example, an arylmagnesium halide such as phenylmagnesium bromide; or an alkylmagnesium halide such as methylmagnesium bromide. The Grignard reagent can be prepared by a method known per se, for example, by reacting an alkyl halide or an aryl halide with metallic magnesium using ether or tetrahydrofuran as a solvent.

When the Knoevenagel condensation reaction is performed in each step, the reagents used are an active methylene compound sandwiched between two electron-withdrawing groups (e.g., malonic acid, diethyl malonate, or malononitrile) and a base (e.g., an organic base, a metal alkoxide, or an inorganic base).

When the Vilsmeier-Haack reaction is performed in each step, the reagents used are phosphoryl chloride and an amide derivative (e.g., N,N-dimethylformamide).

When an alcohol, an alkyl halide, or a sulfonate ester is subjected to an azidation reaction in each step, the azidation agent used is, for example, diphenylphosphoryl azide (DPPA), trimethylsilylazide, or sodium azide. For example, when an alcohol is subjected to azidation, the reaction is performed by a method using diphenylphosphoryl azide and 1,8-diazabicyclo[5.4.0]undec-7-ene (DBU), a method using trimethylsilylazide and a Lewis acid, or the like method.

When a reductive amination reaction is performed in each step, the reductant used is, for example, sodium triacetoxyborohydride, sodium cyanoborohydride, sodium borohydride, hydrogen, or formic acid. When the substrate is an amine compound, the carbonyl compound used is, for example, paraformaldehyde, an aldehyde such as acetaldehyde, or a ketone such as cyclohexanone. When the substrate is a carbonyl compound, the amine used is, for example, ammonia; a primary amine such as methylamine; or a secondary amine such as dimethylamine.

When the Mitsunobu reaction is performed in each step, the reagents used are, for example, an azodicarboxylic acid ester (e.g., diethyl azodicarboxylate (DEAD) or diisopropyl azodicarboxylate (DIAD)) and triphenylphosphine.

When an esterification reaction, an amidation reaction, or a urea formation reaction is performed in each step, the reagent used is, for example, an acyl halide such as acid chloride or acid bromide; or an activated carboxylic acid such as an acid anhydride, an active ester, or a sulfate ester. Examples of the carboxylic acid activator include carbodiimide-based condensing agents, such as 1-ethyl-3-(3-dimethylaminopropyl)carbodiimide hydrochloride (WSCD); triazine-based condensing agents, such as 4-(4,6-dimethoxy-1,3,5-triazin-2-yl)-4-methylmorpholinium chloride-n-hydrate (DMT-MM); carbonate ester-based condensing agents, such as 1,1-carbonyldiimidazole (CDI); diphenylphosphoryl azide (DPPA); benzotriazol-1-yloxy-trisdimethylamino-phosphonium salt (BOP reagent); 2-chloro-1-methyl-pyridinium iodide (Mukaiyama reagent); thionyl chloride; lower alkyl haloformates, such as ethyl chloroformate; O-(7-azabenzotriazol-1-yl)-N,N,N,N-tetramethyluronium hexafluorophosphate (HATU); sulfuric acid; or combinations thereof. When a carbodiimide-based condensing agent is used, an additive such as 1-hydroxybenzotriazole (HOBt), N-hydroxysuccinimide (HOSu), or dimethylaminopyridine (DMAP) may be further added to the reaction.

When a coupling reaction is performed in each step, the metal catalyst used is, for example, a palladium compound such as palladium(II) acetate, tetrakis(triphenylphosphine) palladium(0), dichlorobis(triphenylphosphine)palladium (II), dichlorobis(triethylphosphine)palladium(II), tris(dibenzylideneacetone)dipalladium(0), 1,1-bis (diphenylphosphino)ferrocenepalladium(II) chloride, or palladium(II) acetate; a nickel compound such as tetrakis (triphenylphosphine)nickel(0); a rhodium compound such as tris(triphenylphosphine)rhodium(III) chloride; a cobalt compound; a copper compound such as copper oxide or copper(I) iodide; or a platinum compound. A base may further be added to the reaction. Examples of such a base include inorganic bases and basic salts.

When a thiocarbonylation reaction is performed in each step, the thiocarbonylating agent used is typically phosphorus pentasulfide. Phosphorus pentasulfide may be replaced with a reagent having a 1,3,2,4-dithiadiphosphetane-2,4-disulfide structure, such as 2,4-bis(4-methoxyphenyl)-1,3,2,4-dithiadiphosphetane-2,4-disulfide (Lawesson's reagent).

When the Wohl-Ziegler reaction is performed in each step, the halogenating agent used is, for example, N-iodosuccinimide, N-bromosuccinimide (NBS), N-chlorosuccinimide (NCS), bromine, or sulfuryl chloride. Furthermore, the reaction can be accelerated through addition of heat, light, or a radical initiator such as benzoyl peroxide or azobisisobutyronitrile to the reaction.

When the halogenation reaction of a hydroxy group is performed in each step, the halogenating agent used is, for example, a hydrohalic acid or an inorganic acid halide; specifically, hydrochloric acid, thionyl chloride, phosphorus oxychloride, etc. for chlorination, or 48% hydrobromic acid, etc. for bromination. There may be used a method of preparing an alkyl halide from an alcohol by the reaction between triphenylphosphine and carbon tetrachloride or carbon tetrabromide. Alternatively, there may be used a method of synthesizing an alkyl halide through a two-step reaction process including conversion of an alcohol into a sulfonate ester, and subsequent reaction of the sulfonate ester with lithium bromide, lithium chloride, or sodium iodide.

When the Arbuzov reaction is performed in each step, the reagent used is, for example, an alkyl halide such as ethyl bromoacetate; or a phosphite such as triethyl phosphite or tri(isopropyl)phosphite.

When a sulfonic acid esterification reaction is performed in each step, the sulfonylating agent used is, for example, methanesulfonyl chloride, p-toluenesulfonyl chloride, methanesulfonic anhydride, or p-toluenesulfonic anhydride.

When a hydrolysis reaction is performed in each step, an acid or a base is used as a reagent. In the case of the acid hydrolysis reaction of a tert-butyl ester, formic acid, triethylsilane, or the like may be added in order to reductively trap by-produced tert-butyl cations.

When a dehydration reaction is performed in each step, the dehydrating agents used is, for example, sulfuric acid, phosphorus pentoxide, phosphorus oxychloride, N,N-dicyclohexylcarbodiimide, alumina, or polyphosphoric acid.

When a nitration reaction is performed in each step, the nitrating agent used is, for example, nitric acid, fuming nitric acid, or copper nitrate. The nitration reaction is activated by using, for example, concentrated sulfuric acid or acetic anhydride.

When a halogenation reaction is performed in each step, the halogenating agent used is, for example, N-iodosuccinimide, N-bromosuccinimide (NBS), N-chlorosuccinimide (NCS), iodine monochloride, iodine, bromine, or sulfuryl chloride. In this reaction, an additive such as trifluoroacetic acid may be used for the purpose of activating the halogenating agent.

When an acylation reaction is performed in each step, for example, an amidation reaction, a urea formation reaction, a carbamation reaction, or a thiocarbamation reaction is performed. When a carbamation reaction or a thiocarbamation reaction is performed, the reagent used is, for example, triphosgene, a carbonate ester condensing agent such as 1,1-carbonyldiimidazole (CDI), a chlorocarbonate ester, a chlorocarbonate thioester, or an isothiocyanate.

When a cyclization reaction is performed in each step, the reaction is achieved by the Mitsunobu reaction or an alkylation reaction. When the alkylation reaction is performed, a base is used as a reagent.

Compound (4), compound (5), compound (6), and compound (7) can be produced from compound (1) by the methods described below.

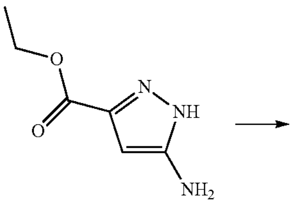

(1)

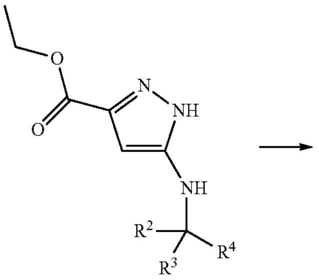

(2)

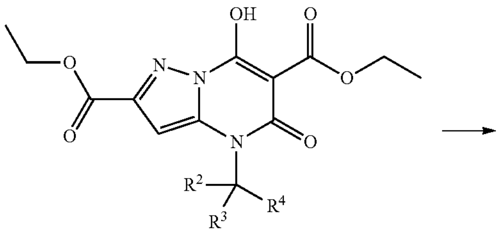

(3)

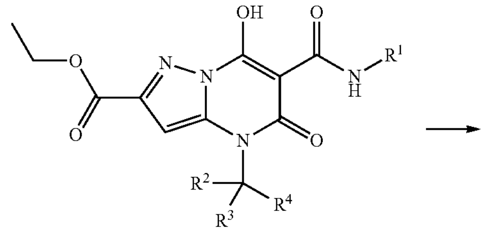

(4)

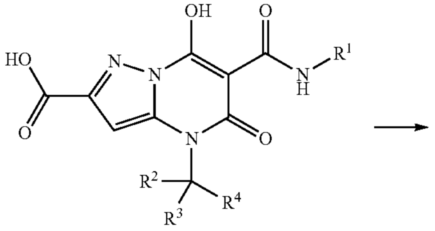

(5)

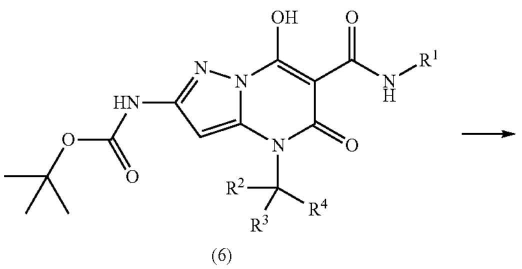

(6)

-continued

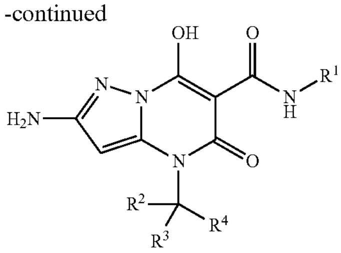

(7)

Compound (2) can be produced by a reductive amination reaction using compound (1), an aldehyde, acetic acid, and a reductant. Examples of the reductant used include sodium triacetoxyborohydride, sodium cyanoborohydride, and sodium borohydride, and examples of the solvent used include tetrahydrofuran.

Compound (1) may be a commercially available product as is. Alternatively, compound (1) may be produced by a method known per se or a method similar thereto.

Compound (3) can be produced by a cyclization reaction using compound (2), triethyl methanetricarboxylate, and a base. Examples of the base used include triethylamine, and examples of the solvent include toluene.

Compound (4) can be produced by an amidation reaction using compound (3) and an amine. Examples of the solvent used include N,N-dimethylacetamide.

Compound (5) can be produced by a hydrolysis reaction using compound (4) and a base. Examples of the base used include potassium trimethylsilanolate, sodium hydroxide, potassium hydroxide, and lithium hydroxide, and examples of the solvent used include tetrahydrofuran, water, and ethanol.

Compound (6) can be produced by an intramolecular rearrangement reaction using compound (5), diphenylphosphoryl azide, a base, and tert-butanol. Examples of the base used include triethylamine.

Compound (7) can be produced by deprotection using compound (6) and an acid. Examples of the acid used include hydrochloric acid and trifluoroacetic acid, and examples of the solvent include 1,4-dioxane and ethyl acetate.

Compound (11) and compound (7) can be produced from compound (8) by the methods described below.

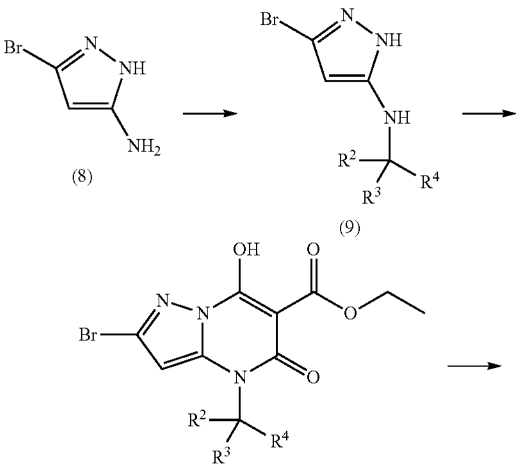

(8) (9) (10)

-continued

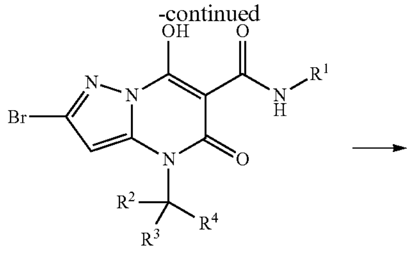

(11)

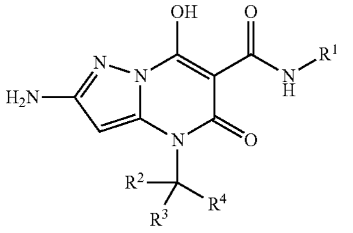

(7)

Compound (9) can be produced by a reductive amination reaction using compound (8), an aldehyde, acetic acid, and a reductant. Examples of the reductant used include sodium triacetoxyborohydride, sodium cyanoborohydride, and sodium borohydride, and examples of the solvent used include tetrahydrofuran and 1,2-dichloroethane.

Compound (8) may be a commercially available product as is. Alternatively, compound (8) may be produced by a method known per se or a method similar thereto.

Compound (10) can be produced by a cyclization reaction using compound (9), triethyl methanetricarboxylate, and a base. Examples of the base used include triethylamine, and examples of the solvent include toluene.

Compound (11) can be produced by an amidation reaction using compound (10) and an amine. Examples of the solvent used include N,N-dimethylacetamide.

Compound (7) can be produced by an amination reaction using compound (11), (2S,4R)-4-hydroxypyrrolidine-2-carboxylic acid, acid carboxamide, copper(I) iodide, potassium carbonate, and aqueous ammonia. Examples of the solvent used include dimethyl sulfoxide.

Compound (15), compound (16), compound (17), compound (18), compound (19), compound (20), and compound (21) can be produced from compound (12) by the methods described below. (In a combination of $R^h$ and $R^i$ in the scheme described below, $R^h$ is a hydrogen atom or a $C_{1-6}$ alkyl group substitutable with one or more substituents independently selected from the substituent group C (substituent group C1 or substituent group C2), and $R^i$ is a hydrogen atom, a $C_{1-6}$ alkyl group substitutable with one or more substituents independently selected from the substituent group C (substituent group C1 or substituent group C2), a $C_{6-14}$ aryl group, a 5- to 14-membered aromatic heterocyclic group or 3- to 14-membered non-aromatic heterocyclic group possibly having one or more substituents independently selected from the substituent group D (D1 or D2); or $R^h$ is a $C_{1-6}$ alkyl group, and $R^i$ is a hydroxy group or a $C_{1-6}$ alkoxy group; or $R^h$ and $R^i$ form, together with the nitrogen atom bonded thereto, a 5- to 14-membered aromatic heterocyclic ring or 3- to 14-membered non-aromatic heterocyclic ring possibly having one or more substituents independently selected from the substituent group D (substituent group D1 or substituent group D2).)

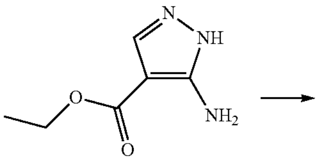

(12)

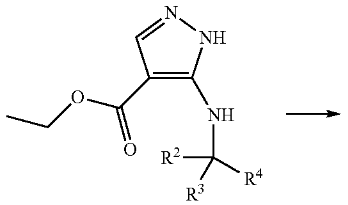

(13)

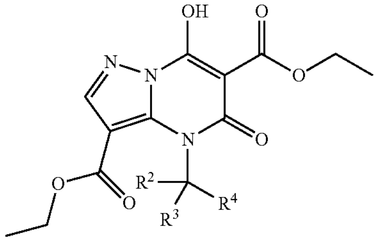

(14)

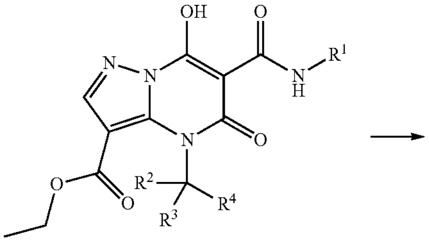

(15)

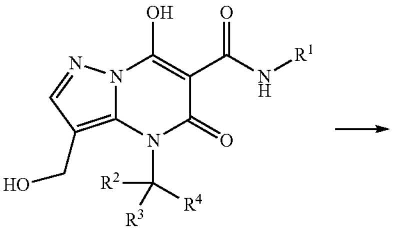

(16)

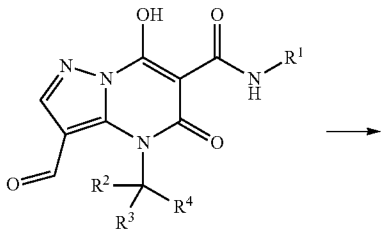

(17)

-continued

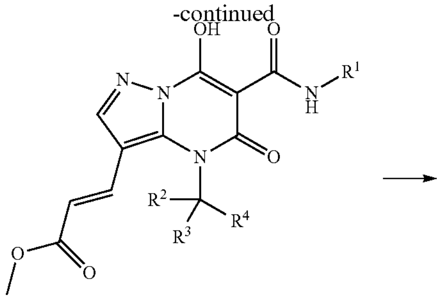

(18)

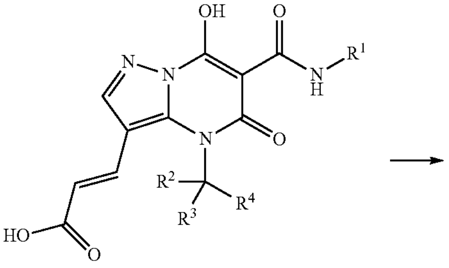

(19)

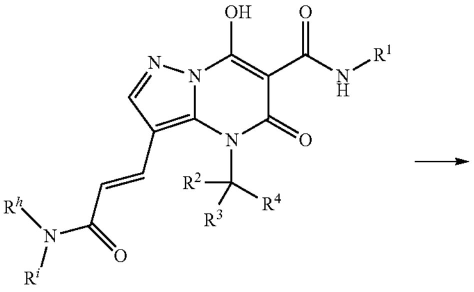

(20)

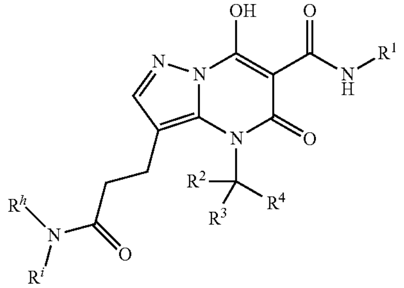

(21)

Compound (13) can be produced by a reductive amination reaction using compound (12), an aldehyde, acetic acid, and a reductant. Examples of the reductant used include sodium triacetoxyborohydride, sodium cyanoborohydride, and sodium borohydride, and examples of the solvent used include tetrahydrofuran and 1,2-dichloroethane.

Compound (12) may be a commercially available product as is. Alternatively, compound (12) may be produced by a method known per se or a method similar thereto.

Compound (14) can be produced by a cyclization reaction using compound (13), triethyl methanetricarboxylate, and a base. Examples of the base used include triethylamine, and examples of the solvent include toluene.

Compound (15) can be produced by an amidation reaction using compound (14) and an amine. Examples of the solvent used include N,N-dimethylacetamide.

Compound (16) can be produced by a reduction reaction using compound (15) and a reductant. Examples of the reductant used include lithium aluminum hydride, and examples of the solvent include tetrahydrofuran.

Compound (17) can be produced by an oxidation reaction using compound (16) and an oxidant. Examples of the oxidant used include 2-iodoxybenzoic acid, and examples of the solvent include dimethyl sulfoxide.

Compound (18) can be produced by the Horner-Emmons reaction using compound (17), sodium hydride, and trimethyl phosphonoacetate. Examples of the solvent used include tetrahydrofuran.

Compound (19) can be produced by a hydrolysis reaction using compound (18) and a base. Examples of the base used include potassium trimethylsilanolate, sodium hydroxide, potassium hydroxide, and lithium hydroxide, and examples of the solvent include tetrahydrofuran, 1,4-dioxane, water, and ethanol.

Compound (20) can be produced by an amidation reaction using compound (19), an amine, 1-(3-dimethylaminopropyl)-3-ethylcarbodiimide hydrochloride, and 1-hydroxybenzotriazole monohydrate. Examples of the solvent used include N,N-dimethylacetamide.

Compound (21) can be produced by a reduction reaction using compound (20), hydrogen, and palladium-carbon. Examples of the solvent used include methanol.

Compound (22) can be produced from compound (11) by the method described below. (In the scheme described below, $R^c$ is a hydrogen atom or a substituent of a substitutable amino group (e.g., a substitutable $C_{1-6}$ alkyl group or a substitutable heterocyclic group).)

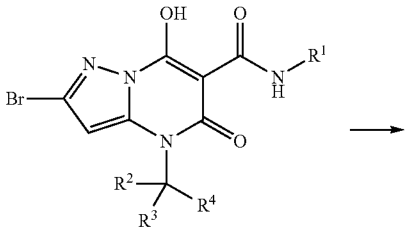

(11)

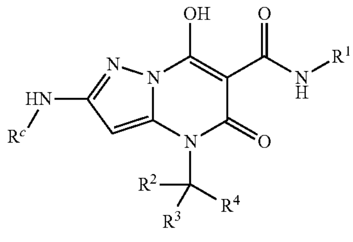

(22)

Compound (22) can be produced by a coupling reaction using compound (11), an amine, a palladium catalyst, a ligand, and a base. Examples of the palladium catalyst used include tris(dibenzylideneacetone)dipalladium(0). Examples of the ligand include 2-di-tert-butylphosphino-2',4',6'-triisopropylbiphenyl and 4,5-bis(diphenylphosphino)-9,9-dimethylxanthene. Examples of the base include sodium tert-butoxide. Examples of the solvent include 1,4-dioxane.

Compound (23) can be produced from compound (11) by the method described below.

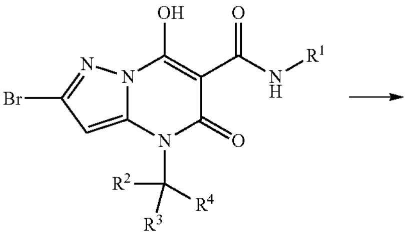

(11)

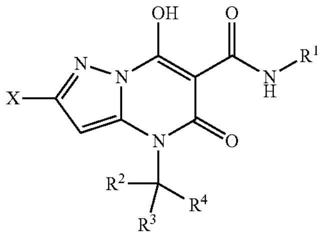

(23)

Compound (23) (a compound wherein X is a substitutable heterocyclic group, hydrocarbon group, or acyl group) can be produced by a coupling reaction using compound (11), a coupling reagent, a metal catalyst, a ligand, and a base. Examples of the coupling reagent used include boronic acid, boronate esters, acrylate esters, imidazole, pyrazole, N1,N2-dimethylethane-1,2-diamine, and pyrrolidone. Examples of the metal catalyst include [1,1'-bis(di-tert-butylphosphino)ferrocene]dichloropalladium(II), palladium(II) acetate, tris(dibenzylideneacetone)dipalladium(0), and copper(I) iodide. Examples of the ligand include 2-dicyclohexylphosphino-2',4',6'-triisopropylbiphenyl, N1,N2-dimethylethane-1,2-diamine, 2-di-tert-butylphosphino-2',4',6'-triisopropylbiphenyl, and 4,5-bis(diphenylphosphino)-9,9-dimethylxanthene. Examples of the base include potassium carbonate, cesium carbonate, sodium tert-butoxide, and triethylamine. Examples of the solvent include 1,4-dioxane, water, N,N-dimethylformamide, dimethyl sulfoxide, and N-methylpyrrolidone.

Compound (24), compound (25), compound (26), and compound (27) can be produced from compound (11) by the methods described below. (In the scheme described below, n is an integer of 1 to 3, and other symbols such as $Z^1$ and $R^{d1}$ have the same meanings as defined above. For example, $Z^1$ is a substitutable methylene group, —N—, or —O—, and $R^{d1}$ is a substitutable $C_{1-6}$ alkyl group, etc.)

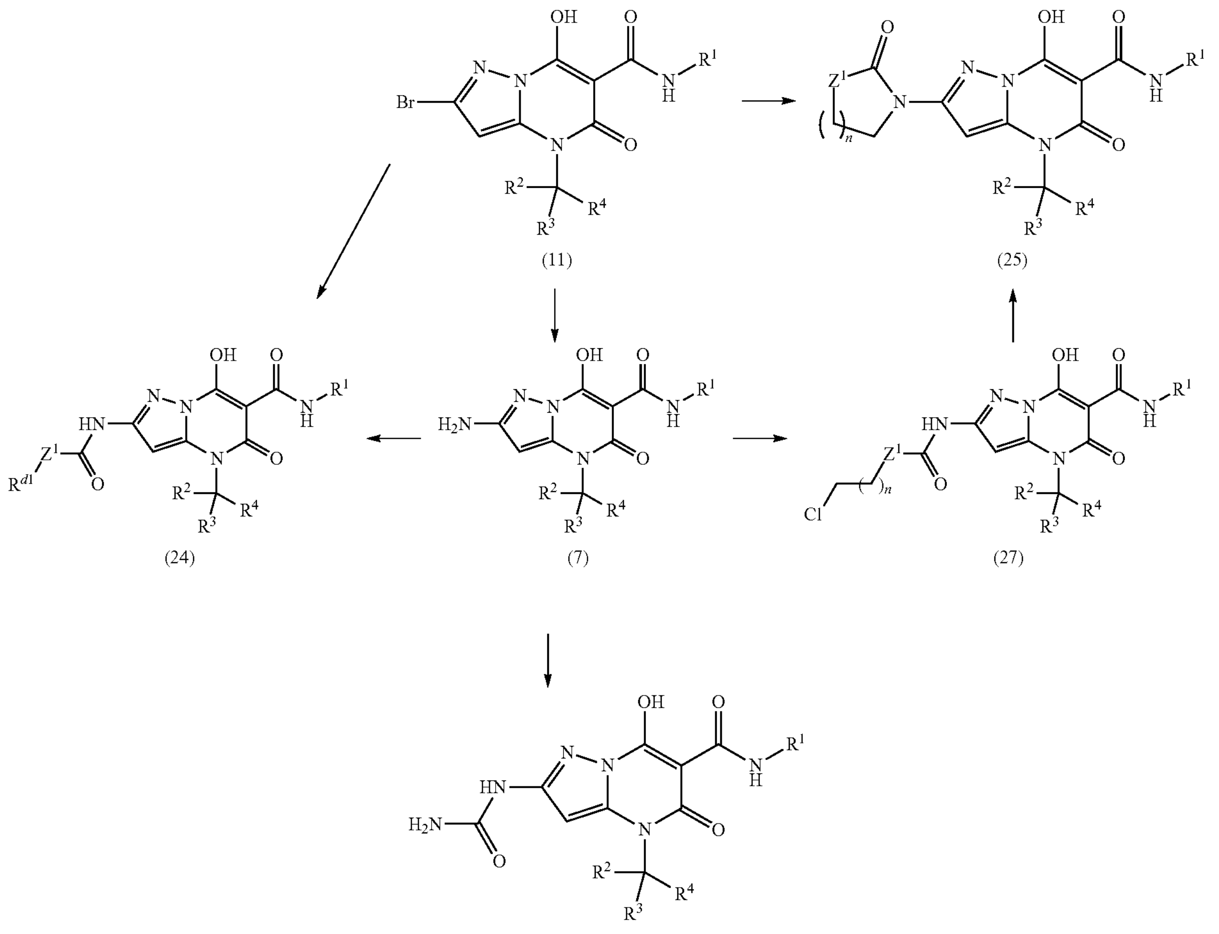

(11) (25) (24) (7) (27) (26)

Compound (24) can be produced by a coupling reaction using compound (11), acylamide, copper(I) iodide, a ligand, and a base. Examples of the ligand used include (1R,2R)—N1,N2-dimethylcyclohexane-1,2-diamine. Examples of the base include potassium carbonate. Examples of the solvent include 1,4-dioxane.

Compound (24) can be produced by an acylation reaction using compound (7), an acylating reagent, pyridine and N,N-dimethyl-4-aminopyridine. Examples of the base used include triethylamine, and examples of the solvent include toluene and tetrahydrofuran.

Compound (24) can be produced by a urea formation reaction using compound (7) and an isocyanate. Examples of the solvent include toluene and tetrahydrofuran.

Compound (24) can be produced by a carbamation reaction using compound (7), chloroformate ester, and a base. Examples of the base used include triethylamine, and examples of the solvent include pyridine, toluene, and tetrahydrofuran.

Compound (25) can be produced by a coupling reaction using compound (11), a saturated cyclic amide, copper(I) iodide, a ligand, and a base. Examples of the saturated cyclic amide used include N1,N2-dimethylethane-1,2-diamine and pyrrolidone. Examples of the ligand include N1,N2-dimethylethane-1,2-diamine. Examples of the base include potassium carbonate. Examples of the solvent include N-methylpyrrolidone.

Compound (26) can be produced by a urea formation reaction using compound (7), trichloroacetyl isocyanate, and a base. Examples of the base used include potassium carbonate, and examples of the solvent include tetrahydrofuran and methanol.

Compound (27) can be produced by an acylation reaction using compound (7), an acylating reagent, pyridine, and N,N-dimethyl-4-aminopyridine. Examples of the base used include triethylamine, and examples of the solvent include toluene and tetrahydrofuran.

Compound (27) can be produced by a urea formation reaction using compound (7) and an isocyanate. Examples of the solvent used include tetrahydrofuran.

Compound (27) can be produced by a carbamation reaction using compound (7), chloroformate ester, and a base. Examples of the base used include triethylamine, and examples of the solvent include pyridine, toluene, and tetrahydrofuran.

Compound (25) can be produced by an intramolecular cyclization reaction using compound (27) and a base. Examples of the base used include potassium tert-butoxide, and examples of the solvent include tetrahydrofuran.

Compound (28) can be produced from compound (5) by the method described below. (In the scheme described below, $R^a$ and $R^b$ have the same meanings as defined above in "acyl group.")

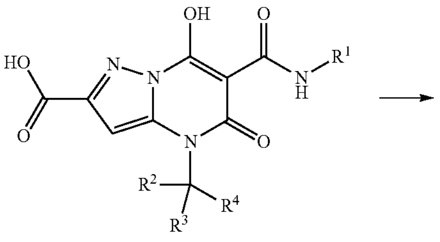

(5)

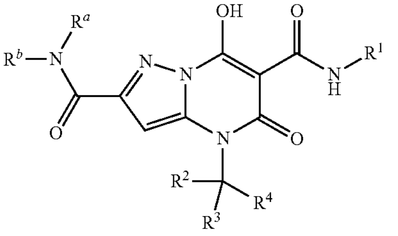

(28)

Compound (28) can be produced by an amidation reaction using compound (5), an amine, 1-(3-dimethylaminopropyl)-3-ethylcarbodiimide hydrochloride, and 1-hydroxybenzotriazole monohydrate. Examples of the solvent used include N,N-dimethylacetamide.

Compound (32) and compound (33) can be produced from compound (29) by the methods described below.

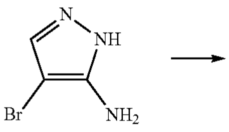

(29)

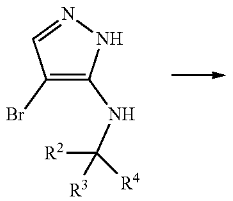

(30)

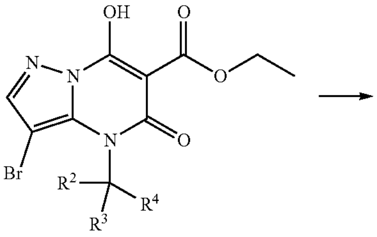

(31)

-continued

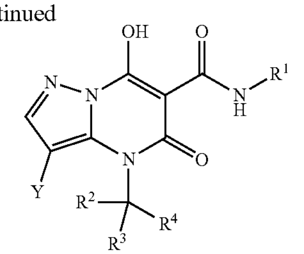

(33)

Compound (30) can be produced by a reductive amination reaction using compound (29), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (29) may be a commercially available product as is. Alternatively, compound (29) may be produced by a method known per se or a method similar thereto.

Compound (31) can be produced by a cyclization reaction using compound (30), triethyl methanetricarboxylate, and a base. Examples of the base used include triethylamine, and examples of the solvent include toluene.

Compound (32) can be produced by an amidation reaction using compound (31) and an amine. Examples of the solvent used include N,N-dimethylacetamide.

Compound (33) (a compound wherein Y is a substitutable heterocyclic group, hydrocarbon group, or acyl group) can be produced by a coupling reaction using compound (32), a coupling reagent, a metal catalyst, a ligand, and a base. Examples of the coupling reagent used include boronic acid, boronate esters, acrylate esters, imidazole, pyrazole, N1,N2-dimethylethane-1,2-diamine, pyrrolidone, and amines. Examples of the metal catalyst used include [1,1'-bis(di-tert-butylphosphino)ferrocene]dichloropalladium(II), palladium (II) acetate, tris(dibenzylideneacetone)dipalladium(0), and copper(I) iodide. Examples of the ligand include 2-dicyclohexylphosphino-2',4',6'-triisopropylbiphenyl, N1,N2-dimethylethane-1,2-diamine, 2-di-tert-butylphosphino-2',4',6'-triisopropylbiphenyl, and 4,5-bis(diphenylphosphino)-9,9-dimethylxanthene. Examples of the base include potassium carbonate, cesium carbonate, sodium tert-butoxide, and triethylamine. Examples of the solvent include 1,4-dioxane, water, N,N-dimethylformamide, dimethyl sulfoxide, and N-methylpyrrolidone.

Compound (34) and compound (35) can be produced from compound (15) by the methods described below. (In the scheme described below, $R^a$ and $R^b$ have the same meanings as defined above in "acyl group.")

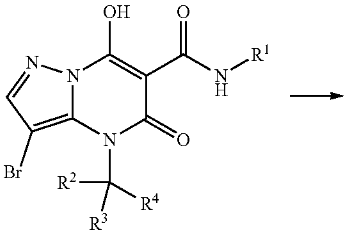

(32)

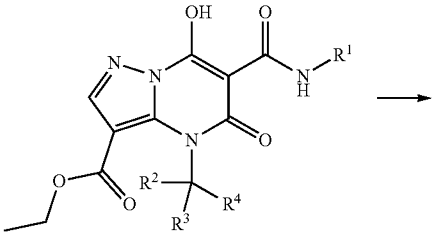

(15)

-continued

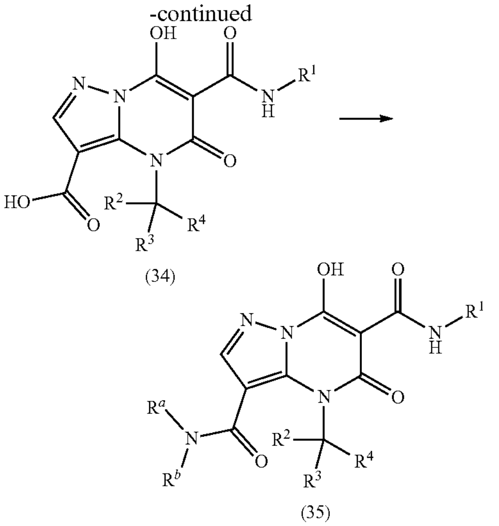

(34)

(35)

Compound (34) can be produced by a hydrolysis reaction using compound (15) and a base. Examples of the base used include potassium trimethylsilanolate, sodium hydroxide, potassium hydroxide, and lithium hydroxide, and examples of the solvent include tetrahydrofuran, 1,4-dioxane, water, and ethanol.

Compound (35) can be produced by an amidation reaction using compound (34), an amine, O-(7-azabenzotriazol-1-yl)-N,N,N',N'-tetramethyluronium hexafluorophosphate, and a base. Examples of the base used include N,N-diisopropylethylamine, and examples of the solvent include N,N-dimethylformamide.

Compound (36), compound (37), and compound (38) can be produced from compound (7) by the methods described below. (In the scheme described below, $P^1$ is a protective group that can be removed under conditions of catalytic reduction reaction, hydrolysis reaction, etc., and other symbols such as $Z^2$ and $R^{d2}$ have the same meanings as defined above. For example, $Z^2$ is a substitutable methylene group or —N—, and $R^{d2}$ is a substitutable $C_{1-6}$ alkyl group, etc.)

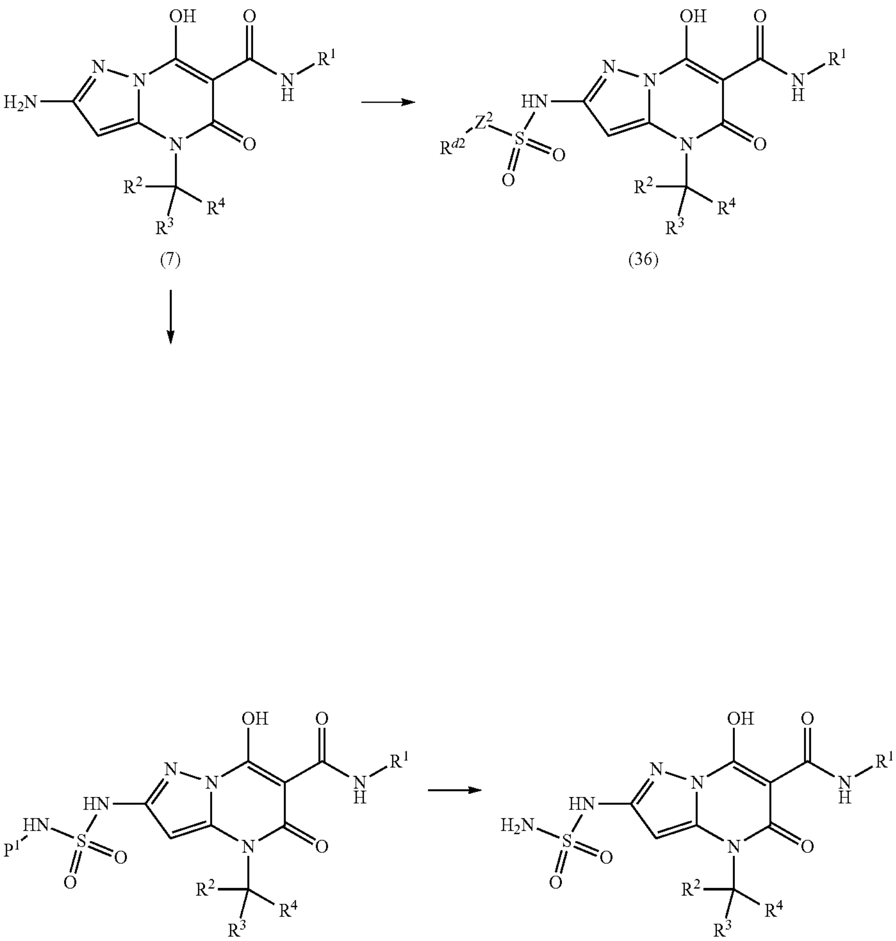

(7)

(36)

(37)

(38)

Compound (36) can be produced by a sulfonylation reaction using compound (7), sulfonyl chloride, and a base. Examples of the base used include triethylamine, and examples of the solvent include pyridine, toluene, and tetrahydrofuran.

Compound (36) can be produced by a sulfamation reaction using compound (7), a chlorosulfonate ester, and a base. Examples of the base used include triethylamine, and examples of the solvent include pyridine, toluene, and tetrahydrofuran.

Compound (37) can be produced by a sulfamoylation reaction using compound (7), tert-butyl (chlorosulfonyl) carbamate, and a base. Examples of the base used include triethylamine, and examples of the solvent include dichloromethane.

Compound (38) can be produced by deprotection using compound (37) and an acid. Examples of the acid used include trifluoroacetic acid.

Compound (39), compound (40), and compound (41) can be produced from compound (4) by the methods described below.

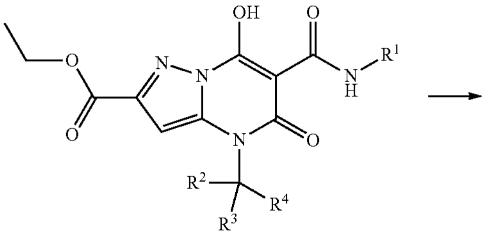

(4)

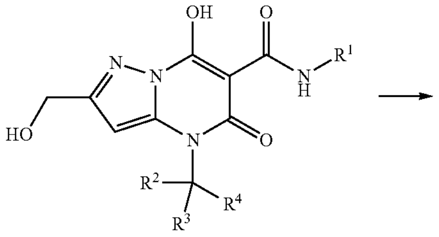

(39)

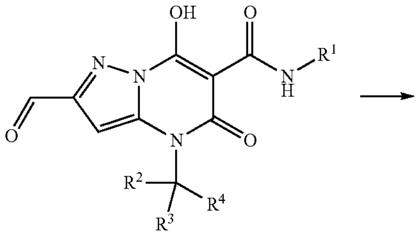

(40)

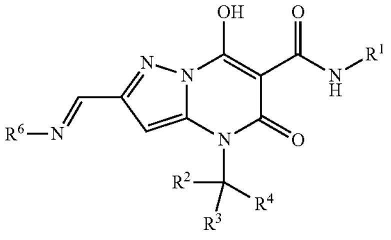

(41)

Compound (39) can be produced by a reduction reaction using compound (4) and a reductant. Examples of the reductant used include lithium aluminum hydride, and examples of the solvent include tetrahydrofuran.

Compound (40) can be produced by an oxidation reaction using compound (39) and an oxidant. Examples of the oxidant used include 2-iodoxybenzoic acid, and examples of the solvent include dimethyl sulfoxide.

Compound (41) can be produced by an oximation reaction using compound (40) and an amine. Examples of the amine used include hydroxylamine hydrochloride and alkoxyamines, and examples of the solvent include methanol.

Compound (42) and compound (43) can be produced from compound (11) by the methods described below.

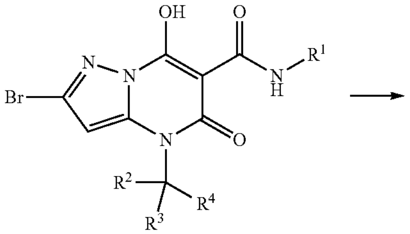

(11)

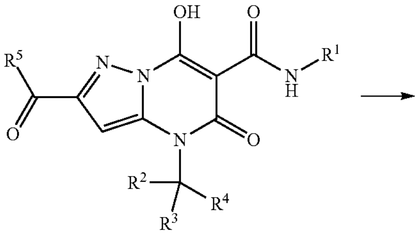

(42)

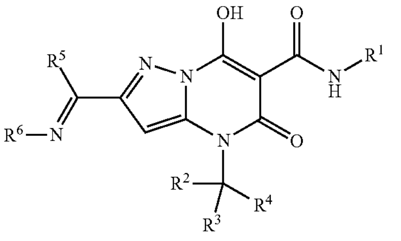

(43)

Compound (42) can be produced by a coupling reaction using compound (11), a tin reagent, and a palladium catalyst. Examples of the tin reagent used include tributyl(1-ethoxyvinyl) tin. Examples of the palladium catalyst include tetrakis(triphenylphosphine) palladium(0). Examples of the solvent include toluene.

Compound (43) can be produced by an oximation reaction using compound (42) and an amine. Examples of the amine used include hydroxylamine hydrochloride and alkoxyamines, and examples of the solvent include methanol.

Compound (44) and compound (45) can be produced from compound (7) by the methods described below.

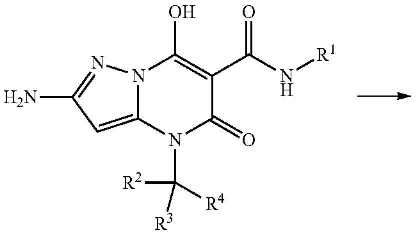

(7)

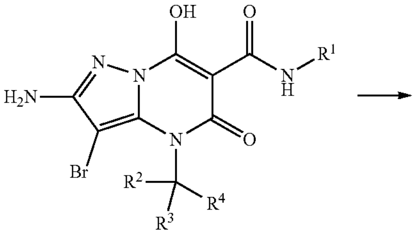

(44)

-continued

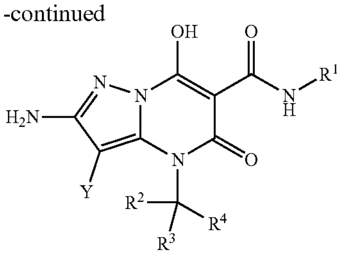

(45)

Compound (44) can be produced by a halogenation reaction using compound (7) and N-bromosuccinimide. Examples of the solvent used include N,N-dimethylformamide and acetonitrile.

Compound (45) can be produced by a coupling reaction using compound (44), a coupling reagent, a palladium catalyst, a ligand, and a base. Examples of the coupling reagent used include boronic acid, boronate esters, and acrylate esters. Examples of the palladium catalyst used include [1,1'-bis(di-tert-butylphosphino)ferrocene]dichloropalladium(II) and palladium(II) acetate. Examples of the ligand include 2-dicyclohexylphosphino-2',4',6'-triisopropylbiphenyl. Examples of the base include potassium carbonate and triethylamine. Examples of the solvent include 1,4-dioxane, water, and N,N-dimethylformamide.

Compound (45), compound (48), compound (49), compound (50), and compound (51) can be produced from compound (2) by the methods described below. (In the scheme described below, $R^a$ and $R^b$ have the same meanings as defined above in "acyl group.")

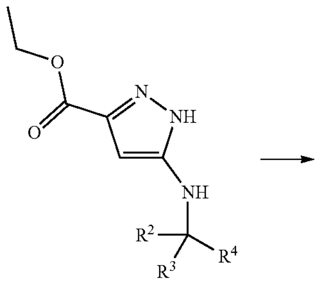

(2)

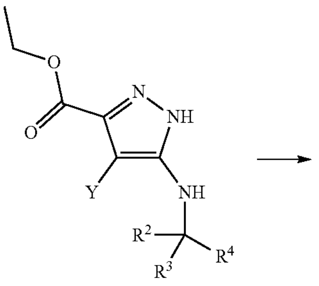

(46)

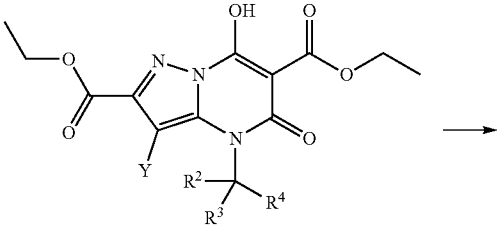

(47)

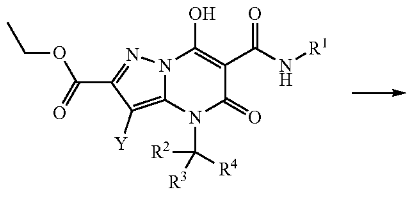

(48)

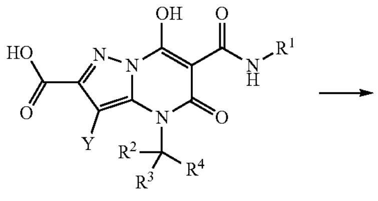

(49)

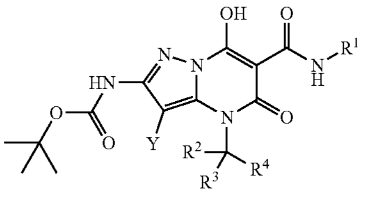

(50)

-continued

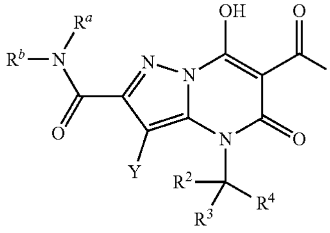

(51)

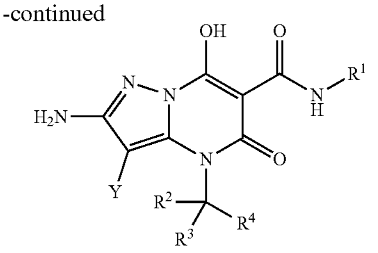

(45)

Compound (46) can be produced by a halogenation reaction using compound (2) and a halogenating reagent. Examples of the halogenating reagent used include N-fluorobenzenesulfonimide and N-bromosuccinimide, and examples of the solvent used include N,N-dimethylformamide and acetonitrile.

Compound (47) can be produced by a cyclization reaction using compound (46), triethyl methanetricarboxylate, and a base. Examples of the base used include triethylamine, and examples of the solvent include toluene.

Compound (48) can be produced by an amidation reaction using compound (47) and an amine. Examples of the solvent used include N,N-dimethylacetamide.

Compound (45) can be produced by deprotection using compound (50) and an acid. Examples of the acid used include hydrochloric acid and trifluoroacetic acid, and examples of the solvent include 1,4-dioxane and ethyl acetate.

Compound (52), compound (53), compound (54), and compound (55) can be produced from compound (45) by the methods described below. (In the scheme described below, n is an integer of 1 to 3, and $Z^1$ and $R^{d1}$ have the same meanings as defined above. For example, $Z^1$ is a substitutable methylene group, —N—, or —O—, and $R^{d1}$ is a substitutable $C_{1-6}$ alkyl group, etc.)

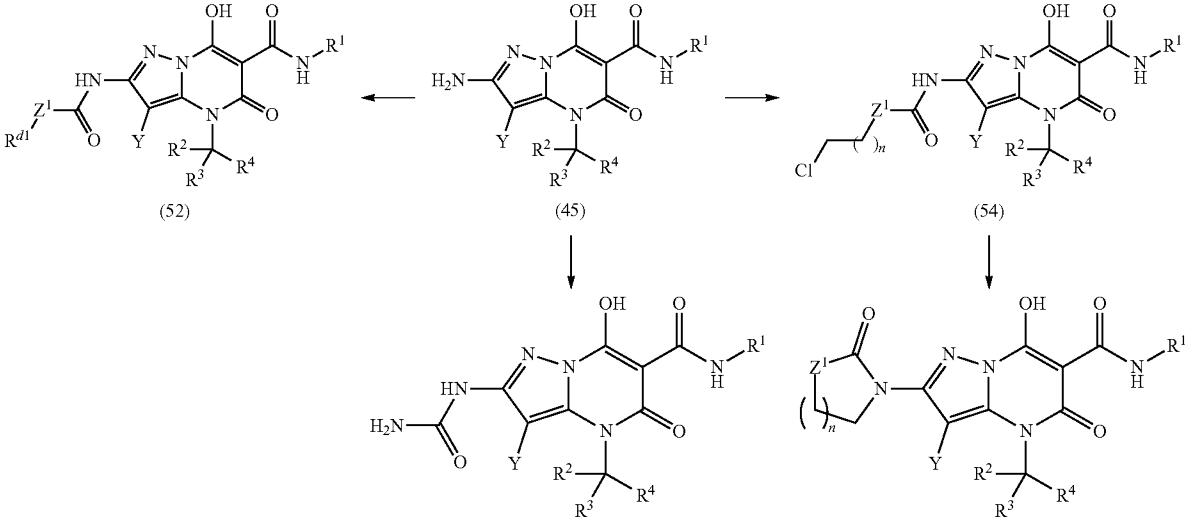

(52) (45) (54)

(53) (55)

Compound (49) can be produced by a hydrolysis reaction using compound (48) and a base. Examples of the base used include potassium trimethylsilanolate, sodium hydroxide, potassium hydroxide, and lithium hydroxide, and examples of the solvent used include 1,4-dioxane, tetrahydrofuran, water, and ethanol.

Compound (50) can be produced by an intramolecular rearrangement reaction using compound (49), diphenylphosphoryl azide, a base, and tert-butanol. Examples of the base used include triethylamine.

Compound (51) can be produced by an amidation reaction using compound (49), an amine, 1-(3-dimethylaminopropyl)-3-ethylcarbodiimide hydrochloride and 1-hydroxybenzotriazole monohydrate. Examples of the solvent used include N,N-dimethylacetamide.

Compound (52) can be produced by an acylation reaction using compound (45), an acylating reagent, pyridine, and N,N-dimethyl-4-aminopyridine. Examples of the base used include triethylamine, and examples of the solvent include toluene and tetrahydrofuran.

Compound (52) can be produced by a urea formation reaction using compound (45) and an isocyanate. Examples of the solvent used include toluene and tetrahydrofuran.

Compound (52) can be produced by a carbamation reaction using compound (45), a chloroformate ester, and a base. Examples of the base used include triethylamine, and examples of the solvent include pyridine, toluene, and tetrahydrofuran.

Compound (53) can be produced by a urea formation reaction using compound (45), trichloroacetyl isocyanate, and a base. Examples of the base used include potassium carbonate, and examples of the solvent include tetrahydrofuran and methanol.

Compound (54) can be produced by an acylation reaction using compound (45), an acylating reagent, pyridine, and N,N-dimethyl-4-aminopyridine. Examples of the base used include triethylamine, and examples of the solvent include toluene and tetrahydrofuran.

Compound (54) can be produced by a urea formation reaction using compound (45) and an isocyanate. Examples of the solvent used include tetrahydrofuran.

Compound (54) can be produced by a carbamation reaction using compound (45), a chloroformate ester, and a base. Examples of the base used include triethylamine, and examples of the solvent include pyridine, toluene, and tetrahydrofuran.

Compound (55) can be produced by an intramolecular cyclization reaction using compound (54) and a base. Examples of the base used include potassium tert-butoxide, and examples of the solvent include tetrahydrofuran.

Compound (56), compound (57), compound (58), compound (59), compound (60), and compound (61) can be produced from compound (44) by the methods described below. (In the scheme described below, m is an integer of 1 to 3; n is an integer of 1 to 3; $R^d$ is a substituent of a substitutable heterocyclic group (e.g., a possibly halogenated $C_{1-6}$ alkyl group); and $P^1$ is a protective group that can be removed under conditions of catalytic reduction reaction, hydrolysis reaction, etc.)

Compound (57) can be produced by deprotection using compound (56) and a catalytic reduction reaction or an acid. Examples of the deprotection reagent used include palladium-carbon, hydrogen, hydrochloric acid, and trifluoroacetic acid, and examples of the solvent include 1,4-dioxane and ethyl acetate.

Compound (58) can be produced by a reductive amination reaction using compound (57), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (59) can be produced by a reduction reaction using compound (56), hydrogen, and palladium-carbon. Examples of the solvent used include methanol.

Compound (60) can be produced by deprotection using compound (59) and a catalytic reduction reaction or an acid. Examples of the deprotection reagent used include palladium-carbon, hydrogen, hydrochloric acid, and trifluoroacetic acid, and examples of the solvent include 1,4-dioxane and ethyl acetate.

Compound (61) can be produced by a reductive amination reaction using compound (60), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

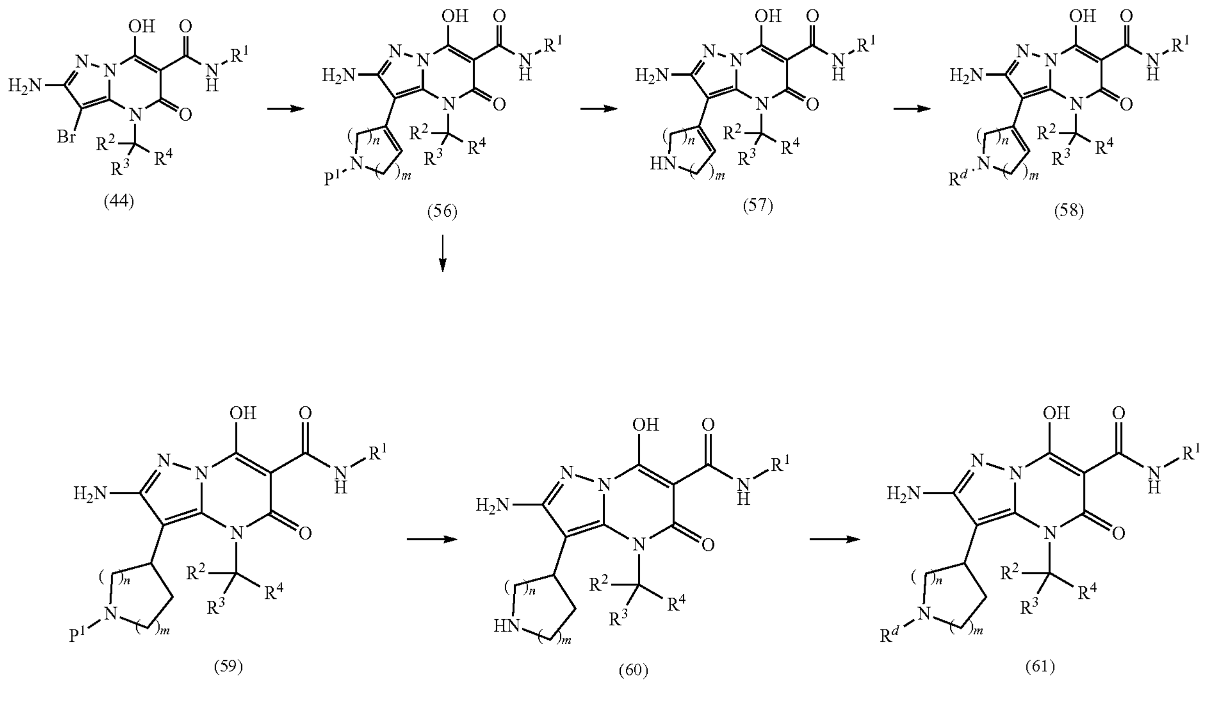

(44) (56) (57) (58)

(59) (60) (61)

Compound (56) can be produced by a coupling reaction using compound (44), a boric acid reagent, a palladium catalyst, and a base. Examples of the boric acid reagent used include boronic acid and boronate esters. Examples of the palladium catalyst include [1,1'-bis(di-tert-butylphosphino)ferrocene]dichloropalladium(II). Examples of the base include potassium carbonate. Examples of the solvent include 1,4-dioxane and water.

Compound (62), compound (63), compound (64), compound (65), compound (66), and compound (67) can be produced from compound (11) by the methods described below. (In the scheme described below, m is an integer of 1 to 3; n is an integer of 1 to 3; $R^d$ is a substituent of a substitutable heterocyclic group (e.g., a possibly halogenated $C_{1-6}$ alkyl group); and $P^1$ is a protective group that can be removed under conditions of catalytic reduction reaction, hydrolysis reaction, etc.)

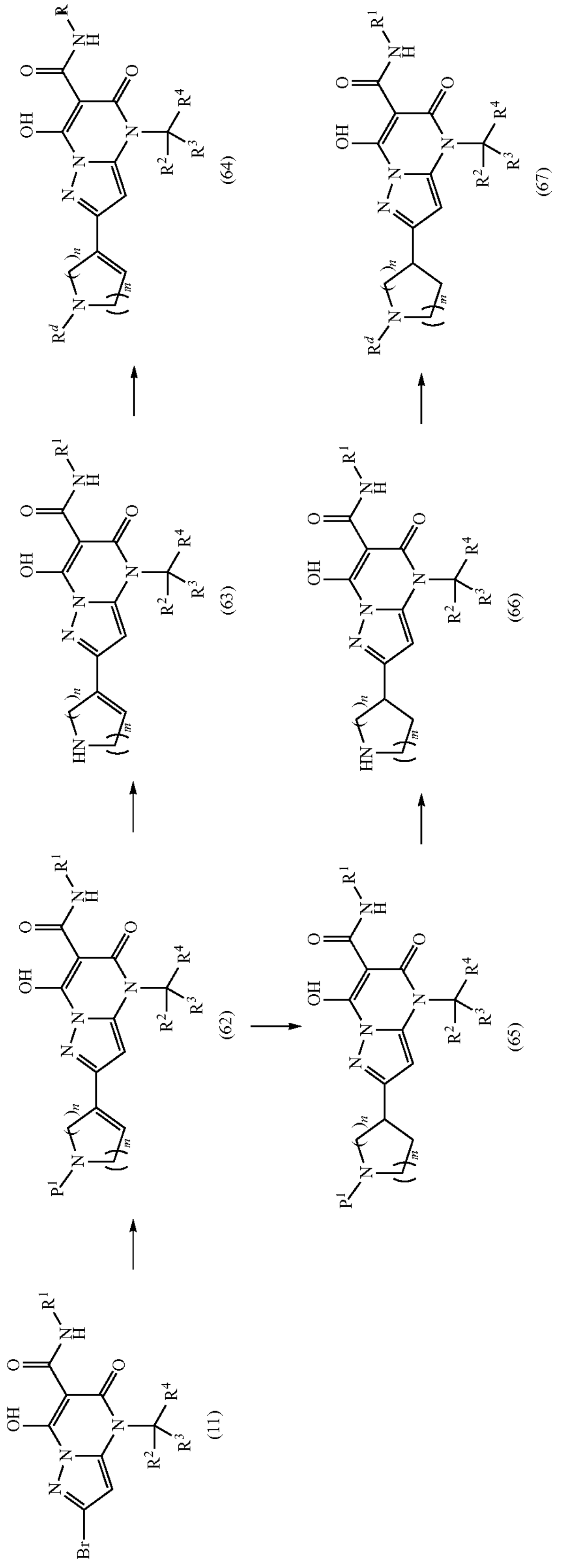
(11) (62) (63) (64) (65) (66) (67)

Compound (62) can be produced by a coupling reaction using compound (11), a boric acid reagent, a palladium catalyst, and a base. Examples of the boric acid reagent used include boronic acid and boronate esters. Examples of the palladium catalyst include [1,1'-bis(di-tert-butylphosphino) ferrocene]dichloropalladium(II). Examples of the base include potassium carbonate. Examples of the solvent include 1,4-dioxane and water.

Compound (63) can be produced by deprotection using compound (62) and a catalytic reduction reaction or an acid. Examples of the deprotection reagent used include palladium-carbon, hydrogen, hydrochloric acid, and trifluoroacetic acid, and examples of the solvent include 1,4-dioxane and ethyl acetate.

Compound (64) can be produced by a reductive amination reaction using compound (63), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (65) can be produced by a reduction reaction using compound (62), hydrogen, and palladium-carbon. Examples of the solvent used include methanol.

Compound (66) can be produced by deprotection using compound (65) and a catalytic reduction reaction or an acid. Examples of the deprotection reagent used include palladium-carbon, hydrogen, hydrochloric acid, and trifluoroacetic acid, and examples of the solvent include 1,4-dioxane and ethyl acetate.

Compound (67) can be produced by a reductive amination reaction using compound (66), an aldehyde, acetic acid, and a reductant. Examples of the reductant used include sodium triacetoxyborohydride, sodium cyanoborohydride and sodium borohydride, and examples of the solvent include tetrahydrofuran and 1,2-dichloroethane.

Compound (23) and compound (68) can be produced from compound (11) by the methods described below.

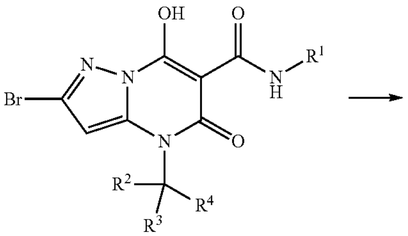

(11)

-continued

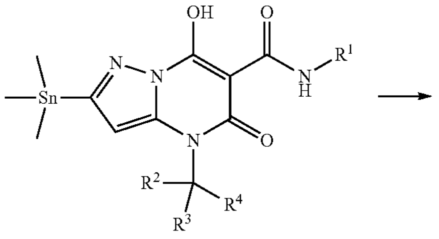

(68)

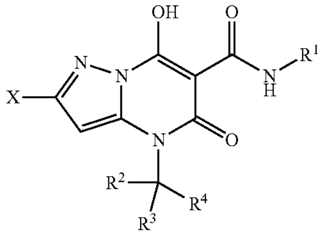

(23)

Compound (68) can be produced by a stannation reaction using compound (11), bis(trimethyltin), and a palladium catalyst. Examples of the palladium catalyst used include tetrakis(triphenylphosphine)palladium(0), and examples of the solvent used include toluene.

Compound (23) can be produced by a coupling reaction using compound (68), an aryl halide, and a palladium catalyst. Examples of the palladium catalyst used include tetrakis(triphenylphosphine)palladium(0), and examples of the solvent used include toluene.

Compound (69), compound (70), compound (71), and compound (72) can be produced from compound (11) by the methods described below. (In the scheme described below, combinations of $R^h$ and $R^i$ are the same as those defined above.)

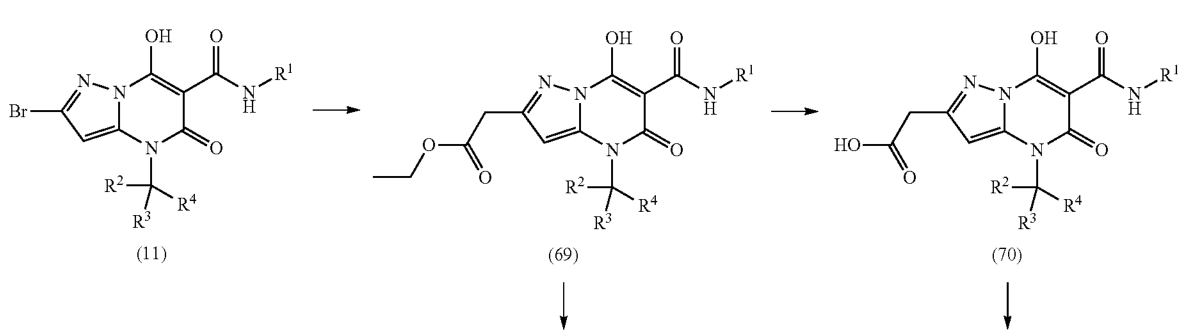

(11) (69) (70)

-continued

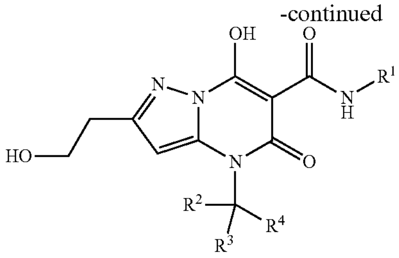

(71)

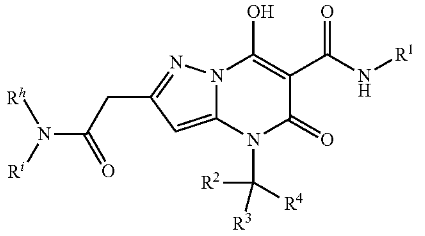

(72)

Compound (69) can be produced by a coupling reaction using compound (11), ethyl acetoacetate palladium catalyst, a ligand, and base: Examples of the palladium catalyst used include palladium(II) acetate. Examples of the ligand include 2-di-tert-butylphosphino-2'-methylbiphenyl. Examples of the base include tripotassium phosphate. Examples of the solvent include toluene.

Compound (70) can be produced by a hydrolysis reaction using compound (69) and a base. Examples of the base used include potassium trimethylsilanolate, sodium hydroxide, potassium hydroxide, and lithium hydroxide, and examples of the solvent include 1,4-dioxane, tetrahydrofuran, water, and ethanol.

Compound (71) can be produced by a reduction reaction using compound (69) and a reductant. Examples of the reductant used include lithium aluminum hydride, and examples of the solvent include tetrahydrofuran.

Compound (72) can be produced by an amidation reaction using compound (70), an amine, 1-(3-dimethylaminopropyl)-3-ethylcarbodiimide hydrochloride, and 1-hydroxybenzotriazole monohydrate. Examples of the solvent used include N,N-dimethylacetamide.

Compound (73), compound (74), compound (75), compound (76), compound (77), and compound (78) can be produced from compound (32) by the methods described below. (In the scheme described below, m is an integer of 1 to 3; n is an integer of 1 to 3; $R^d$ is a substituent of a substitutable heterocyclic group (e.g., a substitutable $C_{1-6}$ alkyl group); and $P^1$ is a protective group that can be removed under conditions of catalytic reduction reaction, hydrolysis reaction, etc.)

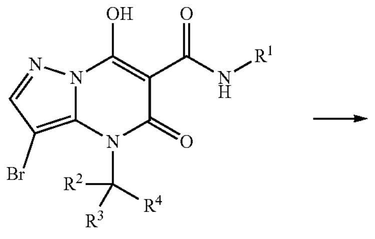

(32)

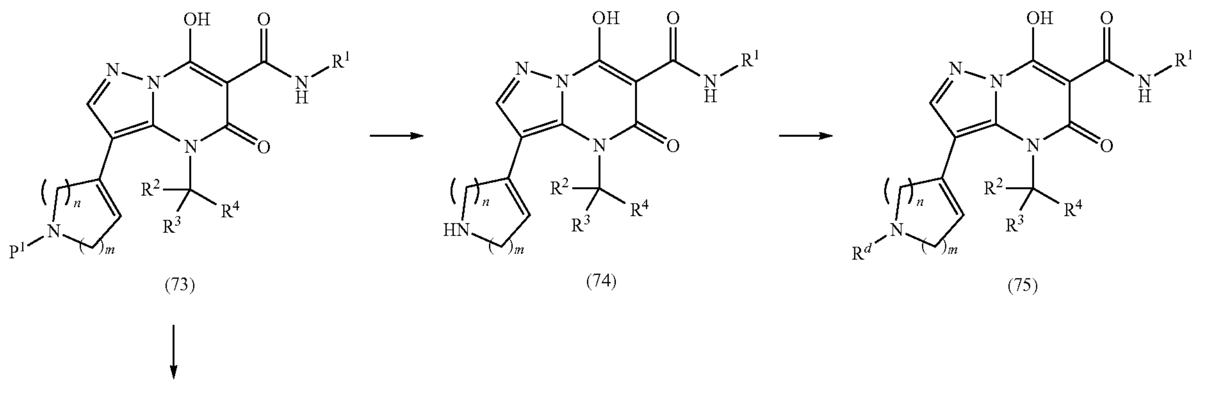

(73) (74) (75)

-continued

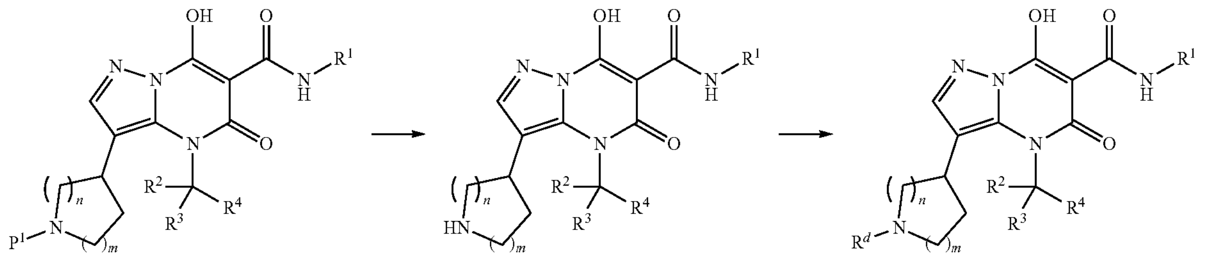

(76) (77) (78)

Compound (73) can be produced by a coupling reaction using compound (32), a boric acid reagent, a palladium catalyst, and a base. Examples of the boric acid reagent used include boronic acid and boronate esters. Examples of the palladium catalyst include [1,1'-bis(di-tert-butylphosphino) ferrocene]dichloropalladium(II). Examples of the base include potassium carbonate. Examples of the solvent include 1,4-dioxane and water.

Compound (74) can be produced by deprotection using compound (73) and a catalytic reduction reaction or an acid. Examples of the deprotection reagent used include palladium-carbon, hydrogen, hydrochloric acid, and trifluoroacetic acid, and examples of the solvent include 1,4-dioxane and ethyl acetate.

Compound (75) can be produced by a reductive amination reaction using compound (74), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (75) can be produced by the Eschweiler-Clarke reaction using compound (74), formaldehyde, and formic acid. Examples of the solvent used include water.

Compound (76) can be produced by a reduction reaction using compound (73), hydrogen, and palladium-carbon. Examples of the solvent used include methanol.

Compound (77) can be produced by deprotection using compound (76) and a catalytic reduction reaction or an acid. Examples of the deprotection reagent used include palladium-carbon, hydrogen, hydrochloric acid, and trifluoroacetic acid, and examples of the solvent include 1,4-dioxane and ethyl acetate.

Compound (78) can be produced by a reductive amination reaction using compound (77), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (78) can be produced by the Eschweiler-Clarke reaction using compound (77), formaldehyde, and formic acid. Examples of the solvent used include water.

Compound (81), compound (82), compound (83), and compound (84) can be produced from compound (8) by the methods described below. (In the scheme described below, $R^c$ is a hydrogen atom or a substituent of a substitutable amino group (e.g., a substitutable $C_{1-6}$ alkyl group or a substitutable heterocyclic group); $R^d$ is, for example, a substitutable $C_{1-6}$ alkyl group, $C_{6-14}$ aryl group, or $C_{7-16}$ aralkyl group; and Re is, for example, a substitutable $C_{1-6}$ alkylene group, $C_{2-6}$ alkenylene group, $C_{2-6}$ alkynylene group, $C_{6-14}$ arylene group, or heterocyclic-diyl group.)

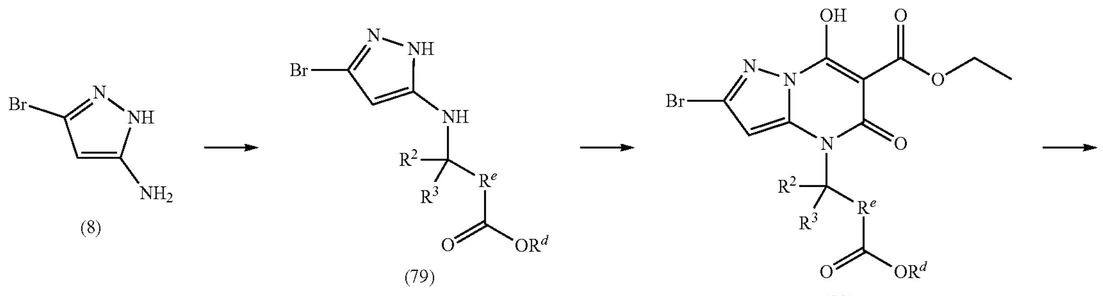

(8) (79) (80)

-continued

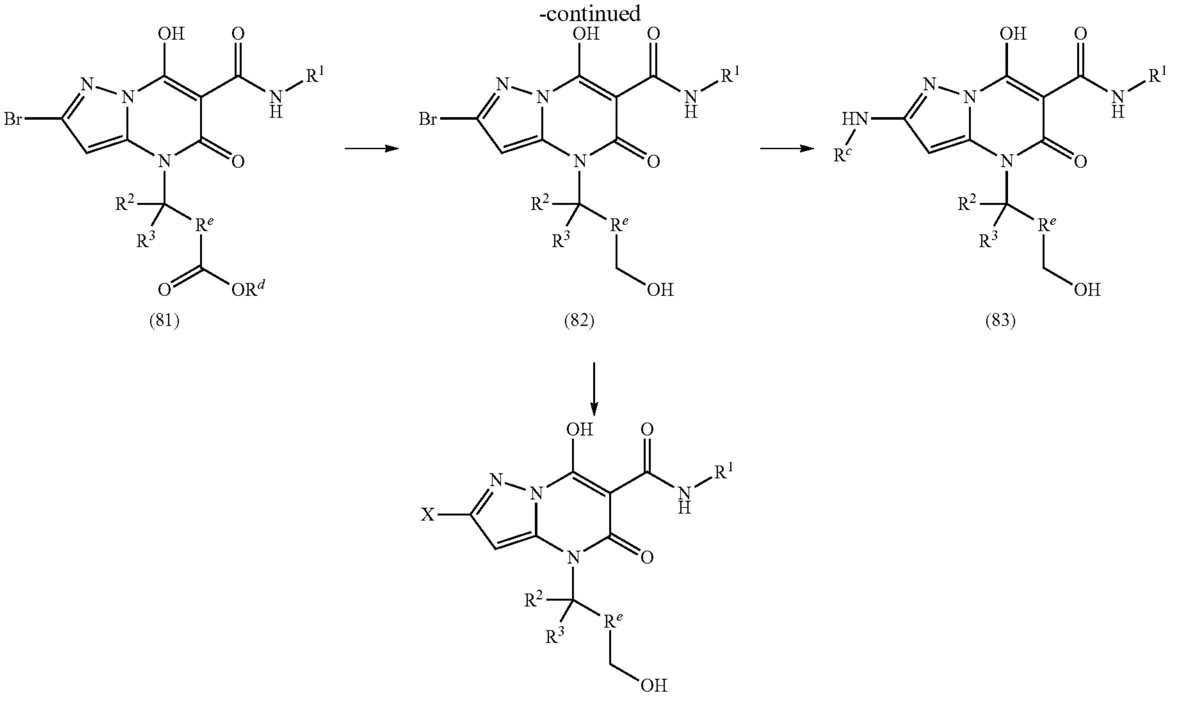

(81) (82) (83) (84)

Compound (79) can be produced by a reductive amination reaction using compound (8), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (80) can be produced by a cyclization reaction using compound (79), triethyl methanetricarboxylate, and a base. Examples of the base used include triethylamine, and examples of the solvent include toluene.

Compound (81) can be produced by an amidation reaction using compound (80) and an amine. Examples of the solvent used include N,N-dimethylacetamide.

Compound (82) can be produced by a reduction reaction using compound (81) and a reductant. Examples of the reductant used include lithium aluminum hydride, and examples of the solvent used include tetrahydrofuran.

Compound (83) can be produced by a coupling reaction using compound (82), an amine, a palladium catalyst, a ligand, and a base. Examples of the palladium catalyst used include tris(dibenzylideneacetone)dipalladium(0). Examples of the ligand include 2-di-tert-butylphosphino-2',4',6'-triisopropylbiphenyl and 4,5-bis(diphenylphosphino)-9,9-dimethylxanthene. Examples of the base include sodium tert-butoxide. Examples of the solvent include 1,4-dioxane.

Compound (84) can be produced by a coupling reaction using compound (82), a coupling reagent, a metal catalyst, a ligand, and a base. Examples of the coupling reagent used include boronic acid, boronate esters, acrylate esters, imidazole, pyrazole, N1,N2-dimethylethane-1,2-diamine, and pyrrolidone. Examples of the metal catalyst include [1,1'-bis(di-tert-butylphosphino)ferrocene]dichloropalladium(II), palladium(II) acetate, tris(dibenzylideneacetone)dipalladium(0), and copper(I) iodide. Examples of the ligand include 2-dicyclohexylphosphino-2',4',6'-triisopropylbiphenyl, N1,N2-dimethylethane-1,2-diamine, 2-di-tert-butylphosphino-2',4',6'-triisopropylbiphenyl, and 4,5-bis(diphenylphosphino)-9,9-dimethylxanthene. Examples of the base include potassium carbonate, cesium carbonate, sodium tert-butoxide, and triethylamine. Examples of the solvent include 1,4-dioxane, water, N,N-dimethylformamide, dimethyl sulfoxide, and N-methylpyrrolidone.

Compound (85) can be produced from compound (17) by the method described below.

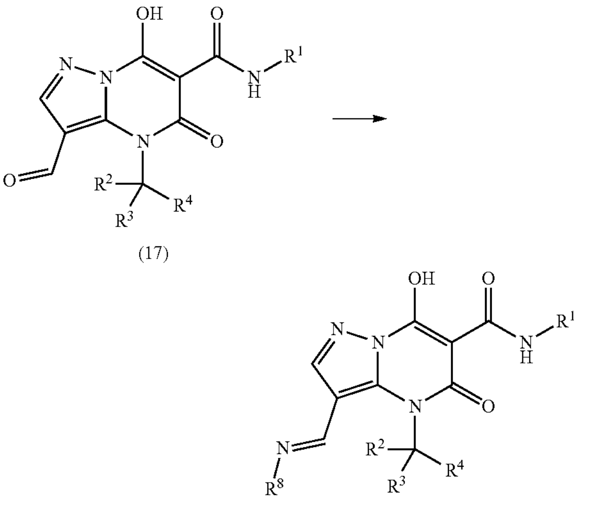

(17) (85)

Compound (85) can be produced by an oximation reaction using compound (17) and an amine. Examples of the amine used include hydroxylamine hydrochloride and alkoxyamines, and examples of the solvent include methanol.

Compound (23) can be produced from compound (86) by the methods described below.

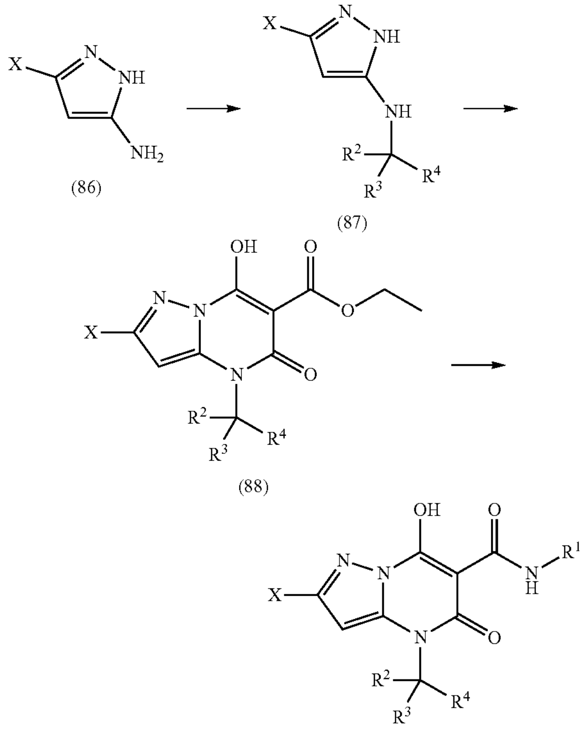

(86) (87) (88) (23)

Compound (87) can be produced by a reductive amination reaction using compound (86), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (86) may be a commercially available product as is, or may be produced by a method known per se or a method similar thereto. Alternatively, compound (86) may be produced by an appropriate combination of such a method with a protection/deprotection reaction, an oxidation-reduction reaction, a hydrolysis reaction, or a condensation reaction such as acylation/amidation/urea formation.

Compound (88) can be produced by a cyclization reaction using compound (87), triethyl methanetricarboxylate, and a base. Examples of the base used include triethylamine, and examples of the solvent include toluene.

Compound (23) can be produced by an amidation reaction using compound (88) and an amine. Examples of the solvent used include N,N-dimethylacetamide.

Compound (33) can be produced from compound (89) by the methods described below.

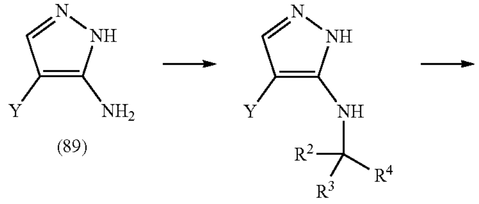

(89) (90)

-continued

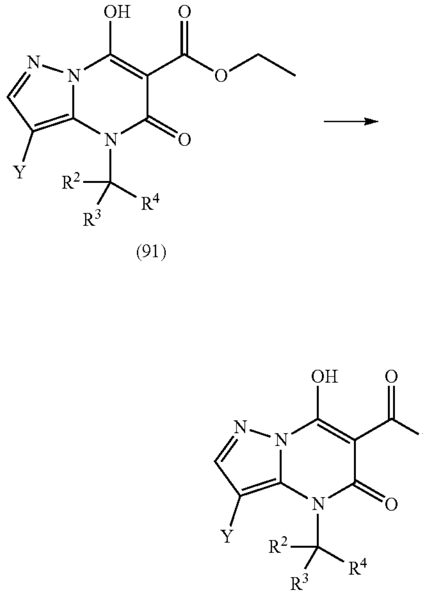

(91) (33)

Compound (90) can be produced by a reductive amination reaction using compound (89), an aldehyde, acetic acid, and a reductant. Examples of the reductant used include sodium triacetoxyborohydride, sodium cyanoborohydride, and sodium borohydride, and examples of the solvent include tetrahydrofuran and 1,2-dichloroethane.

Compound (89) may be a commercially available product as is, or may be produced by a method known per se or a method similar thereto. Alternatively, compound (89) may be produced by an appropriate combination of such a method with a protection/deprotection reaction, an oxidation-reduction reaction, a hydrolysis reaction, or a condensation reaction such as acylation/amidation/urea formation.

Compound (91) can be produced by a cyclization reaction using compound (90), triethyl methanetricarboxylate, and a base. Examples of the base used include triethylamine, and examples of the solvent include toluene.

Compound (33) can be produced by an amidation reaction using compound (91) and an amine. Examples of the solvent used include N,N-dimethylacetamide.

Compound (95) can be produced from compound (92) by the methods described below. (In the scheme described below, the ring A is a substitutable 5- to 7-membered non-aromatic heterocyclic ring or a substitutable 5- or 6-membered nitrogen-containing aromatic heterocyclic ring.)

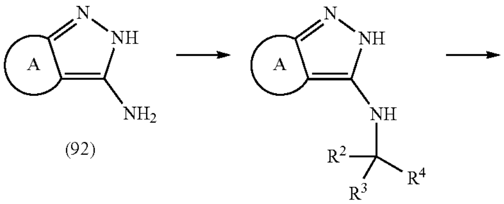

(92) (93)

-continued

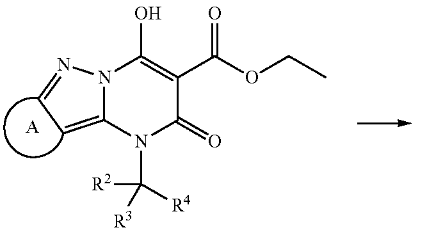

(94)

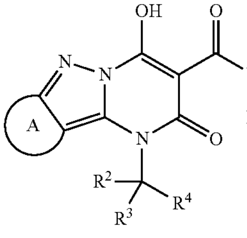

(95)

Compound (93) can be produced by a reductive amination reaction using compound (92), an aldehyde, acetic acid, and a reductant. Examples of the reductant used include sodium triacetoxyborohydride, sodium cyanoborohydride, and sodium borohydride, and examples of the solvent include tetrahydrofuran and dichloromethane.

Compound (92) may be a commercially available product as is, or may be produced by a method known per se or a method similar thereto.

Compound (94) can be produced by a cyclization reaction using compound (93), triethyl methanetricarboxylate, and a base. Examples of the base used include triethylamine, and examples of the solvent include toluene.

Compound (95) can be produced by an amidation reaction using compound (94) and an amine. Examples of the solvent used include N,N-dimethylacetamide.

Compound (100) can be produced from compound (6) by the methods described below.

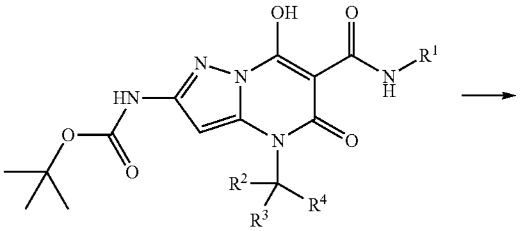

(6)

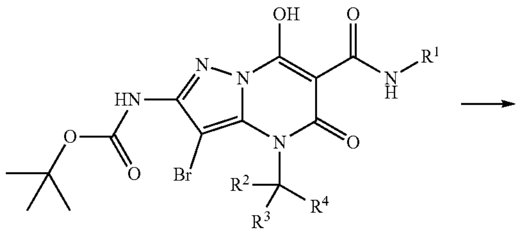

(96)

-continued

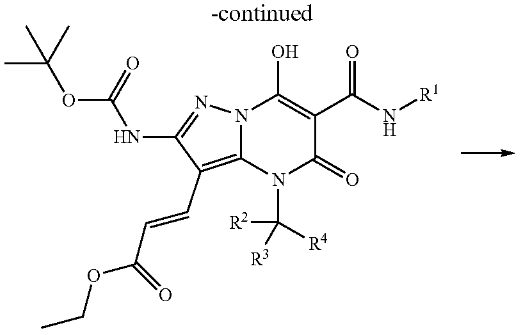

(97)

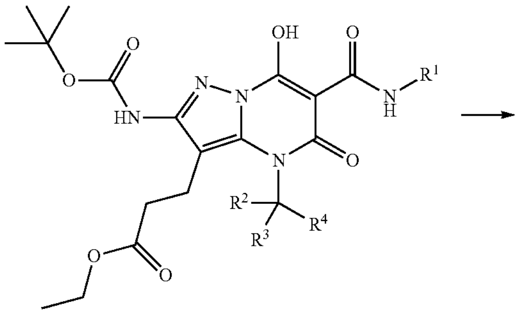

(98)

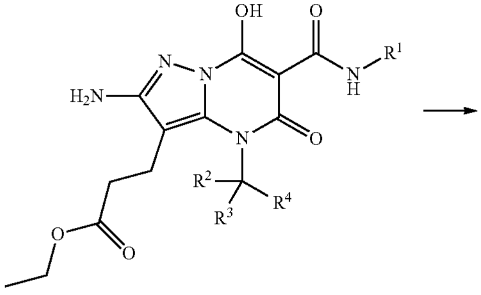

(99)

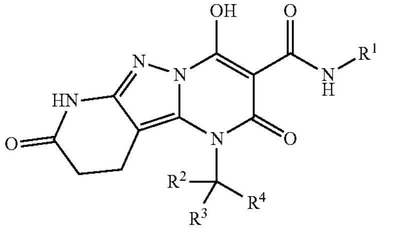

(100)

Compound (96) can be produced by a halogenation reaction using compound (6) and N-bromosuccinimide. Examples of the solvent used include N,N-dimethylformamide and dichloromethane.

Compound (97) can be produced by a coupling reaction using compound (96), a coupling reagent, a palladium catalyst, and a base. Examples of the coupling reagent used include boronic acid, boronate esters, and acrylate esters. Examples of the palladium catalyst include [1,1'-bis(di-tert-butylphosphino)ferrocene]dichloropalladium(II). Examples of the base include potassium carbonate and sodium carbonate. Examples of the solvent include 1,4-dioxane and water.

Compound (98) can be produced by a reduction reaction using compound (97), hydrogen, and palladium-carbon. Examples of the solvent used include ethyl acetate and methanol.

Compound (99) can be produced by deprotection using compound (98) and an acid. Examples of the acid used include hydrochloric acid and trifluoroacetic acid, and examples of the solvent include 1,4-dioxane.

Compound (100) can be produced by an intramolecular cyclization reaction using compound (99) and a base. Examples of the base used include potassium carbonate and sodium hydride, and examples of the solvent include 1,4-dioxane.

Compound (102), compound (103), and compound (104) can be produced from compound (96) by the methods described below. (In the scheme described below, $R^{13}$ is a possibly halogenated $C_{1-6}$ alkyl group, a carbamoyl group, etc.)

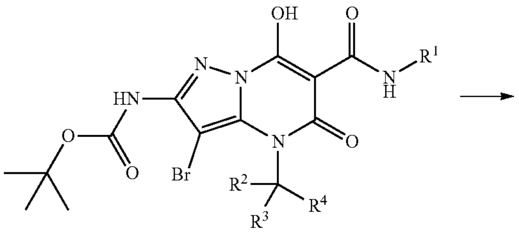

(96)

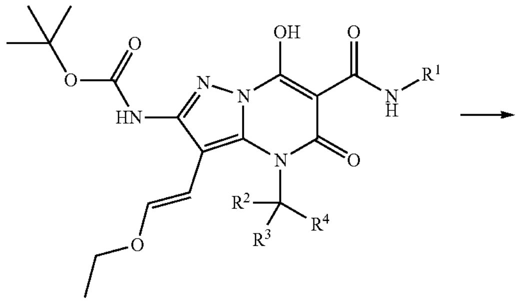

(101)

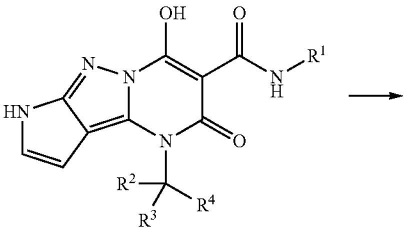

(102)

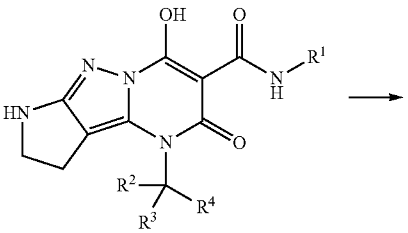

(103)

-continued

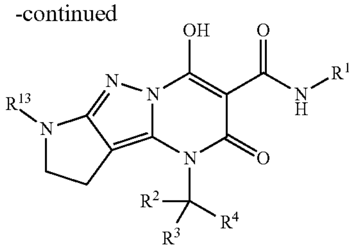

(104)

Compound (101) can be produced by a coupling reaction using compound (96), a coupling reagent, a palladium catalyst, and a base. Examples of the coupling reagent used include boronic acid, boronate esters, and ethyl vinyl ether. Examples of the metal catalyst include [1,1'-bis(di-tert-butylphosphino)ferrocene]dichloropalladium(II). Examples of the base include potassium carbonate and sodium carbonate. Examples of the solvent include 1,4-dioxane and water.

Compound (102) can be produced by deprotection using compound (101) and an acid. Examples of the acid used include hydrochloric acid and trifluoroacetic acid, and examples of the solvent include dichloromethane.

Compound (103) can be produced by a reduction reaction using compound (102) and a reductant. Examples of the reductant used include sodium cyanoborohydride, and examples of the solvent used include acetic acid.

Compound (104) (compound wherein $R^{13}$ is a possibly halogenated $C_{1-6}$ alkyl group, etc.) can be produced by an alkylation reaction using compound (103), an alkylating agent, and a base. Examples of the alkylating agent used include alkyl halides and trifluoromethanesulfonate esters. Examples of the base include N,N-diisopropylethylamine. Examples of the solvent include dimethyl sulfoxide.

Compound (104) (compound wherein $R^{13}$ is a carbamoyl group, etc.) can be produced by a urea formation reaction using compound (103) and an isocyanate. Examples of the isocyanate used include trimethylsilyl isocyanate, and examples of the solvent include dichloromethane.

Compound (108) can be produced from compound (96) by the methods described below.

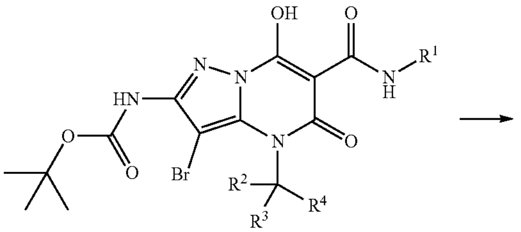

(96)

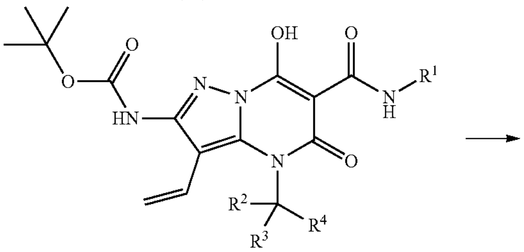

(105)

-continued

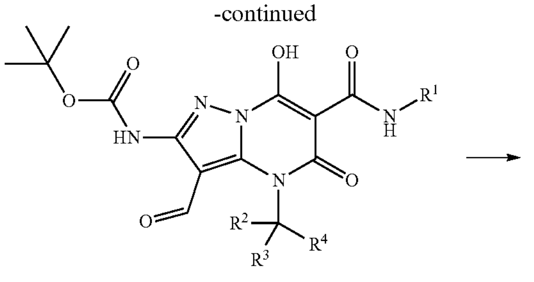

(106)

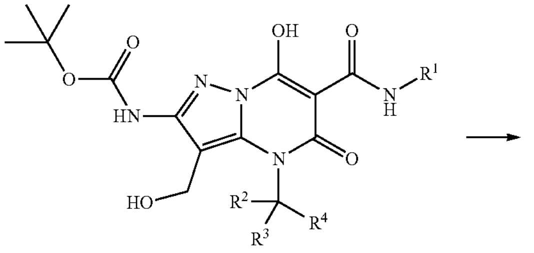

(107)

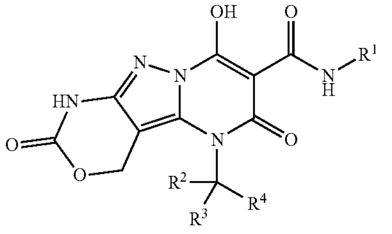

(108)

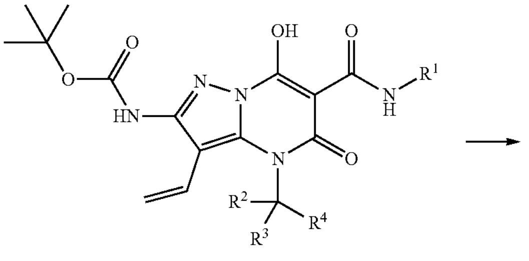

(105)

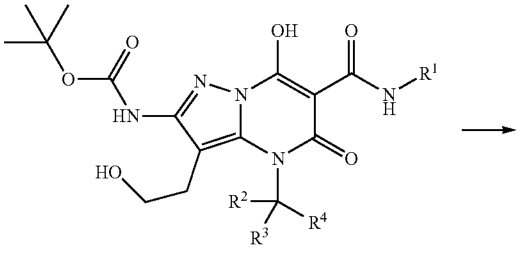

(109)

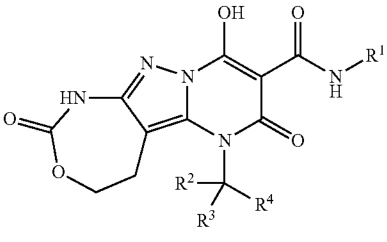

(110)

Compound (105) can be produced by a coupling reaction using compound (96), a coupling reagent, a palladium catalyst, and a base. Examples of the coupling reagent used include vinylboronic acid and potassium vinyltrifluoroborate. Examples of the palladium catalyst include [1,1'-bis(di-tert-butylphosphino)ferrocene]dichloropalladium(II). Examples of the base include potassium carbonate and sodium carbonate. Examples of the solvent include 1,4-dioxane and water.

Compound (106) can be produced by an oxidative cleavage reaction using compound (105), a metal catalyst, and an oxidant. Examples of the metal catalyst used include osmium tetroxide and potassium osmate(VI) dihydrate. Examples of the oxidant include 4-methylmorpholine N-oxide and sodium periodate. Examples of the solvent include tert-butanol and water.

Compound (107) can be produced by a reduction reaction using compound (106) and a reductant. Examples of the reductant used include sodium borohydride, and examples of the solvent include tetrahydrofuran and methanol.

Compound (108) can be produced by an intramolecular cyclization reaction using compound (107) and a base. Examples of the base used include sodium hydride, and examples of the solvent include tetrahydrofuran.

Compound (110) can be produced from compound (105) by the methods described below.

Compound (109) can be produced by a hydroboration/oxidation reaction using compound (105), a borane reagent, an oxidant, and a base. Examples of the borane reagent used include a borane-tetrahydrofuran complex. Examples of the oxidant include hydrogen peroxide and sodium peroxoborate tetrahydrate. Examples of the base include sodium hydroxide. Examples of the solvent include tetrahydrofuran and water.

Compound (110) can be produced by an intramolecular cyclization reaction using compound (109) and a base. Examples of the base used include sodium hydride, and examples of the solvent include N,N-dimethylformamide.

Compound (112) can be produced from compound (106) by the methods described below. (In the scheme described below, $R^{11}$ has the same meaning as defined above).

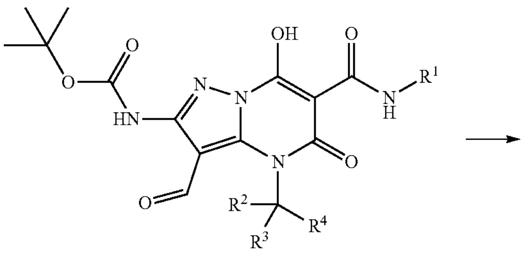

(106)

-continued

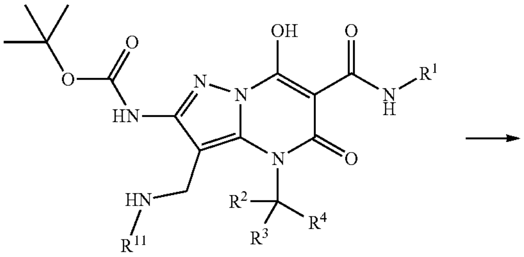

(111)

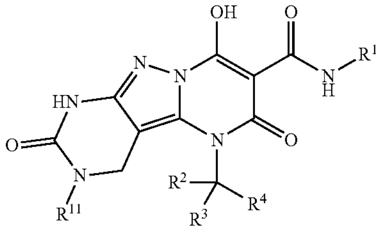

(112)

Compound (111) can be produced by a reductive amination reaction using compound (106), a carbonyl compound such as an aldehyde or a ketone, an acid, and a reductant. Examples of the acid used include acetic acid and tetraethyl orthotitanate. Examples of the reductant include sodium triacetoxyborohydride. Examples of the solvent include toluene and tetrahydrofuran.

Compound (112) can be produced by an intramolecular cyclization reaction using compound (111) and a base. Examples of the base used include sodium hydride and sodium hydroxide, and examples of the solvent include 1,4-dioxane and dimethyl sulfoxide.

Compound (45) and compound (50) can be produced from compound (96) by the methods described below.

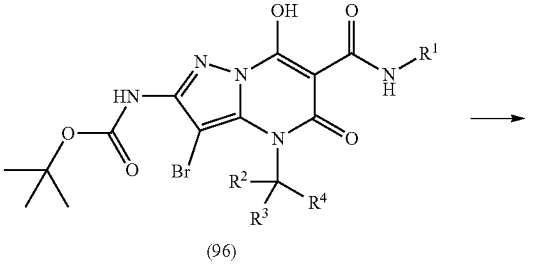

(96)

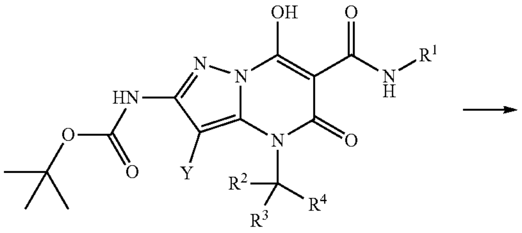

(50)

-continued

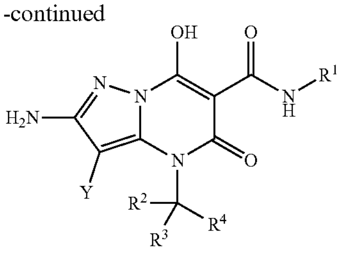

(45)

Compound (50) (compound wherein Y is a substitutable hydrocarbon group) can be produced by a coupling reaction using compound (96), a coupling reagent, a palladium catalyst, and a base. Examples of the coupling reagent used include boronic acid, boronate esters, and acrylate esters. Examples of the palladium catalyst include [1,1'-bis(di-tert-butylphosphino)ferrocene]dichloropalladium(II). Examples of the base include potassium carbonate and sodium carbonate. Examples of the solvent include 1,4-dioxane and water.

Compound (45) (compound wherein Y is a substitutable hydrocarbon group) can be produced by deprotection using compound (50) and an acid. Examples of the acid used include hydrochloric acid and trifluoroacetic acid, and examples of solvent include 1,4-dioxane.

Compound (114) (compound wherein Y is a substitutable hydrocarbon group) can be produced from compound (44) by the methods described below. (In the scheme described below, $R^c$ is a substituent of a substitutable amino group (e.g., a $C_{1-6}$ alkyl group).)

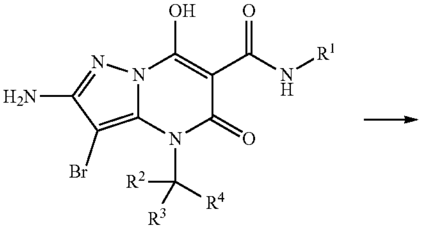

(44)

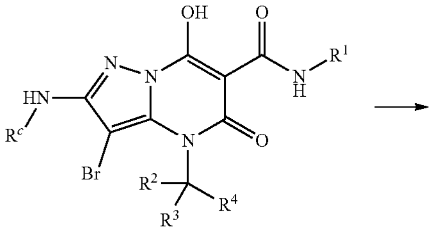

(113)

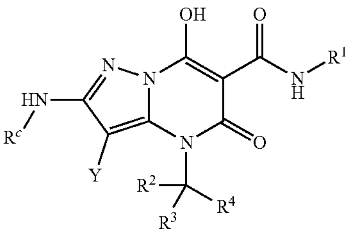

(114)

Compound (113) can be produced by a monoalkylation reaction using compound (44), an orthoester, and a reductant. Examples of the orthoester used include triethyl orthoformate and triethyl orthoacetate. Examples of the reductant include sodium borohydride. Examples of the solvent include methanol.

Compound (114) can be produced by a coupling reaction using compound (113), a: coupling reagent, a palladium catalyst, a ligand, and a base. Examples of the coupling reagent used include boronic acid, boronate esters, and acrylate esters. Examples of the palladium catalyst include [1,1'-bis(di-tert-butylphosphino)ferrocene]dichloropalladium(II). Examples of the base include potassium carbonate and sodium carbonate. Examples of the solvent include 1,4-dioxane and water.

Compound (120) (compound wherein X is a substitutable heterocyclic group, hydrocarbon group, or acyl group) can be produced from compound (87) by the methods described below. (In a combination of $R^h$ and $R^i$ in the scheme described below, $R^h$ is a hydrogen atom or a $C_{1-6}$ alkyl group substitutable with one or more substituents independently selected from the substituent group C2, and $R^i$ is a hydrogen atom, a $C_{1-6}$ alkyl group substitutable with one or more substituents independently selected from the substituent group C2, a $C_{6-14}$ aryl group, a 5- to 14-membered aromatic heterocyclic group or 3- to 14-membered non-aromatic heterocyclic group possibly having one or more substituents independently selected from the substituent group D2; or $R^h$ and $R^i$ form, together with the nitrogen atom bonded thereto, a 3- to 14-membered non-aromatic heterocyclic ring possibly having one or more substituents independently selected from the substituent group D2.)

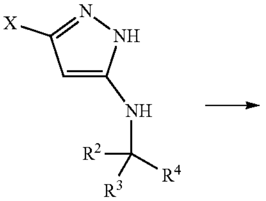

(87)

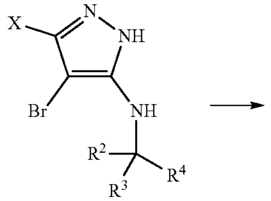

(115)

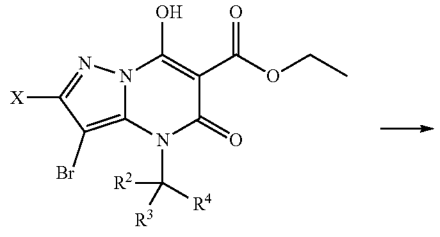

(116)

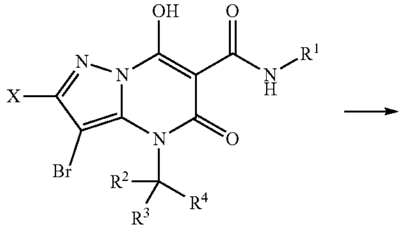

(117)

-continued

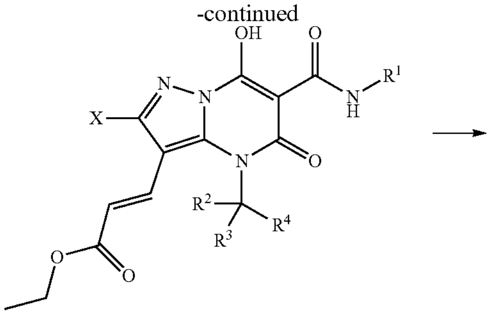

(118)

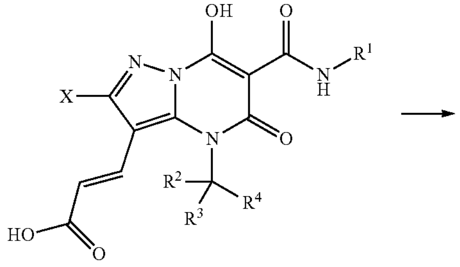

(119)

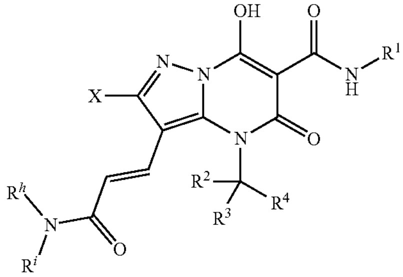

(120)

Compound (115) can be produced by a halogenation reaction using compound (87) and N-bromosuccinimide. Examples of the solvent used include N,N-dimethylformamide and dichloromethane.

Compound (116) can be produced by a cyclization reaction using compound (115), triethyl methanetricarboxylate, and a base. Examples of the base used include N,N-diisopropylethylamine and triethylamine, and examples of the solvent include toluene.

Compound (117) can be produced by an amidation reaction using compound (116) and an amine. Examples of the solvent used include N,N-dimethylacetamide.

Compound (118) can be produced by a coupling reaction using compound (117), a coupling reagent, a palladium catalyst, and a base. Examples of the coupling reagent used include boronic acid, boronate esters, and acrylate esters. Examples of the palladium catalyst include [1,1'-bis(di-tert-butylphosphino)ferrocene]dichloropalladium(II). Examples of the base include potassium carbonate and sodium carbonate. Examples of the solvent include 1,4-dioxane and water.

Compound (119) can be produced by a hydrolysis reaction using compound (118) and a base. Examples of the base used include potassium trimethylsilanolate, sodium hydroxide, potassium hydroxide, and lithium hydroxide, and examples of the solvent include tetrahydrofuran, 1,4-dioxane, water, and ethanol.

Compound (120) can be produced by an amidation reaction using compound (119), an amine, a condensing agent, and an additive. Examples of the condensing agent used include 1-(3-dimethylaminopropyl)-3-ethylcarbodiimide hydrochloride, 1-[bis(dimethylamino)methylene]-1H-1,2,3-triazolo[4,5-b]pyridinium 3-oxide hexafluorophosphate. Examples of the additive include 1-hydroxybenzotriazole monohydrate and 4-dimethylaminopyridine. Examples of the solvent include dichloromethane and N,N-dimethylacetamide.

Compound (121) (compound wherein X is a substitutable heterocyclic group, hydrocarbon group, or acyl group, and Y is a substitutable hydrocarbon group) can be produced from compound (117) by the method described below.

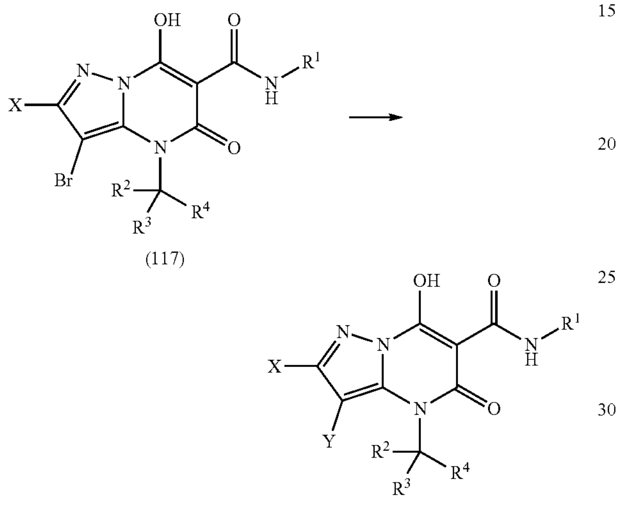

(117)

(121)

Compound (121) can be produced by a coupling reaction using compound (117), a coupling reagent, a palladium catalyst, and a base. Examples of the coupling reagent used include boronic acid and boronate esters. Examples of the palladium catalyst include [1,1'-bis(di-tert-butylphosphino)ferrocene]dichloropalladium(II). Examples of the base include potassium carbonate and sodium carbonate. Examples of the solvent include 1,4-dioxane and water.

In consideration of the type of a substituent of a raw material compound, a raw material compound having a different substituent can be produced according to means known per se by using the compound produced by the aforementioned production method as a raw material.

The compound of Formula (I), which is a product of this reaction, may be produced as a single compound or in the form of a mixture.

When the compound of Formula (I) has isomers such as optical isomers, stereoisomers, positional isomers, or rotational isomers, either of the isomers or the mixture thereof is included in the compound of Formula (I).

For example, when the compound of Formula (I) has optical isomers, the optical isomer resolved from the racemate is also included in the compound of Formula (I). Such an isomer can be prepared as a single product by a synthesis technique known per se or separation technique (e.g., concentration, solvent extraction, column chromatography, or recrystallization).

When the compound of Formula (I) has stereoisomers, the present invention encompasses either of the isomers or the mixture thereof.

The compound of Formula (I) may be in the form of a crystal, and the compound of Formula (I) includes both a single-crystal form and a mixture of crystals. Such a crystal may be produced through crystallization by using a crystallization method known per se. Examples of the crystallization method include crystallization from a solution, crystallization from a vapor, and crystallization from a melt. The resultant crystal is generally analyzed by a method using powder X-ray diffraction. The crystal orientation is determined by, for example, a mechanical method or an optical method.

The compound of Formula (I) may be in the form of a pharmaceutically acceptable co-crystals or co-crystal salts. The term "co-crystals" or "co-crystal salts" as used herein refers to crystalline substances that are composed of two or more unique solids at room temperature, which have different physical properties (e.g., structure, melting point, heat of fusion, hygroscopicity, and stability). Such a co-crystal or co-crystal salt can be produced according to a co-crystallization method known per se.

EXAMPLES

The present invention will next be described in more detail with reference to Synthesis Examples, Evaluation Examples, and Formulation Examples, but the present invention should not be construed as being limited to the following Examples.

A person skilled in the art of organic chemical synthesis can appropriately determine detailed conditions for reactions. The detailed conditions include, for example, the setting of reagent equivalents, solvent amounts, reaction temperatures, etc., determination of the reaction end point, post-treatment methods, and selection of purification methods and conditions. Thus, it should be understood that the phrase "substantially the same reaction, etc." as described herein is a concept obvious to those skilled in the art, and, for example, a reaction based on the same basic principle is performed while supplementing the setting of conditions that can be appropriately determined by those skilled in the art.

In Examples, "NMR" corresponds to nuclear magnetic resonance; "LC/MS" corresponds to high performance liquid chromatography/mass spectrometry; and "(v/v)" corresponds to (volume/volume).

In addition, the description of "Ex" in Tables corresponds to Synthesis Example; "Data" corresponds to physical data; "condition" corresponds to measurement conditions; "R. time" corresponds to the retention time in LC/MS; and "min" corresponds to minutes.

In the description of $^1$H-NMR data, the data correspond to chemical shifts δ (unit: ppm) (splitting pattern, integral value) of signals as measured at 300 MHz with JNM-ECP300 (available from JEOL Ltd.) or JNM-ECX300 (available from JEOL Ltd.) using tetramethylsilane as an internal standard. In $^1$H-NMR data, "s" denotes singlet; "d" denotes doublet; "t" denotes triplet; "dd" denotes doublet of doublet; "m" denotes multiplet; "br" denotes broad; "br s" denotes broad singlet; "J" denotes coupling constant; "$CDCl_3$" denotes deuterated chloroform; and "DMSO-$D_6$" denotes deuterated dimethyl sulfoxide.

Unless otherwise specified, Hi-Flash column (available from Yamazen Corporation), Silica Gel 60 (available from Merck), PSQ60B (available from FUJI SILYSIA CHEMICAL LTD.), or SNAP column (available from Biotage) was used for purification by silica gel column chromatography.

Unless otherwise specified, Xbridge PREP C18 5 μm 19×100 mm or Xselect CSH Prep C18 5 μm 19×100 mm was used for purification by silica gel reversed-phase column chromatography.

Unless otherwise specified, PLC Plate (available from Merck) was used for purification by thin-layer silica gel chromatography.

Initiator Sixty (available from Biotage) was used as a microwave reactor.

LC/MS was measured using the ESI (electrospray ionization) method under the following conditions, wherein "ESI+" corresponds to ESI positive ion mode, and "ESI−" corresponds to ESI negative ion mode. Unless otherwise specified, "numeral/numeral" in each of chromatographic and experimental operations refers to the volume ratio of each solvent.

LC/MS condition 1:

Apparatus: Waters ACQUITY UPLC/SQ Detector

Column: Waters ACQUITY UPLC BEH C18 (1.7 μm, 2.1×50 mm)

Column temperature: 40° C.

Solvent:

Solution A: 0.1% aqueous formic acid solution

Solution B: 0.1% formic acid-acetonitrile solution

Gradient conditions:

The measurement was initiated at a flow rate of 0.6 mL/min and a mixing ratio of solution A and solution B of 90/10, and 0.5 minutes after initiation of the measurement, the mixing ratio of solution A and solution B was linearly changed to 10/90 in 1.5 minutes.

Thereafter, the mixing ratio of solution A and solution B was fixed at 10/90 for 0.8 minutes.

Thereafter, the mixing ratio of solution A and solution B was linearly changed to 90/10 and the flow rate was changed to 0.8 mL/min in 0.1 minutes.

Thereafter, the mixing ratio of solution A and solution B was fixed at 90/10 for 1 minute.

Detection wavelength: UV (254 nm)

LC/MS condition 2:

Apparatus: Waters ACQUITY UPLC H CLASS/SQ Detector 2

Column: Waters ACQUITY UPLC BEH C18 (1.7 μm, 2.1×50 mm)

Column temperature: 40° C.

Solvent:

Solution A: 0.1% aqueous formic acid solution

Solution B: 0.1% formic acid-acetonitrile solution

Gradient Conditions:

The measurement was initiated at a flow rate of 0.6 mL/min and a mixing ratio of solution A and solution B of 90/10, and then the mixing ratio of solution A and solution B was linearly changed to 10/90 in 3 minutes.

Thereafter, the mixing ratio of solution A and solution B was fixed at 10/90 for 0.7 minutes.

Thereafter, the mixing ratio of solution A and solution B was linearly changed to 90/10 and the flow rate was changed to 0.8 mL/min in 0.1 minutes.

Thereafter, the mixing ratio of solution A and solution B was fixed at 90/10 for 1 minute.

Detection wavelength: PDA (190 to 500 nm)

LC/MS Condition 3:

Apparatus: Waters ACQUITY UPLC/Thermo LTQ XL

Column: Waters ACQUITY UPLC BEH C18 (1.7 μm, 2.1×50 mm)

Column temperature: 40° C.

Solvent:

Solution A: 0.1% aqueous formic acid solution

Solution B: 0.1% formic acid-acetonitrile solution

Gradient Conditions:

The measurement was initiated at a flow rate of 0.6 mL/min and a mixing ratio of solution A and solution B of 90/10, and 0.5 minutes after initiation of the measurement, the mixing ratio of solution A and solution B was linearly changed to 10/90 in 2.5 minutes.

Thereafter, the mixing ratio of solution A and solution B was fixed at 10/90 for 0.7 minutes.

Thereafter, the mixing ratio of solution A and solution B was linearly changed to 90/10 and the flow rate was changed to 0.8 mL/min in 0.1 minutes.

Thereafter, the mixing ratio of solution A and solution B was fixed at 90/10 for 1 minute.

Detection wavelength: PDA (190 to 399 nm)

LC/MS Condition 4:

Apparatus: Waters ACQUITY UPLC I CLASS/SQ Detector 2

Column: Waters ACQUITY UPLC BEH C18 (1.7 μm, 2.1×50 mm)

Column temperature: 40° C.

Solvent:

Solution A: 0.1% aqueous formic acid solution

Solution B: 0.1% formic acid-acetonitrile solution

Gradient Conditions:

The measurement was initiated at a flow rate of 0.6 mL/min and a mixing ratio of solution A and solution B of 90/10, and 0.5 minutes after initiation of the measurement, the mixing ratio of solution A and solution B was linearly changed to 10/90 in 3.0 minutes.

Thereafter, the mixing ratio of solution A and solution B was fixed at 10/90 for 0.8 minutes.

Thereafter, the mixing ratio of solution A and solution B was linearly changed to 90/10 and the flow rate was changed to 0.8 mL/min in 0.1 minutes.

Thereafter, the mixing ratio of solution A and solution B was fixed at 90/10 for 1 minute.

Detection wavelength: PDA (190 to 400 nm)

LC/MS Condition 5:

Apparatus: Waters ACQUITY UPLC/SQ Detector

Column: Waters ACQUITY UPLC BEH C18 (1.7 μm, 2.1×50 mm)

Column temperature: 40° C.

Solvent:

Solution A: 0.1% aqueous formic acid solution

Solution B: 0.1% formic acid-acetonitrile solution

Gradient conditions:

The measurement was initiated at a flow rate of 0.6 mL/min and a mixing ratio of solution A and solution B of 95/5, and the mixing ratio of solution A and solution B was linearly changed to 90/10 in 0.5 minutes. 0.5 Minutes after initiation of the measurement, the mixing ratio of solution A and solution B was linearly changed to 40/60 in 1.5 minutes.

Thereafter, the mixing ratio of solution A and solution B was fixed at 40/60 for 0.8 minutes.

Thereafter, the mixing ratio of solution A and solution B was linearly changed to 90/10 and the flow rate was changed to 0.8 mL/min in 0.1 minutes.

Thereafter, the mixing ratio of solution A and solution B was fixed at 90/10 for 1 minute.

Detection wavelength: UV (254 nm)

LC/MS Condition 6:

Apparatus: Waters ACQUITY UPLC/SQ Detector

Column: Waters ACQUITY UPLC BEH C18 (1.7 μm, 2.1×50 mm)

Column temperature: 40° C.

Solvent:

Solution A: 10 mmol aqueous ammonium acetate solution

Solution B: 1 mol/L aqueous ammonium acetate solution-water-acetonitrile (mixing proportions=1/1/9) solution Gradient conditions:

The measurement was initiated at a flow rate of 0.6 mL/min and a mixing ratio of solution A and solution B of 90/10, and 0.5 minutes after initiation of the measurement, the mixing ratio of solution A and solution B was linearly changed to 10/90 in 1.5 minutes.

Thereafter, the mixing ratio of solution A and solution B was fixed at 10/90 for 0.8 minutes.

Thereafter, the mixing ratio of solution A and solution B was linearly changed to 90/10 and the flow rate was changed to 0.8 mL/min in 0.1 minutes.

Thereafter, the mixing ratio of solution A and solution B was fixed at 90/10 for 1 minute.

Detection wavelength: UV (254 nm)

LC/MS Condition 7:

Apparatus: Waters ACQUITY UPLC H CLASS/QDa Detector

Column: Waters ACQUITY UPLC BEH C18 (1.7 μm, 2.1×50 mm)

Column temperature: 40° C.

Solvent:

Solution A: 0.1% aqueous formic acid solution.

Solution B: 0.1% formic acid-acetonitrile solution

Gradient Conditions:

The measurement was initiated at a flow rate of 0.6 mL/min and a mixing ratio of solution A and solution B of 90/10, and then the mixing ratio of solution A and solution B was linearly changed to 10/90 in 3 minutes.

Thereafter, the mixing ratio of solution A and solution B was fixed at 10/90 for 0.7 minutes.

Thereafter, the mixing ratio of solution A and solution B was linearly changed to 90/10 and the flow rate was changed to 0.8 mL/min in 0.1 minutes.

Thereafter, the mixing ratio of solution A and solution B was fixed at 90/10 for 1 minute.

Detection wavelength: PDA (190 to 400 nm)

The symbol "*" (asterisk) described in a structural formula in Examples refers to where the absolute configuration of the structure is undetermined, but the corresponding asymmetric carbon forms a single stereoisomer (i.e., optically active substance). The description of Isomer A and Isomer B refers to where they are different stereoisomers. A compound having no asterisk on an asymmetric carbon atom is in the form of a racemate. When a cyclic compound having two asymmetric carbon centers on the ring is determined to be cis/trans, the name and structural formula of the compound may be marked "cis" or "trans."

Synthesis Example 1

Ethyl 6-(cyclopropylcarbamoyl)-7-hydroxy-4-neopentyl-5-oxo-4,5-dihydropyrazolo[1,5-a]pyrimidine-2-carboxylate (Step A) Ethyl 5-(neopentylamino)-1H-pyrazole-3-carboxylate

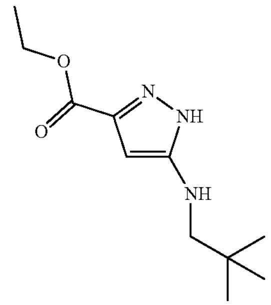 [SMILES: CCOC(=O)c1cc(NCC(C)(C)C)[nH]n1]

2.43 mL of acetic acid was added to a mixture of 5 g of ethyl 5-amino-1H-pyrazole-3-carboxylate, 4.62 mL of pivalaldehyde, and 50 mL of tetrahydrofuran at room temperature, and the resultant mixture was stirred for 17 hours. The reaction mixture was cooled to 0° C., and 1.61 g of sodium borohydride was added to the mixture, followed by stirring at room temperature for four hours. After the reaction mixture was cooled to 0° C., water was added to the reaction mixture, and the mixture was subjected to extraction with ethyl acetate. The organic phase was washed with an aqueous sodium hydrogen carbonate solution and a saturated aqueous sodium chloride solution, and then dried over sodium sulfate. The resultant product was subjected to filtration, and then the filtrate was concentrated under reduced pressure. The resultant residue was purified by silica gel column chromatography (chloroform/methanol=100/0 →95/5 (v/v)), to thereby produce 6.0 g of the title compound as a white solid.

LC/MS: condition 2, retention time=2.06 min

LC/MS (ESI+) m/z; 226.3 $[M+H]^+$ (Step B) Diethyl 7-hydroxy-4-neopentyl-5-oxo-4,5-dihydropyrazolo[1,5-a]pyrimidine-2,6-dicarboxylate

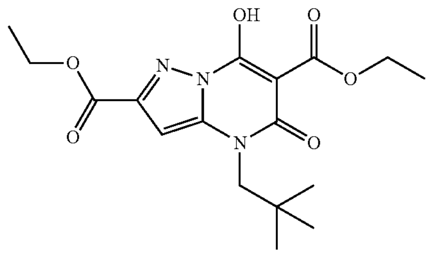 [SMILES: CCOC(=O)c1cc2n(CC(C)(C)C)c(=O)c(C(=O)OCC)c(O)n2n1]

A mixture of 6.0 g of ethyl 5-(neopentylamino)-1H-pyrazole-3-carboxylate produced in step A of Synthesis Example 1, 6.79 mL of triethyl methanetricarboxylate, 11.1 mL of triethylamine, and 30 mL of toluene was stirred at 120° C. for 16 hours: The reaction mixture was concentrated under reduced pressure, and the resultant residue was purified by silica gel column chromatography (chloroform/methanol=100/0→95/5→90/10 (v/v)), to thereby produce 7.6 g of the title compound as a white solid.

LC/MS: condition 2, retention time=1.93 min

LC/MS (ESI+) m/z; 366.3 $[M+H]^+$ (Step C) Ethyl 6-(cyclopropylcarbamoyl)-7-hydroxy-4-neopentyl-5-oxo-4,5-dihydropyrazolo[1,5-a]pyrimidine-2-carboxylate A mixture of 7.5 g of diethyl 7-hydroxy-4-neopentyl-5-oxo-4,5-dihydropyrazolo[1,5-a]pyrimidine-2,6-dicarboxylate produced in step B of Synthesis Example 1, 2.35 g of cyclopropylamine, and 75 mL of N,N-dimethylacetamide was stirred at 120° C. for four hours. The reaction mixture was cooled to room temperature, and 1 M aqueous hydrochloric acid solution was added to the mixture, followed by stirring at room temperature for two hours. The resultant solid was recovered by filtration, and dried under reduced pressure, to thereby produce 7.0 g of the title compound as a white solid.

Synthesis Example 2

6-(Cyclopropylcarbamoyl)-7-hydroxy-4-neopentyl-5-oxo-4,5-dihydropyrazolo[1,5-a]pyrimidine-2-carboxylic acid A mixture of 3.76 g of ethyl 6-(cyclopropylcarbamoyl)-7-hydroxy-4-neopentyl-5-oxo-4,5-dihydropyrazolo[1,5-a]pyrimidine-2-carboxylate produced in step C of Synthesis Example 1, 2.57 g of potassium trimethylsilanolate, and 150 mL of tetrahydrofuran was stirred at room temperature for 14 hours. The reaction mixture was cooled to room temperature, and 1 M aqueous hydrochloric acid solution was added to the mixture, followed by extraction with ethyl acetate. The organic phase was washed with a saturated aqueous sodium chloride solution, and then dried over sodium sulfate. The resultant product was subjected to filtration, and then the filtrate was concentrated under reduced pressure, to thereby produce 3.3 g of the title compound as a white solid.

Synthesis Example 3

Tert-butyl (6-(cyclopropylcarbamoyl)-7-hydroxy-4-neopentyl-5-oxo-4,5-dihydropyrazolo[1,5-a]pyrimidin-2-yl)carbamate A mixture of 9.0 g of 6-(cyclopropylcarbamoyl)-7-hydroxy-4-neopentyl-5-oxo-4,5-dihydropyrazolo[1,5-a]pyrimidine-2-carboxylic acid produced in Synthesis Example 2, 8.3 mL of diphenylphosphoryl azide, 7.19 mL of triethylamine, and 180 mL of tert-butanol was stirred at 100° C. for three hours. The reaction mixture was concentrated under reduced pressure, and the resultant residue was purified by silica gel column chromatography (chloroform/methanol=100/0→95/5→90/10 (v/v)), to thereby produce 7.0 g of the title compound as a white solid.

Synthesis Example 4

2-Amino-N-cyclopropyl-7-hydroxy-4-neopentyl-5-oxo-4,5-dihydropyrazolo[1,5-a]pyrimidine-6-carboxamide hydrochloride A mixture of 1.1 g of tert-butyl (6-(cyclopropylcarbamoyl)-7-hydroxy-4-neopentyl-5-oxo-4,5-dihydropyrazolo[1,5-a]pyrimidin-2-yl)carbamate produced in Synthesis Example 3, 20 mL of 4 M hydrogen chloride ethyl acetate solution, and 20 mL of ethyl acetate was stirred at room temperature for 63 hours. The reaction mixture was concentrated under reduced pressure, to thereby produce 0.921 g of the title compound as a white solid.

Synthesis Example 5

Ethyl 6-(cyclopropylcarbamoyl)-7-hydroxy-4-isobutyl-5-oxo-4,5-dihydropyrazolo[1,5-a]pyrimidine-3-carboxylate (Step A) Ethyl 5-(isobutylamino)-1H-pyrazole-4-carboxylate

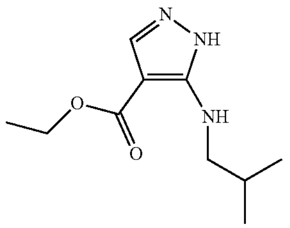

1.11 mL of acetic acid was added to a mixture of 10 g of ethyl 5-amino-1H-pyrazole-4-carboxylate, 5.58 g of isobutyraldehyde, and 200 mL of 1,2-dichloroethane at room temperature, and the resultant mixture was stirred for two hours. To the reaction mixture was added 27.3 g of sodium triacetoxyborohydride at room temperature, and the mixture was stirred at room temperature for 16 hours. An aqueous sodium carbonate solution was added to the reaction mixture until the pH of the mixture was changed to 8 to 9, and the resultant mixture was subjected to extraction with dichloromethane. The organic phase was washed with a saturated aqueous sodium chloride solution, and then dried over sodium sulfate. The resultant product was subjected to filtration, and then the filtrate was concentrated under reduced pressure, to thereby produce 13.8 g of the title compound as a colorless oily product.

LC/MS: condition 4, retention time=1.95 min

LC/MS (ESI+) m/z; 212.0 $[M+H]^+$ (Step B) Diethyl 7-hydroxy-4-isobutyl-5-oxo-4,5-dihydropyrazolo[1,5-a]pyrimidine-3,6-dicarboxylate

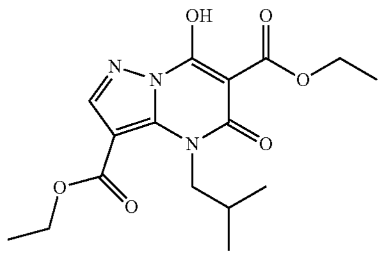 [SMILES: CCOC(=O)c1c(O)n2ncc(C(=O)OCC)c2n(CC(C)C)c1=O]

A mixture of 13.8 g of ethyl 5-(isobutylamino)-1H-pyrazole-4-carboxylate produced in step A of Synthesis Example 5, 25 g of triethyl methanetricarboxylate, 26.9 mL of triethylamine, and 70 mL of toluene was stirred at 120° C. for 87 hours. The reaction mixture was concentrated under reduced pressure, and the resultant residue was purified by silica gel column chromatography (chloroform/methanol=100/0→95/5→90/10 (v/v)), to thereby produce 22.6 g of the title compound as a brown oily product.

LC/MS: condition 4, retention time=2.52 min

LC/MS (ESI+) m/z; 352.0 $[M+H]^+$ (Step C) Ethyl 6-(cyclopropylcarbamoyl)-7-hydroxy-4-isobutyl-5-oxo-4,5-dihydropyrazolo[1,5-a]pyrimidine-3-carboxylate A mixture of 22.6 g of diethyl 7-hydroxy-4-isobutyl-5-oxo-4,5-dihydropyrazolo[1,5-a]pyrimidine-3,6-dicarboxylate produced in step B of Synthesis Example 5, 9.2 g of cyclopropylamine, and 65 mL of N,N-dimethylacetamide was stirred at 120° C. for three hours. The reaction mixture was cooled to room temperature, and 1 M aqueous hydrochloric acid solution was added to the mixture. The resultant solid was recovered by filtration, and then dried under reduced pressure, to thereby produce 14.1 g of the title compound as a white solid.

Synthesis Example 6

N-Cyclopropyl-7-hydroxy-3-(hydroxymethyl)-4-isobutyl-5-oxo-4,5-dihydropyrazolo[1,5-a]pyrimidine-6-carboxamide 45 mL of lithium aluminum hydride (2.0 M tetrahydrofuran solution) was added to a mixture of 10.87 g of ethyl 6-(cyclopropylcarbamoyl)-7-hydroxy-4-isobutyl-5-oxo-4,5-dihydropyrazolo[1,5-a]pyrimidine-3-carboxylate produced in step C of Synthesis Example 5 and 100 mL of tetrahydrofuran at 0° C., and the resultant mixture was stirred at 0° C. for four hours. Sodium sulfate decahydrate was added to the reaction mixture at 0° C., and then chloroform was added to the mixture. The resultant mixture was subjected to filtration, and then the filtrate was concentrated under reduced pressure, to thereby produce 7.9 g of the title compound as a yellow amorphous product.

Synthesis Example 7

N-Cyclopropyl-3-formyl-7-hydroxy-4-isobutyl-5-oxo-4,5-dihydropyrazolo[1,5-a]pyrimidine-6-carboxamide 53.1 g of 2-iodoxybenzoic acid (purity: >39.0%, containing benzoic acid and isophthalic acid as stabilizers) was added to a mixture of 7.9 g of N-cyclopropyl-7-hydroxy-3-(hydroxymethyl)-4-isobutyl-5-oxo-4,5-dihydropyrazolo[1,5-a]pyrimidine-6-carboxamide produced in Synthesis Example 6 and 79 mL of dimethyl sulfoxide at room temperature, and the resultant mixture was stirred at room temperature for four hours and 40 minutes. The reaction mixture was cooled to 0° C., and a saturated aqueous sodium thiosulfate solution was added to the mixture. A saturated aqueous sodium hydrogen carbonate solution was added to the mixture until the pH of the mixture was changed to 6 to 7. Subsequently, water was added to the mixture, and then the resultant solid was recovered by filtration. The solid was washed with water, and then dried under reduced pressure, to thereby produce 6.1 g of the title compound as a brown solid.

Synthesis Example 8

Methyl (E)-3-(6-(cyclopropylcarbamoyl)-7-hydroxy-4-isobutyl-5-oxo-4,5-dihydropyrazolo[1,5-a]pyrimidin-3-yl)acrylate A mixture of 4.48 mL of trimethyl phosphonoacetate and 35 mL of tetrahydrofuran was added to a mixture of 1.13 g of sodium hydride (purity: >55.0%, containing paraffin liquid) and 35 mL of tetrahydrofuran at −4° C. Subsequently, a mixture of 3.52 g of N-cyclopropyl-3-formyl-7-hydroxy-4-isobutyl-5-oxo-4,5-dihydropyrazolo[1,5-a]pyrimidine-6-carboxamide produced in Synthesis Example 7 and 70 mL of tetrahydrofuran was added at −4° C., and the resultant mixture was stirred at −4° C. for 30 minutes. Subsequently, the mixture was stirred at 0° C. for one hour, and then stirred at room temperature for one hour and 30 minutes. The reaction mixture was cooled to 0° C., and then water was added to the mixture. Thereafter, 1 M aqueous hydrochloric acid solution was added to the mixture until the pH of the mixture was changed to 2 to 3, and the mixture was subjected to extraction with chloroform. The organic phase was dried over sodium sulfate, and the resultant product was subjected to filtration. The filtrate was concentrated under reduced pressure, to thereby produce 6.5732 g of the title compound as a brown solid.

Synthesis Example 9

(E)-3-(6-(Cyclopropylcarbamoyl)-7-hydroxy-4-isobutyl-5-oxo-4,5-dihydropyrazolo[1,5-a]pyrimidin-3-yl)acrylic acid 1.4 g of lithium hydroxide monohydrate was added to a mixture of 6.6 g of methyl (E)-3-(6-(cyclopropylcarbamoyl)-7-hydroxy-4-isobutyl-5-oxo-4,5-dihydropyrazolo[1,5-a]pyrimidin-3-yl)acrylate produced in Synthesis Example 8, 40 mL of 1,4-dioxane, and 40 mL of water at room temperature, and the resultant mixture was stirred at 80° C. for eight hours. The reaction mixture was concentrated under reduced pressure (removal of 30 mL of the solvent), and then 1 M aqueous hydrochloric acid solution was added to the mixture until the pH of the mixture was changed to 2. The resultant solid was recovered by filtration, and ethanol was added to the resultant solid. The solid was recovered by filtration, and then dried under reduced pressure, to thereby produce 2.1793 g of the title compound as a brown solid.

Synthesis Example 10

(E)-N-Cyclopropyl-7-hydroxy-4-isobutyl-3-(3-morpholino-3-oxoprop-1-en-1-yl)-5-oxo-4,5-dihydropyrazolo[1,5-a]pyrimidine-6-carboxamide 96.9 μL of triethylamine, 107.2 mg of 1-(3-dimethylaminopropyl)-3-ethylcarbodiimide hydrochloride, 85.6 mg of 1-hydroxybenzotriazole monohydrate, and 48.7 μL of morpholine were added to a mixture of 167.9 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 1.7 mL of N,N-dimethylacetamide at room temperature, and the resultant mixture was stirred at room temperature for 14 hours and 30 minutes. 2 M aqueous hydrochloric acid solution was added to the reaction mixture, and then water was added to the mixture. Thereafter, the resultant mixture was stirred at room temperature for 30 minutes, and the resultant solid was recovered by filtration. The solid was washed with water, and then dried under reduced pressure. The resultant solid was suspended in ethanol, and then the solid was recovered by filtration. The solid was washed with ethanol, and then dried under reduced pressure, to thereby produce 148.5 mg of the title compound as a white solid.

Synthesis Example 11

2-Bromo-N-cyclopropyl-7-hydroxy-4-neopentyl-5-oxo-4,5-dihydropyrazolo[1,5-a]pyrimidine-6-carboxamide (Step A) 3-Bromo-N-neopentyl-1H-pyrazol-5-amine

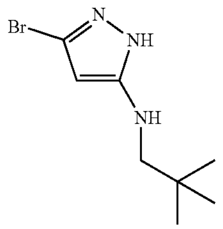

480 mg of acetic acid was added to a mixture of 1 g of 3-bromo-1H-pyrazol-5-amine, 689 mg of pivalaldehyde, and 20 mL of tetrahydrofuran at room temperature, and the resultant mixture was stirred for 17 hours. The reaction mixture was cooled to 0° C., and 303 mg of sodium borohydride was added to the mixture, followed by stirring at room temperature for four hours. After the mixture was cooled to 0° C., water was added to the reaction mixture, and the mixture was subjected to extraction with ethyl acetate. The organic phase was washed with an aqueous sodium hydrogen carbonate solution and a saturated aqueous sodium chloride solution, and then dried over sodium sulfate. The resultant product was subjected to filtration, and the filtrate was concentrated under reduced pressure. The resultant residue was purified by silica gel column chromatography (chloroform/methanol=100/0→95/5 (v/v)), to thereby produce 1.43 g of the title compound as a white solid.

LC/MS: condition 4, retention time=2.18 min

LC/MS (ESI+) m/z; 234.2 $[M+H]^+$ (Step B) Ethyl 2-Bromo-7-hydroxy-4-neopentyl-5-oxo-4,5-dihydropyrazolo[1,5-a]pyrimidine-6-carboxylate

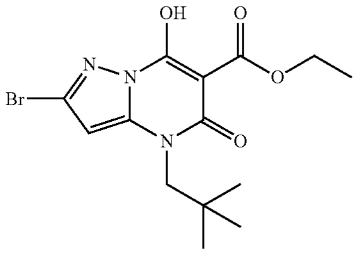 [SMILES: CCOC(=O)c1c(O)n2nc(Br)cc2n(CC(C)(C)C)c1=O]

A mixture of 1.43 g of 3-bromo-N-neopentyl-1H-pyrazol-5-amine produced in step A of Synthesis Example 11, 1.51 mL of triethyl methanetricarboxylate, 2.58 mL of triethylamine, and 7 mL of toluene was stirred at 120° C. for 16 hours. The reaction mixture was concentrated under reduced pressure, and the resultant residue was purified by silica gel column chromatography (chloroform/methanol=100/0→95/5→90/10 (v/v)), to thereby produce 1.39 g of the title compound as a pale brown solid.

LC/MS: condition 2, retention time=2.03 min

LC/MS (ESI+) m/z; 372.3 $[M+H]^+$ (Step C) 2-Bromo-N-cyclopropyl-7-hydroxy-4-neopentyl-5-oxo-4,5-dihydropyrazolo[1,5-a]pyrimidine-6-carboxamide A mixture of 5.0 g of ethyl 2-Bromo-7-hydroxy-4-neopentyl-5-oxo-4,5-dihydropyrazolo[1,5-a]pyrimidine-6-carboxylate produced in step B of Synthesis Example 11, 1.54 g of cyclopropylamine, and 50 mL of N,N-dimethylacetamide was stirred at 120° C. for three hours. The reaction mixture was cooled to room temperature, and 1 M aqueous hydrochloric acid solution was added to the mixture. The mixture was subjected to extraction with ethyl acetate, and the organic phase was washed with water and a saturated aqueous sodium chloride solution, followed by drying over sodium sulfate. The resultant product was subjected to filtration, and then the filtrate was concentrated under reduced pressure, to thereby produce 3.83 g of the title compound as a pale brown solid.

Synthesis Example 12

N-Cyclopropyl-7-hydroxy-4-neopentyl-5-oxo-2-(pyrimidin-4-ylamino)-4,5-dihydropyrazolo[1,5-a]pyrimidine-6-carboxamide A mixture of 76.6 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 38.0 mg of pyrimidin-4-amine, 18.3 mg of tris(dibenzylideneacetone)dipalladium(0), 23.1 mg of 4,5-bis(diphenylphosphino)-9,9-dimethylxanthene, 57.7 mg of sodium tert-butoxide, and 1.6 mL of 1,4-dioxane was stirred at 100° C. overnight. The reaction mixture was cooled to room temperature and subjected to filtration, and then the filtrate was concentrated under reduced pressure. The residue was purified by silica gel column chromatography (chloroform/methanol=99/1→97/3 (v/v)), and then purified by silica gel reversed-phase column chromatography (0.1% formic acid-acetonitrile/0.1% aqueous formic acid solution=40/60→60/40 (v/v)), to thereby produce 5.65 mg of the title compound as a pale brown solid.

Synthesis Example 13

N-Cyclopropyl-7-hydroxy-4-neopentyl-5-oxo-2-(pyrazin-2-ylamino)-4,5-dihydropyrazolo[1,5-a]pyrimidine-6-carboxamide A mixture of 100 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 24.7 mg of pyrazin-2-amine, 11.9 mg of tris(dibenzylideneacetone)dipalladium(0), 11.0 mg of 2-di-tert-butylphosphino-2',4',6'-triisopropylbiphenyl, 37.5 mg of sodium tert-butoxide, and 1 mL of 1,4-dioxane was stirred under microwave irradiation at 120° C. for one hour. The reaction mixture was cooled to room temperature and subjected to filtration, and then the filtrate was concentrated under reduced pressure. The residue was purified by silica gel column chromatography (hexane/ethyl acetate=95/5→60/40→chloroform/methanol=95/5 (v/v)), to thereby produce 5.37 mg of the title compound as a yellow solid.

Synthesis Example 14

2-(2-Aminopyridin-3-yl)-N-cyclopropyl-7-hydroxy-4-neopentyl-5-oxo-4,5-dihydropyrazolo[1,5-a]pyrimidine-6-carboxamide A mixture of 76.6 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 88.0 mg of 3-(4,4,5,5-tetramethyl-1,3,2-dioxaborolan-2-yl)pyridin-2-amine, 13.0 mg of [1,1'-bis(di-tert-butylphosphino)ferrocene]dichloropalladium(II), 82.9 mg of potassium carbonate, 0.77 mL of water, and 0.77 mL of 1,4-dioxane was stirred at 110° C. overnight. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=30/70→60/40 (v/v)), to thereby produce 15.3 mg of the title compound as a pale brown solid.

Synthesis Example 15

N-Cyclopropyl-7-hydroxy-4-neopentyl-5-oxo-2-((5-(trifluoromethyl)pyrazin-2-yl)amino)-4,5-dihydropyrazolo[1,5-a]pyrimidine-6-carboxamide A mixture of 100 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 92.97 mg of 5-(trifluoromethyl)pyrazin-2-amine, 23.8 mg of tris(dibenzylideneacetone)dipalladium (0), 22.1 mg of 2-di-tert-butylphosphino-2',4',6'-triisopropylbiphenyl, 59.4 mg of sodium tert-butoxide, and 1 mL of 1,4-dioxane was stirred under microwave irradiation at 120° C. for one hour. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=40/60→70/30 (v/v)), to thereby produce 18.39 mg of the title compound as a yellow solid.

Synthesis Example 16

N-Cyclopropyl-7-hydroxy-2-((5-methoxypyrazin-2-yl)amino)-4-neopentyl-5-oxo-4,5-dihydropyrazolo[1,5-a]pyrimidine-6-carboxamide A mixture of 50 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 32.5 mg of 5-methoxypyrazin-2-amine, 11.9 mg of tris(dibenzylideneacetone)dipalladium(0), 15.0 mg of 4,5-bis(diphenylphosphino)-9,9-dimethylxanthene, 37.5 mg of sodium tert-butoxide, and 1 mL of 1,4-dioxane was stirred at 110° C. overnight. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=60/40→70/30 (v/v)), to thereby produce 9.12 mg of the title compound as a yellow solid.

Synthesis Example 17

N-Cyclopropyl-7-hydroxy-2-((6-methoxypyrazin-2-yl)amino)-4-neopentyl-5-oxo-4,5-dihydropyrazolo[1,5-a]pyrimidine-6-carboxamide A mixture of 100 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 100 mg of 6-methoxypyrazin-2-amine, 23.8 mg of tris(dibenzylideneacetone)dipalladium(0), 22.1 mg of 2-di-tert-butylphosphino-2',4',6'-triisopropylbiphenyl, 59.4 mg of sodium tert-butoxide, and 1 mL of 1,4-dioxane was stirred under microwave irradiation at 120° C. for one hour. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=60/40→80/20 (v/v)), to thereby produce 42.1 mg of the title compound as a yellow solid.

Synthesis Example 18

2-Amino-N-cyclopropyl-7-hydroxy-4-neopentyl-5-oxo-4,5-dihydropyrazolo[1,5-a]pyrimidine-6-carboxamide A mixture of 516 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 177 mg of (2S,4R)-4-hydroxypyrrolidine-2-carboxylic acid, acid carboxamide, 128.6 mg of copper(I) iodide, 1.87 g of potassium carbonate, 2.5 mL of 28% aqueous ammonia, and 8 mL of dimethyl sulfoxide was stirred in an argon atmosphere under microwave irradiation at 130° C. for one hour. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=50/50→70/30 (v/v)), to thereby produce 10.63 mg of the title compound as a yellow solid.

Synthesis Example 19

Methyl 5-((6-(cyclopropylcarbamoyl)-7-hydroxy-4-neopentyl-5-oxo-4,5-dihydropyrazolo[1,5-a]pyrimidin-2-yl)amino)pyrazine-2-carboxylate A mixture of 95.8 mg of 2-amino-N-cyclopropyl-7-hydroxy-4-neopentyl-5-oxo-4,5-dihydropyrazolo[1,5-a]pyrimidine-6-carboxamide produced in Synthesis Example 18, 103.6 mg of methyl 5-chloropyrazine-2-carboxylate, 27.5 mg of tris(dibenzylideneacetone)dipalladium(0), 34.7 mg of 4,5-bis(diphenylphosphino)-9,9-dimethylxanthene, 95.4 mg of sodium carbonate, and 1 mL of 1,4-dioxane was stirred in an argon atmosphere at 100° C. overnight. The reaction mixture was cooled to room temperature and subjected to filtration, and then the filtrate was concentrated under reduced pressure. The residue was purified by silica gel column chromatography (chloroform/methanol=99/1→97/3 (v/v)), to thereby produce 71.7 mg of the title compound as a brown amorphous product.

Synthesis Example 20

5-((6-(Cyclopropylcarbamoyl)-7-hydroxy-4-neopentyl-5-oxo-4,5-dihydropyrazolo[1,5-a]pyrimidin-2-yl)amino)pyrazine-2-carboxylic acid 13 mg of lithium hydroxide monohydrate was added to a mixture of 70 mg of methyl 5-((6-(cyclopropylcarbamoyl)-7-hydroxy-4-neopentyl-5-oxo-4,5-dihydropyrazolo[1,5-a]pyrimidin-2-yl)amino)pyrazine-2-carboxylate produced in Synthesis Example 19, 0.7 mL of 1,4-dioxane, and 0.7 mL of water at room temperature, and the resultant mixture was stirred at 80° C. for three hours. The reaction mixture was cooled to room temperature, and 1 M aqueous hydrochloric acid solution was added to the mixture until the pH of the mixture was changed to 2. The resultant solid was recovered by filtration, and dried under reduced pressure, to thereby produce 60.2 mg of the title compound as a gray solid.

Synthesis Example 21

2-((5-Carbamoylpyrazin-2-yl)amino)-N-cyclopropyl-7-hydroxy-4-neopentyl-5-oxo-4,5-dihydropyrazolo[1,5-a]pyrimidine-6-carboxamide 26.7 mg of 1-hydroxy-1H-benzotriazole ammonium salt and 26.9 mg of 1-ethyl-3-(3-dimethylaminopropyl)carbodiimide hydrochloride were added to a mixture of 31 mg of 5-((6-(cyclopropylcarbamoyl)-7-hydroxy-4-neopentyl-5-oxo-4,5-dihydropyrazolo[1,5-a]pyrimidin-2-yl)amino)pyrazine-2-carboxylic acid produced in Synthesis Example 20 and 0.6 mL of N,N-dimethylacetamide at 0° C., and the resultant mixture was stirred at room temperature overnight. 1M aqueous hydrochloric acid solution was added to the reaction mixture, and the resultant solid was recovered by filtration. The resultant solid was purified by silica gel reversed-phase column chromatography (acetonitrile/10 mM aqueous ammonium bicarbonate solution=18/82 →27/73 (v/v)), to thereby produce 18.58 mg of the title compound as a white solid.

Synthesis Example 22

2-Bromo-N-cyclopropyl-7-hydroxy-4-isobutyl-5-oxo-4,5-dihydropyrazolo[1,5-a]pyrimidine-6-carboxamide (Step A) 3-Bromo-N-isobutyl-1H-pyrazol-5-amine

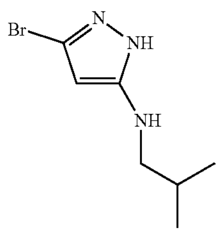

37 mg of acetic acid was added to a mixture of 1 g of 3-bromo-1H-pyrazol-5-amine, 534 mg of isobutyraldehyde, and 30 mL of 1,2-dichloroethane at room temperature, and the resultant mixture was stirred for two hours. To the reaction mixture was added 2.62 g of sodium triacetoxyborohydride at room temperature, and the mixture was stirred at room temperature for 16 hours. An aqueous sodium carbonate solution was added to the reaction mixture until the pH of the mixture was changed to 8 to 9, and the mixture was subjected to extraction with dichloromethane. The organic phase was washed with a saturated aqueous sodium chloride solution, and then dried over sodium sulfate. The resultant product was subjected to filtration, and then the filtrate was concentrated under reduced pressure, to thereby produce 1.35 g of the title compound as a colorless oily product.

LC/MS: condition 4, retention time=1.98 min

LC/MS (ESI+) m/z; 218.2 $[M+H]^+$ (Step B) Ethyl 2-bromo-7-hydroxy-4-isobutyl-5-oxo-4,5-dihydropyrazolo[1,5-a]pyrimidine-6-carboxylate

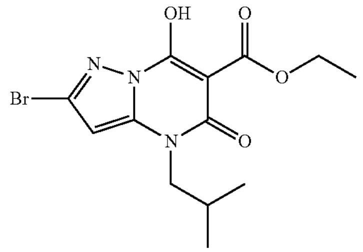 [SMILES: CCOC(=O)c1c(O)n2nc(Br)cc2n(CC(C)C)c1=O]

A mixture of 1.35 g of 3-bromo-N-isobutyl-1H-pyrazol-5-amine produced in step A of Synthesis Example 22, 1.51 mL of triethyl methanetricarboxylate, 2.58 mL of triethylamine, and 7 mL of toluene was stirred at 120° C. for 16 hours. The reaction mixture was concentrated under reduced pressure, and the resultant residue was purified by silica gel column chromatography (chloroform/methanol=100/0→95/5→90/10 (v/v)), to thereby produce 912 mg of the title compound as a pale brown solid.

LC/MS: condition 2, retention time=1.83 min

LC/MS (ESI+) m/z; 360.3. $[M+H]^+$ (Step C) 2-Bromo-N-cyclopropyl-7-hydroxy-4-isobutyl-5-oxo-4,5-dihydropyrazolo[1,5-a]pyrimidine-6-carboxamide A mixture of 2.5 g of ethyl 2-bromo-7-hydroxy-4-isobutyl-5-oxo-4,5-dihydropyrazolo[1,5-a]pyrimidine-6-carboxylate produced in step B of Synthesis Example 22, 13.96 mL of cyclopropylamine, and 12 mL of N,N-dimethylacetamide was stirred under microwave irradiation at 150° C. for one hour. The reaction mixture was cooled to room temperature, and 2 M aqueous hydrochloric acid solution was added to the mixture. The resultant solid was recovered by filtration, and the solid was washed with water and then dried under reduced pressure, to thereby produce 2.51 g of the title compound as a pale brown solid.

Synthesis Example 23

N-Cyclopropyl-7-hydroxy-4-isobutyl-5-oxo-2-(pyrazin-2-ylamino)-4,5-dihydropyrazolo[1,5-a]pyrimidine-6-carboxamide A mixture of 88.37 mg of 2-bromo-N-cyclopropyl-7-hydroxy-4-isobutyl-5-oxo-4,5-dihydropyrazolo[1,5-a]pyrimidine-6-carboxamide produced in step C of Synthesis Example 22, 95.11 mg of pyrazin-2-amine, 21.6 mg of tris(dibenzylideneacetone)dipalladium(0), 27.3 mg of 4,5-bis(diphenylphosphino)-9,9-dimethylxanthene, 68 mg of sodium tert-butoxide, and 1 mL of 1,4-dioxane was stirred in an argon atmosphere at 110° C. overnight. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=50/50→60/40 (v/v)), to thereby produce 16.76 mg of the title compound as a white solid.

Synthesis Example 24

2-(2-Aminopyridin-3-yl)-N-cyclopropyl-7-hydroxy-4-isobutyl-5-oxo-4,5-dihydropyrazolo[1,5-a]pyrimidine-6-carboxamide A mixture of 73.8 mg of 2-bromo-N-cyclopropyl-7-hydroxy-4-isobutyl-5-oxo-4,5-dihydropyrazolo[1,5-a]pyrimidine-6-carboxamide produced in step C of Synthesis Example 22, 88.0 mg of 3-(4,4,5,5-tetramethyl-1,3,2-dioxaborolan-2-yl)pyridin-2-amine, 13.0 mg of [1,1'-bis(di-tert-butylphosphino)ferrocene]dichloropalladium(II), 82.9 mg of potassium carbonate, 0.74 mL of water, and 0.74 mL of 1,4-dioxane was stirred at 110° C. overnight. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=30/70→40/60 (v/v)), to thereby produce 28.9 mg of the title compound as a pale brown solid.

Synthesis Example 25

2-Bromo-N-cyclobutyl-7-hydroxy-4-neopentyl-5-oxo-4,5-dihydropyrazolo[1,5-a]pyrimidine-6-carboxamide A mixture of 2.0 g of ethyl 2-bromo-7-hydroxy-4-neopentyl-5-oxo-4,5-dihydropyrazolo[1,5-a]pyrimidine-6-carboxylate produced in step B of Synthesis Example 11, 764 mg of cyclobutanamine, and 20 mL of N,N-dimethylacetamide was stirred at 120° C. for four hours. The reaction mixture was cooled to room temperature, and 1 M aqueous hydrochloric acid solution was added to the mixture, followed by stirring for two hours. The resultant precipitate was recovered by filtration, and the precipitate was washed with water and then dried under reduced pressure, to thereby produce 2.0 g of the title compound as a skin-color solid.

Synthesis Example 26

N-Cyclobutyl-7-hydroxy-4-neopentyl-5-oxo-2-(pyrazin-2-ylamino)-4,5-dihydropyrazolo[1,5-a]pyrimidine-6-carboxamide A mixture of 79.5 mg of 2-bromo-N-cyclobutyl-7-hydroxy-4-neopentyl-5-oxo-4,5-dihydropyrazolo[1,5-a]pyrimidine-6-carboxamide produced in Synthesis Example 25, 38.0 mg of pyrazin-2-amine, 18.3 mg of tris(dibenzylideneacetone)dipalladium(0), 23.1 mg of 4,5-bis(diphenylphosphino)-9,9-dimethylxanthene, 57.7 mg of sodium tert-butoxide, and 3 mL of 1,4-dioxane was stirred in an argon atmosphere at 110° C. for 15 hours. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=60/40→70/30 (v/v)), to thereby produce 49.5 mg of the title compound as a brown solid.

Synthesis Example 27

2-Bromo-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide (Step A) 3-Bromo-N-((4-methyltetrahydro-2H-pyran-4-yl)methyl)-1H-pyrazol-5-amine

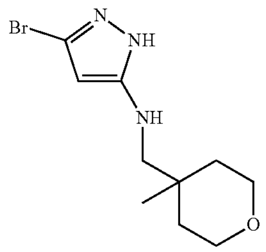

37 mg of acetic acid was added to a mixture of 1 g of 3-bromo-1H-pyrazol-5-amine, 950 mg of 4-methyltetrahydro-2H-pyran-4-carbaldehyde, and 30 mL of 1,2-dichloroethane at room temperature, and the resultant mixture was stirred for two hours. To the reaction mixture was added 2.62 g of sodium triacetoxyborohydride at room temperature, and the mixture was stirred at room temperature for 16 hours. An aqueous sodium carbonate solution was added to the reaction mixture until the pH of the mixture was changed to 8 to 9, and the mixture was subjected to extraction with dichloromethane. The organic phase was washed with a saturated aqueous sodium chloride solution, and then dried over sodium sulfate. The resultant product was subjected to filtration, and then the filtrate was concentrated under reduced pressure, to thereby produce 1.69 g of the title compound as a white solid.

LC/MS: condition 4, retention time=1.76 min

LC/MS (ESI+) m/z; 276.3 $[M+H]^+$ (Step B) Ethyl 2-bromo-7-hydroxy-4-((4-methyltetrahydro-2H-pyran-4-yl)methyl)-5-oxo-4,5-dihydropyrazolo[1,5-a]pyrimidine-6-carboxylate

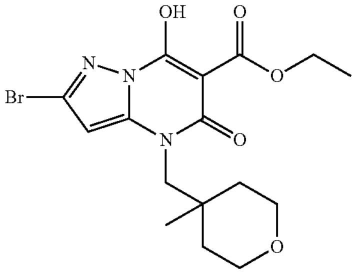 [SMILES: CCOC(=O)c1c(O)n2nc(Br)cc2n(CC2(C)CCOCC2)c1=O]

A mixture of 1.69 g of 3-bromo-N-((4-methyltetrahydro-2H-pyran-4-yl)methyl)-1H-pyrazol-5-amine produced in step A of Synthesis Example 27, 1.51 mL of triethyl methanetricarboxylate, 2.58 mL of triethylamine, and 7 mL of toluene was stirred at 120° C. for 16 hours. The reaction mixture was concentrated under reduced pressure, and the resultant residue was purified by silica gel column chromatography (chloroform/methanol=100/0→95/5→90/10 (v/v)), to thereby produce 1.49 g of the title compound as a white solid.

LC/MS: condition 4, retention time=1.62 min

LC/MS (ESI+) m/z; 416.4 $[M+H]^+$ (Step C) 2-Bromo-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide A mixture of 1.5 g of ethyl 2-bromo-7-hydroxy-4-((4-methyltetrahydro-2H-pyran-4-yl)methyl)-5-oxo-4,5-dihydropyrazolo[1,5-a]pyrimidine-6-carboxylate produced in step B of Synthesis Example 27, 756 µL of cyclopropylamine, and 15 mL of N,N-dimethylacetamide was stirred under microwave irradiation at 130° C. for one hour. The reaction mixture was cooled to room temperature, and 2 M aqueous hydrochloric acid solution was added to the mixture. The resultant solid was recovered by filtration, and the solid was washed with water and then dried under reduced pressure, to thereby produce 1.2 g of the title compound as a pale pink solid.

Synthesis Example 28

N-Cyclopropyl-7-hydroxy-4-((4-methyltetrahydro-2H-pyran-4-yl)methyl)-5-oxo-2-(pyrazin-2-ylamino)-4,5-dihydropyrazolo[1,5-a]pyrimidine-6-carboxamide A mixture of 200 mg of 2-bromo-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide produced in step C of Synthesis Example 27, 67.1 mg of pyrazin-2-amine, 43 mg of tris(dibenzylideneacetone)dipalladium(0), 54.3 mg of 2-di-tert-butyl phosphino-2',4',6'-triisopropylbiphenyl, 135.5 mg of sodium tert-butoxide, and 2 mL of 1,4-dioxane was stirred under microwave irradiation at 120° C. for one hour. The reaction mixture was cooled to room temperature and subjected to filtration, and then the filtrate was concentrated under reduced pressure. The residue was purified by silica gel column chromatography (chloroform/methanol=95/5→50/50 (v/v)), to thereby produce 10.28 mg of the title compound as a yellow solid.

Synthesis Example 29

2-(2-Aminopyridin-3-yl)-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide A mixture of 85.1 mg of 2-bromo-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide produced in step C of Synthesis Example 27, 88.0 mg of 3-(4,4,5,5-tetramethyl-1,3,2-dioxaborolan-2-yl)pyridin-2-amine, 13.0 mg of [1,1'-bis(di-tert-butylphosphino)ferrocene]dichloropalladium(II), 82.9 mg of potassium carbonate, 0.85 mL of water, and 0.85 mL of 1,4-dioxane was stirred at 100° C. overnight. The reaction mixture was cooled to room temperature and subjected to filtration, and then the filtrate was concentrated under reduced pressure. The residue was purified by silica gel column chromatography (chloroform/methanol=99/1→97/3→93/7→90/10 (v/v)). Ethanol was added to the resultant solid, and the resultant solid was recovered by filtration and then dried under reduced pressure, to thereby produce 58.8 mg of the title compound as a white solid.

Synthesis Example 30

2-Bromo-N-cyclobutyl-7-hydroxy-4-((4-methyltetrahydro-2H-pyran-4-yl)methyl)-5-oxo-4,5-dihydropyrazolo[1,5-a]pyrimidine-6-carboxamide A mixture of 2.0 g of ethyl 2-bromo-7-hydroxy-4-((4-methyltetrahydro-2H-pyran-4-yl)methyl)-5-oxo-4,5-dihydropyrazolo[1,5-a]pyrimidine-6-carboxylate produced in step B of Synthesis Example 27, 687 mg of cyclobutanamine, and 20 mL of N,N-dimethylacetamide was stirred at 120° C. for two hours. The reaction mixture was cooled to room temperature, and 1 M aqueous hydrochloric acid solution was added to the mixture, followed by stirring at room temperature for two hours. The resultant solid was recovered by filtration, and then dried under reduced pressure, to thereby produce 2.07 g of the title compound as a white solid.

Synthesis Example 31

N-Cyclobutyl-7-hydroxy-4-((4-methyltetrahydro-2H-pyran-4-yl)methyl)-5-oxo-2-(pyrazin-2-ylamino)-4,5-dihydropyrazolo[1,5-a]pyrimidine-6-carboxamide A mixture of 87.9 mg of 2-bromo-N-cyclobutyl-7-hydroxy-4-((4-methyltetrahydro-2H-pyran-4-yl)methyl)-5-oxo-4,5-dihydropyrazolo[1,5-a]pyrimidine-6-carboxamide produced in Synthesis Example 30, 38.0 mg of pyrazin-2-amine, 18.3 mg of tris(dibenzylideneacetone)dipalladium (0), 23.1 mg of 4,5-bis(diphenylphosphino)-9,9-dimethylxanthene, 57.7 mg of sodium tert-butoxide, and 3 mL of 1,4-dioxane was stirred in an argon atmosphere at 110° C. for 14 hours. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=40/60→70/30 (v/v)), to thereby produce 78.3 mg of the title compound as a pale brown solid.

Synthesis Example 32

N-Cyclopropyl-7-hydroxy-4-neopentyl-5-oxo-2-ureido-4,5-dihydropyrazolo[1,5-a]pyrimidine-6-carboxamide 47.4 µL of trichloroacetyl isocyanate was added to a mixture of 64 mg of 2-amino-N-cyclopropyl-7-hydroxy-4-neopentyl-5-oxo-4,5-dihydropyrazolo[1,5-a]pyrimidine-6-carboxamide produced in Synthesis Example 18 and 1.2 mL of tetrahydrofuran, and the resultant mixture was stirred at room temperature for three hours. To the reaction mixture were added 1.2 mL of methanol and 138.2 mg of potassium carbonate, and the mixture was stirred at room temperature overnight. Water was added to the mixture, and then 1 M aqueous hydrochloric acid solution was added to the mixture until the pH of the mixture was changed to 2. The resultant solid was recovered by filtration, and then dried under reduced pressure, to thereby produce 70.1 mg of the title compound as a white solid.

Synthesis Example 33

N6-Cyclopropyl-7-hydroxy-4-neopentyl-5-oxo-4,5-dihydropyrazolo[1,5-a]pyrimidine-2,6-dicarboxamide 73.0 mg of 1-hydroxy-1H-benzotriazole ammonium salt and 46.0 mg of 1-ethyl-3-(3-dimethylaminopropyl)carbodiimide hydrochloride were added to a mixture of 69.7 mg of 6-(cyclopropylcarbamoyl)-7-hydroxy-4-neopentyl-5-oxo-4,5-dihydropyrazolo[1,5-a]pyrimidine-2-carboxylic acid produced in Synthesis Example 2 and 1.4 mL of N,N-dimethylacetamide at 0° C., and the resultant mixture was stirred at room temperature overnight. 1 M aqueous hydrochloric acid solution was added to the reaction mixture, and the resultant solid was recovered by filtration and then dried under reduced pressure, to thereby produce 60.0 mg of the title compound as a white solid.

Synthesis Example 34

3-Bromo-N-cyclopropyl-7-hydroxy-5-oxo-4-((tetrahydro-2H-pyran-4-yl)methyl)-4,5-dihydropyrazolo[1,5-a]pyrimidine-6-carboxamide (Step A) 4-Bromo-N-((tetrahydro-2H-pyran-4-yl)methyl)-1H-pyrazol-5-amine

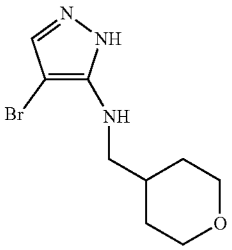 [SMILES: Brc1cn[nH]c1NCC1CCOCC1]

1.37 mL of acetic acid was added to a mixture of 3.24 g of 4-bromo-1H-pyrazol-5-amine, 2.51 g of tetrahydro-2H-pyran-4-carbaldehyde, and 32 mL of tetrahydrofuran at room temperature, and the resultant mixture was stirred for eight hours. The reaction mixture was cooled to 0° C., and 908 mg of sodium borohydride was added to the mixture, followed by stirring at room temperature for 15 hours and 30 minutes. 2 M aqueous hydrochloric acid solution was added to the reaction mixture, and the aqueous phase was washed with diethyl ether. A saturated aqueous sodium hydrogen carbonate solution was added to the aqueous phase until the pH of the mixture was changed to 8, and the mixture was subjected to extraction with ethyl acetate. The organic phase was washed with a saturated aqueous sodium chloride solution, and then dried over sodium sulfate. The resultant product was subjected to filtration, and then the filtrate was concentrated under reduced pressure, to thereby produce 3.1 g of the title compound as a colorless oily product.

LC/MS: condition 3, retention time=1.45 min

LC/MS (ESI+) m/z; 260.06 $[M+H]^+$ (Step B) Ethyl 3-bromo-7-hydroxy-5-oxo-4-((tetrahydro-2H-pyran-4-yl)methyl)-4,5-dihydropyrazolo[1,5-a]pyrimidine-6-carboxylate

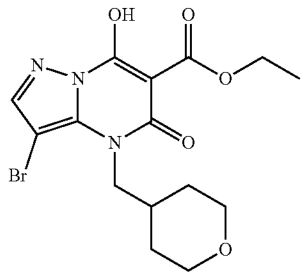 [SMILES: CCOC(=O)c1c(O)n2ncc(Br)c2n(CC2CCOCC2)c1=O]

A mixture of 3.1 g of 4-bromo-N-((tetrahydro-2H-pyran-4-yl)methyl)-1H-pyrazol-5-amine produced in step A of Synthesis Example 34, 3.03 mL of triethyl methanetricarboxylate, 4.96 mL of triethylamine, and 31 mL of toluene was refluxed for six hours and 15 minutes. The reaction mixture was cooled to room temperature, and ethyl acetate and chloroform were added to the mixture. 2 M aqueous hydrochloric acid solution was added to the mixture, and the mixture was subjected to extraction with chloroform. The organic phase was dried over sodium sulfate and subjected to filtration, and then the filtrate was concentrated under reduced pressure. Ethyl acetate was added to the resultant residue, and the solid was recovered by filtration and dried under reduced pressure, to thereby produce 1.5988 g of the title compound as a brown solid.

LC/MS: condition 2, retention time=1.33 min

LC/MS (ESI+) m/z; 400.39 $[M+H]^+$ (Step C) 3-Bromo-N-cyclopropyl-7-hydroxy-5-oxo-4-((tetrahydro-2H-pyran-4-yl)methyl)-4,5-dihydropyrazolo[1,5-a]pyrimidine-6-carboxamide A mixture of 1 g of ethyl 3-bromo-7-hydroxy-5-oxo-4-((tetrahydro-2H-pyran-4-yl)methyl)-4,5-dihydropyrazolo[1,5-a]pyrimidine-6-carboxylate produced in step B of Synthesis Example 34, 0.522 mL of cyclopropylamine, and 7 mL of N,N-dimethylformamide was stirred under microwave irradiation at 120° C. for 30 minutes. The reaction mixture was cooled to room temperature, and 2 M aqueous hydrochloric acid solution was added to the mixture. The resultant solid was recovered by filtration, and the solid was washed with water and then dried under reduced pressure, to thereby produce 750.9 mg of the title compound as a pale brown solid.

Synthesis Example 35

N-Cyclopropyl-3-(3,6-dihydro-2H-pyran-4-yl)-7-hydroxy-5-oxo-4-((tetrahydro-2H-pyran-4-yl)methyl)-4,5-dihydropyrazolo[1,5-a]pyrimidine-6-carboxamide A mixture of 41.2 mg of 3-bromo-N-cyclopropyl-7-hydroxy-5-oxo-4-((tetrahydro-2H-pyran-4-yl)methyl)-4,5-dihydropyrazolo[1,5-a]pyrimidine-6-carboxamide produced in step C of Synthesis Example 34, 31.5 mg of 2-(3,6-dihydro-2H-pyran-4-yl)-4,4,5,5-tetramethyl-1,3,2-dioxaborolane, 3.3 mg of [1,1'-bis(di-tert-butylphosphino)ferrocene]dichloropalladium(II), 41.5 mg of potassium carbonate, 0.42 mL of water, and 0.412 mL of 1,4-dioxane was refluxed overnight. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=40/60→50/50 (v/v)), to thereby produce 17.91 mg of the title compound as a pale brown amorphous product.

Synthesis Example 36

N6-Cyclopropyl-7-hydroxy-N2-methoxy-4-neopentyl-5-oxo-4,5-dihydropyrazolo[1,5-a]pyrimidine-2,6-dicarboxamide 76.7 mg of 1-(3-dimethylaminopropyl)-3-ethylcarbodiimide hydrochloride, 152.1 mg of 1-[bis(dimethylamino)methylene]-1H-1,2,3-triazolo[4,5-b]pyridinium 3-oxide hexafluorophosphate, 139 µL of triethylamine, and 33.4 mg of O-methylhydroxylamine hydrochloride were added to a mixture of 69.7 mg of 6-(cyclopropylcarbamoyl)-7-hydroxy-4-neopentyl-5-oxo-4,5-dihydropyrazolo[1,5-a]pyrimidine-2-carboxylic acid produced in Synthesis Example 2 and 1 mL of N,N-dimethylacetamide, and the resultant mixture was stirred at room" temperature for 15 hours. Water was added to the reaction mixture, and the mixture was subjected to extraction with ethyl acetate. The organic phase was washed with water and a saturated aqueous sodium chloride solution, and then dried over sodium sulfate. The resultant product was subjected to filtration, and then the filtrate was concentrated under reduced pressure. The residue was purified by silica gel reversed-phase column chromatography (0.1% formic acid-acetonitrile/0.1% aqueous formic acid solution=50/50→70/30 (v/v)), to thereby produce 67.3 mg of the title compound as a white solid.

Synthesis Example 37

N6-Cyclopropyl-7-hydroxy-N2-(3-methoxypropyl)-4-neopentyl-5-oxo-4,5-dihydropyrazolo[1,5-a]pyrimidine-2,6-dicarboxamide 76.7 mg of 1-(3-dimethylaminopropyl)-3-ethylcarbodiimide hydrochloride, 152.1 mg of 1-[bis(dimethylamino)methylene]-1H-1,2,3-triazolo[4,5-b]pyridinium 3-oxide hexafluorophosphate, and 35.7 mg of 3-methoxypropan-1-amine were added to a mixture of 69.7 mg of 6-(cyclopropylcarbamoyl)-7-hydroxy-4-neopentyl-5-oxo-4,5-dihydropyrazolo[1,5-a]pyrimidine-2-carboxylic acid produced in Synthesis Example 2 and 1 mL of N,N-dimethylacetamide, and the resultant mixture was stirred at room temperature for 14 hours. Water was added to the reaction mixture, and the mixture was subjected to extraction with ethyl acetate. The organic phase was washed with a saturated aqueous sodium chloride solution, and then dried over sodium sulfate. The resultant product was subjected to filtration, and then the filtrate was concentrated under reduced pressure. The residue was purified by silica gel reversed-phase column chromatography (0.1% formic acid-acetonitrile/0.1% aqueous formic acid solution=50/50→80/20 (v/v)), to thereby produce 54.4 mg of the title compound as a white solid.

The compounds of Synthesis Examples 38 to 50 were produced according to the methods described in the aforementioned Synthesis Examples or methods similar thereto.

Synthesis Example 38

N6-Cyclopropyl-N2-ethyl-7-hydroxy-4-neopentyl-5-oxo-4,5-dihydropyrazolo[1,5-a]pyrimidine-2,6-dicarboxamide Yield: 3.09 mg, white solid Synthesis Example 39

N6-Cyclopropyl-7-hydroxy-4-neopentyl-5-oxo-N2-(pyrazin-2-ylmethyl)-4,5-dihydropyrazolo[1,5-a]pyrimidine-2,6-dicarboxamide Yield: 2.51 mg, white solid r:

Synthesis Example 40

N6-Cyclopropyl-7-hydroxy-N2-(2-morpholinoethyl)-4-neopentyl-5-oxo-4,5-dihydropyrazolo[1,5-a]pyrimidine-2,6-dicarboxamide Yield: 88.7 mg, white solid Synthesis Example 41

N6-Cyclopropyl-7-hydroxy-4-neopentyl-5-oxo-N2-(pyridin-2-yl)-4,5-dihydropyrazolo[1,5-a]pyrimidine-2,6-dicarboxamide Yield: 41.32 mg, white solid Synthesis Example 42

N6-Cyclopropyl-7-hydroxy-N2-(2-hydroxy-2-methylpropyl)-4-neopentyl-5-oxo-4,5-dihydropyrazolo[1,5-a]pyrimidine-2,6-dicarboxamide Yield: 49.1 mg, white solid Synthesis Example 43

N6-Cyclopropyl-7-hydroxy-4-neopentyl-5-oxo-N2-(2,2,2-trifluoroethyl)-4,5-dihydropyrazolo[1,5-a]pyrimidine-2,6-dicarboxamide Yield: 66.6 mg, white solid Synthesis Example 44

N6-Cyclopropyl-7-hydroxy-N2-(3-morpholinopropyl)-4-neopentyl-5-oxo-4,5-dihydropyrazolo[1,5-a]pyrimidine-2,6-dicarboxamide Yield: 69.5 mg, white solid Synthesis Example 45

N6-Cyclopropyl-7-hydroxy-4-neopentyl-5-oxo-N2-(2-(trifluoromethoxy)ethyl)-4,5-dihydropyrazolo[1,5-a]pyrimidine-2,6-dicarboxamide Yield: 71.2 mg, white solid Synthesis Example 46

N6-Cyclopropyl-7-hydroxy-N2-(3-methoxy-3-methylbutyl)-4-neopentyl-5-oxo-4,5-dihydropyrazolo[1,5-a]pyrimidine-2,6-dicarboxamide Yield: 82.9 mg, white solid Synthesis Example 47

N6-Cyclopropyl-7-hydroxy-N2,N2-dimethyl-4-neopentyl-5-oxo-4,5-dihydropyrazolo[1,5-a]pyrimidine-2,6-dicarboxamide Yield: 2.32 mg, white solid Synthesis Example 48

N6-Cyclopropyl-7-hydroxy-4-neopentyl-5-oxo-N2-(2-(pyrazin-2-yl)ethyl)-4,5-dihydropyrazolo[1,5-a]pyrimidine-2,6-dicarboxamide Yield: 8.82 mg, yellow solid Synthesis Example 49

N6-Cyclopropyl-7-hydroxy-4-neopentyl-5-oxo-N2-(pyridin-2-ylmethyl)-4,5-dihydropyrazolo[1,5-a]pyrimidine-2,6-dicarboxamide Yield: 44.01 mg, yellow solid Synthesis Example 50

N6-Cyclopropyl-7-hydroxy-4-neopentyl-5-oxo-N2-(pyrazin-2-yl)-4,5-dihydropyrazolo[1,5-a]pyrimidine-2,6-dicarboxamide Yield: 2.21 mg, yellow oily product Synthesis Example 51

6-(Cyclopropylcarbamoyl)-7-hydroxy-4-isobutyl-5-oxo-4,5-dihydropyrazolo[1,5-a]pyrimidine-3-carboxylic acid 1 mL of 1 M aqueous sodium hydroxide solution was added to a mixture of 100 mg of ethyl 6-(cyclopropylcarbamoyl)-7-hydroxy-4-isobutyl-5-oxo-4,5-dihydropyrazolo[1,5-a]pyrimidine-3-carboxylate produced in step C of Synthesis Example 5 and 1 mL of 1,4-dioxane at room temperature, and the resultant mixture was stirred at 60° C. for seven and a half hours. To the reaction mixture was added 1 M aqueous hydrochloric acid solution, and the resultant solid was recovered by filtration. The resultant solid was washed with water and then dried under reduced pressure, to thereby produce 56.7 mg of the title compound as a white solid.

Synthesis Example 52

N6-Cyclopropyl-7-hydroxy-4-isobutyl-N3-isopropyl-5-oxo-4,5-dihydropyrazolo[1,5-a]pyrimidine-3,6-dicarboxamide 85.2 mg of O-(7-azabenzotriazol-1-yl)-N,N,N',N',-tetramethyluronium hexafluorophosphate and 53.7 μL of N,N-diisopropylethylamine were added to a mixture of 50 mg of 6-(cyclopropylcarbamoyl)-7-hydroxy-4-isobutyl-5-oxo-4,5-dihydropyrazolo[1,5-a]pyrimidine-3-carboxylic acid produced in Synthesis Example 51, 19.3 μL of isopropylamine, and 0.5 mL of N,N-dimethylformamide at 0° C., and the resultant mixture was stirred for three hours. Water was added to the reaction mixture, and the mixture was subjected to extraction with chloroform. The resultant extract was concentrated under reduced pressure, and the residue was purified by silica gel reversed-phase column chromatography (0.1% formic acid-acetonitrile/0.1% aqueous formic acid solution=40/60→60/40 (v/v)), to thereby produce 2.58 mg of the title compound as a white solid.

The compounds of Synthesis Examples 53 to 56 were produced according to the methods described in the aforementioned Synthesis Examples or methods similar thereto.

Synthesis Example 53

N6-Cyclopropyl-N3-(3,3-difluorocyclobutyl)-7-hydroxy-4-isobutyl-5-oxo-4,5-dihydropyrazolo[1,5-a]pyrimidine-3,6-dicarboxamide Yield: 3.20 mg, yellow solid Synthesis Example 54

N-Cyclopropyl-7-hydroxy-4-isobutyl-3-(4-methylpiperazine-1-carbonyl)-5-oxo-4,5-dihydropyrazolo[1,5-a]pyrimidine-6-carboxamide Yield: 54.59 mg, white solid Synthesis Example 55

N6-Cyclobutyl-7-hydroxy-4-neopentyl-5-oxo-4,5-dihydropyrazolo[1,5-a]pyrimidine-2,6-dicarboxamide Yield: 88.7 mg, white solid Synthesis Example 56

2-Amino-N-cyclobutyl-7-hydroxy-4-neopentyl-5-oxo-4,5-dihydropyrazolo[1,5-a]pyrimidine-6-carboxamide hydrochloride Yield: 161.5 mg, white solid Synthesis Example 57

N-Cyclobutyl-7-hydroxy-4-neopentyl-5-oxo-2-(sulfamoylamino)-4,5-dihydropyrazolo[1,5-a]pyrimidine-6-carboxamide 88 mg of tert-butyl (chlorosulfonyl)carbamate was added to a mixture of 90 mg of 2-amino-N-cyclobutyl-7-hydroxy-4-neopentyl-5-oxo-4,5-dihydropyrazolo[1,5-a]pyrimidine-6-carboxamide hydrochloride produced in Synthesis Example 56, 70 μL of triethylamine, and 2 mL of dichloromethane, and the resultant mixture was stirred at room temperature for 16 hours. The reaction mixture was concentrated under reduced pressure, and 2 mL of trifluoroacetic acid was added to the resultant solid, followed by stirring at room temperature for two hours. The reaction mixture was concentrated under reduced pressure, and the residue was purified by silica gel reversed-phase column chromatography (acetonitrile/10 mM aqueous ammonium bicarbonate solution=18/82→27/73 (v/v)), to thereby produce 25.2 mg of the title compound as a white solid.

Synthesis Example 58

N-Cyclopropyl-7-hydroxy-2-(hydroxymethyl)-4-neopentyl-5-oxo-4,5-dihydropyrazolo[1,5-a]pyrimidine-6-carboxamide 570 mg of ethyl 6-(cyclopropylcarbamoyl)-7-hydroxy-4-neopentyl-5-oxo-4,5-dihydropyrazolo[1,5-a]pyrimidine-2-carboxylate produced in step C of Synthesis Example 1 was added to a mixture of 149 mg of lithium aluminum hydride and 14 mL of tetrahydrofuran at 0° C., and the resultant mixture was stirred for two hours. Sodium sulfate decahydrate was added to the reaction mixture at 0° C., and then the resultant mixture was subjected to extraction with chloroform. The organic phase was dried over sodium sulfate and subjected to filtration, and then the filtrate was concentrated under reduced pressure, to thereby produce 550 mg of the title compound as a white solid.

Synthesis Example 59

N-Cyclopropyl-2-formyl-7-hydroxy-4-neopentyl-5-oxo-4,5-dihydropyrazolo[1,5-a]pyrimidine-6-carboxamide 341.7 mg of 2-iodoxybenzoic acid (purity: >39.0%, containing benzoic acid and isophthalic acid as stabilizers) was added to a mixture of 136 mg of N-cyclopropyl-7-hydroxy-2-(hydroxymethyl)-4-neopentyl-5-oxo-4,5-dihydropyrazolo[1,5-a]pyrimidine-6-carboxamide produced in Synthesis Example 58 and 1 mL of dimethyl sulfoxide at room temperature, and the resultant mixture was stirred for three hours. The reaction mixture was cooled to 0° C., and a saturated aqueous sodium thiosulfate solution was added to the mixture. Subsequently, a saturated aqueous sodium hydrogen carbonate solution was added to the resultant mixture until the pH of the mixture was changed to 6 to 7, and the mixture was stirred for 10 minutes. Thereafter, the mixture was subjected to extraction with chloroform, and the organic phase was dried over sodium sulfate. The resultant product was subjected to filtration, and then the filtrate was concentrated under reduced pressure, to thereby produce 120 mg of the title compound as a yellow solid.

Synthesis Example 60

(E)-N-Cyclopropyl-2-((ethoxyimino)methyl)-7-hydroxy-4-neopentyl-5-oxo-4,5-dihydropyrazolo[1,5-a]pyrimidine-6-carboxamide A mixture of 30 mg of N-cyclopropyl-2-formyl-7-hydroxy-4-neopentyl-5-oxo-4,5-dihydropyrazolo[1,5-a]pyrimidine-6-carboxamide produced in Synthesis Example 59, 22 mg of O-ethylhydroxylamine hydrochloride, and 0.6 mL of methanol was stirred at 80° C. for three hours. The reaction mixture was subjected to filtration, and then the filtrate was concentrated under reduced pressure. The residue was purified by silica gel reversed-phase column chromatography (0.1% formic acid-acetonitrile/0.1% aqueous formic acid solution=70/30→90/10 (v/v)), to thereby produce 10.55 mg of the title compound as a yellow oily product.

Synthesis Example 61

2-Acetyl-N-cyclopropyl-7-hydroxy-4-neopentyl-5-oxo-4,5-dihydropyrazolo[1,5-a]pyrimidine-6-carboxamide A mixture of 100 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 157 mg of tributyl(1-ethoxyvinyl) tin, 7.32 mg of tetrakis(triphenylphosphine)palladium(0), and 1 mL of toluene was stirred in an argon atmosphere at 110° C. overnight. The reaction mixture was cooled to room temperature, and 1 M aqueous hydrochloric acid solution was added to the mixture, followed by stirring for five hours and 30 minutes. After addition of water, the mixture was subjected to extraction with ethyl acetate, and the extract was concentrated under reduced pressure. The resultant residue was purified by silica gel column chromatography (chloroform/methanol=100/0→70/30 (v/v)), to thereby produce 51 mg of the title compound as a white solid.

Synthesis Example 62

(E)-N-Cyclopropyl-2-(1-(ethoxyimino)ethy 1)-7-hydroxy-4-neopentyl-5-oxo-4,5-dihydropyrazolo[1,5-a]pyrimidine-6-carboxamide A mixture of 100 mg of 2-acetyl-N-cyclopropyl-7-hydroxy-4-neopentyl-5-oxo-4,5-dihydropyrazolo[1,5-a]pyrimidine-6-carboxamide produced in Synthesis Example 61, 28.7 mg of O-ethylhydroxylamine hydrochloride, and 1 mL of methanol was stirred at 80° C. for one hour. Water was added to the reaction mixture, and the mixture was subjected to extraction with chloroform. The organic phase was dried over sodium sulfate and subjected to filtration, and then the filtrate was concentrated under reduced . . . pressure. The residue was purified by silica gel column chromatography (hexane/ethyl acetate=100/0→30/70 (v/v)), to thereby produce 26.17 mg of the title compound as a yellow solid.

The compounds of Synthesis Examples 63 to 68 were produced according to the methods described in the aforementioned Synthesis Examples or methods similar thereto.

Synthesis Example 63

(E)-N-Cyclopropyl-7-hydroxy-2-((hydroxyimino)methyl)-4-neopentyl-5-oxo-4,5-dihydropyrazolo[1,5-a]pyrimidine-6-carboxamide Yield: 3.29 mg, yellow solid Synthesis Example 64

(E)-N-Cyclopropyl-7-hydroxy-2-(((2-methoxyethoxy)imin o)methyl)-4-neopentyl-5-oxo-4,5-dihydropyrazolo[1,5-a]pyrimidine-6-carboxamide Yield: 15.94 mg, yellow oily product Synthesis Example 65

(E)-2-((((6-(Cyclopropylcarbamoyl)-7-hydroxy-4-neopentyl-5-oxo-4,5-dihydropyrazolo[1,5-a]pyrimidin-2-yl)methylene)amin o)ox y) acetic acid Yield: 2.09 mg, white solid Synthesis Example 66

(E)-2-(((2-Amino-2-oxoethoxy)imino)methyl)-N-cyclopropyl-7-hydroxy-4-neopentyl-5-oxo-4,5-dihydropyrazolo[1,5-a]pyrimidine-6-carboxamide Yield: 5.56 mg, white solid Synthesis Example 67

(E)-2-(((Benzyloxy)imino)methyl)-N-cyclopropyl-7-hydroxy-4-neopentyl-5-oxo-4,5-dihydropyrazolo[1,5-a]pyrimidine-6-carboxamide Yield: 26.69 mg, yellow oily product Synthesis Example 68

(E)-N-Cyclopropyl-7-hydroxy-2-((methoxyimino)methyl)-4-neopentyl-5-oxo-4,5-dihydropyrazolo[1,5-a]pyrimidine-6-carboxamide Yield: 8.11 mg, yellow solid Synthesis Example 69

2-Amino-N-cyclopropyl-7-hydroxy-4-isobutyl-5-oxo-4,5-dihydropyrazolo[1,5-a]pyrimidine-6-carboxamide A mixture of 300 mg of 2-bromo-N-cyclopropyl-7-hydroxy-4-isobutyl-5-oxo-4,5-dihydropyrazolo[1,5-a]pyrimidine-6-carboxamide produced in step C of Synthesis Example 22, 106.5 mg of (2S,4R)-4-hydroxypyrrolidine-2-carboxylic acid, 77.4 mg of copper(I) iodide, 1.69 g of potassium carbonate, 1.5 mL of 28% aqueous ammonia, and 1.5 mL of dimethyl sulfoxide was stirred in an argon atmosphere under microwave irradiation at 140° C. for three hours. The reaction mixture was cooled to room temperature, and the mixture was concentrated under reduced pressure. To the residue were added 20 mL of methanol, 10 mL of chloroform, and diatomaceous earth, and the mixture was stirred and subjected to filtration. The resultant filtrate was concentrated under reduced pressure, and the resultant residue was purified by silica gel reversed-phase column chromatography (acetonitrile/water=5/95→100/0 (v/v)), to thereby produce 98.2 mg of the title compound as a pale green amorphous product.

Synthesis Example 70

2-Amino-N-cyclopropyl-7-hydroxy-4-isobutyl-3-(1-methyl-1,2,3,6-tetrahydropyridin-4-yl)-5-oxo-4,5-dihydropyrazolo[1,5-a]pyrimidine-6-carboxamide A mixture of 80.6 mg of 2-amino-N-cyclopropyl-7-hydroxy-4-isobutyl-5-oxo-4,5-dihydropyrazolo[1,5-a]pyrimidine-6-carboxamide produced in Synthesis Example 69, 56.4 mg of N-bromosuccinimide, and 2 mL of acetonitrile was stirred at 0° C. for 3.5 hours. The reaction mixture was heated to room temperature, and then the mixture was divided into two aliquots. Each aliquot was concentrated under reduced pressure to thereby produce a brown solid. One of the products was used as crude in the subsequent step. A mixture of the resultant crude product, 44.2 mg of 1-methyl-4-(4,4,5,5-tetramethyl-1,3,2-dioxaborolan-2-yl)-1,2,3,6-tetrahydropyridine, 8.6 mg of palladium chloride-1,1'-bis(di-teat-butylphosphino)ferrocene complex, 54.7 mg of potassium carbonate, 0.5 mL of 1,4-dioxane, and 0.5 mL of water was stirred in an argon atmosphere at 100° C. for 14 hours. The reaction mixture was cooled to room temperature, and 4.0 mL of chloroform and diatomaceous earth were added to the mixture. The resultant mixture was stirred and subjected to filtration, and the filtrate was concentrated under reduced pressure. The residue was purified by silica gel reversed-phase column chromatography (0.1% formic acid-acetonitrile/0.1% aqueous formic acid solution=30/70→60/40 (v/v)), to thereby produce 2.9 mg of the title compound as a black amorphous product.

The compound of Synthesis Example 71 was produced according to any of the methods described in the aforementioned Synthesis Examples or a method similar thereto.

Synthesis Example 71

2-Amino-N-cyclopropyl-3-(3,6-dihydro-2H-pyran-4-yl)-7-hydroxy-4-isobutyl-5-oxo-4,5-dihydropyrazolo[1,5-a]pyrimidine-6-carboxamide Yield: 1.4 mg, colorless solid Synthesis Example 72

2-Amino-3-bromo-N-cyclopropyl-7-hydroxy-4-neopentyl-5-oxo-4,5-dihydropyrazolo[1,5-a]pyrimidine-6-carboxamide A mixture of 200 mg of 2-amino-N-cyclopropyl-7-hydroxy-4-neopentyl-5-oxo-4,5-dihydropyrazolo[1,5-a]pyrimidine-6-carboxamide hydrochloride produced in Synthesis Example 4, 100.4 mg of N-bromosuccinimide, and 3 mL of N,N-dimethylformamide was stirred at room temperature for one hour. Water was added to the reaction mixture, and the resultant solid was recovered by filtration. Thereafter, the solid was washed with water, and then dried, to thereby produce 137 mg of the title compound as a yellow solid.

Synthesis Example 73

Tert-butyl (E)-3-(2-amino-6-(cyclopropylcarbamoyl)-7-hydroxy-4-neopentyl-5-oxo-4,5-dihydropyrazolo[1,5-a]pyrimidin-3-yl)acrylate A mixture of 90 mg of 2-amino-3-bromo-N-cyclopropyl-7-hydroxy-4-neopentyl-5-oxo-4,5-dihydropyrazolo[1,5-a]pyrimidine-6-carboxamide produced in Synthesis Example 72, 98.3 μL of tert-butyl acrylate, 5.05 mg of palladium(II) acetate, 31.5 mg of 2-dicyclohexylphosphino-2',4',6'-triisopropylbiphenyl, 125 μL of triethylamine, and 1 mL of N,N-dimethylformamide was stirred under microwave irradiation at 130° C. for one hour. The reaction mixture was cooled to room temperature and subjected to filtration, and the filtrate was concentrated under reduced pressure. The residue was purified by silica gel reversed-phase column chromatography (0.1% formic acid-acetonitrile/0.1% aqueous formic acid solution=40/60→60/40 (v/v)), to thereby produce 0.76 mg of the title compound as a red oily product.

Synthesis Example 74

Ethyl 6-(cyclopropylcarbamoyl)-3-fluoro-7-hydroxy-4-neopentyl-5-oxo-4,5-dihydropyrazolo[1,5-a]pyrimidine-2-carboxylate (Step A) Ethyl 4-fluoro-5-(neopentylamino)-1H-pyrazole-3-carboxylate

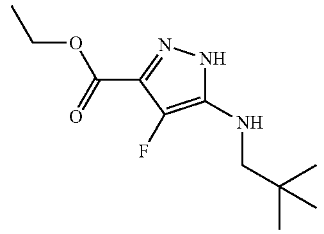 [SMILES: CCOC(=O)c1n[nH]c(NCC(C)(C)C)c1F]

4.2 g of N-fluorobenzenesulfonimide was added to a mixture of 1.5 g of ethyl 5-(neopentylamino)-1H-pyrazole-3-carboxylate produced in step A of Synthesis Example 1 and 60 mL of acetonitrile at 0° C., and the resultant mixture was stirred for three hours and 40 minutes. After addition of water, the mixture was subjected to extraction with chloroform, and the extract was concentrated under reduced pressure. The residue was purified by silica gel column chromatography (chloroform/ethyl acetate=100/0→55/45 (v/v)), to thereby produce 800.2 mg of the title compound as a yellow oily product.

LC/MS: condition 2, retention time=2.27 min

LC/MS (ESI+) m/z; 244.0 $[M+H]^+$ (Step B) Ethyl 6-(cyclopropylcarbamoyl)-3-fluoro-7-hydroxy-4-neopentyl-5-oxo-4,5-dihydropyrazolo[1,5-a]pyrimidine-2-carboxylate Substantially the same reaction as in steps B and C of Synthesis Example 1 was performed by using ethyl 4-fluoro-5-(neopentylamino)-1H-pyrazole-3-carboxylate produced in step A of Synthesis Example 74 in place of ethyl 5-(neopentylamino)-1H-pyrazole-3-carboxylate produced in step A of Synthesis Example 1, to thereby produce 109.28 mg of the title compound as a red solid.

The compounds of Synthesis Examples 75 to 79 were produced according to the methods described in the aforementioned Synthesis Examples or methods similar thereto.

Synthesis Example 75

N6-Cyclopropyl-3-fluoro-7-hydroxy-4-neopentyl-5-oxo-4,5-dihydropyrazolo[1,5-a]pyrimidine-2,6-dicarboxamide Yield: 22.29 mg, white solid Synthesis Example 76

2-Amino-N-cyclopropyl-3-fluoro-7-hydroxy-4-neopentyl-5-oxo-4,5-dihydropyrazolo[1,5-a]pyrimidine-6-carboxamide Yield: 220 mg, white solid Synthesis Example 77

N-Cyclopropyl-3-fluoro-7-hydroxy-4-neopentyl-5-oxo-2-ureido-4,5-dihydropyrazolo[1,5-a]pyrimidine-6-carboxamide Yield: 1.99 mg, yellow solid Synthesis Example 78

2-Amino-N-cyclopropyl-7-hydroxy-4-isobutyl-5-oxo-3-(1,2,3,6-tetrahydropyridin-4-yl)-4,5-dihydropyrazolo[1,5-a]pyrimidine-6-carboxamide dihydrochloride Yield: 2.49 mg, white solid Synthesis Example 79

2-Amino-N-cyclopropyl-3-(3,6-dihydro-2H-pyran-4-yl)-7-hydroxy-4-neopentyl-5-oxo-4,5-dihydropyrazolo[1,5-a]pyrimidine-6-carboxamide Yield: 1.99 mg, white solid Synthesis Example 80

Tert-butyl 4-(6-(cyclopropylcarbamoyl)-7-hydroxy-4-isobutyl-5-oxo-4,5-dihydropyrazolo[1,5-a]pyrimidin-2-yl)-3,6-dihydropyridine-1 (2H)-carboxylate Substantially the same reaction as in Synthesis Example 24 was performed by using tert-butyl 4-(4,4,5,5-tetramethyl-1,3,2-dioxaborolan-2-yl)-3,6-dihydropyridine-1(2H)-carboxylate in place of 3-(4,4,5,5-tetramethyl-1,3,2-dioxaborolan-2-yl)pyridin-2-amine, to thereby produce 66.03 mg of the title compound as a brown solid.

Synthesis Example 81

N-Cyclopropyl-7-hydroxy-4-isobutyl-5-oxo-2-(1,2,3,6-tetrahydropyridin-4-yl)-4,5-dihydropyrazolo[1,5-a]pyrimidine-6-carboxamide hydrochloride A mixture of 20 mg of tert-butyl 4-(6-(cyclopropylcarbamoyl)-7-hydroxy-4-isobutyl-5-oxo-4,5-dihydropyrazolo[1,5-a]pyrimidin-2-yl)-3,6-dihydropyridine-1 (2H)-carboxylate produced in Synthesis Example 80 and 0.4 mL of 4 M hydrogen chloride/1,4-dioxane solution was stirred at room temperature for three hours. The reaction mixture was concentrated under reduced pressure, and then the resultant product was washed with ethyl acetate, to thereby produce 2.93 mg of the title compound as a yellow solid.

Synthesis Example 82

Tert-butyl 4-(6-(cyclopropylcarbamoyl)-7-hydroxy-4-isobutyl-5-oxo-4,5-dihydropyrazolo[1,5-a]pyrimidin-2-yl) piperidine-1-carboxylate A mixture of 38 mg of tert-butyl 4-(6-(cyclopropylcarbamoyl)-7-hydroxy-4-isobutyl-5-oxo-4,5-dihydropyrazolo[1,5-a]pyrimidin-2-yl)-3,6-dihydropyridine-1 (2H)-carboxylate produced in Synthesis Example 80, 19 mg of 10% palladium/carbon (about 55% water-moistened product), and 0.7 mL of methanol was stirred in a hydrogen atmosphere at room temperature for three hours. The reaction mixture was subjected to filtration, and then the filtrate was concentrated under reduced pressure, to thereby produce 20 mg of the title compound as a green solid.

The compounds of Synthesis Examples 83 to 87 were produced according to the methods described in the aforementioned Synthesis Examples or methods similar thereto.

Synthesis Example 83

N-Cyclopropyl-7-hydroxy-4-isobutyl-5-oxo-2-(piperidin-4-yl)-4,5-dihydropyrazolo[1,5-a]pyrimidine-6-carboxamide hydrochloride Yield: 11.22 mg, white solid Synthesis Example 84

Tert-butyl 5-(6-(cyclopropylcarbamoyl)-7-hydroxy-4-isobutyl-5-oxo-4,5-dihydropyrazolo[1,5-a]pyrimidin-2-yl)-3,6-dihydropyridine-1 (2H)-carboxylate Yield: 29.85 mg, yellow solid Synthesis Example 85

N-Cyclopropyl-7-hydroxy-4-isobutyl-5-oxo-2-(1,2,5,6-tetrahydropyridin-3-yl)-4,5-dihydropyrazolo[1,5-a]pyrimidine-6-carboxamide hydrochloride Yield: 3.16 mg, white solid Synthesis Example 86

N-Cyclopropyl-7-hydroxy-4-isobutyl-5-oxo-2-(piperidin-3-yl)-4,5-dihydropyrazolo[1,5-a]pyrimidine-6-carboxamide hydrochloride (racemate)

Yield: 9.82 mg, white solid

Synthesis Example 87

(S)—N-Cyclopropyl-7-hydroxy-2-(3-hydroxypyrrolidin-1-yl)-4-neopentyl-5-oxo-4,5-dihydropyrazolo[1,5-a]pyrimidine-6-carboxamide Yield: 2.5 mg, brown solid Synthesis Example 88

N-Cyclopropyl-7-hydroxy-2-(4-isopropoxypyridin-3-yl)-4-neopentyl-5-oxo-4,5-dihydropyrazolo[1,5-a]pyrimidine-6-carboxamide (Step A) N-Cyclopropyl-7-hydroxy-4-neopentyl-5-oxo-2-(trimethylstannyl)-4,5-dihydropyrazolo[1,5-a]pyrimidine-6-carboxamide

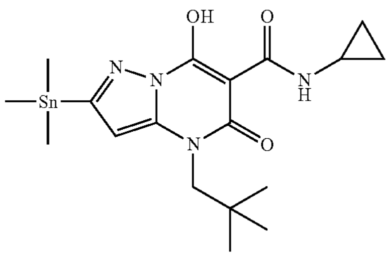 [SMILES: CC(C)(C)Cn1c(=O)c(C(=O)NC2CC2)c(O)n2n[c]([Sn]([CH3])([CH3])[CH3])cc12]

A mixture of 8.43 g of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 2.54 g of tetrakis(triphenylphosphine) palladium(0), 12.25 g of bis(trimethyltin), and 200 mL of toluene was stirred in a nitrogen atmosphere at 110° C. for one hour. A saturated aqueous potassium fluoride solution was added to the reaction mixture, and the mixture was subjected to filtration. Thereafter, the filtrate was subjected to extraction with ethyl acetate. The organic phase was washed with a saturated aqueous potassium fluoride solution, and then dried over sodium sulfate. Thereafter, the resultant product was subjected to filtration, and the filtrate was concentrated under reduced pressure. The residue was purified by silica gel column chromatography (petroleum ether/ethyl acetate=100/0→80/20 (v/v)), to thereby produce 3.8 g of a yellow solid. In a separate batch, a mixture of 36.2 g of 2-bromo-N-cyclopropyl-7-hydroxy-4-neopentyl-5-oxo-4,5-dihydropyrazolo[1,5-a]pyrimidine-6-carboxamide, 10.92 g of tetrakis(triphenylphosphine) palladium(0), 57.25 g of bis(trimethyltin), and 600 mL of toluene was stirred in a nitrogen atmosphere at 110° C. for one hour. A saturated aqueous potassium fluoride solution was added to the reaction mixture, and the mixture was subjected to filtration. The filtrate was subjected to extraction with ethyl acetate. The organic phase was washed with a saturated aqueous potassium fluoride solution, and then dried over sodium sulfate. Thereafter, the resultant product was subjected to filtration, and the filtrate was concentrated under reduced pressure. The residue was purified by silica gel column chromatography (petroleum ether/ethyl acetate=100/0→80/20 (v/v)), to thereby produce 3.1 g of a pure compound and 10.3 g of an impurity-containing yellow solid. A mixture of 10.3 g of the impurity-containing yellow solid and 3.8 g of the above-produced yellow solid was washed with tert-butyl methyl ether, and then the mixture was recovered by filtration. The recovered mixture and 3.1 g of the above-produced pure compound were freeze-dried, to thereby produce 13.81 g of the title compound as a yellow solid.

LC/MS: condition 4, retention time=3.40 min

LC/MS (ESI+) m/z; 469.4 $[M+H]^+$ (Step B) N-Cyclopropyl-7-hydroxy-2-(4-isopropoxypyridin-3-yl)-4-neopentyl-5-oxo-4,5-dihydropyrazolo[1,5-a]pyrimidine-6-carboxamide A mixture of 200 mg of N-cyclopropyl-7-hydroxy-4-neopentyl-5-oxo-2-(trimethylstannyl)-4,5-dihydropyrazolo[1,5-a]pyrimidine-6-carboxamide produced in step A of Synthesis Example 88, 186 mg of 3-bromo-4-isopropoxypyridine, 30.2 mg of tetrakis(triphenylphosphine) palladium (0), and 2 mL of toluene was stirred in an argon atmosphere at 110° C. overnight. The reaction mixture was cooled to room temperature and subjected to filtration, and then the filtrate was concentrated under reduced pressure. The residue was purified by silica gel reversed-phase column chromatography (acetonitrile/10 mM aqueous ammonium bicarbonate solution=36/64→63/37 (v/v)), to thereby produce 34.35 mg of the title compound as an orange oily product.

Synthesis Example 89

Ethyl 2-(6-(cyclopropylcarbamoyl)-7-hydroxy-4-neopentyl-5-oxo-4,5-dihydropyrazolo[1,5-a]pyrimidin-2-yl)acetate A mixture of 191.6 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 126 mg of ethyl acetoacetate, 11.22 mg of palladium(II) acetate, 31.24 mg of 2-di-tert-butylphosphino-2'-methylbiphenyl, 424.5 mg of tripotassium phosphate, and 2 mL of toluene was stirred in an argon atmosphere at 110° C. overnight. The reaction mixture was cooled to room temperature and subjected to filtration, and then the filtrate was concentrated under reduced pressure. The residue was purified by silica gel column chromatography (chloroform/methanol=95/5→70/30 (v/v)), to thereby produce 135 mg of the title compound as a brown solid.

Synthesis Example 90

2-(2-Amino-2-oxoethyl)-N-cyclopropyl-7-hydroxy-4-neopentyl-5-oxo-4,5-dihydropyrazolo[1,5-a]pyrimidine-6-carboxamide A mixture of 50 mg of ethyl 2-(6-(cyclopropylcarbamoyl)-7-hydroxy-4-neopentyl-5-oxo-4,5-dihydropyrazolo[1,5-a]pyrimidin-2-yl)acetat e produced in Synthesis Example 89, 10.7 mg of lithium hydroxide monohydrate, 1 mL of 1,4-dioxane, and 1 mL of water was stirred at 60° C. for one and a half hours. The reaction mixture was cooled to room temperature, and 2 M aqueous hydrochloric acid solution was added to the mixture. The resultant white solid was recovered by filtration, and then dried under reduced pressure. A mixture of 30 mg of the resultant white solid, 31.6 mg of 1-hydroxy-1H-benzotriazole, ammonium salt, 39.9 mg of 1-ethyl-3-(3-dimethylaminopropyl)carbodiimide hydrochloride, and 0.6 mL of N,N-dimethylacetamide was stirred at room temperature overnight. Water was added to the reaction mixture, and then the mixture was subjected to extraction with chloroform. The extract was concentrated under reduced pressure, and the residue was purified by silica gel reversed-phase column chromatography (0.1% formic acid-acetonitrile/0.1% aqueous formic acid solution=40/60→70/30 (v/v)), to thereby produce 2.1 mg of the title compound as a yellow oily product.

Synthesis Example 91

N-Cyclopropyl-7-hydroxy-2-(2-hydroxyethyl)-4-neopentyl-5-oxo-4,5-dihydropyrazolo[1,5-a]pyrimidine-6-carboxamide 50 mg of ethyl 2-(6-(cyclopropylcarbamoyl)-7-hydroxy-4-neopentyl-5-oxo-4,5-dihydropyrazolo[1,5-a]pyrimidin-2-yl)acetat e produced in Synthesis Example 89 was added to a mixture of 14.6 mg of lithium aluminum hydride and 1 mL of tetrahydrofuran at 0° C., and the resultant mixture was stirred for one hour. Sodium sulfate decahydrate was carefully added to the mixture at room temperature, and then the resultant mixture was stirred at room temperature. The reaction mixture was subjected to filtration, and then the filtrate was concentrated under reduced pressure, to thereby produce 3.26 mg of the title compound as a yellow oily product.

Synthesis Example 92

Tert-butyl 5-(6-(cyclopropylcarbamoyl)-7-hydroxy-5-oxo-4-((tetrahydro-2H-pyran-4-yl)methyl)-4,5-dihydropyrazolo[1,5-a]pyrimidin-3-yl)-3,6-dihydropyridine-1(2H)-carboxylate A mixture of 100 mg of 3-bromo-N-cyclopropyl-7-hydroxy-5-oxo-4-((tetrahydro-2H-pyran-4-yl)methyl)-4,5-dihydropyrazolo[1,5-a]pyrimidine-6-carboxamide produced in step C of Synthesis Example 34, 112.8 mg of tert-butyl 5-(4,4,5,5-tetramethyl-1,3,2-dioxaborolan-2-yl)-3,6-dihydropyridine-1 (2H)-carboxylate, 7.9 mg of [1,1'-bis(di-tert-butylphosphino)ferrocene]dichloropalladium(II), 100.8 mg of potassium carbonate, 1 mL of water, and 1 mL of 1,4-dioxane was refluxed in an argon atmosphere overnight. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=50/50→80/20 (v/v)), to thereby produce 53.4 mg of the title compound as a brown amorphous product.

Synthesis Example 93

N-Cyclopropyl-7-hydroxy-5-oxo-4-((tetrahydro-2H-pyran-4-yl)methyl)-3-(1,2,5,6-tetrahydropyridin-3-yl)-4,5-dihydropyrazolo[1,5-a]pyrimidine-6-carboxamide hydrochloride A mixture of 47.3 mg of tert-butyl 5-(6-(cyclopropylcarbamoyl)-7-hydroxy-5-oxo-4-((tetrahydro-2H-pyran-4-yl)methyl)-4,5-dihydropyrazolo[1,5-a]pyrimidin-3-yl)-3,6-dihydropyridine-1 (2H)-carboxylate produced in Synthesis Example 92 and 0.5 mL of 4 M hydrogen chloride/1,4-dioxane solution was stirred at room temperature for four hours. The reaction mixture was concentrated under reduced pressure, to thereby produce 43.7 mg of the title compound as a brown amorphous product.

Synthesis Example 94

N-Cyclopropyl-7-hydroxy-3-(1-methyl-1,2,5,6-tetrahydropyridin-3-yl)-5-oxo-4-((tetrahydro-2H-pyran-4-yl)methyl)-4,5-dihydropyrazolo[1,5-a]pyrimidine-6-carboxamide A mixture of 31.9 mg of N-cyclopropyl-7-hydroxy-5-oxo-4-((tetrahydro-2H-pyran-4-yl)methyl)-3-(1,2,5,6-tetrahydropyridin-3-yl)-4,5-dihydropyrazolo[1,5-a]pyrimidine-6-carboxamide hydrochloride produced in Synthesis Example 93, 0.076 mL of formic acid, and 0.163 mL of 37% aqueous formaldehyde solution was stirred at 80° C. for three hours. The reaction mixture was cooled to room temperature, and chloroform was added to the mixture, followed by addition of a saturated aqueous sodium hydrogen carbonate solution. The organic phase was dried over anhydrous sodium sulfate and subjected to filtration, and then the filtrate was concentrated under reduced pressure. To the residue were added 0.076 mL of formic acid and 0.163 mL of 37% aqueous formaldehyde solution, and the mixture was stirred at 80° C. for two hours. The reaction mixture was cooled to room temperature, and chloroform was added to the mixture, followed by addition of a saturated aqueous sodium hydrogen carbonate solution. The organic phase was washed with a saturated aqueous sodium chloride solution, and then dried over anhydrous sodium sulfate. The resultant product was subjected to filtration, and then the filtrate was concentrated under reduced pressure. The residue was purified by silica gel reversed-phase column chromatography (0.1% formic acid-acetonitrile/0.1% aqueous formic acid solution=10/90→30/70 (v/v)), to thereby produce 8.68 mg of the title compound as a pale yellow amorphous product.

Synthesis Example 95

Methyl 4-((2-bromo-6-(cyclopropylcarbamoyl)-7-hydroxy-5-oxopyrazolo[1,5-a]pyrimidin-4 (5H)-yl) methyl)-3,5-dichlorobenzoate Substantially the same reaction as in steps A, B and C of Synthesis Example 11 was performed by using methyl 3,5-dichloro-4-formylbenzoate in place of pivalaldehyde, to thereby produce 890 mg of the title compound as a brown solid.

Synthesis Example 96

2-Bromo-N-cyclopropyl-4-(2,6-dichloro-4-(hydroxymethyl)benzyl)-7-hydroxy-5-oxo-4,5-dihydropyrazolo[1,5-a]pyrimidine-6-carboxamide A mixture of 890 mg of methyl 4-((2-bromo-6-(cyclopropylcarbamoyl)-7-hydroxy-5-oxopyrazolo[1,5-a]pyrimidin-4 (5H)-yl)methyl)-3,5-dichlorobenzoate produced in Synthesis Example 95 and 9 mL of tetrahydrofuran was stirred at 0° C. for 30 minutes, and then 95.6 mg of lithium aluminum hydride was added to the mixture at 0° C. The resultant mixture was stirred for three hours until the temperature reached room temperature. Sodium sulfate decahydrate was carefully added to the mixture at room temperature, and then the mixture was stirred at room temperature for 30 minutes. The reaction mixture was subjected to filtration, and then the filtrate was concentrated under reduced pressure, to thereby produce 648.3 mg of the title compound as an orange solid.

Synthesis Example 97

2-(2-Aminopyridin-3-yl)-N-cyclopropyl-4-(2,6-dichloro-4-(hydroxymethyl)benzyl)-7-hydroxy-5-oxo-4,5-dihydropyrazolo[1,5-a]pyrimidine-6-carboxamide A mixture of 100.4 mg of 2-bromo-N-cyclopropyl-4-(2,6-dichloro-4-(hydroxymethyl)benzyl)-7-hydroxy-5-oxo-4,5-dihydropyrazolo[1,5-a]pyrimidine-6-carboxamide produced in Synthesis Example 96, 88.0 mg of 3-(4,4,5,5-tetramethyl-1,3,2-dioxaborolan-2-yl)pyridin-2-amine, 13.0 mg of [1,1'-bis(di-tert-butylphosphino)ferrocene]dichloropalladium(II), 82.9 mg of potassium carbonate, 3 mL of water, and 3 mL of 1,4-dioxane was stirred in an argon atmosphere at 110° C. for 12 hours and 45 minutes. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=30/70→40/60 (v/v)), to thereby produce 9.4 mg of the title compound as a pale brown solid.

Synthesis Example 98

2-Acetamido-N-cyclopropyl-7-hydroxy-4-isobutyl-5-oxo-4,5-dihydropyrazolo[1,5-a]pyrimidine-6-carboxamide A mixture of 50 mg of 2-bromo-N-cyclopropyl-7-hydroxy-4-isobutyl-5-oxo-4,5-dihydropyrazolo[1,5-a]pyrimidine-6-carboxamide produced in step C of Synthesis Example 22, 1.9 mg of (1R,2R)—N1,N2-dimethylcyclohexane-1,2-diamine, 2.6 mg of copper(I) iodide, 74.6 mg of potassium carbonate, 8.3 μL of acetic acid, and 1 mL of 1,4-dioxane was stirred in an argon atmosphere at 110° C. for 15 hours. The reaction mixture was cooled to room temperature, and 0.2 mL of water was added to the mixture, followed by stirring. Thereafter, 200 mg of diatomaceous earth and 3 mL of ethyl acetate were added to the mixture, and the resultant mixture was stirred. The mixture was subjected to filtration, and then the filtrate was concentrated under reduced pressure. The residue was purified by silica gel reversed-phase column chromatography (0.1% formic acid-acetonitrile/0.1% aqueous formic acid solution=50/50→70/30 (v/v)), to thereby produce 10.5 mg of the title compound as a colorless solid.

Synthesis Example 99

N-Cyclopropyl-7-hydroxy-4-neopentyl-5-oxo-2-(2-oxoimidazolidin-1-yl)-4,5-dihydropyrazolo[1,5-a]pyrimidine-6-carboxamide A mixture of 76.7 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 52.9 mg of N1,N2-dimethylethane-1,2-diamine, 38.1 mg of copper(I) iodide, 138.2 mg of potassium carbonate, 86.1 mg of imidazolidin-2-one, and 2 mL of N-methylpyrrolidone was stirred in an argon atmosphere under microwave irradiation at 130° C. for three hours. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=40/60→70/30 (v/v)), to thereby produce 6.9 mg of the title compound as a pale brown solid.

Synthesis Example 100

2-(2-Amino-1H-benz[d]imidazol-1-yl)-N-cyclopropyl-7-hydroxy-4-neopentyl-5-oxo-4,5-dihydropyrazolo[1,5-a]pyrimidine-6-carboxamide A mixture of 76.7 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 52.9 mg of N1,N2-dimethylethane-1,2-diamine, 38.1 mg of copper(I) iodide, 138.2 mg of potassium carbonate, 79.9 mg of 1H-benz[d]imidazol-2-amine, and 2 mL of dimethyl sulfoxide was stirred in an argon atmosphere under microwave irradiation at 130° C. for three hours. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=40/60→70/30 (v/v)), to thereby produce 5.1 mg of the title compound as a brown solid.

Synthesis Example 101

2-Acetamido-N-cyclopropyl-7-hydroxy-4-neopentyl-5-oxo-4,5-dihydropyrazolo[1,5-a]pyrimidine-6-carboxamide 11.8 μL of acetic anhydride was added to a mixture of 20 mg of 2-amino-N-cyclopropyl-7-hydroxy-4-neopentyl-5-oxo-4,5-dihydropyrazolo[1,5-a]pyrimidine-6-carboxamide produced in Synthesis Example 18, 25 μL of pyridine, 1.53 mg of N,N-dimethyl-4-aminopyridine, and 0.4 mL of toluene at room temperature, and the resultant mixture was stirred for one hour. 2 M aqueous hydrochloric acid solution was added to the reaction mixture, and then the mixture was subjected to extraction with chloroform. Thereafter, the extract was concentrated under reduced pressure. The residue was purified by silica gel column chromatography (chloroform/methanol=95/5→70/30 (v/v)), to thereby produce 14.69 mg of the title compound as a white solid.

Synthesis Example 102

2-Amino-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide Substantially the same reaction as in Synthesis Example 18 was performed by using 2-bromo-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide produced in step C of Synthesis Example 27 in place of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, to thereby produce 320 mg of the title compound as a brown solid.

Synthesis Example 103

N-Cyclopropyl-7-hydroxy-4-((4-methyltetrahydro-2H-pyran-4-yl)methyl)-5-oxo-2-(2-oxoimidazolidin-1-yl)-4,5-dihydropyrazolo[1,5-a]pyrimidine-6-carboxamide 53.5 μL of 2-chloroethyl isocyanate was added to a mixture of 40 mg of 2-amino-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide produced in Synthesis Example 102 and 0.8 mL of tetrahydrofuran at room temperature, and the resultant mixture was stirred at 80° C. overnight. Subsequently, 52.0 mg of potassium tert-butoxide was added to the reaction mixture, and the mixture was stirred at 80° C. for two hours. The reaction mixture was cooled to room temperature, and water was added to the mixture. Thereafter, the resultant mixture was subjected to extraction with chloroform, and the extract was concentrated under reduced pressure. The residue was purified by silica gel reversed-phase column chromatography (0.1% formic acid-acetonitrile/0.1% aqueous formic acid solution=30/70→60/40 (v/v)), to thereby produce 6.66 mg of the title compound as a white solid.

Synthesis Example 104

3-Bromo-N-cyclopropyl-7-hydroxy-4-isobutyl-5-oxo-4,5-dihydropyrazolo[1,5-a]pyrimidine-6-carboxamide Substantially the same reaction as in steps A, B, and C of Synthesis Example 22 was performed by using 4-bromo-1H-pyrazol-5-amine in place of 3-bromo-1H-pyrazol-5-amine, to thereby produce 400 mg of the title compound as a yellow solid.

Synthesis Example 105

N-Cyclopropyl-7-hydroxy-4-isobutyl-5-oxo-3-((tetrahydro-4H-pyran-4-ylidene)methyl)-4,5-dihydropyrazolo[1,5-a]pyrimidine-6-carboxamide 532 μL of n-butyllithium hexane solution (1.55 M hexane solution) was added to a mixture of 136.2 μL of 2,2,6,6-tetramethylpiperidine and 0.8 mL of tetrahydrofuran at 0° C., and the resultant mixture was stirred for 10 minutes. Thereafter, 80 mg of bis[(pinacolato)boryl]methane was added to the mixture, and the resultant mixture was stirred at 0° C. for 30 minutes. The reaction mixture was cooled to −78° C., and 36.74 μL of tetrahydro-4H-pyran-4-one was added to the mixture, followed by stirring at −78° C. for one hour. The reaction mixture was heated to room temperature, and the mixture was concentrated under reduced pressure. To the residue were added 73.6 mg of 3-bromo-N-cyclopropyl-7-hydroxy-4-isobutyl-5-oxo-4,5-dihydropyrazolo[1,5-a]pyrimidine-6-carboxamide produced in Synthesis Example 104, 13 mg of [1,1'-bis(di-tert-butylphosphino)ferrocene]dichloropalladium(II), 82.9 mg of potassium carbonate, 0.8 mL of 1,4-dioxane, and 0.8 mL of water, and the resultant mixture was stirred at 110° C. overnight. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=60/30→70/30 (v/v)), to thereby produce 1.85 mg of the title compound as a colorless oily product.

Synthesis Example 106

N-Cyclopropyl-7-hydroxy-4-neopentyl-5-oxo-2-(1H-pyrazol-1-yl)-4,5-dihydropyrazolo[1,5-a]pyrimidine-6-carboxamide A mixture of 76.7 mg of 2-bromo-N-cyclopropyl-7-hydroxy-4-neopentyl-5-oxo-4,5-dihydropyrazolo[1,5-a]pyrimidine-6-carboxamide produced in step C of Synthesis Example 11, 40.8 mg of 1H-pyrazole, 38.1 mg of copper(I) iodide, 110.6 mg of potassium carbonate, and 2 mL of N-methylpyrrolidone was stirred in an argon atmosphere under microwave irradiation at 160° C. for three hours. The reaction mixture was cooled to room temperature and subjected to filtration, and then the filtrate was concentrated under reduced pressure. The residue was purified by silica gel reversed-phase column chromatography (0.1% formic acid-acetonitrile/0.1% aqueous formic acid solution=60/40→70/30 (v/v)), to thereby produce 7.0 mg of the title compound as a pale brown solid.

The compounds of Synthesis Examples 107 to 214 were produced according to the methods described in the aforementioned Synthesis Examples or methods similar thereto.

Synthesis Example 107

N-Cyclopropyl-3-(3,6-dihydro-2H-pyran-4-yl)-7-hydroxy-4-((4-methyltetrahydro-2H-pyran-4-yl)methyl)-5-oxo-4,5-dihydropyrazolo[1,5-a]pyrimidine-6-carboxamide Yield: 4.67 mg, brown amorphous product Synthesis Example 108

N-Cyclopropyl-7-hydroxy-5-oxo-4-((tetrahydro-2H-pyran-4-yl)methyl)-3-(2,2,6,6-tetramethyl-3,6-dihydro-2H-pyran-4-yl)-4,5-dihydropyrazolo[1,5-a]pyrimidine-6-carboxamide Yield: 50.4 mg, pale brown solid Synthesis Example 109

N-Cyclopropyl-3-(3,6-dihydro-2H-pyran-4-yl)-7-hydroxy-4-neopentyl-5-oxo-4,5-dihydropyrazolo[1,5-a]pyrimidine-6-carboxamide Yield: 47.6 mg, brown amorphous product Synthesis Example 110

N-Cyclopropyl-4-((4,4-difluorocyclohexyl)methyl)-3-(3,6-dihydro-2H-pyran-4-yl)-7-hydroxy-5-oxo-4,5-dihydropyrazolo[1,5-a]pyrimidine-6-carboxamide Yield: 49.0 mg, pale brown solid Synthesis Example 111

N-Cyclopropyl-4-(2,6-dichlorobenzyl)-3-(3,6-dihydro-2H-pyran-4-yl)-7-hydroxy-5-oxo-4,5-dihydropyrazolo[1,5-a]pyrimidine-6-carboxamide Yield: 28.8 mg, pale brown solid Synthesis Example 112

N-Cyclopropyl-3-(3,6-dihydro-2H-pyran-4-yl)-7-hydroxy-5-oxo-4-(2,4,6-trifluorobenzyl)-4,5-dihydropyrazolo[1,5-a]pyrimidine-6-carboxamide Yield: 78.0 mg, white solid Synthesis Example 113

N-Cyclopropyl-3-(3,6-dihydro-2H-pyran-4-yl)-4-(4-fluorobenzyl)-7-hydroxy-5-oxo-4,5-dihydropyrazolo[1,5-a]pyrimidine-6-carboxamide Yield: 48.0 mg, white solid Synthesis Example 114

N-Cyclopropyl-3-(3,6-dihydro-2H-pyran-4-yl)-4-(3,3-dimethylbutyl)-7-hydroxy-5-oxo-4,5-dihydropyrazolo[1,5-a]pyrimidine-6-carboxamide Yield: 26.6 mg, brown solid Synthesis Example 115

Tert-butyl 4-(6-(cyclopropylcarbamoyl)-7-hydroxy-4-neopentyl-5-oxo-4,5-dihydropyrazolo[1,5-a]pyrimidin-3-yl)-3,6-dihydropyridine-1 (2H)-carboxylate Yield: 20.82 mg, yellow solid Synthesis Example 116

N-Cyclopropyl-7-hydroxy-4-neopentyl-5-oxo-3-(1,2,3,6-tetrahydropyridin-4-yl)-4,5-dihydropyrazolo[1,5-a]pyrimidine-6-carboxamide hydrochloride Yield: 3.48 mg, yellow solid Synthesis Example 117

(R)—N-Cyclopropyl-7-hydroxy-2-(3-hydroxypyrrolidin-1-yl)-4-neopentyl-5-oxo-4,5-dihydropyrazolo[1,5-a]pyrimidine-6-carboxamide Yield: 4.5 mg, brown solid Synthesis Example 118

Tert-butyl 4-(6-(cyclopropylcarbamoyl)-7-hydroxy-5-oxo-4-((tetrahydro-2H-pyran-4-yl)methyl)-4,5-dihydropyrazolo[1,5-a]pyrimidin-3-yl)-3,6-dihydropyridine-1 (2H)-carboxylate Yield: 62.15 mg, brown amorphous product Synthesis Example 119

(E)-N-Cyclopropyl-3-((ethoxyimino)methyl)-7-hydroxy-4-isobutyl-5-oxo-4,5-dihydropyrazolo[1,5-a]pyrimidine-6-carboxamide Yield: 8.03 mg, yellow solid Synthesis Example 120

3-(Cyclohex-1-en-1-yl)-N-cyclopropyl-7-hydroxy-5-oxo-4-((tetrahydro-2H-pyran-4-yl)methyl)-4,5-dihydropyrazolo[1,5-a]pyrimidine-6-carboxamide Yield: 21.8 mg, brown solid Synthesis Example 121

N-Cyclopropyl-3-(3,6-dihydro-2H-pyran-4-yl)-7-hydroxy-4-isobutyl-5-oxo-4,5-dihydropyrazolo[1,5-a]pyrimidine-6-carboxamide Yield: 23.9 mg, pale yellow amorphous product Synthesis Example 122

N-Cyclopropyl-7-hydroxy-4-isobutyl-5-oxo-3-(1,2,3,6-tetrahydropyridin-4-yl)-4,5-dihydropyrazolo[1,5-a]pyrimidine-6-carboxamide hydrochloride Yield: 1.43 mg, brown amorphous product Synthesis Example 123

N-Cyclopropyl-7-hydroxy-3-(1-methyl-1,2,3,6-tetrahydropyridin-4-yl)-4-neopentyl-5-oxo-4,5-dihydropyrazolo[1,5-a]pyrimidine-6-carboxamide Yield: 3.4 mg, white solid Synthesis Example 124

4-(Cyclohexylmethyl)-N-cyclopropyl-3-(3,6-dihydro-2H-pyran-4-yl)-7-hydroxy-5-oxo-4,5-dihydropyrazolo[1,5-a]pyrimidine-6-carboxamide Yield: 54.9 mg, pale brown amorphous product Synthesis Example 125

N-Cyclopropyl-7-hydroxy-4-isobutyl-5-oxo-3-(pyridin-2-yl)-4,5-dihydropyrazolo[1,5-a]pyrimidine-6-carboxamide Yield: 45.02 mg, brown solid Synthesis Example 126

N-Cyclopropyl-3-(3,6-dihydro-2H-pyran-4-yl)-4-(2-ethylbutyl)-7-hydroxy-5-oxo-4,5-dihydropyrazolo[1,5-a]pyrimidine-6-carboxamide Yield: 42.5 mg, pale brown amorphous product Synthesis Example 127

N-Cyclopropyl-7-hydroxy-5-oxo-3-(pyridin-2-yl)-4-((tetrahydro-2H-pyran-4-yl)methyl)-4,5-dihydropyrazolo[1,5-a]pyrimidine-6-carboxamide Yield: 65.11 mg, brown solid Synthesis Example 128

N-Cyclopropyl-7-hydroxy-4-isobutyl-5-oxo-3-(6-(trifluoromethyl)pyridin-3-yl)-4,5-dihydropyrazolo[1,5-a]pyrimidine-6-carboxamide Yield: 2.71 mg, brown amorphous product Synthesis Example 129

N-Cyclopropyl-7-hydroxy-4-isobutyl-3-(1-methyl-1,2,3,6-tetrahydropyridine-4-yl)-5-oxo-4,5-dihydropyrazolo[1,5-a]pyrimidine-6-carboxamide Yield: 5.9 mg, pale yellow amorphous product Synthesis Example 130

N-Cyclopropyl-7-hydroxy-4-isobutyl-5-oxo-3-(piperidin-4-ylidenemethyl)-4,5-dihydropyrazolo[1,5-a]pyrimidine-6-carboxamide hydrochloride Yield: 5.73 mg, yellow solid Synthesis Example 131

N-Cyclopropyl-7-hydroxy-5-oxo-3-phenyl-4-((tetrahydro-2H-pyran-4-yl)methyl)-4,5-dihydropyrazolo[1,5-a]pyrimidine-6-carboxamide Yield: 26.24 mg, brown amorphous product Synthesis Example 132

(E)-N-Cyclopropyl-7-hydroxy-4-isobutyl-3-(((2-morpholino-2-oxoethoxy)imin o)methyl)-5-oxo-4,5-dihydropyrazolo[1,5-a]pyrimidine-6-carboxamide Yield: 27.27 mg, white solid Synthesis Example 133

3-(Cyclohex-1-en-1-yl)-N-cyclopropyl-7-hydroxy-4-isobutyl-5-oxo-4,5-dihydropyrazolo[1,5-a]pyrimidine-6-carboxamide Yield: 1.1 mg, pale yellow amorphous product Synthesis Example 134

N-Cyclopropyl-7-hydroxy-3-(1-methyl-1,2,3,6-tetrahydropyridin-4-yl)-5-oxo-4-((tetrahydro-2H-pyran-4-yl)methyl)-4,5-dihydropyrazolo[1,5-a]pyrimidine-6-carboxamide Yield: 9.13 mg, pale yellow solid Synthesis Example 135

N,2-Dicyclopropyl-7-hydroxy-5-oxo-4-((tetrahydro-2H-pyran-4-yl)methyl)-4,5-dihydropyrazolo[1,5-a]pyrimidine-6-carboxamide Yield: 1900.1 mg, pale brown solid Synthesis Example 136

Methyl 4-(6-(cyclopropylcarbamoyl)-7-hydroxy-4-isobutyl-5-oxo-4,5-dihydropyrazolo[1,5-a]pyrimidin-3-yl)benzoate Yield: 12.32 mg, brown amorphous product Synthesis Example 137

Tert-butyl 4-(6-(cyclopropylcarbamoyl)-7-hydroxy-4-isobutyl-5-oxo-4,5-dihydropyrazolo[1,5-a]pyrimidin-3-yl)-3,6-dihydropyridine-1 (2H)-carboxylate Yield: 14.51 mg, brown amorphous product Synthesis Example 138

N-Cyclopropyl-4-(2,6-dichlorobenzyl)-7-hydroxy-3-(1-methyl-1,2,3,6-tetrahydropyridin-4-yl)-5-oxo-4,5-dihydropyrazolo[1,5-a]pyrimidine-6-carboxamide Yield: 10.7 mg, brown solid Synthesis Example 139

N-Cyclopropyl-4-(4-fluorobenzyl)-7-hydroxy-3-(1-methyl-1,2,3,6-tetrahydropyridin-4-yl)-5-oxo-4,5-dihydropyrazolo[1,5-a]pyrimidine-6-carboxamide Yield: 37.7 mg, pale brown solid Synthesis Example 140

N-Cyclopropyl-7-hydroxy-5-oxo-4-((tetrahydro-2H-pyran-4-yl)methyl)-3-(1,2,3,6-tetrahydropyridin-4-yl)-4,5-dihydropyrazolo[1,5-a]pyrimidine-6-carboxamide hydrochloride Yield: 50.6 mg, pale brown solid Synthesis Example 141

3-(6-Aminopyridin-3-yl)-N-cyclopropyl-7-hydroxy-5-oxo-4-((tetrahydro-2H-pyran-4-yl)methyl)-4,5-dihydropyrazolo[1,5-a]pyrimidine-6-carboxamide Yield: 16.6 mg, pale brown solid Synthesis Example 142

N-Cyclopropyl-7-hydroxy-4-isobutyl-5-oxo-3-(piperidin-4-ylmethyl)-4,5-dihydropyrazolo[1,5-a]pyrimidine-6-carboxamide hydrochloride Yield: 15.86 mg, white solid Synthesis Example 143

N-Cyclopropyl-3-(5,6-dihydro-1,4-dioxin-2-yl)-7-hydroxy-4-isobutyl-5-oxo-4,5-dihydropyrazolo[1,5-a]pyrimidine-6-carboxamide Yield: 25.34 mg, white solid Synthesis Example 144

(E)-N-Cyclopropyl-3-(2-ethoxyvinyl)-7-hydroxy-5-oxo-4-((tetrahydro-2H-pyran-4-yl)methyl)-4,5-dihydropyrazolo[1,5-a]pyrimidine-6-carboxamide Yield: 28.5 mg, pale brown solid Synthesis Example 145

(E)-N-Cyclopropyl-4-((4,4-difluorocyclohexyl)methyl)-3-(2-ethoxyvinyl)-7-hydroxy-5-oxo-4,5-dihydropyrazolo[1,5-a]pyrimidine-6-carboxamide Yield: 29.8 mg, pale brown solid Synthesis Example 146

Tert-butyl 4-((6-(cyclopropylcarbamoyl)-7-hydroxy-4-isobutyl-5-oxo-4,5-dihydropyrazolo[1,5-a]pyrimidin-3-yl)methylene) piperidine-1-carboxylate Yield: 15 mg, yellow oily product Synthesis Example 147

N-Cyclopropyl-4-(2-ethylbutyl)-7-hydroxy-3-(1-methyl-1,2,3,6-tetrahydropyridin-4-yl)-5-oxo-4,5-dihydropyrazolo[1,5-a]pyrimidine-6-carboxamide Yield: 39.3 mg, pale brown amorphous product Synthesis Example 148

N-Cyclopropyl-7-hydroxy-3-(1-methyl-1,2,3,6-tetrahydropyridin-4-yl)-5-oxo-4-(2,4,6-trifluorobenzyl)-4,5-dihydropyrazolo[1,5-a]pyrimidine-6-carboxamide Yield: 58.5 mg, pale brown solid Synthesis Example 149

Tert-butyl (4-(6-(cyclopropylcarbamoyl)-7-hydroxy-4-isobutyl-5-oxo-4,5-dihydropyrazolo[1,5-a]pyrimidin-3-yl)phenyl)carbamate Yield: 1.37 mg, brown amorphous product Synthesis Example 150

3-(3-(Benzyloxy)phenyl)-N-cyclopropyl-7-hydroxy-4-isobutyl-5-oxo-4,5-dihydropyrazolo[1,5-a]pyrimidine-6-carboxamide Yield: 10.07 mg, brown amorphous product Synthesis Example 151

3-(4-(Benzyloxy)phenyl)-N-cyclopropyl-7-hydroxy-4-isobutyl-5-oxo-4,5-dihydropyrazolo[1,5-a]pyrimidine-6-carboxamide Yield: 3.76 mg, brown amorphous product Synthesis Example 152

N,3-Dicyclopropyl-7-hydroxy-4-isobutyl-5-oxo-4,5-dihydropyrazolo[1,5-a]pyrimidine-6-carboxamide Yield: 38.6 mg, pale brown solid Synthesis Example 153

(E)-N-Cyclopropyl-7-hydroxy-4-isobutyl-5-oxo-3-(3-oxo-3-(piperidin-1-yl)prop-1-en-1-yl)-4,5-dihydropyrazolo[1,5-a]pyrimidine-6-carboxamide Yield: 12.76 mg, white amorphous product Synthesis Example 154

(E)-N-Cyclopropyl-7-hydroxy-4-isobutyl-3-(3-(isopropylamino)-3-oxoprop-1-en-1-yl)-5-oxo-4,5-dihydropyrazolo[1,5-a]pyrimidine-6-carboxamide Yield: 49.95 mg, yellow solid Synthesis Example 155

Tert-butyl (E)-3-(6-(cyclopropylcarbamoyl)-7-hydroxy-4-isobutyl-5-oxo-4,5-dihydropyrazolo[1,5-a]pyrimidin-3-yl)acrylate Yield: 12.18 mg, colorless solid Synthesis Example 156

(E)-N-Cyclopropyl-7-hydroxy-4-isobutyl-3-(3-(4-methylpiperazin-1-yl)-3-oxoprop-1-en-1-yl)-5-oxo-4,5-dihydropyrazolo[1,5-a]pyrimidine-6-carboxamide Yield: 8.84 mg, yellow solid Synthesis Example 157

(E)-N-Cyclopropyl-3-(3-(dimethylamino)-3-oxoprop-1-en-1-yl)-7-hydroxy-4-isobutyl-5-oxo-4,5-dihydropyrazolo[1,5-a]pyrimidine-6-carboxamide Yield: 7.36 mg, white solid Synthesis Example 158

(E)-N-Cyclopropyl-3-(3-((3,3-difluorocyclobutyl)amino)-3-oxoprop-1-en-1-yl)-7-hydroxy-4-isobutyl-5-oxo-4,5-dihydropyrazolo[1,5-a]pyrimidine-6-carboxamide Yield: 1.84 mg, white solid Synthesis Example 159

(E)-N-Cyclopropyl-7-hydroxy-3-(3-morpholino-3-oxoprop-1-en-1yl)-5-oxo-4-((tetrahydro-2H-pyran-4-yl)methyl)-4,5-dihydropyrazolo[1,5-a]pyrimidine-6-carboxamide Yield: 1.16 mg, white solid Synthesis Example 160

(E)-3-(3-Amino-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 4.41 mg, white solid Synthesis Example 161

(E)-N-Cyclopropyl-7-hydroxy-3-(3-(hydroxy(methyl)amino)-3-oxoprop-1-en-1-yl)-4-isobutyl-5-oxo-4,5-dihydropyrazolo[1,5-a]pyrimidine-6-carboxamide Yield: 7.0 mg, white solid Synthesis Example 162

(E)-N-Cyclopropyl-7-hydroxy-3-(3-(4-hydroxy-4-(trifluoromethyl) piperidin-1-yl)-3-oxoprope-1-en-1-yl)-5-oxo-4-((tetrahydro-2H-pyran-4-yl)methyl)-4,5-dihydropyrazolo[1,5-a]pyrimidine-6-carboxamide Yield: 0.75 mg, yellow oily product Synthesis Example 163

(E)-N-Cyclopropyl-3-(3-(cis-2,6-dimethylmorpholino)-3-oxoprop-1-en-1-yl)-7-hydroxy-5-oxo-4-((tetrahydro-2H-pyran-4-yl)methyl)-4,5-dihydropyrazolo[1,5-a]pyrimidine-6-carboxamide Yield: 8.99 mg, white solid Synthesis Example 164

N-Cyclopropyl-7-hydroxy-4-isobutyl-3-(3-morpholino-3-oxopropyl)-5-oxo-4,5-dihydropyrazolo[1,5-a]pyrimidine-6-carboxamide Yield: 8.79 mg, white solid Synthesis Example 165

N-Cyclopropyl-7-hydroxy-4-isobutyl-3-(3-(4-methylpiperazin-1-yl)-3-oxopropyl)-5-oxo-4,5-dihydropyrazolo[1,5-a]pyrimidine-6-carboxamide Yield: 15.34 mg, white solid Synthesis Example 166

N-Cyclopropyl-7-hydroxy-4-isobutyl-3-(3-(isopropylamino)-3-oxopropyl)-5-oxo-4,5-dihydropyrazolo[1,5-a]pyrimidine-6-carboxamide Yield: 11.68 mg, white solid Synthesis Example 167

N-Cyclopropyl-3-(3-((3,3-difluorocyclobutyl)amino)-3-oxopropyl)-7-hydroxy-4-isobutyl-5-oxo-4,5-dihydropyrazolo[1,5-a]pyrimidine-6-carboxamide Yield: 12.61 mg, white solid Synthesis Example 168

(E)-N-Cyclopropyl-3-(3-(cis-2,6-dimethylmorpholino)-3-oxoprop-1-en-1-yl)-7-hydroxy-4-neopentyl-5-oxo-4,5-dihydropyrazolo[1,5-a]pyrimidine-6-carboxamide Yield: 15.58 mg, white solid Synthesis Example 169

(E)-N-Cyclopropyl-7-hydroxy-3-(3-morpholino-3-oxoprop-1-en-1-yl)-4-neopentyl-5-oxo-4,5-dihydropyrazolo[1,5-a]pyrimidine-6-carboxamide Yield: 20.56 mg, white amorphous product Synthesis Example 170

(E)-N-Cyclopropyl-7-hydroxy-4-neopentyl-5-oxo-3-(3-oxo-3-((tetrahydro-2H-pyran-4-yl)amino)prop-1-en-1-yl)-4,5-dihydropyrazolo[1,5-a]pyrimidine-6-carboxamide Yield: 12.87 mg, white solid Synthesis Example 171

2-(4-Aminopyridin-3-yl)-N-cyclopropyl-7-hydroxy-4-isobutyl-5-oxo-4,5-dihydropyrazolo[1,5-a]pyrimidine-6-carboxamide Yield: 6.84 mg, white solid Synthesis Example 172

N-Cyclopropyl-7-hydroxy-4-isobutyl-5-oxo-2-(pyridin-4-yl)-4,5-dihydropyrazolo[1,5-a]pyrimidine-6-carboxamide Yield: 16.13 mg, yellow solid Synthesis Example 173

2-(3-Aminopyridin-4-yl)-N-cyclopropyl-7-hydroxy-4-isobutyl-5-oxo-4,5-dihydropyrazolo[1,5-a]pyrimidine-6-carboxamide Yield: 2.07 mg, yellow solid Synthesis Example 174

N-Cyclopropyl-7-hydroxy-4-isobutyl-5-oxo-2-(pyridin-2-ylamino)-4,5-dihydropyrazolo[1,5-a]pyrimidine-6-carboxamide Yield: 4.03 mg, yellow solid Synthesis Example 175

N6-Cyclopropyl-7-hydroxy-4-isobutyl-5-oxo-4,5-dihydropyrazolo[1,5-a]pyrimidine-2,6-dicarboxamide Yield: 3.65 mg, yellow solid Synthesis Example 176

N-Cyclopropyl-7-hydroxy-4-isobutyl-5-oxo-2-(pyridin-2-yl)-4,5-dihydropyrazolo[1,5-a]pyrimidine-6-carboxamide Yield: 13.7 mg, white solid Synthesis Example 177

N-Cyclopropyl-7-hydroxy-4-isobutyl-5-oxo-2-(pyridin-3-yl)-4,5-dihydropyrazolo[1,5-a]pyrimidine-6-carboxamide Yield: 20.33 mg, brown solid Synthesis Example 178

2-(6-Aminopyridin-3-yl)-N-cyclopropyl-7-hydroxy-4-isobutyl-5-oxo-4,5-dihydropyrazolo[1,5-a]pyrimidine-6-carboxamide Yield: 5.45 mg, red solid Synthesis Example 179

2-(5-Aminopyridin-3-yl)-N-cyclopropyl-7-hydroxy-4-isobutyl-5-oxo-4,5-dihydropyrazolo[1,5-a]pyrimidine-6-carboxamide Yield: 8.96 mg, white solid Synthesis Example 180

N-Cyclopropyl-7-hydroxy-4-isobutyl-5-oxo-2-vinyl-4,5-dihydropyrazolo[1,5-a]pyrimidine-6-carboxamide Yield: 6.81 mg, white solid Synthesis Example 181

2-Cyclobutyl-N-cyclopropyl-7-hydroxy-4-isobutyl-5-oxo-4,5-dihydropyrazolo[1,5-a]pyrimidine-6-carboxamide Yield: 19 mg, brown oily product Synthesis Example 182

2-(2-Amino-2-oxoethyl)-N-cyclopropyl-7-hydroxy-4-isobutyl-5-oxo-4,5-dihydropyrazolo[1,5-a]pyrimidine-6-carboxamide Yield: 6.10 mg, yellow solid Synthesis Example 183

N-Cyclopropyl-7-hydroxy-4-neopentyl-5-oxo-2-(1H-pyrazol-5-yl)-4,5-dihydropyrazolo[1,5-a]pyrimidine-6-carboxamide Yield: 23.5 mg, pale brown solid Synthesis Example 184

N-Cyclopropyl-7-hydroxy-4-(3-hydroxy-2,2-dimethylpropyl)-5-oxo-2-(pyrazin-2-ylamino)-4,5-dihydropyrazolo[1,5-a]pyrimidine-6-carboxamide Yield: 2.20 mg, yellow solid Synthesis Example 185

2-(2-Aminopyridin-3-yl)-N-cyclopropyl-7-hydroxy-4-(3-hydroxy-2,2-dimethylpropyl)-5-oxo-4,5-dihydropyrazolo[1,5-a]pyrimidine-6-carboxamide Yield: 6.05 mg, brown solid Synthesis Example 186

N-Cyclopropyl-7-hydroxy-4-neopentyl-5-oxo-2-(pyrimidin-5-ylamino)-4,5-dihydropyrazolo[1,5-a]pyrimidine-6-carboxamide Yield: 3.17 mg, white solid Synthesis Example 187

N-Cyclopropyl-7-hydroxy-4-((4-methyltetrahydro-2H-pyran-4-yl)methyl)-5-oxo-2-ureido-4,5-dihydro-pyrazolo[1,5-a]pyrimidine-6-carboxamide Yield: 5.81 mg, yellow solid Synthesis Example 188

N-Cyclopropyl-7-hydroxy-4-neopentyl-5-oxo-2-((pyrazin-2-ylmethyl)amino)-4,5-dihydropyrazolo[1,5-a]pyrimidine-6-carboxamide Yield: 37.84 mg, yellow solid Synthesis Example 189

N-Cyclopropyl-7-hydroxy-4-neopentyl-5-oxo-2-(pyridazin-4-ylamino)-4,5-dihydropyrazolo[1,5-a]pyrimidine-6-carboxamide Yield: 17.64 mg, white solid Synthesis Example 190

N-Cyclopropyl-7-hydroxy-2-((3-morpholinopropyl)amino)-4-neopentyl-5-oxo-4,5-dihydropyrazolo[1,5-a]pyrimidine-6-carboxamide Yield: 58.1 mg, brown solid Synthesis Example 191

N-Cyclopropyl-7-hydroxy-4-neopentyl-5-oxo-2-(pyridazin-3-ylamino)-4,5-dihydropyrazolo[1,5-a]pyrimidine-6-carboxamide Yield: 38.23 mg, yellow solid Synthesis Example 192

N-Cyclopropyl-7-hydroxy-2-((2-morpholinoethyl)amino)-4-neopentyl-5-oxo-4,5-dihydropyrazolo[1,5-a]pyrimidine-6-carboxamide Yield: 59.4 mg, brown solid Synthesis Example 193

2-(2-Aminophenyl)-N-cyclopropyl-7-hydroxy-4-neopentyl-5-oxo-4,5-dihydropyrazolo[1,5-a]pyrimidine-6-carboxamide Yield: 16.3 mg, white solid Synthesis Example 194

2-(3-Aminopyrazin-2-yl)-N-cyclopropyl-7-hydroxy-4-neopentyl-5-oxo-4,5-dihydropyrazolo[1,5-a]pyrimidine-6-carboxamide hydrochloride Yield: 11 mg, white solid Synthesis Example 195

N-Cyclopropyl-7-hydroxy-2-((4-methoxypyridin-2-yl)amino)-4-neopentyl-5-oxo-4,5-dihydropyrazolo[1,5-a]pyrimidine-6-carboxamide Yield: 19.9 mg, pale brown solid Synthesis Example 196

N-Cyclopropyl-7-hydroxy-4-neopentyl-5-oxo-2-(2-oxopyrrolidin-1-yl)-4,5-dihydropyrazolo[1,5-a]pyrimidine-6-carboxamide Yield: 18.5 mg, white solid Synthesis Example 197

2-(4-Carbamoylpyridin-3-yl)-N-cyclopropyl-7-hydroxy-4-neopentyl-5-oxo-4,5-dihydropyrazolo[1,5-a]pyrimidine-6-carboxamide Yield: 7.3 mg, yellow solid Synthesis Example 198

N-Cyclopropyl-7-hydroxy-2-(4-hydroxypyridin-3-yl)-4-neopentyl-5-oxo-4,5-dihydropyrazolo[1,5-a]pyrimidine-6-carboxamide Yield: 6.24 mg, white solid Synthesis Example 199

2-(2-Amino-6-carbamoylphenyl)-N-cyclopropyl-7-hydroxy-4-neopentyl-5-oxo-4,5-dihydropyrazolo[1,5-a]pyrimidine-6-carboxamide Yield: 1.69 mg, yellow oily product Synthesis Example 200

2-(4-Aminopyrimidin-2-yl)-N-cyclopropyl-7-hydroxy-4-neopentyl-5-oxo-4,5-dihydropyrazolo[1,5-a]pyrimidine-6-carboxamide hydrochloride Yield: 7 mg, pale yellow solid Synthesis Example 201

2-(2-Aminopyrimidin-4-yl)-N-cyclopropyl-7-hydroxy-4-neopentyl-5-oxo-4,5-dihydropyrazolo[1,5-a]pyrimidine-6-carboxamide Yield: 14.7 mg, pale yellow solid Synthesis Example 202

2-(6-Aminopyrazin-2-yl)-N-cyclopropyl-7-hydroxy-4-neopentyl-5-oxo-4,5-dihydropyrazolo[1,5-a]pyrimidine-6-carboxamide hydrochloride Yield: 7.7 mg, pale yellow solid Synthesis Example 203

2-(6-Aminopyridin-2-yl)-N-cyclopropyl-7-hydroxy-4-neopentyl-5-oxo-4,5-dihydropyrazolo[1,5-a]pyrimidine-6-carboxamide hydrochloride Yield: 9.6 mg, white solid Synthesis Example 204

N-Cyclopropyl-7-hydroxy-2-((4-methylpyridin-2-yl)amino)-4-neopentyl-5-oxo-4,5-dihydropyrazolo[1,5-a]pyrimidine-6-carboxamide Yield: 12.8 mg, pale yellow solid Synthesis Example 205

2-(5-Amino-1H-pyrazol-3-yl)-N-cyclopropyl-7-hydroxy-4-neopentyl-5-oxo-4,5-dihydropyrazolo[1,5-a]pyrimidine-6-carboxamide Yield: 7.2 mg, white solid Synthesis Example 206

N-Cyclopropyl-7-hydroxy-4-neopentyl-5-oxo-2-(pyridin-2-ylamino)-4,5-dihydropyrazolo[1,5-a]pyrimidine-6-carboxamide Yield: 4.24 mg, yellow oily product Synthesis Example 207

2-(2-Carbamoylphenyl)-N-cyclopropyl-7-hydroxy-4-((4-methyltetrahydro-2H-pyran-4-yl)methyl)-5-oxo-4,5-dihydropyrazolo[1,5-a]pyrimidine-6-carboxamide Yield: 23.37 mg, white solid Synthesis Example 208

N-Cyclopropyl-7-hydroxy-4-((4-methyltetrahydro-2H-pyran-4-yl)methyl)-5-oxo-2-(2-(2-oxoimidazolidin-1-yl)pyridin-3-yl)-4,5-dihydropyrazolo[1,5-a]pyrimidine-6-carboxamide Yield: 5.96 mg, white solid Synthesis Example 209

N-Cyclopropyl-7-hydroxy-4-neopentyl-5-oxo-2-vinyl-4,5-dihydropyrazolo[1,5-a]pyrimidine-6-carboxamide Yield: 2.58 mg, yellow oily product Synthesis Example 210

2-(2-Amino-5-methylpyridin-3-yl)-N-cyclopropyl-7-hydroxy-4-neopentyl-5-oxo-4,5-dihydropyrazolo[1,5-a]pyrimidine-6-carboxamide Yield: 8.9 mg, pale brown solid Synthesis Example 211

N-Cyclopropyl-7-hydroxy-4-((4-methyltetrahydro-2H-pyran-4-yl)methyl)-5-oxo-2-(2-ureidopyridin-3-yl)-4,5-dihydropyrazolo[1,5-a]pyrimidine-6-carboxamide Yield: 29.62 mg, white solid Synthesis Example 212

2-(2-Amino-3-fluorophenyl)-N-cyclopropyl-7-hydroxy-4-neopentyl-5-oxo-4,5-dihydropyrazolo[1,5-a]pyrimidine-6-carboxamide Yield: 4.5 mg, white solid Synthesis Example 213

N-Cyclopropyl-7-hydroxy-4-neopentyl-5-oxo-2-(2-oxo-1,2-dihydropyridin-3-yl)-4,5-dihydropyrazolo[1,5-a]pyrimidine-6-carboxamide Yield: 6.6 mg, white solid Synthesis Example 214

2-(3-Amino-1H-pyrazol-1-yl)-N-cyclopropyl-7-hydroxy-4-neopentyl-5-oxo-4,5-dihydropyrazolo[1,5-a]pyrimidine-6-carboxamide Yield: 7.0 mg, brown solid The compounds of Synthesis Examples 215 to 258 were produced according to the methods described in the aforementioned Synthesis Examples or methods similar thereto.

Synthesis Example 215

N6-Cyclopropyl-7-hydroxy-4-isobutyl-5-oxo-N3-(pyridin-2-ylmethyl)-4,5-dihydropyrazolo[1,5-a]pyrimidine-3,6-dicarboxamide Yield: 28.08 mg, white solid Synthesis Example 216

N6-Cyclopropyl-7-hydroxy-4-isobutyl-5-oxo-N3-(pyridin-3-ylmethyl)-4,5-dihydropyrazolo[1,5-a]pyrimidine-3,6-dicarboxamide Yield: 29.9 mg, white solid Synthesis Example 217

N6-Cyclopropyl-7-hydroxy-4-isobutyl-5-oxo-N3-(pyridin-4-ylmethyl)-4,5-dihydropyrazolo[1,5-a]pyrimidine-3,6-dicarboxamide Yield: 16.6 mg, white solid Synthesis Example 218

(S)-N6-Cyclopropyl-7-hydroxy-4-isobutyl-5-oxo-N3-(1-(pyridin-2-yl)ethyl)-4,5-dihydropyrazolo[1,5-a]pyrimidine-3,6-dicarboxamide Yield: 30.82 mg, white solid Synthesis Example 219

(R)-N6-Cyclopropyl-7-hydroxy-4-isobutyl-5-oxo-N3-(1-(pyridin-2-yl)ethyl)-4,5-dihydropyrazolo[1,5-a]pyrimidine-3,6-dicarboxamide Yield: 33.22 mg, white solid Synthesis Example 220

N6-Cyclopropyl-7-hydroxy-4-isobutyl-5-oxo-N3-(pyrazin-2-ylmethyl)-4,5-dihydropyrazolo[1,5-a]pyrimidine-3,6-dicarboxamide Yield: 30.36 mg, white solid Synthesis Example 221

N6-Cyclopropyl-7-hydroxy-4-isobutyl-5-oxo-N3-((tetrahydro-2H-pyran-4-yl)methyl)-4,5-dihydropyrazolo[1,5-a]pyrimidine-3,6-dicarboxamide Yield: 36.67 mg, white solid Synthesis Example 222

N6-Cyclopropyl-N3-((3,3-difluorocyclobutyl)methyl)-7-hydroxy-4-isobutyl-5-oxo-4,5-dihydropyrazolo[1,5-a]pyrimidine-3,6-dicarboxamide Yield: 39.36 mg, white solid Synthesis Example 223

N6-Cyclopropyl-7-hydroxy-4-isobutyl-5-oxo-N3-((1,3,5-trimethyl-1H-pyrazol-4-yl)methyl)-4,5-dihydropyrazolo[1,5-a]pyrimidine-3,6-dicarboxamide Yield: 15.0 mg, pale yellow solid Synthesis Example 224

N6-Cyclopropyl-7-hydroxy-4-isobutyl-N3-((5-methylpyrazin-2-yl)methyl)-5-oxo-4,5-dihydropyrazolo[1,5-a]pyrimidine-3,6-dicarboxamide Yield: 30.59 mg, pale yellow solid Synthesis Example 225

N6-Cyclopropyl-7-hydroxy-4-isobutyl-5-oxo-N3-(pyridin-2-yl)-4,5-dihydropyrazolo[1,5-a]pyrimidine-3,6-dicarboxamide Yield: 8.0 mg, white solid Synthesis Example 226

N6-Cyclopropyl-7-hydroxy-4-isobutyl-5-oxo-N3-((6-(trifluoromethyl)pyridin-3-yl)methyl)-4,5-dihydropyrazolo[1,5-a]pyrimidine-3,6-dicarboxamide Yield: 25.39 mg, white solid Synthesis Example 227

N-Cyclopropyl-7-hydroxy-4-isobutyl-3-(morpholine-4-carbonyl)-5-oxo-4,5-dihydropyrazolo[1,5-a]pyrimidine-6-carboxamide Yield: 49.3 mg, white solid Synthesis Example 228

N6-Cyclopropyl-7-hydroxy-4-isobutyl-N3-((5-methylpyridin-2-yl)methyl)-5-oxo-4,5-dihydropyrazolo[1,5-a]pyrimidine-3,6-dicarboxamide Yield: 10.1 mg, white solid Synthesis Example 229

N6-Cyclopropyl-N3-((1,3-dimethyl-1H-pyrazol-5-yl)methyl)-7-hydroxy-4-isobutyl-5-oxo-4,5-dihydropyrazolo[1,5-a]pyrimidine-3,6-dicarboxamide Yield: 6.1 mg, white solid Synthesis Example 230

N6-Cyclopropyl-7-hydroxy-4-isobutyl-N3-methyl-5-oxo-N3-(pyridin-3-ylmethyl)-4,5-dihydropyrazolo[1,5-a]pyrimidine-3,6-dicarboxamide Yield: 36.43 mg, white amorphous product Synthesis Example 231

N6-Cyclopropyl-7-hydroxy-4-isobutyl-5-oxo-N3-(pyrimidin-2-ylmethyl)-4,5-dihydropyrazolo[1,5-a]pyrimidine-3,6-dicarboxamide Yield: 60.36 mg, white solid Synthesis Example 232

N3-(4-Cyanobenzyl)-N6-cyclopropyl-7-hydroxy-4-isobutyl-5-oxo-4,5-dihydropyrazolo[1,5-a]pyrimidine-3,6-dicarboxamide Yield: 49.48 mg, white solid Synthesis Example 233

N6-Cyclopropyl-N3-(2-fluorobenzyl)-7-hydroxy-4-isobutyl-5-oxo-4,5-dihydropyrazolo[1,5-a]pyrimidine-3,6-dicarboxamide Yield: 69.44 mg, white solid Synthesis Example 234

N6-Cyclopropyl-N3-(2,4-difluorobenzyl)-7-hydroxy-4-isobutyl-5-oxo-4,5-dihydropyrazolo[1,5-a]pyrimidine-3,6-dicarboxamide Yield: 79.05 mg, pale yellow solid Synthesis Example 235

N6-Cyclopropyl-N3-((3-fluoropyridin-2-yl)methyl)-7-hydroxy-4-isobutyl-5-oxo-4,5-dihydropyrazolo[1,5-a]pyrimidine-3,6-dicarboxamide Yield: 31.6 mg, white solid Synthesis Example 236

(E)-N-Cyclopropyl-7-hydroxy-4-isobutyl-5-oxo-3-(2-(pyrazin-2-yl) vinyl)-4,5-dihydropyrazolo[1,5-a]pyrimidine-6-carboxamide Yield: 29.48 mg, white solid Synthesis Example 237

(E)-N-Cyclopropyl-7-hydroxy-4-isobutyl-5-oxo-3-(2-(tetrahydro-2H-pyran-4-yl) vinyl)-4,5-dihydropyrazolo[1,5-a]pyrimidine-6-carboxamide Yield: 9.6 mg, white solid Synthesis Example 238

(E)-N-Cyclopropyl-3-(2-(3,5-dimethylisoxazol-4-yl) vinyl)-7-hydroxy-4-isobutyl-5-oxo-4,5-dihydropyrazolo[1,5-a]pyrimidine-6-carboxamide Yield: 10.53 mg, pale yellow solid Synthesis Example 239

N-Cyclopropyl-7-hydroxy-4-isobutyl-5-oxo-3-(1,2,5,6-tetrahydropyridin-3-yl)-4,5-dihydropyrazolo[1,5-a]pyrimidine-6-carboxamide hydrochloride Yield: 200.7 mg, pale brown solid Synthesis Example 240

(E)-N-Cyclopropyl-7-hydroxy-4-isobutyl-5-oxo-3-(2-(thiazol-4-yl) vinyl)-4,5-dihydropyrazolo[1,5-a]pyrimidine-6-carboxamide Yield: 3.37 mg, white solid Synthesis Example 241

(E)-N-Cyclopropyl-7-hydroxy-4-isobutyl-5-oxo-3-(2-(piperidin-4-yl) vinyl)-4,5-dihydropyrazolo[1,5-a]pyrimidine-6-carboxamide hydrochloride Yield: 8.68 mg, white solid Synthesis Example 242

(E)-N-Cyclopropyl-7-hydroxy-4-isobutyl-3-(2-(4-methyltetrahydro-2H-pyran-4-yl) vinyl)-5-oxo-4,5-dihydropyrazolo[1,5-a]pyrimidine-6-carboxamide Yield: 6.41 mg, pale yellow oily product Synthesis Example 243

(E)-N-Cyclopropyl-3-(3,3-dimethylbut-1-en-1-yl)-7-hydroxy-4-isobutyl-5-oxo-4,5-dihydropyrazolo[1,5-a]pyrimidine-6-carboxamide Yield: 29.95 mg, pale brown solid Synthesis Example 244

(E)-3-(2-(1-Acetylpiperidin-4-yl) vinyl)-N-cyclopropyl-7-hydroxy-4-isobutyl-5-oxo-4,5-dihydropyrazolo[1,5-a]pyrimidine-6-carboxamide Yield: 22.17 mg, yellow solid Synthesis Example 245

(E)-3-(2-(1-Acetyl-4-methylpiperidin-4-yl) vinyl)-N-cyclopropyl-7-hydroxy-4-isobutyl-5-oxo-4,5-dihydropyrazolo[1,5-a]pyrimidine-6-carboxamide Yield: 9.78 mg, yellow amorphous product Synthesis Example 246

(E)-N-Cyclopropyl-3-(2-cyclopropylvinyl)-7-hydroxy-4-isobutyl-5-oxo-4,5-dihydropyrazolo[1,5-a]pyrimidine-6-carboxamide Yield: 6.57 mg, pale brown solid Synthesis Example 247

(E)-N-Cyclopropyl-7-hydroxy-4-isobutyl-5-oxo-3-(2-(pyridin-3-yl) vinyl)-4,5-dihydropyrazolo[1,5-a]pyrimidine-6-carboxamide Yield: 5.0 mg, white solid Synthesis Example 248

(E)-N-Cyclopropyl-7-hydroxy-4-isobutyl-5-oxo-3-(2-(6-(trifluoromethyl)pyridine-3-yl) vinyl)-4,5-dihydropyrazolo[1,5-a]pyrimidine-6-carboxamide Yield: 18.3 mg, white solid Synthesis Example 249

(E)-N-Cyclopropyl-7-hydroxy-4-isobutyl-5-oxo-3-(2-(1-(2,2,2-trifluoroethyl) piperidin-4-yl) vinyl)-4,5-dihydropyrazolo[1,5-a]pyrimidine-6-carboxamide Yield: 11.71 mg, brown amorphous product Synthesis Example 250

N-Cyclopropyl-7-hydroxy-4-isobutyl-5-oxo-3-(2-(pyridin-3-yl)ethyl)-4,5-dihydropyrazolo[1,5-a]pyrimidine-6-carboxamide Yield: 6.0 mg, white solid Synthesis Example 251

N-Cyclopropyl-7-hydroxy-4-isobutyl-5-oxo-3-(2-(6-(trifluoromethyl)pyridin-3-yl)ethyl)-4,5-dihydropyrazolo[1,5-a]pyrimidine-6-carboxamide Yield: 5.0 mg, white solid Synthesis Example 252

(E)-3-(6-(Cyclopropylcarbamoyl)-7-hydroxy-4-isobutyl-5-oxo-4,5-dihydropyrazolo[1,5-a]pyrimidin-3-yl)-2-methylacrylic acid Yield: 64.55 mg, yellow solid Synthesis Example 253

(E)-N-Cyclopropyl-3-(3-(4,4-difluoropiperidin-1-yl)-2-methyl-3-oxoprop-1-en-1-yl)-7-hydroxy-4-isobutyl-5-oxo-4,5-dihydropyrazolo[1,5-a]pyrimidine-6-carboxamide Yield: 13.25 mg, yellow solid Synthesis Example 254

(E)-N-Cyclopropyl-7-hydroxy-4-isobutyl-3-(2-methyl-3-morpholino-3-oxoprop-1-en-1-yl)-5-oxo-4,5-dihydropyrazolo[1,5-a]pyrimidine-6-carboxamide Yield: 5.93 mg, white solid Synthesis Example 255

(E)-N-Cyclopropyl-3-(3-(4-(3,3-difluorocyclobutyl)piperazin-1-yl)-2-methyl-3-oxoprop-1-en-1-yl)-7-hydroxy-4-isobutyl-5-oxo-4,5-dihydropyrazolo[1,5-a]pyrimidine-6-carboxamide Yield: 15.03 mg, pale orange amorphous product Synthesis Example 256

(E)-N-Cyclopropyl-3-(3-(3,3-difluoropyrrolidin-1-yl)-2-methyl-3-oxoprop-1-en-1-yl)-7-hydroxy-4-isobutyl-5-oxo-4,5-dihydropyrazolo[1,5-a]pyrimidine-6-carboxamide Yield: 2.66 mg, pale yellow solid.

Synthesis Example 257

(E)-N-Cyclopropyl-7-hydroxy-4-isobutyl-3-(3-(isopropylamino)-2-methyl-3-oxoprop-1-en-1-yl)-5-oxo-4,5-dihydropyrazolo[1,5-a]pyrimidine-6-carboxamide Yield: 6.75 mg, pale yellow solid Synthesis Example 258

(E)-3-(3-((Cyanomethyl)(methyl)amino)-2-methyl-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 23.63 mg, pale yellow solid Synthesis Example 259

N-Cyclopropyl-7-hydroxy-4-isobutyl-5-oxo-3-((pyridin-3-yloxy)methyl)-4,5-dihydropyrazolo[1,5-a]pyrimidine-6-carboxamide 50.6 μL of diisopropyl azodicarboxylate was added to a mixture of 54.4 mg of N-cyclopropyl-7-hydroxy-3-(hydroxymethyl)-4-isobutyl-5-oxo-4,5-dihydropyrazolo[1,5-a]pyrimidine-6-carboxamide produced in Synthesis Example 6, 48.5 mg of pyridin-3-ol, 66.9 mg of triphenylphosphine, and 2 mL of tetrahydrofuran at 0° C., and the resultant mixture was stirred at room temperature for 16 hours. The reaction mixture was purified by silica gel reversed-phase column chromatography (0.1% formic acid-acetonitrile/0.1% aqueous formic acid solution=30/70→60/40 (v/v)), to thereby produce 5.2 mg of the title compound as a white solid.

Synthesis Example 260

N-Cyclopropyl-7-hydroxy-4-isobutyl-5-oxo-3-(phenoxymethyl)-4,5-dihydropyrazolo[1,5-a]pyrimidine-6-carboxamide Substantially the same reaction as in Synthesis Example 259 was performed by using phenol in place of pyridin-3-ol, to thereby produce 7.53 mg of the title compound as a yellow solid.

Synthesis Example 261

3-Cyano-N-cyclopropyl-7-hydroxy-4-isobutyl-5-oxo-4,5-dihydropyrazolo[1,5-a]pyrimidine-6-carboxamide 27.8 mg of hydroxylamine hydrochloride was added to a mixture of 63.7 mg of N-cyclopropyl-3-formyl-7-hydroxy-4-isobutyl-5-oxo-4,5-dihydropyrazolo[1,5-a]pyrimidine-6-carboxamide produced in Synthesis Example 7 and 2 mL of methanol, and the resultant mixture was stirred at room temperature for two hours. The reaction mixture was concentrated under reduced pressure, and 1 mL of tetrahydrofuran and 357 μL of a solution of propylphosphonic anhydride in ethyl acetate were added to the residue. The resultant mixture was stirred under heating at 50° C. for hours. Water and 1 mL of 1 M hydrochloric acid were added to the reaction mixture, and the mixture was subjected to extraction with 15 mL of ethyl acetate. The organic phase was dried over sodium sulfate and subjected to filtration, and then the filtrate was concentrated under reduced pressure. The residue was purified by silica gel column chromatography (chloroform/methanol=100/0→95/5 (v/v)), to thereby produce 12.13 mg of the title compound as a white solid.

Synthesis Example 262

N-Cyclopropyl-7-hydroxy-4-isobutyl-5-oxo-3-((tetrahydro-2H-pyran-4-carboxamido) methyl)-4,5-dihydropyrazolo[1,5-a]pyrimidine-6-carboxamide A mixture of 160.2 mg of N-cyclopropyl-7-hydroxy-3-(hydroxymethyl)-4-isobutyl-5-oxo-4,5-dihydropyrazolo[1,5-a]pyrimidine-6-carboxamide produced in Synthesis Example 6, 3 mL of tetrahydrofuran, and 0.3 mL of N,N-dimethylacetamide was cooled to 0° C., and 0.269 mL of diphenylphosphoryl azide and 0.187 mL of 1,8-diazabicyclo[5.4.0]-7-undecene were added to the mixture at 0° C., followed by stirring at room temperature for three hours. Water was added to the reaction mixture, and the mixture was subjected to extraction three times with ethyl acetate. The organic phase was washed with a saturated aqueous sodium chloride solution. The organic phase was dried over sodium sulfate and subjected to filtration, and then the filtrate was concentrated under reduced pressure, to thereby produce a white solid. Subsequently, 80 mg of 10% palladium/carbon (about 55% water-moistened product) was added to a mixture of the resultant white solid, 4 mL of tetrahydrofuran, and 4 mL of methanol, and the mixture was stirred in a hydrogen atmosphere at room temperature for three hours. The reaction mixture was subjected to Celite filtration, and then the filtrate was concentrated, to thereby produce 160 mg of 3-(aminomethyl)-N-cyclopropyl-7-hydroxy-4-isobutyl-5-oxo-4,5-dihydropyrazolo[1,5-a]pyrimidine-6-carboxamide as a brown amorphous product. A mixture of 63.9 mg of the resultant 3-(aminomethyl)-N-cyclopropyl-7-hydroxy-4-isobutyl-5-oxo-4,5-dihydropyrazolo[1,5-a]pyrimidine-6-carboxamide and 1.2 mL of dichloromethane was cooled to 0° C., and 0.11 mL of triethylamine and 0.0495 mL of tetrahydro-2H-pyran-4-carbonyl chloride were added to the mixture at 0° C., followed by stirred at room temperature for three hours. 1 M hydrochloric acid was added to the reaction mixture, and the mixture was subjected to extraction with 20 mL of chloroform. The organic phase was subjected to diatomaceous earth filtration, and then the filtrate was concentrated under reduced pressure. The residue was purified by silica gel column chromatography (chloroform/methanol=100/0→97/3 (v/v)), to thereby produce 56.4 mg of the title compound as a white solid.

Synthesis Example 263

N-Cyclopropyl-3-((4,4-difluorocyclohexane-1-carboxamido) methyl)-7-hydroxy-4-isobutyl-5-oxo-4,5-dihydropyrazolo[1,5-a]pyrimidine-6-carboxamide 76.3 mg of 1-(3-dimethylaminopropyl)-3-ethylcarbodiimide hydrochloride, 61.3 mg of 1-hydroxybenzotriazole monohydrate, 0.11 mL of triethylamine, and 65.7 mg of 4,4-difluorocyclohexanecarboxylic acid were added to a mixture of 63.9 mg of 3-(aminomethyl)-N-cyclopropyl-7-hydroxy-4-isobutyl-5-oxo-4,5-dihydropyrazolo[1,5-a]pyrimidine-6-carboxamide produced in Synthesis Example 262 and 1.2 mL of dichloromethane at 0° C., and the resultant mixture was stirred at room temperature for 40 hours. 1 M hydrochloric acid was added to the reaction mixture, and the mixture was subjected to extraction with 20 mL of chloroform. The organic phase was subjected to diatomaceous earth filtration, and then the filtrate was concentrated under reduced pressure. The residue was purified by silica gel column chromatography (chloroform/methanol=100/0→97/3 (v/v)), to thereby produce 39.7 mg of the title compound as a white solid.

Synthesis Example 264

N-Cyclopropyl-7-hydroxy-4-isobutyl-3-(2-morpholino-2-oxoethyl)-5-oxo-4,5-dihydropyrazolo[1,5-a]pyrimidine-6-carboxamide 30.5 μL of methyl((methylsulfinyl)methyl) sulfane and 8.8 mg of sodium hydroxide were added to a mixture of 63.7 mg of N-cyclopropyl-3-formyl-7-hydroxy-4-isobutyl-5-oxo-4,5-dihydropyrazolo[1,5-a]pyrimidine-6-carboxamide produced in Synthesis Example 7 and 1 mL of tetrahydrofuran, and the resultant mixture was stirred at 70° C. for six hours. A saturated aqueous ammonium chloride solution was added to the reaction mixture, and the mixture was subjected to extraction with 15 mL of ethyl acetate. The organic phase was dried over sodium sulfate and subjected to filtration, and then the filtrate was concentrated under reduced pressure. Subsequently, 1.69 mL of a hydrogen chloride methanol solution (containing 5 to 10% hydrogen chloride) was added to a mixture of the resultant residue and 0.4 mL of dehydrated methanol, and the resultant mixture was stirred at 45° C. for three hours. The reaction mixture was concentrated under reduced pressure, and 0.4 mL of dehydrated methanol and 3.31 mL of a hydrogen chloride methanol solution (containing 5 to 10% hydrogen chloride) were added to the mixture, followed by stirring at 45° C. for six hours. The reaction mixture was concentrated under reduced pressure. To the resultant residue were added 1 mL of 1,4-dioxane, 0.5 mL of water, and 42.0 mg of lithium hydroxide monohydrate, and the resultant mixture was stirred at 100° C. for four hours. Water was added to the reaction mixture, and the mixture was subjected to extraction with ethyl acetate. 1 M hydrochloric acid was added to the resultant aqueous phase, and the mixture was subjected to extraction with ethyl acetate. The organic phase was dried over sodium sulfate and subjected to filtration, and then the filtrate was concentrated under reduced pressure. Thereafter, 19.1 mg of 1-(3-dimethylaminopropyl)-3-ethylcarbodiimide hydrochloride, 15.3 mg of 1-hydroxybenzotriazole monohydrate, and 13.0 μL of morpholine were added to a mixture of the resultant residue and 1 mL of N,N-dimethylacetamide at 0° C., and the resultant mixture was stirred at room temperature for 16 hours. 1 M hydrochloric acid and water were added to the reaction mixture, and the mixture was subjected to extraction with ethyl acetate. The organic phase was dried over sodium sulfate and subjected to filtration, and then the filtrate was concentrated under reduced pressure. The residue was purified by silica gel column chromatography (chloroform/ethyl acetate=20/1→1/1→chloroform/methanol=20/1 (v/v)), and then the resultant product was dried under reduced pressure, to thereby produce 3.46 mg of the title compound as a white solid.

Synthesis Example 265

(E)-N-Cyclopropyl-7-hydroxy-3-(3-hydroxy-3-methylbut-1-en-1-yl)-4-isobutyl-5-oxo-4,5-dihydropyrazolo[1,5-a]pyrimidine-6-carboxamide In an argon atmosphere, a solution of 25.0 mg of methyl (E)-3-(6-(cyclopropylcarbamoyl)-7-hydroxy-4-isobutyl-5-oxo-4,5-dihydropyrazolo[1,5-a]pyrimidin-3-yl)acrylate produced in Synthesis Example 8 in 1 mL of tetrahydrofuran was added dropwise to 0.29 mL of methylmagnesium bromide (12% tetrahydrofuran solution, about 1 mol/L) at 0° C., and the resultant mixture was stirred at 0° C. for 30 minutes. Subsequently, 1 mL of a saturated aqueous ammonium chloride solution was added to the reaction mixture, and the mixture was subjected to extraction with ethyl acetate. The organic phase was concentrated under reduced pressure, and the residue was purified by silica gel reversed-phase column chromatography (0.1% formic acid-acetonitrile/0.1% aqueous formic acid solution=50/50→60/40 (v/v)), to thereby produce 5.99 mg of the title compound as a white solid.

Synthesis Example 266

(E)-N-Cyclopropyl-3-(2-(5,5-dimethyl-4,5-dihydrooxazol-2-yl) vinyl)-7-hydroxy-4-isobutyl-5-oxo-4,5-dihydropyrazolo[1,5-a]pyrimidine-6-carboxamide 45.5 μL of methanesulfonic acid was added to a solution of 43.1 mg of (E)-N-cyclopropyl-7-hydroxy-3-(3-((2-hydroxy-2-methylpropyl)amino)-3-oxoprop-1-en-1-yl)-4-isobutyl-5-oxo-4,5-dihydropyrazolo[1,5-a]pyrimidine-6-carboxamide produced in Synthesis Example 507 in 1 mL of 1,2-dichloroethane, and the resultant mixture was stirred under reflux with heating for three hours. The reaction mixture was concentrated under reduced pressure, and a saturated aqueous ammonium chloride solution was added to the mixture, followed by extraction with 15 mL of chloroform. The organic phase was dried over sodium sulfate and subjected to filtration, and then the filtrate was concentrated under reduced pressure. The residue was purified by silica gel reversed-phase column chromatography (0.1% formic acid-acetonitrile/0.1% aqueous formic acid solution=30/70→60/40 (v/v)), to thereby produce 25.37 mg of the title compound as a white solid.

Synthesis Example 267

(E)-N-Cyclopropyl-7-hydroxy-4-isobutyl-5-oxo-3-(2-(5-oxo-4,5-dihydro-1,2,4-oxadiazol-3-yl) vinyl)-4,5-dihydropyrazolo[1,5-a]pyrimidine-6-carboxamide 125.64 mg of sodium hydride (60% purity) was added to a solution of 333.88 mg of diethyl cyanomethylphosphonate in 5 mL of tetrahydrofuran at 0 to 5° C. The resultant mixture was stirred at 0 to 5° C. for 30 minutes, and then a solution of 400 mg of N-cyclopropyl-3-formyl-7-hydroxy-4-isobutyl-5-oxo-4,5-dihydropyrazolo[1,5-a]pyrimidine-6-carboxamide produced in Synthesis Example 7 in 5 mL of tetrahydrofuran was added to the mixture at 0 to 5° C., followed by stirring at room temperature for three hours. Diluted sulfuric acid was added to the reaction mixture to achieve a pH of 3 to 4, and then the mixture was diluted with 30 ml of water, followed by extraction with ethyl acetate (10 mL×3). The organic phase was dried over sodium sulfate and subjected to filtration, and then the filtrate was concentrated under reduced pressure. The residue was suspended in 5 mL of methyl tert-butyl ether and then recovered by filtration, to thereby produce 210 mg of a white solid. Subsequently, 61.93 mg of hydroxylamine (50% purity) was added to a mixture of 160 mg of the resultant white solid and 5 mL of ethanol, and the resultant mixture was stirred at 80° C. for six hours. The reaction mixture was concentrated under reduced pressure. To the resultant residue were added 5 mL of 1,4-dioxane, 110.44 mg of 1,1'-carbonyldiimidazole, and 103.69 mg of 1,8-diazabicyclo[5.4.0]-7-undecene, and the mixture was stirred at 100° C. for 16 hours. To the reaction mixture were further added. 110.44 mg of 1,1'-carbonyldiimidazole and 103.69 mg of 1,8-diazabicyclo [5.4.0]-7-undecene, and the mixture was further stirred at 100° C. for 24 hours. Diluted sulfuric acid was added to the reaction mixture to achieve a pH of 3 to 4, and then the mixture was diluted with 10 mL of water, followed by extraction with ethyl acetate (15 mL×3). The organic phase was dried over sodium sulfate and subjected to filtration, and then the filtrate was concentrated under reduced pressure. The residue was purified by preparative high-performance liquid chromatography (Welch Xtimate C18 (25 mm×150 mm, 5 μm); acetonitrile/0.225% aqueous formic acid solution=40/60 →70/30 (v/v)), to thereby produce 28.4 mg of the title compound as a pale yellow solid.

Synthesis Example 268

(E)-N-Cyclopropyl-7-hydroxy-4-isobutyl-3-(2-(5-methyl-1,3,4-thiadiazol-2-yl) vinyl)-5-oxo-4,5-dihydropyrazolo[1,5-a]pyrimidine-6-carboxamide 381.4 mg of 1-(3-dimethylaminopropyl)-3-ethylcarbodiimide hydrochloride, 45.9 mg of 1-hydroxybenzotriazole monohydrate, and 148.2 mg of acetohydrazide were added to a mixture of 360.4 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 4 mL of N, N-dimethylacetamide at 0° C., and the resultant mixture was stirred at room temperature for 16 hours. 1 M hydrochloric acid was added to the reaction mixture, and the resultant solid was recovered by filtration and then dried under reduced pressure, to thereby produce 400.6 mg of (E)-3-(3-(2-acetylhydrazineyl)-3-oxoprop-1-en-1-yl)-N-cyclopropyl-7-hydroxy-4-isobutyl-5-oxo-4,5-dihydropyrazolo[1,5-a]pyrimidine-6-carboxamide as a white solid. A mixture of 104.1 mg of the resultant (E)-3-(3-(2-acetylhydrazineyl)-3-oxoprop-1-en-1-yl)-N-cyclopropyl-7-hydroxy-4-isobutyl-5-oxo-4,5-dihydropyrazolo[1,5-a]pyrimidine-6-carboxamide, 101.1 mg of 2,4-bis(4-methoxyphenyl)-1,3-dithia-2,4-diphosphetane 2,4-disulfide, and 2 mL of 1,4-dioxane was stirred at 100° C. for one hour. The reaction mixture was cooled to room temperature, and then concentrated under reduced pressure. The residue was purified by silica gel column chromatography (chloroform/methanol=99/1→97/3 (v/v)). Ethanol was added to the residue, and the resultant solid was recovered by filtration, followed by washing with ethanol, to thereby produce 51.5 mg of the title compound as a brown solid.

Synthesis Example 269

(E)-N-Cyclopropyl-7-hydroxy-4-isobutyl-3-(2-(5-methyl-1,3,4-oxadiazol-2-yl) vinyl)-5-oxo-4,5-dihydropyrazolo[1,5-a]pyrimidine-6-carboxamide A mixture of 104.1 mg of (E)-3-(3-(2-acetylhydrazineyl)-3-oxoprop-1-en-1-yl)-N-cyclopropyl-7-hydroxy-4-isobutyl-5-oxo-4,5-dihydropyrazolo[1,5-a]pyrimidine-6-carboxamide produced in Synthesis Example 268, 65.5 mg of (methoxycarbonylsulfamoyl) triethylammonium hydroxide inner salt, and 2 mL of 1,4-dioxane was stirred under microwave irradiation at 100° C. for 10 minutes. The reaction mixture was cooled to room temperature, and then concentrated under reduced pressure. The residue was purified by silica gel column chromatography (chloroform/ethyl acetate=90/10→50/50 (v/v)), to thereby produce 7.61 mg of the title compound as a white solid.

Synthesis Example 270

2-Bromo-N-cyclopropyl-7-hydroxy-4-(2-methoxy-2-methylpropyl)-5-oxo-4,5-dihydropyrazolo[1,5-a]pyrimidine-6-carboxamide Substantially the same reaction as in steps A, B, and C of Synthesis Example 11 was performed by using 2-methoxy-2-methylpropanal in place of pivalaldehyde, to thereby produce 962 mg of the title compound as a white solid.

Synthesis Example 271

2-(2-Aminopyridin-3-yl)-N-cyclopropyl-7-hydroxy-4-(2-methoxy-2-methylpropyl)-5-oxo-4,5-dihydropyrazolo[1,5-a]pyrimidine-6-carboxamide Substantially the same reaction as in Synthesis Example 14 was performed by using 2-bromo-N-cyclopropyl-7-hydroxy-4-(2-methoxy-2-methylpropyl)-5-oxo-4,5-dihydropyrazolo[1,5-a]pyrimidine-6-carboxamide produced in Synthesis Example 270 in place of 2-bromo-N-cyclopropyl-7-hydroxy-4-neopentyl-5-oxo-4,5-dihydropyrazolo[1,5-a]pyrimidine-6-carboxamide, to thereby produce 5.3 mg of the title compound as a white solid.

Synthesis Example 272

2-Bromo-7-hydroxy-4-neopentyl-5-oxo-N-(2,2,2-trifluoroethyl)-4,5-dihydropyrazolo[1,5-a]pyrimidine-6-carboxamide Substantially the same reaction as in step C of Synthesis Example 11 was performed by using 2,2,2-trifluoroethan-1-amine in place of cyclopropylamine, to thereby produce 3.60 g of the title compound as a white solid.

Synthesis Example 273

2-Bromo-7-hydroxy-4-isobutyl-5-oxo-N-(2,2,2-trifluoroethyl)-4,5-dihydropyrazolo[1,5-a]pyrimidine-6-carboxamide Substantially the same reaction as in step C of Synthesis Example 22 was performed by using 2,2,2-trifluoroethan-1-amine in place of cyclopropylamine, to thereby produce 3.90 g of the title compound as a white solid.

Synthesis Example 274

N-Cyclopropyl-7-hydroxy-4-neopentyl-5-oxo-2-(piperidin-1-ylmethyl)-4,5-dihydropyrazolo[1,5-a]pyrimidine-6-carboxamide 0.0429 mL of acetic acid was added to a mixture of 83.6 mg of N-cyclopropyl-2-formyl-7-hydroxy-4-neopentyl-5-oxo-4,5-dihydropyrazolo[1,5-a]pyrimidine-6-carboxamide produced in Synthesis Example 59, 0.0297 mL of piperidine, and 1 mL of dichloromethane at room temperature, and the resultant mixture was stirred at room temperature for five minutes. Furthermore, 79.5 mg of sodium triacetoxyborohydride was added to the mixture at room temperature, and the resultant mixture was stirred at room temperature for two hours. A saturated aqueous sodium hydrogen carbonate solution was added to the reaction mixture, and the mixture was subjected to extraction with chloroform. The organic phase was washed with a saturated aqueous sodium chloride solution, and then dried over anhydrous sodium sulfate. The resultant product was subjected to filtration, and then the filtrate was concentrated under reduced pressure. The residue was purified by silica gel reversed-phase column chromatography (0.1% formic acid-acetonitrile/0.1% aqueous formic acid solution=30/70→50/50 (v/v)), to thereby produce 24.42 mg of the title compound as a pale brown solid.

The compounds of Synthesis Examples 275 to 277 were produced according to the methods described in the aforementioned Synthesis Examples or methods similar thereto.

Synthesis Example 275

N6-Cyclopropyl-7-hydroxy-4-(2-methoxy-2-methylpropyl)-5-oxo-4,5-dihydropyrazolo[1,5-a]pyrimidine-2,6-dicarboxamide Yield: 61.9 mg, pale brown solid Synthesis Example 276

N6-Cyclopropyl-4-((4,4-difluorocyclohexyl)methyl)-7-hydroxy-5-oxo-4,5-dihydropyrazolo[1,5-a]pyrimidine-2,6-dicarboxamide Yield: 60.5 mg, pale brown solid Synthesis Example 277

N6-Cyclopropyl-7-hydroxy-5-oxo-4-(3,3,3-trifluoro-2,2-dimethylpropyl)-4,5-dihydropyrazolo[1,5-a]pyrimidine-2,6-dicarboxamide Yield: 34.24 mg, pale brown solid Synthesis Example 278

N-Cyclopropyl-7-hydroxy-2-(2-hydroxypropan-2-yl)-4-neopentyl-5-oxo-4,5-dihydropyrazolo[1,5-a]pyrimidine-6-carboxamide 2.143 mL of methylmagnesium bromide (1.4 M tetrahydrofuran:toluene solution (1:3)) was added to 188.2 mg of ethyl 6-(cyclopropylcarbamoyl)-7-hydroxy-4-neopentyl-5-oxo-4,5-dihydropyrazolo[1,5-a]pyrimidine-2-carboxylate produced in Synthesis Example 1 at 0° C., and the resultant mixture was stirred at room temperature for 10 minutes. Subsequently, 10 mL of 1 M hydrochloric acid was added to the reaction mixture, and the mixture was subjected to extraction with 20 mL of chloroform. The resultant extract was subjected to diatomaceous earth filtration, and then the filtrate was concentrated under reduced pressure. The resultant residue was purified by thin-layer chromatography (chloroform/methanol=15/1 (v/v)) and silica gel column chromatography (chloroform/methanol=30/1 (v/v)), to thereby produce 8.3 mg of the title compound as a white amorphous product.

Synthesis Example 279

2-Cyano-N-cyclopropyl-7-hydroxy-4-neopentyl-5-oxo-4,5-dihydropyrazolo[1,5-a]pyrimidine-6-carboxamide 4 mL of aqueous ammonia was added to 188.2 mg of ethyl 6-(cyclopropylcarbamoyl)-7-hydroxy-4-neopentyl-5-oxo-4, 5-dihydropyrazolo[1,5-a]pyrimidine-2-carboxylate produced in Synthesis Example 1, and the resultant mixture was stirred under microwave irradiation with heating at 120° C. for one hour. The reaction mixture was cooled to room temperature, and 5 mL of water was added to the mixture. The precipitated solid was recovered by filtration, and then dried under reduced pressure. To a solution of the resultant solid in 4 mL of pyridine was added 1.400 mL of trifluoroacetic anhydride at 0° C., and the mixture was stirred at room temperature for one hour. Subsequently, 10 mL of 1 M aqueous sodium hydroxide solution was added to the reaction mixture, and the mixture was stirred at room temperature for 16 hours. The reaction mixture was concentrated under reduced pressure, and 10 mL of 1 M hydrochloric acid was added to the mixture, followed by extraction with 20 mL of chloroform. The resultant extract was subjected to diatomaceous earth filtration, and then the filtrate was concentrated under reduced pressure. The residue was purified by silica gel column chromatography (chloroform/ethyl acetate=3/1 (v/v)). Thereafter, 10 mL of methanol was added to the resultant residue, and the precipitated solid was recovered by filtration, to thereby produce 190.1 mg of the title compound as a pale yellow solid.

Synthesis Example 280

2-(1-Aminopropyl)-N-cyclopropyl-7-hydroxy-4-neopentyl-5-oxo-4,5-dihydropyrazolo[1,5-a]pyrimidine-6-carboxamide hydrochloride (racemate)

769.7 mg of potassium trimethylsilanolate was added to a solution of 752.8 mg of ethyl 6-(cyclopropylcarbamoyl)-7-hydroxy-4-neopentyl-5-oxo-4,5-dihydropyrazolo[1,5-a]pyrimidine-2-carboxylate produced in Synthesis Example 1 in 10 mL of tetrahydrofuran, and the resultant mixture was stirred under reflux with heating for one hour. The reaction mixture was cooled to room temperature, and 10 mL of dichloromethane, 585.2 mg of N,O-dimethylhydroxylamine hydrochloride, 272.2 mg of 3H-[1,2,3]-triazolo[4,5-b]pyridin-3-ol, and 575.1 mg of 1-ethyl-3-(3-dimethylaminopropyl)carbodiimide hydrochloride were added to the mixture, followed by stirring at room temperature for 16 hours. The reaction mixture was concentrated under reduced pressure, and 30 mL of 1 M hydrochloric acid was added to the mixture. The precipitated solid was recovered by filtration, and washed with water, followed by drying under reduced pressure, to thereby produce a pale yellowish brown solid. Subsequently, 2 mL of ethylmagnesium bromide (1 M tetrahydrofuran solution) was added to a solution of 195.7 mg of the resultant pale yellowish brown solid in 2 mL of tetrahydrofuran at 0° C., and the resultant mixture was stirred at room temperature for 10 minutes. To the reaction mixture were added 347.5 mg of hydroxylamine hydrochloride, 5 mL of methanol, and 1 mL of water, and the mixture was stirred under reflux with heating for 10 minutes. The reaction mixture was cooled to room temperature, and 15 mL of chloroform was added to the mixture. The resultant mixture was subjected to diatomaceous earth filtration, and then the filtrate was concentrated under reduced pressure. The residue was purified by silica gel column chromatography (chloroform/ethyl acetate=2/1 (v/v)). To the resultant residue were added 327.0 mg of zince (powder) and 5 mL of acetic acid, and the mixture was stirred at room temperature for 16 hours. Subsequently, 10 mL of chloroform was added to the resultant mixture, and the mixture was subjected to Celite filtration. The filtrate was concentrated under reduced pressure, and 2 mL of saturated aqueous ammonia was added to the reaction mixture, followed by concentration under reduced pressure. To the resultant product were added 1 mL of water, 1 mL of methanol, and 5 mL of chloroform, and the mixture was subjected to diatomaceous earth filtration. Thereafter, the filtrate was concentrated under reduced pressure, and the residue was purified by silica gel reversed-phase column chromatography (0.1% formic acid-acetonitrile/0.1% aqueous formic acid solution=30/70→40/60 (v/v)). Subsequently, the resultant solid was suspended in 2 mL of acetonitrile, and then recovered by filtration, to thereby produce 9.61 mg of 2-(1-aminopropyl)-N-cyclopropyl-7-hydroxy-4-neopentyl-5-oxo-4,5-dihydropyrazolo[1,5-a]pyrimidine-6-carboxamide as a white solid. To 3.66 mg of the resultant 2-(1-aminopropyl)-N-cyclopropyl-7-hydroxy-4-neopentyl-5-oxo-4,5-dihydropyrazolo[1,5-a]pyrimidine-6-carboxamide was added 0.1 mL of 4 M hydrogen chloride 1,4-dioxane solution, and the resultant mixture was stirred at room temperature for five minutes. Thereafter, the mixture was concentrated under reduced pressure, to thereby produce 4.03 mg of the title compound as a white solid.

The compounds of Synthesis Examples 281 to 317 were produced according to the methods described in the aforementioned Synthesis Examples or methods similar thereto.

Synthesis Example 281

N-Cyclopropyl-7-hydroxy-2-(2-methoxypyridine-3-yl)-4-neopentyl-5-oxo-4,5-dihydropyrazolo[1,5-a]pyrimidine-6-carboxamide Yield: 32.3 mg, white solid

Synthesis Example 282

N-Cyclopropyl-7-hydroxy-2-(4-methoxypyridine-3-yl)-4-neopentyl-5-oxo-4,5-dihydropyrazolo[1,5-a]pyrimidine-6-carboxamide Yield: 17.2 mg, pale brown solid

Synthesis Example 283

N-Cyclopropyl-2-(2-fluoropyridine-3-yl)-7-hydroxy-4-neopentyl-5-oxo-4,5-dihydropyrazolo[1,5-a]pyrimidine-6-carboxamide Yield: 9.3 mg, pale brown solid

Synthesis Example 284

N-Cyclopropyl-7-hydroxy-4-neopentyl-5-oxo-2-(2-(trifluoromethyl)pyridin-3-yl)-4,5-dihydropyrazolo[1,5-a]pyrimidine-6-carboxamide Yield: 6.04 mg, pale brown amorphous product

Synthesis Example 285

2-(2-Amino-5-fluoropyridin-3-yl)-N-cyclopropyl-7-hydroxy-4-neopentyl-5-oxo-4,5-dihydropyrazolo[1,5-a]pyrimidine-6-carboxamide Yield: 4.2 mg, pale brown solid Synthesis Example 286

N-Cyclopropyl-7-hydroxy-4-neopentyl-5-oxo-2-(1H-pyrazol-4-yl)-4,5-dihydropyrazolo[1,5-a]pyrimidine-6-carboxamide Yield: 13.75 mg, white solid Synthesis Example 287

N-Cyclopropyl-7-hydroxy-2-(4-methyl-1H-pyrazol-5-yl)-4-neopentyl-5-oxo-4,5-dihydropyrazolo[1,5-a]pyrimidine-6-carboxamide Yield: 14.2 mg, pale yellow solid Synthesis Example 288

N-Cyclopropyl-7-hydroxy-4-neopentyl-5-oxo-2-(pyrimidin-5-yl)-4,5-dihydropyrazolo[1,5-a]pyrimidine-6-carboxamide Yield: 4.31 mg, pale brown solid Synthesis Example 289

2-(2-Aminopyrimidin-5-yl)-N-cyclopropyl-7-hydroxy-4-neopentyl-5-oxo-4,5-dihydropyrazolo[1,5-a]pyrimidine-6-carboxamide Yield: 18.4 mg, pale brown solid Synthesis Example 290

2-(2-Aminopyridin-3-yl)-N-cyclopropyl-7-hydroxy-5-oxo-4-((tetrahydro-2H-pyran-4-yl)methyl)-4,5-dihydropyrazolo[1,5-a]pyrimidine-6-carboxamide Yield: 12.71 mg, white solid Synthesis Example 291

2-(2-Amino-5-cyanopyridin-3-yl)-N-cyclopropyl-7-hydroxy-4-neopentyl-5-oxo-4,5-dihydropyrazolo[1,5-a]pyrimidine-6-carboxamide Yield: 2.42 mg, pale brown solid Synthesis Example 292

2-(4-Cyano-1H-pyrazol-3-yl)-N-cyclopropyl-7-hydroxy-4-neopentyl-5-oxo-4,5-dihydropyrazolo[1,5-a]pyrimidine-6-carboxamide Yield: 5.0 mg, white solid Synthesis Example 293

2-(2-Cyanopyridin-3-yl)-N-cyclopropyl-7-hydroxy-4-neopentyl-5-oxo-4,5-dihydropyrazolo[1,5-a]pyrimidine-6-carboxamide Yield: 7.0 mg, pale yellow solid Synthesis Example 294

2-(4-Cyanopyridin-3-yl)-N-cyclopropyl-7-hydroxy-4-neopentyl-5-oxo-4,5-dihydropyrazolo[1,5-a]pyrimidine-6-carboxamide Yield: 20.5 mg, yellow solid Synthesis Example 295

N-Cyclopropyl-2-(4-fluoropyridin-3-yl)-7-hydroxy-4-neopentyl-5-oxo-4,5-dihydropyrazolo[1,5-a]pyrimidine-6-carboxamide Yield: 30.1 mg, yellow solid Synthesis Example 296

2-(3-Cyano-1H-pyrazol-5-yl)-N-cyclopropyl-7-hydroxy-4-neopentyl-5-oxo-4,5-dihydropyrazolo[1,5-a]pyrimidine-6-carboxamide Yield: 27.79 mg, white solid Synthesis Example 297

N-Cyclopropyl-2-(2-(difluoromethyl)pyridin-3-yl)-7-hydroxy-4-neopentyl-5-oxo-4,5-dihydropyrazolo[1,5-a]pyrimidine-6-carboxamide Yield: 21.8 mg, pale yellow solid Synthesis Example 298

N-Cyclopropyl-7-hydroxy-4-neopentyl-5-oxo-2-(4-(trifluoromethyl)-1H-pyrazol-3-yl)-4,5-dihydropyrazolo[1,5-a]pyrimidine-6-carboxamide Yield: 5.1 mg, pale yellow solid Synthesis Example 299

N-Cyclopropyl-7-hydroxy-4-neopentyl-5-oxo-2-(pyridin-2-yl)-4,5-dihydropyrazolo[1,5-a]pyrimidine-6-carboxamide Yield: 4.73 mg, pale brown solid Synthesis Example 300

N-Cyclopropyl-7-hydroxy-2-(5-methoxypyrazin-2-yl)-4-neopentyl-5-oxo-4,5-dihydropyrazolo[1,5-a]pyrimidine-6-carboxamide Yield: 2.01 mg, white solid Synthesis Example 301

2-(5-Cyano-1H-pyrazol-4-yl)-N-cyclopropyl-7-hydroxy-4-neopentyl-5-oxo-4,5-dihydropyrazolo[1,5-a]pyrimidine-6-carboxamide Yield: 7.6 mg, pale brown solid Synthesis Example 302

N-Cyclopropyl-7-hydroxy-4-neopentyl-5-oxo-2-(pyrazin-2-yl)-4,5-dihydropyrazolo[1,5-a]pyrimidine-6-carboxamide Yield: 1.83 mg, brown solid Synthesis Example 303

N-Cyclopropyl-7-hydroxy-2-(5-methylpyrazin-2-yl)-4-neopentyl-5-oxo-4,5-dihydropyrazolo[1,5-a]pyrimidine-6-carboxamide Yield: 12.11 mg, pale brown solid Synthesis Example 304

N-Cyclopropyl-2-(5-fluoropyrazin-2-yl)-7-hydroxy-4-neopentyl-5-oxo-4,5-dihydropyrazolo[1,5-a]pyrimidine-6-carboxamide Yield: 9.0 mg, pale brown solid Synthesis Example 305

2-(4-Chloro-1H-pyrazol-5-yl)-N-cyclopropyl-7-hydroxy-4-neopentyl-5-oxo-4,5-dihydropyrazolo[1,5-a]pyrimidine-6-carboxamide Yield: 10.59 mg, white solid Synthesis Example 306

N-Cyclopropyl-7-hydroxy-4-neopentyl-5-oxo-2-(1H-pyrazolo[3,4-b]pyridin-3-yl)-4,5-dihydropyrazolo[1,5-a]pyrimidine-6-carboxamide Yield: 30.1 mg, yellow solid Synthesis Example 307

N-Cyclopropyl-7-hydroxy-4-neopentyl-5-oxo-2-(1H-pyrazolo[4,3-c]pyridin-3-yl)-4,5-dihydropyrazolo[1,5-a]pyrimidine-6-carboxamide hydrochloride Yield: 16.1 mg, white solid Synthesis Example 308

N-Cyclopropyl-7-hydroxy-2-(4-(methylamino)pyridin-3-yl)-4-neopentyl-5-oxo-4,5-dihydropyrazolo[1,5-a]pyrimidine-6-carboxamide Yield: 1.89 mg, pale yellow solid Synthesis Example 309

N-Cyclopropyl-7-hydroxy-2-(2-(methylamino)pyridin-3-yl)-4-neopentyl-5-oxo-4,5-dihydropyrazolo[1,5-a]pyrimidine-6-carboxamide Yield: 7.16 mg, pale brown solid Synthesis Example 310

2-(3-Carbamoyl-1-methyl-1H-pyrazol-4-yl)-N-cyclopropyl-7-hydroxy-4-neopentyl-5-oxo-4,5-dihydropyrazolo[1,5-a]pyrimidine-6-carboxamide Yield: 6.2 mg, pale yellow solid Synthesis Example 311

N-Cyclopropyl-7-hydroxy-2-(4-(morpholine-4-carbonyl)-1H-pyrazol-5-yl)-4-neopentyl-5-oxo-4,5-dihydropyrazolo[1,5-a]pyrimidine-6-carboxamide Yield: 4.65 mg, white solid Synthesis Example 312

2-(3-Carbamoyl-1H-pyrazol-4-yl)-N-cyclopropyl-7-hydroxy-4-neopentyl-5-oxo-4,5-dihydropyrazolo[1,5-a]pyrimidine-6-carboxamide Yield: 5.08 mg, pale brown solid Synthesis Example 313

N-Cyclopropyl-2-(4-(4,4-difluoropiperidine-1-carbonyl)-1H-pyrazol-5-yl)-7-hydroxy-4-neopentyl-5-oxo-4,5-dihydropyrazolo[1,5-a]pyrimidine-6-carboxamide hydrochloride Yield: 13.4 mg, white solid Synthesis Example 314

N-Cyclopropyl-2-(4-(dimethylcarbamoyl)-1H-pyrazol-5-yl)-7-hydroxy-4-neopentyl-5-oxo-4,5-dihydropyrazolo[1,5-a]pyrimidine-6-carboxamide hydrochloride Yield: 5.1 mg, white solid Synthesis Example 315

N-Cyclopropyl-7-hydroxy-4-neopentyl-5-oxo-2-(4-(((tetrahydro-2H-pyran-4-yl)methyl)carbamoyl)-1H-pyrazol-5-yl)-4,5-dihydropyrazolo[1,5-a]pyrimidine-6-carboxamide hydrochloride Yield: 12.8 mg, white solid Synthesis Example 316

N-Cyclopropyl-2-(4-(3,3-difluoropyrrolidine-1-carbonyl)-1H-pyrazol-5-yl)-7-hydroxy-4-neopentyl-5-oxo-4,5-dihydropyrazolo[1,5-a]pyrimidine-6-carboxamide hydrochloride Yield: 8.36 mg, white solid Synthesis Example 317

2-(3-Amino-1H-pyrazol-4-yl)-N-cyclopropyl-7-hydroxy-4-neopentyl-5-oxo-4,5-dihydropyrazolo[1,5-a]pyrimidine-6-carboxamide Yield: 5.3 mg, pale brown solid Synthesis Example 318

N-Cyclopropyl-2,7-dihydroxy-4-isobutyl-5-oxo-4,5-dihydropyrazolo[1,5-a]pyrimidine-6-carboxamide A mixture of 1.98 g of 3-amino-1H-pyrazol-5-ol, 80 mL of dichloromethane, and 12 mL of acetic acid was cooled to 0° C., and 1.826 mL of isobutyraldehyde was added to the mixture at 0° C., followed by stirring at 0° C. for 10 minutes. Subsequently, 5.09 g of sodium triacetoxyborohydride was slowly added to the mixture at 0° C., and the mixture was stirred at 0° C. for 30 minutes and at room temperature for 30 minutes. The reaction mixture was concentrated under reduced pressure, and 30 mL of water was added to the mixture, followed by extraction with 60 mL of chloroform. The organic phase was washed with a saturated aqueous sodium chloride solution, and then dried over sodium sulfate. The resultant product was subjected to filtration, and then the filtrate was concentrated under reduced pressure. To the resultant residue were added 2.87 g of triethyl methanetricarboxylate and 6.005 mL of N,N-diisopropylethylamine, and the resultant mixture was stirred under reflux with heating for four hours. The reaction mixture was cooled to room temperature, and 20 mL of N, N-dimethylacetamide and 3.073 mL of cyclopropylamine were added to the mixture, followed by stirring at 120° C. for three hours. After completion of the reaction, the resultant product was concentrated under reduced pressure. The resultant residue was purified by silica gel column chromatography (chloroform/methanol=30/1 (v/v)). The residue was suspended in 20 mL of isopropanol and then recovered by filtration, to thereby produce 715.80 mg of the title compound as a white solid.

The compounds of Synthesis Examples 319 to 360 were produced according to the methods described in the aforementioned Synthesis Examples or methods similar thereto.

Synthesis Example 319

N-Cyclopropyl-7-hydroxy-4-isobutyl-2-methyl-5-oxo-4,5-dihydropyrazolo[1,5-a]pyrimidine-6-carboxamide Yield: 65.94 mg, white amorphous product Synthesis Example 320

N-Cyclopropyl-7-hydroxy-2-methyl-4-neopentyl-5-oxo-4,5-dihydropyrazolo[1,5-a]pyrimidine-6-carboxamide Yield: 494.24 mg, white amorphous product Synthesis Example 321

N-Cyclopropyl-7-hydroxy-4-(2-methoxy-2-methylpropyl)-5-oxo-2-(pyrazin-2-ylamino)-4,5-dihydropyrazolo[1,5-a]pyrimidine-6-carboxamide Yield: 10.63 mg, pale brown solid Synthesis Example 322

N-Cyclopropyl-2-((5-fluoropyrazin-2-yl)amino)-7-hydroxy-4-neopentyl-5-oxo-4,5-dihydropyrazolo[1,5-a]pyrimidine-6-carboxamide Yield: 23.47 mg, pale brown solid Synthesis Example 323

2-((5-Cyanopyrazin-2-yl)amino)-N-cyclopropyl-7-hydroxy-4-neopentyl-5-oxo-4,5-dihydropyrazolo[1,5-a]pyrimidine-6-carboxamide Yield: 6.14 mg, pale brown solid Synthesis Example 324

2-((6-Cyanopyrazin-2-yl)amino)-N-cyclopropyl-7-hydroxy-4-neopentyl-5-oxo-4,5-dihydropyrazolo[1,5-a]pyrimidine-6-carboxamide Yield: 8.17 mg, pale brown solid.

Synthesis Example 325

2-((2-Cyanopyrimidin-4-yl)amino)-N-cyclopropyl-7-hydroxy-4-neopentyl-5-oxo-4,5-dihydropyrazolo[1,5-a]pyrimidine-6-carboxamide Yield: 4.51 mg, pale brown solid Synthesis Example 326

(S)—N-Cyclopropyl-7-hydroxy-4-neopentyl-5-oxo-2-((1-(pyridin-2-yl)ethyl)amino)-4,5-dihydropyrazolo[1,5-a]pyrimidine-6-carboxamide Yield: 36.61 mg, pale brown amorphous product Synthesis Example 327

(R)—N-Cyclopropyl-7-hydroxy-4-neopentyl-5-oxo-2-((1-(pyridin-2-yl)ethyl)amino)-4,5-dihydropyrazolo[1,5-a]pyrimidine-6-carboxamide Yield: 22.42 mg, pale brown amorphous product Synthesis Example 328

N-Cyclopropyl-7-hydroxy-2-((3-methylpyrazin-2-yl)amino)-4-neopentyl-5-oxo-4,5-dihydropyrazolo[1,5-a]pyrimidine-6-carboxamide Yield: 65.2 mg, white solid Synthesis Example 329

2-((6-Cyanopyrimidin-4-yl)amino)-N-cyclopropyl-7-hydroxy-4-neopentyl-5-oxo-4,5-dihydropyrazolo[1,5-a]pyrimidine-6-carboxamide Yield: 2.3 mg, white solid Synthesis Example 330

N-Cyclopropyl-7-hydroxy-2-((6-methylpyrazin-2-yl)amino)-4-neopentyl-5-oxo-4,5-dihydropyrazolo[1,5-a]pyrimidine-6-carboxamide Yield: 4.04 mg, pale brown solid Synthesis Example 331

N-Cyclopropyl-7-hydroxy-4-neopentyl-5-oxo-2-((6-(trifluoromethyl)pyrazin-2-yl)amino)-4,5-dihydropyrazolo[1,5-a]pyrimidine-6-carboxamide Yield: 28.05 mg, pale brown solid Synthesis Example 332

N-Cyclopropyl-7-hydroxy-2-((2-methoxypyrimidin-4-yl)amino)-4-neopentyl-5-oxo-4,5-dihydropyrazolo[1,5-a]pyrimidine-6-carboxamide Yield: 6.6 mg, pale yellow solid Synthesis Example 333

N-Cyclopropyl-7-hydroxy-2-((5-methylpyrazin-2-yl)amino)-4-neopentyl-5-oxo-4,5-dihydropyrazolo[1,5-a]pyrimidine-6-carboxamide Yield: 20.59 mg, brown solid Synthesis Example 334

N-Cyclopropyl-7-hydroxy-2-((2-methylpyrimidin-4-yl)amino)-4-neopentyl-5-oxo-4,5-dihydropyrazolo[1,5-a]pyrimidine-6-carboxamide Yield: 21.73 mg, pale brown solid Synthesis Example 335

N-Cyclopropyl-7-hydroxy-2-((5-(morpholine-4-carbonyl) pyrazin-2-yl)amino)-4-neopentyl-5-oxo-4,5-dihydropyrazolo[1,5-a]pyrimidine-6-carboxamide Yield: 46.32 mg, white solid Synthesis Example 336

N-Cyclopropyl-7-hydroxy-4-neopentyl-5-oxo-2-((5-propylpyrazin-2-yl)amino)-4,5-dihydropyrazolo[1,5-a]pyrimidine-6-carboxamide Yield: 5.2 mg, pale brown solid Synthesis Example 337

N-Cyclopropyl-2-((5-(difluoromethyl)pyrazin-2-yl)amino)-7-hydroxy-4-neopentyl-5-oxo-4,5-dihydropyrazolo[1,5-a]pyrimidine-6-carboxamide Yield: 9.81 mg, pale brown solid Synthesis Example 338

N-Cyclopropyl-2-((5-ethoxypyrazin-2-yl)amino)-7-hydroxy-4-neopentyl-5-oxo-4,5-dihydropyrazolo[1,5-a]pyrimidine-6-carboxamide Yield: 2.77 mg, pale brown solid Synthesis Example 339

N-Cyclopropyl-7-hydroxy-2-((6-methylpyrimidin-4-yl)amino)-4-neopentyl-5-oxo-4,5-dihydropyrazolo[1,5-a]pyrimidine-6-carboxamide Yield: 40.8 mg, brown solid Synthesis Example 340

N-Cyclopropyl-7-hydroxy-2-((5-methylpyrimidin-4-yl)amino)-4-neopentyl-5-oxo-4,5-dihydropyrazolo[1,5-a]pyrimidine-6-carboxamide Yield: 5.5 mg, pale brown solid Synthesis Example 341

(R)-2-(3-Aminopyrrolidin-1-yl)-N-cyclopropyl-7-hydroxy-4-neopentyl-5-oxo-4,5-dihydropyrazolo[1,5-a]pyrimidine-6-carboxamide Yield: 16.1 mg, brown solid Synthesis Example 342

(S)-2-(3-Aminopyrrolidin-1-yl)-N-cyclopropyl-7-hydroxy-4-neopentyl-5-oxo-4,5-dihydropyrazolo[1,5-a]pyrimidine-6-carboxamide Yield: 11.21 mg, brown solid Synthesis Example 343

2-(Cyclohexylamino)-N-cyclopropyl-7-hydroxy-4-neopentyl-5-oxo-4,5-dihydropyrazolo[1,5-a]pyrimidine-6-carboxamide Yield: 38.84 mg, pale brown amorphous product Synthesis Example 344

N-Cyclopropyl-2-((5-(1,1-difluoroethyl)pyrazin-2-yl)amino)-7-hydroxy-4-neopentyl-5-oxo-4,5-dihydropyrazolo[1,5-a]pyrimidine-6-carboxamide Yield: 2.0 mg, pale brown solid Synthesis Example 345

2-((6-Carbamoylpyrazin-2-yl)amino)-N-cyclopropyl-7-hydroxy-4-neopentyl-5-oxo-4,5-dihydropyrazolo[1,5-a]pyrimidine-6-carboxamide Yield: 12.8 mg, brown solid Synthesis Example 346

N-Cyclopropyl-7-hydroxy-2-((1-methyl-1H-pyrazol-3-yl)amino)-4-neopentyl-5-oxo-4,5-dihydropyrazolo[1,5-a]pyrimidine-6-carboxamide Yield: 17.69 mg, pale yellow amorphous product.

Synthesis Example 347

7-Hydroxy-4-neopentyl-5-oxo-2-(pyrazin-2-ylamino)-N-(2,2,2-trifluoroethyl)-4,5-dihydropyrazolo[1,5-a]pyrimidine-6-carboxamide Yield: 36.6 mg, white solid Synthesis Example 348

7-Hydroxy-4-isobutyl-5-oxo-2-(pyrazin-2-ylamino)-N-(2,2,2-trifluoroethyl)-4,5-dihydropyrazolo[1,5-a]pyrimidine-6-carboxamide Yield: 28.7 mg, white solid Synthesis Example 349

N-Cyclopropyl-7-hydroxy-2-((5-(2-hydroxypropan-2-yl) pyrazin-2-yl)amino)-4-neopentyl-5-oxo-4,5-dihydropyrazolo[1,5-a]pyrimidine-6-carboxamide Yield: 1.56 mg, pale brown solid Synthesis Example 350

N-Cyclopropyl-7-hydroxy-5-oxo-2-(pyrazin-2-ylamino)-4-((tetrahydro-2H-pyran-4-yl)methyl)-4,5-dihydropyrazolo[1,5-a]pyrimidine-6-carboxamide Yield: 5.54 mg, pale brown solid Synthesis Example 351

2-((2-Carbamoylpyrimidin-4-yl)amino)-N-cyclopropyl-7-hydroxy-4-neopentyl-5-oxo-4,5-dihydropyrazolo[1,5-a]pyrimidine-6-carboxamide Yield: 27.34 mg, white solid Synthesis Example 352

N-Cyclopropyl-7-hydroxy-4-neopentyl-5-oxo-2-((5-((2,2,2-trifluoroethyl)carbamoyl) pyrazin-2-yl) amino)-4,5-dihydropyrazolo[1,5-a]pyrimidine-6-carboxamide Yield: 54.96 mg, pale orange solid Synthesis Example 353

N-Cyclopropyl-2-((5-((2,2-difluoroethyl)carbamoyl) pyrazin-2-yl)amino)-7-hydroxy-4-neopentyl-5-oxo-4,5-dihydropyrazolo[1,5-a]pyrimidine-6-carboxamide Yield: 12.35 mg, white solid Synthesis Example 354

N-Cyclopropyl-7-hydroxy-2-((5-((2-hydroxy-2-methylpropyl)carbamoyl) pyrazin-2-yl)amino)-4-neopentyl-5-oxo-4,5-dihydropyrazolo[1,5-a]pyrimidine-6-carboxamide Yield: 29.51 mg, white solid Synthesis Example 355

N-Cyclopropyl-2-((5-(4,4-difluoropiperidine-1-carbonyl) pyrazin-2-yl)amino)-7-hydroxy-4-neopentyl-5-oxo-4,5-dihydropyrazolo[1,5-a]pyrimidine-6-carboxamide Yield: 25.27 mg, white solid Synthesis Example 356

N-Cyclopropyl-2-((6-fluoropyrazin-2-yl)amino)-7-hydroxy-4-neopentyl-5-oxo-4,5-dihydropyrazolo[1,5-a]pyrimidine-6-carboxamide Yield: 15.69 mg, pale brown solid Synthesis Example 357

N-Cyclopropyl-7-hydroxy-2-((1-methyl-1H-imidazol-2-yl)amino)-4-neopentyl-5-oxo-4,5-dihydropyrazolo[1,5-a]pyrimidine-6-carboxamide Yield: 8.1 mg, white solid Synthesis Example 358

2-((5-((Cyanomethyl)(methyl)carbamoyl) pyrazin-2-yl)amino)-N-cyclopropyl-7-hydroxy-4-neopentyl-5-oxo-4,5-dihydropyrazolo[1,5-a]pyrimidine-6-carboxamide Yield: 32.9 mg, white solid Synthesis Example 359

2-((5-(4-Cyanopiperidine-1-carbonyl) pyrazin-2-yl) amino)-N-cyclopropyl-7-hydroxy-4-neopentyl-5-oxo-4,5-dihydropyrazolo[1,5-a]pyrimidine-6-carboxamide Yield: 30.3 mg, white solid Synthesis Example 360

(S)—N-Cyclopropyl-7-hydroxy-2-((5-(3-hydroxypyrrolidine-1-carbonyl) pyrazin-2-yl)amino)-4-neopentyl-5-oxo-4,5-dihydropyrazolo[1,5-a]pyrimidine-6-carboxamide Yield: 4.08 mg, pale yellow solid Synthesis Example 361

N-Cyclopropyl-7-hydroxy-4-neopentyl-2-(oxazol-2-ylamino)-5-oxo-4,5-dihydropyrazolo[1,5-a]pyrimidine-6-carboxamide 121 μL of 4-fluorophenyl chloroformate was added to a mixture of 95.8 mg of 2-amino-N-cyclopropyl-7-hydroxy-4-neopentyl-5-oxo-4,5-dihydropyrazolo[1,5-a]pyrimidine-6-carboxamide produced in Synthesis Example 18, 72.6 μL of pyridine, and 3 mL of dichloromethane at 0° C., and the resultant mixture was stirred at room temperature for two hours. To the reaction mixture were added 2 mL of pyridine, 1 mL of 1,4-dioxane, and 65.0 μL of 2,2-dimethoxyethan-1-amine at room temperature, and the mixture was stirred at 100° C. for 16 hours. A saturated aqueous ammonium chloride solution was added to the reaction mixture, and the mixture was subjected to extraction with ethyl acetate. The organic phase was dried over sodium sulfate and subjected to filtration, and then the filtrate was concentrated under reduced pressure and then purified by silica gel column chromatography (chloroform/methanol=19/1 (v/v)). Subsequently, concentrated hydrochloric acid/methanol (0.6 mL/0.6 mL) was added to a solution of 60.0 mg of the resultant residue in 2 mL of methanol at 0° C., and the mixture was stirred at 50° C. for three hours. Water was added to the reaction mixture, and the precipitated solid was recovered by filtration and then dried under reduced pressure. The resultant solid was purified by silica gel reversed-phase column chromatography (0.1% formic acid-acetonitrile/0.1% aqueous formic acid solution=45/55 (v/v)), to thereby produce 12.38 mg of the title compound as a white solid.

Synthesis Example 362

(E)-N-Cyclopropyl-2-(((dimethylamino)methylene)amino)-7-hydroxy-4-neopentyl-5-oxo-4,5-dihydropyrazolo[1,5-a]pyrimidine-6-carboxamide hydrochloride 25.6 mg of (chloromethylene)dimethyliminium chloride was added to a solution of 31.9 mg of 2-amino-N-cyclopropyl-7-hydroxy-4-neopentyl-5-oxo-4,5-dihydropyrazolo[1,5-a]pyrimidine-6-carboxamide produced in Synthesis Example 18 in 2 mL of N,N-dimethylformamide, and the resultant mixture was stirred at 50° C. for one hour. The reaction mixture was cooled to room temperature, and the precipitated solid was recovered by filtration. The resultant product was washed with 1 mL of N,N-dimethylformamide and 5 mL of ethyl acetate, and then dried under reduced pressure, to thereby produce 7.34 mg of the title compound as a white solid.

The compound of Synthesis Example 363 was produced according to any of the methods described in the aforementioned Synthesis Examples or a method similar thereto.

Synthesis Example 363

(E)-N-Cyclopropyl-2-(((dimethylamino)methylene)amino)-7-hydroxy-4-isobutyl-5-oxo-4,5-dihydropyrazolo[1,5-a]pyrimidine-6-carboxamide hydrochloride Yield: 22.85 mg, white solid Synthesis Example 364

(E)-N-Cyclopropyl-4-((1-fluorocyclopropyl)methyl)-7-hydroxy-3-(3-morpholino-3-oxoprop-1-en-1-yl)-5-oxo-4,5-dihydropyrazolo[1,5-a]pyrimidine-6-carboxamide Substantially the same reaction as in Synthesis Example 5 or Synthesis Example 10 was performed by using 1-fluorocyclopropane-1-carbaldehyde in place of isobutyraldehyde, to thereby produce 40.8 mg of the title compound as a white solid.

The compounds of Synthesis Examples 365 to 380 were produced according to the methods described in the aforementioned Synthesis Examples or methods similar thereto.

Synthesis Example 365

(E)-N-Cyclopropyl-7-hydroxy-4-(2-methoxy-2-methylpropyl)-3-(3-morpholino-3-oxoprop-1-en-1-yl)-5-oxo-4,5-dihydropyrazolo[1,5-a]pyrimidine-6-carboxamide Yield: 55.78 mg, white solid Synthesis Example 366

(E)-N-Cyclopropyl-7-hydroxy-4-((1-methylcyclopropyl)methyl)-3-(3-morpholino-3-oxoprop-1-en-1-yl)-5-oxo-4,5-dihydropyrazolo[1,5-a]pyrimidine-6-carboxamide Yield: 72.6 mg, white solid Synthesis Example 367

(E)-3-(3-(3-Oxa-8-azabicyclo[3.2.1]octan-8-yl)-3-oxoprop-1-en-1-yl)-N-cyclopropyl-7-hydroxy-4-((1-methylcyclopropyl)methyl)-5-oxo-4,5-dihydropyrazolo[1,5-a]pyrimidine-6-carboxamide Yield: 11.64 mg, white solid Synthesis Example 368

(E)-3-(3-(8-Oxa-3-azabicyclo[3.2.1]octan-3-yl)-3-oxoprop-1-en-1-yl)-N-cyclopropyl-7-hydroxy-4-((1-methylcyclopropyl)methyl)-5-oxo-4,5-dihydropyrazolo[1,5-a]pyrimidine-6-carboxamide Yield: 13.09 mg, white solid Synthesis Example 369

(S,E)-N-Cyclopropyl-7-hydroxy-4-((1-methylcyclopropyl)methyl)-3-(3-(3-methylmorpholino)-3-oxoprop-1-en-1-yl)-5-oxo-4,5-dihydropyrazolo[1,5-a]pyrimidine-6-carboxamide Yield: 127.9 mg, white amorphous product Synthesis Example 370

(R,E)-N-Cyclopropyl-7-hydroxy-4-((1-methylcyclopropyl)methyl)-3-(3-(3-methylmorpholino)-3-oxoprop-1-en-1-yl)-5-oxo-4,5-dihydropyrazolo[1,5-a]pyrimidine-6-carboxamide Yield: 149.3 mg, white amorphous product Synthesis Example 371

(S,E)-N-Cyclopropyl-7-hydroxy-3-(3-(3-(methoxymethyl) morpholino)-3-oxoprop-1-en-1-yl)-4-((1-methylcyclopropyl)methyl)-5-oxo-4,5-dihydropyrazolo[1,5-a]pyrimidine-6-carboxamide Yield: 92.6 mg, white amorphous product Synthesis Example 372

(R,E)-N-Cyclopropyl-7-hydroxy-3-(3-(3-(methoxymethyl) morpholino)-3-oxoprop-1-en-1-yl)-4-((1-methylcyclopropyl)methyl)-5-oxo-4,5-dihydropyrazolo[1,5-a]pyrimidine-6-carboxamide Yield: 90.5 mg, white amorphous product Synthesis Example 373

3-((E)-3-((1R,4R)-2-Oxa-5-azabicyclo[2.2.1]heptan-5-yl)-3-oxoprop-1-en-1-yl)-N-cyclopropyl-7-hydroxy-4-((1-methylcyclopropyl)methyl)-5-oxo-4,5-dihydropyrazolo[1,5-a]pyrimidine-6-carboxamide Yield: 45.5 mg, white amorphous product Synthesis Example 374

3-((E)-3-((1S,4S)-2-Oxa-5-azabicyclo[2.2.1]heptan-5-yl)-3-oxoprop-1-en-1-yl)-N-cyclopropyl-7-hydroxy-4-((1-methylcyclopropyl)methyl)-5-oxo-4,5-dihydropyrazolo[1,5-a]pyrimidine-6-carboxamide Yield: 27.4 mg, white amorphous product Synthesis Example 375

3-((E)-3-((1S,4S)-2-Oxa-5-azabicyclo[2.2.1]heptan-5-yl)-3-oxoprop-1-en-1-yl)-N-cyclopropyl-4-((1-fluorocyclopropyl)methyl)-7-hydroxy-5-oxo-4,5-dihydropyrazolo[1,5-a]pyrimidine-6-carboxamide Yield: 22.89 mg, white amorphous product Synthesis Example 376

(E)-3-(3-(3-Oxa-8-azabicyclo[3.2.1]octan-8-yl)-3-oxoprop-1-en-1-yl)-N-cyclopropyl-4-((1-fluorocyclopropyl)methyl)-7-hydroxy-5-oxo-4,5-dihydropyrazolo[1,5-a]pyrimidine-6-carboxamide Yield: 16.93 mg, white solid Synthesis Example 377

3-((E)-3-((1R,4R)-2-Oxa-5-azabicyclo[2.2.1]heptan-5-yl)-3-oxoprop-1-en-1-yl)-N-cyclopropyl-4-((1-fluorocyclopropyl)methyl)-7-hydroxy-5-oxo-4,5-dihydropyrazolo[1,5-a]pyrimidine-6-carboxamide Yield: 17.9 mg, white amorphous product Synthesis Example 378

(E)-3-(3-(8-Oxa-3-azabicyclo[3.2.1]octan-3-yl)-3-oxoprop-1-en-1-yl)-N-cyclopropyl-4-((1-fluorocyclopropyl)methyl)-7-hydroxy-5-oxo-4,5-dihydropyrazolo[1,5-a]pyrimidine-6-carboxamide Yield: 35.87 mg, white amorphous product Synthesis Example 379

(S,E)-N-Cyclopropyl-4-((1-fluorocyclopropyl) methyl)-7-hydroxy-3-(3-(3-methylmorpholino)-3-oxoprop-1-en-1-yl)-5-oxo-4.5-dihydropyrazolo[1,5-a]pyrimidine-6-carboxamide Yield: 18.67 mg, white solid Synthesis Example 380

(R,E)-N-Cyclopropyl-4-((1-fluorocyclopropyl) methyl)-7-hydroxy-3-(3-(3-methylmorpholino)-3-oxoprop-1-en-1-yl)-5-oxo-4,5-dihydropyrazolo[1,5-a]pyrimidine-6-carboxamide Yield: 15.45 mg, white solid Synthesis Example 381

(E)-4-(Cyclobutylmethyl)-N-cyclopropyl-7-hydroxy-3-(3-morpholino-3-oxoprop-1-en-1-yl)-5-oxo-4,5-dihydropyrazolo[1,5-a]pyrimidine-6-carboxamide (Step A) 4-(Cyclobutylmethyl)-N-cyclopropyl-3-formyl-7-hydroxy-5-oxo-4,5-dihydropyrazolo[1,5-a] pyrimidine-6-carboxamide

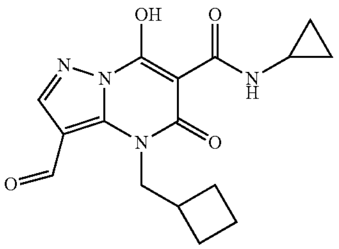 [SMILES: O=Cc1cnn2c(O)c(C(=O)NC3CC3)c(=O)n(CC3CCC3)c12]

Substantially the same reaction as in Synthesis Example 5 to Synthesis Example 7 was performed by using cyclobutanecarbaldehyde in place of isobutyraldehyde, to thereby produce 354 mg of the title compound as a yellow solid.

(Step B) (E)-4-(Cyclobutylmethyl)-N-cyclopropyl-7-hydroxy-3-(3-morpholino-3-oxoprop-1-en-1-yl)-5-oxo-4,5-dihydropyrazolo[1,5-a]pyrimidine-6-carboxamide 107.15 mg of sodium hydride (60% purity) was added to a solution of 426.36 mg of diethyl(2-morpholino-2-oxoethyl)phosphonate in 5 mL of N,N-dimethylformamide at 0 to 5° C. The resultant mixture was stirred at 0 to 5° C. for 30 minutes, and then a solution of 354 mg of 4-(cyclobutylmethyl)-N-cyclopropyl-3-formyl-7-hydroxy-5-oxo-4,5-dihydropyrazolo[1,5-a]pyrimidine-6-carboxamide produced in step A of Synthesis Example 381 in 5 mL of N,N-dimethylformamide was added to the mixture at 0 to 5° C., followed by stirring at room temperature for two hours. Diluted sulfuric acid was added to the reaction mixture to achieve a pH of 3 to 4, and then the mixture was diluted with 20 mL of water. The precipitated solid was recovered by filtration, and washed with 5 mL of water and 5 mL of methyl tert-butyl ether. The resultant solid was suspended in methyl tert-butyl ether/ethanol (5 mL/0.5 mL), and then recovered by filtration and washed with 5 mL of hexane. The resultant solid was dried under reduced pressure, to thereby produce 228.5 mg of the title compound as a white solid.

The compounds of Synthesis Examples 382 and 383 were produced according to the methods described in the aforementioned Synthesis Examples or methods similar thereto.

Synthesis Example 382

(S,E)-N-cyclopropyl-4-((1-fluorocyclopropyl) methyl)-7-hydroxy-3-(3-(3-(methoxymethyl) morpholino)-3-oxoprop-1-en-1-yl)-5-oxo-4,5-dihydropyrazolo[1,5-a]pyrimidine-6-carboxamide Yield: 33.2 mg, white amorphous product Synthesis Example 383

(R,E)-N-Cyclopropyl-4-((1-fluorocyclopropyl) methyl)-7-hydroxy-3-(3-(3-(methoxymethyl) morpholino)-3-oxoprop-1-en-1-yl)-5-oxo-4,5-dihydropyrazolo[1,5-a]pyrimidine-6-carboxamide Yield: 25.41 mg, white amorphous product Synthesis Example 384

(E)-N-Cyclopropyl-7-hydroxy-4-(2-methoxypropyl)-3-(3-morpholino-3-oxoprop-1-en-1-yl)-5-oxo-4,5-dihydropyrazolo[1,5-a]pyrimidine-6-carboxamide (Isomer A)

Synthesis Example 385

(E)-N-Cyclopropyl-7-hydroxy-4-(2-methoxypropyl)-3-(3-morpholino-3-oxoprop-1-en-1-yl)-5-oxo-4,5-dihydropyrazolo[1,5-a]pyrimidine-6-carboxamide (Isomer B)

Substantially the same reaction as in Synthesis Example 5, Synthesis Example 6, Synthesis Example 7, and step B of Synthesis Example 381 was performed by using 2-methoxypropanal in place of isobutyraldehyde, to thereby produce 920 mg of a racemic mixture of (E)-N-cyclopropyl-7-hydroxy-4-(2-methoxypropyl)-3-(3-morpholino-3-oxoprop-1-en-1-yl)-5-oxo-4,5-dihydropyrazolo[1,5-a]pyrimidine-6-carboxamide. The racemic mixture was optically resolved by SFC (apparatus: Waters Prep 80q, column: DAICEL CHIRALCEL OD-H (30 mm×250 mm, 5 μm), column temperature: 38° C., mobile phase: carbon dioxide/ethanol (0.1% aqueous ammonia (28%))=70/30, flow rate: 70 mL/min). The fraction with a retention time of 17 min (Isomer A) and the fraction with a retention time of 19 min (Isomer B) were concentrated under reduced pressure, and each of the resultant solids was suspended in 2 mL of methyl tert-butyl ether. The resultant suspensions were concentrated under reduced pressure, to thereby produce 70.3 mg of the title compound (Isomer A) as a white solid and 102.0 mg of the title compound (Isomer B) as a white solid.

The compounds of Synthesis Examples 386 and 387 were produced according to the methods described in the aforementioned Synthesis Examples or methods similar thereto.

Synthesis Example 386

(E)-N-Cyclopropyl-7-hydroxy-4-((4-methyltetrahydro-2H-pyran-4-yl)methyl)-3-(3-morpholino-3-oxoprop-1-en-1-yl)-5-oxo-4,5-dihydropyrazolo[1,5-a]pyrimidine-6-carboxamide Yield: 6.3 mg, white amorphous product Synthesis Example 387

(E)-N-Cyclopropyl-4-(cyclopropylmethyl)-7-hydroxy-3-(3-morpholino-3-oxoprop-1-en-1-yl)-5-oxo-4,5-dihydropyrazolo[1,5-a]pyrimidine-6-carboxamide Yield: 33.3 mg, white solid Synthesis Example 388

(E)-N-Cyclopropyl-7-hydroxy-3-(3-morpholino-3-oxoprop-1-en-1-yl)-5-oxo-4-(3,3,3-trifluoro-2-methylpropyl)-4,5-dihydropyrazolo[1,5-a]pyrimidine-6-carboxamide (Isomer A)

Synthesis Example 389

(E)-N-Cyclopropyl-7-hydroxy-3-(3-morpholino-3-oxoprop-1-en-1-yl)-5-oxo-4-(3,3,3-trifluoro-2-methylpropyl)-4,5-dihydropyrazolo[1,5-a]pyrimidine-6-carboxamide (Isomer B)

A racemic mixture of (E)-N-cyclopropyl-7-hydroxy-3-(3-morpholino-3-oxoprop-1-en-1-yl)-5-oxo-4-(3,3,3-trifluoro-2-methylpropyl)-4,5-dihydropyrazolo[1,5-a]pyrimidine-6-carboxamide was produced according to any of the methods described in the aforementioned Synthesis Examples or a method similar thereto. The racemic mixture was optically resolved by SFC (apparatus: Waters Prep 80, column: DAICEL CHIRALPAK IG (30 mmϕ×250 mm, 10 μm), column temperature: 40° C., mobile phase: carbon dioxide/isopropanol=60/40, flow rate: 80 mL/min). The fraction with a retention time of 9.34 min (Isomer A) and the fraction with a retention time of 12.40 min (Isomer B) were concentrated under reduced pressure, to thereby produce 136.3 mg of the title compound (Isomer A) as a white solid and 82.6 mg of the title compound (Isomer B) as a white solid.

Synthesis Example 390

(E)-N-Cyclopropyl-4-(2-fluoro-2-methylpropyl)-7-hydroxy-3-(3-morpholino-3-oxoprop-1-en-1-yl)-5-oxo-4,5-dihydropyrazolo[1,5-a]pyrimidine-6-carboxamide Substantially the same reaction as in Synthesis Example 5, Synthesis Example 6, Synthesis Example 7, and step B of Synthesis Example 381 was performed by using 2-fluoro-2-methylpropanal in place of isobutyraldehyde, to thereby produce 165.3 mg of the title compound as a white solid.

Synthesis Example 391

N-Cyclopropyl-4-hydroxy-1-neopentyl-2-oxo-1,2-dihydropyrido[2',3':3,4] pyrazolo[1,5-a]pyrimidine-3-carboxamide 4.24 g of sodium triacetoxyborohydride and 3.313 mL of pivalaldehyde were added to a mixture of 1.34 g of 1H-pyrazolo[3,4-b]pyridin-3-amine and 5 mL of trifluoroacetic acid at 0° C., and the resultant mixture was stirred at room temperature for 30 minutes. The reaction mixture was concentrated under reduced pressure, and a saturated aqueous sodium hydrogen carbonate solution was added to the mixture, followed by extraction with 50 mL of dichloromethane. The organic phase was washed with a saturated aqueous sodium hydrogen carbonate solution and a saturated aqueous sodium chloride solution, and then dried over sodium sulfate. The resultant product was subjected to filtration, and then the filtrate was concentrated under reduced pressure. The residue was purified by silica gel column chromatography (hexane/ethyl acetate=1/2). To 1.79 g of the resultant solid were added 2.65 g of triethyl methanetricarboxylate, 3.667 mL of triethylamine, and 10 mL of toluene, and the resultant mixture was stirred under reflux with heating for 40 hours. The reaction mixture was concentrated under reduced pressure, and the resultant residue was purified by silica gel column chromatography (chloroform/methanol=100/0→95/5→90/10 (v/v)). To 2.71 g of the resultant solid were added 2.737 mL of cyclopropylamine and 10 mL of N, N-dimethylacetamide, and the resultant mixture was stirred at 120° C. for two hours. The reaction mixture was concentrated under reduced pressure, and 841.0 mg of ammonium chloride and 25 mL of water were added to the mixture. The precipitated solid was recovered by filtration and washed with 20 mL of water, and then dried under reduced pressure, to thereby produce 2.00 g of the title compound as a yellow solid.

The compounds of Synthesis Examples 392 and 393 were produced according to the methods described in the aforementioned Synthesis Examples or methods similar thereto.

Synthesis Example 392

N-Cyclopropyl-7-hydroxy-10-neopentyl-9-oxo-9,10-dihydropyrazino[2',3': 3,4] pyrazolo[1,5-a]pyrimidine-8-carboxamide Yield: 54.58 mg, yellow solid Synthesis Example 393

N-Cyclopropyl-4-hydroxy-8-methoxy-1-neopentyl-2-oxo-1,2-dihydropyrido[2',3': 3,4] pyrazolo[1,5-a] pyrimidine-3-carboxamide Yield: 30.52 mg, pale brown solid Synthesis Example 394

N-Cyclopropyl-4-hydroxy-1-neopentyl-2,8-dioxo-1, 2,7,8-tetrahydropyrido[2',3': 3,4] pyrazolo[1,5-a] pyrimidine-3-carboxamide 0.0838 mL of chlorotrimethylsilane and 149.4 mg of potassium iodide were added to a mixture of 115.6 mg of N-cyclopropyl-4-hydroxy-8-methoxy-1-neopentyl-2-oxo-1, 2-dihydropyrido[2',3': 3,4] pyrazolo[1,5-a]pyrimidine-3-carboxamide produced in Synthesis Example 393 and 3 mL of acetonitrile, and the resultant mixture was stirred at 60° C. for two hours. Water was added to the reaction mixture, and the mixture was subjected to extraction with ethyl acetate. The organic phase was washed with a saturated aqueous sodium chloride solution, and the organic phase was dried over sodium sulfate. The resultant product was subjected to filtration, and then the filtrate was concentrated under reduced pressure. The residue was purified by silica gel column chromatography (chloroform/methanol=100/0→95/5 (v/v)), and then the resultant solid was washed with ethanol, to thereby produce 26.0 mg of the title compound as a white solid.

Synthesis Example 395

N-Cyclopropyl-7-hydroxy-4-neopentyl-5-oxo-4,5-dihydro-1H-pyrrolo[2',3': 3,4] pyrazolo[1,5-a]pyrimidine-6-carboxamide (Step A) Tert-butyl (3-bromo-6-(cyclopropylcarbamoyl)-7-hydroxy-4-neopentyl-5-oxo-4,5-dihydropyrazolo[1,5-a]pyrimidin-2-yl)carbamate

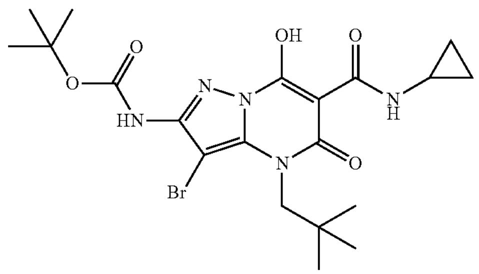 [SMILES: CC(C)(C)Cn1c(=O)c(C(=O)NC2CC2)c(O)n2nc(NC(=O)OC(C)(C)C)c(Br)c12]

213.6 mg of N-bromosuccinimide was added to a solution of 419.5 mg of tert-butyl (6-(cyclopropylcarbamoyl)-7-hydroxy-4-neopentyl-5-oxo-4,5-dihydropyrazolo[1,5-a]pyrimidin-2-yl)carbamate produced in Synthesis Example 3 in 1.2 mL of N, N-dimethylformamide, and the resultant mixture was stirred at room temperature for 20 hours. Subsequently, 5 mL of water was added to the mixture, and the precipitated solid was recovered by filtration. The solid was washed with 5 mL of water and 1 mL of diisopropyl ether, and then dried under reduced pressure, to thereby produce 294.9 mg of the title compound as a white solid.

LC/MS: condition 2, retention time=3.12 min

LC/MS (ESI+) m/z; 498.4, 500.4 $[M+H]^+$ (Step B) N-Cyclopropyl-7-hydroxy-4-neopentyl-5-oxo-4,5-dihydro-1H-pyrrolo[2',3':3,4] pyrazolo[1,5-a]pyrimidine-6-carboxamide A mixture of 49.8 mg tert-butyl (3-bromo-6-(cyclopropylcarbamoyl)-7-hydroxy-4-neopentyl-5-oxo-4,5-dihydropyrazolo[1,5-a]pyrimidin-2-yl)carbamate produced in step A of Synthesis Example 395, 59.4 mg of (E)-1-ethoxyethene-2-boronic acid pinacol ester, 6.5 mg of [1,1'-bis(di-tert-butylphosphino)ferrocene]dichloropalladium(II), 69.1 mg of potassium carbonate, 0.1 mL of water, and 0.4 mL of 1,4-dioxane was refluxed with heating in an argon atmosphere for two hours. The reaction mixture was cooled to room temperature, and 1 mL of a saturated aqueous ammonium chloride solution and 10 mL of chloroform were added to the mixture. The mixture was subjected to diatomaceous earth filtration, and then the filtrate was concentrated under reduced pressure. To the resultant residue was added 1 mL of trifluoroacetic acid, and the resultant mixture was stirred at room temperature. The reaction mixture was concentrated under reduced pressure, and the residue was purified by silica gel column chromatography (ethyl acetate). Diethyl ether was added to the resultant product, and the solid was recovered by filtration, to thereby produce 9.45 mg of the title compound as a white solid.

Synthesis Example 396

N-Cyclopropyl-7-hydroxy-4-neopentyl-5-oxo-2,3,4,5-tetrahydro-1H-pyrrolo[2',3':3,4] pyrazolo[1,5-a]pyrimidine-6-carboxamide 44.0 mg of cyanosodium borohydride was added to a solution of 39.6 mg of N-cyclopropyl-7-hydroxy-4-neopentyl-5-oxo-4,5-dihydro-1H-pyrrolo[2',3':3,4] pyrazolo[1,5-a]pyrimidine-6-carboxamide produced in step B of Synthesis Example 395 in 1 mL of acetic acid, and the resultant mixture was stirred at room temperature for 20 hours. The reaction mixture was concentrated under reduced pressure, and 5 mL of a saturated aqueous sodium hydrogen carbonate solution was added to the mixture, followed by extraction with 10 mL of chloroform. The organic phase was subjected to diatomaceous earth filtration, and then the filtrate was concentrated under reduced pressure. The residue was purified by silica gel reversed-phase column chromatography (0.1% formic acid-acetonitrile/0.1% aqueous formic acid solution=50/50 (v/v)), to thereby produce 1.64 mg of the title compound as a white solid.

Synthesis Example 397

N6-Cyclopropyl-7-hydroxy-4-neopentyl-5-oxo-2,3,4,5-tetrahydro-1H-pyrrolo[2',3':3,4] pyrazolo[1,5-a]pyrimidine-1,6-dicarboxamide 35.4 mg of trimethylsilyl isocyanate was added to a solution of 21.2 mg of N-cyclopropyl-7-hydroxy-4-neopentyl-5-oxo-2,3,4,5-tetrahydro-1H-pyrrolo[2',3':3,4] pyrazolo[1,5-a]pyrimidine-6-carboxamide produced in Synthesis Example 396 in 0.5 mL of dichloromethane, and the resultant mixture was stirred at room temperature for two hours. The reaction mixture was concentrated under reduced pressure. The residue was suspended in diethyl ether, and the resultant solid was recovered by filtration and then dried under reduced pressure, to thereby produce 6.95 mg of the title compound as a pale brown solid.

Synthesis Example 398

N-Cyclopropyl-7-hydroxy-4-neopentyl-5-oxo-1-(2,2,2-trifluoroethyl)-2,3,4,5-tetrahydro-1H-pyrrolo[2',3':3,4] pyrazolo[1,5-a]pyrimidine-6-carboxamide 0.0314 mL of N,N-diisopropylethylamine and 9.7 μL of 2,2,2-trifluoroethyl trifluoromethanesulfonate were added to a solution of 21.2 mg of N-cyclopropyl-7-hydroxy-4-neopentyl-5-oxo-2,3,4,5-tetrahydro-1H-pyrrolo[2',3':3,4] pyrazolo[1,5-a]pyrimidine-6-carboxamide produced in Synthesis Example 396 in 0.5 mL of dimethyl sulfoxide, and the resultant mixture was stirred at room temperature overnight. Subsequently, 2.0 mL of a saturated aqueous ammonium chloride solution was added to the reaction mixture, and the mixture was subjected to extraction with 10 mL of chloroform. The organic phase was subjected to diatomaceous earth filtration, and then the filtrate was concentrated under reduced pressure. The residue was purified by silica gel reversed-phase column chromatography (0.1% formic acid-acetonitrile/0.1% aqueous formic acid solution=30/70→60/40 (v/v)), to thereby produce 0.52 mg of the title compound as a pale brown oily product.

The compound of Synthesis Example 399 was produced according to any of the methods described in the aforementioned Synthesis Examples or a method similar thereto.

Synthesis Example 399

N-Cyclopropyl-7-hydroxy-4-isobutyl-5-oxo-4,5-dihydro-1H-pyrrolo[2',3':3,4] pyrazolo[1,5-a]pyrimidine-6-carboxamide Yield: 27.23 mg, white solid Synthesis Example 400

N-Cyclopropyl-8-hydroxy-5-neopentyl-2,6-dioxo-1,2,5,6-tetrahydro-4H-pyrimido[1',2':1,5] pyrazolo[3,4-d][1,3]oxazine-7-carboxamide (Step A) Tert-butyl (6-(cyclopropylcarbamoyl)-7-hydroxy-4-neopentyl-5-oxo-3-vinyl-4,5-dihydropyrazolo[1,5-a]pyrimidin-2-yl)carbamate

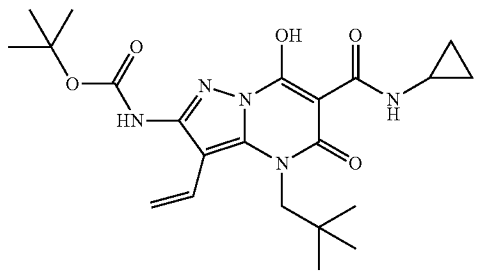 [SMILES: C=Cc1c(NC(=O)OC(C)(C)C)nn2c(O)c(C(=O)NC3CC3)c(=O)n(CC(C)(C)C)c12]

A solution of 2.49 g of tert-butyl (3-bromo-6-(cyclopropylcarbamoyl)-7-hydroxy-4-neopentyl-5-oxo-4,5-dihydropyrazolo[1,5-a]pyrimidin-2-yl)carbamate produced in step A of Synthesis Example 395, 2.01 g of potassium vinyltrifluoroborate, 325.9 mg of [1,1'-bis(di-tert-butylphosphino) ferrocene]dichloropalladium(II), 2.07 g of potassium carbonate in 1,4-dioxane (24 mL)/water (6 mL) was refluxed with heating in an argon atmosphere for three hours. The reaction mixture was cooled to room temperature, and 10 mL of a saturated aqueous ammonium chloride solution and 20 mL of chloroform were added to the mixture. The resultant mixture was subjected to diatomaceous earth filtration, and then the filtrate was concentrated under reduced pressure. The residue was purified by silica gel column chromatography (chloroform), to thereby produce 1.35 g of the title compound as a brown amorphous product. LC/MS: condition 3, retention time=2.80 min LC/MS (ESI+) m/z; 446.1 $[M+H]^+$ (Step B) Tert-butyl (6-(cyclopropylcarbamoyl)-3-formyl-7-hydroxy-4-neopentyl-5-oxo-4,5-dihydro-pyrazolo[1,5-a]pyrimidin-2-yl)carbamate

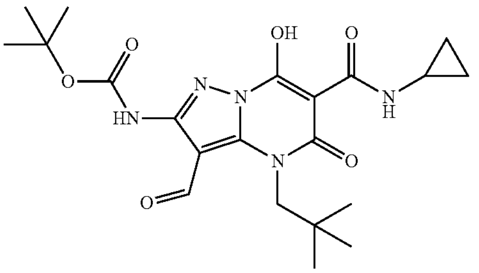 [SMILES: CC(C)(C)Cn1c(=O)c(C(=O)NC2CC2)c(O)n2nc(NC(=O)OC(C)(C)C)c(C=O)c12]

4 mL of water, 57.7 mg of potassium osmate (VI) dihydrate, and 0.629 mL of 4-methylmorpholine N-oxide (50% aqueous solution) were added to a solution of 1.35 g of tert-butyl (6-(cyclopropylcarbamoyl)-7-hydroxy-4-neopentyl-5-oxo-3-vinyl-4,5-dihydropyrazolo[1,5-a]pyrimidin-2-yl)carbamate produced in step A of Synthesis Example 400 in 12 mL of tert-butanol, and the resultant mixture was stirred at room temperature for 40 hours. To the reaction mixture was added 1.29 g of sodium periodate, and the mixture was stirred at room temperature for three hours. To the reaction mixture was added 30 mL of water, and the precipitated solid was recovered by filtration. The resultant product was washed with 30 mL of water. The resultant solid was dried under reduced pressure, to thereby produce 1.21 g of the title compound as a brown solid.

LC/MS: condition 3, retention time=2.73 min

LC/MS (ESI+) m/z; 447.9 $[M+H]^+$ (Step C) N-Cyclopropyl-8-hydroxy-5-neopentyl-2,6-dioxo-1,2,5,6-tetrahydro-4H-pyrimido[1',2':1,5]pyrazolo[3,4-d][1,3]oxazine-7-carboxamide 3 mL of tetrahydrofuran, 15.1 mg of sodium borohydride, and 0.2 mL of methanol were added to 89.5 mg of tert-butyl (6-(cyclopropylcarbamoyl)-3-formyl-7-hydroxy-4-neopentyl-5-oxo-4,5-dihydropyrazolo[1,5-a]pyrimidin-2-yl)carbamate produced in step B of Synthesis Example 400, and the resultant mixture was stirred at room temperature for 30 minutes. To the reaction mixture was added 2 mL of a saturated aqueous ammonium chloride solution, and the mixture was subjected to extraction with 10 mL of chloroform. The organic phase was subjected to diatomaceous earth filtration, and the filtrate was concentrated under reduced pressure. To the residue were added 2 mL of tetrahydrofuran and 26.2 mg of sodium hydride (55% purity, dispersed in liquid paraffin), and the resultant mixture was stirred under reflux with heating for six hours. To the reaction mixture was added 2 mL of a saturated aqueous ammonium chloride solution, and the mixture was subjected to extraction with 10 mL of chloroform. The organic phase was subjected to diatomaceous earth filtration, and the filtrate was concentrated under reduced pressure. The residue was purified by silica gel column chromatography (chloroform→chloroform/methanol=50/1 (v/v)). The residue was suspended in 2 mL of diethyl ether, and the resultant solid was recovered by filtration, to thereby produce 12.04 mg of the title compound as a white solid.

Synthesis Example 401

N-Cyclopropyl-9-hydroxy-6-neopentyl-2,7-dioxo-1,2,4,5,6,7-hexahydropyrimido[1',2': 1,5] pyrazolo[3,4-d][1,3]oxazepine-8-carboxamide (Step A) Tert-butyl (6-(cyclopropylcarbamoyl)-7-hydroxy-3-(2-hydroxyethyl)-4-neopentyl-5-oxo-4,5-dihydropyrazolo[1,5-a]pyrimidin-2-yl)carbamate

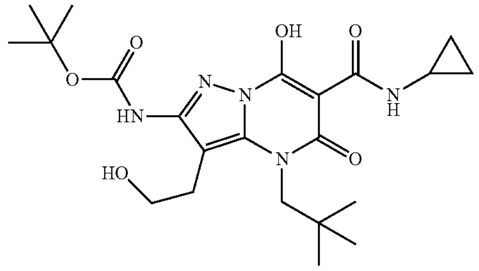 [SMILES: CC(C)(C)Cn1c(=O)c(C(=O)NC2CC2)c(O)n2nc(NC(=O)OC(C)(C)C)c(CCO)c12]

2.4 mL of borane-tetrahydrofuran complex (about 0.94 mol/L tetrahydrofuran solution) was added to a solution of 409 mg of tert-butyl (6-(cyclopropylcarbamoyl)-7-hydroxy-4-neopentyl-5-oxo-3-vinyl-4,5-dihydropyrazolo[1,5-a]pyrimidin-2-yl)carbamate produced in step A of Synthesis Example 400 in 2.0 mL of tetrahydrofuran, and the resultant mixture was stirred at room temperature for 15 hours. To the reaction mixture were added 708 mg of sodium peroxoborate tetrahydrate and 4.6 mL of an aqueous sodium hydroxide solution, and the mixture was stirred at room temperature for one hour. To the reaction mixture was added 4.0 mL of a saturated aqueous ammonium chloride solution, and the mixture was subjected to extraction with 15 mL of ethyl acetate. The organic phase was subjected to diatomaceous earth filtration, and the filtrate was concentrated under reduced pressure. The residue was purified by silica gel column chromatography (chloroform/hexane=4/1→chloroform (v/v)), to thereby produce 57.0 mg of the title compound as a yellow solid.

LC/MS: condition 3, retention time=2.57 min

LC/MS (ESI+) m/z; 464.1 $[M+H]^+$ (Step B) N-Cyclopropyl-9-hydroxy-6-neopentyl-2,7-dioxo-1,2,4,5,6,7-hexahydropyrimido[11,2': 1,5] pyrazolo[3,4-d][1,3]oxazepine-8-carboxamide 0.4 mL of N,N-dimethylformamide and 14 mg of sodium hydride (55% purity, dispersed in liquid paraffin) were added to 46 mg of tert-butyl (6-(cyclopropylcarbamoyl)-7-hydroxy-3-(2-hydroxyethyl)-4-neopentyl-5-oxo-4,5-dihydropyrazolo[1,5-a]pyrimidin-2-yl)carbamate produced in step A of Synthesis Example 401, and the resultant mixture was stirred at 90° C. for six hours. To the reaction mixture was added 2 mL of a saturated aqueous ammonium chloride solution, and the mixture was subjected to extraction with 5 mL of ethyl acetate. The organic phase was subjected to diatomaceous earth filtration, and the filtrate was concentrated under reduced pressure. The residue was purified by silica gel reversed-phase column chromatography (0.1% formic acid-acetonitrile/0.1% aqueous formic acid solution=30/70→60/40 (v/v)), to thereby produce 6.8 mg of the title compound as a white solid.

Synthesis Example 402

N-Cyclopropyl-7-hydroxy-4-neopentyl-2,5-dioxo-2,3,4,5-tetrahydro-1H-pyrrolo[2',3': 3,4] pyrazolo[1,5-a]pyrimidine-6-carboxamide (Step A) 2-Amino-1-(2,4-dimethoxybenzyl)-5-oxo-4,5-dihydro-1H-pyrrole-3-carbonitrile

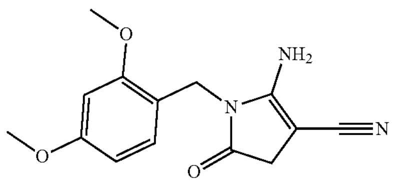 [SMILES: COc1ccc(CN2C(=O)CC(C#N)=C2N)c(OC)c1]

0.866 mL of bromoacetyl bromide was added dropwise to a solution of 1.506 mL of 2,4-dimethoxybenzylamine and 1.701 mL of N,N-diisopropylethylamine in 20 mL of dichloromethane at −10° C., and the resultant mixture was stirred at room temperature for minutes. To the reaction mixture was added 10 mL of 1 M hydrochloric acid. The organic phase was subjected to diatomaceous earth filtration, and the filtrate was concentrated under reduced pressure, to thereby produce 2-bromo-N-(2,4-dimethoxybenzyl) acetamide as a brown solid. Subsequently, 0.666 mL of malononitrile and 4.15 g of potassium carbonate were added to a solution of the resultant 2-bromo-N-(2,4-dimethoxybenzyl) acetamide in 40 mL of ethanol, and the resultant mixture was stirred at room temperature for 30 minutes, followed by stirring under reflux with heating for 30 minutes. The reaction mixture was cooled to room temperature, and 10 mL of water was added to the mixture, followed by extraction with 100 mL of chloroform. The organic phase was dried over sodium sulfate and subjected to filtration, and then the filtrate was concentrated under reduced pressure. The residue was purified by silica gel column chromatography (chloroform/ethyl acetate=3/2). The resultant residue was suspended in 5 mL of diisopropyl ether, and the resultant solid was recovered by filtration, to thereby produce 1.05 g of the title compound as a pale yellow solid.

LC/MS: condition 2, retention time=1.61 min

LC/MS (ESI+) m/z; 274.1 $[M+H]^+$ (Step B) 6-(2,4-Dimethoxybenzyl)-3-(neopentylamino)-4,6-dihydropyrrolo[2,3-c]pyrazol-5 (1H)-one

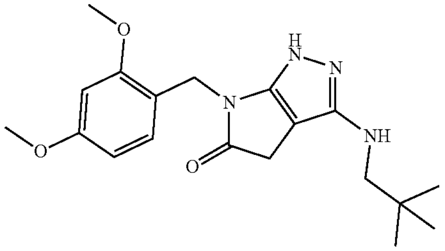 [SMILES: COc1ccc(CN2C(=O)Cc3c(NCC(C)(C)C)n[nH]c32)c(OC)c1]

2.430 mL of hydrazine monohydrate was added to 10 mL of acetic acid at 0° C., and the mixture was adjusted to room temperature. Thereafter, 273.3 mg of 2-amino-1-(2,4-dimethoxybenzyl)-5-oxo-4,5-dihydro-1H-pyrrole-3-carbonitrile produced in step A of Synthesis Example 402 was added to the mixture at room temperature, and the resultant mixture was stirred at 60° C. for 25 minutes. To the reaction mixture was added 20 mL of ice water, and the mixture was concentrated under reduced pressure. To the resultant residue was added 50 mL of a saturated aqueous sodium hydrogen carbonate solution, and the mixture was subjected to extraction with ethyl acetate (50 mL×2). The organic phase was dried over sodium sulfate and subjected to filtration, and then the filtrate was concentrated under reduced pressure. To the resultant residue were added 2 mL of dichloromethane, 0.221 mL of pivalaldehyde, 423.9 mg of sodium triacetoxyborohydride, and 0.5 mL of acetic acid, and the resultant mixture was stirred at room temperature for two hours. The reaction mixture was concentrated under reduced pressure, and 20 mL of a saturated aqueous sodium hydrogen carbonate solution was added to the mixture, followed by extraction with 20 mL of chloroform. The organic phase was subjected to diatomaceous earth filtration, and then the filtrate was concentrated under reduced pressure. The residue was purified by silica gel column chromatography (hexane/ethyl acetate=1/2 (v/v)), to thereby produce 160.6 mg of the title compound as a pale yellow amorphous product.

LC/MS: condition 3, retention time=2.03 min

LC/MS (ESI+) m/z; 359.1 $[M+H]^+$ (Step C) N-Cyclopropyl-7-hydroxy-4-neopentyl-2,5-dioxo-2,3,4,5-tetrahydro-1H-pyrrolo[2',3': 3,4] pyrazolo[1,5-a]pyrimidine-6-carboxamide A mixture of 161.3 mg of 6-(2,4-dimethoxybenzyl)-3-(neopentylamino)-4,6-dihydropyrrolo[2,3-c]pyrazol-5 (1H)-one produced in step B of Synthesis Example 402, 135.9 mg of triethyl methanetricarboxylate, 0.188 mL of triethylamine, and 1 mL of toluene was stirred under reflux with heating for 16 hours. The reaction mixture was concentrated under reduced pressure, and the residue was purified by silica gel column chromatography (chloroform/methanol=20/1→10/1 (v/v)). To the residue were added 0.130 mL of cyclopropylamine and 1 mL of N, N-dimethylacetamide, and the resultant mixture was stirred at 120° C. for one hour. The reaction mixture was concentrated under reduced pressure, and 5 mL of 1 M hydrochloric acid was added to the mixture, followed by extraction with 10 mL of chloroform. The organic phase was concentrated under reduced pressure, and the residue was purified by silica gel column chromatography (chloroform). To the residue were added 0.201 mL of anisole and 4 mL of trifluoroacetic acid, and the mixture was refluxed with heating for 24 hours. The reaction mixture was concentrated under reduced pressure, and the residue was purified by silica gel column chromatography (chloroform/methanol=30/1 (v/v)). The residue was suspended in 2 mL of ethyl acetate, and the resultant solid was recovered by filtration and dried under reduced pressure, to thereby produce 22.3 mg of the title compound as a white solid.

Synthesis Example 403

N-Cyclopropyl-4-hydroxy-1-neopentyl-2,8-dioxo-1,2,7,8,9,10-hexahydropyrido[2',3':3,4] pyrazolo[1,5-a]pyrimidine-3-carboxamide (Step A) Ethyl (E)-3-(2-((tert-butoxycarbonyl)amino)-6-(cyclopropylcarbamoyl)-7-hydroxy-4-neopentyl-5-oxo-4,5-dihydropyrazolo[1,5-a]pyrimidin-3-yl)acrylate

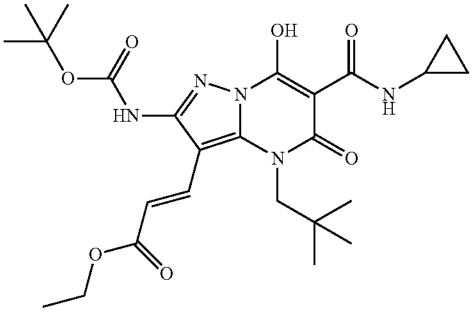 [SMILES: CCOC(=O)/C=C/c1c(NC(=O)OC(C)(C)C)nn2c(O)c(C(=O)NC3CC3)c(=O)n(CC(C)(C)C)c12]

A solution of 498.4 mg of tert-butyl (3-bromo-6-(cyclopropylcarbamoyl)-7-hydroxy-4-neopentyl-5-oxo-4,5-dihydropyrazolo[1,5-a]pyrimidin-2-yl)carbamate produced in step A of Synthesis Example 395, 678.2 mg of ethyl (E)-3-(4,4,5,5-tetramethyl-1,3,2-dioxaborolan-2-yl)acrylate, 65.2 mg of [1,1'-bis(di-tert-butylphosphino)ferrocene]dichloropalladium(II), 691.1 mg of potassium carbonate in 1,4-dioxane (4 mL)/water (1 mL) was refluxed with heating in an argon atmosphere for 90 minutes. The reaction mixture was cooled to room temperature, and 5 mL of a saturated aqueous ammonium chloride solution and 20 mL of chloroform were added to the mixture. The resultant mixture was subjected to diatomaceous earth filtration, and then the filtrate was concentrated under reduced pressure. The residue was purified by silica gel column chromatography (chloroform). The residue was suspended in 5 mL of diisopropyl ether, and the resultant solid was recovered by filtration, to thereby produce 201.9 mg of the title compound as a white solid.

LC/MS: condition 3, retention time=2.84 min

LC/MS (ESI+) m/z; 518.0 $[M+H]^+$ (Step B) N-Cyclopropyl-4-hydroxy-1-neopentyl-2,8-dioxo-1,2,7,8,9,10-hexahydropyrido[2',3':3,4] pyrazolo[1,5-a]pyrimidine-3-carboxamide 50.0 mg of 10% palladium/carbon (about 55% water-moistened product), 5 mL of methanol, and 5 mL of ethyl acetate were added to 201.9 mg of ethyl (E)-3-(2-((tert-butoxycarbonyl)amino)-6-(cyclopropylcarbamoyl)-7-hydroxy-4-neopentyl-5-oxo-4,5-dihydropyrazolo[1,5-a]pyrimidin-3-yl)acrylate produced in step A of Synthesis Example 403, and the resultant mixture was stirred in a hydrogen (1 atm) atmosphere at room temperature for 16 hours. The reaction mixture was subjected to Celite filtration, and then the filtrate was concentrated under reduced pressure. To the residue was added 5 mL of trifluoroacetic acid, and the mixture was stirred at room temperature for 10 minutes. The reaction mixture was concentrated under reduced pressure, and then dried under reduced pressure. To the residue were added 269.5 mg of potassium carbonate and 10 mL of 1,4-dioxane, and the resultant mixture was refluxed with heating for 30 minutes. The reaction mixture was concentrated under reduced pressure, and then 4 mL of 1 M hydrochloric acid was added to the mixture, followed by extraction with 20 mL of chloroform. The organic phase was subjected to diatomaceous earth filtration, and then the filtrate was concentrated under reduced pressure. The residue was purified by silica gel column chromatography (chloroform/ethyl acetate=1/1 (v/v)). The residue was suspended in 5 mL of ethyl acetate, and the resultant solid was recovered by filtration, to thereby produce 104.1 mg of the title compound as a white solid.

The compound of Synthesis Example 404 was produced according to any of the methods described in the aforementioned Synthesis Examples or a method similar thereto.

Synthesis Example 404

N-Cyclopropyl-4-hydroxy-1-isobutyl-2,8-dioxo-1,2,7,8,9,10-hexahydropyrido[2',3':3,4] pyrazolo[1,5-a] pyrimidine-3-carboxamide Yield: 15.0 mg, white solid Synthesis Example 405

N-Cyclopropyl-8-hydroxy-5-neopentyl-2,6-dioxo-3-(tetrahydro-2H-pyran-4-yl)-1,2,3,4,5,6-hexahydropyrazolo[1,5-a:3,4-d'] dipyrimidine-7-carboxamide A solution of 103 mg of tert-butyl (6-(cyclopropylcarbamoyl)-3-formyl-7-hydroxy-4-neopentyl-5-oxo-4,5-dihydropyrazolo[1,5-a]pyrimidin-2-yl)carbamate produced in step B of Synthesis Example 400 and 116 mg of tetrahydro-2H-pyran-4-amine in 0.5 mL of toluene was refluxed with heating for five hours. To the reaction mixture were added 0.0744 mL of acetic acid and 195 mg of sodium triacetoxyborohydride, and the mixture was stirred at room temperature for one hour. To the reaction mixture was added 3.0 mL of a saturated aqueous sodium hydrogen carbonate solution, and the mixture was subjected to extraction with 10 mL of chloroform. The organic phase was subjected to diatomaceous earth filtration, and then the filtrate was concentrated under reduced pressure, to thereby produce 120 mg of a pale yellow solid. To 90.5 mg of the resultant pale yellow solid were added 0.152 mL of 4 M aqueous sodium hydroxide solution and 0.4 mL of 1,4-dioxane, and the resultant mixture was refluxed with heating for six hours. 1 M Hydrochloric acid was added to the reaction mixture, and then the mixture was subjected to extraction with chloroform. The organic phase was subjected to diatomaceous earth filtration, and then the filtrate was concentrated under reduced pressure. The residue was purified by silica gel column chromatography (dichloromethane/methanol/hexane=90/5/5 (v/v)), to thereby produce 11.0 mg of the title compound as a white solid.

The compounds of Synthesis Examples 406 to 410 were produced according to the methods described in the aforementioned Synthesis Examples or methods similar thereto.

Synthesis Example 406

N-Cyclopropyl-8-hydroxy-3-methyl-5-neopentyl-2,6-dioxo-1,2,3,4,5,6-hexahydropyrazolo[1,5-a:3,4-d'] dipyrimidine-7-carboxamide Yield: 9.55 mg, white solid Synthesis Example 407

N-Cyclopropyl-3-(4,4-difluorocyclohexyl)-8-hydroxy-5-neopentyl-2,6-dioxo-1,2,3,4,5,6-hexahydropyrazolo[1,5-a:3,4-d'] dipyrimidine-7-carboxamide Yield: 14.9 mg, white solid Synthesis Example 408

N,3-Dicyclopropyl-8-hydroxy-5-neopentyl-2,6-dioxo-1,2,3,4,5,6-hexahydropyrazolo[1,5-a:3,4-d'] dipyrimidine-7-carboxamide Yield: 9.28 mg, white solid Synthesis Example 409

N-Cyclopropyl-8-hydroxy-5-neopentyl-2,6-dioxo-3-((tetrahydro-2H-pyran-4-yl)methyl)-1,2,3,4,5,6-hexahydropyrazolo[1,5-a:3,4-d'] dipyrimidine-7-carboxamide Yield: 3:71 mg, white solid Synthesis Example 410

N-Cyclopropyl-3-(3,3-difluorocyclobutyl)-8-hydroxy-5-neopentyl-2,6-dioxo-1,2,3,4,5,6-hexahydropyrazolo[1,5-a:3,4-d'] dipyrimidine-7-carboxamide Yield: 23.1 mg, pale yellow solid Synthesis Example 411

(E)-2-Amino-N-cyclopropyl-7-hydroxy-3-(3-morpholino-3-oxoprop-1-en-1-yl)-4-neopentyl-5-oxo-4,5-dihydropyrazolo[1,5-a]pyrimidine-6-carboxamide (Step A) (E)-3-(2-((Tert-butoxycarbonyl)amino)-6-(cyclopropylcarbamoyl)-7-hydroxy-4-neopentyl-5-oxo-4,5-dihydropyrazolo[1,5-a]pyrimidin-3-yl) acrylic acid

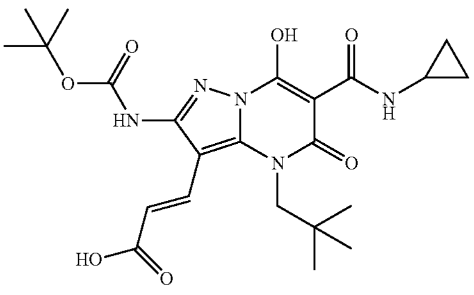 [SMILES: CC(C)(C)Cn1c(=O)c(C(=O)NC2CC2)c(O)n2nc(NC(=O)OC(C)(C)C)c(/C=C/C(=O)O)c12]

14.3 mg of lithium hydroxide monohydrate was added to a mixture of 88.0 mg of ethyl (E)-3-(2-((tert-butoxycarbonyl)amino)-6-(cyclopropylcarbamoyl)-7-hydroxy-4-neopentyl-5-oxo-4,5-dihydropyrazolo[1,5-a]pyrimidin-3-yl) acrylate produced in step A of Synthesis Example 403, 0.8 mL of 1,4-dioxane, and 0.8 mL of water at room temperature, and the resultant mixture was stirred at 80° C. for one hour. To the reaction mixture was added 1 M hydrochloric acid, and the mixture was subjected to extraction with chloroform twice. The organic phase was washed with a saturated aqueous sodium chloride solution, and then dried over sodium sulfate. The resultant product was subjected to filtration, and then the filtrate was concentrated under reduced pressure, to thereby produce 81.7 mg of the title compound as a white solid.

LC/MS: condition 2, retention time=2.54 min

LC/MS (ESI+) m/z; 490.4 $[M+H]^+$ (Step B) Tert-butyl (E)-(6-(cyclopropylcarbamoyl)-7-hydroxy-3-(3-morpholino-3-oxoprop-1-en-1-yl)-4-neopentyl-5-oxo-4,5-dihydropyrazolo[1,5-a]pyrimidine-2-yl)carbamate

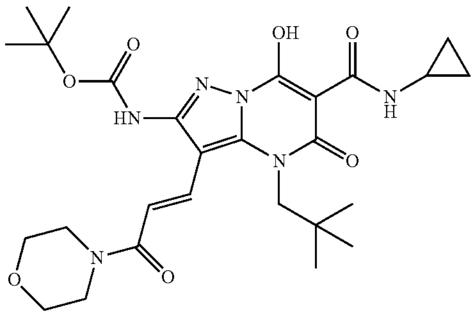 [SMILES: CC(C)(C)Cn1c(=O)c(C(=O)NC2CC2)c(O)n2nc(NC(=O)OC(C)(C)C)c(/C=C/C(=O)N3CCOCC3)c12]

76.3 mg of 1-(3-dimethylaminopropyl)-3-ethylcarbodiimide hydrochloride, 61.3 mg of 1-hydroxybenzotriazole monohydrate, and 0.0291 mL of morpholine were added to a mixture of 72.1 mg of (E)-3-(2-((tert-butoxycarbonyl) amino)-6-(cyclopropylcarbamoyl)-7-hydroxy-4-neopentyl-5-oxo-4,5-dihydropyrazolo[1,5-a]pyrimidin-3-yl)acrylic acid produced in step A of Synthesis Example 411 and 2 mL of N,N-dimethylacetamide at 0° C., and the resultant mixture was stirred at room temperature for 70 hours. To the reaction mixture was added 1 M hydrochloric acid, and the precipitated solid was recovered by filtration. The resultant solid was dried under reduced pressure, to thereby produce 65.2 mg of the title compound as a white solid.

LC/MS: condition 2, retention time=2.58 min

LC/MS (ESI+) m/z; 559.6 $[M+H]^+$ (Step C) (E)-2-Amino-N-cyclopropyl-7-hydroxy-3-(3-morpholino-3-oxoprop-1-en-1-yl)-4-neopentyl-5-oxo-4,5-dihydropyrazolo[1,5-a]pyrimidine-6-carboxamide A mixture of 2 mL of tert-butyl (E)-(6-(cyclopropylcarbamoyl)-7-hydroxy-3-(3-morpholino-3-oxoprop-1-en-1-yl)-4-neopentyl-5-oxo-4,5-dihydropyrazolo[1,5-a]pyrimidine-2-yl)carbamate produced in step B of Synthesis Example 411 and 2 mL of 4 M hydrogen chloride 1,4-dioxane solution was stirred at room temperature for four hours. The reaction mixture was concentrated under reduced pressure. The residue was suspended in ethyl acetate, and the resultant solid was recovered by filtration. A saturated aqueous sodium hydrogen carbonate solution was added to the resultant solid, and the mixture was subjected to extraction with chloroform. The organic phase was washed with a saturated aqueous sodium chloride solution and then dried over anhydrous sodium sulfate, and the resultant product was concentrated under reduced pressure, to thereby produce 52.9 mg of the title compound as a white solid.

Synthesis Example 412

Ethyl (E)-3-(2-((tert-butoxycarbonyl)amino)-6-(cyclopropylcarbamoyl)-7-hydroxy-4-isobutyl-5-oxo-4,5-dihydropyrazolo[1,5-a]pyrimidin-3-yl)acrylate (Step A) Ethyl 5-(isobutylamino)-1H-pyrazole-3-carboxylate

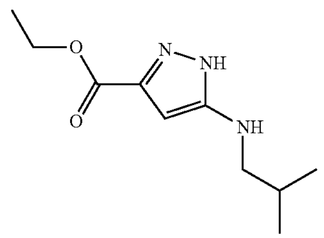

2.4 mL of acetic acid was added to a mixture of 5 g of ethyl 5-amino-1H-pyrazole-3-carboxylate, 3.03 g of isobutyraldehyde, and 50 mL of 1,2-dichloroethane at room temperature, and the resultant mixture was stirred for 16 hours. To the reaction mixture was added 13.6 g of sodium triacetoxyborohydride, and the mixture was stirred at room temperature for four hours. An aqueous sodium hydrogen carbonate solution was added to the reaction mixture, and the mixture was subjected to extraction with ethyl acetate. The organic phase was washed with a saturated aqueous sodium chloride solution, and then dried over sodium sulfate. The resultant product was subjected to filtration, and then the filtrate was concentrated under reduced pressure, to thereby produce 10.6 g of the title compound as a brown solid.

LC/MS: condition 2, retention time=1.90 min

LC/MS (ESI+) m/z; 212.3 $[M+H]^+$ (Step B) Diethyl 7-hydroxy-4-isobutyl-5-oxo-4,5-dihydropyrazolo[1,5-a]pyrimidine-2,6-dicarboxylate

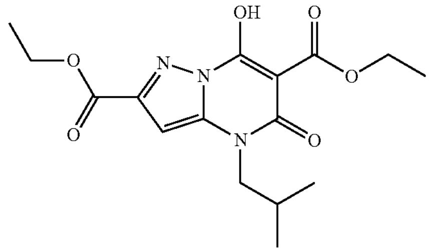 [SMILES: CCOC(=O)c1cc2n(CC(C)C)c(=O)c(C(=O)OCC)c(O)n2n1]

A mixture of 6.80 g of ethyl 5-(isobutylamino)-1H-pyrazole-3-carboxylate produced in step A of Synthesis Example 412, 9.72 g of triethyl methanetricarboxylate, 13.5 mL of triethylamine, and 35 mL of toluene was stirred at 120° C. for 42 hours. The reaction mixture was concentrated under reduced pressure, and the resultant residue was purified by silica gel column chromatography (chloroform/methanol=100/0→95/5 (v/v)), to thereby produce 11.84 g of the title compound as a brown oily product.

LC/MS: condition 2, retention time=1.86 min

LC/MS (ESI+) m/z; 352.4 $[M+H]^+$ (Step C) Ethyl 6-(cyclopropylcarbamoyl)-7-hydroxy-4-isobutyl-5-oxo-4,5-dihydropyrazolo[1,5-a]pyrimidine-2-carboxylate

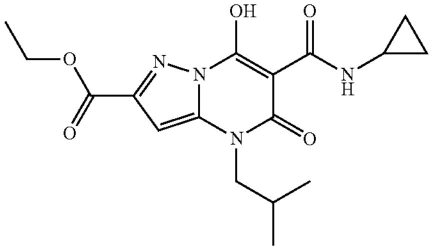 [SMILES: CCOC(=O)c1cc2n(CC(C)C)c(=O)c(C(=O)NC3CC3)c(O)n2n1]

A mixture of 11.31 g of diethyl 7-hydroxy-4-isobutyl-5-oxo-4,5-dihydropyrazolo[1,5-a]pyrimidine-2,6-dicarboxylate produced in step B of Synthesis Example 412, 6.727 mL of cyclopropylamine, and 70 mL of N,N-dimethylacetamide was stirred at 120° C. for four hours. The reaction mixture was cooled to room temperature, and 1 M hydrochloric acid was added to the mixture, followed by stirring at room temperature for two hours. The precipitated solid was recovered by filtration, and then dried under reduced pressure, to thereby produce 7.38 g of the title compound as a pale brown solid.

LC/MS: condition 2, retention time=2.78 min

LC/MS (ESI+) m/z; 363.4 $[M+H]^+$ (Step D) 6-(Cyclopropylcarbamoyl)-7-hydroxy-4-isobutyl-5-oxo-4,5-dihydropyrazolo[1,5-a]pyrimidine-2-carboxylic acid

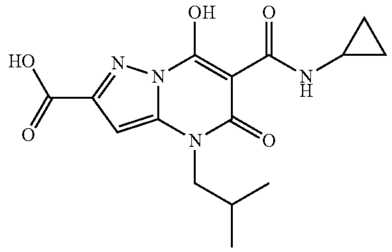 [SMILES: CC(C)Cn1c(=O)c(C(=O)NC2CC2)c(O)n2nc(C(=O)O)cc12]

A mixture of 7.32 g of ethyl 6-(cyclopropylcarbamoyl)-7-hydroxy-4-isobutyl-5-oxo-4,5-dihydropyrazolo[1,5-a]pyrimidine-2-carboxylate produced in step C of Synthesis Example 412, 5.18 g of potassium trimethylsilanolate, and 140 mL of 1,4-dioxane was stirred at room temperature for 16 hours. The reaction mixture was concentrated under reduced pressure, and then 1 M hydrochloric acid was added to the mixture, followed by extraction with ethyl acetate. The organic phase was washed with a saturated aqueous sodium chloride solution, and then dried over sodium sulfate. The resultant product was subjected to filtration, and then the filtrate was concentrated under reduced pressure, to thereby produce 7.09 g of the title compound as a white solid.

LC/MS: condition 2, retention time=2.26 min

LC/MS (ESI+) m/z; 335.3 $[M+H]^+$ (Step E) Tert-butyl (6-(cyclopropylcarbamoyl)-7-hydroxy-4-isobutyl-5-oxo-4,5-dihydropyrazolo[1,5-a]pyrimidin-2-yl)carbamate

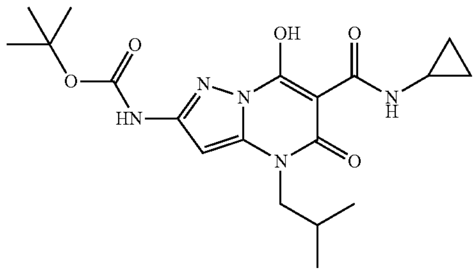 [SMILES: CC(C)Cn1c(=O)c(C(=O)NC2CC2)c(O)n2nc(NC(=O)OC(C)(C)C)cc12]

A mixture of 1.82 g of 6-(cyclopropylcarbamoyl)-7-hydroxy-4-isobutyl-5-oxo-4,5-dihydropyrazolo[1,5-a]pyrimidine-2-carboxylic acid produced in step D of Synthesis Example 412, 1.613 mL of diphenylphosphoryl azide, 2.091 mL of triethylamine, and 40 mL of tert-butanol was stirred at 100° C. for five hours. The reaction mixture was concentrated under reduced pressure, and the resultant residue was purified by silica gel column chromatography (chloroform/methanol=100/0→95/5 (v/v)), to thereby produce 2.031 g of the title compound as a white solid.

LC/MS: condition 4, retention time=3.13 min

LC/MS (ESI+) m/z; 406.5 $[M+H]^+$ (Step F) Tert-butyl (3-bromo-6-(cyclopropylcarbamoyl)-7-hydroxy-4-isobutyl-5-oxo-4,5-dihydropyrazolo[1,5-a]pyrimidin-2-yl)carbamate

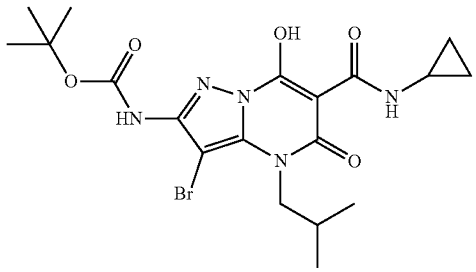 [SMILES: CC(C)Cn1c(=O)c(C(=O)NC2CC2)c(O)n2nc(NC(=O)OC(C)(C)C)c(Br)c12]

1.07 g of N-bromosuccinimide was added to a solution of 2.03 g of tert-butyl (6-(cyclopropylcarbamoyl)-7-hydroxy-4-isobutyl-5-oxo-4,5-dihydropyrazolo[1,5-a]pyrimidin-2-yl)carbamate produced in step E of Synthesis Example 412 in 6 mL of N, N-dimethylacetamide, and the resultant mixture was stirred at room temperature for 20 hours. Water was added to the reaction mixture, and the precipitated solid was recovered by filtration and washed with water. The resultant solid was dried under reduced pressure, to thereby produce 2.309 g of the title compound as a white solid.

LC/MS: condition 2, retention time=2.75 min

LC/MS (ESI+) m/z; 484.4, 486.4 $[M+H]^+$ (Step G) Ethyl (E)-3-(2-((tert-butoxycarbonyl)amino)-6-(cyclopropylcarbamoyl)-7-hydroxy-4-isobutyl-5-oxo-4,5-dihydropyrazolo[1,5-a]pyrimidin-3-yl)acrylate A solution of 968.7 mg of tert-butyl (3-bromo-6-(cyclopropylcarbamoyl)-7-hydroxy-4-isobutyl-5-oxo-4,5-dihydropyrazolo[1,5-a]pyrimidin-2-yl)carbamate produced in step F of Synthesis Example 412, 1.36 g of ethyl (E)-3-(4,4,5,5-tetramethyl-1,3,2-dioxaborolan-2-yl)acrylate, 130.4 mg of [1,1'-bis(di-tert-butylphosphino)ferrocene]dichloropalladium(II), 1.38 g of potassium carbonate in 1,4-dioxane (8 mL)/water (2 mL) was refluxed with heating in an argon atmosphere for two hours. The reaction mixture was cooled to room temperature, and 5 mL of a saturated aqueous ammonium chloride solution and 20 mL of chloroform were added to the mixture. The organic phase was subjected to diatomaceous earth filtration, and then the filtrate was concentrated under reduced pressure. The residue was purified by silica gel column chromatography (chloroform/methanol=100/0→97/3 (v/v)). The residue was suspended in 10 mL of diisopropyl ether, and the resultant solid was recovered by filtration and then dried under reduced pressure, to thereby produce 452.7 mg of the title compound as a pale brown solid.

Synthesis Example 413

Tert-butyl (E)-(6-(cyclopropylcarbamoyl)-3-(3-(4,4-difluoropiperidin-1-yl)-3-oxoprop-1-en-1-yl)-7-hydroxy-4-isobutyl-5-oxo-4,5-dihydropyrazolo[1,5-a]pyrimidin-2-yl)carbamate (Step A) (E)-3-(2-((Tert-butoxycarbonyl)amino)-6-(cyclopropylcarbamoyl)-7-hydroxy-4-isobutyl-5-oxo-4,5-dihydropyrazolo[1,5-a]pyrimidin-3-yl)acrylic acid

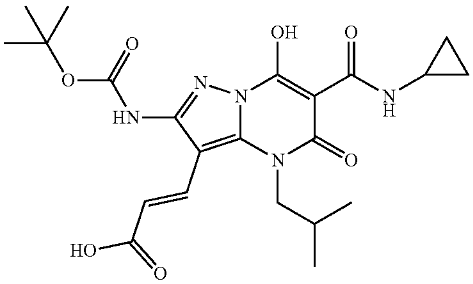 [SMILES: CC(C)Cn1c(=O)c(C(=O)NC2CC2)c(O)n2nc(NC(=O)OC(C)(C)C)c(/C=C/C(=O)O)c12]

16.8 mg of lithium hydroxide monohydrate was added to a mixture of 100.7 mg of ethyl (E)-3-(2-((tert-butoxycarbonyl)amino)-6-(cyclopropylcarbamoyl)-7-hydroxy-4-isobutyl-5-oxo-4,5-dihydropyrazolo[1,5-a]pyrimidin-3-yl)acrylate produced in step G of Synthesis Example 412, 2 mL of 1,4-dioxane, and 2 mL of water at room temperature, and the resultant mixture was stirred at 50° C. for three hours. 1 M Hydrochloric acid was added to the reaction mixture, and the mixture was subjected to extraction with 100 mL of chloroform twice. The organic phase was dried over sodium sulfate and subjected to filtration, and then the filtrate was concentrated under reduced pressure, to thereby produce 84.9 mg of the title compound as a pale yellow solid.

LC/MS: condition 2, retention time=2.32 min

LC/MS (ESI+) m/z; 476.5 $[M+H]^+$ (Step B) Tert-butyl (E)-(6-(cyclopropylcarbamoyl)-3-(3-(4,4-difluoropiperidin-1-yl)-3-oxoprop-1-en-1-yl)-7-hydroxy-4-isobutyl-5-oxo-4,5-dihydropyrazolo[1,5-a]pyrimidin-2-yl)carbamate 38.1 mg of 1-(3-dimethylaminopropyl)-3-ethylcarbodiimide hydrochloride, 30.6 mg of 1-hydroxybenzotriazole monohydrate, 0.0418 mL of triethylamine, and 31.5 mg of 4,4-difluoropiperidine hydrochloride were added to a mixture of 47.6 mg of (E)-3-(2-((tert-butoxycarbonyl)amino)-6-(cyclopropylcarbamoyl)-7-hydroxy-4-isobutyl-5-oxo-4,5-dihydropyrazolo[1,5-a]pyrimidin-3-yl)acrylic acid produced in step A of Synthesis Example 413 and 1 mL of N,N-dimethylacetamide at 0° C., and the resultant mixture was stirred at room temperature for 70 hours. 1 M Hydrochloric acid was added to the reaction mixture, and the precipitated solid was recovered by filtration and then dried under reduced pressure, to thereby produce 43.1 mg of the title compound as a pale yellow solid.

Synthesis Example 414

(E)-2-Amino-N-cyclopropyl-3-(3-(4,4-difluoropiperidin-1-yl)-3-oxoprop-1-en-1-yl)-7-hydroxy-4-isobutyl-5-oxo-4,5-dihydropyrazolo[1,5-a]pyrimidine-6-carboxamide hydrochloride A mixture of 34.7 mg of tert-butyl (E)-(6-(cyclopropylcarbamoyl)-3-(3-(4,4-difluoropiperidin-1-yl)-3-oxoprop-1-en-1-yl)-7-hydroxy-4-isobutyl-5-oxo-4,5-dihydropyrazolo[1,5-a]pyrimidin-2-yl)carbamate produced in step B of Synthesis Example 413 and 1 mL of 4 M hydrogen chloride 1,4-dioxane solution was stirred at room temperature for three hours. The reaction mixture was concentrated under reduced pressure, and the resultant solid was suspended in ethyl acetate. The resultant solid was recovered by filtration, and then dried under reduced pressure, to thereby produce 24.2 mg of the title compound as a white solid.

The compounds of Synthesis Examples 415 to 423 were produced according to the methods described in the aforementioned Synthesis Examples or methods similar thereto.

Synthesis Example 415

Tert-butyl (E)-(6-(cyclopropylcarbamoyl)-7-hydroxy-4-isobutyl-3-(3-morpholino-3-oxoprop-1-en-1-yl)-5-oxo-4,5-dihydropyrazolo[1,5-a]pyrimidin-2-yl)carbamate Yield: 40.6 mg, white solid Synthesis Example 416

(E)-2-Amino-N-cyclopropyl-7-hydroxy-4-isobutyl-3-(3-morpholino-3-oxoprop-1-en-1-yl)-5-oxo-4,5-dihydropyrazolo[1,5-a]pyrimidine-6-carboxamide Yield: 10.0 mg, white solid Synthesis Example 417

(S,E)-2-Amino-N-cyclopropyl-7-hydroxy-4-isobutyl-3-(3-(3-methylmorpholino)-3-oxoprop-1-en-1-yl)-5-oxo-4,5-dihydropyrazolo[1,5-a]pyrimidine-6-carboxamide hydrochloride Yield: 18.92 mg, white solid Synthesis Example 418

(R,E)-2-Amino-N-cyclopropyl-7-hydroxy-4-isobutyl-3-(3-(3-methylmorpholino)-3-oxoprop-1-en-1-yl)-5-oxo-4,5-dihydropyrazolo[1,5-a]pyrimidine-6-carboxamide hydrochloride Yield: 24.26 mg, pale yellow solid Synthesis Example 419

(E)-2-Amino-N-cyclopropyl-4-(cyclopropylmethyl)-7-hydroxy-3-(3-morpholino-3-oxoprop-1-en-1-yl)-5-oxo-4,5-dihydropyrazolo[1,5-a]pyrimidine-6-carboxamide hydrochloride Yield: 2.5 mg, white solid Synthesis Example 420

(E)-2-Amino-N-cyclopropyl-4-(cyclopropylmethyl)-3-(3-(4,4-difluoropiperidin-1-yl)-3-oxoprop-1-en-1-yl)-7-hydroxy-5-oxo-4,5-dihydropyrazolo[1,5-a]pyrimidine-6-carboxamide hydrochloride Yield: 11.2 mg, white solid Synthesis Example 421

(S,E)-2-Amino-3-(3-(4,4-difluoropiperidin-1-yl)-3-oxoprop-1-en-1-yl)-7-hydroxy-4-isobutyl-5-oxo-N-(1,1,1-trifluoropropan-2-yl)-4,5-dihydropyrazolo[1,5-a]pyrimidine-6-carboxamide hydrochloride Yield: 8.04 mg, pale brown solid Synthesis Example 422

2-Amino-N-cyclopropyl-3-((E)-3-((3S,5S)-3,5-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 7.5 mg, brown solid Synthesis Example 423

(E)-3-(3-(3-Oxa-9-azabicyclo[3.3.1]nonan-9-yl)-3-oxoprop-1-en-1-yl)-2-amino-N-cyclopropyl-7-hydroxy-4-isobutyl-5-oxo-4,5-dihydropyrazolo[1,5-a]pyrimidine-6-carboxamide hydrochloride Yield: 15.1 mg, pale yellow solid Synthesis Example 424

(E)-N-Cyclopropyl-7-hydroxy-3-(3-morpholino-3-oxoprop-1-en-1-yl)-4-neopentyl-5-oxo-2-ureido-4,5-dihydropyrazolo[1,5-a]pyrimidine-6-carboxamide 23.2 μL of 2,2,2-trichloroacetyl isocyanate was added to a mixture of 44.9 mg of (E)-2-amino-N-cyclopropyl-7-hydroxy-3-(3-morpholino-3-oxoprop-1-en-1-yl)-4-neopentyl-5-oxo-4,5-dihydropyrazolo[1,5-a]pyrimidine-6-carboxamide produced in step C of Synthesis Example 411 and 1 mL of tetrahydrofuran at 0° C., and the resultant mixture was stirred at room temperature for one hour. To the reaction mixture was added 1 mL of methanol, and the mixture was concentrated under reduced pressure. To the resultant residue were added 1 mL of methanol and 67.7 mg of potassium carbonate, and the resultant mixture was stirred at room temperature for four hours. Water and a saturated aqueous ammonium chloride solution were added to the reaction mixture, and the mixture was subjected to extraction with 10 mL of chloroform. The organic phase was dried over sodium sulfate and subjected to filtration, and then the filtrate was concentrated under reduced pressure. The residue was purified by silica gel column chromatography (chloroform/ethyl acetate=100/0→20/1→4/1→chloroform/methanol=20/1 (v/v)), to thereby produce 16.2 mg of the title compound as a pale yellow solid.

The compound of Synthesis Example 425 was produced according to any of the methods described in the aforementioned Synthesis Examples or a method similar thereto.

Synthesis Example 425

Methyl (E)-(6-(cyclopropylcarbamoyl)-7-hydroxy-4-isobutyl-3-(3-morpholino-3-oxoprop-1-en-1-yl)-5-oxo-4,5-dihydropyrazolo[1,5-a]pyrimidin-2-yl)carbamate Yield: 28.53 mg, brown solid Synthesis Example 426

(E)-N-Cyclopropyl-7-hydroxy-4-isobutyl-2-(methylamino)-3-(3-morpholino-3-oxoprop-1-en-1-yl)-5-oxo-4,5-dihydropyrazolo[1,5-a]pyrimidine-6-carboxamide (Step A) 3-Bromo-N-cyclopropyl-7-hydroxy-4-isobutyl-2-(methylamino)-5-oxo-4,5-dihydropyrazolo[1,5-a]pyrimidine-6-carboxamide

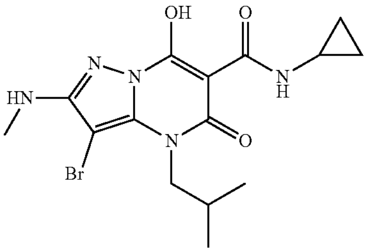 [SMILES: CNc1nn2c(O)c(C(=O)NC3CC3)c(=O)n(CC(C)C)c2c1Br]

5 mL of trifluoroacetic acid was added to 484.4 mg of tert-butyl (3-bromo-6-(cyclopropylcarbamoyl)-7-hydroxy-4-isobutyl-5-oxo-4,5-dihydropyrazolo[1,5-a]pyrimidin-2-yl)carbamate produced in step F of Synthesis Example 412, and the resultant mixture was stirred at room temperature for one minute, followed by concentration under reduced pressure. To the resultant residue was added 10 mL of triethyl orthoformate, and the mixture was stirred at 110° C. for two hours. The reaction mixture was concentrated under reduced pressure, and then dried under reduced pressure. To the resultant residue were added 10 mL of ethanol and 227.0 mg of sodium borohydride, and the mixture was stirred at 60° C. for six hours. Furthermore, 75.7 mg of sodium borohydride was added to the mixture, and the mixture was stirred at 60° C. for two hours. The reaction mixture was cooled to room temperature, and 10 mL of 1 M hydrochloric acid was added to the mixture, followed by extraction with chloroform (30 mL×3). The organic phase was dried over sodium sulfate and subjected to filtration, and then the filtrate was concentrated under reduced pressure. The residue was purified by silica gel column chromatography (chloroform/methanol=40/1 (v/v)), to thereby produce 398.3 mg of the title compound as a pale brown solid.

LC/MS: condition 3, retention time=2.52 min

LC/MS (ESI+) m/z; 398.1, 400.1 $[M+H]^+$ (Step B) Ethyl (E)-3-(6-(cyclopropylcarbamoyl)-7-hydroxy-4-isobutyl-2-(methylamino)-5-oxo-4,5-dihydropyrazolo[1,5-a]pyrimidin-3-yl)acrylate

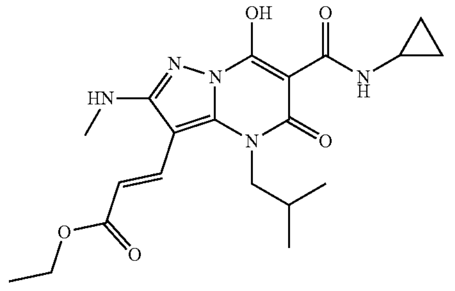 [SMILES: CCOC(=O)/C=C/c1c(NC)nn2c(O)c(C(=O)NC3CC3)c(=O)n(CC(C)C)c12]

A solution of 398.3 mg of 3-bromo-N-cyclopropyl-7-hydroxy-4-isobutyl-2-(methylamino)-5-oxo-4,5-dihydropyrazolo[1,5-a]pyrimidine-6-carboxamide produced in step A of Synthesis Example 426, 678.2 mg of ethyl (E)-3-(4,4,5,5-tetramethyl-1,3,2-dioxaborolan-2-yl)acrylate, 65.2 mg of [1,1'-bis(di-tert-butylphosphino)ferrocene]dichloropalladium(II), 552.8 mg of potassium carbonate in 1,4-dioxane (6 mL)/water (1.5 mL) was refluxed with heating in an argon atmosphere for six hours. The reaction mixture was concentrated under reduced pressure. The residue was purified by silica gel column chromatography (chloroform/methanol=40/1 (v/v)) and silica gel column chromatography (hexane/ethyl acetate=1/1→ethyl acetate (v/v)), to thereby produce 203.4 mg of the title compound as a brownish-red solid LC/MS: condition 3, retention time=2.60 min LC/MS (ESI+) m/z; 418.2 $[M+H]^+$ (Step C) (E)-N-Cyclopropyl-7-hydroxy-4-isobutyl-2-(methylamino)-3-(3-morpholino-3-oxoprop-1-en-1-yl)-5-oxo-4,5-dihydropyrazolo[1,5-a]pyrimidine-6-carboxamide A mixture of 204.6 mg of ethyl (E)-3-(6-(cyclopropylcarbamoyl)-7-hydroxy-4-isobutyl-2-(methylamino)-5-oxo-4,5-dihydropyrazolo[1,5-a]pyrimidin-3-yl)acrylate produced in step B of Synthesis Example 426, 1 mL of tetrahydrofuran, and 0.98 mL of 1 M aqueous sodium hydroxide solution was stirred under reflux with heating for six hours. The reaction mixture was cooled to room temperature, and 1 mL of 1 M hydrochloric acid was added to the mixture, followed by concentration under reduced pressure. To the residue were added 10 mL of chloroform and 1 mL of methanol, and the resultant mixture was subjected to diatomaceous earth filtration, followed by concentration of the filtrate under reduced pressure. To the residue were added 3 mL of dichloromethane, 0.171 mL of morpholine, and 186.9 mg of 1-(3-dimethylaminopropyl)-3-ethylcarbodiimide hydrochloride, and the resultant mixture was stirred at room temperature for 16 hours. The reaction mixture was purified by silica gel column chromatography (ethyl acetate→chloroform/methanol=40/1 (v/v)), to thereby produce 92.15 mg of the title compound as a pale brown amorphous product.

The compounds of Synthesis Examples 427 to 432 were produced according to the methods described in the aforementioned Synthesis Examples or methods similar thereto.

Synthesis Example 427

(E)-N-Cyclopropyl-7-hydroxy-4-isobutyl-2-(methylamino)-5-oxo-3-(3-oxo-3-(pyrrolidin-1-yl)prop-1-en-1-yl)-4,5-dihydropyrazolo[1,5-a]pyrimidine-6-carboxamide Yield: 77.11 mg, white amorphous product Synthesis Example 428

(E)-N-Cyclopropyl-3-(3-(3,3-difluoropyrrolidin-1-yl)-3-oxoprop-1-en-1-yl)-7-hydroxy-4-isobutyl-2-(methylamino)-5-oxo-4,5-dihydropyrazolo[1,5-a]pyrimidine-6-carboxamide Yield: 91.28 mg, white amorphous product Synthesis Example 429

(S,E)-N-Cyclopropyl-3-(3-(3-fluoropyrrolidin-1-yl)-3-oxoprop-1-en-1-yl)-7-hydroxy-4-isobutyl-2-(methylamino)-5-oxo-4,5-dihydropyrazolo[1,5-a]pyrimidine-6-carboxamide Yield: 91.38 mg, white amorphous product Synthesis Example 430

(S,E)-N-Cyclopropyl-7-hydroxy-4-isobutyl-2-(methylamino)-3-(3-(3-methylmorpholino)-3-oxoprop-1-en-1-yl)-5-oxo-4,5-dihydropyrazolo[1,5-a]pyrimidine-6-carboxamide Yield: 66.15 mg, white amorphous product Synthesis Example 431

(E)-3-(3-(8-Oxa-3-azabicyclo[3.2.1]octan-3-yl)-3-oxoprop-1-en-1-yl)-N-cyclopropyl-7-hydroxy-4-isobutyl-2-(methylamino)-5-oxo-4,5-dihydropyrazolo[1,5-a]pyrimidine-6-carboxamide Yield: 87.6 mg, white amorphous product Synthesis Example 432

N-Cyclopropyl-3-((E)-3-((3S,5S)-3,5-dimethylmorpholino)-3-oxoprop-1-en-1-yl)-7-hydroxy-4-isobutyl-2-(methylamino)-5-oxo-4,5-dihydropyrazolo[1,5-a]pyrimidine-6-carboxamide Yield: 60.94 mg, white amorphous product Synthesis Example 433

(E)-2-Amino-N-cyclopropyl-7-hydroxy-4-neopentyl-5-oxo-3-(2-(tetrahydro-2H-pyran-4-yl) vinyl)-4,5-dihydropyrazolo[1,5-a]pyrimidine-6-carboxamide hydrochloride (Step A) Tert-butyl (E)-(6-(cyclopropylcarbamoyl)-7-hydroxy-4-neopentyl-5-oxo-3-(2-(tetrahydro-2H-pyran-4-yl) vinyl)-4,5-dihydropyrazolo[1,5-a]pyrimidin-2-yl)carbamate

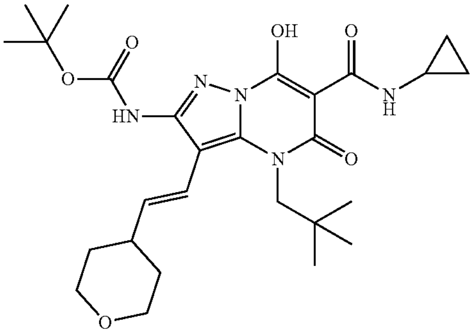 [SMILES: CC(C)(C)Cn1c(=O)c(C(=O)NC2CC2)c(O)n2nc(NC(=O)OC(C)(C)C)c(/C=C/C3CCOCC3)c12]

A mixture of 249.2 mg of tert-butyl (3-bromo-6-(cyclopropylcarbamoyl)-7-hydroxy-4-neopentyl-5-oxo-4,5-dihydropyrazolo[1,5-a]pyrimidin-2-yl)carbamate produced in step A of Synthesis Example 395, 357.2 mg of (E)-4,4,5,5-tetramethyl-2-(2-(tetrahydro-2H-pyran-4-yl) vinyl)-1,3,2-dioxaborolane, 32.6 mg of [1,1'-bis(di-tert-butylphosphino) ferrocene]dichloropalladium(II), 345.5 mg of potassium carbonate, 2.5 mL of 1,4-dioxane, and 2.5 mL of water was refluxed with heating in an argon atmosphere for five hours. The reaction mixture was cooled to room temperature, and diatomaceous earth was added to the mixture, followed by concentration under reduced pressure. The residue was purified by silica gel column chromatography (hexane/ethyl acetate=50/50 (v/v)), to thereby produce 149.4 mg of the title compound as a pale brown amorphous product LC/MS: condition 2, retention time=2.79 min LC/MS (ESI+) m/z; 530.2 $[M+H]^+$ (Step B) (E)-2-Amino-N-cyclopropyl-7-hydroxy-4-neopentyl-5-oxo-3-(2-(tetrahydro-2H-pyran-4-yl) vinyl)-4,5-dihydropyrazolo[1,5-a]pyrimidine-6-carboxamide hydrochloride A mixture of 158.9 mg of tert-butyl (E)-(6-(cyclopropylcarbamoyl)-7-hydroxy-4-neopentyl-5-oxo-3-(2-(tetrahydro-2H-pyran-4-yl) vinyl)-4,5-dihydropyrazolo[1,5-a]pyrimidin-2-yl)carbamate produced in step A of Synthesis Example 433 and 1.5 mL of 4 M hydrogen chloride 1,4-dioxane solution was stirred at room temperature for three hours. The reaction mixture was concentrated under reduced pressure, and ethyl acetate was added to the mixture. The resultant solid was recovered by filtration, and then dried under reduced pressure, to thereby produce 67.01 mg of the title compound as a white solid.

The compounds of Synthesis Examples 434 to 446 were produced according to the methods described in the aforementioned Synthesis Examples or methods similar thereto.

Synthesis Example 434

(E)-2-Amino-N-cyclopropyl-7-hydroxy-4-isobutyl-5-oxo-3-(2-(tetrahydro-2H-pyran-4-yl) vinyl)-4,5-dihydropyrazolo[1,5-a]pyrimidine-6-carboxamide hydrochloride Yield: 45.5 mg, brown amorphous product Synthesis Example 435

2-Amino-N-cyclopropyl-7-hydroxy-4-isobutyl-5-oxo-3-vinyl-4,5-dihydropyrazolo[1,5-a]pyrimidine-6-carboxamide Yield: 14.18 mg, white solid Synthesis Example 436

2-Amino-N-cyclopropyl-3-ethyl-7-hydroxy-4-neopentyl-5-oxo-4,5-dihydropyrazolo[1,5-a]pyrimidine-6-carboxamide hydrochloride Yield: 10.73 mg, white solid Synthesis Example 437

2-Amino-N-cyclopropyl-7-hydroxy-3-methyl-4-neopentyl-5-oxo-4,5-dihydropyrazolo[1,5-a]pyrimidine-6-carboxamide hydrochloride Yield: 10.5 mg, orange solid Synthesis Example 438

(E)-2-Amino-N-cyclopropyl-7-hydroxy-4-neopentyl-5-oxo-3-(prop-1-en-1-yl)-4,5-dihydropyrazolo[1,5-a]pyrimidine-6-carboxamide hydrochloride Yield: 37.73 mg, white solid Synthesis Example 439

(E)-2-Amino-N-cyclopropyl-3-(3,3-dimethylbut-1-en-1-yl)-7-hydroxy-4-isobutyl-5-oxo-4,5-dihydropyrazolo[1,5-a]pyrimidine-6-carboxamide hydrochloride Yield: 2.5 mg, pale yellow solid Synthesis Example 440

(E)-2-Amino-N-cyclopropyl-3-(2-cyclopropylvinyl)-7-hydroxy-4-neopentyl-5-oxo-4,5-dihydropyrazolo[1,5-a]pyrimidine-6-carboxamide hydrochloride Yield: 11.15 mg, white solid Synthesis Example 441

(E)-2-Amino-3-(2-cyclohexylvinyl)-N-cyclopropyl-7-hydroxy-4-isobutyl-5-oxo-4,5-dihydropyrazolo[1,5-a]pyrimidine-6-carboxamide Yield: 2.16 mg, pale brown solid Synthesis Example 442

(E)-2-Amino-N-cyclopropyl-7-hydroxy-3-(3-methylbut-1-en-1-yl)-4-neopentyl-5-oxo-4,5-dihydropyrazolo[1,5-a]pyrimidine-6-carboxamide hydrochloride Yield: 9.14 mg, white solid Synthesis Example 443

(E)-2-Amino-N-cyclopropyl-7-hydroxy-5-oxo-4-((tetrahydro-2H-pyran-4-yl)methyl)-3-(2-(tetrahydro-2H-pyran-4-yl) vinyl)-4,5-dihydropyrazolo[1,5-a]pyrimidine-6-carboxamide hydrochloride Yield: 4.94 mg, white solid Synthesis Example 444

(E)-2-Amino-N-cyclopropyl-7-hydroxy-4-neopentyl-5-oxo-3-(2-(tetrahydrofuran-3-yl) vinyl)-4,5-dihydropyrazolo[1,5-a]pyrimidine-6-carboxamide hydrochloride (racemate)

Yield: 14.4 mg, pale brown solid

Synthesis Example 445

(E)-2-Amino-N-cyclopropyl-7-hydroxy-4-((4-methyltetrahydro-2H-pyran-4-yl)methyl)-5-oxo-3-(2-(tetrahydro-2H-pyran-4-yl) vinyl)-4,5-dihydropyrazolo[1,5-a]pyrimidine-6-carboxamide hydrochloride Yield: 14.7 mg, white solid Synthesis Example 446

(E)-N-Cyclopropyl-7-hydroxy-4-isobutyl-2-(methylamino)-5-oxo-3-(2-(tetrahydro-2H-pyran-4-yl) vinyl)-4,5-dihydropyrazolo[1,5-a]pyrimidine-6-carboxamide Yield: 6.0 mg, pale yellow amorphous product Synthesis Example 447

2-Amino-3-chloro-N-cyclopropyl-7-hydroxy-4-neopentyl-5-oxo-4,5-dihydropyrazolo[1,5-a]pyrimidine-6-carboxamide hydrochloride 1 mL of N, N-dimethylformamide and 80.1 mg of N-chlorosuccinimide were added to 177.9 mg of 2-amino-N-cyclopropyl-7-hydroxy-4-neopentyl-5-oxo-4,5-dihydropyrazolo[1,5-a]pyrimidine-6-carboxamide hydrochloride produced in Synthesis Example 4, and the resultant mixture was stirred at 50° C. for 60 minutes. The reaction mixture was cooled to room temperature, and the precipitated solid was recovered by filtration. The resultant product was washed with 2 mL of N, N-dimethylformamide and 5 mL of ethyl acetate, and then dried under reduced pressure, to thereby produce 36.46 mg of the title compound as a white solid.

Synthesis Example 448

2-(2-Aminopyridin-3-yl)-3-bromo-N-cyclopropyl-7-hydroxy-4-neopentyl-5-oxo-4,5-dihydropyrazolo[1,5-a]pyrimidine-6-carboxamide (Step A) 3-Bromo-N-cyclopropyl-7-hydroxy-2-iodo-4-neopentyl-5-oxo-4,5-dihydropyrazolo[1,5-a]pyrimidine-6-carboxamide

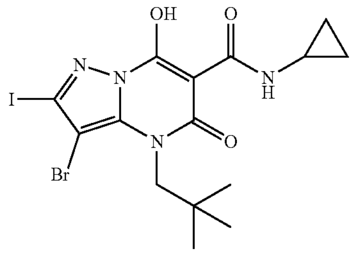 [SMILES: CC(C)(C)Cn1c(=O)c(C(=O)NC2CC2)c(O)n2nc(I)c(Br)c12]

0.0806 mL of diiodomethane and 0.0799 mL of isoamyl nitrite were added to a solution of 199.1 mg of 2-amino-3-bromo-N-cyclopropyl-7-hydroxy-4-neopentyl-5-oxo-4,5-dihydropyrazolo[1,5-a]pyrimidine-6-carboxamide produced in Synthesis Example 72 in 2 mL of acetonitrile, and the resultant mixture was stirred under reflux with heating for four hours. The reaction mixture was concentrated under reduced pressure, and then purified by silica gel column chromatography (hexane/ethyl acetate=I/O→1/1 (v/v)), to thereby produce 152.5 mg of the title compound as a yellow amorphous product.

LC/MS: condition 3, retention time=2.99 min

LC/MS (ESI+) m/z; 509.0, 511.0 $[M+H]^+$ (Step B) 2-(2-Aminopyridin-3-yl)-3-bromo-N-cyclopropyl-7-hydroxy-4-neopentyl-5-oxo-4,5-dihydropyrazolo[1,5-a]pyrimidine-6-carboxamide A solution of 152.7 mg of 3-bromo-N-cyclopropyl-7-hydroxy-2-iodo-4-neopentyl-5-oxo-4,5-dihydropyrazolo[1,5-a]pyrimidine-6-carboxamide produced in step A of Synthesis Example 448, 66.0 mg of 3-(4,4,5,5-tetramethyl-1,3,2-dioxaborolan-2-yl)pyridine-2-amine, 12.2 mg of [1,1'-diphenylferrocene]dichloropalladium(II), 82.9 mg of potassium carbonate in 1,4-dioxane (2 mL)/water (0.5 mL) was refluxed with heating in an argon atmosphere for one hour. The reaction mixture was cooled to room temperature, and 1 mL of a saturated aqueous ammonium chloride solution and 5 mL of chloroform were added to the mixture. The resultant mixture was subjected to diatomaceous earth filtration, and then the filtrate was concentrated under reduced pressure. The residue was purified by silica gel column chromatography (chloroform/methanol=20/1 (v/v)). The residue was suspended in 2 mL of ethanol, and the resultant solid was recovered by filtration and then dried under reduced pressure, to thereby produce 73.9 mg of the title compound as a pale brown solid.

Synthesis Example 449

(E)-2-(2-Aminopyridin-3-yl)-N-cyclopropyl-7-hydroxy-4-isobutyl-3-(3-morpholino-3-oxoprop-1-en-1-yl)-5-oxo-4,5-dihydropyrazolo[1,5-a]pyrimidine-6-carboxamide (Step A) 3-Bromo-N-cyclopropyl-7-hydroxy-2-iodo-4-isobutyl-5-oxo-4,5-dihydropyrazolo[1,5-a]pyrimidine-6-carboxamide

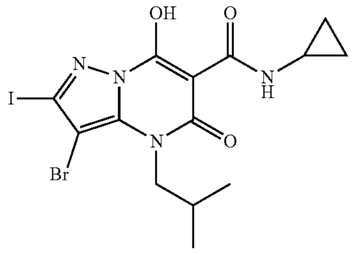 [SMILES: CC(C)Cn1c(=O)c(C(=O)NC2CC2)c(O)n2nc(I)c(Br)c12]

587.3 mg of N-bromosuccinimide was added to a solution of 916.0 mg of 2-amino-N-cyclopropyl-7-hydroxy-4-isobutyl-5-oxo-4,5-dihydropyrazolo[1,5-a]pyrimidine-6-carboxamide produced in Synthesis Example 69 in 15 mL of N,N-dimethylformamide, and the resultant mixture was stirred at room temperature for 30 minutes. The precipitated solid was recovered by filtration and washed with 10 mL of N,N-dimethylformamide and 10 mL of hexane, and then dried under reduced pressure, to thereby produce a white solid. To the resultant white solid were added 15 mL of acetonitrile, 0.304 mL of diiodomethane, and 0.269 mL of tert-butyl nitrite, and the resultant mixture was stirred under reflux with heating for 10 minutes. After completion of the reaction, the mixture was cooled to room temperature, and silica gel was added to the mixture, followed by concentration under reduced pressure. The residue was purified by silica gel column chromatography (hexane/ethyl acetate=1/1 (v/v)), to thereby produce 622.1 mg of the title compound as a yellow solid.

LC/MS: condition 3, retention time=2.90 min

LC/MS (ESI+) m/z; 495.0, 497.1 $[M+H]^+$ (Step B) 2-(2-Aminopyridin-3-yl)-3-bromo-N-cyclopropyl-7-hydroxy-4-isobutyl-5-oxo-4,5-dihydropyrazolo[1,5-a]pyrimidine-6-carboxamide

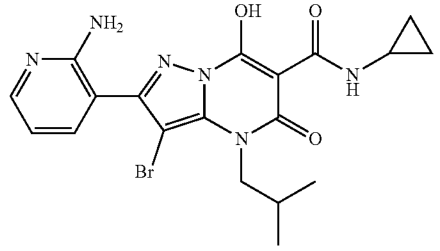 [SMILES: CC(C)Cn1c(=O)c(C(=O)NC2CC2)c(O)n2nc(-c3cccnc3N)c(Br)c12]

A solution of 152.7 mg of 3-bromo-N-cyclopropyl-7-hydroxy-2-iodo-4-isobutyl-5-oxo-4,5-dihydropyrazolo[1,5-a]pyrimidine-6-carboxamide produced in step A of Synthesis Example 449, 331.8 mg of 3-(4,4,5,5-tetramethyl-1,3,2-dioxaborolan-2-yl)pyridine-2-amine, 51.3 mg of [1,1'-diphenylferrocene]dichloropalladium(II), 347.3 mg of potassium carbonate in 1,4-dioxane (8 mL)/water (2 mL) was refluxed with heating in an argon atmosphere for one hour. The reaction mixture was cooled to room temperature, and 4 mL of a saturated aqueous ammonium chloride solution and 20 mL of chloroform were added to the mixture. The resultant mixture was subjected to diatomaceous earth filtration, and then the filtrate was concentrated under reduced pressure. The residue was purified by silica gel column chromatography (chloroform/methanol=20/1→10/1 (v/v)), to thereby produce 448.3 mg of the title compound as a pale brown solid.

LC/MS: condition 3, retention time=2.20 min

LC/MS (ESI+) m/z; 461.1, 463.1 $[M+H]^+$ (Step C) (E)-2-(2-Aminopyridin-3-yl)-N-cyclopropyl-7-hydroxy-4-isobutyl-3-(3-morpholino-3-oxoprop-1-en-1-yl)-5-oxo-4,5-dihydropyrazolo[1,5-a]pyrimidine-6-carboxamide A solution of 448.3 mg of 2-(2-aminopyridin-3-yl)-3-bromo-N-cyclopropyl-7-hydroxy-4-isobutyl-5-oxo-4,5-dihydropyrazolo[1,5-a]pyrimidine-6-carboxamide produced in step B of Synthesis Example 449, 639.6 mg of ethyl (E)-3-(4,4,5,5-tetramethyl-1,3,2-dioxaborolan-2-yl)acrylate, 61.5 mg of [1,1'-bis(di-tert-butylphosphino)ferrocene]dichloropalladium(II), 521.3 mg of potassium carbonate in 1,4-dioxane (4 mL)/water (1 mL) was refluxed with heating in an argon atmosphere for six hours. The reaction mixture was concentrated under reduced pressure, and then purified by silica gel column chromatography (chloroform/methanol=10/1 (v/v)) and silica gel column chromatography (hexane/ethyl acetate=1/1→ethyl acetate→chloroform/methanol=10/1 (v/v)). To the resultant residue were added 1 mL of tetrahydrofuran and 0.548 mL of 1 M aqueous sodium hydroxide solution, and the resultant mixture was stirred at room temperature for 16 hours. The reaction mixture was concentrated under reduced pressure. To the resultant residue were added 3 mL of dichloromethane, 0.119 mL of morpholine, and 156.8 mg of 1-(3-dimethylaminopropyl)-3-ethylcarbodiimide hydrochloride, and the resultant mixture was stirred at room temperature for 16 hours. The reaction mixture was purified by silica gel column chromatography (chloroform→chloroform/methanol=20/1 (v/v)).

The residue was suspended in 1 mL of diethyl ether, and the resultant solid was recovered by filtration and then dried under reduced pressure, to thereby produce 38.29 mg of the title compound as a pale brown solid.

Synthesis Example 450

(E)-N6-Cyclopropyl-7-hydroxy-4-isobutyl-3-(3-morpholino-3-oxoprop-1-en-1-yl)-5-oxo-4,5-dihydropyrazolol1,5-a]pyrimidine-2,6-dicarboxamide (Step A) Ethyl 4-bromo-5-(isobutylamino)-1H-pyrazole-3-carboxylate

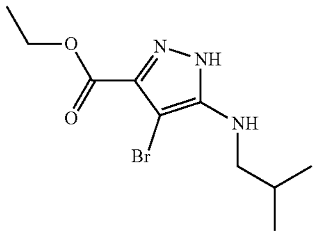 [SMILES: CCOC(=O)c1n[nH]c(NCC(C)C)c1Br]

3.83 g of N-bromosuccinimide was added to a solution of 4.33 g of ethyl 5-(isobutylamino)-1H-pyrazole-3-carboxylate produced in step A of Synthesis Example 412 in 80 mL of dichloromethane at −10° C., and the resultant mixture was stirred at −10° C. for 30 minutes. To the reaction mixture was added 50 mL of water, and the organic phase was separated and the organic phase was washed with water (50 mL×2). The organic phase was dried over sodium sulfate and subjected to filtration, and then the filtrate was concentrated under reduced pressure, to thereby produce 5.94 g of the title compound as a pale yellow solid.

LC/MS: condition 3, retention time=2.16 min

LC/MS (ESI+) m/z; 290, 292 $[M+H]^+$ (Step B) Ethyl 3-bromo-6-(cyclopropylcarbamoyl)-7-hydroxy-4-isobutyl-5-oxo-4,5-dihydropyrazolo[1,5-a]pyrimidine-2-carboxylate

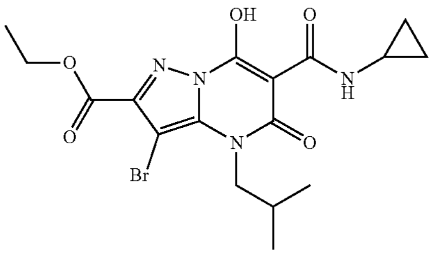 [SMILES: CCOC(=O)c1nn2c(O)c(C(=O)NC3CC3)c(=O)n(CC(C)C)c2c1Br]

4.34 g of triethyl methanetricarboxylate, 5 mL of toluene, and 6.360 mL of N,N-diisopropylethylamine were added to 2.71 g of ethyl 4-bromo-5-(isobutylamino)-1H-pyrazole-3-carboxylate produced in step A of Synthesis Example 450, and the resultant mixture was stirred under reflux with heating for one hour. To the reaction mixture were added 20 mL of N,N-dimethylacetamide and 1.302 mL of cyclopropylamine, and the resultant mixture was stirred at 90° C. for 90 minutes. The reaction mixture was concentrated under reduced pressure and purified by silica gel column chromatography (hexane/ethyl acetate=1/1 (v/v)), to thereby produce 3.11 g of the title compound as a brown solid.

LC/MS: condition 3, retention time=2.80 min

LC/MS (ESI+) m/z; 441.1, 443.1 $[M+H]^+$ (Step C) 3-Bromo-N6-cyclopropyl-7-hydroxy-4-isobutyl-5-oxo-4,5-dihydropyrazolo[1,5-a]pyrimidine-2,6-dicarboxamide

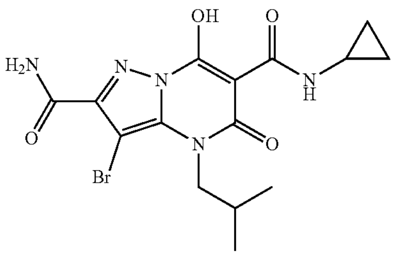 [SMILES: CC(C)Cn1c(=O)c(C(=O)NC2CC2)c(O)n2nc(C(N)=O)c(Br)c12]

2.41 g of potassium trimethylsilanolate was added to a solution of 2.76 g of ethyl 3-bromo-6-(cyclopropylcarbamoyl)-7-hydroxy-4-isobutyl-5-oxo-4,5-dihydropyrazolo[1,5-a]pyrimidine-2-carboxylate produced in step B of Synthesis Example 450 in 30 mL of tetrahydrofuran, and the resultant mixture was stirred under reflux with heating for two hours. The reaction mixture was cooled to room temperature, and 20 mL of 1 M hydrochloric acid was added to the mixture, followed by extraction with 20 mL of chloroform. The organic phase was subjected to diatomaceous earth filtration, and the filtrate was concentrated under reduced pressure. To the resultant residue were added 3 mL of acetonitrile, 158.1 mg of ammonium bicarbonate, 0.0403 mL of pyridine, and 436.5 mg of di-tert-butyl dicarbonate, and the resultant mixture was stirred at room temperature for 16 hours. The reaction mixture was concentrated under reduced pressure, and the residue was purified by silica gel column chromatography (hexane/ethyl acetate=1/2→ethyl acetate→chloroform/methanol=30/1 (v/v)), to thereby produce 1.04 g of the title compound as a pale orange solid.

LC/MS: condition 2, retention time=2.27 min

LC/MS (ESI+) m/z; 412.2, 414.2 $[M+H]^+$ (Step D) Ethyl (E)-3-(2-carbamoyl-6-(cyclopropylcarbamoyl)-7-hydroxy-4-isobutyl-5-oxo-4,5-dihydropyrazolo[1,5-a]pyrimidin-3-yl)acrylate

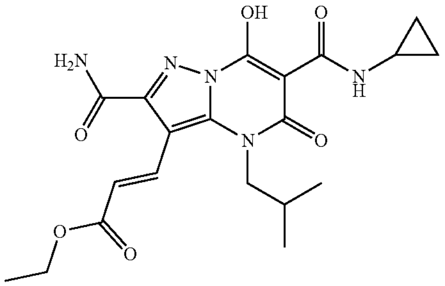 [SMILES: CCOC(=O)/C=C/c1c(C(N)=O)nn2c(O)c(C(=O)NC3CC3)c(=O)n(CC(C)C)c12]

A solution of 131.9 mg of 3-bromo-N6-cyclopropyl-7-hydroxy-4-isobutyl-5-oxo-4,5-dihydropyrazolo[1,5-a]pyrimidine-2,6-dicarboxamide produced in step C of Synthesis Example 450, 217.0 mg of ethyl (E)-3-(4,4,5,5-tetramethyl-1,3,2-dioxaborolan-2-yl)acrylate, 20.9 mg of [1,1'-bis(di-tert-butylphosphino)ferrocene]dichloropalladium(II), 221.1 mg of potassium carbonate in 1,4-dioxane (2 mL)/water (0.5 mL) was refluxed. with heating in an argon atmosphere for one hour. The reaction mixture was cooled to room temperature and subjected to filtration, and then the filtrate was concentrated under reduced pressure. The residue was purified by silica gel column chromatography (chloroform/methanol=99/1 (v/v)), to thereby produce 132.4 mg of the title compound as a brown oily product.

LC/MS: condition 2, retention time=2.39 min

LC/MS (ESI+) m/z; 432.4 $[M+H]^+$ (Step E) (E)-3-(2-Carbamoyl-6-(cyclopropylcarbamoyl)-7-hydroxy-4-isobutyl-5-oxo-4,5-dihydropyrazolo[1,5-a]pyrimidin-3-yl)acrylic acid

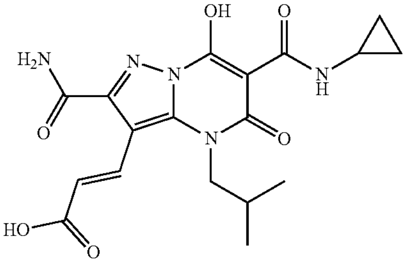 [SMILES: CC(C)Cn1c(=O)c(C(=O)NC2CC2)c(O)n2nc(C(N)=O)c(/C=C/C(=O)O)c12]

25.2 mg of lithium hydroxide monohydrate was added to a mixture of 129.4 mg of ethyl (E)-3-(2-carbamoyl-6-(cyclopropylcarbamoyl)-7-hydroxy-4-isobutyl-5-oxo-4,5-dihydropyrazolo[1,5-a]pyrimidin-3-yl)acrylate produced in step D of Synthesis Example 450, 2 mL of tetrahydrofuran, and 2 mL of water at room temperature, and the resultant mixture was stirred at room temperature for three hours. The reaction mixture was concentrated under reduced pressure, and water and ethyl acetate were added to the mixture, followed by extraction with water. 1 M Hydrochloric acid was added to the aqueous phase, and the mixture was subjected to extraction with 100 mL of ethyl acetate twice. The organic phase was washed with a saturated aqueous sodium chloride solution, and then dried over sodium sulfate. The resultant product was subjected to filtration, and then the filtrate was concentrated under reduced pressure, to thereby produce 69.0 mg of the title compound as a pale brown amorphous product LC/MS: condition 2, retention time=1.98 min LC/MS (ESI+) m/z; 404.3 $[M+H]^+$ (Step F) (E)-N6-Cyclopropyl-7-hydroxy-4-isobutyl-3-(3-morpholino-3-oxoprop-1-en-1-yl)-5-oxo-4,5-dihydropyrazolo[1,5-a]pyrimidine-2,6-dicarboxamide 65.2 mg of 1-(3-dimethylaminopropyl)-3-ethylcarbodiimide hydrochloride, 52.4 mg of 1-hydroxybenzotriazole monohydrate, and 0.0298 mL of morpholine were added to a mixture of 69.0 mg of (E)-3-(2-carbamoyl-6-(cyclopropylcarbamoyl)-7-hydroxy-4-isobutyl-5-oxo-4,5-dihydropyrazolo[1,5-a]pyrimidin-3-yl)acrylic acid produced in step E of Synthesis Example 450 and 2 mL of dichloromethane at 0° C., and the resultant mixture was stirred at room temperature for 16 hours. The reaction mixture was concentrated under reduced pressure, and 1 M hydrochloric acid was added to the mixture, followed by extraction with ethyl acetate. The organic phase was washed with a saturated aqueous sodium chloride solution, and then dried over anhydrous sodium sulfate. The resultant product was subjected to filtration, and then the filtrate was concentrated under reduced pressure. The residue was purified by silica gel column chromatography (chloroform/ethyl acetate=100/0→50/50 (v/v)→chloroform/methanol=90/10 (v/v)), to thereby produce 15.4 mg of the title compound as a white solid.

The compound of Synthesis Example 451 was produced according to any of the methods described in the aforementioned Synthesis Examples or a method similar thereto.

Synthesis Example 451

(E)-N6-Cyclopropyl-7-hydroxy-4-isobutyl-5-oxo-3-(2-(tetrahydro-2H-pyran-4-yl) vinyl)-4,5-dihydropyrazolo[1,5-a]pyrimidine-2,6-dicarboxamide Yield: 18.2 mg, white solid Synthesis Example 452

(E)-N-Cyclopropyl-7-hydroxy-4-isobutyl-5-oxo-3-(3-oxo-3-(pyrrolidin-1-yl)prop-1-en-1-yl)-4,5-dihydropyrazolo[1,5-a]pyrimidine-6-carboxamide 76.3 mg of 1-(3-dimethylaminopropyl)-3-ethylcarbodiimide hydrochloride, 61.3 mg of 1-hydroxybenzotriazole monohydrate, and 33 μL of pyrrolidine were added to a mixture of 72.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 2 mL of N,N-dimethylacetamide at 0° C., and the resultant mixture was stirred at room temperature for 16 hours. Water was added to the reaction mixture, and the precipitated solid was recovered by filtration and then dried under reduced pressure, to thereby produce 81.0 mg of the title compound as a white solid.

Synthesis Example 453

(E)-N-Cyclopropyl-3-(3-(3,3-difluoropyrrolidin-1-yl)-3-oxoprop-1-en-1-yl)-7-hydroxy-4-isobutyl-5-oxo-4,5-dihydropyrazolo[1,5-a]pyrimidine-6-carboxamide 76.3 mg of 1-(3-dimethylaminopropyl)-3-ethylcarbodiimide hydrochloride, 61.3 mg of 1-hydroxybenzotriazole monohydrate, 57.4 mg of 3,3-fluoropyrrolidine hydrochloride, and 83.6 µL of triethylamine were added to a mixture of 72.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 2 mL of N,N-dimethylacetamide at 0° C., and the resultant mixture was stirred at room temperature for 19.5 hours. 1 M Hydrochloric acid was added to the reaction mixture, and the precipitated solid was recovered by filtration and then dried under reduced pressure, to thereby produce 77.8 mg of the title compound as a white solid.

Synthesis Example 454

(S,E)-N-Cyclopropyl-3-(3-(3-fluoropyrrolidin-1-yl)-3-oxoprop-1-en-1-yl)-7-hydroxy-4-isobutyl-5-oxo-4,5-dihydropyrazolo[1,5-a]pyrimidine-6-carboxamide 76.3 mg of 1-(3-dimethylaminopropyl)-3-ethylcarbodiimide hydrochloride, 61.3 mg of 1-hydroxybenzotriazole monohydrate, 50.2 mg of(S)-3-fluoropyrrolidine hydrochloride, and 83.6 µL of triethylamine were added to a mixture of 72.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 2 mL of N,N-dimethylacetamide at 0° C., and the resultant mixture was stirred at room temperature for 23 hours. 1 M Hydrochloric acid and water were added to the reaction mixture, and the precipitated solid was recovered by filtration and then dried under reduced pressure, to thereby produce 83.4 mg of the title compound as a white solid.

Synthesis Example 455

(S,E)-N-Cyclopropyl-7-hydroxy-4-isobutyl-3-(3-(3-methylmorpholino)-3-oxoprop-1-en-1-yl)-5-oxo-4,5-dihydropyrazolo[1,5-a]pyrimidine-6-carboxamide 76.3 mg of 1-(3-dimethylaminopropyl)-3-ethylcarbodiimide hydrochloride, 61.3 mg of 1-hydroxybenzotriazole monohydrate, and 40.5 mg of(S)-3-methylmorpholine were added to a mixture of 72.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 2 mL of N,N-dimethylacetamide at 0° C., and the resultant mixture was stirred at room temperature for 19 hours. 1 M Hydrochloric acid and water were added to the reaction mixture, and the mixture was subjected to extraction with chloroform. The organic phase was dried over sodium sulfate and subjected to filtration, and then the filtrate was concentrated under reduced pressure. The residue was purified by silica gel reversed-phase column chromatography (mobile phase A: 10 mM ammonium bicarbonate-acetonitrile:water (90:10) solution, mobile phase B: 10 mM aqueous ammonium bicarbonate solution, A/B=50/50→60/40 (v/v)), to thereby produce 23.6 mg of the title compound as a white amorphous product.

Synthesis Example 456

(E)-3-(3-(8-Oxa-3-azabicyclo[3.2.1]octan-3-yl)-3-oxoprop-1-en-1-yl)-N-cyclopropyl-7-hydroxy-4-isobutyl-5-oxo-4,5-dihydropyrazolo[1,5-a]pyrimidine-6-carboxamide 114.4 mg of 1-(3-dimethylaminopropyl)-3-ethylcarbodiimide hydrochloride, 91.9 mg of 1-hydroxybenzotriazole monohydrate, 89.8 mg of 8-oxa-3-azabicyclo[3.2.1]octane hydrochloride, and 125 µL of triethylamine were added to a mixture of 108.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 2 mL of N,N-dimethylacetamide at 0° C., and the resultant mixture was stirred at room temperature for 16 hours. 1 M Hydrochloric acid was added to the reaction mixture, and the precipitated solid was recovered by filtration and then dried under reduced pressure, to thereby produce 84.43 mg of the title compound as a white solid.

Synthesis Example 457

N-Cyclopropyl-3-((E)-3-((3S,5S)-3,5-dimethylmorpholino)-3-oxoprop-1-en-1-yl)-7-hydroxy-4-isobutyl-5-oxo-4,5-dihydropyrazolo[1,5-a]pyrimidine-6-carboxamide 114.4 mg of 1-(3-dimethylaminopropyl)-3-ethylcarbodiimide hydrochloride, 91.9 mg of 1-hydroxybenzotriazole monohydrate, 91.0 mg of (3S,5S)-3,5-dimethylmorpholine hydrochloride, and 83.6 µL of triethylamine were added to a mixture of 108.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 1 mL of N,N-dimethylacetamide at 0° C., and the resultant mixture was stirred at room temperature for 16 hours. 1 M Hydrochloric acid and water were added to the reaction mixture, and the precipitated solid was recovered by filtration and then dried under reduced pressure. The residue was purified by silica gel reversed-phase column chromatography (mobile phase A: 10 mM ammonium bicarbonate-acetonitrile: water (90:10) solution, mobile phase B: 10 mM aqueous ammonium bicarbonate solution, A/B=20/80→30/70 (v/v)), to thereby produce 75.45 mg of the title compound as a white amorphous product.

Synthesis Example 458

(S,E)-N-Cyclopropyl-7-hydroxy-4-isobutyl-3-(3-(2-methylpyrrolidin-1-yl)-3-oxoprop-1-en-1-yl)-5-oxo-4,5-dihydropyrazolo[1,5-a]pyrimidine-6-carboxamide 152.6 mg of 1-(3-dimethylaminopropyl)-3-ethylcarbodiimide hydrochloride, 122.5 mg of 1-hydroxybenzotriazole monohydrate, 145.9 mg of(S)-2-methylpyrrolidine hydrochloride, and 0.167 mL of triethylamine were added to a mixture of 144.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 2 mL of N,N-dimethylacetamide at 0° C., and the resultant mixture was stirred at room temperature for two days. 1 M Hydrochloric acid and water were added to the reaction mixture, and the precipitated solid was recovered by filtration and then dried under reduced pressure, to thereby produce 116.3 mg of the title compound as a pale purple solid.

The compounds of Synthesis Examples 459 to 543 were produced according to the methods described in the aforementioned Synthesis Examples or methods similar thereto.

Synthesis Example 459

(E)-N-Cyclopropyl-3-(3-(3,3-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 155.2 mg, white solid Synthesis Example 460

(E)-N-Cyclopropyl-3-(3-(4-(3,3-difluorocyclobutyl)piperazin-1-yl)-3-oxoprop-1-en-1-yl)-7-hydroxy-4-isobutyl-5-oxo-4,5-dihydropyrazolo[1,5-a]pyrimidine-6-carboxamide Yield: 100.0 mg, white solid Synthesis Example 461

(E)-3-(3-(1,4-Oxazepan-4-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 69.7 mg, white solid Synthesis Example 462

(E)-N-Cyclopropyl-7-hydroxy-4-isobutyl-3-(3-(4-isopropylpiperazin-1-yl)-3-oxoprop-1-en-1-yl)-5-oxo-4,5-dihydropyrazolo[1,5-a]pyrimidine-6-carboxamide Yield: 84.4 mg, white solid Synthesis Example 463

(E)-N-Cyclopropyl-3-(3-(4-fluoropiperidin-1-yl)-3-oxoprop-1-en-1-yl)-7-hydroxy-4-isobutyl-5-oxo-4,5-dihydropyrazolo[1,5-a]pyrimidine-6-carboxamide Yield: 89.0 mg, white solid Synthesis Example 464

(E)-N-Cyclopropyl-3-(3-(4,4-difluoropiperidin-1-yl)-3-oxoprop-1-en-1-yl)-7-hydroxy-4-isobutyl-5-oxo-4,5-dihydropyrazolo[1,5-a]pyrimidine-6-carboxamide Yield: 91.1 mg, white solid Synthesis Example 465

(E)-N-Cyclopropyl-7-hydroxy-4-isobutyl-5-oxo-3-(3-oxo-3-(4-(trifluoromethoxy) piperidin-1-yl)prop-1-en-1-yl)-4,5-dihydropyrazolo[1,5-a]pyrimidine-6-carboxamide Yield: 100.0 mg, white solid Synthesis Example 466

(E)-N-Cyclopropyl-3-(3-(4-(difluoromethyl) piperidin-1-yl)-3-oxoprop-1-en-1-yl)-7-hydroxy-4-isobutyl-5-oxo-4,5-dihydropyrazolo[1,5-a]pyrimidine-6-carboxamide Yield: 94.0 mg, white solid Synthesis Example 467

(E)-N-Cyclopropyl-7-hydroxy-3-(3-(4-hydroxy-4-methylpiperidin-1-yl)-3-oxoprop-1-en-1-yl)-4-isobutyl-5-oxo-4,5-dihydropyrazolo[1,5-a]pyrimidine-6-carboxamide Yield: 57.13 mg, white solid Synthesis Example 468

(E)-3-(3-(4-Cyanopiperidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 88.1 mg, white solid Synthesis Example 469

(E)-N-Cyclopropyl-3-(3-(4-(1,1-difluoroethyl) piperidin-1-yl)-3-oxoprop-1-en-1-yl)-7-hydroxy-4-isobutyl-5-oxo-4,5-dihydropyrazolo[1,5-a]pyrimidine-6-carboxamide Yield: 48.5 mg, white solid Synthesis Example 470

(E)-N-Cyclopropyl-7-hydroxy-4-isobutyl-3-(3-(4-methoxy-4-methylpiperidin-1-yl)-3-oxoprop-1-en-1-yl)-5-oxo-4,5-dihydropyrazolo[1,5-a]pyrimidine-6-carboxamide Yield: 90.2 mg, white solid Synthesis Example 471

(E)-N-Cyclopropyl-3-(3-(4-cyclopropylpiperazin-1-yl)-3-oxoprop-1-en-1-yl)-7-hydroxy-4-isobutyl-5-oxo-4,5-dihydropyrazolo[1,5-a]pyrimidine-6-carboxamide Yield: 50.1 mg, white solid Synthesis Example 472

(E)-3-(3-(4-Cyclobutylpiperazin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 86.3 mg, white solid Synthesis Example 473

(E)-N-Cyclopropyl-7-hydroxy-4-isobutyl-3-(3-(4-isopropylpiperidin-1-yl)-3-oxoprop-1-en-1-yl)-5-oxo-4,5-dihydropyrazolo[1,5-a]pyrimidine-6-carboxamide Yield: 89.1 mg, white solid Synthesis Example 474

(E)-N-Cyclopropyl-7-hydroxy-3-(3-(4-(2-hydroxypropan-2-yl) piperidin-1-yl)-3-oxoprop-1-en-1-yl)-4-isobutyl-5-oxo-4,5-dihydropyrazolo[1,5-a]pyrimidine-6-carboxamide Yield: 77.9 mg, white solid Synthesis Example 475

(E)-N-Cyclopropyl-7-hydroxy-4-isobutyl-3-(3-(4-(methoxymethyl) piperidin-1-yl)-3-oxoprop-1-en-1-yl)-5-oxo-4,5-dihydropyrazolo[1,5-a]pyrimidine-6-carboxamide Yield: 59.7 mg, white solid Synthesis Example 476

(E)-N-Cyclopropyl-7-hydroxy-3-(3-(4-hydroxypiperidin-1-yl)-3-oxoprop-1-en-1-yl)-4-isobutyl-5-oxo-4,5-dihydropyrazolo[1,5-a]pyrimidine-6-carboxamide Yield: 63.2 mg, white solid Synthesis Example 477

(E)-3-(3-(4-Carbamoylpiperidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 87.38 mg, white solid Synthesis Example 478

(E)-N-Cyclopropyl-7-hydroxy-4-isobutyl-5-oxo-3-(3-oxo-3-(4-((tetrahydro-2H-pyran-4-yl)oxy) piperidin-1-yl)prop-1-en-1-yl)-4,5-dihydropyrazolo[1,5-a]pyrimidine-6-carboxamide Yield: 99.3 mg, white solid Synthesis Example 479

(E)-N-Cyclopropyl-3-(3-(3,3-dimethylpyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 76.16 mg, white solid Synthesis Example 480

(E)-N-Cyclopropyl-7-hydroxy-4-isobutyl-5-oxo-3-(3-oxo-3-(4-(trifluoromethyl) piperidine-1-yl)prop-1-en-1-yl)-4,5-dihydropyrazolo[1,5-a]pyrimidine-6-carboxamide Yield: 25.04 mg, white solid Synthesis Example 481

(R,E)-N-Cyclopropyl-3-(3-(3-fluoropyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 75.72 mg, white solid Synthesis Example 482

(S,E)-3-(3-(3-Cyanopyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 76.51 mg, white solid Synthesis Example 483

(R,E)-3-(3-(3-Cyanopyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 77.51 mg, white solid Synthesis Example 484

(S,E)-N-Cyclopropyl-7-hydroxy-4-isobutyl-5-oxo-3-(3-oxo-3-(2-(trifluoromethyl)pyrrolidine-1-yl)prop-1-en-1-yl)-4,5-dihydropyrazolo[1,5-a]pyrimidine-6-carboxamide Yield: 82.41 mg, white solid Synthesis Example 485

(R,E)-N-Cyclopropyl-7-hydroxy-4-isobutyl-5-oxo-3-(3-oxo-3-(2-(trifluoromethyl)pyrrolidine-1-yl)prop-1-en-1-yl)-4,5-dihydropyrazolo[1,5-a]pyrimidine-6-carboxamide Yield: 55.75 mg, white solid Synthesis Example 486

(S,E)-3-(3-(2-Carbamoylpyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 72.7 mg, white solid Synthesis Example 487

(R,E)-3-(3-(2-Carbamoylpyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 73.03 mg, white solid Synthesis Example 488

(E)-N-Cyclopropyl-7-hydroxy-4-isobutyl-3-(3-(4-(methylsulfonyl) piperidin-1-yl)-3-oxoprop-1-en-1-yl)-5-oxo-4,5-dihydropyrazolo[1,5-a]pyrimidine-6-carboxamide Yield: 80.59 mg, white solid Synthesis Example 489

(E)-N-Cyclopropyl-3-(3-(2,2-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 67.8 mg, white solid Synthesis Example 490

N-Cyclopropyl-3-((E)-3-((2S,6S)-2,6-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 83.28 mg, white solid Synthesis Example 491

N-Cyclopropyl-3-((E)-3-((2R,6R)-2,6-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 89.81 mg, white solid Synthesis Example 492

(E)-N-Cyclopropyl-7-hydroxy-4-isobutyl-3-(3-((4-methyltetrahydro-2H-pyran-4-yl)amino)-3-oxoprop-1-en-1-yl)-5-oxo-4,5-dihydropyrazolo[1,5-a]pyrimidine-6-carboxamide Yield: 61.57 mg, white amorphous product Synthesis Example 493

(E)-N-Cyclopropyl-3-(3-((2-cyclopropylpropan-2-yl)amino)-3-oxoprop-1-en-1-yl)-7-hydroxy-4-isobutyl-5-oxo-4,5-dihydropyrazolo[1,5-a]pyrimidine-6-carboxamide Yield: 51.3 mg, white amorphous product Synthesis Example 494

(R,E)-N-Cyclopropyl-7-hydroxy-4-isobutyl-3-(3-(3-methylmorpholino)-3-oxoprop-1-en-1-yl)-5-oxo-4,5-dihydropyrazolo[1,5-a]pyrimidine-6-carboxamide Yield: 33.8 mg, white amorphous product Synthesis Example 495

(S,E)-3-(3-(2-Cyanopyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 11.2 mg, pale brown solid Synthesis Example 496

(R,E)-3-(3-(2-Cyanopyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 2.5 mg, pale brown solid Synthesis Example 497

(E)-N-Cyclopropyl-3-(3-(cyclopropyl(methyl)amino)-3-oxoprop-1-en-1-yl)-7-hydroxy-4-isobutyl-5-oxo-4,5-dihydropyrazolo[1,5-a]pyrimidine-6-carboxamide Yield: 73.75 mg, white solid Synthesis Example 498

(E)-3-(3-((Cyanomethyl)(methyl)amino)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 58.62 mg, pale yellow solid Synthesis Example 499

(E)-N-Cyclopropyl-7-hydroxy-4-isobutyl-3-(3-(methyl((tetrahydro-2H-pyran-4-yl)methyl)amino)-3-oxoprop-1-en-1-yl)-5-oxo-4,5-dihydropyrazolo[1,5-a]pyrimidine-6-carboxamide Yield: 74.24 mg, white solid Synthesis Example 500

(E)-N-Cyclopropyl-7-hydroxy-3-(3-(3-hydroxy-3-methylpyrrolidin-1-yl)-3-oxoprop-1-en-1-yl)-4-isobutyl-5-oxo-4,5-dihydropyrazolo[1,5-a]pyrimidine-6-carboxamide (racemate)

Yield: 6.33 mg, white solid

Synthesis Example 501

(S,E)-N-Cyclopropyl-7-hydroxy-3-(3-(3-hydroxy-pyrrolidin-1-yl)-3-oxoprop-1-en-1-yl)-4-isobutyl-5-oxo-4,5-dihydropyrazolo[1,5-a]pyrimidine-6-carboxamide Yield: 66.29 mg, white solid Synthesis Example 502

(R,E)-N-Cyclopropyl-7-hydroxy-3-(3-(3-hydroxy-pyrrolidin-1-yl)-3-oxoprop-1-en-1-yl)-4-isobutyl-5-oxo-4,5-dihydropyrazolo[1,5-a]pyrimidine-6-carboxamide Yield: 71.8 mg, white solid Synthesis Example 503

(E)-N-Cyclopropyl-7-hydroxy-4-isobutyl-3-(3-(isopropyl(methyl)amino)-3-oxoprop-1-en-1-yl)-5-oxo-4,5-dihydropyrazolo[1,5-a]pyrimidine-6-carboxamide Yield: 29.9 mg, white amorphous product Synthesis Example 504

(E)-N-Cyclopropyl-3-(3-(diethylamino)-3-oxoprop-1-en-1-yl)-7-hydroxy-4-isobutyl-5-oxo-4,5-dihydropyrazolo[1,5-a]pyrimidine-6-carboxamide Yield: 49.2 mg, white solid Synthesis Example 505

(E)-N-Cyclopropyl-7-hydroxy-4-isobutyl-5-oxo-3-(3-oxo-3-(4-(2,2,3,3,3-pentafluoropropyl) piperazin-1-yl)prop-1-en-1-yl)-4,5-dihydropyrazolo[1,5-a]pyrimidine-6-carboxamide Yield: 4.99 mg, white solid Synthesis Example 506

(E)-N-Cyclopropyl-7-hydroxy-4-isobutyl-5-oxo-3-(3-oxo-3-(4-(2,2,2-trifluoroethyl) piperazin-1-yl)prop-1-en-1-yl)-4,5-dihydropyrazolo[1,5-a]pyrimidine-6-carboxamide Yield: 100.51 mg, white solid Synthesis Example 507

(E)-N-Cyclopropyl-7-hydroxy-3-(3-((2-hydroxy-2-methylpropyl)amino)-3-oxoprop-1-en-1-yl)-4-isobutyl-5-oxo-4,5-dihydropyrazolo[1,5-a]pyrimidine-6-carboxamide Yield: 103.4 mg, white solid Synthesis Example 508

(E)-N-Cyclopropyl-7-hydroxy-4-isobutyl-5-oxo-3-(3-oxo-3-(piperazin-1-yl)prop-1-en-1-yl)-4,5-dihydropyrazolo[1,5-a]pyrimidine-6-carboxamide hydrochloride Yield: 224.0 mg, white solid Synthesis Example 509

(E)-N-Cyclopropyl-7-hydroxy-4-isobutyl-3-(3-(methyl (2,2,2-trifluoroethyl)amino)-3-oxoprop-1-en-1-yl)-5-oxo-4,5-dihydropyrazolo[1,5-a]pyrimidine-6-carboxamide Yield: 95.32 mg, white solid Synthesis Example 510

(S,E)-N-Cyclopropyl-7-hydroxy-3-(3-(2-(hydroxymethyl)pyrrolidin-1-yl)-3-oxoprop-1-en-1-yl)-4-isobutyl-5-oxo-4,5-dihydropyrazolo[1,5-a]pyrimidine-6-carboxamide Yield: 171.34 mg, white solid Synthesis Example 511

(E)-N-Cyclopropyl-3-(3-(6,6-difluoro-3-azabicyclo[3.1.0]hexan-3-yl)-3-oxoprop-1-en-1-yl)-7-hydroxy-4-isobutyl-5-oxo-4,5-dihydropyrazolo[1,5-a]pyrimidine-6-carboxamide Yield: 203.94 mg, white solid Synthesis Example 512

(S,E)-3-(3-(3-Carbamoylpyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 151.79 mg, white solid Synthesis Example 513

(R,E)-3-(3-(3-Carbamoylpyrrolidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 165.17 mg, white solid Synthesis Example 514

(E)-N-Cyclopropyl-3-(3-(1,1-dioxidothiomorpholino)-3-oxoprop-1-en-1-yl)-7-hydroxy-4-isobutyl-5-oxo-4,5-dihydropyrazolo[1,5-a]pyrimidine-6-carboxamide Yield: 109.51 mg, white solid Synthesis Example 515

(E)-N-Cyclopropyl-3-(3-(dicyclopropylamino)-3-oxoprop-1-en-1-yl)-7-hydroxy-4-isobutyl-5-oxo-4,5-dihydropyrazolo[1,5-a]pyrimidine-6-carboxamide Yield: 27.14 mg, pale yellow amorphous product Synthesis Example 516

(E)-N-Cyclopropyl-7-hydroxy-4-isobutyl-5-oxo-3-(3-oxo-3-(3-oxopyrrolidin-1-yl)prop-1-en-1-yl)-4,5-dihydropyrazolo[1,5-a]pyrimidine-6-carboxamide Yield: 15.85 mg, gray solid Synthesis Example 517

(E)-N-Cyclopropyl-7-hydroxy-4-isobutyl-3-(3-((2-methoxyethyl)amino)-3-oxoprop-1-en-1-yl)-5-oxo-4,5-dihydropyrazolo[1,5-a]pyrimidine-6-carboxamide Yield: 101.3 mg, white solid Synthesis Example 518

(E)-N-Cyclopropyl-7-hydroxy-3-(3-((2-hydroxy-2-methylpropyl)(methyl)amino)-3-oxoprop-1-en-1-yl)-4-isobutyl-5-oxo-4,5-dihydropyrazolo[1,5-a]pyrimidine-6-carboxamide Yield: 149.81 mg, pale yellow amorphous product Synthesis Example 519

(E)-N-Cyclopropyl-7-hydroxy-4-isobutyl-3-(3-((2-methoxyethyl)(methyl)amino)-3-oxoprop-1-en-1-yl)-5-oxo-4,5-dihydropyrazolo[1,5-a]pyrimidine-6-carboxamide Yield: 94.5 mg, pale yellow amorphous product Synthesis Example 520

(R,E)-N-Cyclopropyl-7-hydroxy-3-(3-(3-(hydroxymethyl) piperidin-1-yl)-3-oxoprop-1-en-1-yl)-4-isobutyl-5-oxo-4,5-dihydropyrazolo[1,5-a]pyrimidine-6-carboxamide Yield: 133.8 mg, pale yellow solid Synthesis Example 521

(S,E)-N-Cyclopropyl-7-hydroxy-3-(3-(2-(hydroxymethyl) morpholino)-3-oxoprop-1-en-1-yl)-4-isobutyl-5-oxo-4,5-dihydropyrazolo[1,5-a]pyrimidine-6-carboxamide Yield: 132.0 mg, pale brown solid Synthesis Example 522

(E)-N-Cyclopropyl-3-(3-(ethyl(methyl)amino)-3-oxoprop-1-en-1-yl)-7-hydroxy-4-isobutyl-5-oxo-4,5-dihydropyrazolo[1,5-a]pyrimidine-6-carboxamide Yield: 148.85 mg, white solid Synthesis Example 523

(E)-N-Cyclopropyl-7-hydroxy-4-isobutyl-3-(3-(methyl(tetrahydro-2H-pyran-4-yl)amino)-3-oxoprop-1-en-1-yl)-5-oxo-4,5-dihydropyrazolo[1,5-a]pyrimidine-6-carboxamide Yield: 71.56 mg, white amorphous product Synthesis Example 524

(E)-3-(3-((2-Cyanoethyl)(methyl)amino)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 140.55 mg, white solid Synthesis Example 525

(S,E)-N-Cyclopropyl-7-hydroxy-3-(3-(3-(hydroxymethyl) morpholino)-3-oxoprop-1-en-1-yl)-4-isobutyl-5-oxo-4,5-dihydropyrazolo[1,5-a]pyrimidine-6-carboxamide Yield: 49.04 mg, white solid Synthesis Example 526

(R,E)-N-Cyclopropyl-7-hydroxy-3-(3-(3-(hydroxymethyl) morpholino)-3-oxoprop-1-en-1-yl)-4-isobutyl-5-oxo-4,5-dihydropyrazolo[1,5-a]pyrimidine-6-carboxamide Yield: 68.83 mg, white solid Synthesis Example 527

(E)-N-Cyclobutyl-7-hydroxy-4-isobutyl-3-(3-morpholino-3-oxoprop-1-en-1-yl)-5-oxo-4,5-dihydropyrazolo[1,5-a]pyrimidine-6-carboxamide Yield: 38.0 mg, white solid Synthesis Example 528

(S,E)-N-Cyclopropyl-7-hydroxy-3-(3-(3-(hydroxymethyl) piperidin-1-yl)-3-oxoprop-1-en-1-yl)-4-isobutyl-5-oxo-4,5-dihydropyrazolo[1,5-a]pyrimidine-6-carboxamide Yield: 132.3 mg, white solid Synthesis Example 529

(R,E)-N-Cyclopropyl-7-hydroxy-4-isobutyl-5-oxo-3-(3-oxo-3-(2-(trifluoromethyl) morpholino)prop-1-en-1-yl)-4,5-dihydropyrazolo[1,5-a]pyrimidine-6-carboxamide Yield: 49.71 mg, white solid Synthesis Example 530

(S,E)-N-Cyclopropyl-7-hydroxy-4-isobutyl-5-oxo-3-(3-oxo-3-(2-(trifluoromethyl) morpholino)prop-1-en-1-yl)-4,5-dihydropyrazolo[1,5-a]pyrimidine-6-carboxamide Yield: 42.96 mg, white solid Synthesis Example 531

(S,E)-N-Cyclopropyl-7-hydroxy-4-isobutyl-3-(3-(3-(methoxymethyl) morpholino)-3-oxoprop-1-en-1-yl)-5-oxo-4,5-dihydropyrazolo[1,5-a]pyrimidine-6-carboxamide Yield: 63.38 mg, white amorphous product Synthesis Example 532

(R,E)-N-Cyclopropyl-7-hydroxy-4-isobutyl-3-(3-(3-(methoxymethyl) morpholino)-3-oxoprop-1-en-1-yl)-5-oxo-4,5-dihydropyrazolo[1,5-a]pyrimidine-6-carboxamide Yield: 76.15 mg, white amorphous product Synthesis Example 533

(E)-3-(3-(3-Oxa-8-azabicyclo[3.2.1]octan-8-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 122.82 mg, white solid Synthesis Example 534

(S,E)-N-Cyclopropyl-7-hydroxy-4-isobutyl-5-oxo-3-(3-oxo-3-(3-(trifluoromethyl) morpholino)prop-1-en-1-yl)-4,5-dihydropyrazolo[1,5-a]pyrimidine-6-carboxamide Yield: 9.44 mg, yellow amorphous product Synthesis Example 535

(E)-3-(3-(1,2-Oxazinan-2-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 129.27 mg, white solid Synthesis Example 536

(R,E)-N-Cyclopropyl-7-hydroxy-4-isobutyl-3-(3-(2-methylpyrrolidine-1-yl)-3-oxoprop-1-en-1-yl)-5-oxo-4,5-dihydropyrazolo[1,5-a]pyrimidine-6-carboxamide Yield: 72.31 mg, pale brown solid Synthesis Example 537

(E)-N-Cyclopropyl-3-(3-(2,2-dimethylpyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 163.03 mg, white solid Synthesis Example 538

3-((E)-3-((1R,4R)-2-Oxa-5-azabicyclo[2.2.1]heptan-5-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 99.1 mg, white solid Synthesis Example 539

3-((E)-3-((1S,4S)-2-Oxa-5-azabicyclo[2.2.1]heptan-5-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 104.2 mg, white solid Synthesis Example 540

(R,E)-N-Cyclopropyl-3-(3-(3-ethylmorpholino)-3-oxoprop-1-en-1-yl)-7-hydroxy-4-isobutyl-5-oxo-4,5-dihydropyrazolo[1,5-a]pyrimidine-6-carboxamide Yield: 115.34 mg, pale yellow amorphous product Synthesis Example 541

(E)-N-Cyclopropyl-7-hydroxy-4-isobutyl-5-oxo-3-(3-oxo-3-(7-oxa-4-azaspiro[2.5]octan-4-yl)prop-1-en-1-yl)-4,5-dihydropyrazolo[1,5-a]pyrimidine-6-carboxamide Yield: 57.3 mg, pale yellow amorphous product Synthesis Example 542

(E)-3-(3-(3-Oxa-9-azabicyclo[3.3.1]nonan-9-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 66.0 mg, white solid Synthesis Example 543

(E)-3-(3-(1,2-Oxazepan-2-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 86.36 mg, pale yellow amorphous product Synthesis Example 544

(S,E)-N-Cyclopropyl-3-(3-(3-ethylmorpholino)-3-oxoprop-1-en-1-yl)-7-hydroxy-4-isobutyl-5-oxo-4,5-dihydropyrazolo[1,5-a]pyrimidine-6-carboxamide 152.6 mg of 1-(3-dimethylaminopropyl)-3-ethylcarbodiimide hydrochloride, 122.5 mg of 1-hydroxybenzotriazole monohydrate, 182.0 mg of(S)-3-ethylmorpholine hydrochloride, and 0.167 mL of triethylamine were added to a mixture of 144.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 2 mL of N,N-dimethylacetamide at 0° C., and the resultant mixture was stirred at room temperature for two days. 1 M Hydrochloric acid and water were added to the reaction mixture, and the mixture was subjected to extraction with chloroform. The organic phase was dried over sodium sulfate and then concentrated under reduced pressure. The residue was purified by silica gel reversed-phase column chromatography (mobile phase A: 10 mM ammonium bicarbonate-acetonitrile:water (90:10) solution, mobile phase B: 10 mM aqueous ammonium bicarbonate solution, A/B=20/80→30/70 (v/v)), to thereby produce 65.17 mg of the title compound as a white amorphous product.

The compounds of Synthesis Examples 545 to 549 were produced according to the methods described in the aforementioned Synthesis Examples or methods similar thereto.

Synthesis Example 545

(S,E)-7-Hydroxy-4-isobutyl-3-(3-morpholino-3-oxoprop-1-en-1-yl)-5-oxo-N-(1,1,1-trifluoropropan-2-yl)-4,5-dihydropyrazolo[1,5-a]pyrimidine-6-carboxamide Yield: 94.7 mg, white solid Synthesis Example 546

(E)-N-Cyclopropyl-3-(3-(4,4-difluoro-2-methylpiperidin-1-yl)-3-oxoprop-1-en-1-yl)-7-hydroxy-4-isobutyl-5-oxo-4,5-dihydropyrazolo[1,5-a]pyrimidine-6-carboxamide (racemate)

Yield: 180.0 mg, pale brown solid

Synthesis Example 547

(E)-N-Cyclopropyl-7-hydroxy-4-isobutyl-5-oxo-3-(3-oxo-3-(8-oxa-5-azaspiro[3.5]nonan-5-yl)prop-1-en-1-yl)-4,5-dihydropyrazolo[1,5-a]pyrimidine-6-carboxamide Yield: 68.0 mg, white amorphous product Synthesis Example 548

(R,E)-N-Cyclopropyl-7-hydroxy-4-isobutyl-3-(3-(2-(methoxymethyl)pyrrolidin-1-yl)-3-oxoprop-1-en-1-yl)-5-oxo-4,5-dihydropyrazolo[1,5-a]pyrimidine-6-carboxamide Yield: 132.2 mg, white amorphous product Synthesis Example 549

(S,E)-N-Cyclopropyl-7-hydroxy-4-isobutyl-3-(3-(2-(methoxymethyl)pyrrolidine-1-yl)-3-oxoprop-1-en-1-yl)-5-oxo-4,5-dihydropyrazolo[1,5-a]pyrimidine-6-carboxamide Yield: 122.3 mg, white amorphous product Synthesis Example 550

(E)-N-Cyclopropyl-7-hydroxy-4-isobutyl-5-oxo-3-(3-oxo-3-(3-(2,2,2-trifluoroethyl) morpholino)prop-1-en-1-yl)-4,5-dihydropyrazolo[1,5-a]pyrimidine-6-carboxamide (Isomer A)

Synthesis Example 551

(E)-N-Cyclopropyl-7-hydroxy-4-isobutyl-5-oxo-3-(3-oxo-3-(3-(2,2,2-trifluoroethyl) morpholino)prop-1-en-1-yl)-4,5-dihydropyrazolo[1,5-a]pyrimidine-6-carboxamide (Isomer B)

114.4 mg of 1-(3-dimethylaminopropyl)-3-ethylcarbodiimide hydrochloride, 18.4 mg of 1-hydroxybenzotriazole monohydrate, and 81.2 mg of 3-(2,2,2-trifluoroethyl) morpholine were added to a mixture of 144.1 mg of (E)-3-(6-(cyclopropylcarbamoyl)-7-hydroxy-4-isobutyl-5-oxo-4,5-dihydropyrazolo[1,5-a]pyrimidin-3-yl)acrylic acid produced in Synthesis Example 9 and 1.4 mL of N,N-dimethylacetamide at 0° C., and the resultant mixture was stirred at room temperature for 16 hours. 1 M Hydrochloric acid was added to the reaction mixture, and the precipitated solid was recovered by filtration and then purified by silica gel reversed-phase column chromatograph (0.1% formic acid-acetonitrile/0.1% aqueous formic acid solution=50/50→70/30 (v/v)), to thereby produce 78.69 mg of a racemic mixture of (E)-N-cyclopropyl-7-hydroxy-4-isobutyl-5-oxo-3-(3-oxo-3-(3-(2,2,2-trifluoroethyl) morpholino)prop-1-en-1-yl)-4,5-dihydropyrazolo[1,5-a]pyrimidine-6-carboxamide as a pale brown solid. The racemic mixture was optically resolved by SFC (apparatus: Waters Prep15 SFC, column: DAICEL CHIRALPAK IG (20 mmϕ×250 mm, 5 μm), column temperature: room temperature, mobile phase: carbon dioxide/methanol=65/35, flow rate: 15 mL/min). The fraction with a retention time of 27.72 min (Isomer A) and the fraction with a retention time 31.95 min (Isomer B) were concentrated under reduced pressure, to thereby produce 26.1 mg of the title compound (Isomer A) as a pale brown solid and 27.4 mg of the title compound (Isomer B) as a pale brown solid.

The compounds of Synthesis Examples 552 to 562 were produced according to the methods described in the aforementioned Synthesis Examples or methods similar thereto.

Synthesis Example 552

(E)-7-Hydroxy-4-isobutyl-3-(3-morpholino-3-oxoprop-1-en-1-yl)-5-oxo-N-(2,2,2-trifluoroethyl)-4,5-dihydropyrazolo[1,5-a]pyrimidine-6-carboxamide Yield: 13.5 mg, white solid Synthesis Example 553

(E)-3-(3-(Azetidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 62.2 mg, white solid Synthesis Example 554

(E)-N-Cyclopropyl-3-(3-(3-fluoroazetidin-1-yl)-3-oxoprop-1-en-1-yl)-7-hydroxy-4-isobutyl-5-oxo-4,5-dihydropyrazolo[1,5-a]pyrimidine-6-carboxamide Yield: 93.9 mg, white solid Synthesis Example 555

(E)-N-Cyclopropyl-3-(3-(3,3-difluoroazetidin-1-yl)-3-oxoprop-1-en-1-yl)-7-hydroxy-4-isobutyl-5-oxo-4,5-dihydropyrazolo[1,5-a]pyrimidine-6-carboxamide Yield: 103.4 mg, white solid Synthesis Example 556

N-Cyclopropyl-3-((E)-3-((3R,5R)-3,5-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 80.5 mg, white solid Synthesis Example 557

N-Cyclopropyl-3-((E)-3-(cis-3,5-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 30.2 mg, white solid Synthesis Example 558

(E)-N-Cyclopropyl-7-hydroxy-4-isobutyl-3-(3-(3-methoxyazetidin-1-yl)-3-oxoprop-1-en-1-yl)-5-oxo-4,5-dihydropyrazolo[1,5-a]pyrimidine-6-carboxamide Yield: 117 mg, white solid Synthesis Example 559

(E)-N-Cyclopropyl-7-hydroxy-4-isobutyl-5-oxo-3-(3-oxo-3-(8-oxa-2-azaspiro[4.5]decan-2-yl)prop-1-en-1-yl)-4,5-dihydropyrazolo[1,5-a]pyrimidine-6-carboxamide Yield: 62.0 mg, white solid Synthesis Example 560

(S,E)-N-Cyclopropyl-7-hydroxy-4-isobutyl-3-(3-(3-methoxypyrrolidine-1-yl)-3-oxoprop-1-en-1-yl)-5-oxo-4,5-dihydropyrazolo[1,5-a]pyrimidine-6-carboxamide Yield: 101.4 mg, white amorphous product Synthesis Example 561

(R,E)-N-Cyclopropyl-7-hydroxy-4-isobutyl-3-(3-(3-methoxypyrrolidine-1-yl)-3-oxoprop-1-en-1-yl)-5-oxo-4,5-dihydropyrazolo[1,5-a]pyrimidine-6-carboxamide Yield: 121.4 mg, white amorphous product Synthesis Example 562

(R,E)-N-Cyclopropyl-3-(3-(2-ethylpyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 26.9 mg, white amorphous product Synthesis Example 563

(E)-N-Cyclopropyl-7-hydroxy-4-isobutyl-2-methyl-3-(3-morpholino-3-oxoprop-1-en-1-yl)-5-oxo-4,5-dihydropyrazolo[1,5-a]pyrimidine-6-carboxamide (Step A) 4-Bromo-N-isobutyl-3-methyl-1H-pyrazol-5-amine

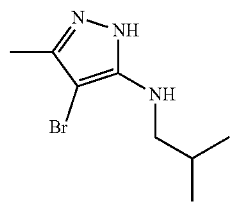

2.738 mL of isobutyraldehyde and 17.5 mL of acetic acid were added to a mixture of 2.91 g of 3-methyl-1H-pyrazol-5-amine and 100 mL of dichloromethane at 0° C., and the resultant mixture was stirred at 0° C. for 10 minutes. To the reaction mixture was added 9.54 g of sodium triacetoxyborohydride at 0° C., and the mixture was stirred at 0° C. for 30 minutes and at room temperature for 30 minutes. The reaction mixture was concentrated under reduced pressure, and 25.20 g of sodium hydrogen carbonate and 150 mL of water were added to the mixture, followed by extraction with ethyl acetate. The organic phase was dried over sodium sulfate and subjected to filtration, and then the filtrate was concentrated under reduced pressure. To the resultant residue was added 180 mL of dichloromethane, and then 5.34 g of N-bromosuccinimide was added to the mixture at −10° C., followed by stirring at −10° C. for 10 minutes. To the reaction mixture was added 50 mL of a saturated aqueous sodium thiosulfate solution, and the mixture was stirred at room temperature for 10 minutes. The organic phase was separated and dried over sodium sulfate. The resultant product was subjected to filtration, and then the filtrate was concentrated under reduced pressure. The residue was purified by silica gel column chromatography (ethyl acetate), to thereby produce 6.94 g of the title compound as a pale brown solid.

LC/MS: condition 2, retention time=1.62 min

LC/MS (ESI+) m/z; 232.1, 234.1 $[M+H]^+$ (Step B) 3-Bromo-N-cyclopropyl-7-hydroxy-4-isobutyl-2-methyl-5-oxo-4,5-dihydropyrazolo[1,5-a] pyrimidine-6-carboxamide

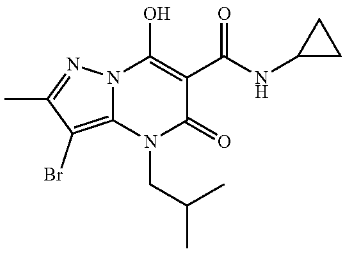 [SMILES: Cc1nn2c(O)c(C(=O)NC3CC3)c(=O)n(CC(C)C)c2c1Br]

6.803 mL of N,N-diisopropylethylamine and 4.64 g of triethyl methanetricarboxylate were added to 2.32 g of 4-bromo-N-isobutyl-3-methyl-1H-pyrazol-5-amine produced in step A of Synthesis Example 563, and the resultant mixture was stirred at 130° C. for 90 minutes. The reaction mixture was cooled to room temperature, and 5.571 mL of cyclopropylamine was added to the mixture, followed by stirring at 130° C. for 90 minutes. The reaction mixture was concentrated under reduced pressure, and the residue was purified by silica gel column chromatography (chloroform/methanol→20/1 (v/v)). The resultant residue was suspended in 10 mL of diisopropyl ether, and the resultant solid was recovered by filtration, to thereby produce 1.18 g of the title compound as a white solid.

LC/MS: condition 2, retention time=2.64 min

LC/MS (ESI+) m/z; 383.1, 385.2 $[M+H]^+$ (Step C) Ethyl (E)-3-(6-(cyclopropylcarbamoyl)-7-hydroxy-4-isobutyl-2-methyl-5-oxo-4,5-dihydropyrazolo[1,5-a]pyrimidin-3-yl)acrylate

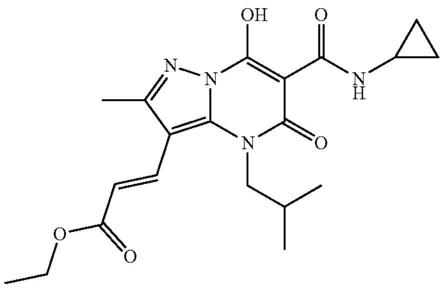 [SMILES: CCOC(=O)/C=C/c1c(C)nn2c(O)c(C(=O)NC3CC3)c(=O)n(CC(C)C)c12]

A solution of 2.27 g of 3-bromo-N-cyclopropyl-7-hydroxy-4-isobutyl-2-methyl-5-oxo-4,5-dihydropyrazolo[1,5-a]pyrimidine-6-carboxamide produced in step B of Synthesis Example 563, 4.02 g of ethyl (E)-3-(4,4,5,5-tetramethyl-1,3,2-dioxaborolan-2-yl)acrylate, 386.5 mg of [1,1'-bis(di-tert-butylphosphino)ferrocene]dichloropalladium(II), 3.28 g of potassium carbonate in 1,4-dioxane (24 mL)/water (6 mL) was refluxed with heating in an argon atmosphere for two hours. To the reaction mixture was added 25 mL of 1 M hydrochloric acid, and the mixture was subjected to extraction with 50 mL of chloroform. The organic phase was dried over sodium sulfate and subjected to filtration, and then the filtrate was concentrated under reduced pressure. The residue was purified by silica gel column chromatography (hexane/ethyl acetate=1/1 (v/v)). The resultant solid was suspended in 10 mL of diisopropyl ether, and the solid was recovered by filtration, to thereby produce 1.24 g of the title compound as a white solid.

LC/MS: condition 3, retention time=2.68 min

LC/MS (ESI+) m/z; 403.2 $[M+H]^+$ (Step D) (E)-3-(6-(Cyclopropylcarbamoyl)-7-hydroxy-4-isobutyl-2-methyl-5-oxo-4,5-dihydropyrazolo[1,5-a]pyrimidin-3-yl)acrylic acid

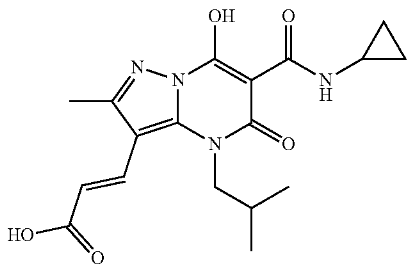 [SMILES: Cc1nn2c(O)c(C(=O)NC3CC3)c(=O)n(CC(C)C)c2c1/C=C/C(=O)O]

15 mL of ethanol and 9.15 mL of 1 M aqueous sodium hydroxide solution were added to 1.27 g of ethyl (E)-3-(6-(cyclopropylcarbamoyl)-7-hydroxy-4-isobutyl-2-methyl-5-oxo-4,5-dihydropyrazolo[1,5-a]pyrimidin-3-yl)acrylate produced in step C of Synthesis Example 563, and the resultant mixture was stirred under reflux with heating for two hours. The reaction mixture was cooled to room temperature, and 10 mL of 1 M hydrochloric acid was added to the mixture, followed by extraction with 80 mL of chloroform. The organic phase was dried over anhydrous sodium sulfate and subjected to filtration, and then the filtrate was concentrated under reduced pressure, to thereby produce 1.15 g of the title compound as a white solid.

LC/MS: condition 3, retention time=2.13 min

LC/MS (ESI+) m/z; 375.1 $[M+H]^+$ (Step E) (E)-N-Cyclopropyl-7-hydroxy-4-isobutyl-2-methyl-3-(3-morpholino-3-oxoprop-1-en-1-yl)-5-oxo-4,5-dihydropyrazolo[1,5-a]pyrimidine-6-carboxamide 3 mL of dichloromethane, 0.171 mL of morpholine, and 186.9 mg of 1-(3-dimethylaminopropyl)-3-ethylcarbodiimide hydrochloride were added to 115.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. The reaction mixture was purified by silica gel column chromatography (ethyl acetate→chloroform/methanol=40/1 (v/v)), to thereby produce 47.74 mg of the title compound as a white solid.

Synthesis Example 564

(E)-N-Cyclopropyl-7-hydroxy-4-isobutyl-2-methyl-5-oxo-3-(3-oxo-3-(pyrrolidin-1-yl)prop-1-en-1-yl)-4,5-dihydropyrazolo[1,5-a]pyrimidine-6-carboxamide 1 mL of dichloromethane, 43.7 mg of pyrrolidine, and 195.5 mg of 1-(3-dimethylaminopropyl)-3-ethylcarbodiimide hydrochloride were added to 76.8 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. The reaction mixture was concentrated under reduced pressure, and 5 mL of methanol and 5 mL of 1 M hydrochloric acid were added to the mixture. Methanol was distilled off under reduced pressure, and the precipitated solid was recovered by filtration. The resultant solid was washed with water and diethyl ether, and then dried under reduced pressure, to thereby produce 65.81 mg of the title compound as a white solid.

Synthesis Example 565

(E)-N-Cyclopropyl-3-(3-(3,3-difluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 2 mL of dichloromethane (2 mL), 107.7 mg of 3,3-difluoropyrrolidine hydrochloride, 0.105 mL of triethylamine, and 143.0 mg of 1-(3-dimethylaminopropyl)-3-ethylcarbodiimide hydrochloride were added to 93.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563, and the resultant mixture was stirred at room temperature for one hour. The reaction mixture was concentrated under reduced pressure, and 5 mL of methanol and 5 mL of 1 M hydrochloric acid were added to the mixture. Methanol was distilled off under reduced pressure, and the precipitated solid was recovered by filtration. The resultant solid was washed with water and diethyl ether, and then dried under reduced pressure, to thereby produce 110.06 mg of the title compound as a white solid.

Synthesis Example 566

(S,E)-N-Cyclopropyl-3-(3-(3-fluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 2 mL of dichloromethane, 94.2 mg of(S)-3-fluoropyrrolidine hydrochloride, 0.105 mL of triethylamine, and 143.0 mg of 1-(3-dimethylaminopropyl)-3-ethylcarbodiimide hydrochloride were added to 93.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. The reaction mixture was concentrated under reduced pressure, and 5 mL of methanol and 5 mL of 1 M hydrochloric acid were added to the mixture. Methanol was distilled off under reduced pressure, and the precipitated solid was recovered by filtration. The resultant solid was washed with water and diethyl ether, and then dried under reduced pressure, to thereby produce 105.07 mg of the title compound as a white solid.

Synthesis Example 567

N-Cyclopropyl-3-((E)-3-((3S,5S)-3,5-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide 2 mL of dichloromethane, 113.7 mg of (3S,5S)-3,5-dimethylmorpholine hydrochloride, 0.0627 mL of triethylamine, and 114.1 mg of 1-[bis(dimethylamino)methylene]-1H-1,2,3-triazolo[4,5-b]pyridinium 3-oxide hexafluorophosphate were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. The reaction mixture was concentrated under reduced pressure, and 5 mL of diethyl ether was added to the mixture. The organic phase was washed with 1 M hydrochloric acid (2 mL×3). The organic phase was subjected to diatomaceous earth filtration, and the filtrate was concentrated under reduced pressure. The residue was purified by silica gel column chromatography (hexane/ethyl acetate=1/1→ethyl acetate), to thereby produce 27.95 mg of the title compound as a white amorphous product.

Synthesis Example 568

(S,E)-N-Cyclopropyl-7-hydroxy-4-isobutyl-2-methyl-3-(3-(3-methylmorpholino)-3-oxoprop-1-en-1-yl)-5-oxo-4,5-dihydropyrazolo[1,5-a]pyrimidine-6-carboxamide 1 mL of dichloromethane, 50.6 mg of(S)-3-methylmorpholine, and 143.0 mg of 1-(3-dimethylaminopropyl)-3-ethylcarbodiimide hydrochloride were added to 93.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563, and the resultant mixture was stirred at room temperature for one hour. The reaction mixture was concentrated under reduced pressure, and 5 mL of methanol and 5 mL of 1 M hydrochloric acid were added to the mixture. Methanol was distilled off under reduced pressure, and the precipitated solid was recovered by filtration. The resultant solid was washed with water and diethyl ether, and then dried under reduced pressure, to thereby produce 74.81 mg of the title compound as a white solid.

Synthesis Example 569

(E)-3-(3-(8-Oxa-3-azabicyclo[3.2.1]octan-3-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 1 mL of dichloromethane, 56.6 mg of 8-oxa-3-azabicyclo[3.2.1]octane, and 143.0 mg of 1-(3-dimethylaminopropyl)-3-ethylcarbodiimide hydrochloride were added to 93.6 mg of (E)-3-(6-(cyclopropylcarbamoyl)-7-hydroxy-4-isobutyl- 2-methyl-5-oxo-4,5-dihydropyrazolo[1,5-a]pyrimidin-3-yl) acrylic acid produced in step D of Synthesis Example 563, and the resultant mixture was stirred at room temperature for one hour. The reaction mixture was concentrated under reduced pressure, and 5 mL of methanol and 5 mL of 1 M hydrochloric acid were added to the mixture. Methanol was distilled off under reduced pressure, and the precipitated solid was recovered by filtration. The resultant solid was washed with water and diethyl ether, and then dried under reduced pressure, to thereby produce 99.97 mg of the title compound as a white solid.

Synthesis Example 570

(R,E)-N-Cyclopropyl-7-hydroxy-4-isobutyl-2-methyl-3-(3-(3-methylmorpholino)-3-oxoprop-1-en-1-yl)-5-oxo-4,5-dihydropyrazolo[1,5-a]pyrimidine-6-carboxamide 1 mL of dichloromethane, 50.6 mg of (R)-3-methylmorpholine, and 143.0 mg of 1-(3-dimethylaminopropyl)-3-ethylcarbodiimide hydrochloride were added to 93.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563, and the resultant mixture was stirred at room temperature for one hour. To the reaction mixture was added 2 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (ethyl acetate), to thereby produce 63.47 mg of the title compound as a white amorphous product.

The compounds of Synthesis Examples 571 to 573 were produced according to the methods described in the aforementioned Synthesis Examples or methods similar thereto.

Synthesis Example 571

(E)-N-Cyclopropyl-3-(3-(4-fluoropiperidin-1-yl)-3-oxoprop-1-en-1-yl)-7-hydroxy-4-isobutyl-2-methyl-5-oxo-4,5-dihydropyrazolo[1,5-a]pyrimidine-6-carboxamide Yield: 77.37 mg, white solid Synthesis Example 572

(E)-N-Cyclopropyl-3-(3-(cyclopropyl(methyl)amino)-3-oxoprop-1-en-1-yl)-7-hydroxy-4-isobutyl-2-methyl-5-oxo-4,5-dihydropyrazolo[1,5-a]pyrimidine-6-carboxamide Yield: 66.62 mg, white solid Synthesis Example 573

(R,E)-N-Cyclopropyl-3-(3-(3-ethylmorpholino)-3-oxoprop-1-en-1-yl)-7-hydroxy-4-isobutyl-2-methyl-5-oxo-4,5-dihydropyrazolo[1,5-a]pyrimidine-6-carboxamide Yield: 78.24 mg, white amorphous product Synthesis Example 574

(E)-N-Cyclopropyl-7-hydroxy-4-isobutyl-2-methyl-3-(3-(4-methylpiperazin-1-yl)-3-oxoprop-1-en-1-yl)-5-oxo-4,5-dihydropyrazolo[1,5-a]pyrimidine-6-carboxamide 1 mL of dichloromethane, 0.0440 mL of 1-methylpiperazine, and 143.0 mg of 1-(3-dimethylaminopropyl)-3-ethylcarbodiimide hydrochloride were added to 93.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563, and the resultant mixture was stirred at room temperature for one hour. To the reaction mixture was added 0.5 mL of a saturated aqueous ammonium chloride solution, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=10/1 (v/v)), to thereby produce 83.17 mg of the title compound as a white amorphous product.

The compound of Synthesis Example 575 was produced according to any of the methods described in the aforementioned Synthesis Examples or a method similar thereto.

Synthesis Example 575

(E)-N-Cyclopropyl-7-hydroxy-2-methyl-3-(3-morpholino-3-oxoprop-1-en-1-yl)-5-oxo-4-((tetrahydro-2H-pyran-4-yl)methyl)-4,5-dihydropyrazolo[1,5-a]pyrimidine-6-carboxamide Yield: 4.5 mg, pale brown solid Synthesis Example 576

N-Cyclopropyl-3-((E)-3-((3R,5R)-3,5-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide 1 mL of dichloromethane, 60.7 mg of (3R,5R)-3,5-dimethylmorpholine hydrochloride, 0.0558 mL of triethylamine, 24.4 mg of 4-dimethylaminopyridine, and 114.4 mg of 1-(3-dimethylaminopropyl)-3-ethylcarbodiimide hydrochloride were added to 74.9 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 0.5 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=50/1 (v/v)), to thereby produce 49.9 mg of the title compound as a white amorphous product.

The compounds of Synthesis Examples 577 and 578 were produced according to the methods described in the aforementioned Synthesis Examples or methods similar thereto.

Synthesis Example 577

(S,E)-N-Cyclopropyl-7-hydroxy-4-isobutyl-3-(3-(3-methoxypyrrolidin-1-yl)-3-oxoprop-1-en-1-yl)-2-methyl-5-oxo-4,5-dihydropyrazolo[1,5-a]pyrimidine-6-carboxamide Yield: 44.6 mg, white solid Synthesis Example 578

(R,E)-N-Cyclopropyl-7-hydroxy-4-isobutyl-3-(3-(3-methoxypyrrolidin-1-yl)-3-oxoprop-1-en-1-yl)-2-methyl-5-oxo-4,5-dihydropyrazolo[1,5-a]pyrimidine-6-carboxamide Yield: 14.88 mg, white solid Synthesis Example 579

(E)-N-Cyclopropyl-3-(3-(4,4-difluoropiperidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 0.0627 mL of triethylamine, 18.3 mg of 4-dimethylaminopyridine, and 47.3 mg of 4,4-difluoropiperidine hydrochloride were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration and then the filtrate was concentrated under reduced pressure. The residue was purified by silica gel column chromatography (chloroform/methanol=99/1 (v/v)), and then the resultant product was recrystallized from 2 mL of ethanol, to thereby produce 30.4 mg of the title compound as a white solid.

The compounds of Synthesis Examples 580 and 581 were produced according to the methods described in the aforementioned Synthesis Examples or methods similar thereto.

Synthesis Example 580

(S,E)-N-Cyclopropyl-7-hydroxy-4-isobutyl-2-methyl-3-(3-(2-methylpyrrolidin-1-yl)-3-oxoprop-1-en-1-yl)-5-oxo-4,5-dihydropyrazolo[1,5-a]pyrimidine-6-carboxamide Yield: 32.5 mg, white solid Synthesis Example 581

(R,E)-N-Cyclopropyl-7-hydroxy-4-isobutyl-2-methyl-3-(3-(2-methylpyrrolidin-1-yl)-3-oxoprop-1-en-1-yl)-5-oxo-4,5-dihydropyrazolo[1,5-a]pyrimidine-6-carboxamide Yield: 27.6 mg, white solid Synthesis Example 582

(E)-N-Cyclopropyl-7-hydroxy-2-methyl-3-(3-morpholino-3-oxoprop-1-en-1-yl)-4-neopentyl-5-oxo-4,5-dihydropyrazolo[1,5-a]pyrimidine-6-carboxamide (Step A) 4-Bromo-3-methyl-N-neopentyl-1H-pyrazol-5-amine

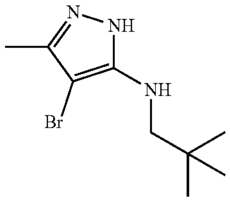

1.656 mL of pivalaldehyde and 8 mL of acetic acid were added to a mixture of 1.46 g of 3-methyl-1H-pyrazol-5-amine and 50 mL of dichloromethane at-10° C., and the resultant mixture was stirred at-10° C. for 10 minutes. To the reaction mixture was added 4.77 g of sodium triacetoxyborohydride at −10° C., and the mixture was stirred at −10° C. for 30 minutes and at room temperature for 30 minutes. The reaction mixture was concentrated under reduced pressure, and 12.60 g of sodium hydrogen carbonate and 75 mL of water were added to the mixture, followed by extraction with ethyl acetate. The organic phase was dried over sodium sulfate and subjected to filtration, and then the filtrate was concentrated under reduced pressure. To the resultant residue was added 90 mL of dichloromethane, and then 2.67 g of N-bromosuccinimide was added to the mixture at −10° C., followed by stirring at-10° C. for 10 minutes. To the reaction mixture was added 25 mL of a saturated aqueous sodium thiosulfate solution, and the mixture was stirred at room temperature for 10 minutes. The organic phase was separated and dried over sodium sulfate. The resultant product was subjected to filtration, and then the filtrate was concentrated under reduced pressure. The residue was purified by silica gel column chromatography (hexane/ethyl acetate=80/20→60/40 (v/v)), to thereby produce 3.64 g of the title compound as a colorless oily product.

LC/MS: condition 2, retention time=1.86 min

LC/MS (ESI+) m/z; 246.0, 248.0 $[M+H]^+$ (Step B) 3-Bromo-N-cyclopropyl-7-hydroxy-2-methyl-4-neopentyl-5-oxo-4,5-dihydropyrazolo[1,5-a]pyrimidine-6-carboxamide

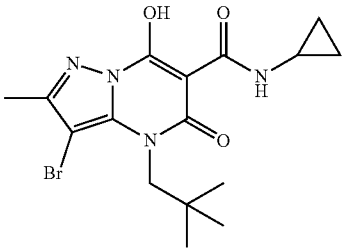 [SMILES: Cc1nn2c(O)c(C(=O)NC3CC3)c(=O)n(CC(C)(C)C)c2c1Br]

10.1 mL of N,N-diisopropylethylamine and 6.87 g of triethyl methanetricarboxylate were added to 3.64 g of 4-bromo-3-methyl-N-neopentyl-1H-pyrazol-5-amine produced in step A of Synthesis Example 582, and the resultant mixture was stirred at 130° C. for five hours. The reaction mixture was cooled to room temperature, and 4.122 mL of cyclopropylamine was added to the mixture, followed by stirring at 130° C. for three hours. The reaction mixture was concentrated under reduced pressure, and 30 mL of 1 M hydrochloric acid was added to the mixture, followed by extraction with 200 mL of chloroform. The organic phase was dried over sodium sulfate and subjected to filtration, and then the filtrate was concentrated under reduced pressure. The residue was purified by silica gel column chromatography (chloroform/methanol=100/0→99/1 (v/v)), to thereby produce 3.9878 g of the title compound as a brown oily product.

LC/MS: condition 2, retention time=2.71 min

LC/MS (ESI+) m/z; 397.0, 399.0 $[M+H]^+$ (Step C) Ethyl (E)-3-(6-(cyclopropylcarbamoyl)-7-hydroxy-2-methyl-4-neopentyl-5-oxo-4,5-dihydropyrazolo[1,5-a]pyrimidin-3-yl)acrylate

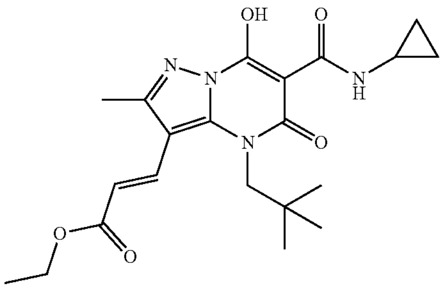 [SMILES: CCOC(=O)/C=C/c1c(C)nn2c(O)c(C(=O)NC3CC3)c(=O)n(CC(C)(C)C)c12]

A solution of 993.2 mg of 3-bromo-N-cyclopropyl-7-hydroxy-2-methyl-4-neopentyl-5-oxo-4,5-dihydropyrazolo [1,5-a]pyrimidine-6-carboxamide produced in step B of Synthesis Example 582, 1.70 g of ethyl (E)-3-(4,4,5,5-tetramethyl-1,3,2-dioxaborolan-2-yl)acrylate, 162.9 mg of [1,1'-bis(di-tert-butylphosphino)ferrocene]dichloropalladium(II), 1.73 g of potassium carbonate in 1,4-dioxane (24 mL)/water (2.5 mL) was refluxed with heating in an argon atmosphere for one hour. The reaction mixture was cooled to room temperature, and diatomaceous earth was added to the mixture. The resultant mixture was concentrated under reduced pressure, and the residue was purified by silica gel column chromatography (hexane/ethyl acetate=50/50 (v/v)), to thereby produce 318.6 mg of the title compound as a pale brown amorphous product.

LC/MS: condition 2, retention time=2.71 min

LC/MS (ESI+) m/z; 417.2 $[M+H]^+$ (Step D) (E)-3-(6-(Cyclopropylcarbamoyl)-7-hydroxy-2-methyl-4-neopentyl-5-oxo-4,5-dihydropyrazolo[1,5-a]pyrimidin-3-yl)acrylic acid

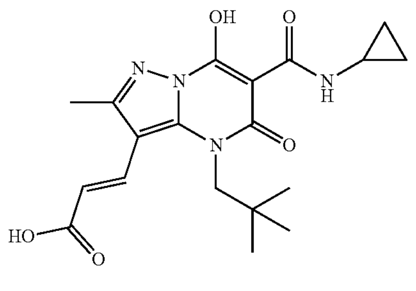 [SMILES: Cc1nn2c(O)c(C(=O)NC3CC3)c(=O)n(CC(C)(C)C)c2c1/C=C/C(=O)O]

3 mL of ethanol and 2.28 mL of 1 M aqueous sodium hydroxide solution were added to 316.5 mg of ethyl (E)-3-(6-(cyclopropylcarbamoyl)-7-hydroxy-2-methyl-4-neopentyl-5-oxo-4,5-dihydropyrazolo[1,5-a]pyrimidin-3-yl)acrylate produced in step C of Synthesis Example 582, and the resultant mixture was stirred under reflux with heating for two hours. The reaction mixture was cooled to room temperature, and 10 mL of 1 M hydrochloric acid was added to the mixture, followed by extraction with 80 mL of chloroform. The organic phase was dried over anhydrous sodium sulfate and subjected to filtration, and then the filtrate was concentrated under reduced pressure, to thereby produce 251.8 mg of the title compound as a pale brown solid.

LC/MS: condition 2, retention time=2.22 min

LC/MS (ESI+) m/z; 389.2 $[M+H]^+$ (Step E) (E)-N-Cyclopropyl-7-hydroxy-2-methyl-3-(3-morpholino-3-oxoprop-1-en-1-yl)-4-neopentyl-5-oxo-4,5-dihydropyrazolo[1,5-a]pyrimidine-6-carboxamide 1.5 mL of dichloromethane, 114.4 mg of 1-(3-dimethylaminopropyl)-3-ethylcarbodiimide hydrochloride, 24.4 mg of 4-dimethylaminopyridine, and 0.0348 mL of morpholine were added to 77.7 mg of (E)-3-(6-(cyclopropylcarbamoyl)-7-hydroxy-2-methyl-4-neopentyl-5-oxo-4,5-dihydropyrazolo[1,5-a]pyrimidin-3-yl)acrylic acid produced in step D of Synthesis Example 582 at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), and then the resultant product was recrystallized from 2 mL of ethanol, to thereby produce 53.8 mg of the title compound as a white solid.

Synthesis Example 583

(E)-N-Cyclopropyl-7-hydroxy-4-isobutyl-2-methyl-5-oxo-3-(2-(tetrahydro-2H-pyran-4-yl) vinyl)-4,5-dihydropyrazolo[1,5-a]pyrimidine-6-carboxamide A mixture of 76.7 mg of 3-bromo-N-cyclopropyl-7-hydroxy-4-isobutyl-2-methyl-5-oxo-4,5-dihydropyrazolo[1,5-a]pyrimidine-6-carboxamide produced in step B of Synthesis Example 563, 238.1 mg of (E)-4,4,5,5-tetramethyl-2-(2-(tetrahydro-2H-pyran-4-yl) vinyl)-1,3,2-dioxaborolane, 13.0 mg of [1,1'-bis(di-tert-butylphosphino)ferrocene]dichloropalladium(II), 138.2 mg of potassium carbonate, 1 mL of 1,4-dioxane, and 1 mL of water was refluxed with heating in an argon atmosphere for 16 hours. The reaction mixture was cooled to room temperature, and diatomaceous earth was added to the mixture, followed by concentration under reduced pressure. The residue was purified by silica gel column chromatography (chloroform/methanol=100/0→99/1→95/5 (v/v)), and then the resultant product was recrystallized from ethanol, to thereby produce 25.0 mg of the title compound as a white solid.

The compounds of Synthesis Examples 584 and 585 were produced according to the methods described in the aforementioned Synthesis Examples or methods similar thereto.

Synthesis Example 584

(E)-N-Cyclopropyl-7-hydroxy-2-methyl-4-neopentyl-5-oxo-3-(2-(tetrahydro-2H-pyran-4-yl) vinyl)-4,5-dihydropyrazolo[1,5-a]pyrimidine-6-carboxamide Yield: 25.0 mg, white solid Synthesis Example 585

(E)-N-Cyclopropyl-7-hydroxy-2-(methylamino)-4-((4-methyltetrahydro-2H-pyran-4-yl)methyl)-5-oxo-3-(2-(tetrahydro-2H-pyran-4-yl) vinyl)-4,5-dihydropyrazolo[1,5-a]pyrimidine-6-carboxamide Yield: 9.03 mg, brown amorphous product Synthesis Example 586

(E)-N-Cyclopropyl-2-ethyl-7-hydroxy-4-isobutyl-3-(3-morpholino-3-oxoprop-1-en-1-yl)-5-oxo-4,5-dihydropyrazolo[1,5-a]pyrimidine-6-carboxamide Yield: 50.0 mg, white solid (Step A) 4-Bromo-3-ethyl-N-isobutyl-1H-pyrazol-5-amine

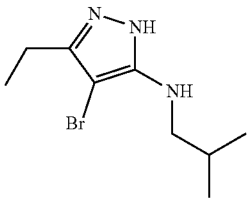

1.734 mL of isobutyraldehyde and 8 mL of acetic acid were added to a mixture of 2.11 g of 3-ethyl-1H-pyrazol-5-amine and 50 mL of dichloromethane at-10° C., and the resultant mixture was stirred at −10° C. for 10 minutes. To the reaction mixture was added 6.04 g of sodium triacetoxyborohydride at-10° C., and the mixture was stirred at −10° C. for 30 minutes and at room temperature for 30 minutes. The reaction mixture was concentrated under reduced pressure, and 15.96 g of sodium hydrogen carbonate and 75 mL of water were added to the mixture, followed by extraction with ethyl acetate. The organic phase was dried over sodium sulfate and subjected to filtration, and then the filtrate was concentrated under reduced pressure. To the resultant residue was added 90 mL of dichloromethane, and then 3.38 g of N-bromosuccinimide was added to the mixture at −10° C., followed by stirring at −10° C. for 10 minutes. To the reaction mixture was added 25 mL of a saturated aqueous sodium thiosulfate solution, and the mixture was stirred at room temperature for 10 minutes. The organic phase was separated and dried over sodium sulfate. The resultant product was subjected to filtration, and then the filtrate was concentrated under reduced pressure. The residue was purified by silica gel column chromatography (hexane/ethyl acetate=80/20→60/40 (v/v)), to thereby produce 2.8021 g of the title compound as a brown solid.

LC/MS: condition 2, retention time=1.84 min

LC/MS (ESI+) m/z; 246.2, 248.2 $[M+H]^+$ (Step B) 3-Bromo-N-cyclopropyl-2-ethyl-7-hydroxy-4-isobutyl-5-oxo-4,5-dihydropyrazolo[1,5-a]pyrimidine-6-carboxamide

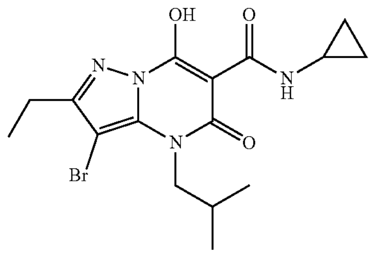 [SMILES: CCc1nn2c(O)c(C(=O)NC3CC3)c(=O)n(CC(C)C)c2c1Br]

7.721 mL of N,N-diisopropylethylamine and 5.27 g of triethyl methanetricarboxylate were added to 2.79 g of 4-bromo-3-ethyl-N-isobutyl-1H-pyrazol-5-amine produced in step A of Synthesis Example 586, and the resultant mixture was stirred at 130° C. for five hours. The reaction mixture was concentrated under reduced pressure, and then the residue was purified by silica gel column chromatography (chloroform/methanol=100/0→99/1 (v/v)). To the resultant residue were added 5 mL of N,N-dimethylformamide and 3.161 mL of cyclopropylamine, and the resultant mixture was stirred at 130° C. for two hours. The reaction mixture was cooled to room temperature, and then 10 mL of 1 M hydrochloric acid was added to the mixture, followed by stirring at room temperature for one hour. The precipitated solid was recovered by filtration and washed with water, and then dried under reduced pressure, to thereby produce 465.5 mg of the title compound as a pale brown solid.

LC/MS: condition 2, retention time=2.82 min

LC/MS (ESI+) m/z; 397.3, 399.3 $[M+H]^+$ (Step C) Ethyl (E)-3-(6-(cyclopropylcarbamoyl)-2-ethyl-7-hydroxy-4-isobutyl-5-oxo-4,5-dihydropyrazolo[1,5-a]pyrimidin-3-yl)acrylate

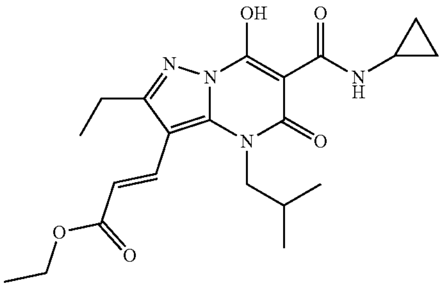 [SMILES: CCOC(=O)/C=C/c1c(CC)nn2c(O)c(C(=O)NC3CC3)c(=O)n(CC(C)C)c12]

A solution of 298.0 mg of 3-bromo-N-cyclopropyl-2-ethyl-7-hydroxy-4-isobutyl-5-oxo-4,5-dihydropyrazolo[1,5-a]pyrimidine-6-carboxamide produced in step B of Synthesis Example 586, 508.7 mg of ethyl (E)-3-(4,4,5,5-tetramethyl-1,3,2-dioxaborolan-2-yl)acrylate, 48.9 mg of [1,1'-bis(di-tert-butylphosphino)ferrocene]dichloropalladium(II), 518.3 mg of potassium carbonate in 1,4-dioxane (3 mL)/water (1 mL) was refluxed with heating in an argon atmosphere for one hour. The reaction mixture was cooled to room temperature, and then diatomaceous earth was added to the mixture, followed by concentration under reduced pressure. The residue was purified by silica gel column chromatography (hexane/ethyl acetate=50/50 (v/v)), to thereby produce 228.6 mg of the title compound as a pale brown solid.

LC/MS: condition 2, retention time=2.79 min

LC/MS (ESI+) m/z; 417.4. $[M+H]^+$ (Step D) (E)-3-(6-(Cyclopropylcarbamoyl)-2-ethyl-7-hydroxy-4-isobutyl-5-oxo-4,5-dihydropyrazolo[1,5-a]pyrimidin-3-yl)acrylic acid

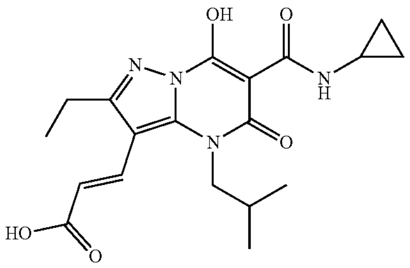 [SMILES: CCc1nn2c(O)c(C(=O)NC3CC3)c(=O)n(CC(C)C)c2c1/C=C/C(=O)O]

2.3 mL of ethanol and 1.62 mL of 1 M aqueous sodium hydroxide solution were added to 224.9 mg of ethyl (E)-3-(6-(cyclopropylcarbamoyl)-2-ethyl-7-hydroxy-4-isobutyl-5-oxo-4,5-dihydropyrazolo[1,5-a]pyrimidin-3-yl)acrylate produced in step C of Synthesis Example 586, and the resultant mixture was stirred under reflux with heating for two hours. The reaction mixture was cooled to room temperature, and 2 mL of 1 M hydrochloric acid was added to the mixture, followed by stirring at room temperature for 10 minutes. The precipitated solid was recovered by filtration and then dried under reduced pressure, to thereby produce 171.7 mg of the title compound as a pale brown solid.

LC/MS: condition 2, retention time=2.25 min

LC/MS (ESI+) m/z; 389.4 $[M+H]^+$ (Step E) (E)-N-Cyclopropyl-2-ethyl-7-hydroxy-4-isobutyl-3-(3-morpholino-3-oxoprop-1-en-1-yl)-5-oxo-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 18.3 mg of 4-dimethylaminopyridine, and 0.0281 mL of morpholine were added to 58.3 mg of (E)-3-(6-(cyclopropylcarbamoyl)-2-ethyl-7-hydroxy-4-isobutyl-5-oxo-4,5-dihydropyrazolo[1,5-a]pyrimidin-3-yl)acrylic acid produced in step D of Synthesis Example 586 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), and then the resultant product was recrystallized from ethanol, to thereby produce 50.0 mg of the title compound as a white solid.

The compounds of Synthesis Examples 587 to 607 were produced according to the methods described in the aforementioned Synthesis Examples or methods similar thereto.

Synthesis Example 587

(S,E)-N-Cyclopropyl-3-(3-(2-(dimethylcarbamoyl)pyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 91.25 mg, brown solid Synthesis Example 588

(E)-3-(3-(2-Azabicyclo[3.1.0]hexan-2-yl)-3-oxoprop-1-en-1-yl)-N-cyclopropyl-7-hydroxy-4-isobutyl-5-oxo-4,5-dihydropyrazolo[1,5-a]pyrimidine-6-carboxamide (racemate)

Yield: 38.29 mg, white solid

Synthesis Example 589

(R,E)-N-Cyclopropyl-7-hydroxy-3-(3-(2-(2-hydroxypropan-2-yl) pyrrolidin-1-yl)-3-oxoprop-1-en-1-yl)-4-isobutyl-5-oxo-4,5-dihydropyrazolo[1,5-a]pyrimidine-6-carboxamide Yield: 99.9 mg, white solid Synthesis Example 590

N-Cyclopropyl-3-((E)-3-((2R,5R)-2,5-dimethylpyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 18.85 mg, white solid Synthesis Example 591

N-Cyclopropyl-3-((E)-3-((2S,5S)-2,5-dimethylpyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 44.26 mg, white solid Synthesis Example 592

N-Cyclopropyl-3-((E)-3-(cis-2,5-dimethylpyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 42.69 mg, white amorphous product Synthesis Example 593

(E)-N-Cyclopropyl-3-(3-(2-cyclopropylpyrrolidin-1-yl)-3-oxoprop-1-en-1-yl)-7-hydroxy-4-isobutyl-5-oxo-4,5-dihydropyrazolo[1,5-a]pyrimidine-6-carboxamide (racemate)

Yield: 79.27 mg, white amorphous product

Synthesis Example 594

(E)-N-Cyclopropyl-3-(3-(2,3-dihydro-1H-pyrrolo[2,3-b]pyridin-1-yl)-3-oxoprop-1-en-1-yl)-7-hydroxy-4-isobutyl-5-oxo-4,5-dihydropyrazolo[1,5-a]pyrimidine-6-carboxamide Yield: 36.28 mg, white solid Synthesis Example 595

(E)-N-Cyclopropyl-7-hydroxy-4-isobutyl-5-oxo-3-(3-oxo-3-(3-(trifluoromethyl)pyrrolidin-1-yl)prop-1-en-1-yl)-4,5-dihydropyrazolo[1,5-a]pyrimidine-6-carboxamide (racemate)

Yield: 115.7 mg, white solid

Synthesis Example 596

(E)-N-Cyclopropyl-3-(3-(3-(difluoromethyl)pyrrolidin-1-yl)-3-oxoprop-1-en-1-yl)-7-hydroxy-4-isobutyl-5-oxo-4,5-dihydropyrazolo[1,5-a]pyrimidine-6-carboxamide (racemate)

Yield: 53.2 mg, white solid

Synthesis Example 597

N-Cyclopropyl-3-((E)-3-(cis-2,6-dimethylpiperidin-1-yl)-3-oxoprop-1-en-1-yl)-7-hydroxy-4-isobutyl-5-oxo-4,5-dihydropyrazolo[1,5-a]pyrimidine-6-carboxamide Yield: 24.61 mg, white amorphous product Synthesis Example 598

(S,E)-N-Cyclopropyl-7-hydroxy-3-(3-(3-(2-hydroxypropan-2-yl) pyrrolidin-1-yl)-3-oxoprop-1-en-1-yl)-4-isobutyl-5-oxo-4,5-dihydropyrazolo[1,5-a]pyrimidine-6-carboxamide Yield: 35.77 mg, white solid Synthesis Example 599

(R,E)-N-Cyclopropyl-7-hydroxy-4-isobutyl-3-(3-(2-isopropylpyrrolidin-1-yl)-3-oxoprop-1-en-1-yl)-5-oxo-4,5-dihydropyrazolo[1,5-a]pyrimidine-6-carboxamide Yield: 95.56 mg, white solid Synthesis Example 600

(S,E)-N-Cyclopropyl-7-hydroxy-4-isobutyl-3-(3-(2-isopropylpyrrolidin-1-yl)-3-oxoprop-1-en-1-yl)-5-oxo-4,5-dihydropyrazolo[1,5-a]pyrimidine-6-carboxamide Yield: 105.32 mg, white solid Synthesis Example 601

(R,E)-N-Cyclopropyl-3-(3-(2-(difluoromethyl)pyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 63.64 mg, white solid Synthesis Example 602

(R,E)-N-Cyclopropyl-7-hydroxy-4-isobutyl-5-oxo-3-(3-oxo-3-(3-phenylmorpholino)prop-1-en-1-yl)-4,5-dihydropyrazolo[1,5-a]pyrimidine-6-carboxamide Yield: 39.92 mg, white solid Synthesis Example 603

(S,E)-N-Cyclopropyl-7-hydroxy-4-isobutyl-5-oxo-3-(3-oxo-3-(2-(pyridin-3-yl) pyrrolidin-1-yl)prop-1-en-1-yl)-4,5-dihydropyrazolo[1,5-a]pyrimidine-6-carboxamide Yield: 63.72 mg, white solid Synthesis Example 604

(E)-N-Cyclopropyl-7-hydroxy-4-isobutyl-3-(3-(methyl((1-methyl-1H-pyrazol-3-yl)methyl)amino)-3-oxoprop-1-en-1-yl)-5-oxo-4,5-dihydropyrazolo[1,5-a]pyrimidine-6-carboxamide Yield: 86.65 mg, white solid Synthesis Example 605

(S,E)-N-Cyclopropyl-3-(3-(2-ethylpyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 62.04 mg, white solid Synthesis Example 606

(S,E)-N-Cyclopropyl-7-hydroxy-4-isobutyl-5-oxo-3-(3-oxo-3-(3-phenylmorpholino)prop-1-en-1-yl)-4,5-dihydropyrazolo[1,5-a]pyrimidine-6-carboxamide Yield: 77.8 mg, white solid Synthesis Example 607

(R,E)-N-Cyclopropyl-7-hydroxy-4-isobutyl-5-oxo-3-(3-oxo-3-(2-phenylpyrrolidin-1-yl)prop-1-en-1-yl)-4,5-dihydropyrazolo[1,5-a]pyrimidine-6-carboxamide Yield: 83.91 mg, white solid Synthesis Example 608

(E)-N-Cyclopropyl-3-(3-(6,6-difluoro-3-azabicyclo[3.1.0]hexan-3-yl)-3-oxoprop-1-en-1-yl)-7-hydroxy-4-isobutyl-2-methyl-5-oxo-4,5-dihydropyrazolo[1,5-a]pyrimidine-6-carboxamide 1 mL of dichloromethane, 43.6 mg of 6,6-difluoro-3-azabicyclo[3.1.0]hexane hydrochloride, 8.6 mg of 4-dimethylaminopyridine, 80.1 mg of 1-(3-dimethylaminopropyl)-3-ethylcarbodiimide hydrochloride, and 58.5 μL of triethylamine were added to 52.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 2 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (hexane/ethyl acetate=1/1→30/70→0/100 (v/v)), to thereby produce 51.02 mg of the title compound as a white solid.

Synthesis Example 609

(E)-3-(3-(2-Azabicyclo[3.1.0]hexan-2-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide (racemate)

1 mL of dichloromethane, 33.5 mg of 2-azabicyclo[3.1.0]hexane hydrochloride, 8.6 mg of 4-dimethylaminopyridine, 80.1 mg of 1-(3-dimethylaminopropyl)-3-ethylcarbodiimide hydrochloride, and 58.5 μL of triethylamine were added to 52.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 2 mL of 1 M hydrochloric acid, and the mixture was followed by extraction with 5 mL of dichloromethane. The organic phase was subjected to diatomaceous earth filtration, and the filtrate was concentrated under reduced pressure. The residue was purified by silica gel column chromatography (hexane/ethyl acetate=1/1→30/70→0/100 (v/v)), to thereby produce 17.79 mg of the title compound as a white solid.

Synthesis Example 610

(R,E)-N-Cyclopropyl-3-(3-(2-ethylpyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 1 mL of dichloromethane, 29.8 mg of (R)-2-ethylpyrrolidine, 0.0836 mL of triethylamine, and 85.8 mg of 1-(3-dimethylaminopropyl)-3-ethylcarbodiimide hydrochloride were added to 56.2 mg of (E)-3-(6-(cyclopropylcarbamoyl)-7-hydroxy-4-isobutyl-2-methyl-5-oxo-4,5-dihydropyrazolo [1,5-a]pyrimidin-3-yl)acrylic acid produced in step D of Synthesis Example 563, and the resultant mixture was stirred at room temperature for 16 hours. To the reaction mixture was added 2.0 mL of a saturated aqueous ammonium chloride solution, and the mixture was subjected to extraction with 5.0 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 16.7 mg of the title compound as a pale brown solid.

Synthesis Example 611

(R,E)-N-Cyclopropyl-7-hydroxy-3-(3-(2-(2-hydroxypropan-2-yl) pyrrolidin-1-yl)-3-oxoprop-1-en-1-yl)-4-isobutyl-2-methyl-5-oxo-4,5-dihydropyrazolo[1,5-a]pyrimidine-6-carboxamide 1 mL of dichloromethane, 37.3 mg of (R)-2-(pyrrolidin-2-yl)propan-2-ol hydrochloride, 0.125 mL of triethylamine, and 85.8 mg of 1-(3-dimethylaminopropyl)-3-ethylcarbodiimide hydrochloride were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 2.0 mL of a saturated aqueous ammonium chloride solution, and the mixture was subjected to extraction with 5.0 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 19.2 mg of the title compound as a pale yellow solid.

Synthesis Example 612

(R,E)-N-Cyclopropyl-7-hydroxy-4-isobutyl-3-(3-(2-(methoxymethyl)pyrrolidin-1-yl)-3-oxoprop-1-en-1-yl)-2-methyl-5-oxo-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 18.3 mg of 4-dimethylaminopyridine, and 34.6 mg of (R)-2-(methoxymethyl)pyrrolidine were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 64.5 mg of the title compound as a white amorphous product.

Synthesis Example 613

(S,E)-N-Cyclopropyl-7-hydroxy-4-isobutyl-3-(3-(2-(methoxymethyl)pyrrolidin-1-yl)-3-oxoprop-1-en-1-yl)-2-methyl-5-oxo-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 18.3 mg of 4-dimethylaminopyridine, and 34.6 mg of(S)-2-(methoxymethyl)pyrrolidine were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 52.9 mg of the title compound as a white amorphous product.

Synthesis Example 614

(E)-N-Cyclopropyl-7-hydroxy-4-isobutyl-2-methyl-5-oxo-3-(3-oxo-3-(3-(trifluoromethyl)pyrrolidin-1-yl)prop-1-en-1-yl)-4,5-dihydropyrazolo[1,5-a]pyrimidine-6-carboxamide (racemate)

1.5 mL of dichloromethane, 115.0 mg of 1-(3-dimethylaminopropyl)-3-ethylcarbodiimide hydrochloride, 0.0836 mL of triethylamine, 18.3 mg of 4-dimethylaminopyridine, and 70.2 mg of 3-(trifluoromethyl)pyrrolidine hydrochloride were added to 74.9 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 87.9 mg of the title compound as a pale brown solid.

Synthesis Example 615

(E)-N-Cyclopropyl-3-(3-(4-(3,3-difluorocyclobutyl)piperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 18.3 mg of 4-dimethylaminopyridine, and 52.9 mg of 1-(3,3-difluorocyclobutyl) piperazine were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 40 hours. To the reaction mixture were added 2 mL of water and 20 mL of chloroform, and the mixture was subjected to diatomaceous earth filtration. Thereafter, the filtrate was concentrated under reduced pressure. The residue was purified by silica gel column chromatography (chloroform/methanol=99/1→97/3 (v/v)). Ethanol was added to the residue, and the resultant solid was recovered by filtration and then dried under reduced pressure, to thereby produce 41.3 mg of the title compound as a white solid.

Synthesis Example 616

N-Cyclopropyl-3-((E)-3-((2R,5R)-2,5-dimethylpyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 1 mL of dichloromethane, 34.6 mg of (2R,5R)-2,5-dimethylpyrrolidine hydrochloride, 0.142 mL of triethylamine, and 97.3 mg of 1-(3-dimethylaminopropyl)-3-ethylcarbodiimide hydrochloride were added to 63.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 20 hours. To the reaction mixture was added 2.0 mL of a saturated aqueous ammonium chloride solution, and the mixture was subjected to extraction with 5.0 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 42.0 mg of the title compound as a yellow amorphous product.

Synthesis Example 617

N-Cyclopropyl-3-((E)-3-((2S,5S)-2,5-dimethylpyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 1.5 mL of dichloromethane, 34.6 mg of (2S,5S)-2,5-dimethylpyrrolidine hydrochloride, 0.142 mL of triethylamine, and 97.3 mg of 1-(3-dimethylaminopropyl)-3-ethylcarbodiimide hydrochloride were added to 63.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 20 hours. To the reaction mixture was added 2.0 mL of a saturated aqueous ammonium chloride solution, and the mixture was subjected to extraction with 5.0 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 37.9 mg of the title compound as a yellow amorphous product.

Synthesis Example 618

N-Cyclopropyl-3-((E)-3-(cis-2,5-dimethylpyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 1.5 mL of dichloromethane, 34.6 mg of cis-2,5-dimethylpyrrolidine hydrochloride, 0.142 mL of triethylamine, and 97.3 mg of 1-(3-dimethylaminopropyl)-3-ethylcarbodiimide hydrochloride were added to 63.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 20 hours. To the reaction mixture was added 2.0 mL of a saturated aqueous ammonium chloride solution, and the mixture was subjected to extraction with 5.0 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 31.7 mg of the title compound as a pale yellow amorphous product.

Synthesis Example 619

(E)-N-Cyclopropyl-3-(3-(2-cyclopropylpyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide (racemate)

2.0 mL of dichloromethane, 53.2 mg of 2-cyclopropylpyrrolidine hydrochloride, 0.201 mL of triethylamine, and 114 mg of 1-(3-dimethylaminopropyl)-3-ethylcarbodiimide hydrochloride were added to 89.9 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 20 hours. To the reaction mixture was added 2.0 mL of a saturated aqueous ammonium chloride solution, and the mixture was subjected to extraction with 6.0 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 72.3 mg of the title compound as a yellow solid.

Synthesis Example 620

(S,E)-N-Cyclopropyl-7-hydroxy-4-isobutyl-3-(3-(3-(methoxymethyl)pyrrolidin-1-yl)-3-oxoprop-1-en-1-yl)-2-methyl-5-oxo-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 18.3 mg of 4-dimethylaminopyridine, and 34.5 mg of(S)-3-(methoxymethyl)pyrrolidine were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563 at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 62.8 mg of the title compound as a white amorphous product.

Synthesis Example 621

(R,E)-N-Cyclopropyl-7-hydroxy-4-isobutyl-3-(3-(3-(methoxymethyl)pyrrolidin-1-yl)-3-oxoprop-1-en-1-yl)-2-methyl-5-oxo-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 18.3 mg of 4-dimethylaminopyridine, and 34.5 mg of (R)-3-(methoxymethyl)pyrrolidine were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563 at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 48.2 mg of the title compound as a white amorphous product.

Synthesis Example 622

(E)-N-Cyclopropyl-3-(3-(3-(difluoromethyl)pyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide (racemate)

1.5 mL of dichloromethane, 115.0 mg of 1-(3-dimethylaminopropyl)-3-ethylcarbodiimide hydrochloride, 0.0836 mL of triethylamine, 24.4 mg of 4-dimethylaminopyridine, and 63.0 mg of 3-(difluoromethyl)pyrrolidine hydrochloride were added to 77.7 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), and the resultant product was recrystallized from ethanol, to thereby produce 84.4 mg of the title compound as a pale brown solid.

Synthesis Example 623

(S,E)-N-Cyclopropyl-7-hydroxy-3-(3-(3-(2-hydroxypropan-2-yl) pyrrolidine-1-yl)-3-oxoprop-1-en-1-yl)-4-isobutyl-2-methyl-5-oxo-4,5-dihydropyrazolo[1,5-a]pyrimidine-6-carboxamide 1 mL of dichloromethane, 46.4 mg of(S)-2-(pyrrolidin-3-yl)propan-2-ol hydrochloride, 8.6 mg of 4-dimethylaminopyridine, 80.1 mg of 1-(3-dimethylaminopropyl)-3-ethylcarbodiimide hydrochloride, and 58.5 μL of triethylamine were added to 52.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 16 hours. To the reaction mixture was added 2 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (hexane/ethyl acetate=1/1→30/70→0/100→chloroform/methanol=100/0→98/2) (v/v)). To the residue was added 3 mL of ethyl acetate, and the precipitated solid was recovered by filtration and then dried under reduced pressure, to thereby produce 38.98 mg of the title compound as a pale brown solid.

Synthesis Example 624

N-Cyclopropyl-3-((E)-3-((3S,5S)-3,5-dimethylmorpholino)-3-oxoprop-1-en-1-yl)-7-hydroxy-2-methyl-4-neopentyl-5-oxo-4,5-dihydropyrazolo[1,5-a]pyrimidine-6-carboxamide 1.2 mL of dichloromethane, 85.8 mg of 1-(3-dimethylaminopropyl)-3-ethylcarbodiimide hydrochloride, 18.3 mg of 4-dimethylaminopyridine, 0.0627 mL of triethylamine, and 45.5 mg of (3S,5S)-3,5-dimethylmorpholine hydrochloride were added to 58.3 mg of (E)-3-(6-(cyclopropylcarbamoyl)-7-hydroxy-2-methyl-4-neopentyl-5-oxo-4,5-dihydropyrazolo[1,5-a]pyrimidin-3-yl)acrylic acid produced in step D of Synthesis Example 582 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), and the resultant produced was recrystallized from 2 mL of ethanol, to thereby produce 21.3 mg of the title compound as a white solid.

Synthesis Example 625

(S,E)-N-Cyclopropyl-7-hydroxy-2-methyl-3-(3-(3-methylmorpholino)-3-oxoprop-1-en-1-yl)-4-neopentyl-5-oxo-4,5-dihydropyrazolo[1,5-a]pyrimidine-6-carboxamide 1.2 mL of dichloromethane, 85.8 mg of 1-(3-dimethylaminopropyl)-3-ethylcarbodiimide hydrochloride, 18.3 mg of 4-dimethylaminopyridine, and 30.3 mg of(S)-3-methylmorpholine were added to 58.3 mg of (E)-3-(6-(cyclopropylcarbamoyl)-7-hydroxy-2-methyl-4-neopentyl-5-oxo-4,5-dihydropyrazolo[1,5-a]pyrimidin-3-yl)acrylic acid produced in step D of Synthesis Example 582 at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 57.8 mg of the title compound as a white amorphous product.

Synthesis Example 626

N-Cyclopropyl-3-((E)-3-((3S,5S)-3,5-dimethylmorpholino)-3-oxoprop-1-en-1-yl)-2-ethyl-7-hydroxy-4-isobutyl-5-oxo-4,5-dihydropyrazolo[1,5-a]pyrimidine-6-carboxamide 1.2 mL of dichloromethane, 85.8 mg of 1-(3-dimethylaminopropyl)-3-ethylcarbodiimide hydrochloride, 18.3 mg of 4-dimethylaminopyridine, 0.0627 mL of triethylamine, and 45.5 mg of (3S,5S)-3,5-dimethylmorpholine hydrochloride were added to 58.3 mg of (E)-3-(6-(cyclopropylcarbamoyl)-2-ethyl-7-hydroxy-4-isobutyl-5-oxo-4,5-dihydropyrazolo[1,5-a]pyrimidin-3-yl)acrylic acid produced in step D of Synthesis Example 586 at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), and then the resultant product was recrystallized from diisopropyl ether, to thereby produce 51.8 mg of the title compound as a pale brown solid.

Synthesis Example 627

(E)-N-Cyclopropyl-3-(3-(3,3-difluoropyrrolidin-1-yl)-3-oxoprop-1-en-1-yl)-7-hydroxy-2-methyl-4-neopentyl-5-oxo-4,5-dihydropyrazolo[1,5-a]pyrimidine-6-carboxamide 1.2 mL of dichloromethane, 85.8 mg of 1-(3-dimethylaminopropyl)-3-ethylcarbodiimide hydrochloride, 18.3 mg of 4-dimethylaminopyridine, 0.0627 mL of triethylamine, and 43.1 mg of 3,3-difluoropyrrolidine hydrochloride were added to 58.3 mg of (E)-3-(6-(cyclopropylcarbamoyl)-7-hydroxy-2-methyl-4-neopentyl-5-oxo-4,5-dihydropyrazolo[1,5-a]pyrimidin-3-yl)acrylic acid produced in step D of Synthesis Example 582 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 56.8 mg of the title compound as a white amorphous product.

Synthesis Example 628

N-Cyclopropyl-7-hydroxy-4-isobutyl-2-methyl-5-oxo-3-((E)-3-oxo-3-((3aR,6aS)-tetrahydro-1H-furo[3,4-c]pyrrol-5 (3H)-yl)prop-1-en-1-yl)-4,5-dihydropyrazolo[1,5-a]pyrimidine-6-carboxamide 1.2 mL of dichloromethane, 86.3 mg of 1-(3-dimethylaminopropyl)-3-ethylcarbodiimide hydrochloride, 0.0627 mL of triethylamine, 18.3 mg of 4-dimethylaminopyridine, and 44.9 mg of (3aR,6aS)-hexahydro-1H-furo[3,4-c]pyrrole hydrochloride were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1→97/3→90/10 (v/v)), and the resultant product was recrystallized from 2 mL of diisopropyl ether, to thereby produce 48.1 mg of the title compound as a pale brown solid.

Synthesis Example 629

(R,E)-N-Cyclopropyl-7-hydroxy-4-isobutyl-3-(3-(2-isopropylpyrrolidin-1-yl)-3-oxoprop-1-en-1-yl)-2-methyl-5-oxo-4,5-dihydropyrazolo[1,5-a]pyrimidine-6-carboxamide 2 mL of dichloromethane, 50.9 mg of 1-(3-dimethylaminopropyl)-3-ethylcarbodiimide hydrochloride, 0.056 mL of triethylamine, 16.3 mg of 4-dimethylaminopyridine, and 40.0 mg of (R)-2-isopropylpyrrolidine hydrochloride were added to 50.0 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 16 hours. To the reaction mixture were added 2 mL of 1 M hydrochloric acid and water, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5 (v/v)), to thereby produce 45.6 mg of the title compound as a pale yellow amorphous product.

Synthesis Example 630

(S,E)-N-Cyclopropyl-7-hydroxy-4-isobutyl-3-(3-(2-isopropylpyrrolidin-1-yl)-3-oxoprop-1-en-1-yl)-2-methyl-5-oxo-4,5-dihydropyrazolo[1,5-a]pyrimidine-6-carboxamide Substantially the same reaction as in Synthesis Example 629 was performed by using(S)-2-isopropylpyrrolidine hydrochloride in place of (R)-2-isopropylpyrrolidine hydrochloride, to thereby produce 53.0 mg of the title compound as a white amorphous product.

Synthesis Example 631

(E)-N-Cyclopropyl-7-hydroxy-4-isobutyl-2-methyl-5-oxo-3-(3-oxo-3-(8-oxa-1-azaspiro[4.5]decan-1-yl)prop-1-en-1-yl)-4,5-dihydropyrazolo[1,5-a]pyrimidine-6-carboxamide 2 mL of dichloromethane, 50.9 mg of 1-(3-dimethylaminopropyl)-3-ethylcarbodiimide hydrochloride, 16.3 mg of 4-dimethylaminopyridine, and 37.7 mg of 8-oxa-1-azaspiro[4.5]decane were added to 50.0 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 16 hours. To the reaction mixture were added 2 mL of 1 M hydrochloric acid and water, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5 (v/v)), to thereby produce 64.3 mg of the title compound as a white solid.

Synthesis Example 632

(R,E)-N-Cyclopropyl-3-(3-(2-(difluoromethyl)pyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide 1.5 mL of dichloromethane, 42.5 mg of (R)-2-(difluoromethyl)pyrrolidine hydrochloride, 0.125 mL of triethylamine, and 85.8 mg of 1-(3-dimethylaminopropyl)-3-ethylcarbodiimide hydrochloride were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 20 hours. To the reaction mixture was added 2.0 mL of a saturated aqueous ammonium chloride solution, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 43.8 mg of the title compound as a pale brown solid.

Synthesis Example 633

(S,E)-N-Cyclopropyl-7-hydroxy-4-isobutyl-2-methyl-5-oxo-3-(3-oxo-3-(2-(pyridin-3-yl) pyrrolidin-1-yl)prop-1-en-1-yl)-4,5-dihydropyrazolo[1,5-a]pyrimidine-6-carboxamide 1.5 mL of dichloromethane, 44.1 mg of(S)-3-(pyrrolidin-2-yl)pyridine, 0.125 mL of triethylamine, and 143 mg of 1-(3-dimethylaminopropyl)-3-ethylcarbodiimide hydrochloride were added to 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 2.0 mL of a saturated aqueous ammonium chloride solution, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=100/0→97/3 (v/v)), to thereby produce 45.5 mg of the title compound as a pale brown solid.

Synthesis Example 634

(S,E)-N-Cyclopropyl-3-(3-(2-(difluoromethyl)pyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 632 was performed by using(S)-2-(difluoromethyl)pyrrolidine hydrochloride in place of (R)-2-(difluoromethyl)pyrrolidine hydrochloride, to thereby produce 44.9 mg of the title compound as a pale brown solid.

Synthesis Example 635

(R,E)-N-Cyclopropyl-7-hydroxy-4-isobutyl-2-methyl-5-oxo-3-(3-oxo-3-(2-(pyridin-2-yl) pyrrolidin-1-yl)prop-1-en-1-yl)-4,5-dihydropyrazolo[1,5-a]pyrimidine-6-carboxamide Substantially the same reaction as in Synthesis Example 633 was performed by using (R)-2-(pyrrolidin-2-yl)pyridine in place of(S)-3-(pyrrolidin-2-yl)pyridine, to thereby produce 23.4 mg of the title compound as a pale brown solid.

Synthesis Example 636

(E)-N-Cyclopropyl-7-hydroxy-4-isobutyl-2-methyl-3-(3-(methyl(pyrazin-2-ylmethyl)amino)-3-oxoprop-1-en-1-yl)-5-oxo-4,5-dihydropyrazolo[1,5-a]pyrimidine-6-carboxamide Substantially the same reaction as in Synthesis Example 632 was performed by using N-methyl-1-(pyrazin-2-yl)methanamine in place of (R)-2-(difluoromethyl)pyrrolidine hydrochloride, to thereby produce 57.2 mg of the title compound as a pale brown solid.

Synthesis Example 637

(E)-N-Cyclopropyl-7-hydroxy-4-isobutyl-2-methyl-3-(3-(methyl(pyridin-3-ylmethyl)amino)-3-oxoprop-1-en-1-yl)-5-oxo-4,5-dihydropyrazolo[1,5-a]pyrimidine-6-carboxamide Substantially the same reaction as in Synthesis Example 632 was performed by using N-methyl-1-(pyridin-3-yl) methanamine in place of (R)-2-(difluoromethyl)pyrrolidine hydrochloride, to thereby produce 33.3 mg of the title compound as a pale yellow solid.

Synthesis Example 638

(E)-N-Cyclopropyl-7-hydroxy-4-isobutyl-2-methyl-3-(3-(methyl(pyridin-2-ylmethyl)amino)-3-oxoprop-1-en-1-yl)-5-oxo-4,5-dihydropyrazolo[1,5-a]pyrimidine-6-carboxamide Substantially the same reaction as in Synthesis Example 632 was performed by using N-methyl-1-(pyridin-2-yl) methanamine in place of (R)-2-(difluoromethyl)pyrrolidine hydrochloride, to thereby produce 35.2 mg of the title compound as a green solid.

Synthesis Example 639

(E)-N-Cyclopropyl-7-hydroxy-4-isobutyl-2-methyl-3-(3-(methyl((1-methyl-1H-pyrazol-3-yl)methyl) amino)-3-oxoprop-1-en-1-yl)-5-oxo-4,5-dihydropyrazolo[1,5-a]pyrimidine-6-carboxamide Substantially the same reaction as in Synthesis Example 632 was performed by using N-methyl-1-(1-methyl-1H-pyrazol-3-yl)methanamine in place of (R)-2-(difluoromethyl)pyrrolidine hydrochloride, to thereby produce 60.6 mg of the title compound as a pale brown solid.

Synthesis Example 640

(S,E)-N-Cyclopropyl-3-(3-(2-ethylpyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 632 was performed by using(S)-2-ethylpyrrolidine hydrochloride in place of (R)-2-(difluoromethyl)pyrrolidine hydrochloride, to thereby produce 24.3 mg of the title compound as a pale yellow solid.

Synthesis Example 641

N-Cyclopropyl-3-((E)-3-(cis-3,5-dimethylmorpholino)-3-oxoprop-1-en-1-yl)-7-hydroxy-4-isobutyl-2-methyl-5-oxo-4,5-dihydropyrazolo[1,5-a] pyrimidine-6-carboxamide 1 mL of dichloromethane, 60.7 mg of cis-3,5-dimethylmorpholine hydrochloride, 0.0558 mL of triethylamine, 24.4 mg of 4-dimethylaminopyridine, and 114.4 mg of 1-(3-dimethylaminopropyl)-3-ethylcarbodiimide hydrochloride were added to 74.9 mg of (E)-3-(6-(cyclopropylcarbamoyl)-7-hydroxy-4-isobutyl-2-methyl-5-oxo-4,5-dihydropyrazolo [1,5-a]pyrimidin-3-yl)acrylic acid produced in step D of Synthesis Example 563, and the resultant mixture was stirred at room temperature for 16 hours. To the reaction mixture was added 0.5 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=50/1), to thereby produce 18.0 mg of the title compound as a white amorphous product.

Synthesis Example 642

(R,E)-N-Cyclopropyl-7-hydroxy-4-isobutyl-2-methyl-5-oxo-3-(3-oxo-3-(3-phenylmorpholino) prop-1-en-1-yl)-4,5-dihydropyrazolo[1,5-a]pyrimidine-6-carboxamide 2 mL of dichloromethane, 38.1 mg of 1-(3-dimethylaminopropyl)-3-ethylcarbodiimide hydrochloride, 12.2 mg of 4-dimethylaminopyridine, and 32.6 mg of (R)-3-phenylmorpholine were added to 37.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 16 hours. To the reaction mixture were added 2 mL of 1 M hydrochloric acid and water, and the mixture was subjected to extraction with chloroform. The organic phase was dried over sodium sulfate and subjected to filtration, and then the filtrate. was concentrated under reduced pressure. The residue was purified by silica gel column chromatography (chloroform/methanol=100/0→95/5 (v/v)), to thereby produce 41.4 mg of the title compound as a white amorphous product.

Synthesis Example 643

(S,E)-N-Cyclopropyl-7-hydroxy-4-isobutyl-2-methyl-5-oxo-3-(3-oxo-3-(3-phenylmorpholino) prop-1-en-1-yl)-4,5-dihydropyrazolo[1,5-a]pyrimidine-6-carboxamide Substantially the same reaction as in Synthesis Example 642 was performed by using(S)-3-phenylmorpholine in place of (R)-3-phenylmorpholine, to thereby produce 58.2 mg of the title compound as a white amorphous product.

Synthesis Example 644

N-Cyclopropyl-3-((E)-3-((2R,5R)-2,5-dimethylmorpholino)-3-oxoprop-1-en-1-yl)-7-hydroxy-4-isobutyl-2-methyl-5-oxo-4,5-dihydropyrazolo[1,5-a] pyrimidine-6-carboxamide 1 mL of dichloromethane, 42.5 mg of (2R,5R)-2,5-dimethylmorpholine hydrochloride, 8.6 mg of 4-dimethylaminopyridine, 80.1 mg of 1-(3-dimethylaminopropyl)-3-ethylcarbodiimide hydrochloride, and 58.5 μL of triethylamine were added to 52.4 mg of (E)-3-(6-(cyclopropylcarbamoyl)-7-hydroxy-4-isobutyl-2-methyl-5-oxo-4,5-dihydropyrazolo [1,5-a]pyrimidin-3-yl)acrylic acid produced in step D of Synthesis Example 563, and the resultant mixture was stirred at room temperature for 16 hours. To the reaction mixture was added 2 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (hexane/ethyl acetate=50/50→30/70→0/100 (v/v)), to thereby produce 33.78 mg of the title compound as a white solid.

Synthesis Example 645

N-Cyclopropyl-3-((E)-3-((2S,5S)-2,5-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 644 was performed by using (2S,5S)-2,5-dimethylmorpholine in place of (2R,5R)-2,5-dimethylmorpholine hydrochloride, to thereby produce 30.95 mg of the title compound as a white solid.

Synthesis Example 646

N-Cyclopropyl-3-((E)-3-((2S,5R)-2,5-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 644 was performed by using (2S,5R)-2,5-dimethylmorpholine in place of (2R,5R)-2,5-dimethylmorpholine hydrochloride, to thereby produce 36.88 mg of the title compound as a white solid.

Synthesis Example 647

N-Cyclopropyl-3-((E)-3-((2R,5S)-2,5-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 644 was performed by using (2R,5S)-2,5-dimethylmorpholine in place of (2R,5R)-2,5-dimethylmorpholine hydrochloride, to thereby produce 30.79 mg of the title compound as a white solid.

Synthesis Example 648

N-Cyclopropyl-3-((E)-3-(cis-3,4-difluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 644 was performed by using cis-3,4-difluoropyrrolidine hydrochloride in place of (2R,5R)-2,5-dimethylmorpholine hydrochloride, to thereby produce 30.82 mg of the title compound as a white solid.

Synthesis Example 649

N-Cyclopropyl-3-((E)-3-(trans-3,4-difluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide (racemate)

Substantially the same reaction as in Synthesis Example 644 was performed by using trans-3,4-difluoropyrrolidine hydrochloride in place of (2R,5R)-2,5-dimethylmorpholine hydrochloride, to thereby produce 18.95 mg of the title compound as a white solid.

Synthesis Example 650

(E)-N-Cyclopropyl-3-(3-(3,3-difluoro-8-azabicyclo[3.2.1]octan-8-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 644 was performed by using 3,3-difluoro-8-azabicyclo[3.2.1]octane hydrochloride in place of (2R,5R)-2,5-dimethylmorpholine hydrochloride, to thereby produce 14.81 mg of the title compound as a white solid.

Synthesis Example 651

(E)-N-Cyclopropyl-3-(3-(8,8-difluoro-3-azabicyclo[3.2.1]octan-3-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 644 was performed by using 8,8-difluoro-3-azabicyclo[3.2.1]octane hydrochloride in place of (2R,5R)-2,5-dimethylmorpholine hydrochloride, to thereby produce 35.16 mg of the title compound as a white solid.

Synthesis Example 652

(E)-N-Cyclopropyl-7-hydroxy-4-isobutyl-2-methyl-5-oxo-3-(3-oxo-3-(4-azaspiro[2.4]heptan-4-yl)prop-1-en-1-yl)-4,5-dihydropyrazolo[1,5-a]pyrimidine-6-carboxamide Substantially the same reaction as in Synthesis Example 644 was performed by using 4-azaspiro[2.4]heptane hydrochloride in place of (2R,5R)-2,5-dimethylmorpholine hydrochloride, to thereby produce 27.24 mg of the title compound as a white solid.

Synthesis Example 653

(S,E)-N-Cyclopropyl-2-ethyl-7-hydroxy-4-isobutyl-3-(3-(3-methylmorpholino)-3-oxoprop-1-en-1-yl)-5-oxo-4,5-dihydropyrazolo[1,5-a]pyrimidine-6-carboxamide 1 mL of dichloromethane, 43.1 mg of 1-(3-dimethylaminopropyl)-3-ethylcarbodiimide hydrochloride, 9.2 mg of 4-dimethylaminopyridine, and 15.2 mg of(S)-3-methylmorpholine were added to 29.1 mg of (E)-3-(6-(cyclopropylcarbamoyl)-2-ethyl-7-hydroxy-4-isobutyl-5-oxo-4,5-dihydropyrazolo[1,5-a]pyrimidin-3-yl)acrylic acid produced in step D of Synthesis Example 586 at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), and then the resultant product was recrystallized from diisopropyl ether, to thereby produce 18.9 mg of the title compound as a white solid.

Synthesis Example 654

(R,E)-N-Cyclopropyl-2-ethyl-7-hydroxy-3-(3-(2-(2-hydroxypropan-2-yl) pyrrolidin-1-yl)-3-oxoprop-1-en-1-yl)-4-isobutyl-5-oxo-4,5-dihydropyrazolo[1,5-a]pyrimidine-6-carboxamide 1 mL of dichloromethane, 43.1 mg of 1-(3-dimethylaminopropyl)-3-ethylcarbodiimide hydrochloride, 9.2 mg of 4-dimethylaminopyridine, 0.0312 mL of triethylamine, and 24.8 mg of (R)-2-(pyrrolidin-2-yl)propan-2-ol hydrochloride were added to 29.1 mg of (E)-3-(6-(cyclopropylcarbamoyl)-2-ethyl-7-hydroxy-4-isobutyl-5-oxo-4,5-dihydropyrazolo[1,5-a]pyrimidin-3-yl)acrylic acid produced in step D of Synthesis Example 586 at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 27.6 mg of the title compound as a white amorphous product.

Synthesis Example 655

(R,E)-N-Cyclopropyl-7-hydroxy-3-(3-(2-(2-hydroxypropan-2-yl) pyrrolidin-1-yl)-3-oxoprop-1-en-1-yl)-2-methyl-4-neopentyl-5-oxo-4,5-dihydropyrazolo[1,5-a]pyrimidine-6-carboxamide 1 mL of dichloromethane, 42.9 mg of 1-(3-dimethylaminopropyl)-3-ethylcarbodiimide hydrochloride, 9.2 mg of 4-dimethylaminopyridine, 0.0314 mL of triethylamine, and 24.8 mg of (R)-2-(pyrrolidin-2-yl)propan-2-ol hydrochloride were added to 29.1 mg of (E)-3-(6-(cyclopropylcarbamoyl)-7-hydroxy-2-methyl-4-neopentyl-5-oxo-4,5-dihydropyrazolo[1,5-a]pyrimidin-3-yl)acrylic acid produced in step D of Synthesis Example 582 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)) and then recrystallized from diisopropyl ether, to thereby produce 20.2 mg of the title compound as a white solid.

Synthesis Example 656

(E)-N-Cyclopropyl-3-(3-(3,3-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide 1 mL of dichloromethane, 46.1 mg of 3,3-dimethylmorpholine, 24.4 mg of 4-dimethylaminopyridine, and 114.4 mg of 1-(3-dimethylaminopropyl)-3-ethylcarbodiimide hydrochloride were added to 74.9 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. To the reaction mixture was added 0.5 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (ethyl acetate), to thereby produce 71.0 mg of the title compound as a white solid.

Synthesis Example 657

(E)-N-Cyclopropyl-3-(3-(2,2-dimethylmorpholino)-3-oxoprop-1-en-1-yl)-7-hydroxy-4-isobutyl-2-methyl-5-oxo-4,5-dihydropyrazolo[1,5-a]pyrimidine-6-carboxamide 1 mL of dichloromethane, 46.1 mg of 2,2-dimethylmorpholine, 24.4 mg of 4-dimethylaminopyridine, and 114.4 mg of 1-(3-dimethylaminopropyl)-3-ethylcarbodiimide hydrochloride were added to 74.9 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. To the reaction mixture was added 0.5 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (ethyl acetate), to thereby produce 74.8 mg of the title compound as a white amorphous product.

Synthesis Example 658

(E)-3-(3-(3-Oxa-8-azabicyclo[3.2.1]octan-8-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 1 mL of dichloromethane, 45.3 mg of 3-oxa-8-azabicyclo[3.2.1]octane, 24.4 mg of 4-dimethylaminopyridine, and 114.4 mg of 1-(3-dimethylaminopropyl)-3-ethylcarbodiimide hydrochloride were added to 74.9 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. To the reaction mixture was added 0.5 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=50/1 (v/v)). To the residue was added 1 mL of ethanol, and the precipitated solid was recovered by filtration and then dried under reduced pressure, to thereby produce 70.0 mg of the title compound as a white solid.

Synthesis Example 659

(S,E)-N-Cyclopropyl-3-(3-(3-ethylmorpholino)-3-oxoprop-1-en-1-yl)-7-hydroxy-4-isobutyl-2-methyl-5-oxo-4,5-dihydropyrazolo[1,5-a]pyrimidine-6-carboxamide 1 mL of dichloromethane, 57.5 mg of 1-(3-dimethylaminopropyl)-3-ethylcarbodiimide hydrochloride, 12.2 mg of 4-dimethylaminopyridine, and 23.0 mg of(S)-3-ethylmorpholine were added to 37.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 40 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 36.9 mg of the title compound as a white amorphous product.

Synthesis Example 660

Tert-butyl (E)-1-(3-(6-(cyclopropylcarbamoyl)-7-hydroxy-4-isobutyl-2-methyl-5-oxo-4,5-dihydropyrazolo[1,5-a]pyrimidin-3-yl)acryloyl)-1,7-diazaspiro[4.5]decane-7-carboxylate (racemate)

2 mL of dichloromethane, 76.3 mg of 1-(3-dimethylaminopropyl)-3-ethylcarbodiimide hydrochloride, 24.4 mg of 4-dimethylaminopyridine, and 96.1 mg of tert-butyl 1,7-diazaspiro[4.5]decane-7-carboxylate were added to 74.9 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 16 hours. To the reaction mixture were added 2 mL of 1 M hydrochloric acid and water, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5 (v/v)), to thereby produce 95.6 mg of the title compound as a yellow solid.

Synthesis Example 661

Tert-butyl (E)-1-(3-(6-(cyclopropylcarbamoyl)-7-hydroxy-4-isobutyl-2-methyl-5-oxo-4,5-dihydropyrazolo[1,5-a]pyrimidin-3-yl)acryloyl)-1,8-diazaspiro[4.5]decane-8-carboxylate 6 mL of dichloromethane, 305.1 mg of 1-(3-dimethylaminopropyl)-3-ethylcarbodiimide hydrochloride, 97.7 mg of 4-dimethylaminopyridine, and 230.7 mg of tert-butyl 1,8-diazaspiro[4.5]decane-8-carboxylate were added to 299.5 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 16 hours. To the reaction mixture were added 6 mL of 1 M hydrochloric acid and water, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5 (v/v)), to thereby produce 494.4 mg of the title compound as a pale yellow solid.

Synthesis Example 662

(E)-N-Cyclopropyl-7-hydroxy-4-isobutyl-2-methyl-3-(3-(7-methyl-1,7-diazaspiro[4.5]decan-1-yl)-3-oxoprop-1-en-1-yl)-5-oxo-4,5-dihydropyrazolo[1,5-a]pyrimidine-6-carboxamide (racemate)

2 mL of 4 M hydrogen chloride 1,4-dioxane solution was added to 95.6 mg of tert-butyl (E)-1-(3-(6-(cyclopropylcarbamoyl)-7-hydroxy-4-isobutyl-2-methyl-5-oxo-4,5-dihydropyrazolo[1,5-a]pyrimidin-3-yl)acryloyl)-1,7-diazaspiro[4.5]decane-7-carboxylate produced in Synthesis Example 660, and the resultant mixture was stirred at room temperature for one hour. The reaction mixture was concentrated under reduced pressure, to thereby produce 83.1 mg of (E)-N-cyclopropyl-7-hydroxy-4-isobutyl-2-methyl-5-oxo-3-(3-oxo-3-(1,7-diazaspiro[4.5]decan-1-yl)prop-1-en-1-yl)-4,5-dihydropyrazolo[1,5-a]pyrimidine-6-carboxamide hydrochloride as a pale yellow amorphous product.

Subsequently, 20 μL of 37% aqueous formaldehyde solution was added to a mixture of 26.7 mg of the resultant (E)-N-cyclopropyl-7-hydroxy-4-isobutyl-2-methyl-5-oxo-3-(3-oxo-3-(1,7-diazaspiro[4.5]decan-1-yl)prop-1-en-1-yl)-4,5-dihydropyrazolo[1,5-a]pyrimidine-6-carboxamide hydrochloride and 1 mL of dichloromethane at 0° C., and the resultant mixture was stirred at 0° C. for 10 minutes. To the reaction mixture was added 31.8 mg of sodium triacetoxyborohydride at 0° C., and the mixture was stirred at room temperature for one hour. To the reaction mixture was added 2 mL of a saturated aqueous sodium chloride solution, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5→90/10 (v/v)), to thereby produce 8.25 mg of the title compound as a white solid.

Synthesis Example 663

(E)-3-(3-(7-Acetyl-1,7-diazaspiro[4.5]decan-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide (racemate)

5.9 mg of acetyl chloride and 0.0209 mL of triethylamine were added to a solution of 26.7 mg of (E)-N-cyclopropyl-7-hydroxy-4-isobutyl-2-methyl-5-oxo-3-(3-oxo-3-(1,7-diazaspiro[4.5]decan-1-yl)prop-1-en-1-yl)-4,5-dihydropyrazolo[1,5-a]pyrimidine-6-carboxamide hydrochloride produced in Synthesis Example 662 in 1 mL of dichloromethane, and the resultant mixture was stirred at room temperature for one hour. To the reaction mixture was added 2 mL of a saturated aqueous ammonium chloride solution, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5 (v/v)), to thereby produce 15.0 mg of the title compound as a white amorphous product.

Synthesis Example 664

(E)-N-Cyclopropyl-7-hydroxy-4-isobutyl-2-methyl-3-(3-(8-methyl-1,8-diazaspiro[4.5]decan-1-yl)-3-oxoprop-1-en-1-yl)-5-oxo-4,5-dihydropyrazolo[1,5-a]pyrimidine-6-carboxamide 8 mL of 4 M hydrogen chloride 1,4-dioxane solution was added to 494.4 mg of tert-butyl (E)-1-(3-(6-(cyclopropylcarbamoyl)-7-hydroxy-4-isobutyl-2-methyl-5-oxo-4,5-dihydropyrazolo[1,5-a]pyrimidin-3-yl)acryloyl)-1,8-diazaspiro[4.5]decane-8-carboxylate produced in Synthesis Example 661, and the resultant mixture was stirred at room temperature for one hour. The reaction mixture was concentrated under reduced pressure, to thereby produce 288.3 mg of (E)-N-cyclopropyl-7-hydroxy-4-isobutyl-2-methyl-5-oxo-3-(3-oxo-3-(1,8-diazaspiro[4.5]decan-1-yl)prop-1-en-1-yl)-4,5-dihydropyrazolo[1,5-a]pyrimidine-6-carboxamide hydrochloride as a white solid.

Subsequently, 20 μL of 37% aqueous formaldehyde solution was added to a mixture of 26.7 mg of the resultant (E)-N-cyclopropyl-7-hydroxy-4-isobutyl-2-methyl-5-oxo-3-(3-oxo-3-(1,8-diazaspiro[4.5]decan-1-yl)prop-1-en-1-yl)-4,5-dihydropyrazolo[1,5-a]pyrimidine-6-carboxamide hydrochloride and 1 mL of dichloromethane at 0° C., and the resultant mixture was stirred at 0° C. for 10 minutes. To the reaction mixture was added 31.8 mg of sodium triacetoxyborohydride at 0° C., and the mixture was stirred at room temperature for one hour. To the reaction mixture was added 2 mL of a saturated aqueous sodium chloride solution, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→80/20 (v/v)). Diisopropyl ether was added to the residue, and the precipitated solid was recovered by filtration, to thereby produce 15.74 mg of the title compound as a white solid.

Synthesis Example 665

(E)-3-(3-(8-Acetyl-1,8-diazaspiro[4.5]decan-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 5.9 mg of acetyl chloride and 0.0209 mL of triethylamine were added to a solution of 26.7 mg of (E)-N-cyclopropyl-7-hydroxy-4-isobutyl-2-methyl-5-oxo-3-(3-oxo-3-(1,8-diazaspiro[4.5]decan-1-yl)prop-1-en-1-yl)-4,5-dihydropyrazolo[1,5-a]pyrimidine-6-carboxamide hydrochloride produced in Synthesis Example 664 in 1 mL of dichloromethane, and the resultant mixture was stirred at room temperature for one hour. To the reaction mixture was added 2 mL of a saturated aqueous ammonium chloride solution, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5→90/10 (v/v)). Diisopropyl ether was added to the residue, and the precipitated solid was recovered by filtration, to thereby produce 21.72 mg of the title compound as a white solid.

Synthesis Example 666

(E)-N-Cyclopropyl-7-hydroxy-4-isobutyl-2-methyl-5-oxo-3-(3-oxo-3-(8-(2,2,2-trifluoroethyl)-1,8-diazaspiro[4.5]decan-1-yl)prop-1-en-1-yl)-4,5-dihydropyrazolo[1,5-a]pyrimidine-6-carboxamide 34.8 mg of 2,2,2-trifluoroethyl trifluoromethanesulfonate and 0.0262 mL of N,N-diisopropylethylamine were added to a solution of 26.7 mg of (E)-N-cyclopropyl-7-hydroxy-4-isobutyl-2-methyl-5-oxo-3-(3-oxo-3-(1,8-diazaspiro[4.5]decan-1-yl)prop-1-en-1-yl)-4,5-dihydropyrazolo[1,5-a]pyrimidine-6-carboxamide hydrochloride produced in Synthesis Example 664 in 1 mL of acetonitrile, and the resultant mixture was stirred at 50° C. for 24 hours. To the reaction mixture was added 2 mL of a saturated aqueous ammonium chloride solution, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5→80/20 (v/v)), to thereby produce 10.46 mg of the title compound as a white solid.

Synthesis Example 667

(E)-N-Cyclopropyl-3-(3-(8-ethyl-1,8-diazaspiro[4.5]decan-1-yl)-3-oxoprop-1-en-1-yl)-7-hydroxy-4-isobutyl-2-methyl-5-oxo-4,5-dihydropyrazolo[1,5-a]pyrimidine-6-carboxamide 385.4 mg of acetaldehyde (about 2% by weight N,N-dimethylformamide solution) was added to a mixture of 26.7 mg of (E)-N-cyclopropyl-7-hydroxy-4-isobutyl-2-methyl-5-oxo-3-(3-oxo-3-(1,8-diazaspiro[4.5]decan-1-yl)prop-1-en-1-yl)-4,5-dihydropyrazolo[1,5-a]pyrimidine-6-carboxamide hydrochloride produced in Synthesis Example 664 and 1 mL of dichloromethane at 0° C., and the resultant mixture was stirred at 0° C. for 10 minutes. To the reaction mixture was added 31.8 mg of sodium triacetoxyborohydride at 0° C., and the mixture was stirred at room temperature for one hour. To the reaction mixture was added 2 mL of a saturated aqueous sodium chloride solution, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5→80/20 (v/v)), to thereby produce 20.9 mg of the title compound as a white solid.

Synthesis Example 668

(E)-N-Cyclopropyl-3-(3-(5-fluoroindolin-1-yl)-3-oxoprop-1-en-1-yl)-7-hydroxy-4-isobutyl-2-methyl-5-oxo-4,5-dihydropyrazolo[1,5-a]pyrimidine-6-carboxamide 2 mL of dichloromethane, 50.9 mg of 1-(3-dimethylaminopropyl)-3-ethylcarbodiimide hydrochloride, 16.3 mg of 4-dimethylaminopyridine, and 36.6 mg of 5-fluoroindoline were added to 50.0 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 at 0° C., and the resultant mixture was stirred at room temperature for 16 hours. To the reaction mixture were added 2 mL of 1 M hydrochloric acid and water, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→95/5 (v/v)), to thereby produce 52.04 mg of the title compound as a white solid.

Synthesis Example 669

(E)-3-(3-(5-Cyanoindolin-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide Substantially the same reaction as in Synthesis Example 668 was performed by using indoline-5-carbonitrile in place of 5-fluoroindoline, to thereby produce 45.68 mg of the title compound as a white solid.

Synthesis Example 670

(E)-3-(3-(5-Bromoindolin-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide Substantially the same reaction as in Synthesis Example 668 was performed by using 5-bromoindoline in place of 5-fluoroindoline, to thereby produce 40.6 mg of the title compound as a white solid.

Synthesis Example 671

(S,E)-N-Cyclopropyl-3-(3-(4-(3,3-difluorocyclobutyl)-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide (Step A)

(S,E)-N-Cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride 2 mL of dichloromethane, 128.2 mg of tert-butyl (S)-3-methylpiperazine-1-carboxylate, 19.5 mg of 4-dimethylaminopyridine, and 183.1 mg of 1-(3-dimethylaminopropyl)-3-ethylcarbodiimide hydrochloride were added to 119.8 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563, and the resultant mixture was stirred at room temperature for 16 hours. To the reaction mixture was added 2 mL of 1 M hydrochloric acid, and the mixture was subjected to extraction with chloroform/methanol (10 mL/0.5 mL). The organic phase was dried over sodium sulfate and subjected to filtration, and then the filtrate was concentrated under reduced pressure. The residue was purified by silica gel column chromatography (hexane/ethyl acetate=50/50→30/70→15/85 (v/v)), to thereby produce 121.5 mg of tert-butyl (S,E)-4-(3-(6-(cyclopropylcarbamoyl)-7-hydroxy-4-isobutyl-2-methyl-5-oxo-4,5-dihydropyrazolo[1,5-a]pyrimidin-3-yl)acryloyl)-3-methylpiperazine-1-carboxylate as a pale yellow solid.

Subsequently, 2 mL of 4 M hydrogen chloride 1,4-dioxane solution was added to 116.9 mg of the resultant tert-butyl (S,E)-4-(3-(6-(cyclopropylcarbamoyl)-7-hydroxy-4-isobutyl-2-methyl-5-oxo-4,5-dihydropyrazolo[1,5-a]pyrimidin-3-yl)acryloyl)-3-methylpiperazine-1-carboxylate, and the resultant mixture was stirred at room temperature for one hour. The reaction mixture was concentrated under reduced pressure. The residue was suspended in 5 mL of ethyl acetate, and the resultant solid was recovered by filtration and then dried under reduced pressure, to thereby produce 74.99 mg of the title compound as a white solid.

LC/MS: condition 7, retention time=1.66 min

LC/MS (ESI+) m/z; 457.2 $[M+H]^+$

Step B (S,E)-N-Cyclopropyl-3-(3-(4-(3,3-difluorocyclobutyl)-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide 26.0 mg of 3,3-difluorocyclobutan-1-one was added to a mixture of 34.5 mg of (S,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride produced in step A of Synthesis Example 671 and 1 mL of dichloromethane at 0° C., and the resultant mixture was stirred at room temperature for five minutes. To the reaction mixture was added 44.5 mg of sodium triacetoxyborohydride at 0° C., and the mixture was stirred at 0° C. for 30 minutes. To the reaction mixture was added 2 mL of a saturated aqueous sodium hydrogen carbonate solution, and the mixture was subjected to extraction with 10 mL of chloroform. The organic phase was dried over sodium sulfate and subjected to filtration, and then the filtrate was concentrated under reduced pressure. The residue was purified by silica gel column chromatography (chloroform/methanol=100/0→97/3→95/5 (v/v)), to thereby produce 17.4 mg of the title compound as a white solid.

Synthesis Example 672

(E)-N-Cyclopropyl-3-(3-(4,4-difluoro-2-methylpiperidin-1-yl)-3-oxoprop-1-en-1-yl)-7-hydroxy-4-isobutyl-2-methyl-5-oxo-4,5-dihydropyrazolo[1,5-a]pyrimidine-6-carboxamide (racemate)

1 mL of dichloromethane, 48.1 mg of 4,4-difluoro-2-methylpiperidine hydrochloride, 8.6 mg of 4-dimethylaminopyridine, 80.1 mg of 1-(3-dimethylaminopropyl)-3-ethylcarbodiimide hydrochloride, and 58.5 μL of triethylamine were added to 52.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 2 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (hexane/ethyl acetate=50/50→30/70→0/100 (v/v)), to thereby produce 27.0 mg of the title compound as a pale yellow solid.

Synthesis Example 673

(R,E)-N-Cyclopropyl-7-hydroxy-4-isobutyl-2-methyl-5-oxo-3-(3-oxo-3-(2-phenylpyrrolidin-1-yl)prop-1-en-1-yl)-4,5-dihydropyrazolo[1,5-a]pyrimidine-6-carboxamide Substantially the same reaction as in Synthesis Example 633 was performed by using (R)-2-phenylpyrrolidine in place of(S)-3-(pyrrolidin-2-yl)pyridine, to thereby produce 39.2 mg of the title compound as a pale brown solid.

Synthesis Example 674

(S,E)-N-Cyclopropyl-7-hydroxy-4-isobutyl-2-methyl-5-oxo-3-(3-oxo-3-(2-phenylpyrrolidin-1-yl)prop-1-en-1-yl)-4,5-dihydropyrazolo[1,5-a]pyrimidine-6-carboxamide Substantially the same reaction as in Synthesis Example 633 was performed by using(S)-2-phenylpyrrolidine in place of(S)-3-(pyrrolidin-2-yl)pyridine, to thereby produce 42.9 mg of the title compound as a pale brown solid.

Synthesis Example 675

(E)-N-Cyclopropyl-3-(3-(2,3-dihydro-1H-pyrido[3,4-b][1,4]oxazin-1-yl)-3-oxoprop-1-en-1-yl)-7-hydroxy-4-isobutyl-2-methyl-5-oxo-4,5-dihydropyrazolo[1,5-a]pyrimidine-6-carboxamide 40.8 mg of 2,3-dihydro-1H-pyrido[3,4-b][1,4]oxazine, 0.107 mL of N,N-diisopropylethylamine, and 114 mg of O-(7-azabenzotriazol-1-yl)-N,N,N',N'-tetramethyluronium hexafluorophosphate were added to a solution of 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 in 1.0 mL of N,N-dimethylformamide, and the resultant mixture was stirred at room temperature for one hour. The reaction mixture was stirred at 60° C. for four hours. The reaction mixture was cooled to room temperature, and 2.0 mL of a saturated aqueous ammonium chloride solution was added to the mixture, followed by extraction with 5 mL of chloroform. The organic phase was subjected to diatomaceous earth filtration, and the filtrate was concentrated under reduced pressure. The residue was purified by silica gel column chromatography (chloroform/methanol=100/0→95/5 (v/v)), to thereby produce 57.8 mg of the title compound as a yellow solid.

Synthesis Example 676

(E)-N-Cyclopropyl-3-(3-(2,3-dihydro-1H-pyrido[2,3-b] 1,4]oxazin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 675 was performed by using 2,3-dihydro-1H-pyrido[2,3-b][1,4]oxazine in place of 2,3-dihydro-1H-pyrido[3,4-b][1,4]oxazine, to thereby produce 16.6 mg of the title compound as a pale brown solid.

Synthesis Example 677

(S,E)-N-Cyclopropyl-7-hydroxy-3-(3-(2-(2-hydroxypropan-2-yl) pyrrolidin-1-yl)-3-oxoprop-1-en-1-yl)-4-isobutyl-2-methyl-5-oxo-4,5-dihydropyrazolo[1,5-a]pyrimidine-6-carboxamide 1.5 mL of dichloromethane, 39.5 mg of(S)-2-(pyrrolidin-2-yl)propan-2-ol, 0.142 mL of triethylamine, and 97.3 mg of 1-(3-dimethylaminopropyl)-3-ethylcarbodiimide hydrochloride were added to 63.6 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 2.0 mL of a saturated aqueous ammonium chloride solution, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=100/0→50/1 (v/v)), to thereby produce 36.1 mg of the title compound as a pale yellow solid.

Synthesis Example 678

(E)-N-Cyclopropyl-7-hydroxy-4-isobutyl-3-(3-(8-isopropyl-1,8-diazaspiro[4.5]decan-1-yl)-3-oxoprop-1-en-1-yl)-2-methyl-5-oxo-4,5-dihydropyrazolo[1,5-a]pyrimidine-6-carboxamide 0.0208 mL of triethylamine was added to a mixture of 26.7 mg of (E)-N-cyclopropyl-7-hydroxy-4-isobutyl-2-methyl-5-oxo-3-(3-oxo-3-(1,8-diazaspiro[4.5]decan-1-yl)prop-1-en-1-yl)-4,5-dihydropyrazolo[1,5-a]pyrimidine-6-carboxamide hydrochloride produced in Synthesis Example 664 and 1 mL of acetone at 0° C., and the resultant mixture was stirred at 0° C. for 10 minutes. To the reaction mixture was added 31.8 mg of sodium triacetoxyborohydride at 0° C., and the mixture was stirred at room temperature for two hours. To the reaction mixture was added 2 mL of a saturated aqueous sodium chloride solution, and the mixture was subjected to extraction with chloroform. The organic phase was dried over sodium sulfate and subjected to filtration, and then the filtrate was concentrated under reduced pressure. The residue was purified by silica gel column chromatography (chloroform/methanol=100/0→80/20 (v/v)). To the residue was added 2 mL of a saturated aqueous sodium chloride solution, and the mixture was subjected to extraction with chloroform, followed by concentration under reduced pressure, to thereby produce 9.87 mg of the title compound as a white solid.

Synthesis Example 679

(R,E)-N-Cyclopropyl-7-hydroxy-4-isobutyl-2-methyl-3-(3-(2-methylmorpholino)-3-oxoprop-1-en-1-yl)-5-oxo-4,5-dihydropyrazolo[1,5-a]pyrimidine-6-carboxamide 0.5 mL of dichloromethane, 14.2 mg of (R)-2-methylmorpholine, 8.6 mg of 4-dimethylaminopyridine, and 40.0 mg of 1-(3-dimethylaminopropyl)-3-ethylcarbodiimide hydrochloride were added to 26.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. To the reaction mixture was added 0.5 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=50/1 (v/v)), to thereby produce 25.6 mg of the title compound as a pale brown amorphous product.

Synthesis Example 680

(S,E)-N-Cyclopropyl-7-hydroxy-4-isobutyl-2-methyl-3-(3-(2-methylmorpholino)-3-oxoprop-1-en-1-yl)-5-oxo-4,5-dihydropyrazolo[1,5-a]pyrimidine-6-carboxamide 0.5 mL of dichloromethane, 19.3 mg of(S)-2-methylmorpholine hydrochloride, 8.6 mg of 4-dimethylaminopyridine, 0.0195 mL of triethylamine, and 40.0 mg of 1-(3-dimethylaminopropyl)-3-ethylcarbodiimide hydrochloride were added to 26.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. To the reaction mixture was added 0.5 mL of 1 M hydrochloric acid, and the mixture was subjected to extraction with 5 mL of dichloromethane. The organic phase was subjected to diatomaceous earth filtration, and the filtrate was concentrated under reduced pressure. The residue was purified by silica gel column chromatography (chloroform/methanol=50/1 (v/v)), to thereby produce 26.9 mg of the title compound as a pale brown amorphous product.

Synthesis Example 681

(E)-3-(3-((Cyanomethyl)(methyl)amino)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, and 10.5 mg of 2-(methylamino) acetonitrile were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)). The residue was suspended in diisopropyl ether, and the resultant solid was recovered by filtration and then dried under reduced pressure, to thereby produce 14.2 mg of the title compound as a white solid.

Synthesis Example 682

(R,E)-N-Cyclopropyl-7-hydroxy-4-isobutyl-3-(3-(3-(methoxymethyl) morpholino)-3-oxoprop-1-en-1-yl)-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 0.0314 mL of triethylamine, 9.2 mg of 4-dimethylaminopyridine, and 25.1 mg of (R)-3-(methoxymethyl) morpholine hydrochloride were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 16.6 mg of the title compound as a pale brown amorphous product.

Synthesis Example 683

(S,E)-N-Cyclopropyl-7-hydroxy-4-isobutyl-3-(3-(3-(methoxymethyl) morpholino)-3-oxoprop-1-en-1-yl)-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 0.0314 mL of triethylamine, 9.2 mg of 4-dimethylaminopyridine, and 25.1 mg of(S)-3-(methoxymethyl) morpholine hydrochloride were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 23.2 mg of the title compound as a pale brown amorphous product.

Synthesis Example 684

(E)-3-(3-(4-Cyanopiperidin-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, and 0.0167 mL of piperidine-4-carbonitrile were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)). The residue was suspended in diisopropyl ether, and the resultant solid was recovered by filtration and then dried under reduced pressure, to thereby produced 22.3 mg of the title compound as a white solid.

Synthesis Example 685

(E)-N-Cyclopropyl-7-hydroxy-4-isobutyl-2-methyl-5-oxo-3-(3-oxo-3-(4-(2,2,2-trifluoroethyl) piperazin-1-yl)prop-1-en-1-yl)-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, and 25.2 mg of 1-(2,2,2-trifluoroethyl) piperazine were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 16 hours. To the reaction mixture were added 2 mL of a saturated aqueous ammonium chloride solution and 20 mL of chloroform, and the mixture was subjected to diatomaceous earth filtration. Thereafter, the filtrate was concentrated under reduced pressure. The residue was purified by silica gel column chromatography (chloroform/methanol=99/1 v/v)). The residue was suspended in diisopropyl ether, and the resultant solid was recovered by filtration and then dried under reduced pressure, to thereby produce 26.9 mg of the title compound as a white solid.

Synthesis Example 686

(E)-N-Cyclopropyl-7-hydroxy-3-(3-((2-hydroxy-2-methylpropyl)(methyl)amino)-3-oxoprop-1-en-1-yl)-4-isobutyl-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, and 15.5 mg of 2-methyl-1-(methylamino)propan-2-ol were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 25.5 mg of the title compound as a pale brown amorphous product.

Synthesis Example 687

(E)-3-(3-((2-Cyanoethyl)(methyl)amino)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, and 0.0139 mL of 3-(methylamino)propanenitrile were added to a mixture of 28.1 mg of (E)-3-(6-(cyclopropylcarbamoyl)-7-hydroxy-. 4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)) and then recrystallized from ethanol, to thereby produce 13.8 mg of the title compound as a white solid.

Synthesis Example 688

(S,E)-3-(3-(3-Cyanopyrrolidin-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, 0.0314 mL of triethylamine, and 19.9 mg of(S)-pyrrolidine-3-carbonitrile hydrochloride were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 24.5 mg of the title compound as a pale brown amorphous product.

Synthesis Example 689

(R,E)-3-(3-(3-Cyanopyrrolidin-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, 0.0314 mL of triethylamine, and 19.9 mg of (R)-pyrrolidine-3-carbonitrile hydrochloride were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 23.0 mg of the title compound as a pale brown amorphous product.

Synthesis Example 690

(E)-3-(3-((Cyanomethyl)(methyl)amino)-3-oxoprop-1-en-1-yl)-N-cyclopropyl-7-hydroxy-2-methyl1-4-neopentyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, and 10.5 mg of 2-(methylamino) acetonitrile were added to a mixture of 29.1 mg of (E)-3-(6-(cyclopropylcarbamoyl)-7-hydroxy-2-methyl-4-neopentyl-5-oxo-4,5-dihydropyrazolo[1,5-a]pyrimidin-3-yl)acrylic acid produced in step D of Synthesis Example 582 and 1 mL of dichloromethane at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)). The residue was suspended in diisopropyl ether, and the resultant solid was recovered by filtration and then dried under reduced pressure, to thereby produce 21.6 mg of the title compound as a white solid.

Synthesis Example 691

(S,E)-N-Cyclopropyl-3-(3-(3-ethylmorpholino)-3-oxoprop-1-en-1-yl)-7-hydroxy-2-methyl-4-neopentyl-5-oxo-4,5-dihydropyrazolo[1,5-a]pyrimidine-6-carboxamide Substantially the same reaction as in Synthesis Example 690 was performed by using(S)-3-ethylmorpholine in place of 2-(methylamino) acetonitrile, to thereby produce 31.2 mg of the title compound as a pale brown amorphous product.

Synthesis Example 692

(E)-N-Cyclopropyl-3-(3-(4-(3,3-difluorocyclobutyl) piperazin-1-yl)-3-oxoprop-1-en-1-yl)-7-hydroxy-2-methyl-4-neopentyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, 0.0314 mL of triethylamine, and 31.9 mg of 1-(3,3-difluorocyclobutyl) piperazine dihydrochloride were added to a mixture of 29.1 mg of (E)-3-(6-(cyclopropylcarbamoyl)-7-hydroxy-2-methyl-4-neopentyl-5-oxo-4,5-dihydropyrazolo [1,5-a]pyrimidin-3-yl)acrylic acid produced in step D of Synthesis Example 582 and 1 mL of dichloromethane at 0° C., and the resultant mixture was stirred at room temperature for 16 hours. To the reaction mixture were added 2 mL of a saturated aqueous ammonium chloride solution and 20 mL of chloroform, and the mixture was subjected to diatomaceous earth filtration. Thereafter, the filtrate was concentrated under reduced pressure. The residue was purified by silica gel column chromatography (chloroform/methanol=99/1→97/3 (v/v)). The residue was suspended in diisopropyl ether, and the resultant solid was recovered by filtration and then dried under reduced pressure, to thereby produce 18.1 mg of the title compound as a white solid.

Synthesis Example 693

(R,E)-N-Cyclopropyl-7-hydroxy-3-(3-(3-(methoxymethyl) morpholino)-3-oxoprop-1-en-1-yl)-2-methyl-4-neopentyl-5-oxo-4,5-dihydropyrazolo[1,5-a]pyrimidine-6-carboxamide Substantially the same reaction as in Synthesis Example 692 was performed by using (R)-3-(methoxymethyl) morpholine hydrochloride in place of 1-(3,3-difluorocyclobutyl) piperazine dihydrochloride, to thereby produce 31.2 mg of the title compound as a pale brown amorphous product.

Synthesis Example 694

(S,E)-N-Cyclopropyl-7-hydroxy-3-(3-(3-(methoxymethyl) morpholino)-3-oxoprop-1-en-1-yl)-2-methyl-4-neopentyl-5-oxo-4,5-dihydropyrazolo[1,5-a]pyrimidine-6-carboxamide Substantially the same reaction as in Synthesis Example 692 was performed by using(S)-3-(methoxymethyl) morpholine hydrochloride in place of 1-(3,3-difluorocyclobutyl) piperazine dihydrochloride, to thereby produce 25.9 mg of the title compound as a pale brown amorphous product.

Synthesis Example 695

(E)-N-Cyclopropyl-3-(3-(2,3-dihydro-4H-pyrido[4,3-b][1,4]oxazin-4-yl)-3-oxoprop-1-en-1-yl)-7-hydroxy-4-isobutyl-2-methyl-5-oxo-4,5-dihydropyrazolo[1,5-a]pyrimidine-6-carboxamide 40.8 mg of 3,4-dihydro-2H-pyrido[4,3-b][1,4]oxazine, 0.107 mL of N,N-diisopropylethylamine, and 114 mg of O-(7-azabenzotriazol-1-yl)-N,N,N',N'-tetramethyluronium hexafluorophosphate were added to a solution of 56.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563 in 1.0 mL of N,N-dimethylformamide, and the resultant mixture was stirred at room temperature for one hour. To the reaction mixture was added 2.0 mL of a saturated aqueous ammonium chloride solution, and the mixture was subjected to extraction with 5 mL of chloroform. The organic phase was subjected to diatomaceous earth filtration, and the filtrate was concentrated under reduced pressure. The residue was purified by reversed-phase silica gel column chromatography (0.1% trifluoroacetic acid-acetonitrile/0.1% aqueous trifluoroacetic acid solution=70/30 →100/0 (v/v)), to thereby produce 6.94 mg of the title compound as a pale brown solid.

Synthesis Example 696

(E)-N-Cyclopropyl-3-(3-(2,3-dihydro-4H-benz[b][1.4]oxazin-4-yl)-3-oxoprop-1-en-1-yl)-7-hydroxy-4-isobutyl-2-methyl-5-oxo-4,5-dihydropyrazolo[1,5-a]pyrimidine-6-carboxamide 36.2 mg of 3,4-dihydro-2H-benz[b] [1,4]oxazine, 0.107 mL of N,N-diisopropylethylamine, and 102 mg of O-(7-azabenzotriazol-1-yl)-N,N,N',N'-tetramethyluronium hexafluorophosphate were added to a solution of 50.2 mg of (E)-3-(6-(cyclopropylcarbamoyl)-7-hydroxy-4-isobutyl-2-methyl-5-oxo-4,5-dihydropyrazolo[1,5-a]pyrimidin-3-yl) acrylic acid produced in step D of Synthesis Example 563 in 1.0 mL of N,N-dimethylformamide, and the resultant mixture was stirred at room temperature for one hour. The reaction mixture was stirred at 60° C. overnight. The reaction mixture was cooled to room temperature, and 2.0 mL of a saturated aqueous ammonium chloride solution was added to the mixture, followed by extraction with 5 mL of chloroform. The organic phase was subjected to diatomaceous earth filtration, and the filtrate was concentrated under reduced pressure. The residue was purified by silica gel column chromatography (chloroform/methanol=100/0→98/2 (v/v)). To the residue was added 3.0 mL of hexane, and the precipitated solid was recovered by filtration and then dried under reduced pressure, to thereby produce 31.9 mg of the title compound as a pale brown solid.

Synthesis Example 697

(R,E)-N-Cyclopropyl-3-(3-(4-(3,3-difluorocyclobutyl)-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide Step A (R,E)-N-Cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride Substantially the same reaction as in step A of Synthesis Example 671 was performed by using tert-butyl (R)-3-methylpiperazine-1-carboxylate in place of tert-butyl (S)-3-methylpiperazine-1-carboxylate, to thereby produce 76.1 mg of the title compound as a white solid.

LC/MS: condition 2, retention time=1.77 min

LC/MS (ESI+) m/z; 457.5 $[M+H]^+$

Step B (R,E)-N-Cyclopropyl-3-(3-(4-(3,3-difluorocyclobutyl)-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in step B of Synthesis Example 671 was performed by using (R,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride produced in step A of Synthesis Example 697 in place of (S,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride, to thereby produce 12.91 mg of the title compound as a white solid.

Synthesis Example 698

(E)-N-Cyclopropyl-3-(3-(4-((3,3-difluorocyclobutyl)methyl) piperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide To 93.1 mg of tert-butyl piperazine-1-carboxylate were added 1 mL of acetonitrile, 218 μL of N,N-diisopropylethylamine, and 70.7 μL of 3-(bromomethyl)-1,1-difluorocyclobutane, and the resultant mixture was stirred at room temperature for one hour and then at 65° C. for 16 hours. The reaction mixture was cooled to room temperature, and then concentrated under reduced pressure. To the residue was added 2 mL of 4 M hydrogen chloride dioxane solution, and the resultant mixture was stirred at room temperature for one hour. The reaction mixture was concentrated under reduced pressure, and then suspended in 3 mL of ethyl acetate. The resultant solid was recovered by filtration, and then dried under reduced pressure, to thereby produce 102.51 mg of 1-((3,3-difluorocyclobutyl)methyl) piperazine hydrochloride as a pale yellow solid.

Subsequently, 1 mL of dichloromethane, 27.2 mg of the above-produced 1-((3,3-difluorocyclobutyl)methyl) piperazine hydrochloride, 4.9 mg of 4-dimethylaminopyridine, 45.8 mg of 1-(3-dimethylaminopropyl)-3-ethylcarbodiimide hydrochloride, and 33.5 μL of triethylamine were added to 30.0 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 1 mL of water, and the mixture was subjected to extraction with chloroform/methanol (6 mL/0.5 mL). The organic phase was dried over sodium sulfate and subjected to filtration, and then the filtrate was concentrated under reduced pressure. The residue was purified by silica gel column chromatography (chloroform/methanol=100/0→98/2→95/5 (v/v)), to thereby produce 10.24 mg of the title compound as a white solid.

Synthesis Example 699

(E)-N-Cyclopropyl-3-(3-(2,3-dihydro-1H-pyrrolo[2,3-c]pyridin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 698 was performed by using 2,3-dihydro-1H-pyrrolo[2,3-c]pyridine in place of 1-((3,3-difluorocyclobutyl)methyl) piperazine hydrochloride, to thereby produce 17.98 mg of the title compound as a pale brown solid.

Synthesis Example 700

(R,E)-N-Cyclopropyl-7-hydroxy-3-(3-(3-(2-hydroxypropan-2-yl) pyrrolidin-1-yl)-3-oxoprop-1-en-1-yl)-4-isobutyl-2-methyl-5-oxo-4,5-dihydropyrazolo[1,5-a]pyrimidine-6-carboxamide 1 mL of dichloromethane, 25.8 mg of (R)-2-(pyrrolidin-3-yl)propan-2-ol, 6.1 mg of 4-dimethylaminopyridine, and 57.2 mg of 1-(3-dimethylaminopropyl)-3-ethylcarbodiimide hydrochloride were added to 36.0 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for one hour. To the reaction mixture was added 2 mL of 1 M hydrochloric acid, and the mixture was subjected to extraction with 20 mL of chloroform. The organic phase was dried over sodium sulfate and subjected to filtration, and then the filtrate was concentrated under reduced pressure. The resultant product was purified by silica gel column chromatography (chloroform/methanol=100/0→98/2→95/5 (v/v)), to thereby produce 28.61 mg of the title compound as a white solid.

Synthesis Example 701

(S,E)-N-Cyclopropyl-3-(3-(2,4-dimethylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide 12.9 μL of 37% aqueous formaldehyde solution was added to a mixture of 34.5 mg of (S,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride produced in step A of Synthesis Example 671 and 1 mL of dichloromethane, and the resultant mixture was stirred at room temperature for five minutes. To the reaction mixture was added 31.8 mg of sodium triacetoxyborohydride, and the mixture was stirred at room temperature for one hour. To the reaction mixture was added 2 mL of a saturated aqueous sodium hydrogen carbonate solution, and the mixture was subjected to extraction with 10 mL of chloroform. The organic phase was dried over sodium sulfate and subjected to filtration, and then the filtrate was concentrated under reduced pressure. The resultant product was purified by silica gel column chromatography (chloroform/methanol=100/0→95/5 →90/10 (v/v)), to thereby produce 6.38 mg of the title compound as a white solid.

Synthesis Example 702

(R,E)-N-Cyclopropyl-3-(3-(2,4-dimethylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 701 was performed by using (R,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride produced in step A of Synthesis Example 697 in place of (S,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride, to thereby produce 8.07 mg of the title compound as a white solid.

Synthesis Example 703

(S,E)-N-Cyclopropyl-3-(3-(4-((3,3-difluorocyclobutyl)methyl)-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 698 was performed by using tert-butyl(S)-2-methylpiperazine-1-carboxylate in place of tert-butyl piperazine-1-carboxylate, to thereby produce 16.06 mg of the title compound as a white solid.

Synthesis Example 704

(R,E)-N-Cyclopropyl-3-(3-(4-((3,3-difluorocyclobutyl)methyl)-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 698 was performed by using tert-butyl (R)-2-methylpiperazine-1-carboxylate in place of tert-butyl piperazine-1-carboxylate, to thereby produce 31.44 mg of the title compound as a white solid.

Synthesis Example 705

(E)-N-Cyclopropyl-3-(3-(2,3-dihydro-1H-pyrrolo[3,2-c]pyridin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 698 was performed by using 2,3-dihydro-1H-pyrrolo[3,2-c]pyridine hydrochloride in place of 1-((3,3-difluorocyclobutyl)methyl) piperazine hydrochloride, to thereby produce 19.01 mg of the title compound as a yellow solid.

Synthesis Example 706

(E)-N-Cyclopropyl-7-hydroxy-4-isobutyl-2-methyl-5-oxo-3-(3-oxo-3-(7-oxa-4-azaspiro[2.5]octan-4-yl)prop-1-en-1-yl)-4,5-dihydropyrazolo[1,5-a]pyrimidine-6-carboxamide 1 mL of dichloromethane, 29.9 mg of 7-oxa-4-azaspiro[2.5]octane hydrochloride, 6.1 mg of 4-dimethylaminopyridine, 57.2 mg of 1-(3-dimethylaminopropyl)-3-ethylcarbodiimide hydrochloride, and 41.8 μL of triethylamine were added to 37.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563, and the resultant mixture was stirred at room temperature for 16 hours. To the reaction mixture was added 1 mL of 1 M hydrochloric acid, and the mixture was subjected to extraction with 5 mL of chloroform. The organic phase was dried over sodium sulfate and subjected to filtration, and then the filtrate was concentrated under reduced pressure. The resultant product was purified by silica gel column chromatography (hexane/ethyl acetate=50/50→30/70→20/80→0/100 (v/v)), to thereby produce 2.7 mg of the title compound as a white solid.

Synthesis Example 707

(S,E)-N-Cyclopropyl-3-(3-(4-ethyl-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide 308.4 mg of acetaldehyde (about 2% by weight N,N-dimethylformamide solution) was added to a mixture of 19.7 mg (S,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride produced in step A of Synthesis Example 671 and 0.8 mL of dichloromethane, and the resultant mixture was stirred at room temperature for five minutes. To the reaction mixture was added 25.4 mg of sodium triacetoxyborohydride, and the mixture was stirred room temperature for one hour. To the reaction mixture was added 2 mL of a saturated aqueous sodium hydrogen carbonate solution, and the mixture was subjected to extraction with 10 mL of chloroform. The organic phase was dried over sodium sulfate and subjected to filtration, and then the filtrate was concentrated under reduced pressure. The resultant product was purified by silica gel column chromatography (chloroform/methanol=100/0→95/5 →90/10 (v/v)), to thereby produce 8.46 mg of the title compound as a white solid.

The compounds of Synthesis Examples 708 to 748 were produced according to the methods described in the aforementioned Synthesis Examples or methods similar thereto.

Synthesis Example 708

N-Cyclopropyl-7-hydroxy-4-isobutyl-5-oxo-3-((E)-3-oxo-3-((3aR,6aS)-tetrahydro-1H-furo[3,4-c]pyrrol-5 (3H)-yl)prop-1-en-1-yl)-4,5-dihydropyrazolo[1,5-a]pyrimidine-6-carboxamide Yield: 47.6 mg, white solid Synthesis Example 709

(E)-N-Cyclopropyl-7-hydroxy-4-isobutyl-3-(3-(methyl(pyrazin-2-ylmethyl)amino)-3-oxoprop-1-en-1-yl)-5-oxo-4,5-dihydropyrazolo[1,5-a]pyrimidine-6-carboxamide Yield: 70.1 mg, white solid Synthesis Example 710

(E)-N-Cyclopropyl-7-hydroxy-4-isobutyl-3-(3-(methyl(pyridin-2-ylmethyl)amino)-3-oxoprop-1-en-1-yl)-5-oxo-4,5-dihydropyrazolo[1,5-a]pyrimidine-6-carboxamide Yield: 68.2 mg, pale blue solid Synthesis Example 711

(E)-N-Cyclopropyl-7-hydroxy-4-isobutyl-3-(3-(methyl(pyrimidin-2-ylmethyl)amino)-3-oxoprop-1-en-1-yl)-5-oxo-4,5-dihydropyrazolo[1,5-a]pyrimidine-6-carboxamide Yield: 33.9 mg, white solid Synthesis Example 712

(E)-N-Cyclopropyl-7-hydroxy-4-isobutyl-3-(3-(methyl(pyridin-3-ylmethyl)amino) . . . 3-oxoprop-1-en-1-yl)-5-oxo-4,5-dihydropyrazolo[1,5-a]pyrimidine-6-carboxamide Yield: 47.6 mg, white solid Synthesis Example 713

(S,E)-N-Cyclopropyl-3-(3-(2,4-dimethylpiperazin-1-yl)-3-oxoprop-1-en-1-yl)-7-hydroxy-4-isobutyl-5-oxo-4,5-dihydropyrazolo[1,5-a]pyrimidine-6-carboxamide Yield: 18.0 mg, white solid Synthesis Example 714

(E)-N-Cyclopropyl-3-(3-(4-((3,3-difluorocyclobutyl) methyl) piperazin-1-yl)-3-oxoprop-1-en-1-yl)-7-hydroxy-4-isobutyl-5-oxo-4,5-dihydropyrazolo[1,5-a]pyrimidine-6-carboxamide Yield: 19.5 mg, white solid Synthesis Example 715

(R,E)-N-Cyclopropyl-3-(3-(4-(3,3-difluorocyclobutyl)-2-methylpiperazin-1-yl)-3-oxoprop-1-en-1-yl)-7-hydroxy-4-isobutyl-5-oxo-4,5-dihydropyrazolo[1,5-a]pyrimidine-6-carboxamide Yield: 15.8 mg, white solid Synthesis Example 716

N-Cyclopropyl-3-((E)-3-((2R,5R)-2,5-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 23.8 mg, white solid Synthesis Example 717

N-Cyclopropyl-3-((E)-3-((2S,5S)-2,5-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 26.6 mg, white solid Synthesis Example 718

N-Cyclopropyl-3-((E)-3-((2S,5R)-2,5-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 27.3 mg, white solid Synthesis Example 719

(E)-N-Cyclopropyl-3-(3-(3,3-difluoro-8-azabicyclo[3.2.1]octan-8-yl)-3-oxoprop-1-en-1-yl)-7-hydroxy-4-isobutyl-5-oxo-4,5-dihydropyrazolo[1,5-a]pyrimidine-6-carboxamide Yield: 26.4 mg, white solid Synthesis Example 720

(E)-N-Cyclopropyl-3-(3-(8,8-difluoro-3-azabicyclo[3.2.1]octan-3-yl)-3-oxoprop-1-en-1-yl)-7-hydroxy-4-isobutyl-5-oxo-4,5-dihydropyrazolo[1,5-a]pyrimidine-6-carboxamide Yield: 26.6 mg, white solid Synthesis Example 721

(E)-N-Cyclopropyl-7-hydroxy-4-isobutyl-5-oxo-3-(3-oxo-3-(4-azaspiro[2.4]heptan-4-yl)prop-1-en-1-yl)-4,5-dihydropyrazolo[1,5-a]pyrimidine-6-carboxamide Yield: 22.9 mg, white solid Synthesis Example 722

N-Cyclopropyl-3-((E)-3-(cis-3,4-difluoropyrrolidin-1-yl)-3-oxoprop-1-en-1-yl)-7-hydroxy-4-isobutyl-5-oxo-4,5-dihydropyrazolo[1,5-a]pyrimidine-6-carboxamide Yield: 29.3 mg, white solid Synthesis Example 723

N-Cyclopropyl-3-((E)-3-(trans-3,4-difluoropyrrolidin-1-yl)-3-oxoprop-1-en-1-yl)-7-hydroxy-4-isobutyl-5-oxo-4,5-dihydropyrazolo[1,5-a]pyrimidine-6-carboxamide (racemate)

Yield: 21.7 mg, white solid

Synthesis Example 724

(E)-N-Cyclopropyl-3-(3-(5,6-dihydro-7H-pyrrolo[2,3-d]pyrimidin-7-yl)-3-oxoprop-1-en-1-yl)-7-hydroxy-4-isobutyl-5-oxo-4,5-dihydropyrazolo[1,5-a]pyrimidine-6-carboxamide Yield: 15.8 mg, yellow solid Synthesis Example 725

(E)-N-Cyclopropyl-7-hydroxy-3-(3-(indolin-1-yl)-3-oxoprop-1-en-1-yl)-4-isobutyl-5-oxo-4,5-dihydropyrazolo[1,5-a]pyrimidine-6-carboxamide Yield: 62.8 mg, white solid Synthesis Example 726

(S,E)-N-Cyclopropyl-3-(3-(4-(3,3-difluorocyclobutyl)-2-methylpiperazin-1-yl)-3-oxoprop-1-en-1-yl)-7-hydroxy-4-isobutyl-5-oxo-4,5-dihydropyrazolo[1,5-a]pyrimidine-6-carboxamide Yield: 16.8 mg, white solid Synthesis Example 727

(S,E)-N-Cyclopropyl-7-hydroxy-4-isobutyl-5-oxo-3-(3-oxo-3-(2-phenylpyrrolidin-1-yl)prop-1-en-1-yl)-4,5-dihydropyrazolo[1,5-a]pyrimidine-6-carboxamide Yield: 44.9 mg, white solid Synthesis Example 728

(E)-N-Cyclopropyl-3-(3-(2,3-dihydro-1H-pyrido[3,4-b][1,4]oxazin-1-yl)-3-oxoprop-1-en-1-yl)-7-hydroxy-4-isobutyl-5-oxo-4,5-dihydropyrazolo[1,5-a]pyrimidine-6-carboxamide Yield: 34.4 mg, pale yellow solid Synthesis Example 729

(E)-N-Cyclopropyl-3-(3-(2,3-dihydro-1H-pyrido[2,3-b][1,4]oxazin-1-yl)-3-oxoprop-1-en-1-yl)-7-hydroxy-4-isobutyl-5-oxo-4,5-dihydropyrazolo[1,5-a]pyrimidine-6-carboxamide Yield: 6.1 mg, pale brown solid Synthesis Example 730

(S,E)-N-Cyclopropyl-7-hydroxy-3-(3-(2-(2-hydroxypropan-2-yl) pyrrolidin-1-yl)-3-oxoprop-1-en-1-yl)-4-isobutyl-5-oxo-4,5-dihydropyrazolo[1,5-a]pyrimidine-6-carboxamide Yield: 16.6 mg, white solid Synthesis Example 731

(E)-N-Cyclopropyl-3-(3-(5-fluoroindolin-1-yl)-3-oxoprop-1-en-1-yl)-7-hydroxy-4-isobutyl-5-oxo-4,5-dihydropyrazolo[1,5-a]pyrimidine-6-carboxamide Yield: 37.2 mg, white solid Synthesis Example 732

(E)-3-(3-(5-Cyanoindolin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 30.7 mg, pale yellow solid Synthesis Example 733

Tert-butyl (E)-1-(3-(6-(cyclopropylcarbamoyl)-7-hydroxy-4-isobutyl-5-oxo-4,5-dihydropyrazolo[1,5-a]pyrimidin-3-yl)acryloyl)-1,8-diazaspiro[4.5]decane-8-carboxylate Yield: 119.3 mg, white solid Synthesis Example 734

(E)-3-(3-(3-Cyanoazetidin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 106.5 mg, white solid Synthesis Example 735

(E)-3-(3-(5-Bromoindolin-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 52.1 mg, white solid Synthesis Example 736

(E)-N-Cyclopropyl-7-hydroxy-4-isobutyl-3-(3-(8-methyl-1,8-diazaspiro[4.5]decan-1-yl)-3-oxoprop-1-en-1-yl)-5-oxo-4,5-dihydropyrazolo[1,5-a]pyrimidine-6-carboxamide Yield: 9.3 mg, white solid Synthesis Example 737

(E)-3-(3-(8-Acetyl-1,8-diazaspiro[4.5]decan-1-yl)-3-oxoprop-1-en-1-yl)-N-cyclopropyl-7-hydroxy-4-isobutyl-5-oxo-4,5-dihydropyrazolo[1,5-a]pyrimidine-6-carboxamide Yield: 27.7 mg, white solid Synthesis Example 738

(E)-N-Cyclopropyl-3-(3-(2,3-dihydro-4H-pyrido[4,3-b][1,4]oxazin-4-yl)-3-oxoprop-1-en-1-yl)-7-hydroxy-4-isobutyl-5-oxo-4,5-dihydropyrazolo[1,5-a]pyrimidine-6-carboxamide Yield: 4.3 mg, pale brown solid Synthesis Example 739

(E)-N-Cyclopropyl-3-(3-(2,3-dihydro-4H-benz[b][1,4]oxazin-4-yl)-3-oxoprop-1-en-1-yl)-7-hydroxy-4-isobutyl-5-oxo-4,5-dihydropyrazolo[1,5-a]pyrimidine-6-carboxamide Yield: 66.2 mg, pale brown solid Synthesis Example 740

(E)-N-Cyclopropyl-3-(3-(2,3-dihydro-1H-pyrrolo[3,2-c]pyridin-1-yl)-3-oxoprop-1-en-1-yl)-7-hydroxy-4-isobutyl-5-oxo-4,5-dihydropyrazolo[1,5-a]pyrimidine-6-carboxamide Yield: 14.2 mg, yellow solid Synthesis Example 741

N-Cyclopropyl-3-((E)-3-((2R,5S)-2,5-dimethylmorpholino)-3-oxoprop-1-en-1-yl)-7-hydroxy-4-isobutyl-5-oxo-4,5-dihydropyrazolo[1,5-a]pyrimidine-6-carboxamide Yield: 13.1 mg, white solid Synthesis Example 742

(E)-N-Cyclopropyl-3-(3-(2,3-dihydro-1H-pyrrolo[2,3-c]pyridin-1-yl)-3-oxoprop-1-en-1-yl)-7-hydroxy-4-isobutyl-5-oxo-4,5-dihydropyrazolo[1,5-a]pyrimidine-6-carboxamide Yield: 38.2 mg, white solid Synthesis Example 743

(R,E)-N-Cyclopropyl-7-hydroxy-3-(3-(3-(2-hydroxypropan-2-yl) pyrrolidin-1-yl)-3-oxoprop-1-en-1-yl)-4-isobutyl-5-oxo-4,5-dihydropyrazolo[1,5-a]pyrimidine-6-carboxamide Yield: 36.1 mg, white solid Synthesis Example 744

(S,E)-N-Cyclopropyl-3-(3-(4-((3,3-difluorocyclobutyl)methyl)-2-methylpiperazin-1-yl)-3-oxoprop-1-en-1-yl)-7-hydroxy-4-isobutyl-5-oxo-4,5-dihydropyrazolo[1,5-a]pyrimidine-6-carboxamide Yield: 22.6 mg, white solid Synthesis Example 745

(R,E)-N-Cyclopropyl-3-(3-(4-((3,3-difluorocyclobutyl)methyl)-2-methylpiperazin-1-yl)-3-oxoprop-1-en-1-yl)-7-hydroxy-4-isobutyl-5-oxo-4,5-dihydropyrazolo[1,5-a]pyrimidine-6-carboxamide Yield: 31.4 mg, white solid Synthesis Example 746

(E)-N-Cyclopropyl-7-hydroxy-4-isobutyl-3-(3-(8-isopropyl-1,8-diazaspiro[4.5]decan-1-yl)-3-oxoprop-1-en-1-yl)-5-oxo-4,5-dihydropyrazolo[1,5-a]pyrimidine-6-carboxamide Yield: 4.2 mg, white solid Synthesis Example 747

(E)-N-Cyclopropyl-4-(2-fluoro-2-methylpropyl)-7-hydroxy-2-methyl-3-(3-morpholino-3-oxoprop-1-en-1-yl)-5-oxo-4,5-dihydropyrazolo[1,5-a]pyrimidine-6-carboxamide Yield: 64.8 mg, white solid Synthesis Example 748

(R,E)-N-Cyclopropyl-7-hydroxy-4-isobutyl-5-oxo-3-(3-oxo-3-(2-(pyridin-3-yl) pyrrolidin-1-yl)prop-1-en-1-yl)-4,5-dihydropyrazolo[1,5-a]pyrimidine-6-carboxamide Yield: 8.4 mg, pale brown solid Synthesis Example 749

(R,E)-3-(3-(2-Cyanopyrrolidin-1-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide 43.1 mg of 1-(3-dimethylaminopropyl)-3-ethylcarbodiimide hydrochloride, 9.2 mg of 4-dimethylaminopyridine, 0.0314 mL of triethylamine, and 19.9 mg of (R)-pyrrolidine-2-carbonitrile hydrochloride were added to a mixture of 28.1 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 16 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel reversed-phase column chromatography (0.1% trifluoroacetic acid-acetonitrile/0.1% aqueous trifluoroacetic acid solution=40/60 →50/50 (v/v)), to thereby produce 20.1 mg of the title compound as a pale brown amorphous product.

Synthesis Example 750

(E)-N-Cyclopropyl-7-hydroxy-4-isobutyl-3-(3-((2-methoxyethyl)(methyl)amino)-3-oxoprop-1-en-1-yl)-2-methyl-5-oxo-4,5-dihydropyrazolo[1,5-a]pyrimidine-6-carboxamide 57.5 mg of 1-(3-dimethylaminopropyl)-3-ethylcarbodiimide hydrochloride, 12.2 mg of 4-dimethylaminopyridine, and 17.8 mg of 2-methoxy-N-methylethan-1-amine were added to a mixture of 37.4 mg of (E)-3-(6-(cyclopropylcarbamoyl)-7-hydroxy-4-isobutyl-2-methyl-5-oxo-4,5-dihydropyrazolo[1,5-a]pyrimidin-3-yl)acrylic acid produced in step D of Synthesis Example 563 and 1 mL of dichloromethane at 0° C., and the resultant mixture was stirred at room temperature for 60 hours. To the reaction mixture were added 2 mL of 1 M hydrochloric acid and 20 mL of chloroform, and the mixture was subjected to diatomaceous earth filtration. Thereafter, the filtrate was concentrated under reduced pressure. The residue was purified by silica gel column chromatography (chloroform/methanol=99/1 (v/v)), to thereby produce 26.8 mg of the title compound as a brown solid.

Synthesis Example 751

(R,E)-N-Cyclopropyl-3-(3-(4-ethyl-2-methylpiperazin-1-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 707 was performed by using (R,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride produced in step A of Synthesis Example 697 in place of (S,E)-N-cyclopropyl-7-hydroxy-4-isobutyl-2-methyl-3-(3-(2-methylpiperazin-1-yl)-3-oxoprop-1-en-1-yl)-5-oxo-4,5-dihydropyrazolo[1,5-a]pyrimidine-6-carboxamide hydrochloride, to thereby produce 9.59 mg of the title compound as a white solid.

Synthesis Example 752

(E)-N-Cyclopropyl-3-(3-(5,6-dihydro-7H-pyrrolo[2,3-d]pyrimidin-7-yl)-3-oxoprop-1-en-1-yl)-7-hydroxy-4-isobutyl-2-methyl-5-oxo-4,5-dihydropyrazolo[1,5-a]pyrimidine-6-carboxamide Substantially the same reaction as in Synthesis Example 706 was performed by using 6,7-dihydro-5H-pyrrolo[2,3-d]pyrimidine dihydrochloride in place of 7-oxa-4-azaspiro[2.5]octane hydrochloride, to thereby produce 10.38 mg of the title compound as a white solid.

Synthesis Example 753

3-((E)-3-((1S,4S)-2-Oxa-5-azabicyclo[2.2.1]heptan-5-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide Substantially the same reaction as in Synthesis Example 680 was performed by using (1S,4S)-2-oxa-5-azabicyclo[2.2.1]heptane hydrochloride in place of (S)-2-methylmorpholine hydrochloride, to thereby produce 17.5 mg of the title compound as a pale brown solid.

Synthesis Example 754

3-((E)-3-((1R,4R)-2-Oxa-5-azabicyclo[2.2.1]heptan-5-yl)-3-oxoprop-1-en-1-yl)-N-cyclopropyl-7-hydroxy-4-isobutyl-2-methyl-5-oxo-4,5-dihydropyrazolo[1,5-a]pyrimidine-6-carboxamide Substantially the same reaction as in Synthesis Example 680 was performed by using (1R,4R)-2-oxa-5-azabicyclo[2.2.1]heptane hydrochloride in place of (S)-2-methylmorpholine hydrochloride, to thereby produce 21.7 mg of the title compound as a pale brown solid.

Synthesis Example 755

N-Cyclopropyl-3-((E)-3-(trans-3,4-difluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide (Isomer A)

Synthesis Example 756

N-Cyclopropyl-3-((E)-3-(trans-3,4-difluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide (Isomer B)

N-Cyclopropyl-3-((E)-3-(trans-3,4-difluoropyrrolidin-1-yl)-3-oxoprop-1-en-1-yl)-7-hydroxy-4-isobutyl-2-methyl-5-oxo-4,5-dihydropyrazolo[1,5-a]pyrimidine-6-carboxamide (racemate) produced in Synthesis Example 649 was optically resolved by SFC (apparatus: Waters Prep15 SFC, column: DAICEL CHIRALPAK IG (20 mm×250 mm, 5 μm), column temperature: 40° C., mobile phase: carbon dioxide/methanol=60/40, flow rate: 15 mL/min). The fraction with a retention time of 31.90 min (Isomer A) and the fraction with a retention time of 38.73 min (Isomer B) were concentrated under reduced pressure, to thereby produce 10.8 mg of the title compound (Isomer A) as a pale brown solid and 11.7 mg of the title compound (Isomer B) as a pale brown solid.

Next will be shown the chemical structural formulae of the compounds synthesized in the aforementioned Synthesis Examples.

Ex 1

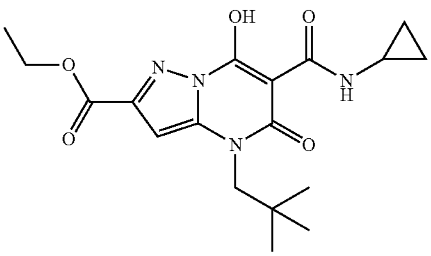

Ex 2

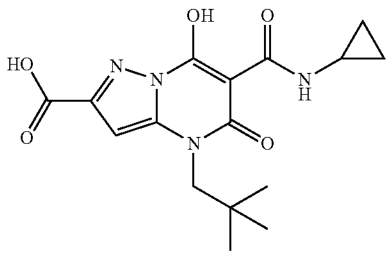

-continued
Ex 3
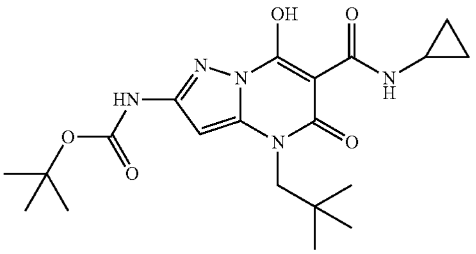
Ex 4
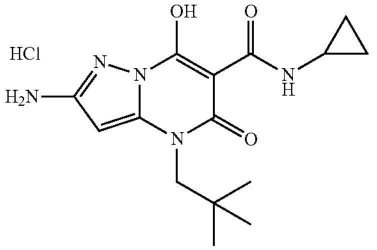
Ex 5
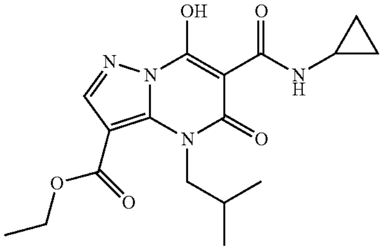
Ex 6
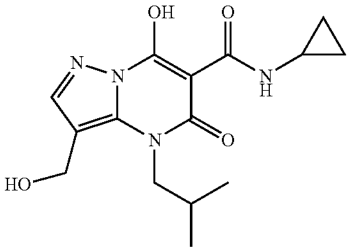
Ex 7
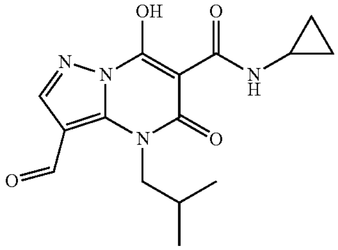
Ex 8
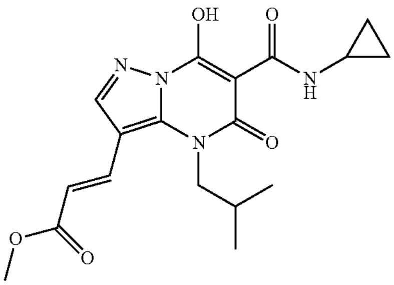
-continued
Ex 9
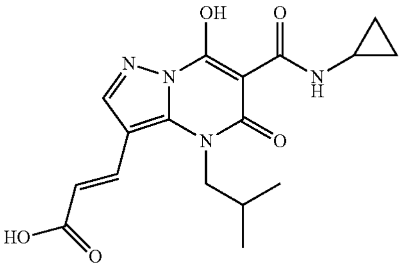
Ex 10
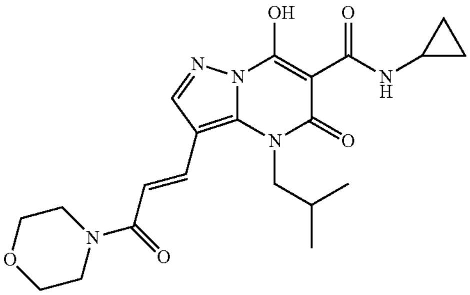
Ex 11
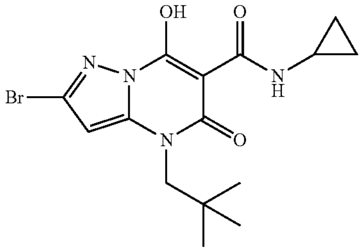
Ex 12
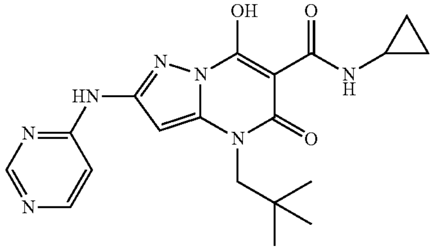
Ex 13
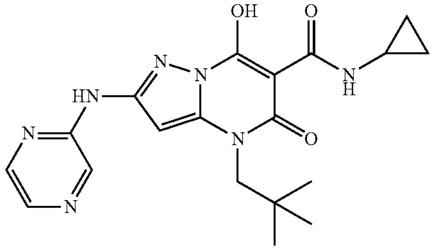
Ex 14
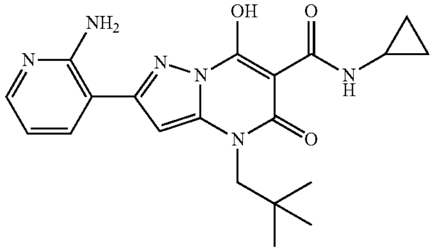

-continued
Ex 15
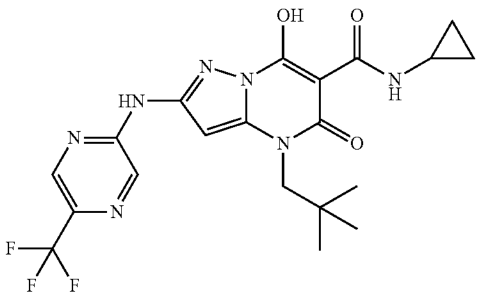
Ex 16
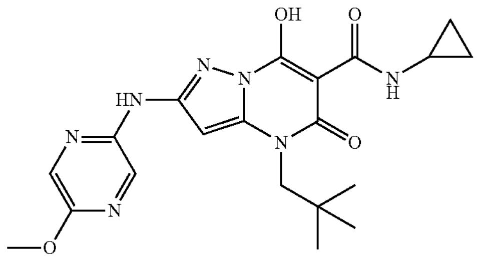
Ex 17
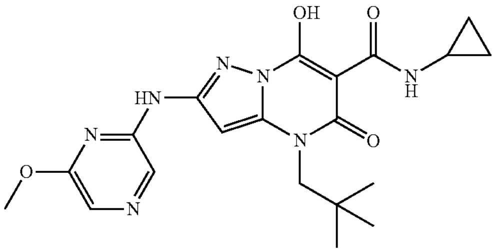
Ex 18
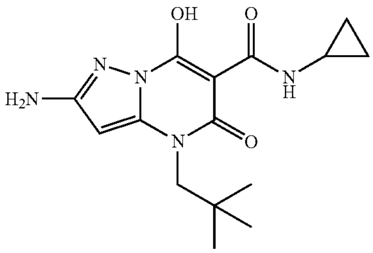
Ex 19
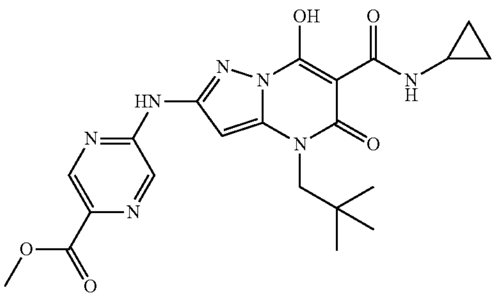
-continued
Ex 20
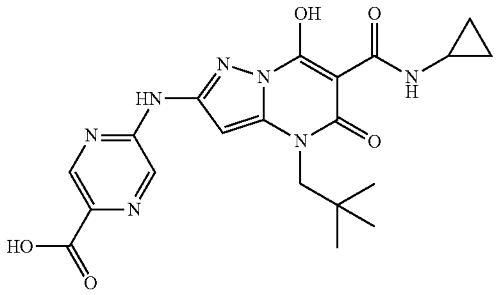
Ex 21
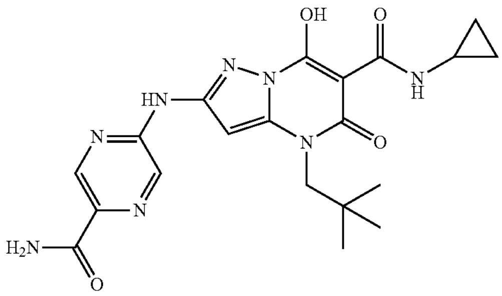
Ex 22
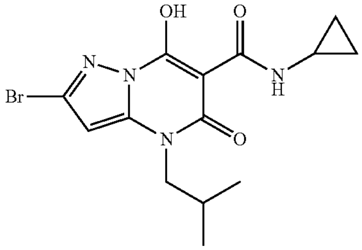
Ex 23
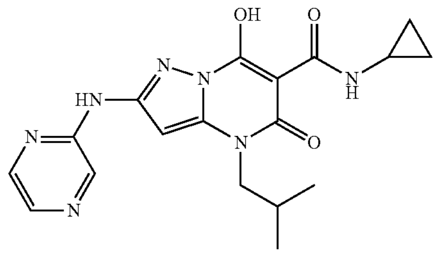
Ex 24
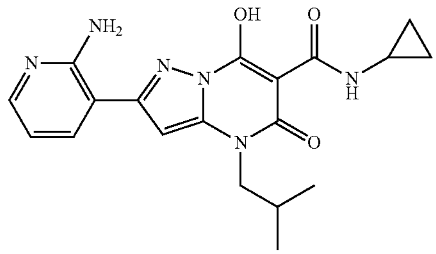

-continued
Ex 25
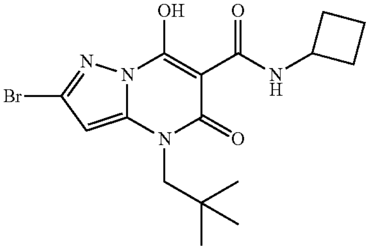
Ex 26
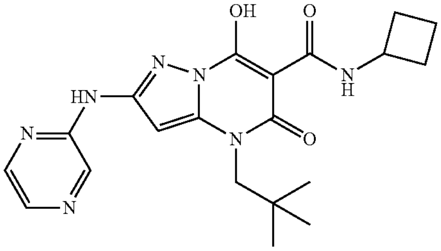
Ex 27
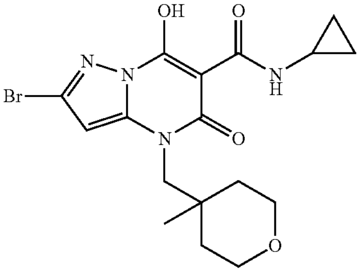
Ex 28
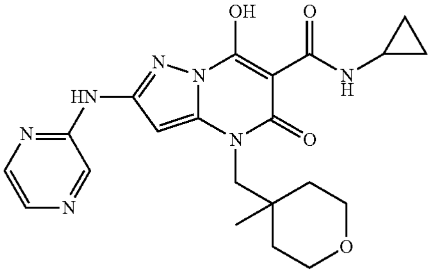
Ex 29
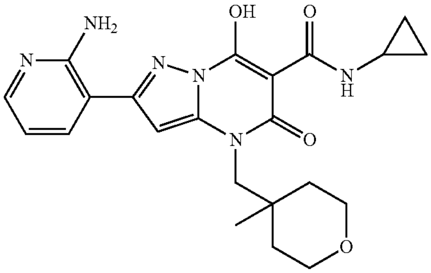
Ex 30
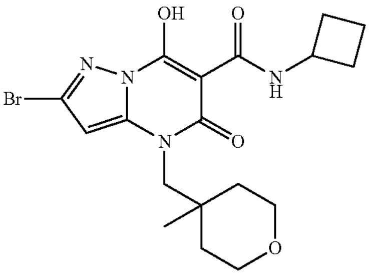
-continued
Ex 31
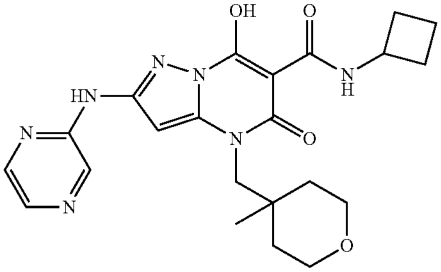
Ex 32
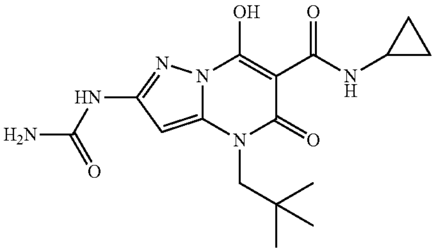
Ex 33
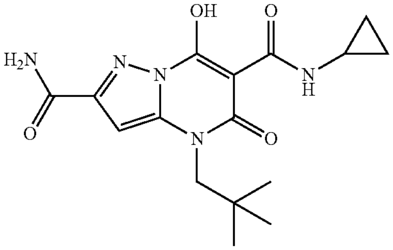
Ex 34
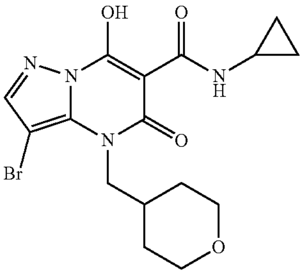
Ex 35
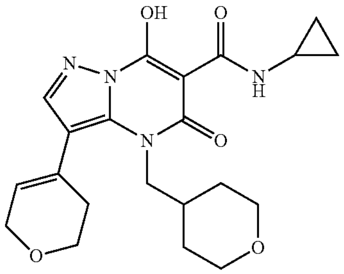
Ex 36
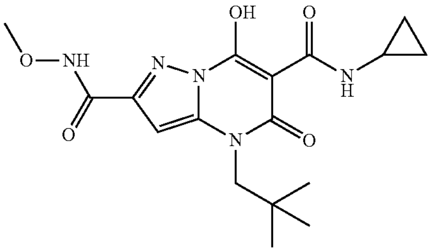

-continued
Ex 37
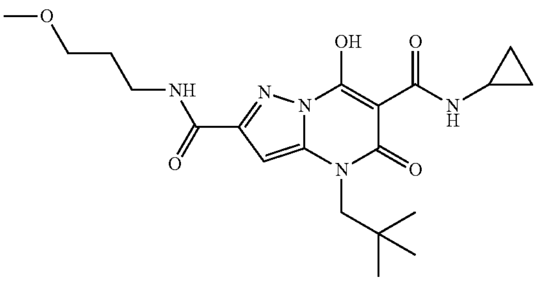
Ex 38
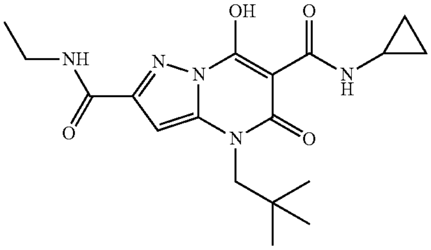
Ex 39
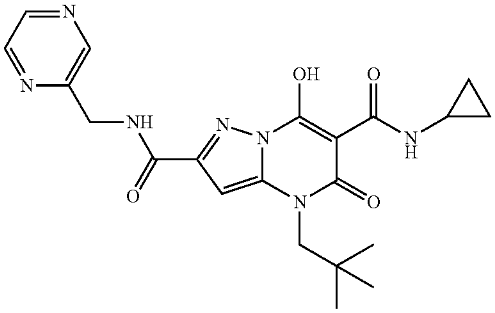
Ex 40
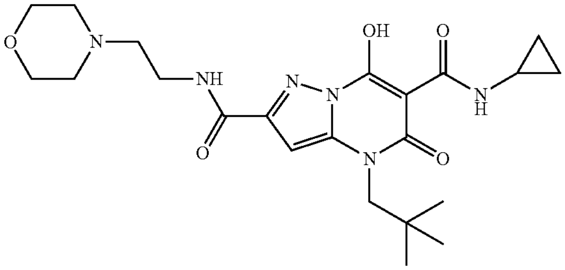
Ex 41
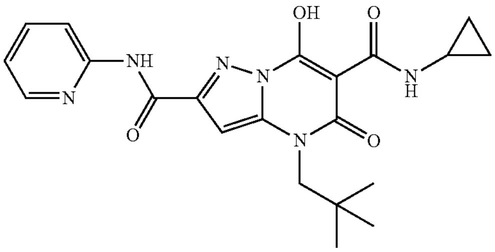
-continued
Ex 42
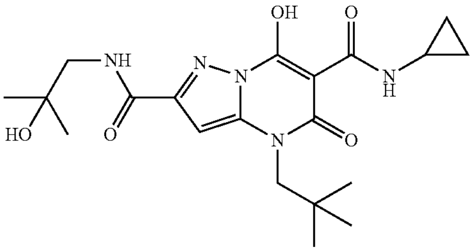
Ex 43
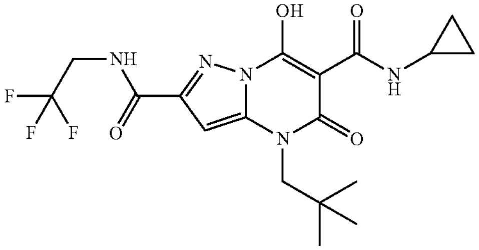
Ex 44
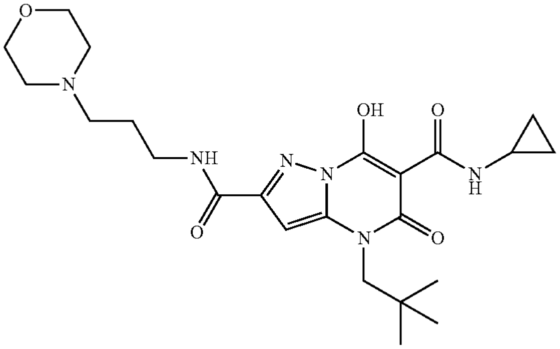
Ex 45
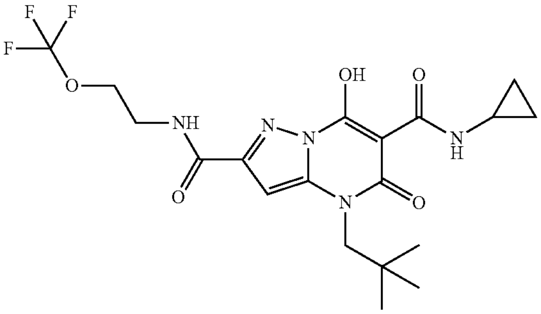
Ex 46
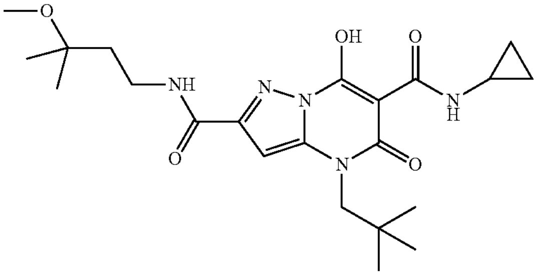

Ex 47
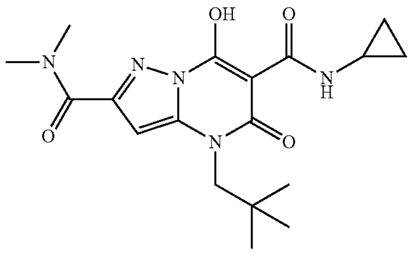
Ex 48
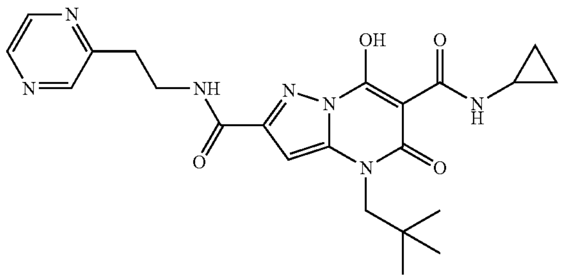
Ex 49
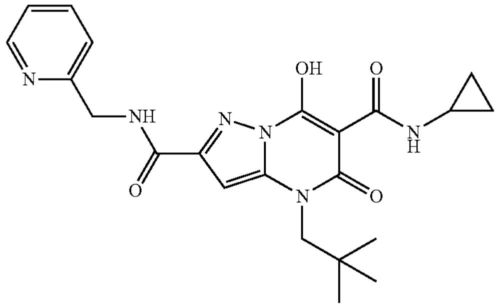
Ex 50
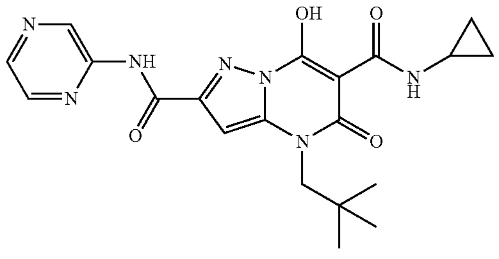
Ex 51
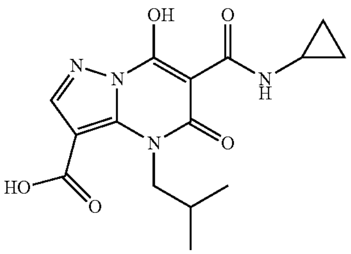
Ex 52
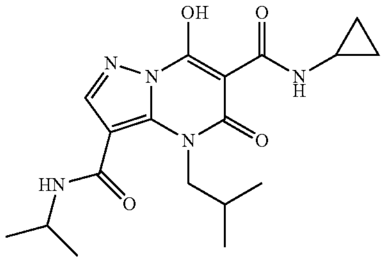
Ex 53
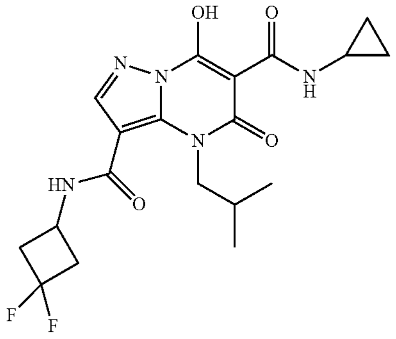
Ex 54
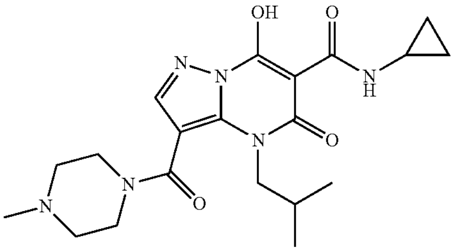
Ex 55
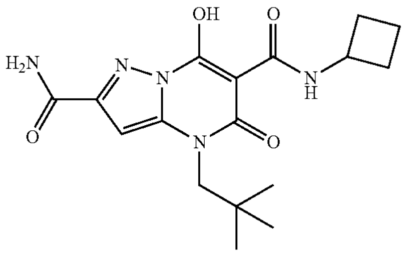
Ex 56
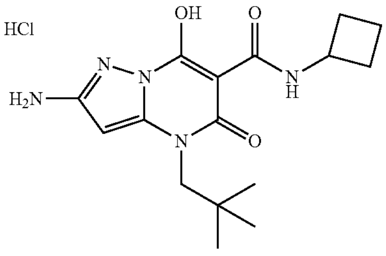
Ex 57
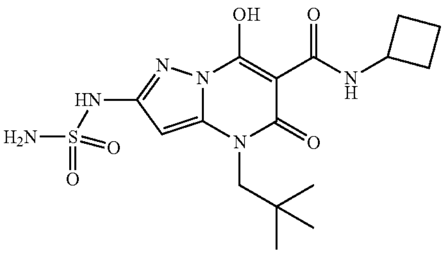

-continued
Ex 58
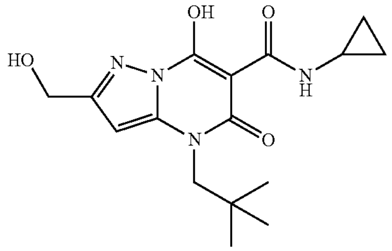
Ex 59
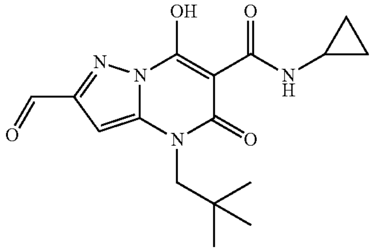
Ex 60
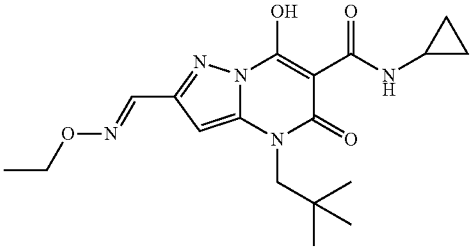
Ex 61
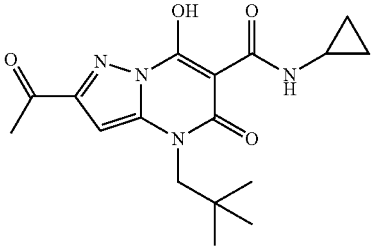
Ex 62
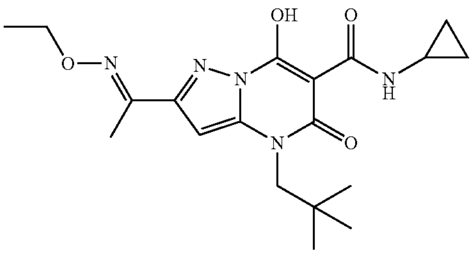
Ex 63
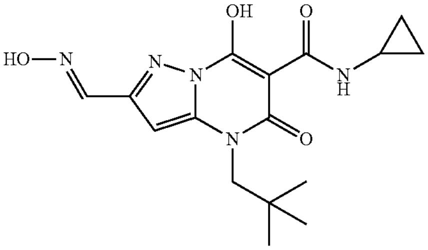
-continued
Ex 64
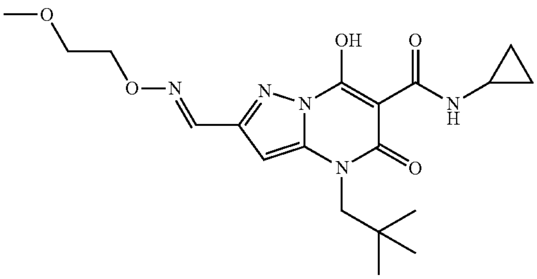
Ex 65
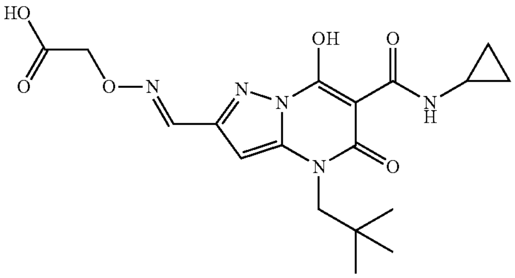
Ex 66
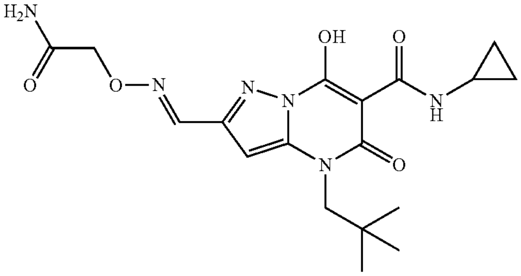
Ex 67
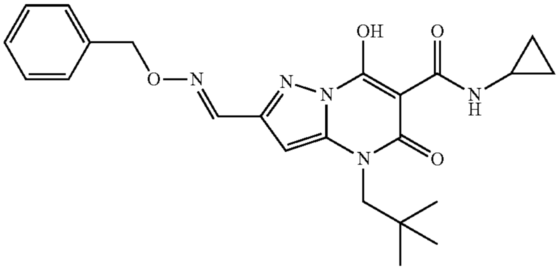
Ex 68
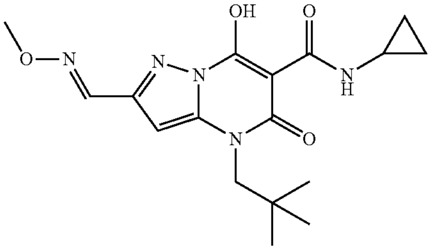

-continued
Ex 69
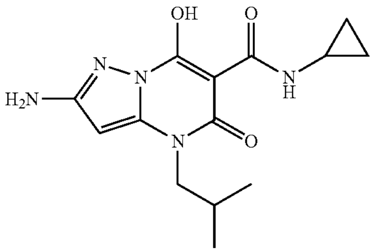
Ex 70
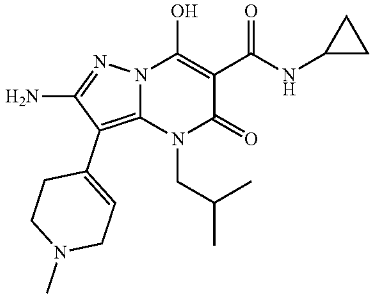
Ex 71
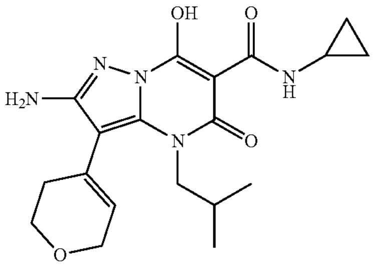
Ex 72
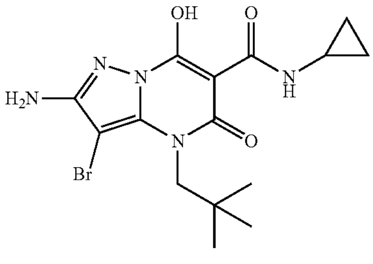
Ex 73
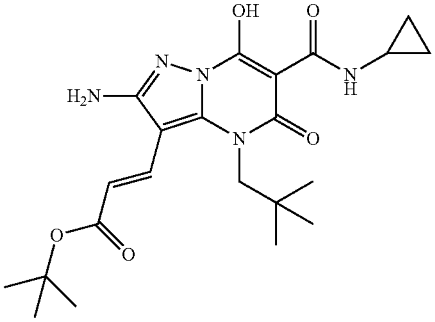
-continued
Ex 74
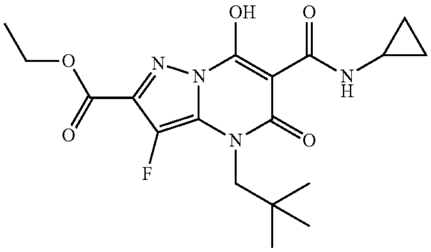
Ex 75
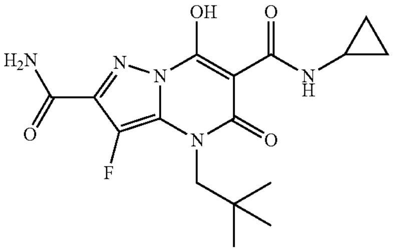
Ex 76
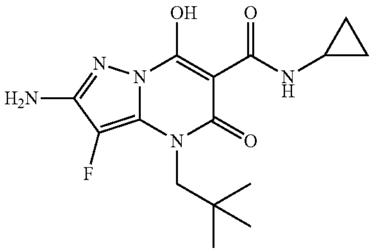
Ex 77
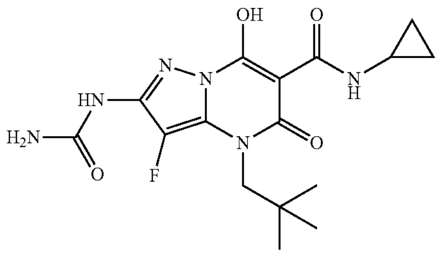
Ex 78
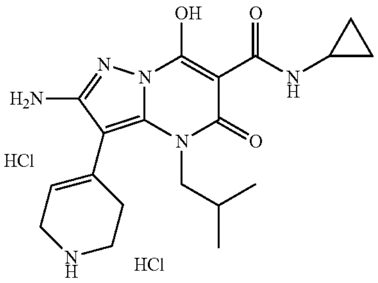
Ex 79
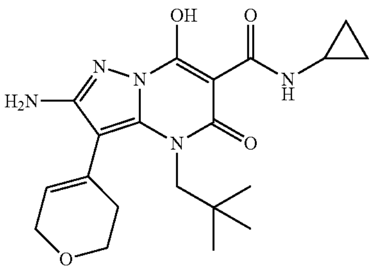

-continued
Ex 80
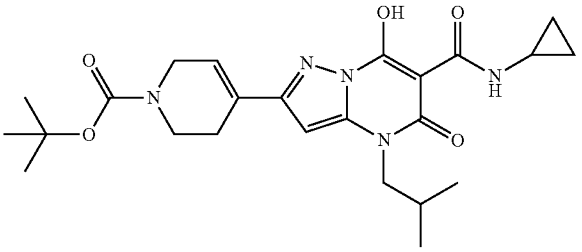
Ex 81
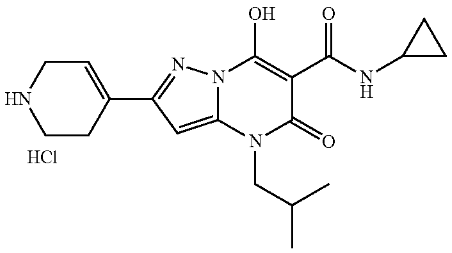
Ex 82
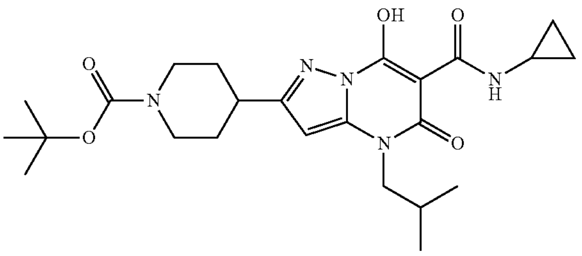
Ex 83
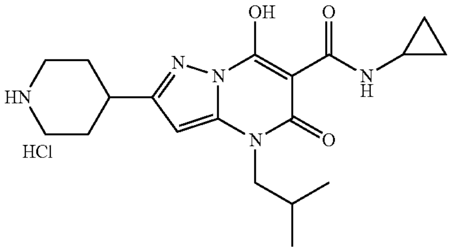
Ex 84
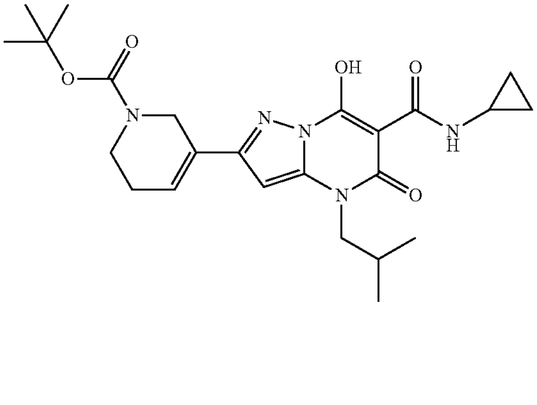
-continued
Ex 85
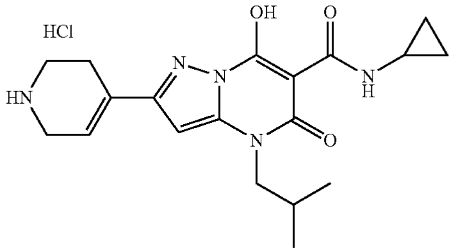
Ex 86
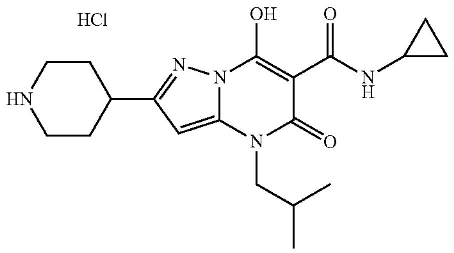
Ex 87
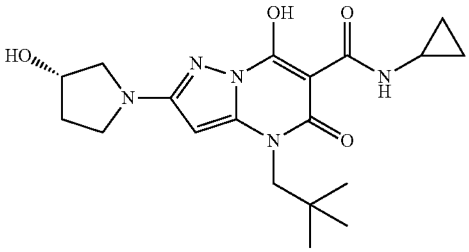
Ex 88
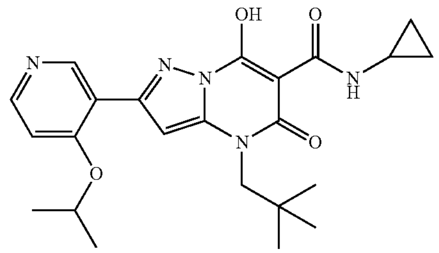
Ex 89
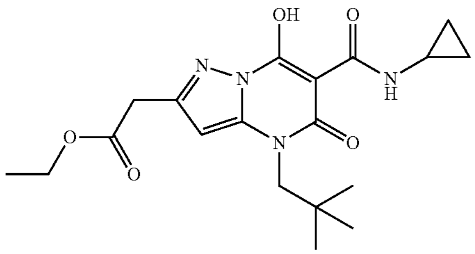
Ex 90
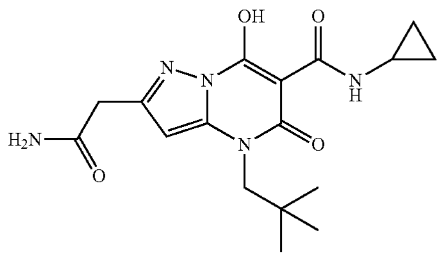

-continued
Ex 91
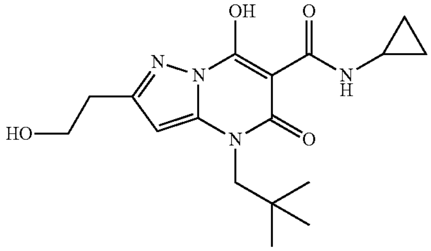
Ex 92
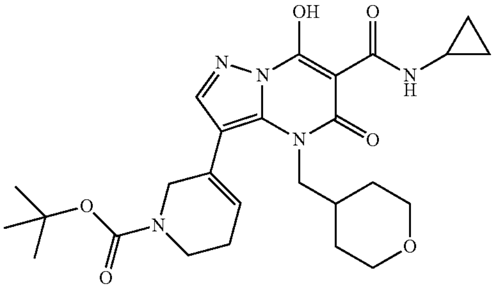
Ex 93
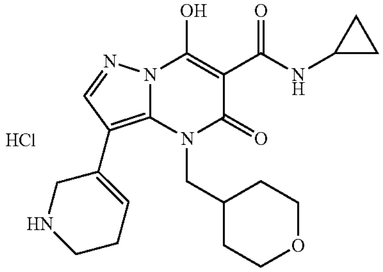
Ex 94
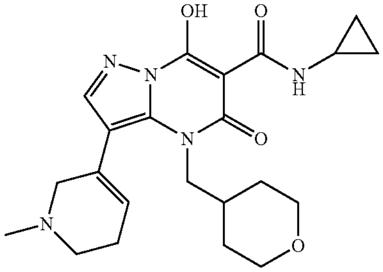
Ex 95
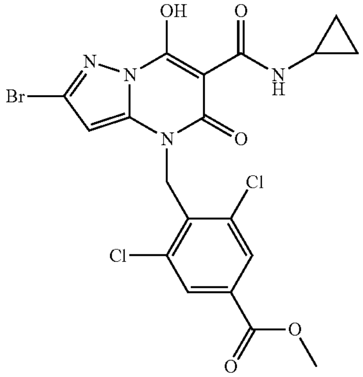
-continued
Ex 96
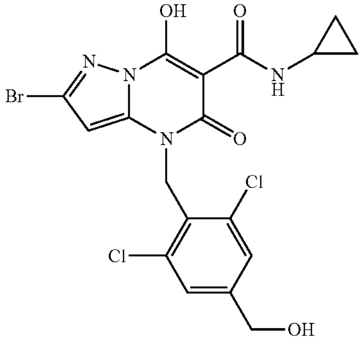
Ex 97
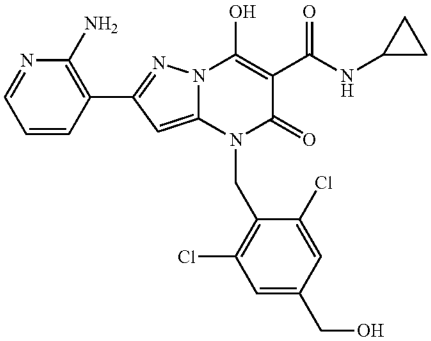
Ex 98
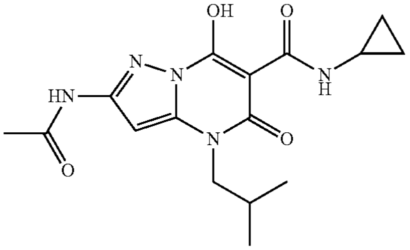
Ex 99
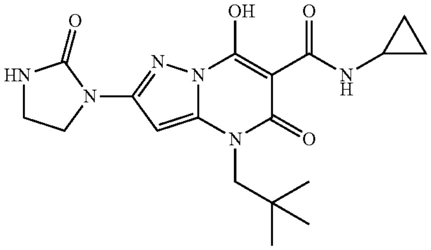
Ex 100
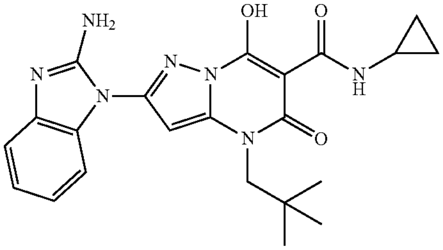

Ex 101
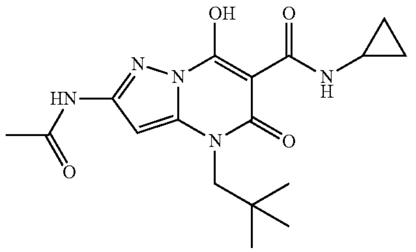
Ex 102
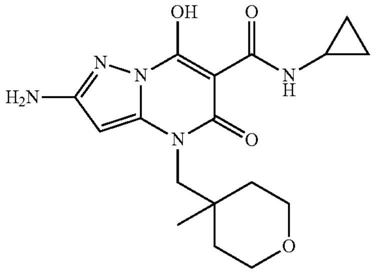
Ex 103
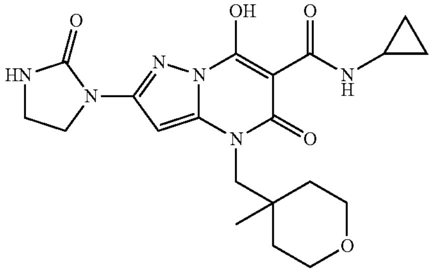
Ex 104
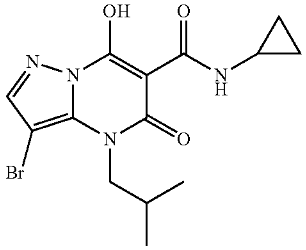
Ex 105
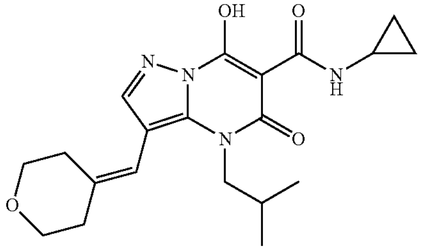
Ex 106
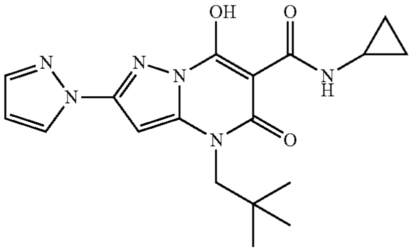
Ex 107
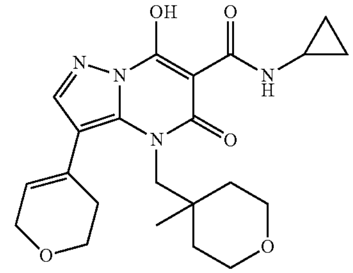
Ex 108
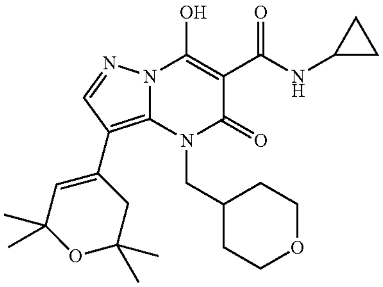
Ex 109
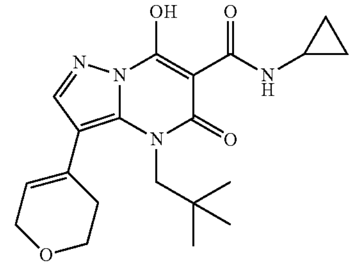
Ex 110
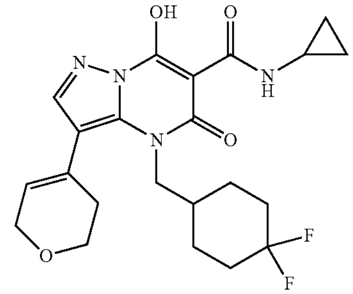
Ex 111
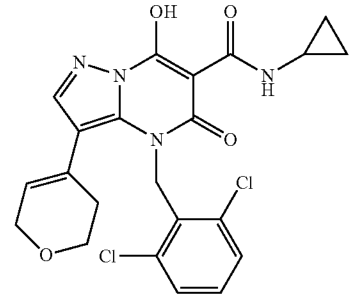

-continued
Ex 112
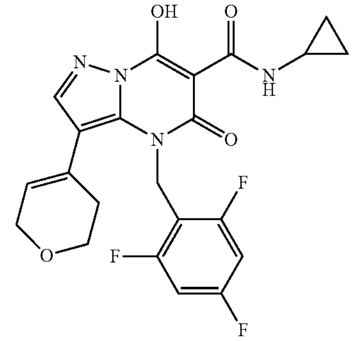
Ex 113
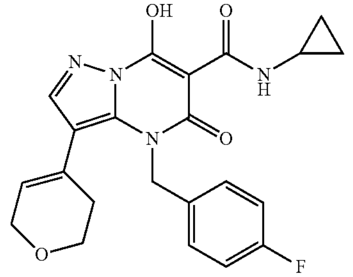
Ex 114
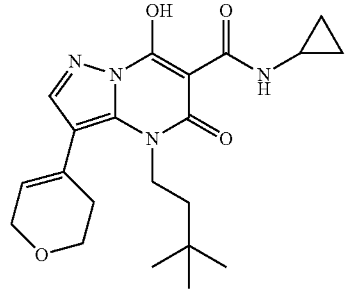
Ex 115
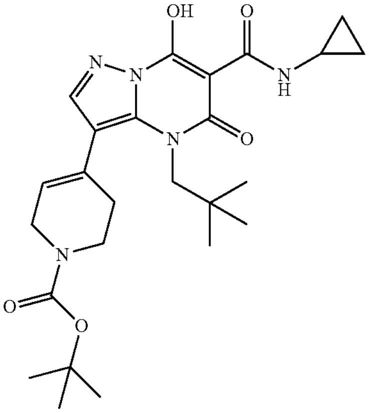
Ex 116
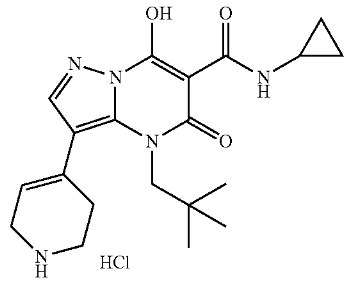
HCl
-continued
Ex 117
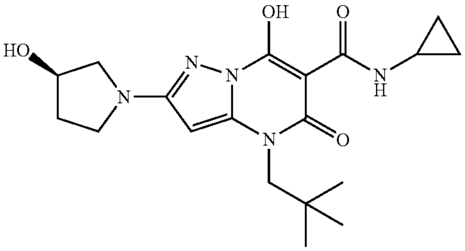
Ex 118
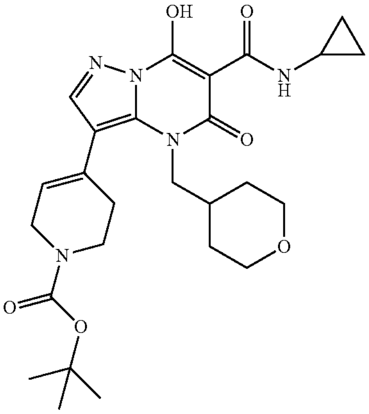
Ex 119
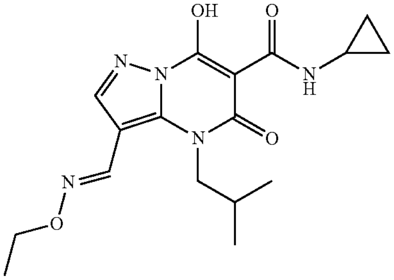
Ex 120
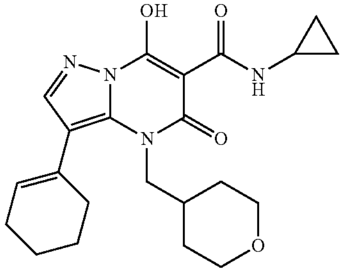
Ex 121
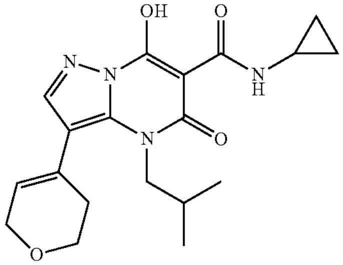

-continued
Ex 122
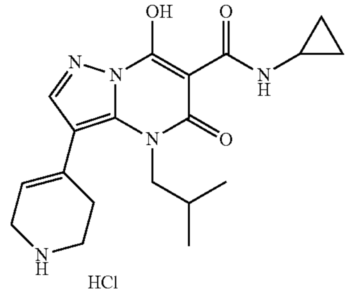
Ex 123
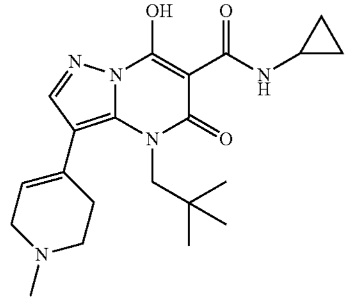
Ex 124
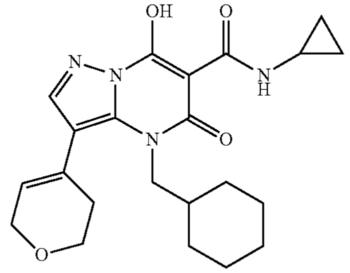
Ex 125
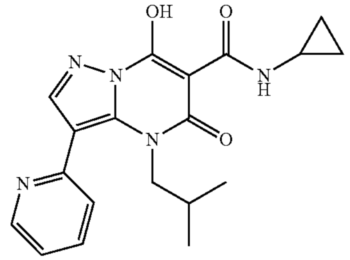
Ex 126
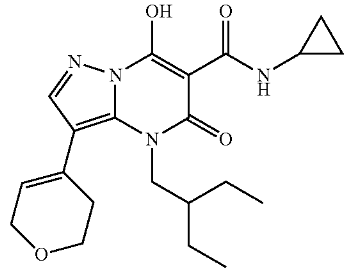
-continued
Ex 127
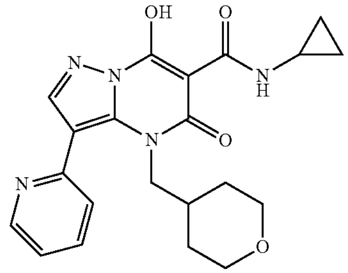
Ex 128
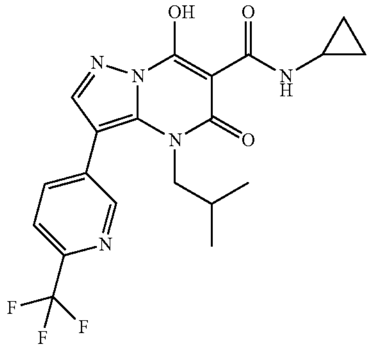
Ex 129
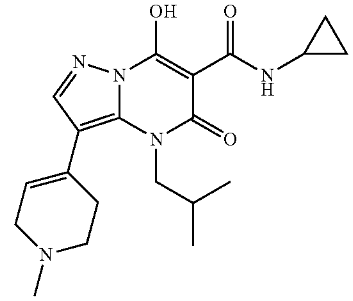
Ex 130
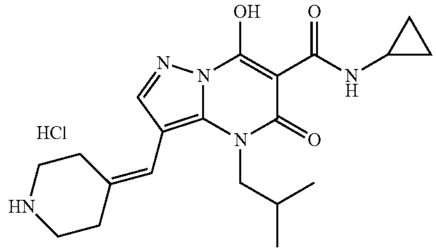
Ex 131
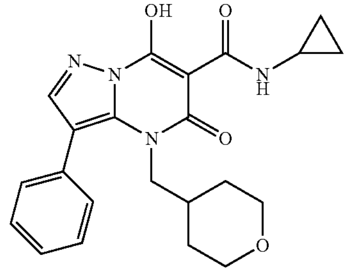

Ex 132
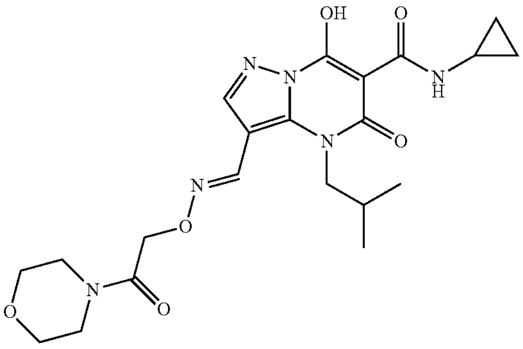
Ex 133
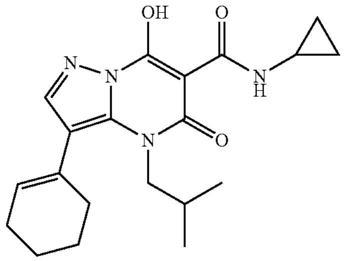
Ex 134
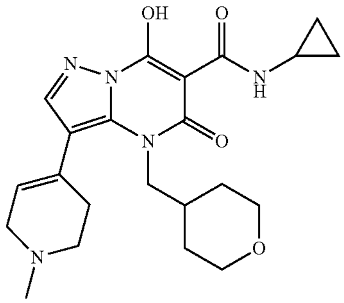
Ex 135
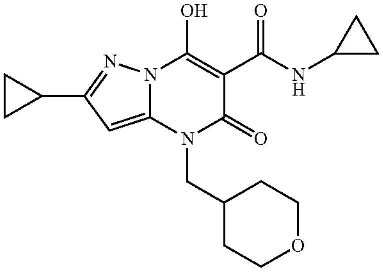
Ex 136
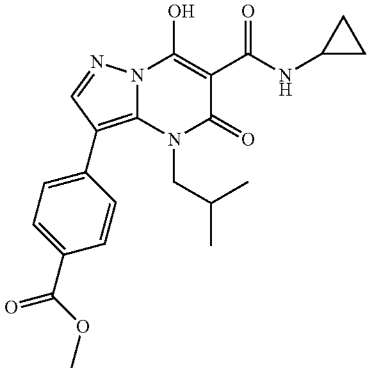
Ex 137
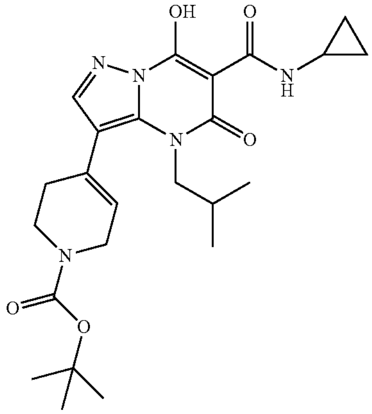
Ex 138
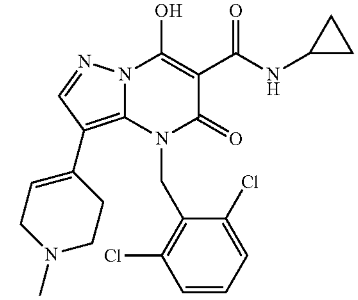
Ex 139
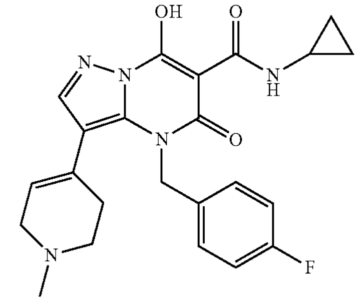
Ex 140
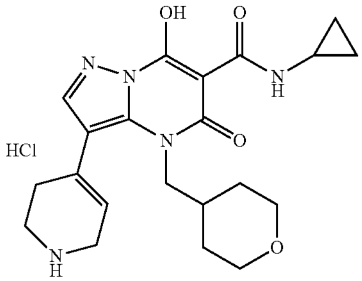
Ex 141
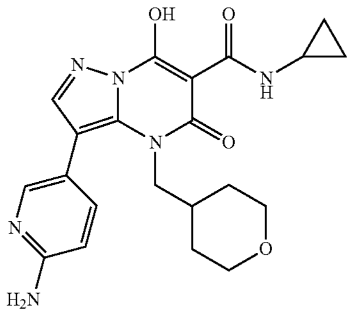

Ex 142
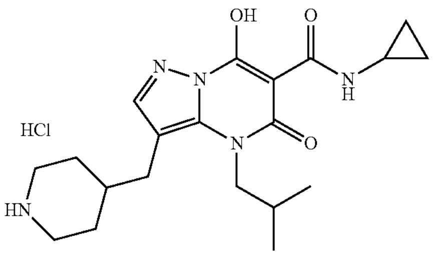
Ex 143
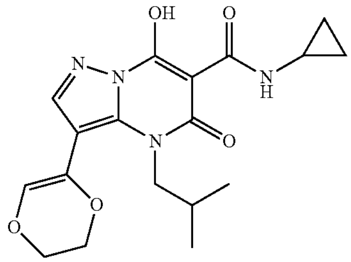
Ex 144
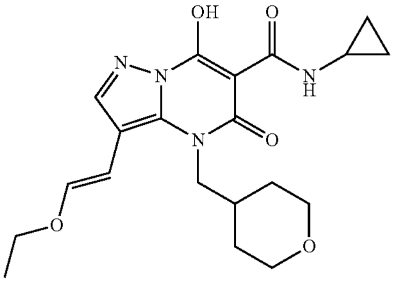
Ex 145
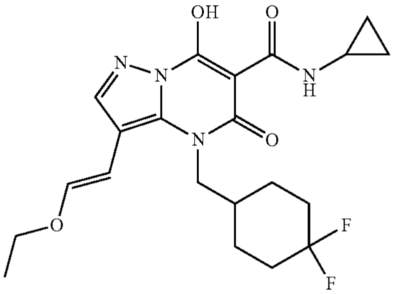
Ex 146
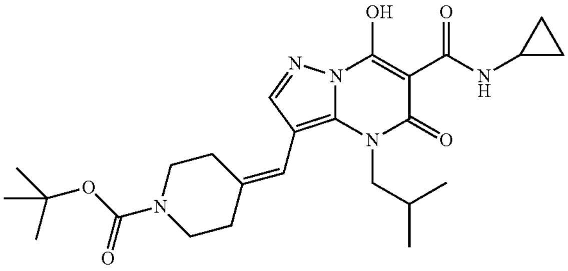
Ex 147
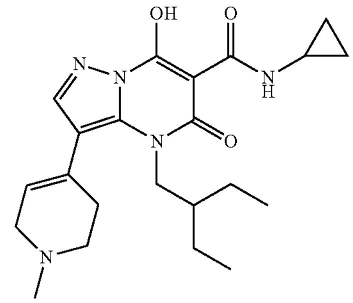
Ex 106
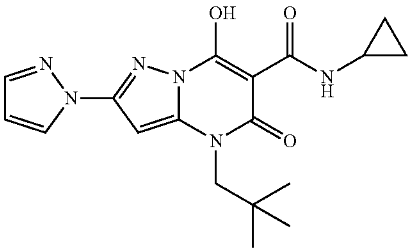
Ex 107
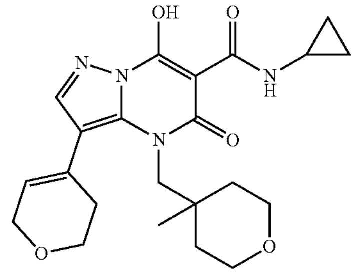
Ex 108
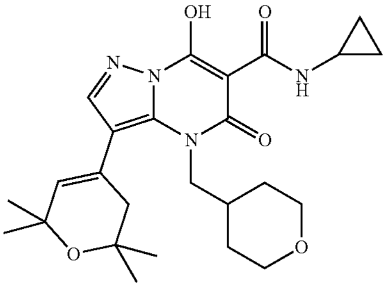
Ex 109
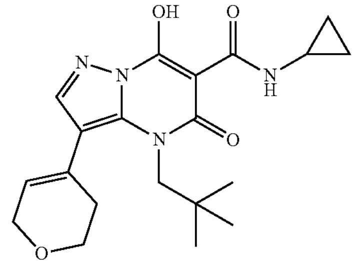

-continued
Ex 110
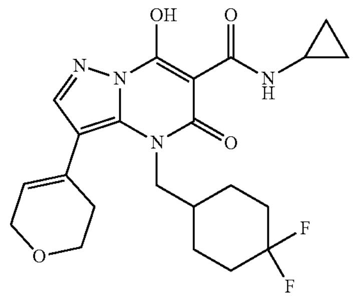
Ex 111
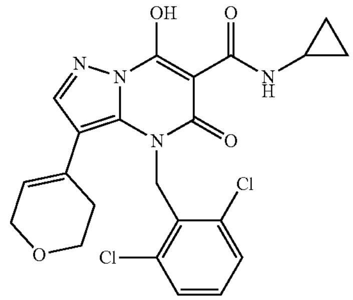
Ex 112
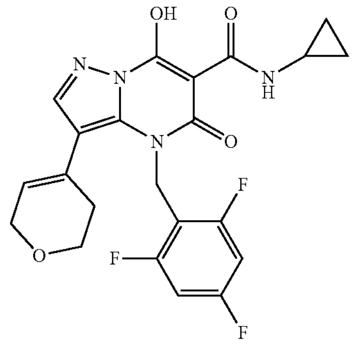
Ex 113
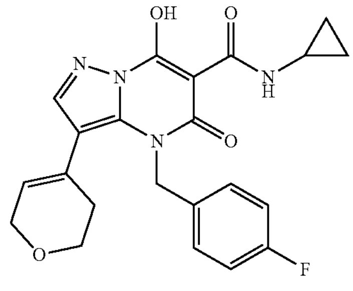
Ex 114
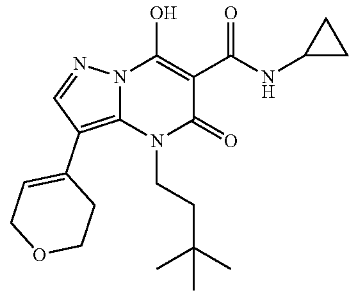
-continued
Ex 115
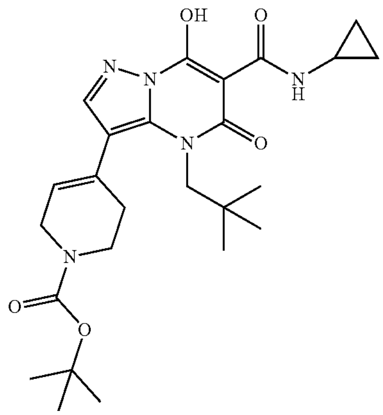
Ex 116
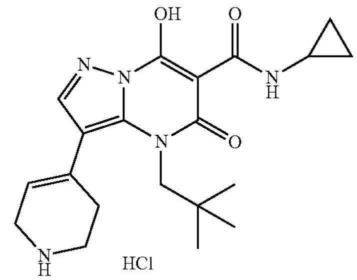
Ex 117
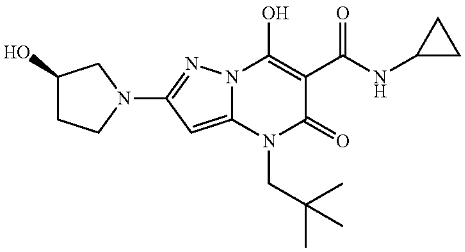
Ex 118
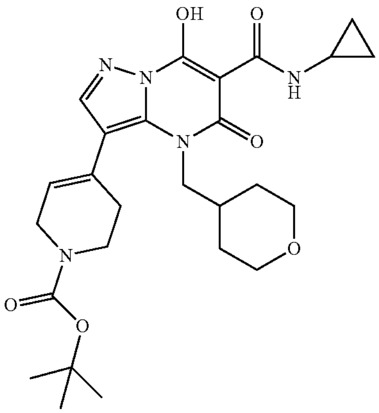
Ex 119
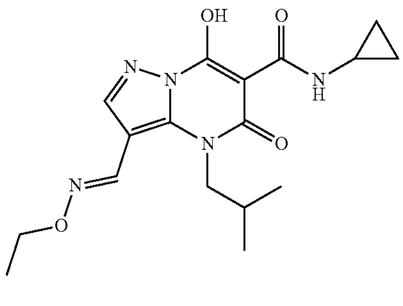

-continued
Ex 120
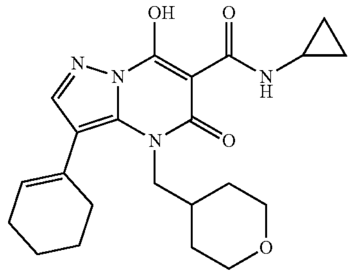
Ex 121
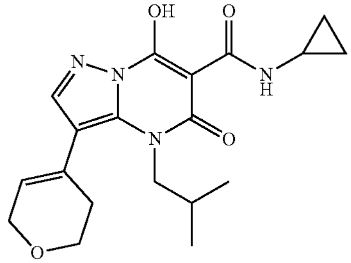
Ex 122
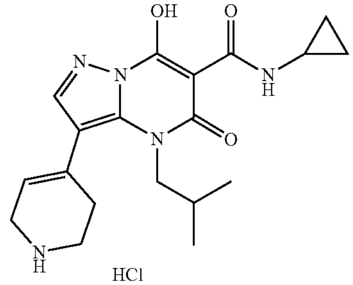
HCl
Ex 123
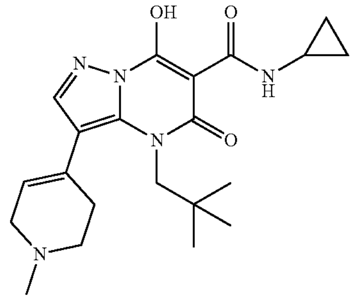
Ex 124
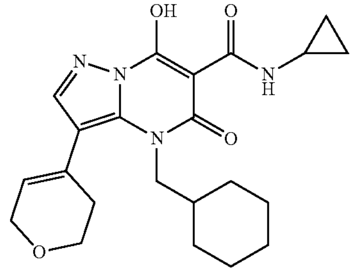
-continued
Ex 125
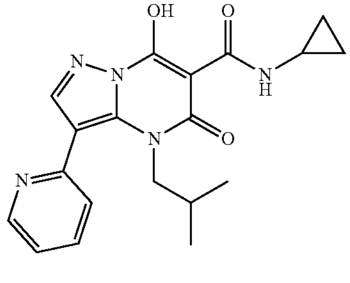
Ex 126
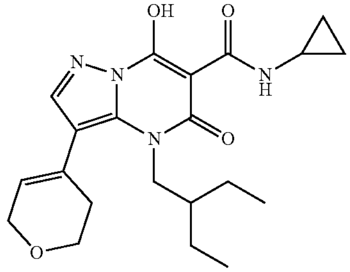
Ex 148
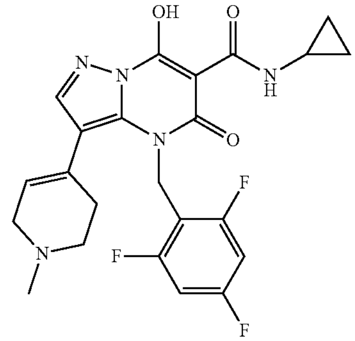
Ex 149
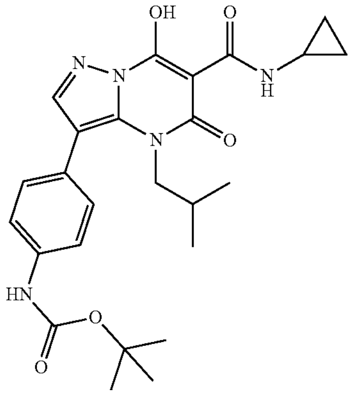

-continued
Ex 150
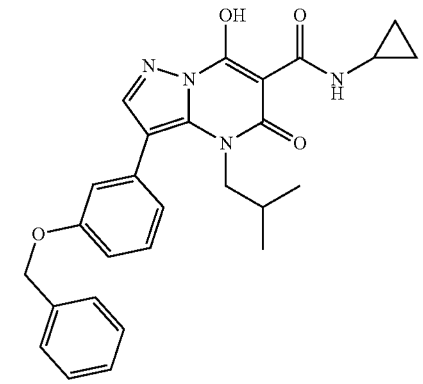
Ex 151
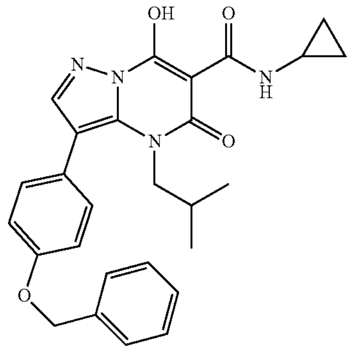
Ex 152
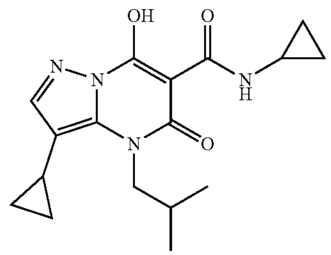
Ex 153
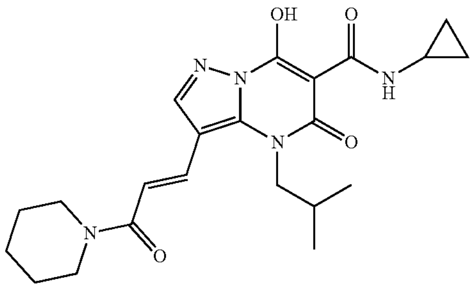
Ex 154
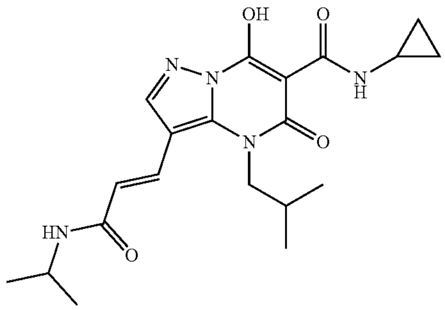
-continued
Ex 155
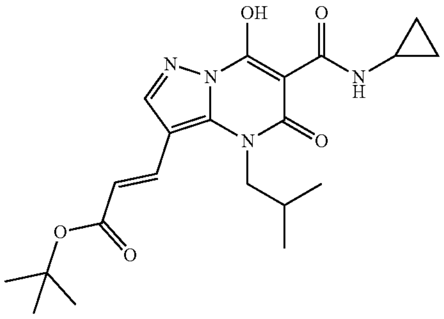
Ex 156
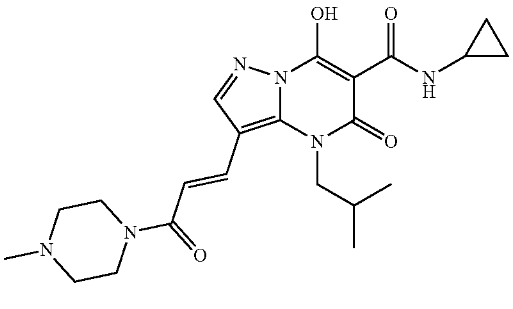
Ex 157
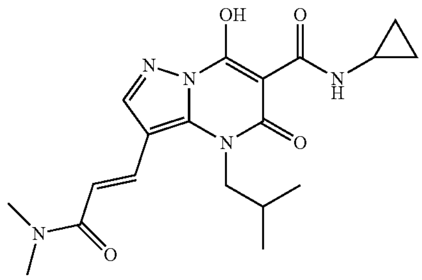
Ex 158
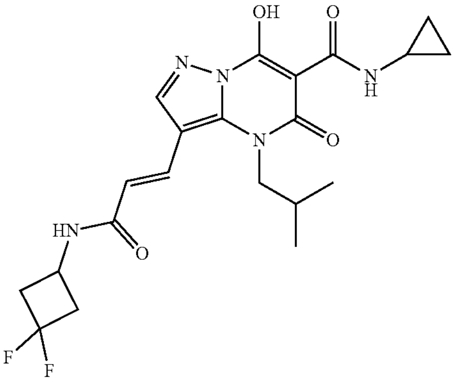
Ex 159
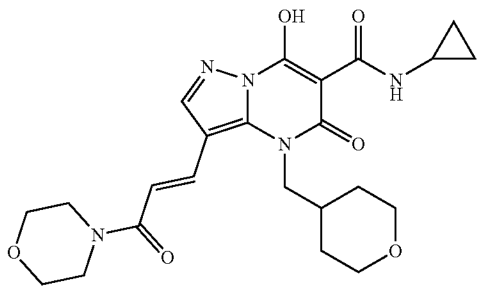

-continued
Ex 160
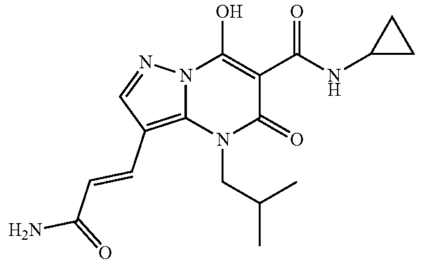
Ex 161
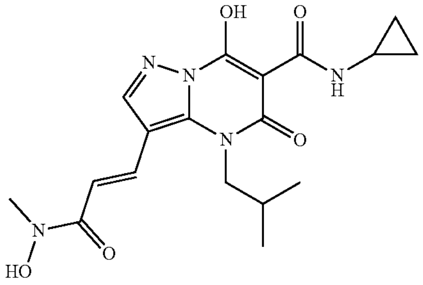
Ex 162
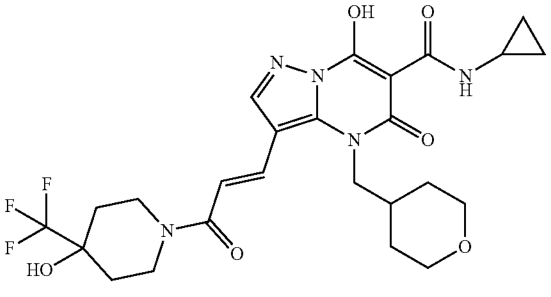
Ex 163
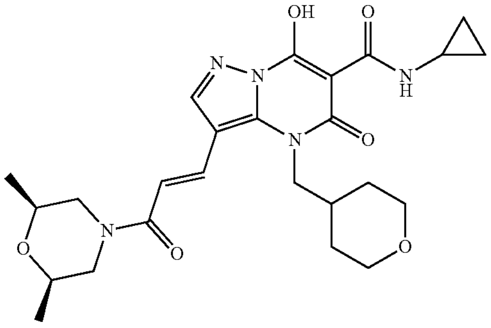
Ex 164
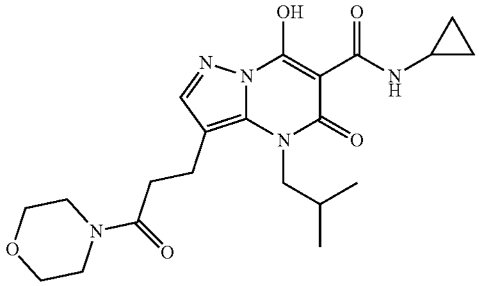
-continued
Ex 165
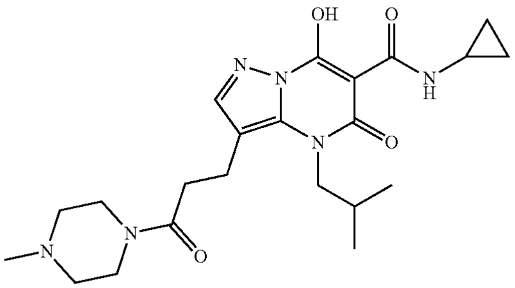
Ex 166
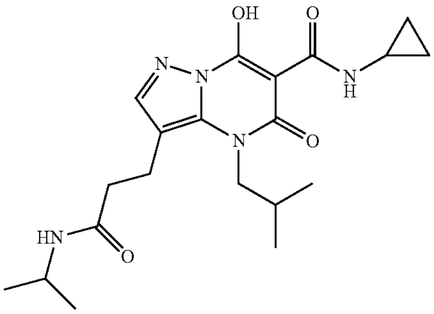
Ex 167
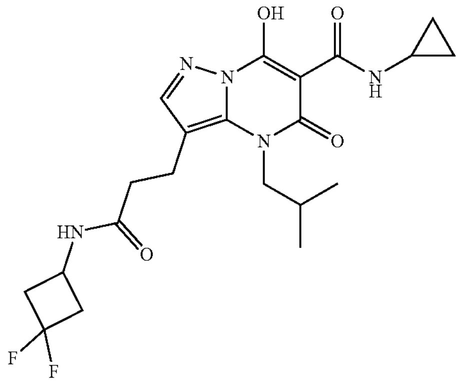
Ex 168
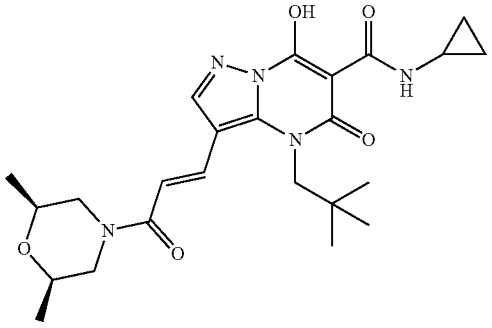

Ex 169
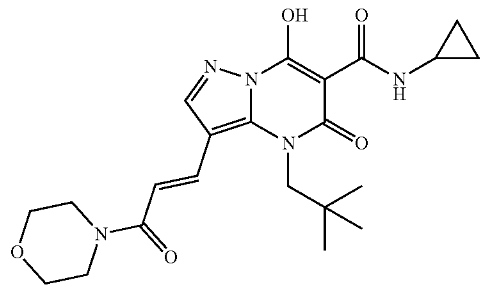
Ex 170
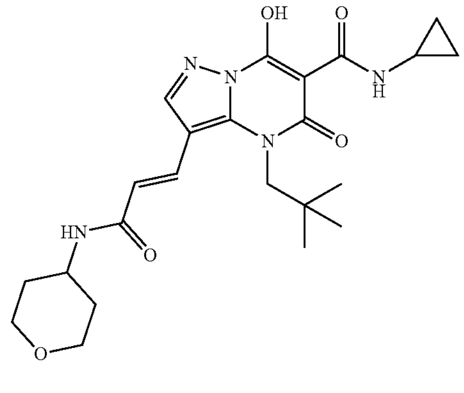
Ex 171
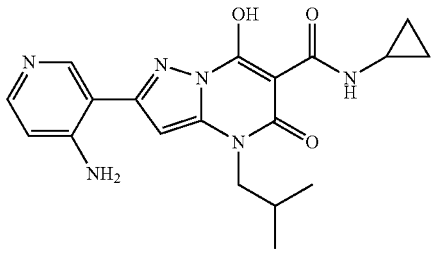
Ex 172
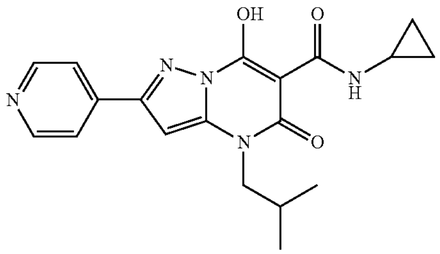
Ex 173
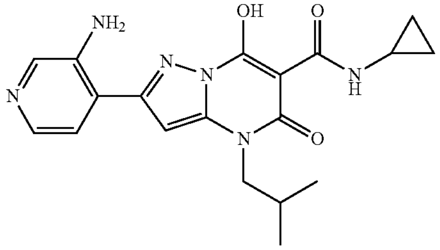
-continued
Ex 174
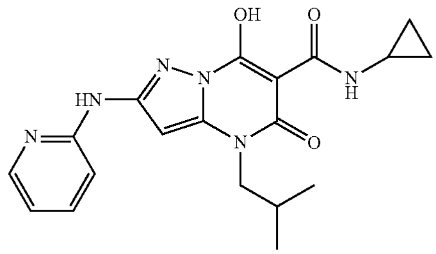
Ex 175
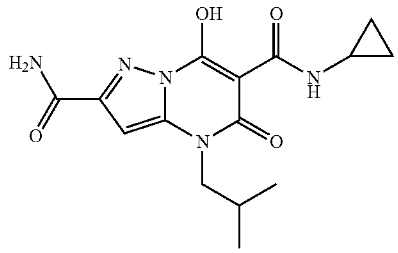
Ex 176
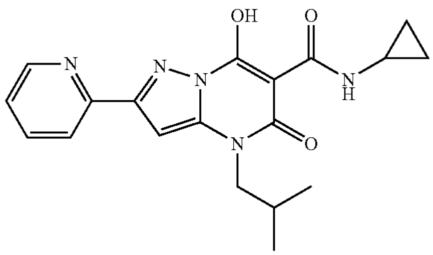
Ex 177
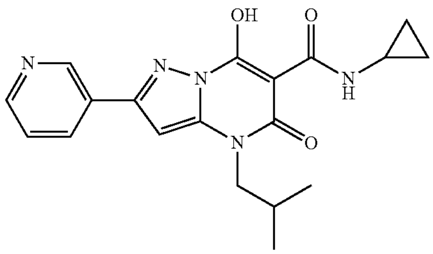
Ex 178
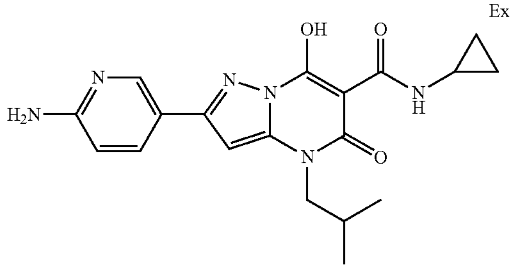
Ex 179
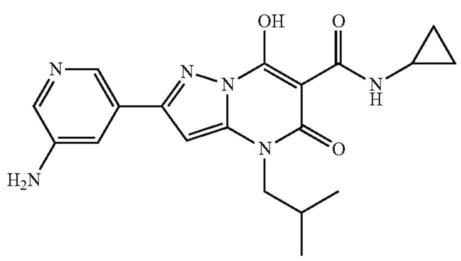

-continued
Ex 180
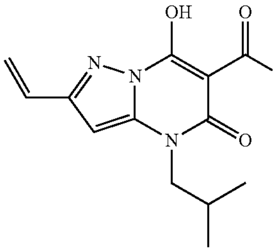
Ex 181
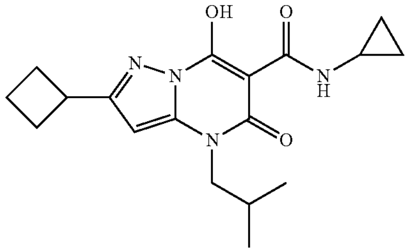
Ex 182
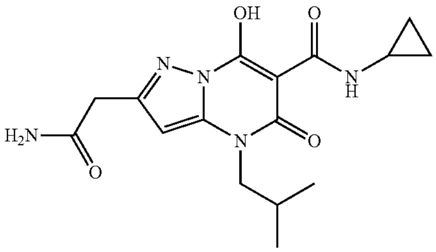
Ex 183
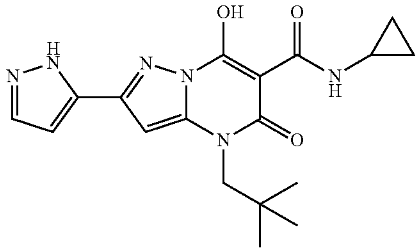
Ex 184
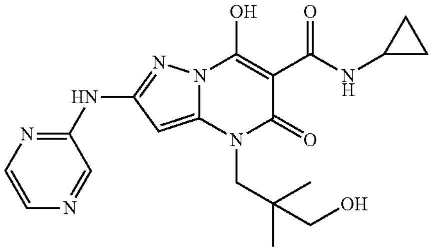
Ex 185
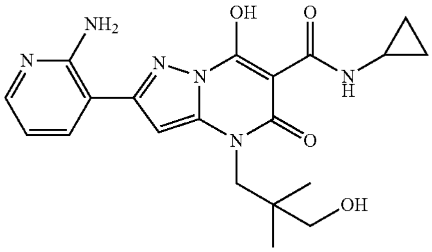
-continued
Ex 186
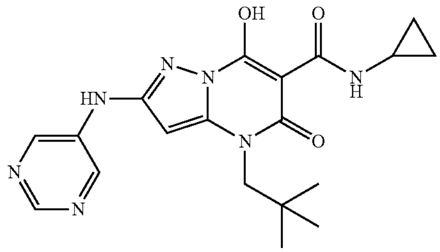
Ex 187
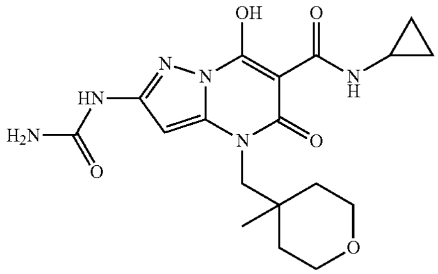
Ex 188
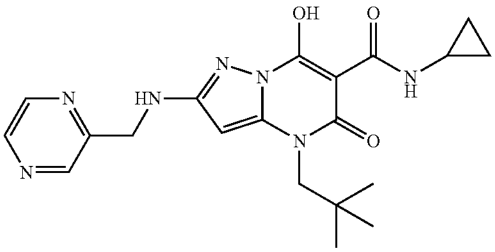
Ex 189
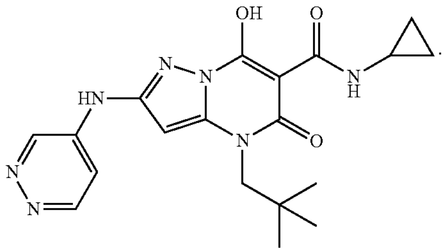
Ex 190
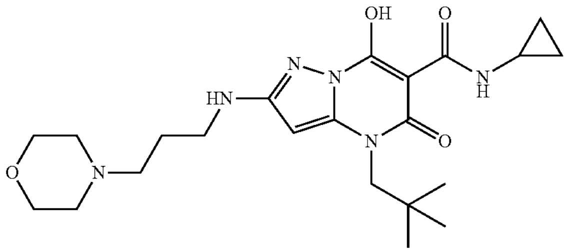

-continued
Ex 191
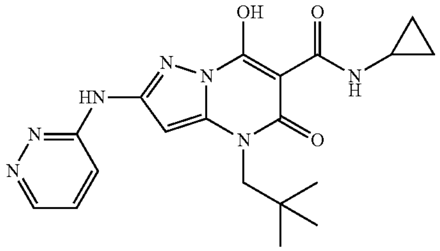
Ex 192
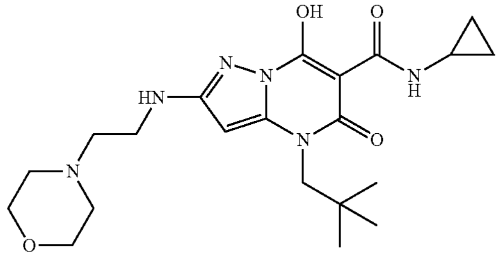
Ex 193
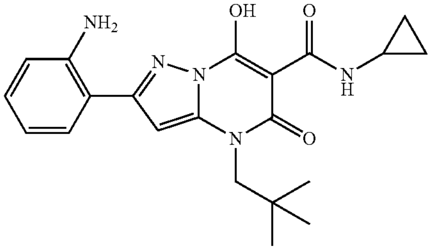
Ex 194
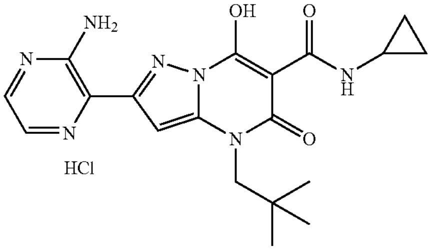
Ex 195
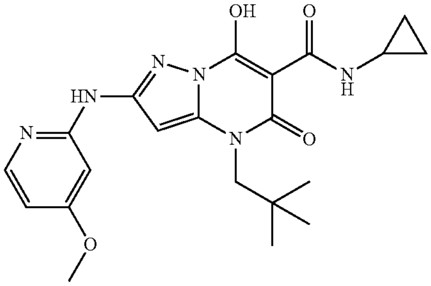
Ex 196
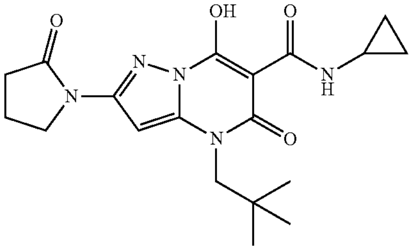
-continued
Ex 197
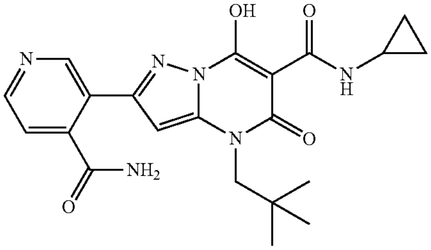
Ex 198
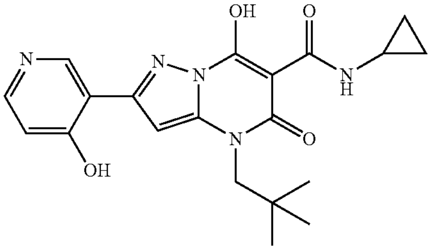
Ex 199
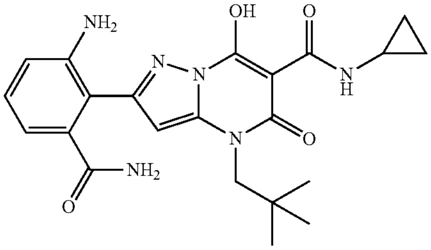
Ex 200
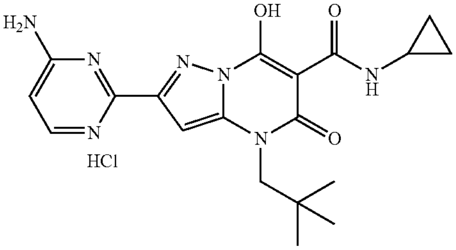
Ex 201
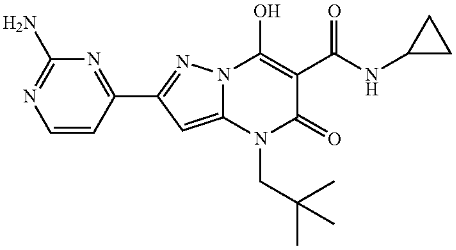
Ex 202
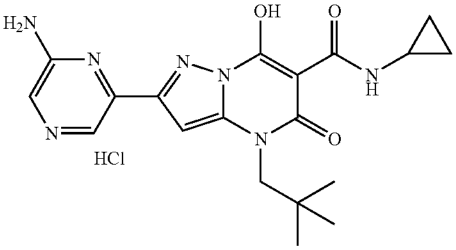

-continued
Ex 203
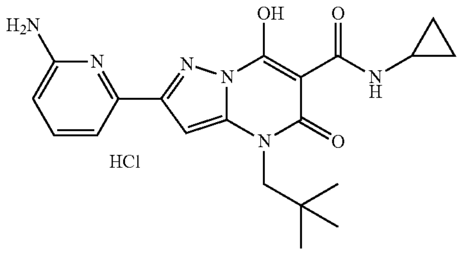
Ex 204
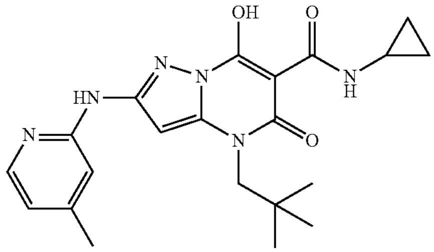
Ex 205
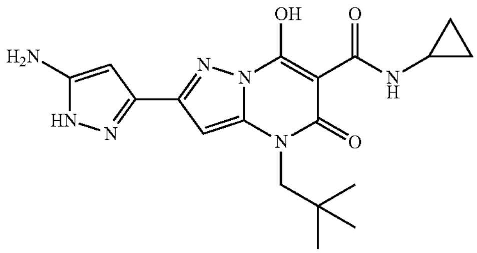
Ex 206
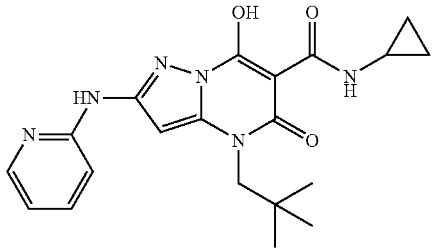
Ex 207
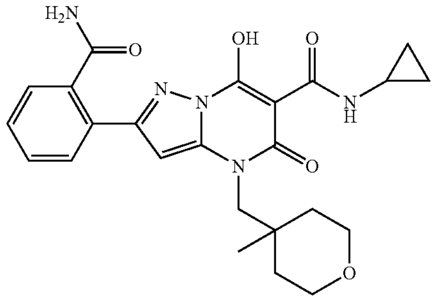
-continued
Ex 208
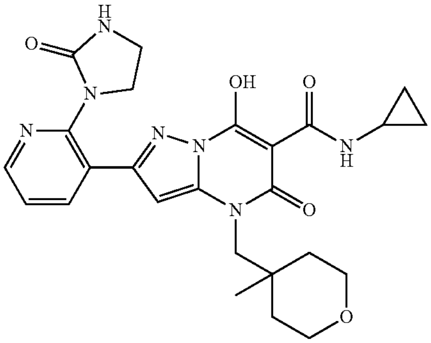
Ex 209
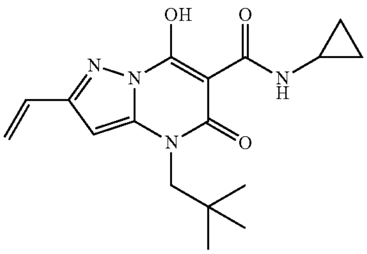
Ex 210
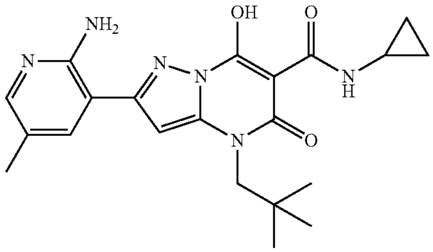
Ex 211
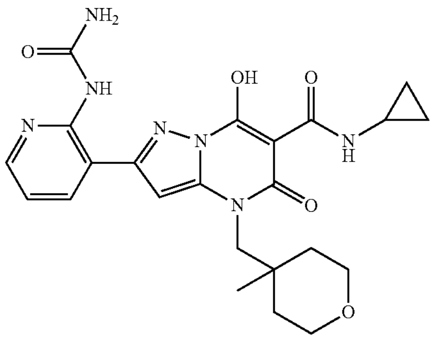
Ex 212
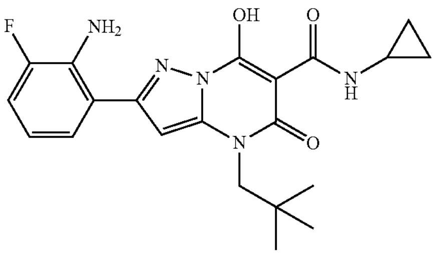

-continued
Ex 213
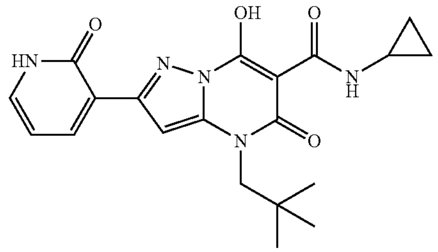
Ex 214
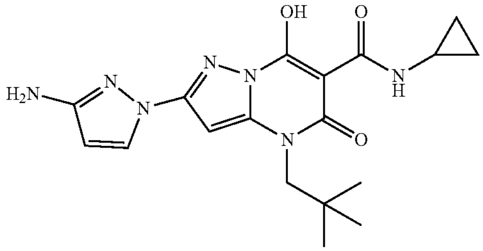
Ex 215
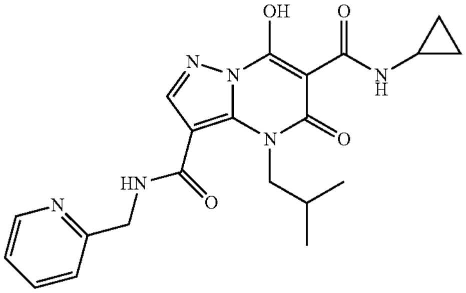
Ex 216
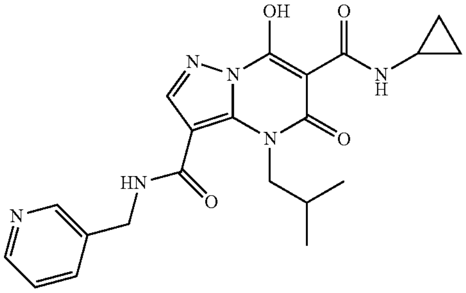
Ex 217
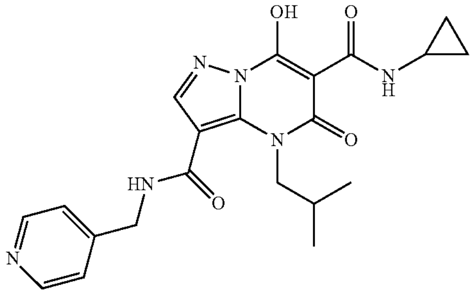
-continued
Ex 218
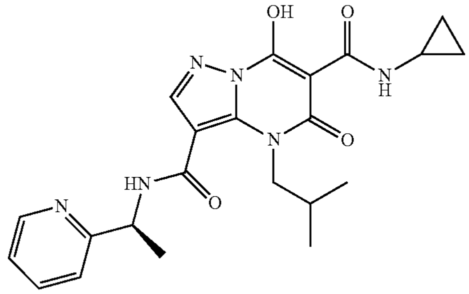
Ex 219
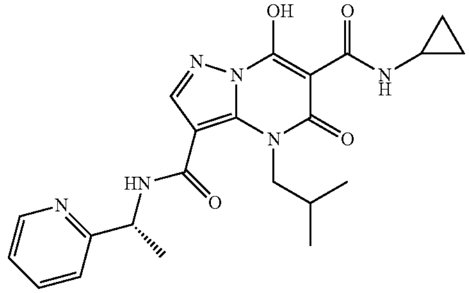
Ex 220
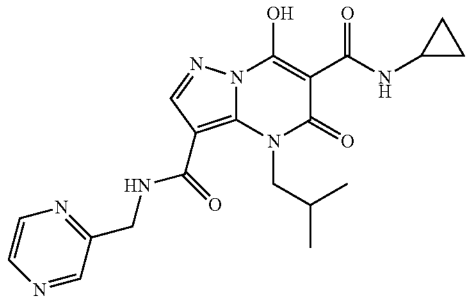
Ex 221
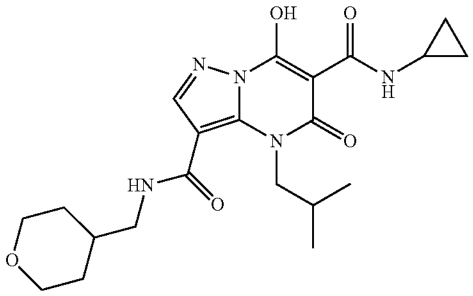
Ex 222
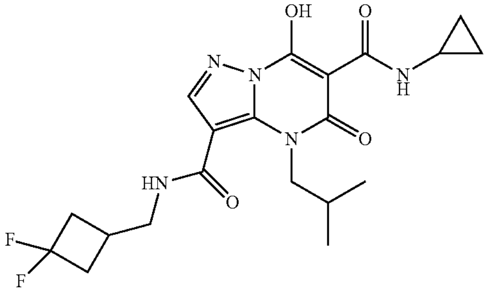

-continued
Ex 223
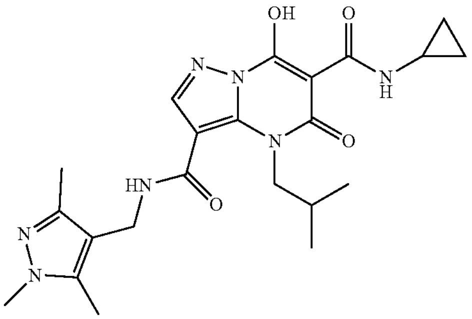
Ex 224
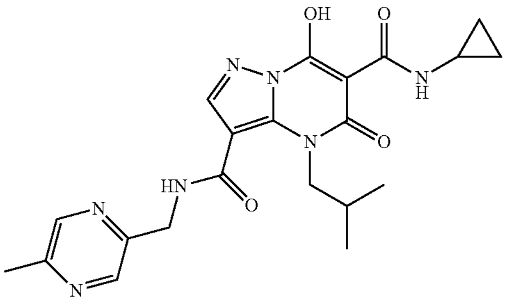
Ex 225
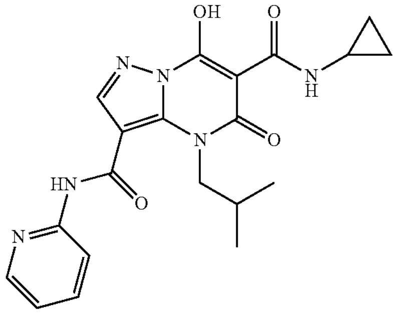
Ex 226
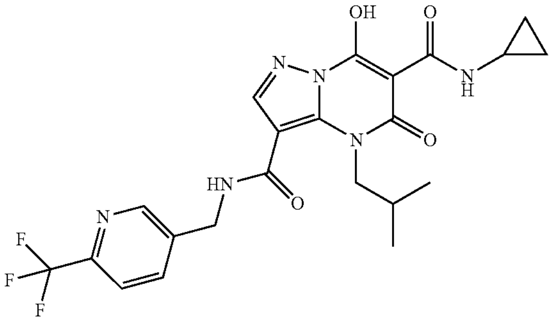
Ex 227
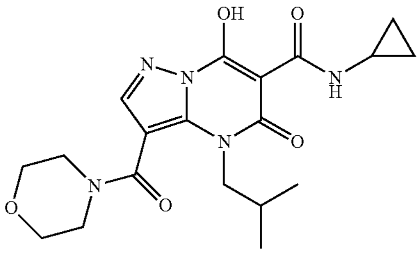
-continued
Ex 228
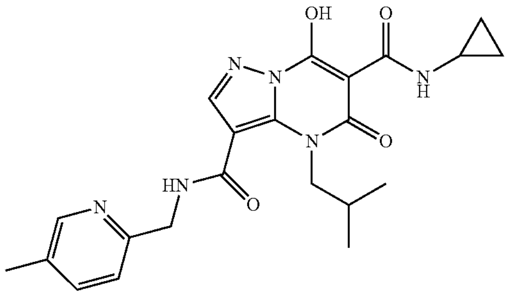
Ex 229
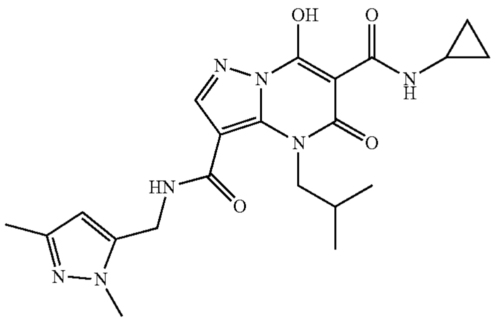
Ex 230
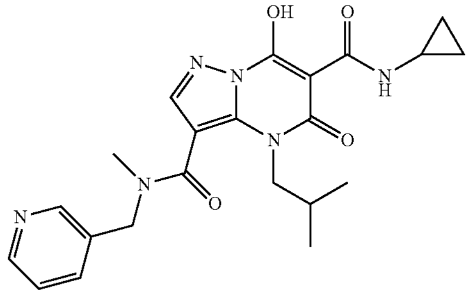
Ex 231
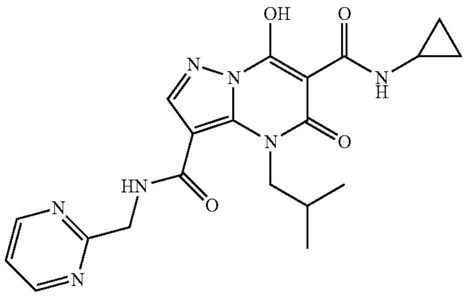
Ex 232
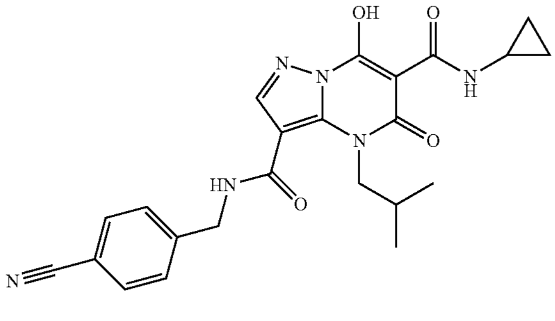

-continued
Ex 233
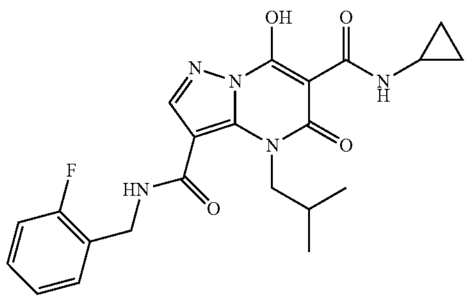
Ex 234
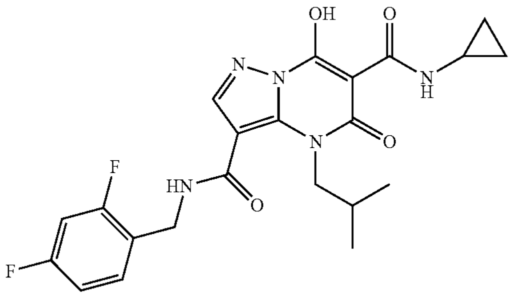
Ex 235
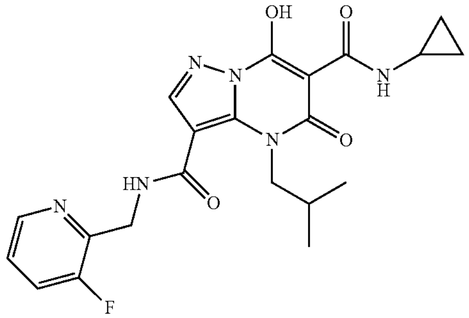
Ex 236
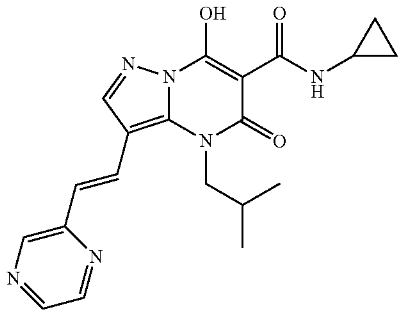
Ex 237
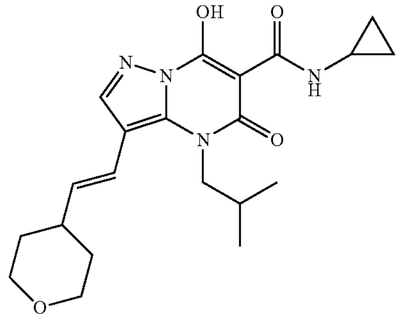
-continued
Ex 238
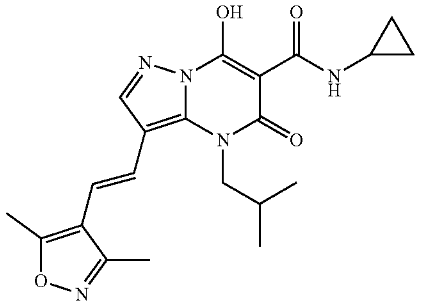
Ex 239
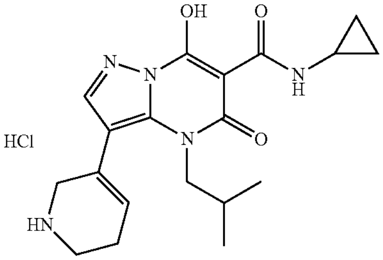
Ex 240
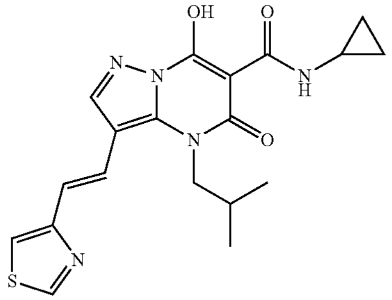
Ex 241
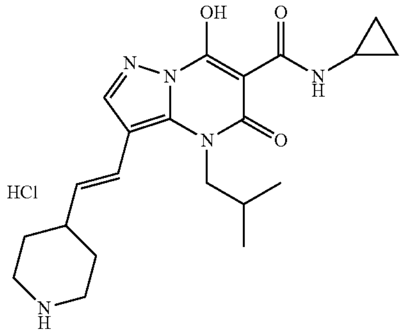
Ex 242
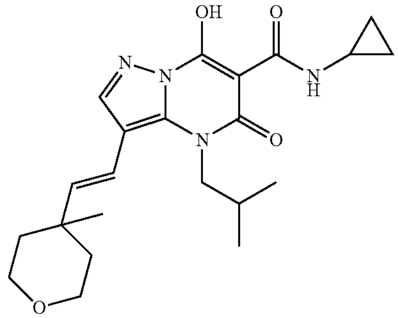

Ex 243
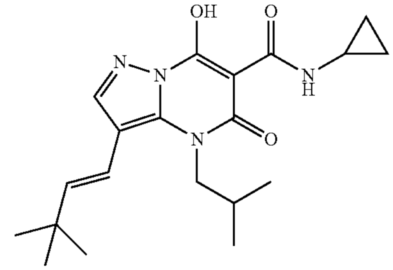
Ex 244
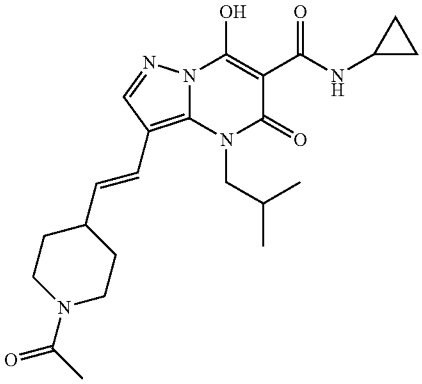
Ex 245
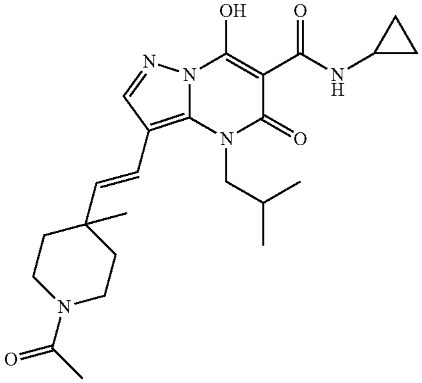
Ex 246
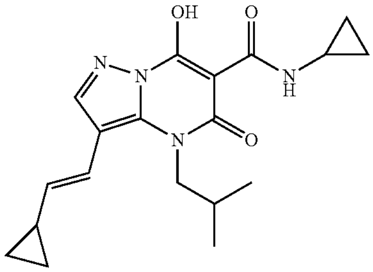
Ex 247
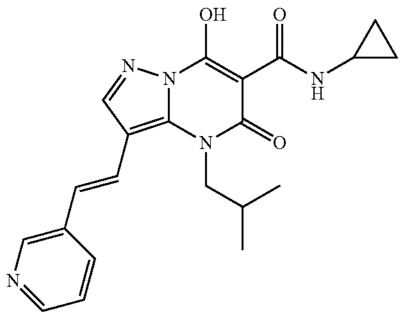
Ex 248
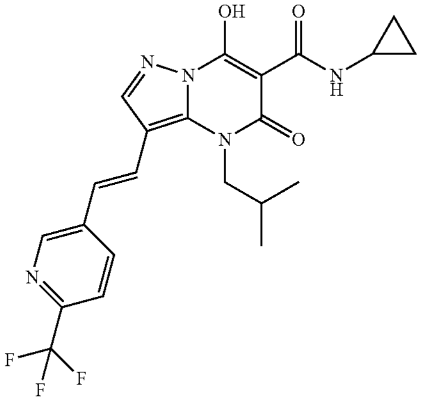
Ex 249
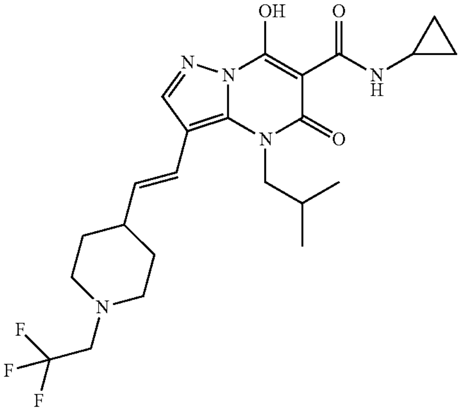
Ex 250
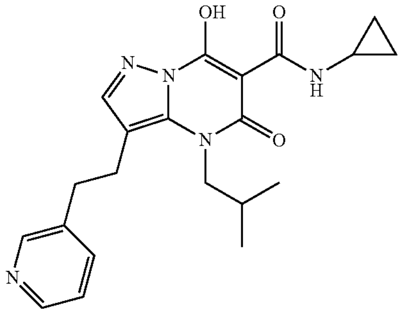
Ex 251
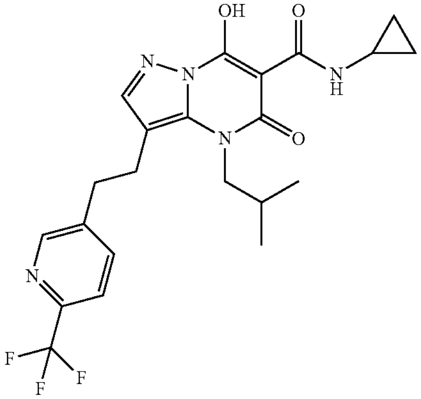

-continued
Ex 252
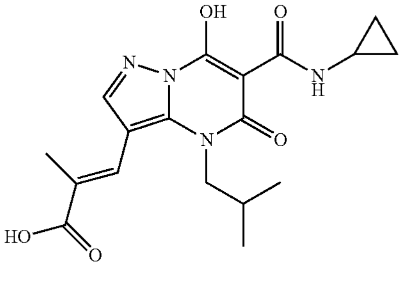
Ex 253
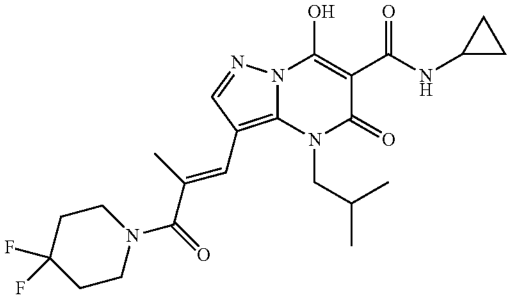
Ex 254
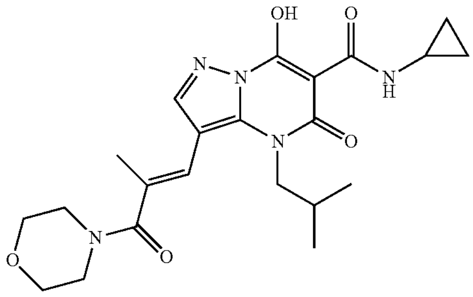
Ex 255
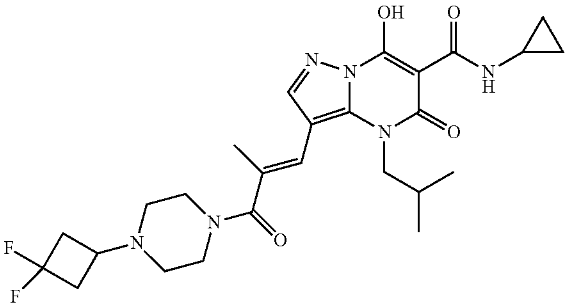
Ex 256
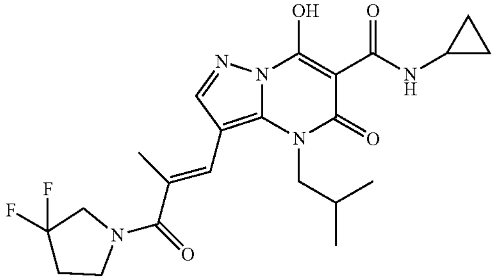
-continued
Ex 257
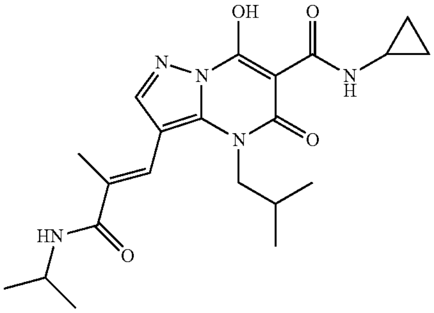
Ex 258
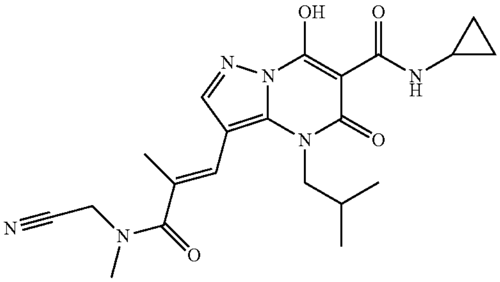
Ex 259
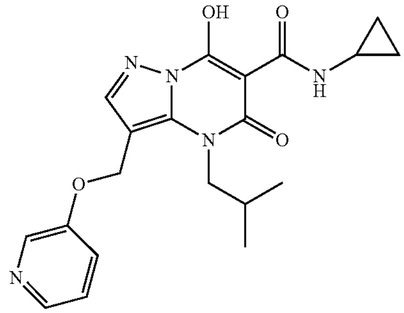
Ex 260
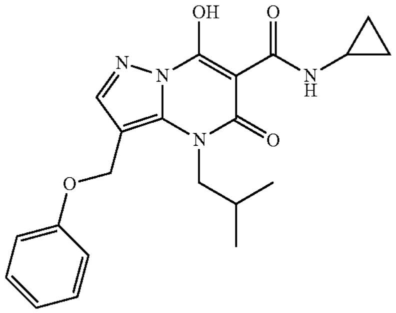
Ex 261
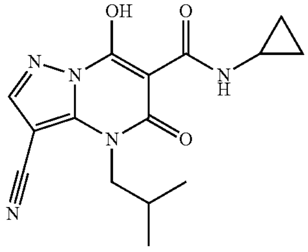

-continued
Ex 262
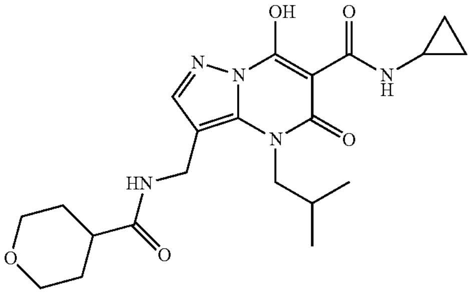
Ex 263
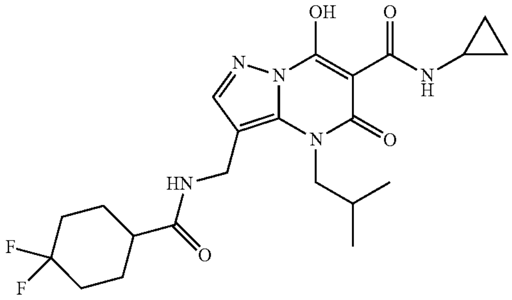
Ex 264
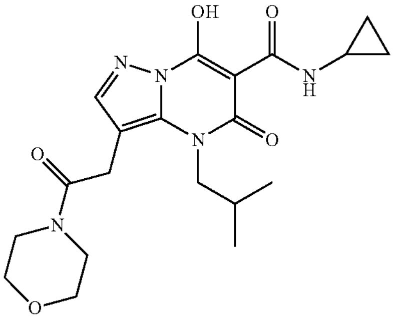
Ex 265
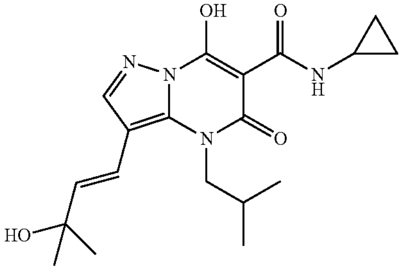
Ex 266
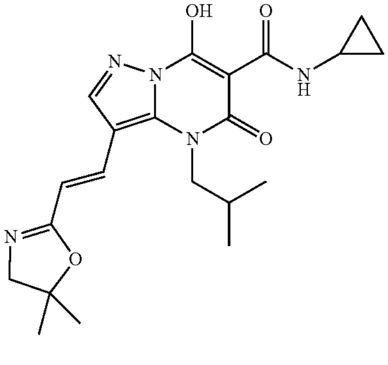
-continued
Ex 267
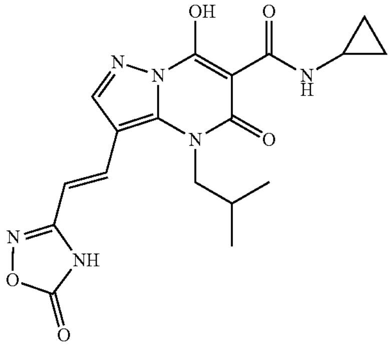
Ex 268
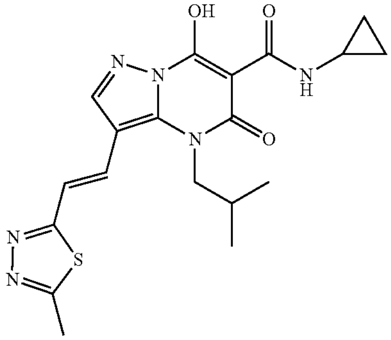
Ex 269
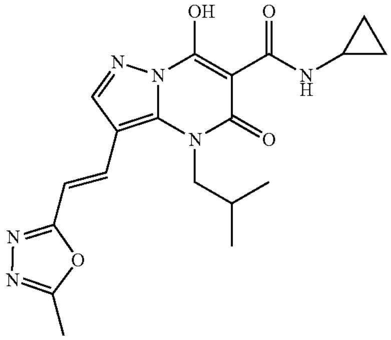
Ex 270
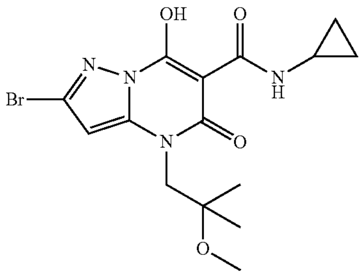
Ex 271
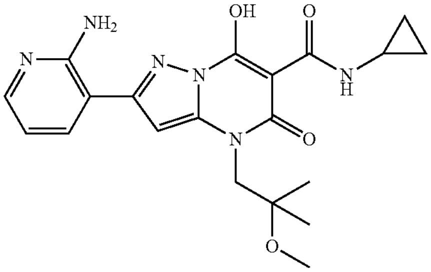

-continued
Ex 272
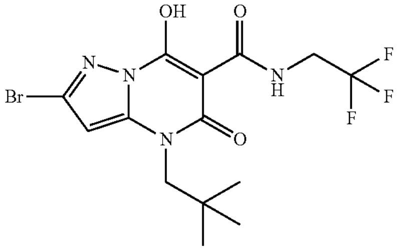
Ex 273
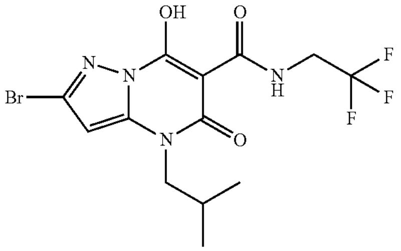
Ex 274
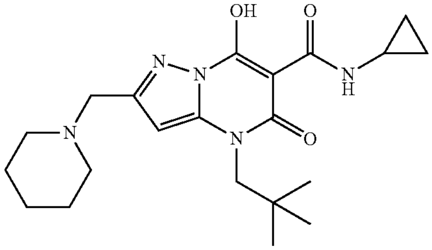
Ex 275
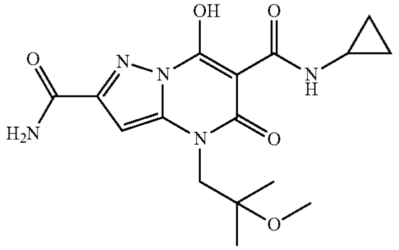
Ex 276
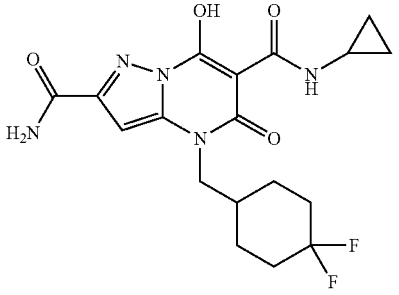
Ex 277
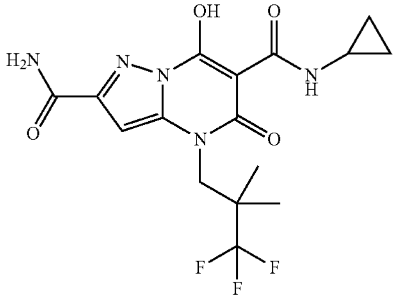
-continued
Ex 278
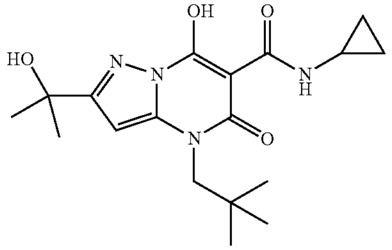
Ex 279
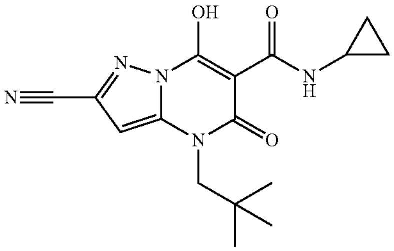
Ex 280
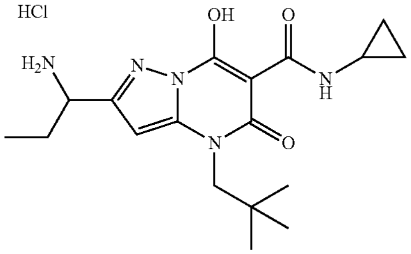
Ex 281
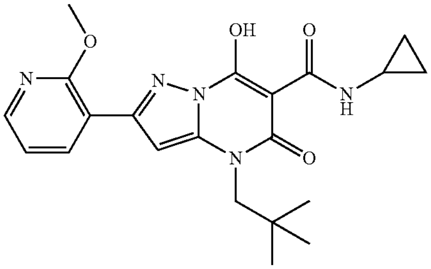
Ex 282
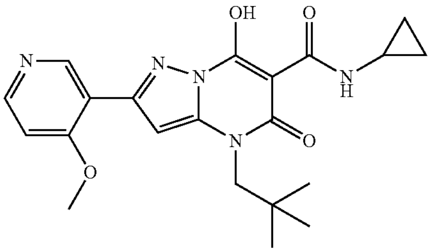
Ex 283
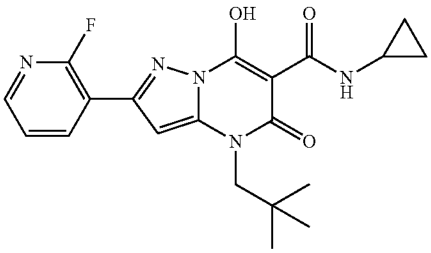

-continued
Ex 284
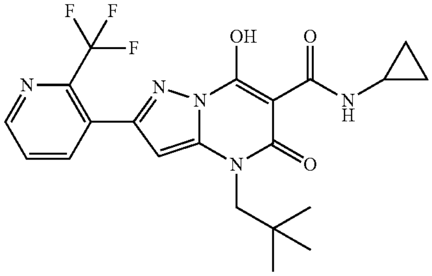
Ex 285
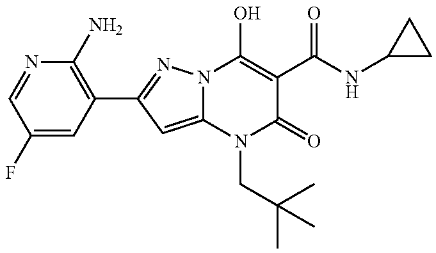
Ex 286
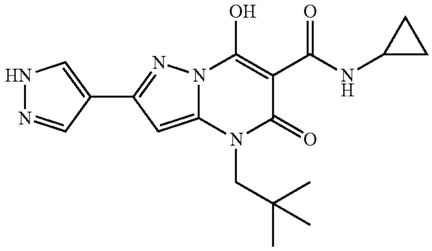
Ex 287
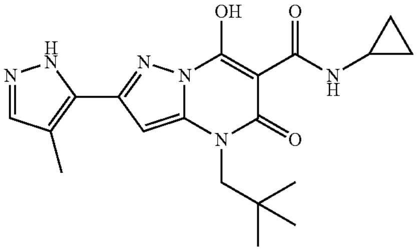
Ex 288
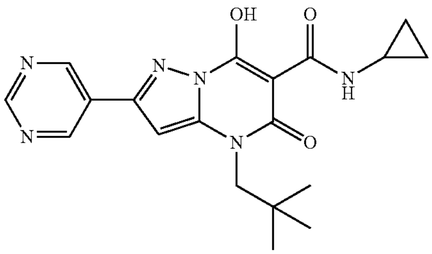
Ex 289
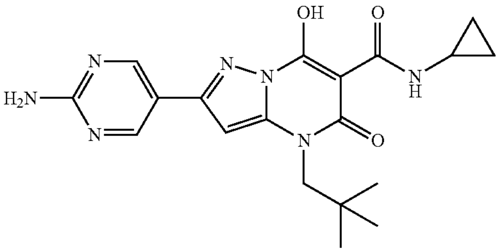
-continued
Ex 290
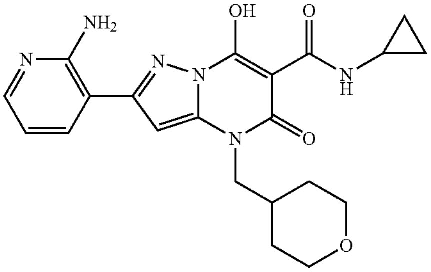
Ex 291
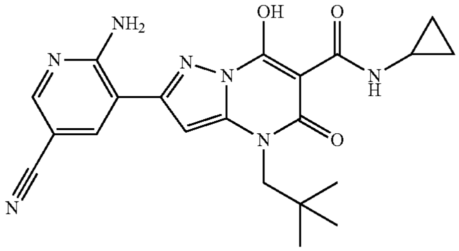
Ex 292
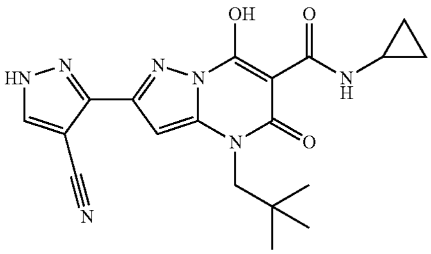
Ex 293
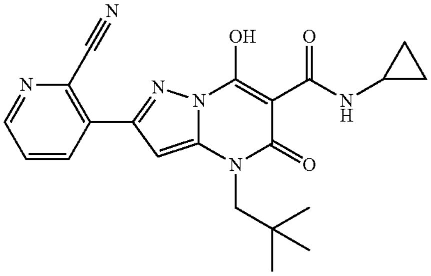
Ex 294
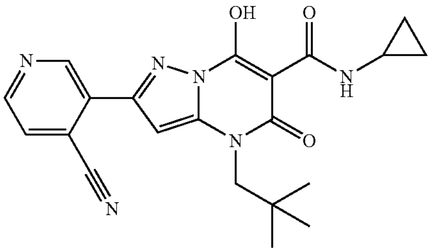
Ex 295
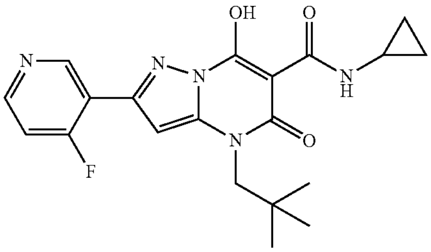

-continued
Ex 296
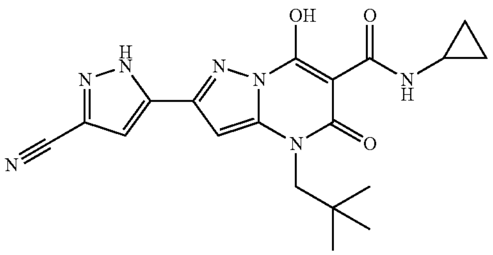
Ex 297
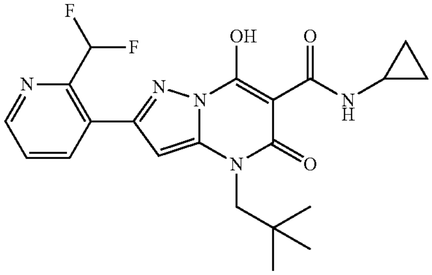
Ex 298
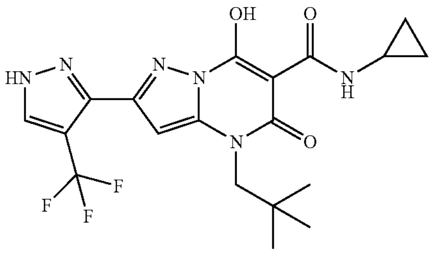
Ex 299
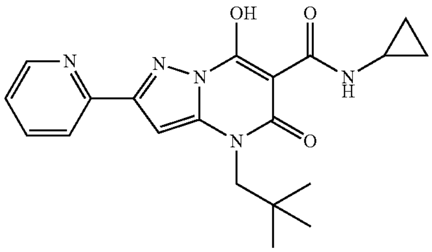
Ex 300
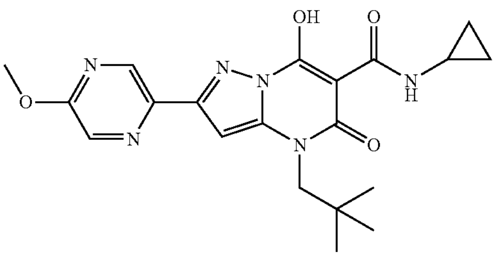
-continued
Ex 301
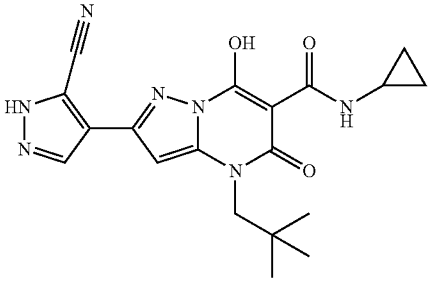
Ex 302
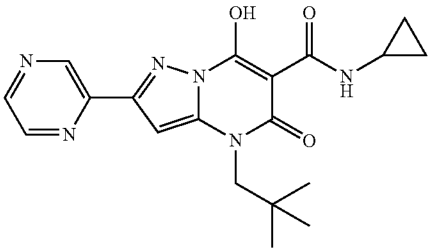
Ex 303
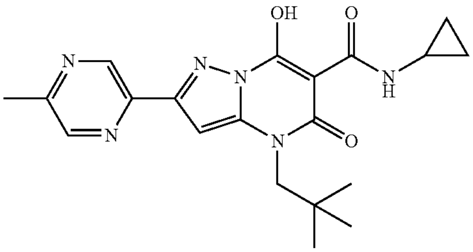
Ex 304
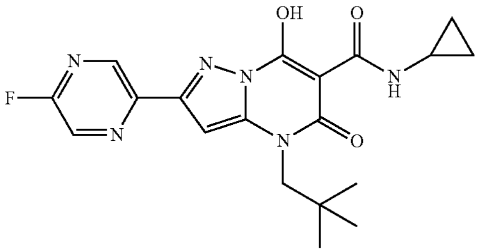
Ex 305
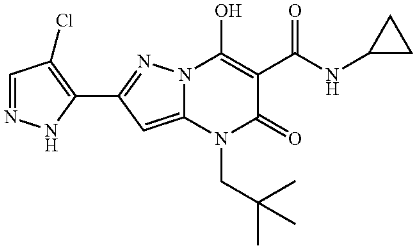
Ex 306
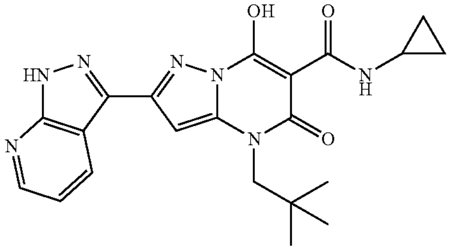

-continued
Ex 307
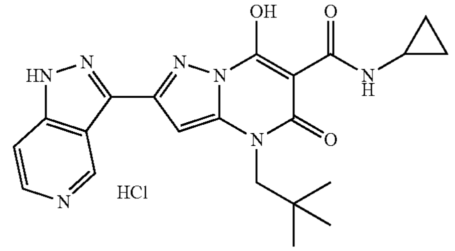
Ex 308
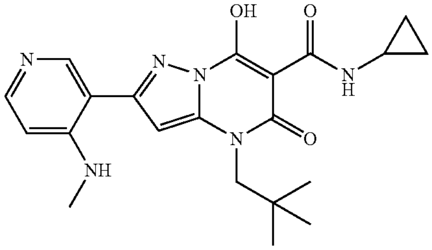
Ex 309
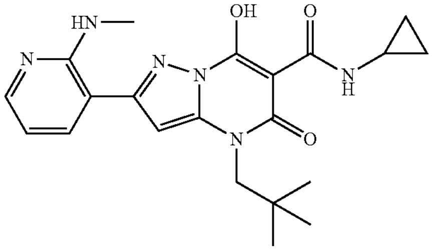
Ex 310
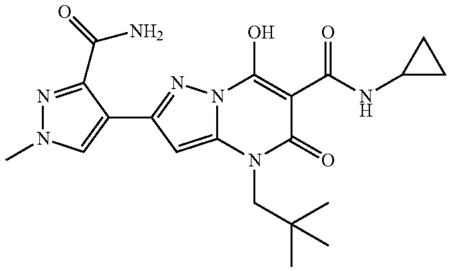
Ex 311
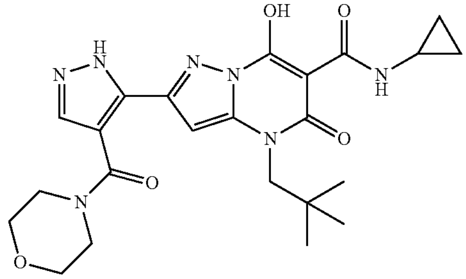
Ex 312
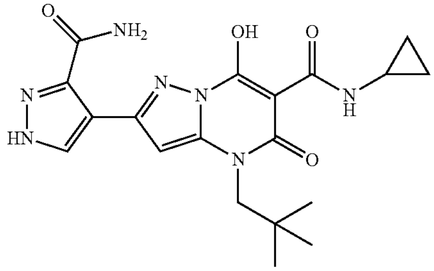
-continued
Ex 313
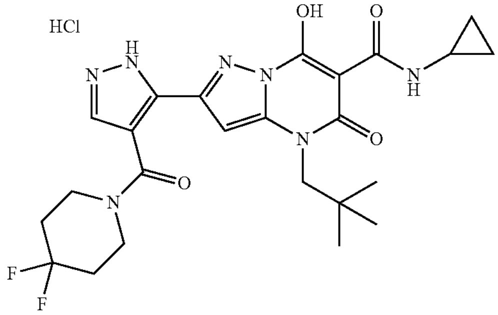
Ex 314
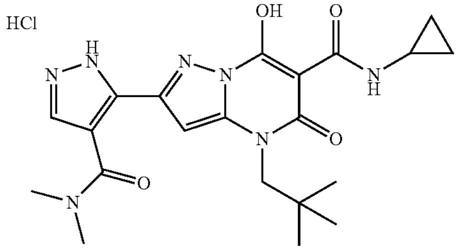
Ex 315
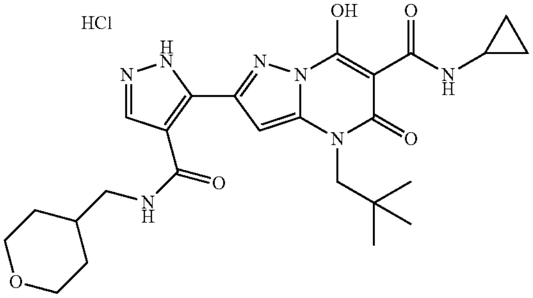
Ex 316
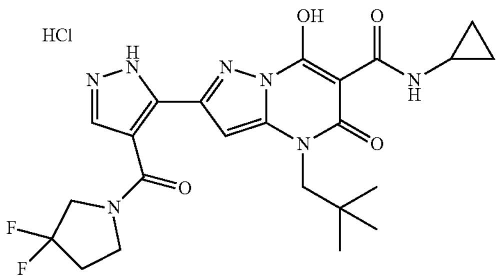
Ex 317
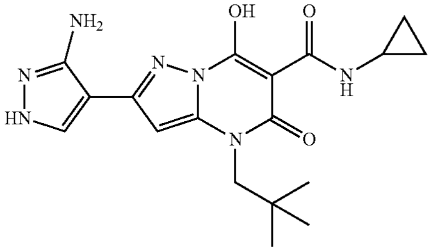

-continued
Ex 318
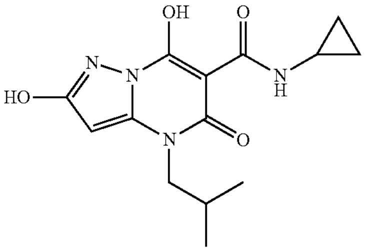
Ex 319
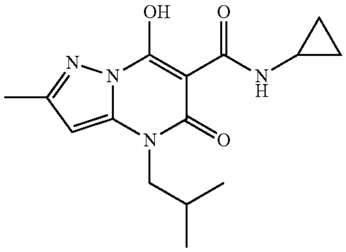
Ex 320
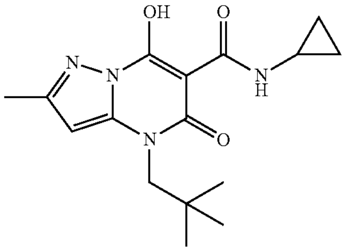
Ex 321
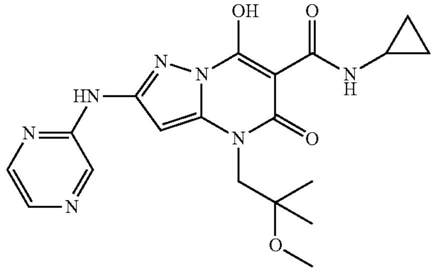
Ex 322
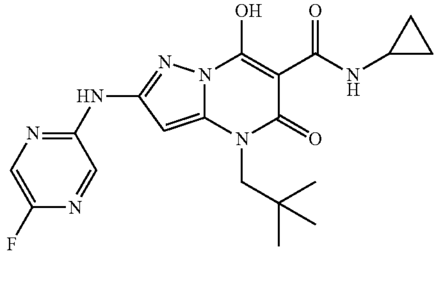
Ex 323
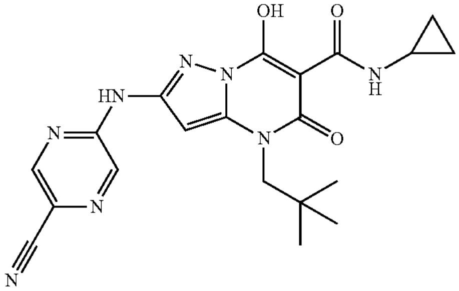
-continued
Ex 324
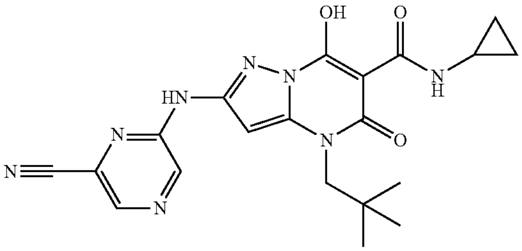
Ex 325
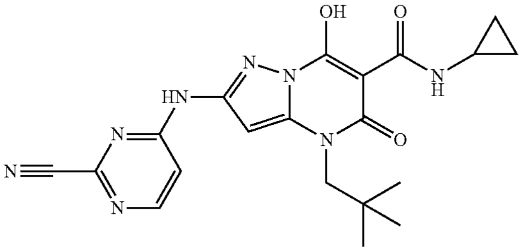
Ex 326
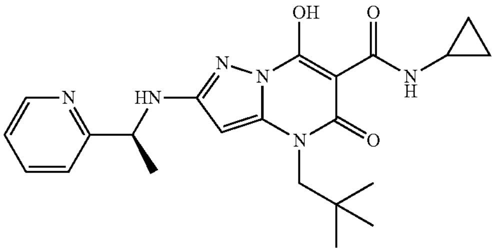
Ex 327
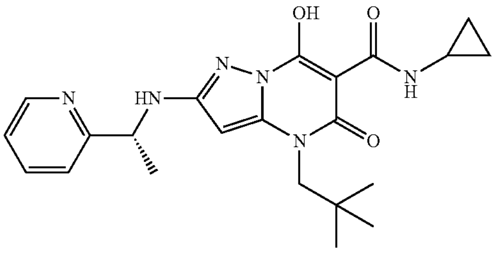
Ex 328
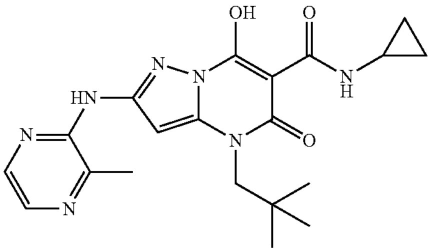

-continued
Ex 329
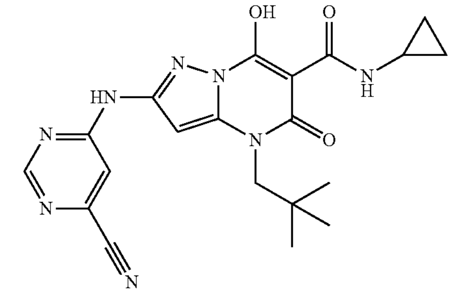
Ex 330
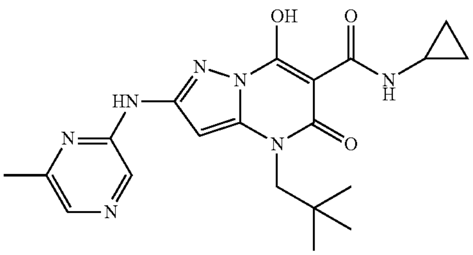
Ex 331
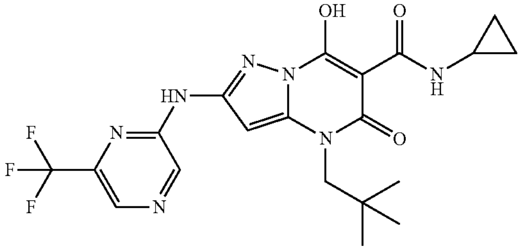
Ex 332
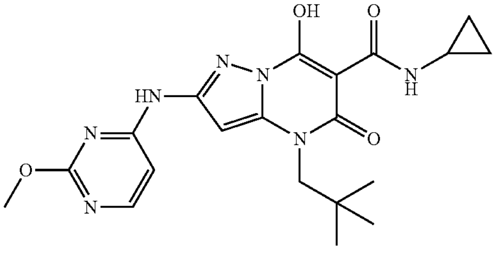
Ex 333
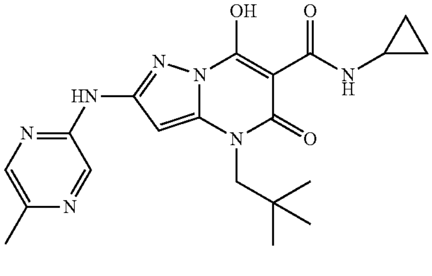
-continued
Ex 334
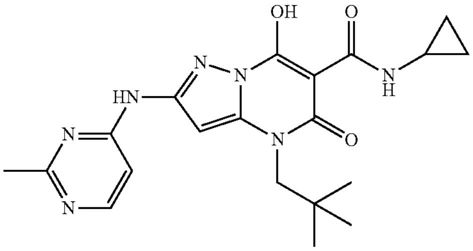
Ex 335
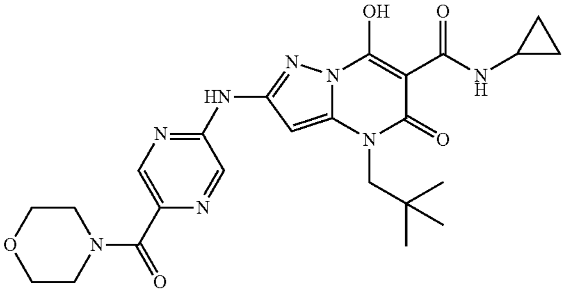
Ex 336
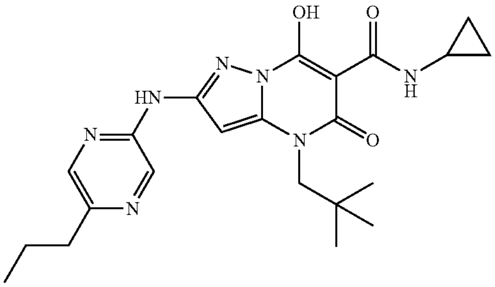
Ex 337
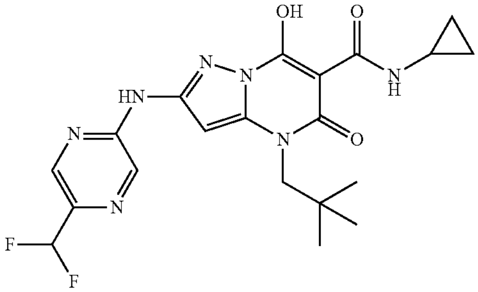
Ex 338
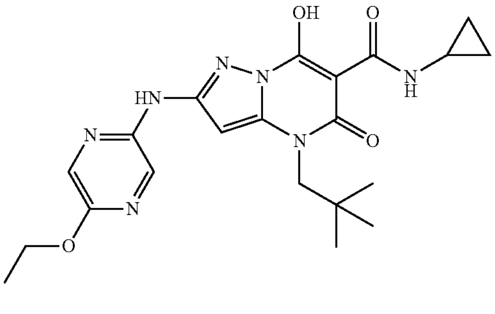

-continued
Ex 339
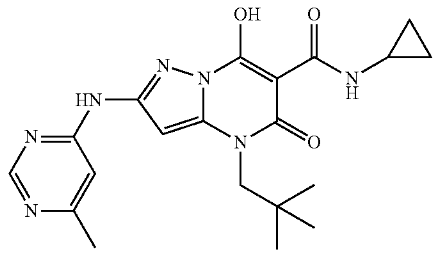
Ex 340
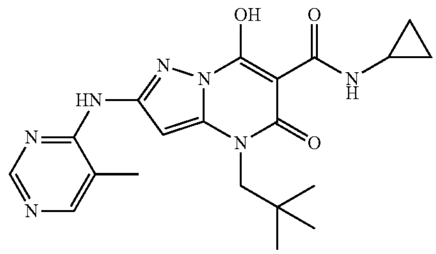
Ex 341
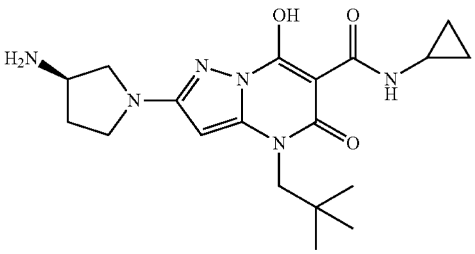
Ex 342
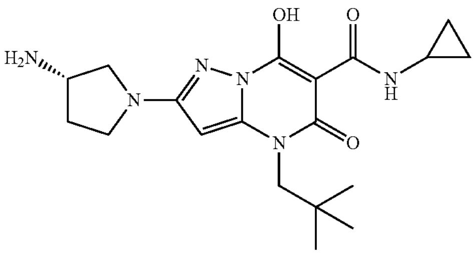
Ex 343
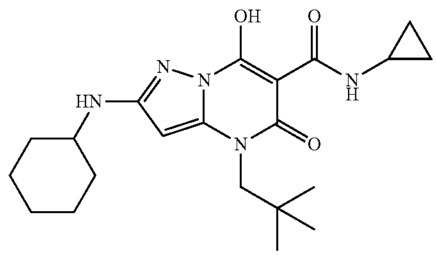
-continued
Ex 344
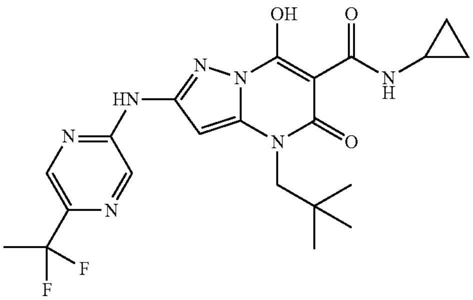
Ex 345
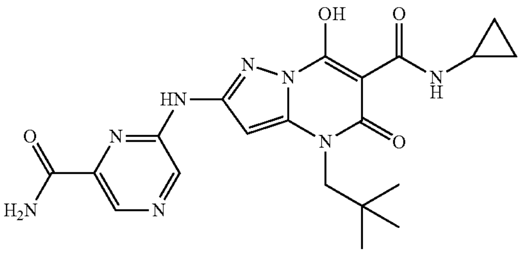
Ex 346
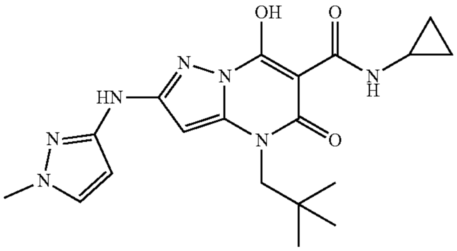
Ex 347
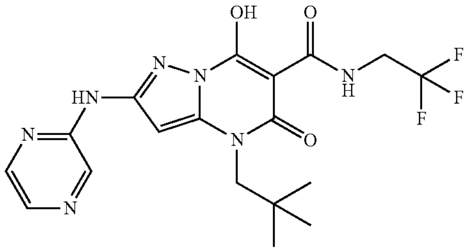
Ex 348
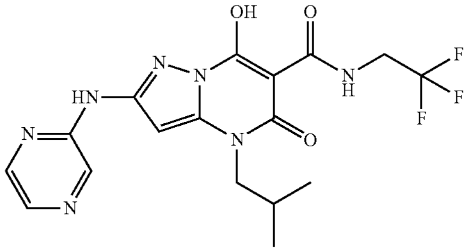

-continued
Ex 349
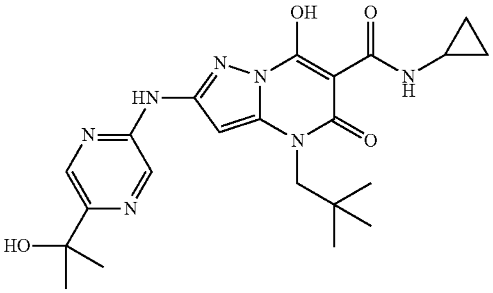
Ex 350
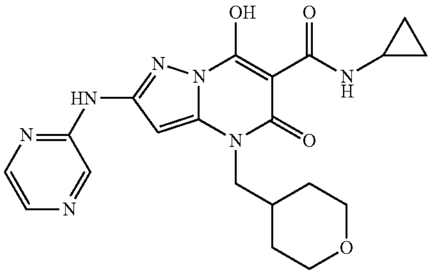
Ex 351
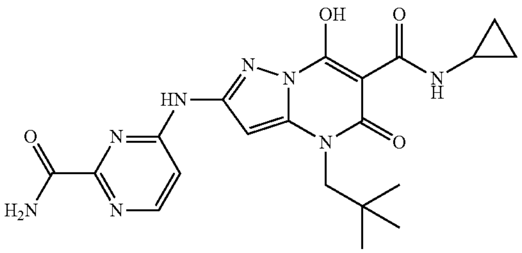
Ex 352
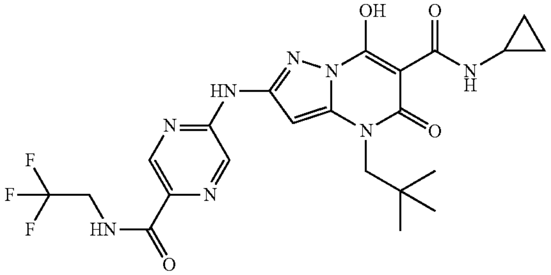
Ex 353
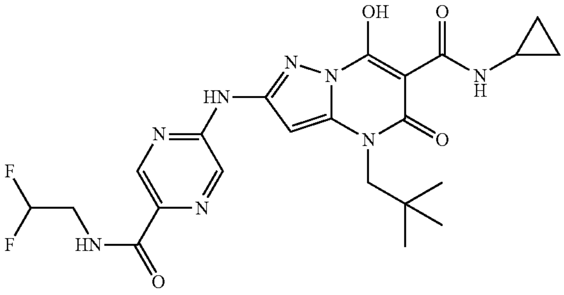
-continued
Ex 354
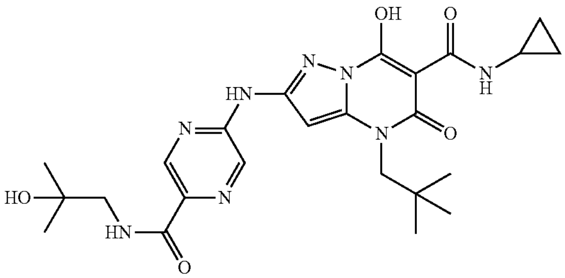
Ex 355
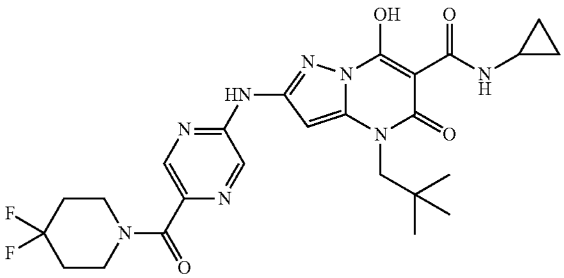
Ex 356
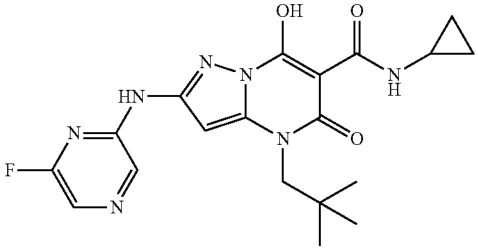
Ex 357
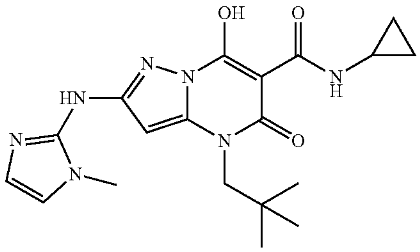
Ex 358
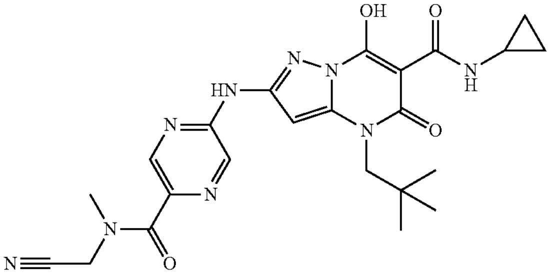

-continued
Ex 359
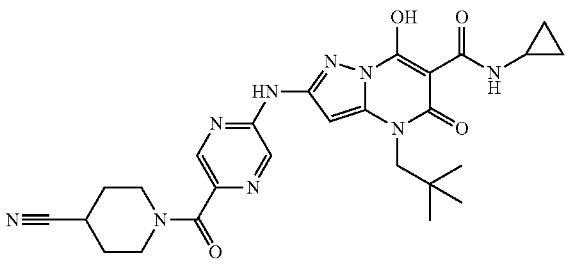
Ex 360
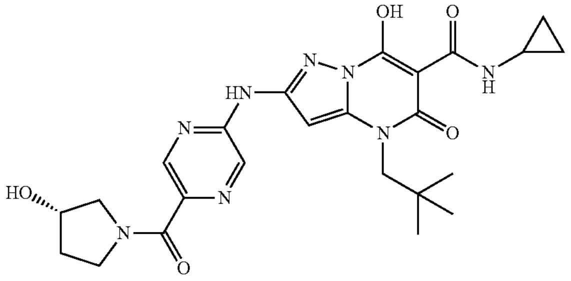
Ex 361
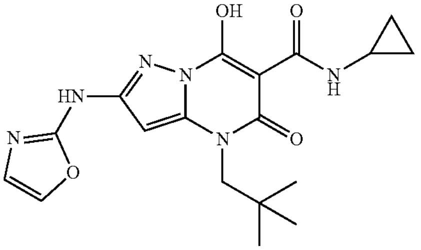
Ex 362
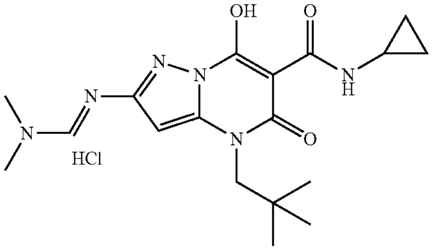
Ex 363
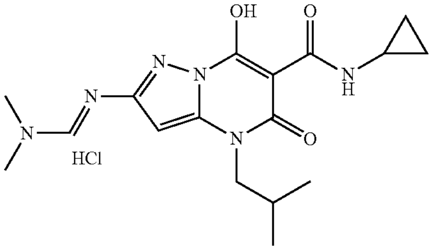
-continued
Ex 364
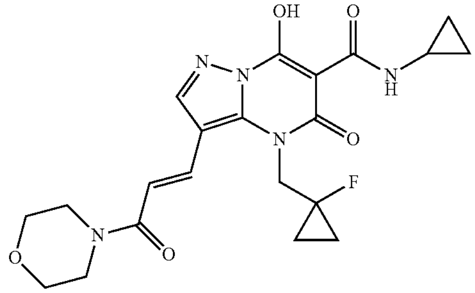
Ex 365
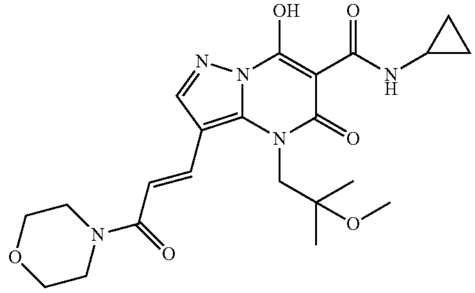
Ex 366
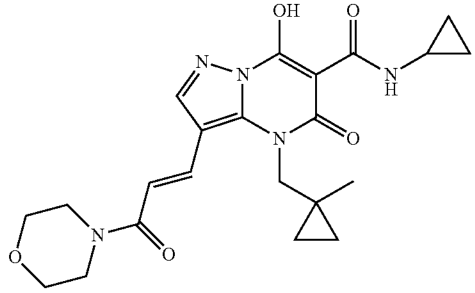
Ex 367
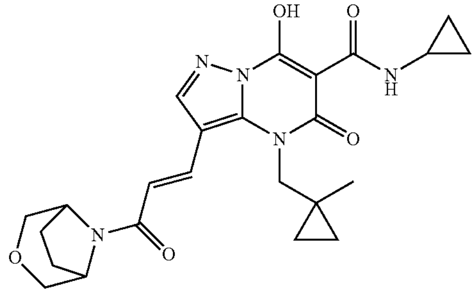
Ex 368
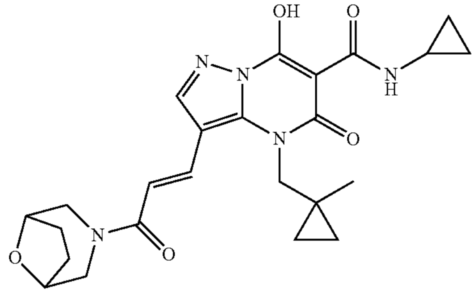

Ex 369
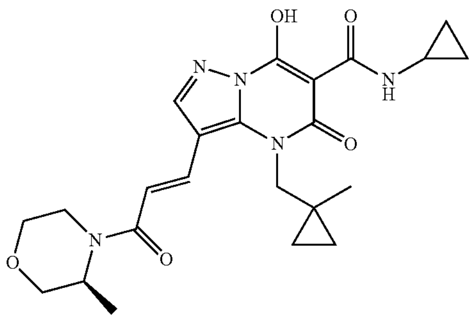
Ex 370
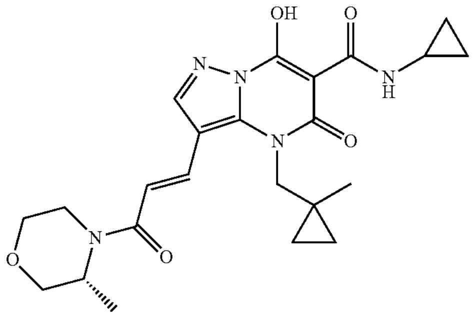
Ex 371
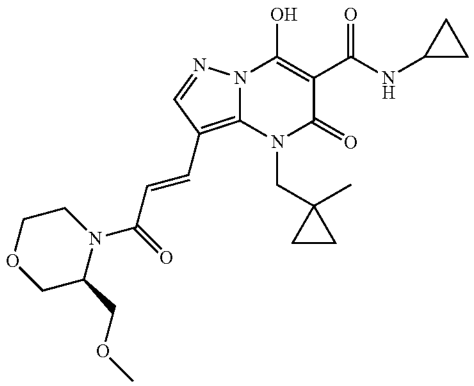
Ex 372
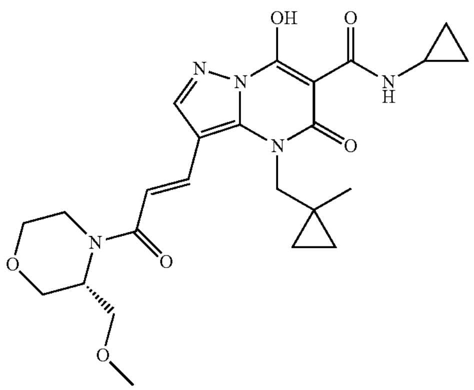
Ex 373
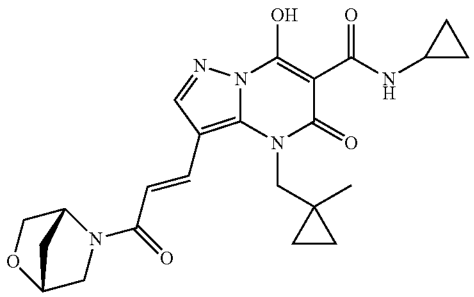
Ex 374
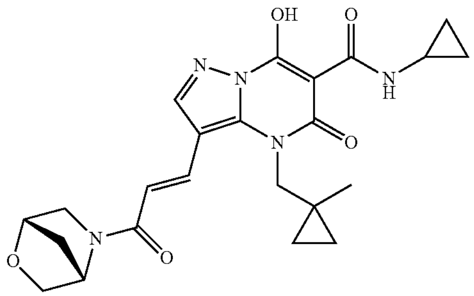
Ex 375
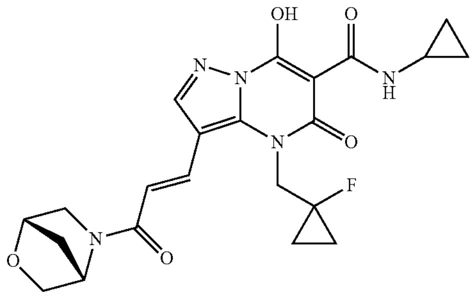
Ex 376
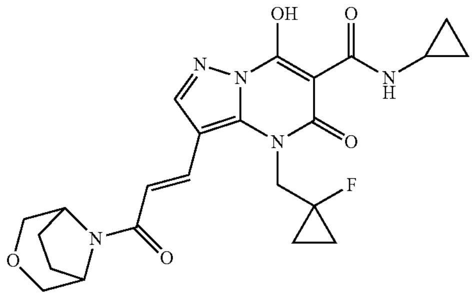
Ex 377
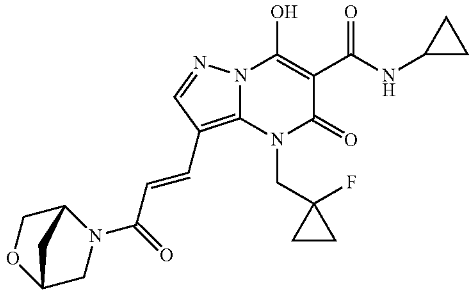

-continued
Ex 378
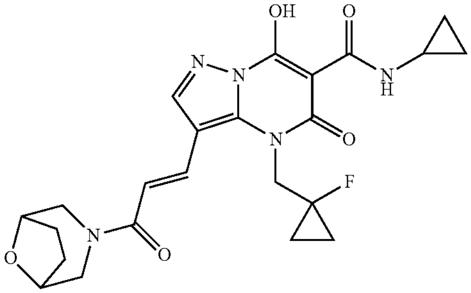
Ex 379
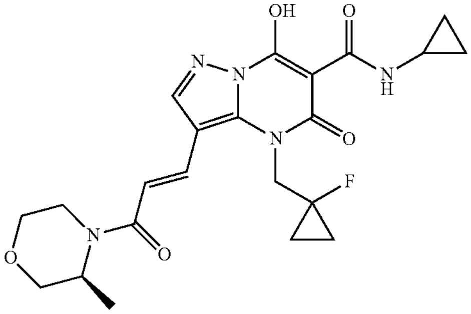
Ex 380
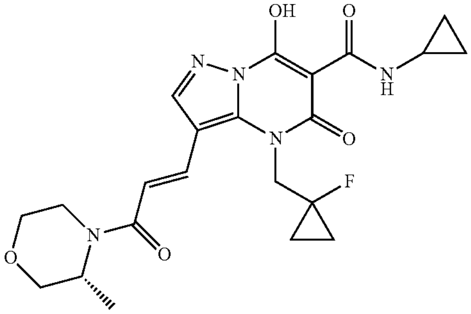
Ex 381
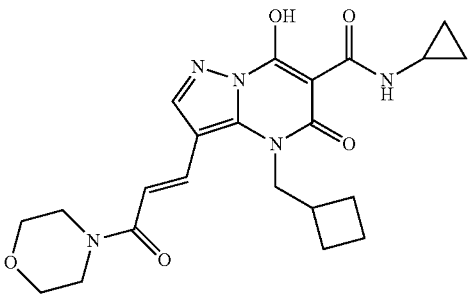
-continued
Ex 382
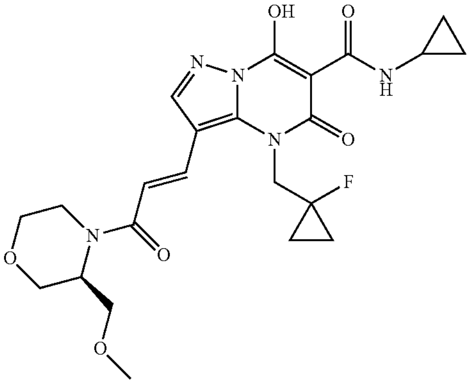
Ex 383
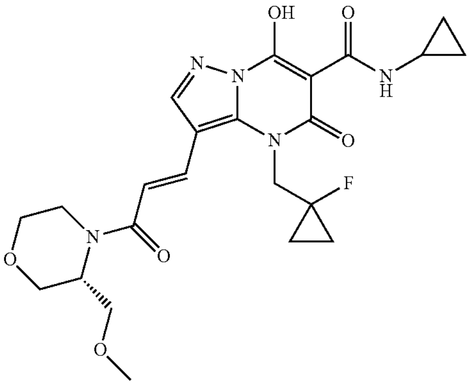
Ex 384
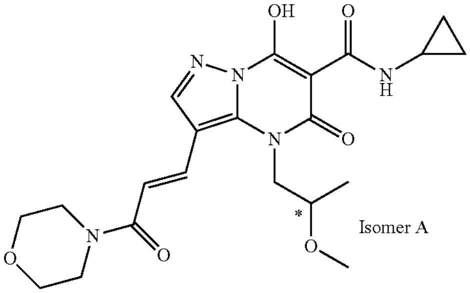
Isomer A
Ex 385
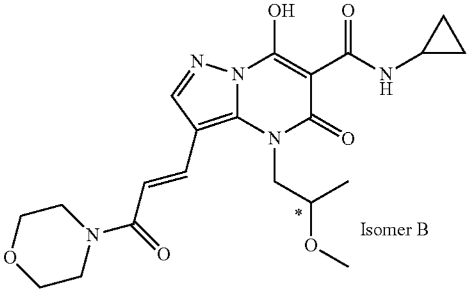
Isomer B Ex 386
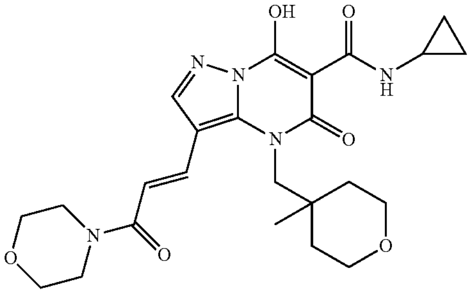
Ex 387
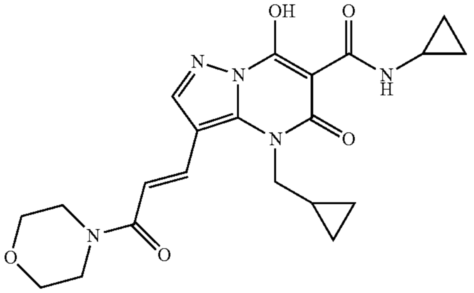
Ex 388
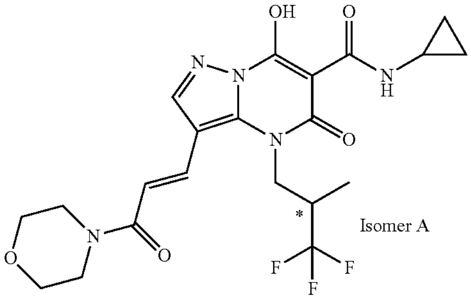
Isomer A
Ex 389
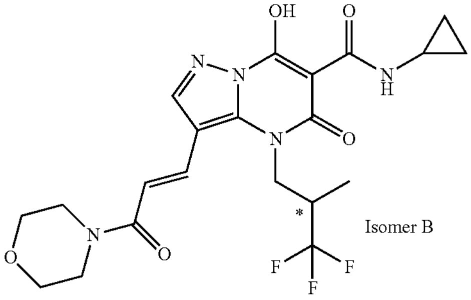
Isomer B
Ex 390
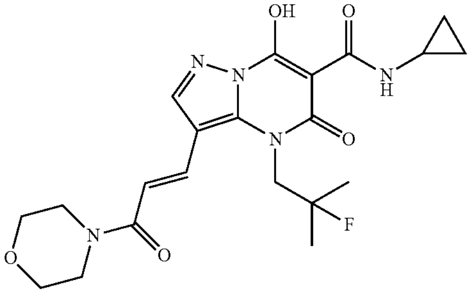
Ex 391
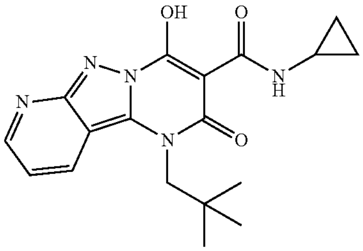
Ex 392
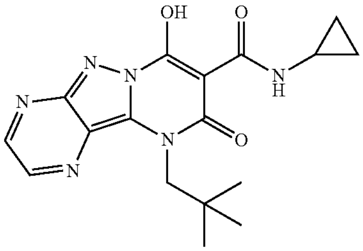
Ex 393
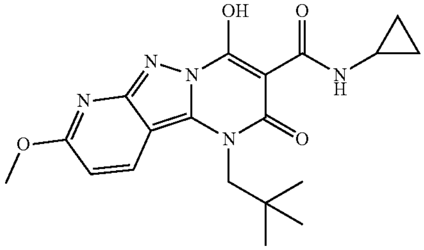
Ex 394
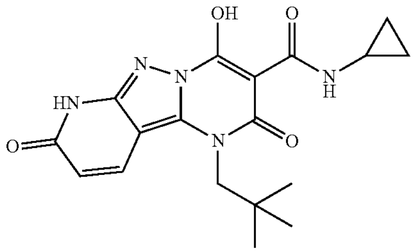
Ex 395
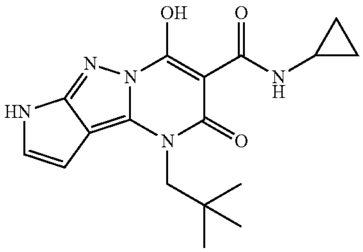
Ex 396
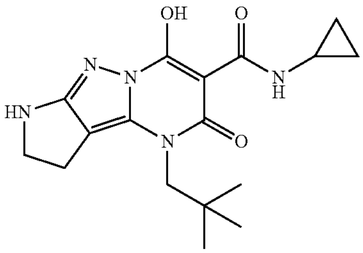

Ex 397
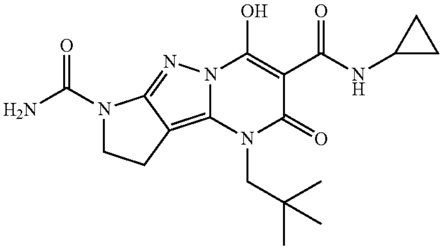
Ex 398
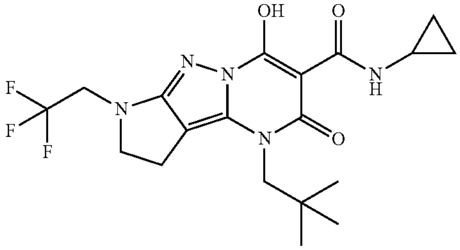
Ex 399
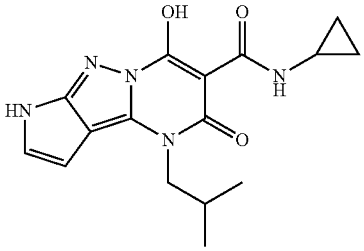
Ex 400
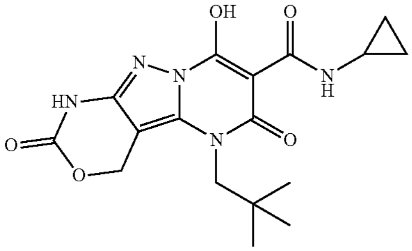
Ex 401
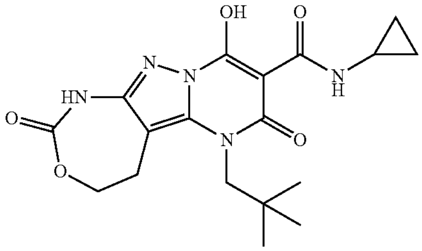
Ex 402
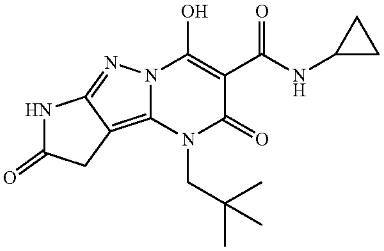
Ex 403
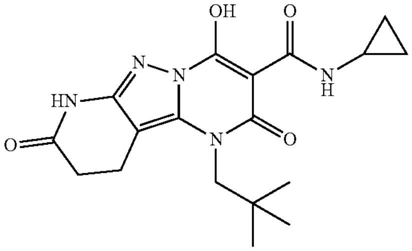
Ex 404
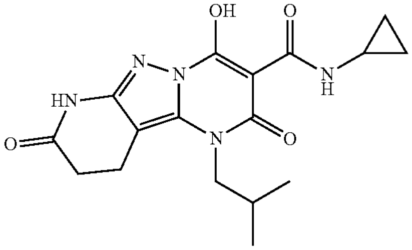
Ex 405
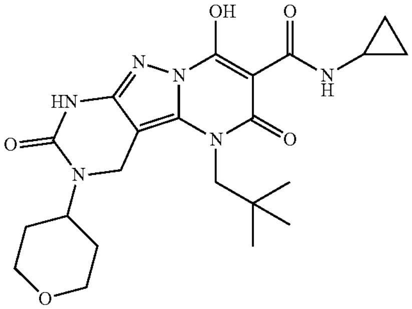
Ex 406
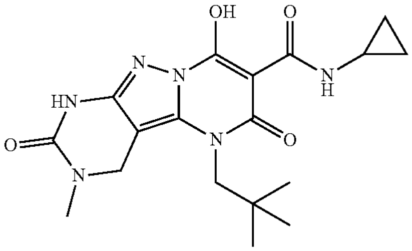
Ex 407
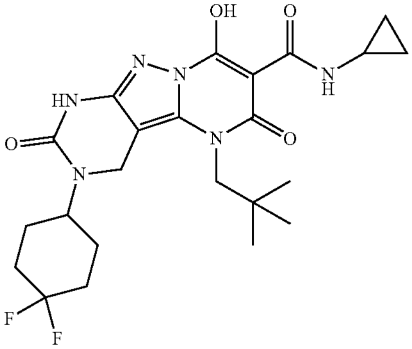

-continued
Ex 408
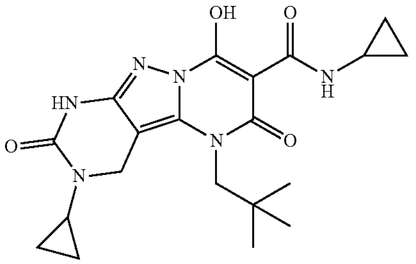
Ex 409
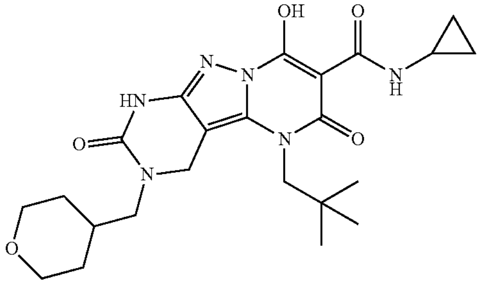
Ex 410
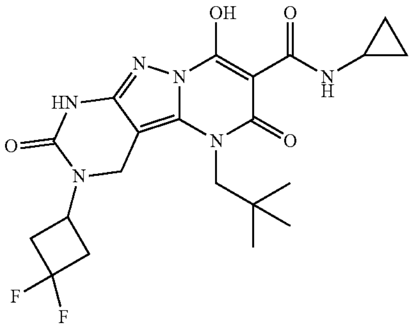
Ex 411
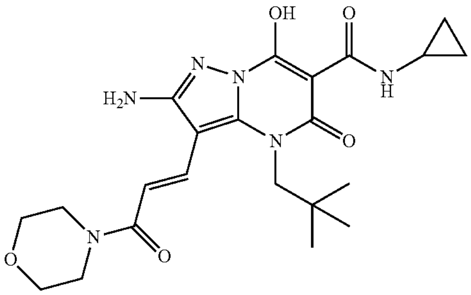
Ex 412
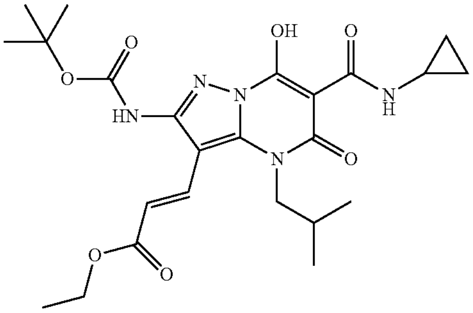
-continued
Ex 413
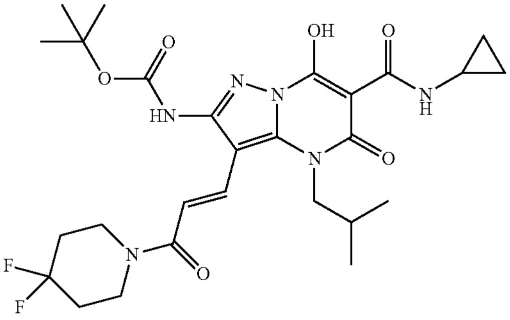
Ex 414
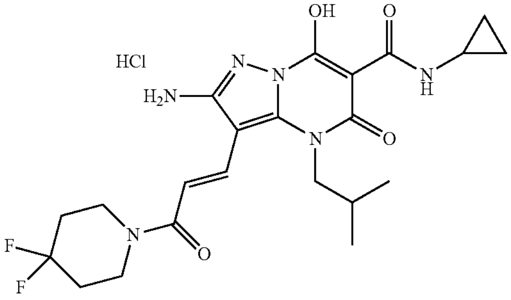
Ex 415
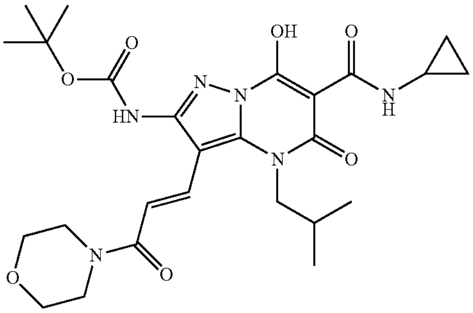
Ex 416
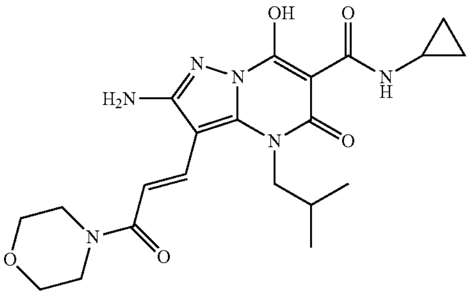
Ex 417
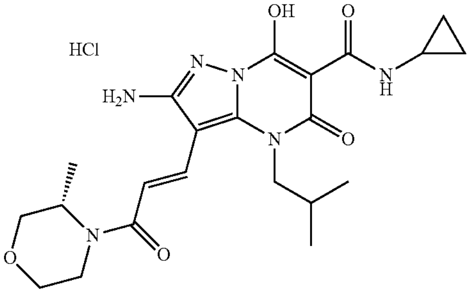

-continued
Ex 418
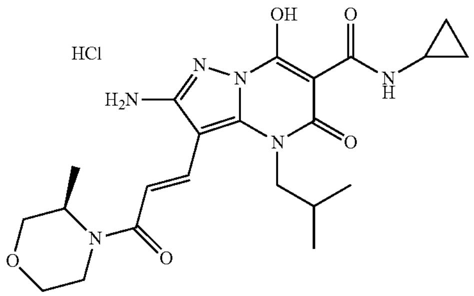
Ex 419
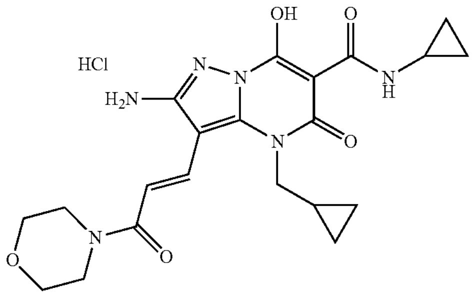
Ex 420
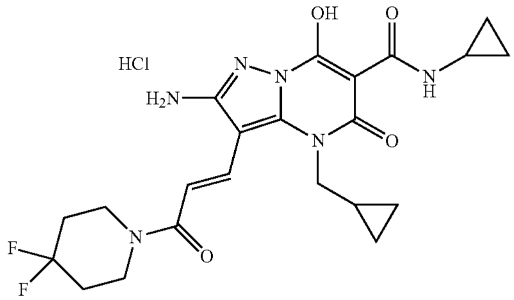
Ex 421
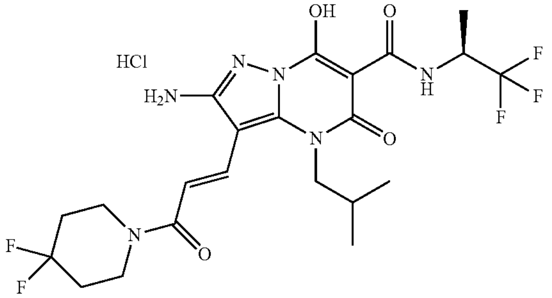
Ex 422
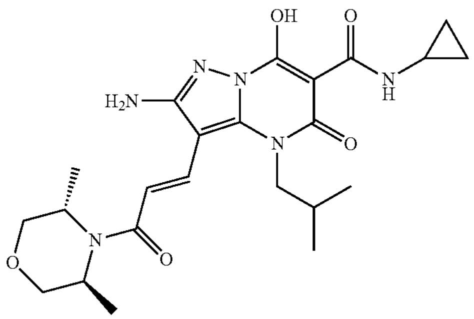
-continued
Ex 423
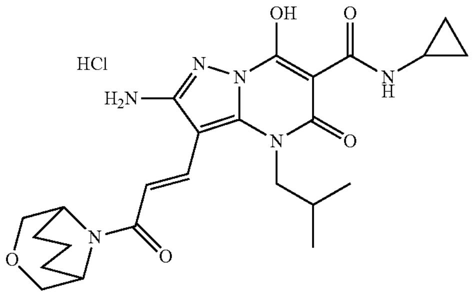
Ex 424
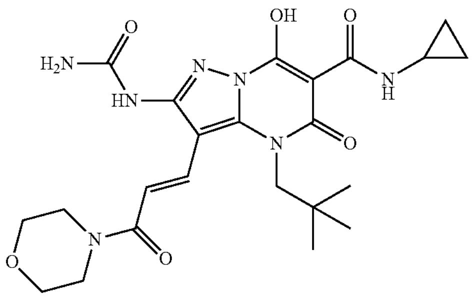
Ex 425
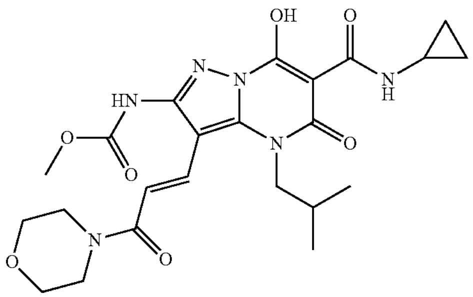
Ex 426
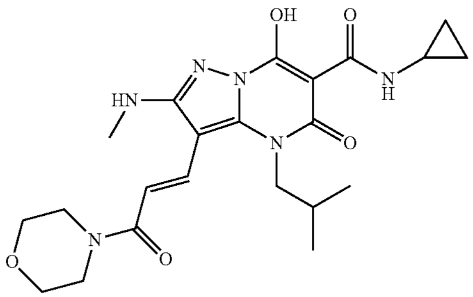
Ex 427
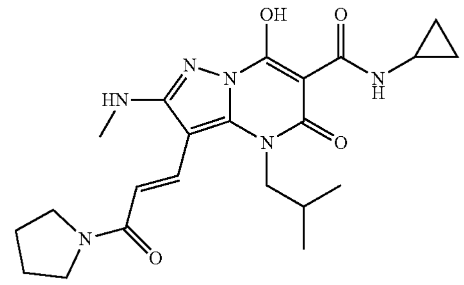

-continued
Ex 428
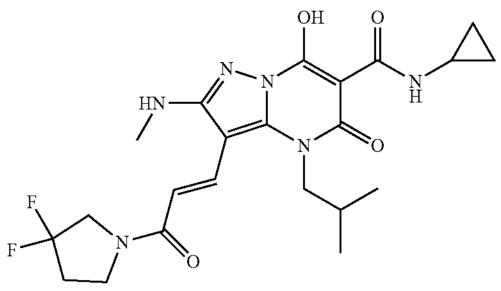
Ex 429
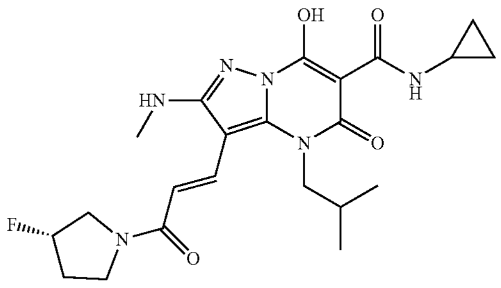
Ex 430
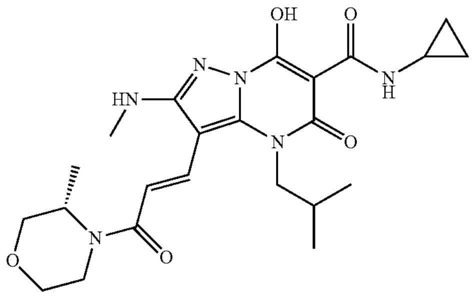
Ex 431
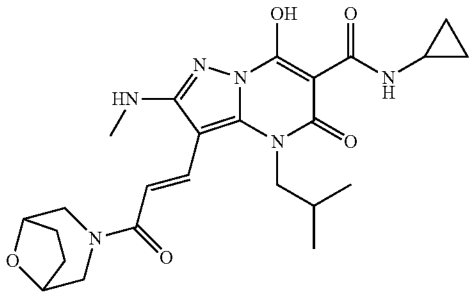
Ex 432
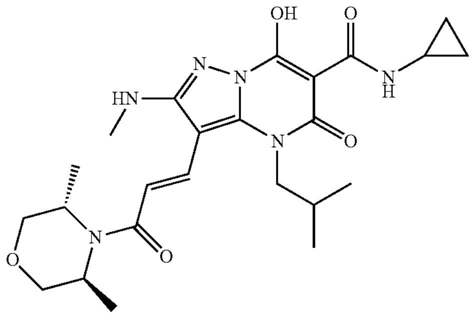
-continued
Ex 433
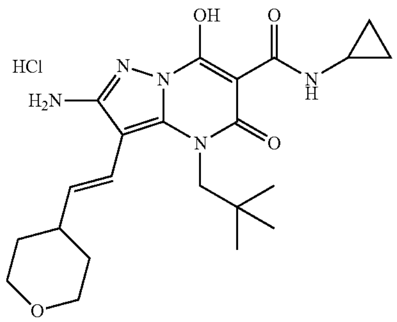
Ex 434
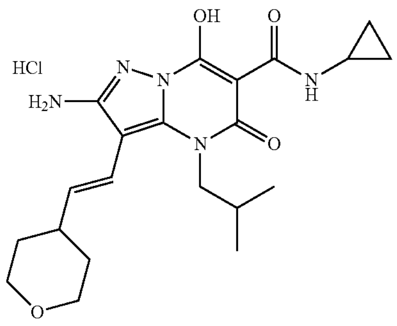
Ex 435
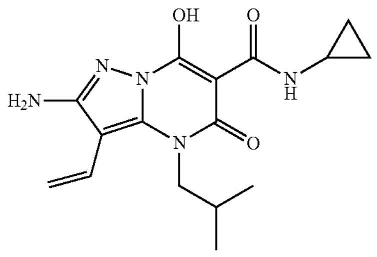
Ex 436
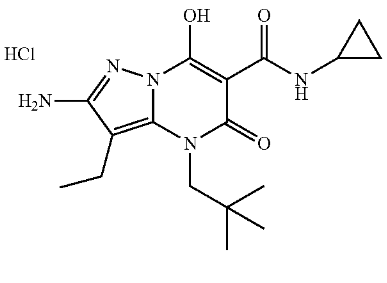
Ex 437
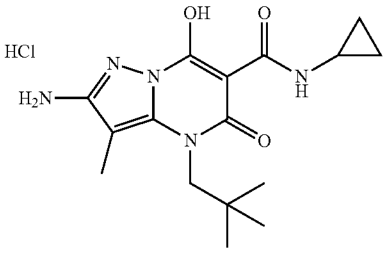

-continued
Ex 438
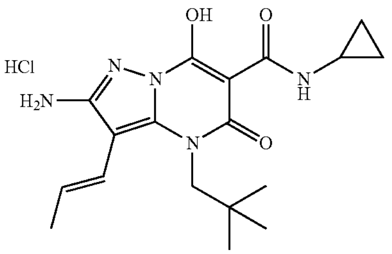
Ex 439
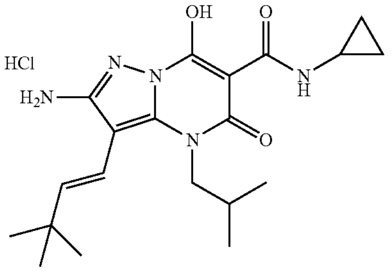
Ex 440
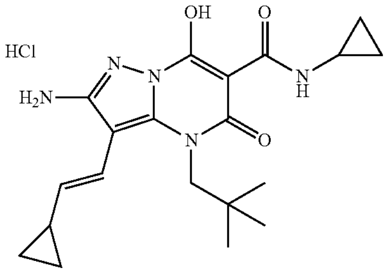
Ex 441
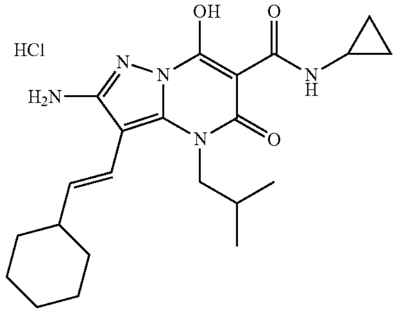
Ex 442
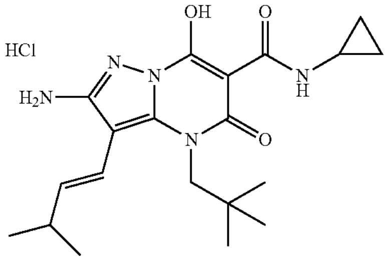
-continued
Ex 443
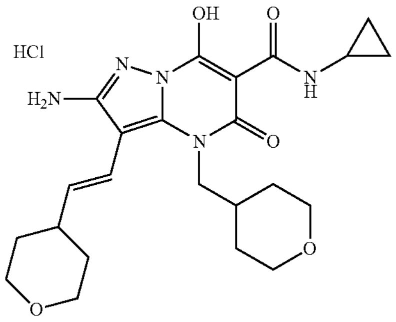
Ex 444
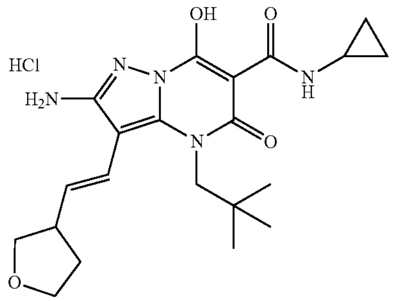
Ex 445
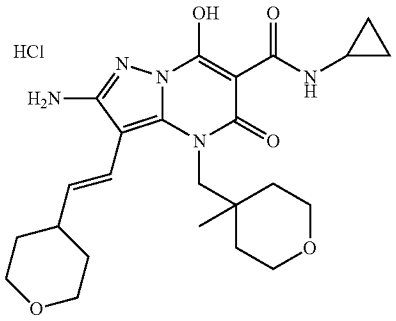
Ex 446
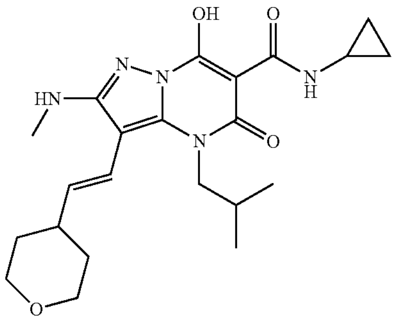
Ex 447
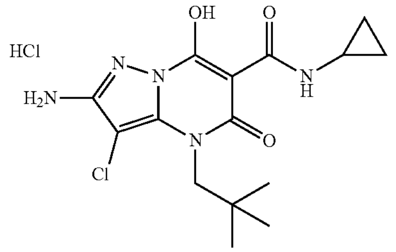

Ex 448
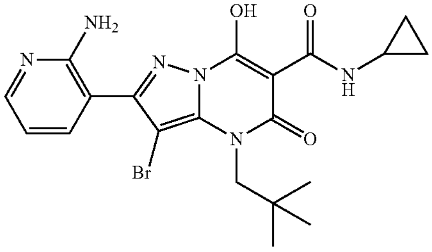
Ex 449
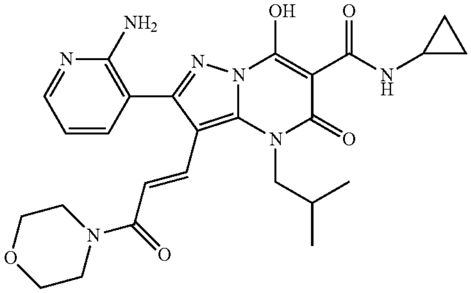
Ex 450
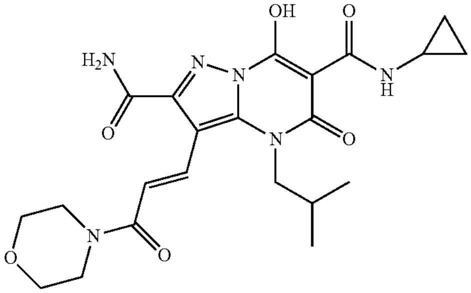
Ex 451
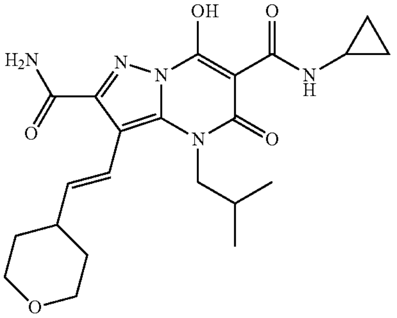
Ex 452
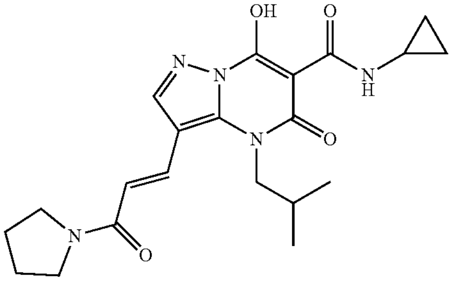
Ex 453
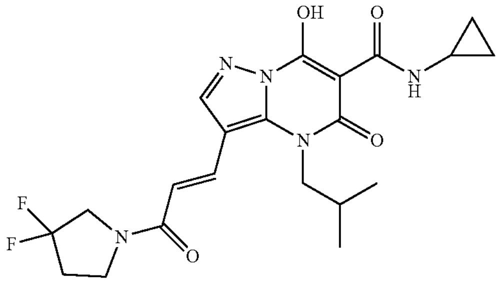
Ex 454
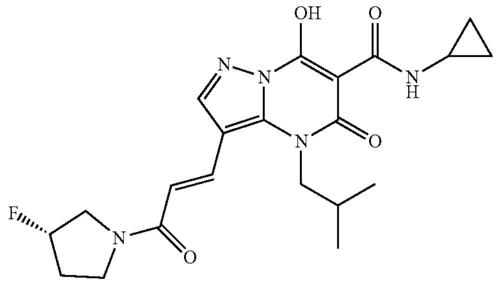
Ex 455
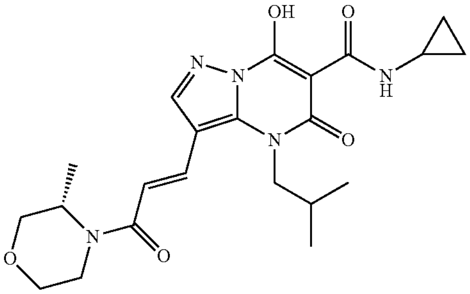
Ex 456
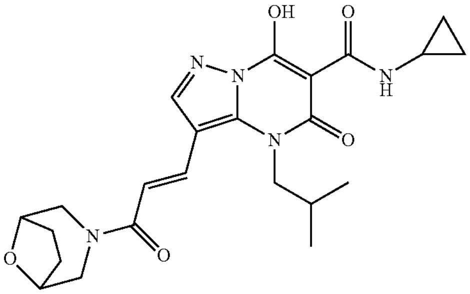
Ex 457
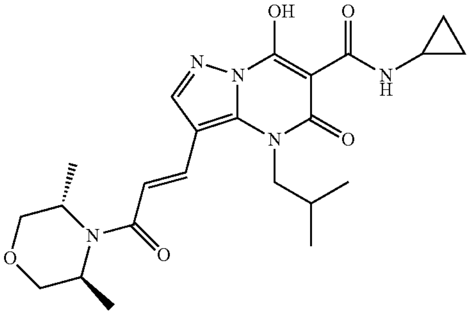

-continued
Ex 458
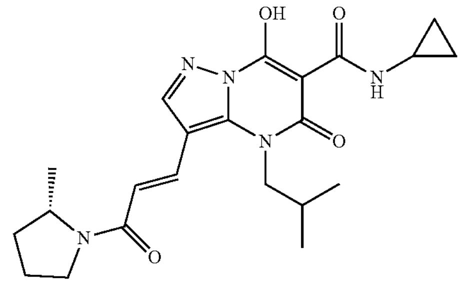
Ex 459
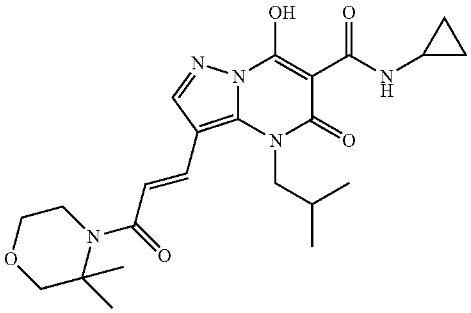
Ex 460
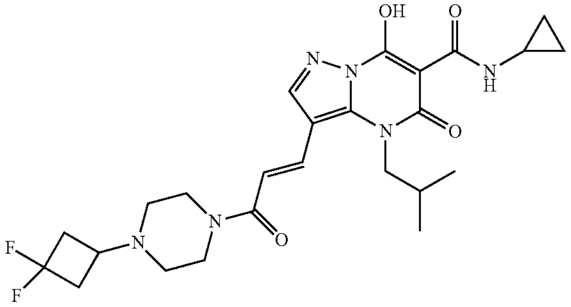
Ex 461
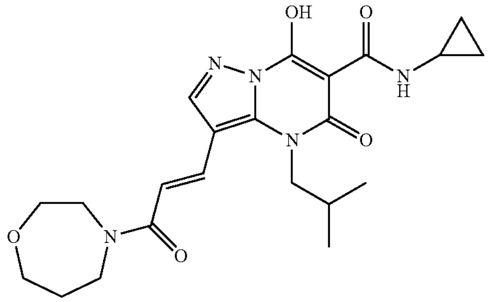
Ex 462
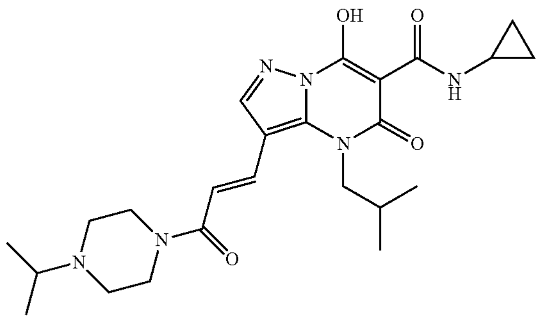
-continued
Ex 463
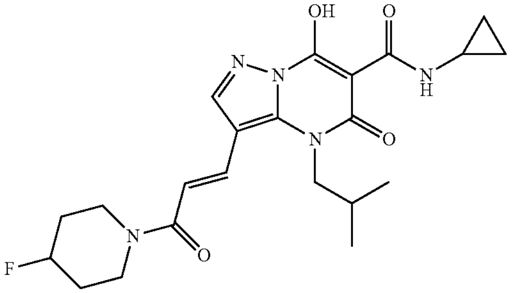
Ex 464
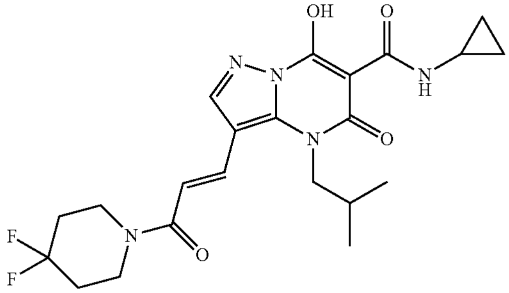
Ex 465
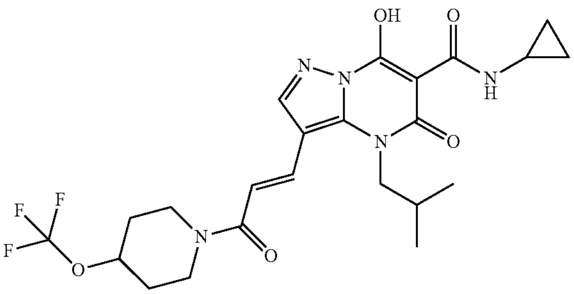
Ex 466
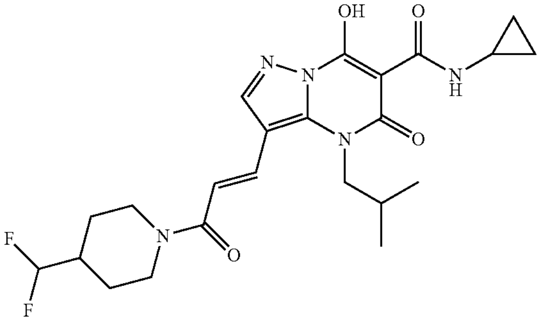

Ex 467
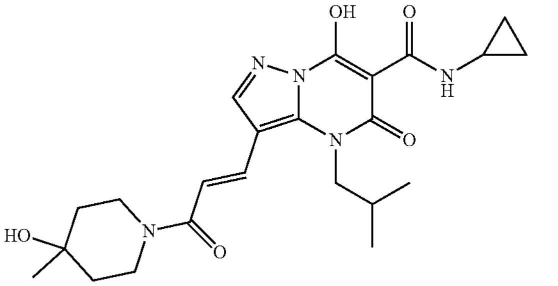
Ex 468
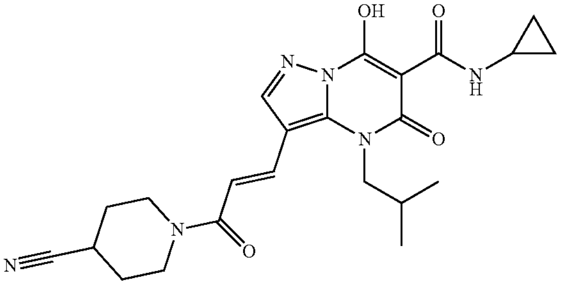
Ex 469
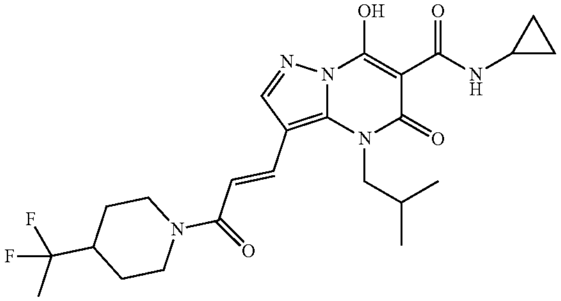
Ex 470
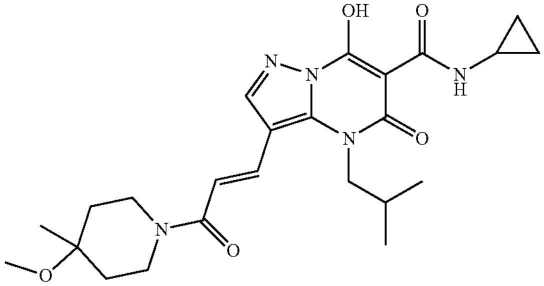
Ex 471
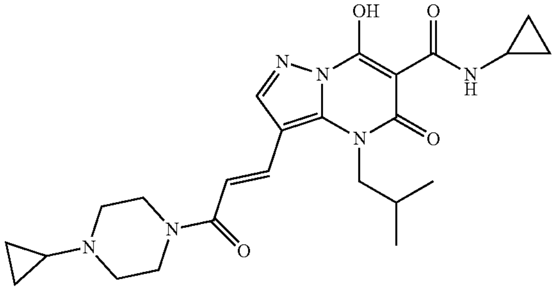
-continued
Ex 472
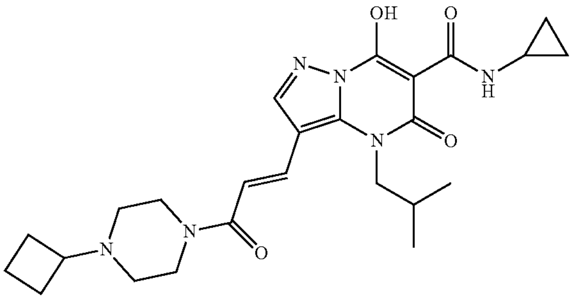
Ex 473
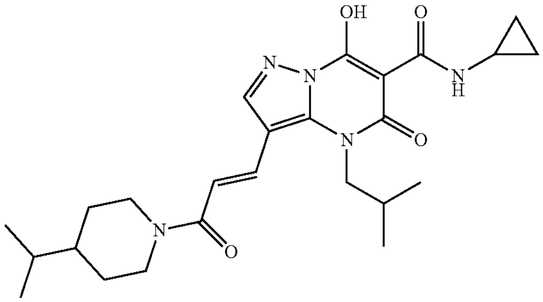
Ex 474
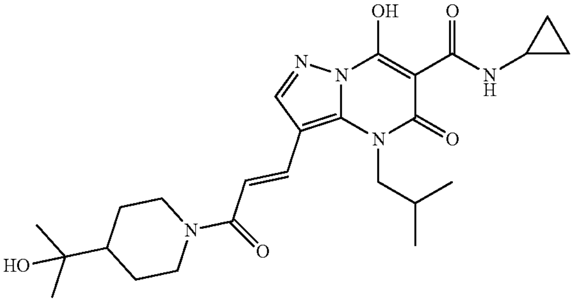
Ex 475
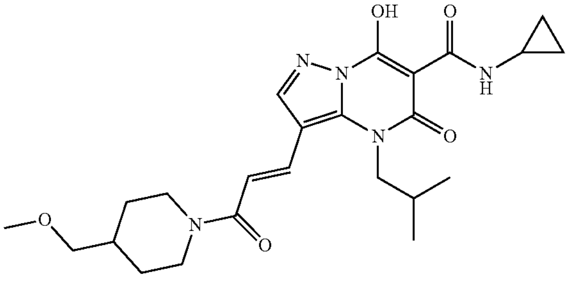
Ex 476
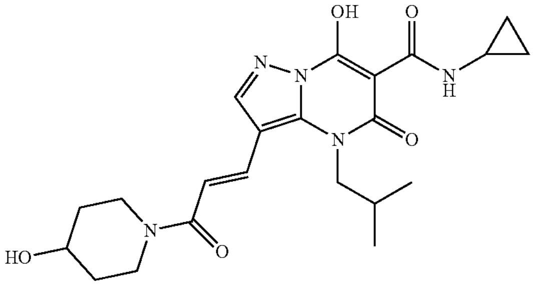

-continued
Ex 477
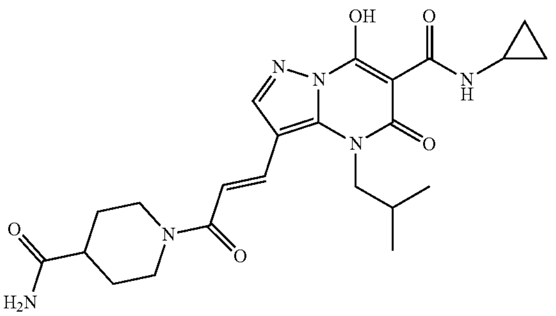
Ex 478
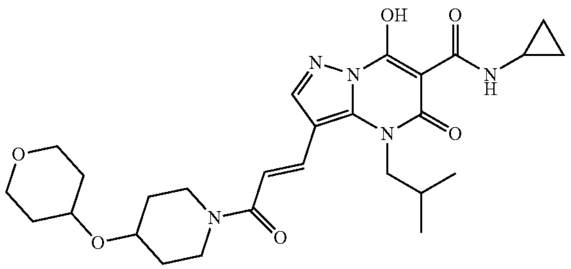
Ex 479
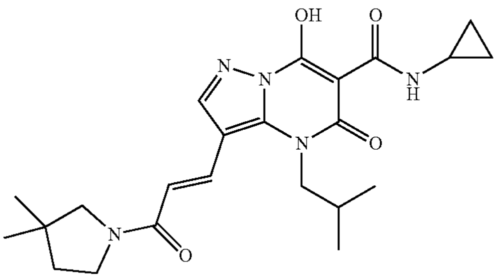
Ex 480
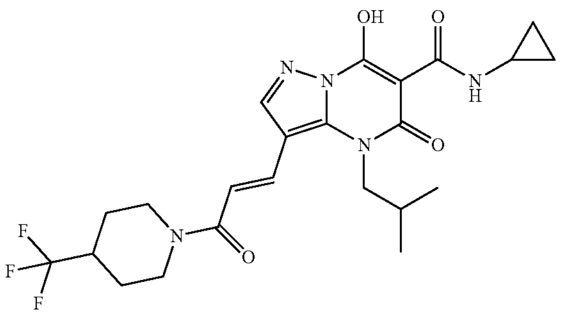
Ex 481
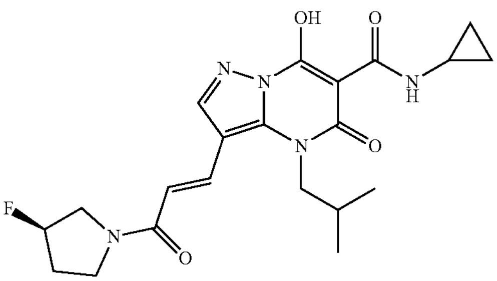
-continued
Ex 482
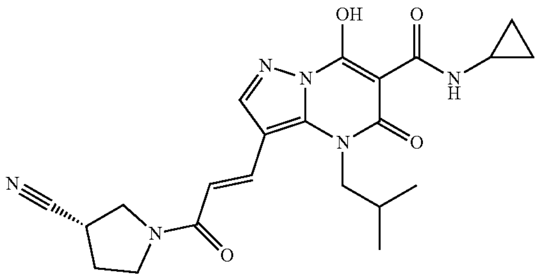
Ex 483
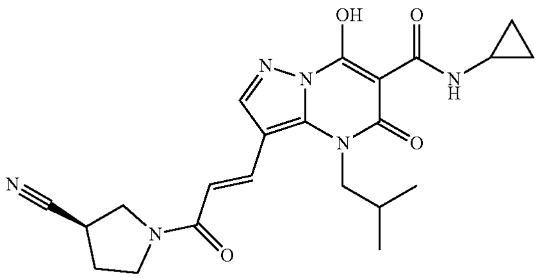
Ex 484
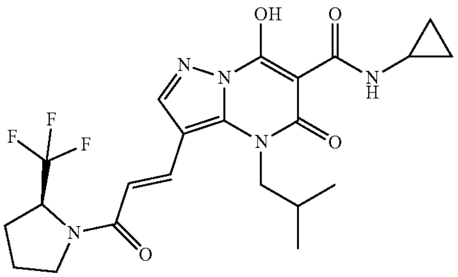
Ex 485
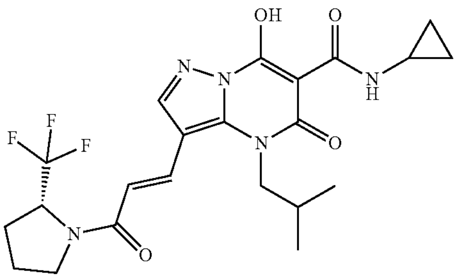
Ex 486
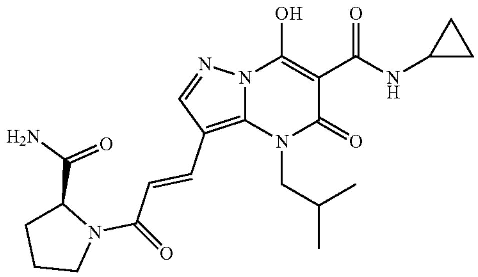

Ex 487
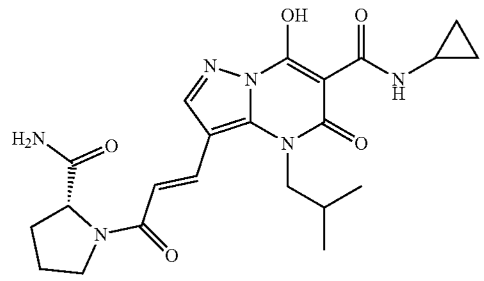
Ex 488
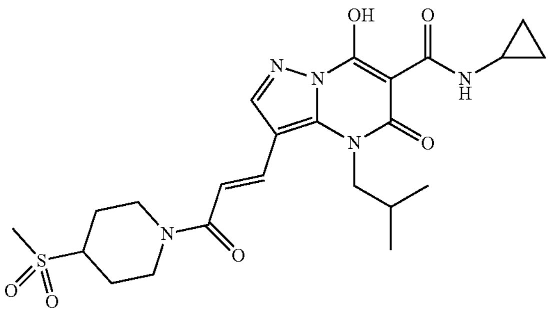
Ex 489
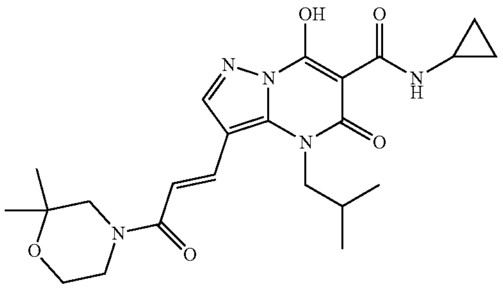
Ex 490
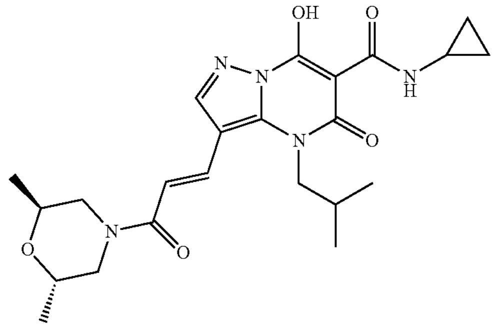
Ex 491
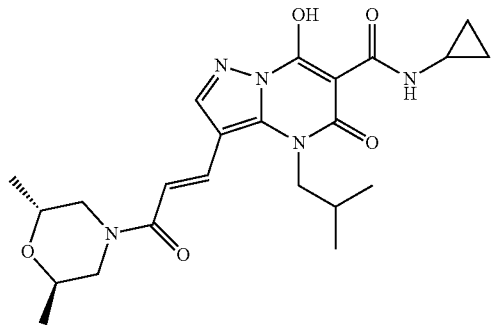
Ex 492
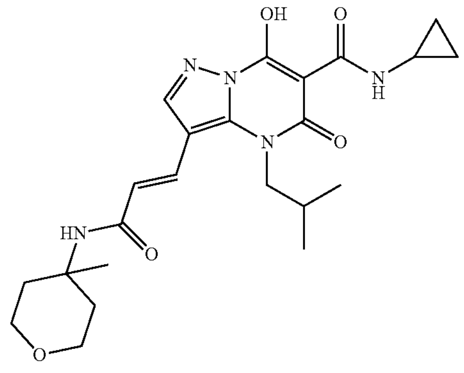
Ex 493
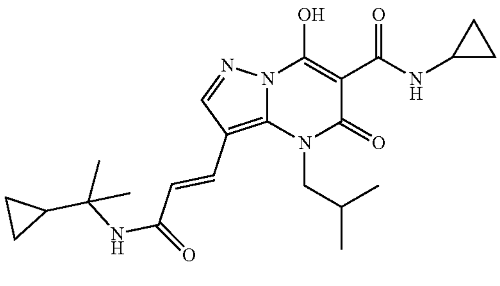
Ex 494
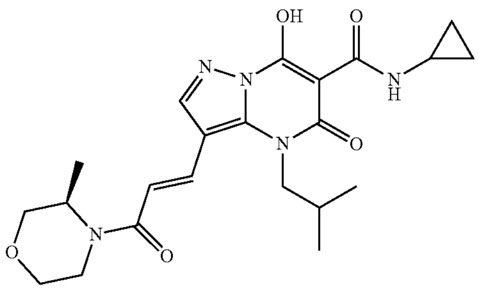
Ex 495
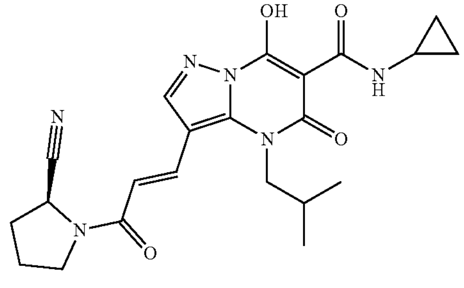
Ex 496
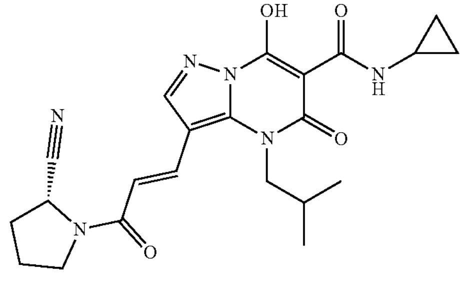

-continued
Ex 497
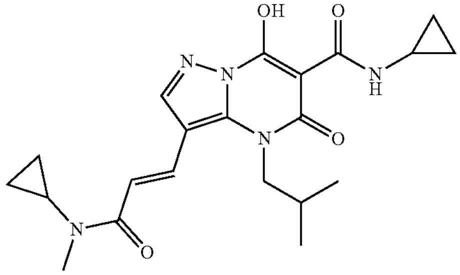
Ex 498
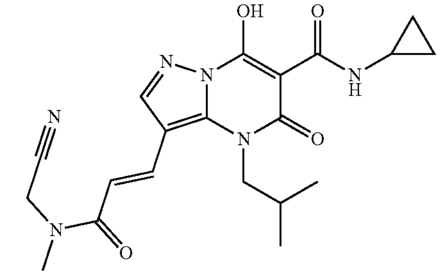
Ex 499
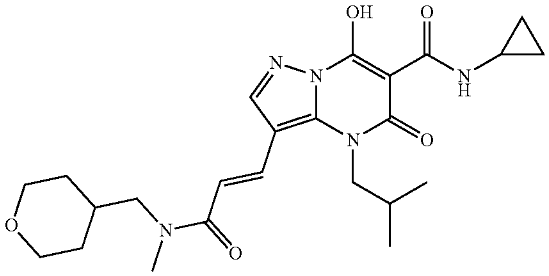
Ex 500
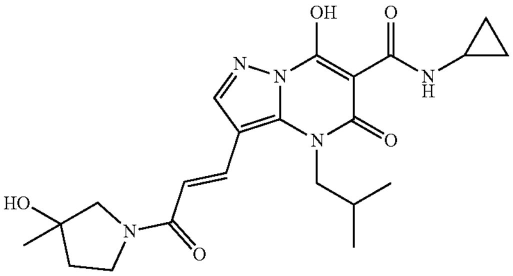
Ex 501
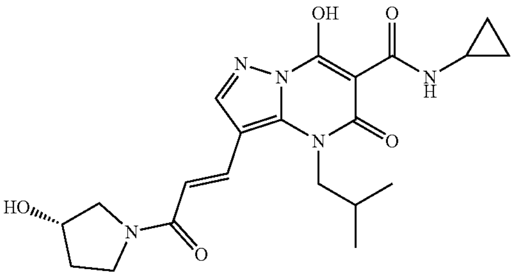
-continued
Ex 502
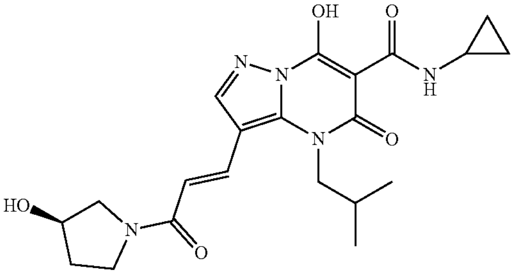
Ex 503
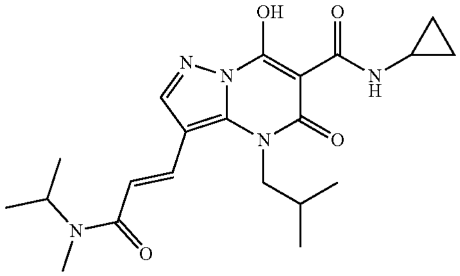
Ex 504
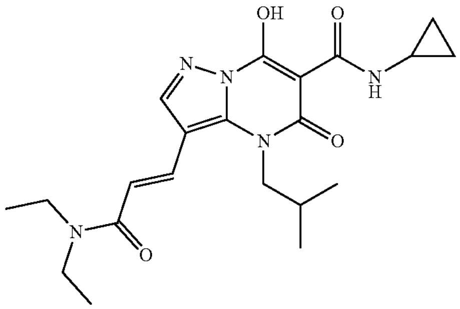
Ex 505
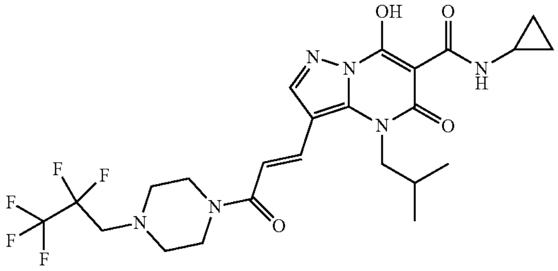
Ex 506
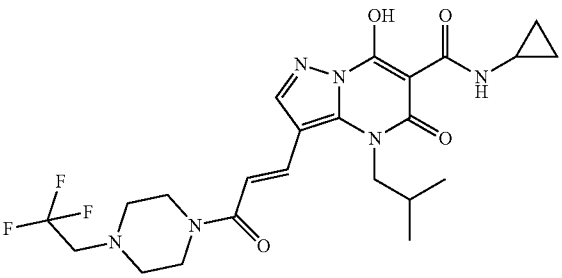

-continued
Ex 507
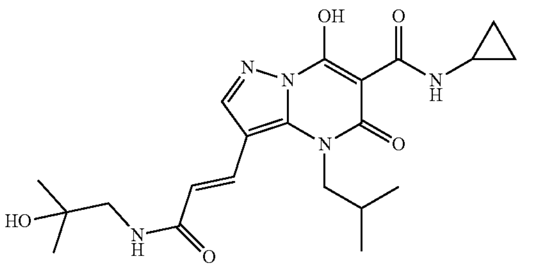
Ex 508
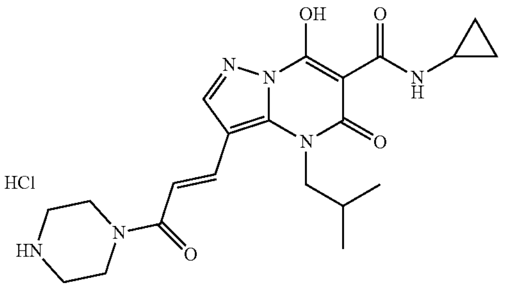
Ex 509
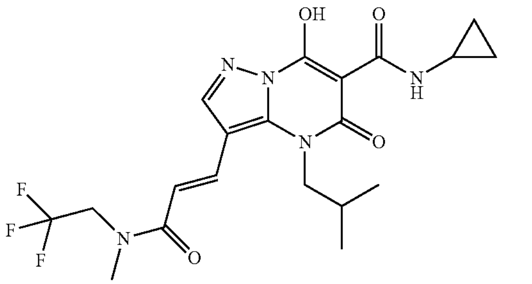
Ex 510
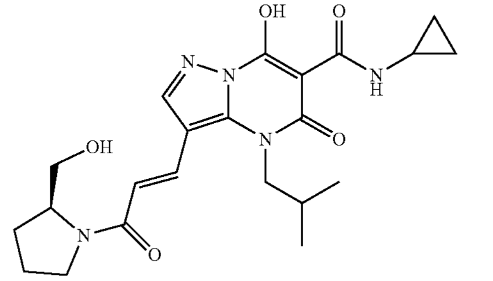
Ex 511
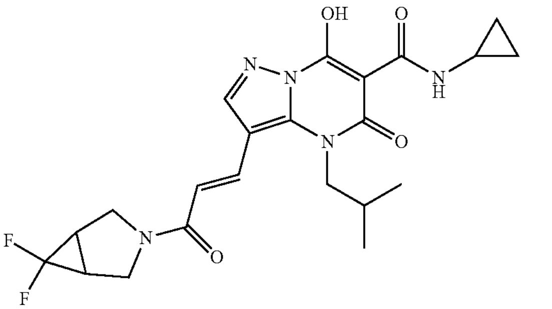
-continued
Ex 512
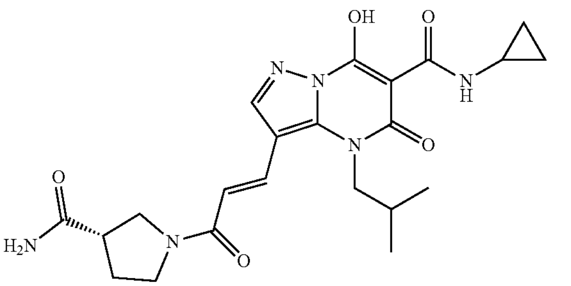
Ex 513
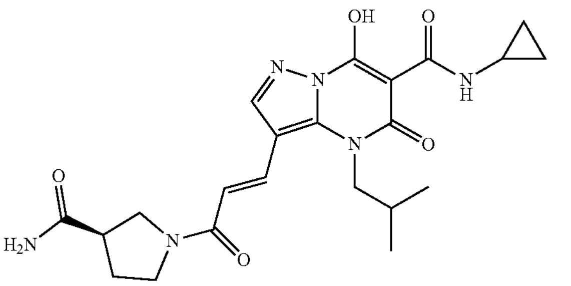
Ex 514
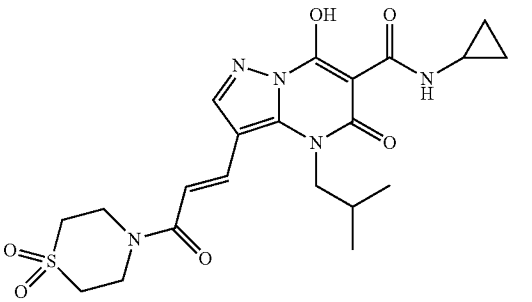
Ex 515
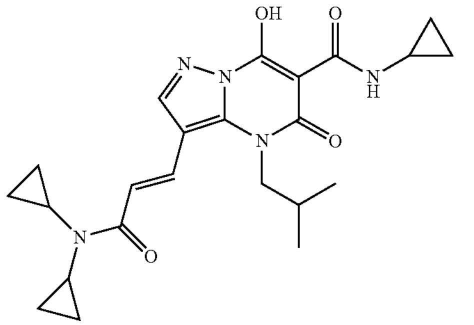
Ex 516
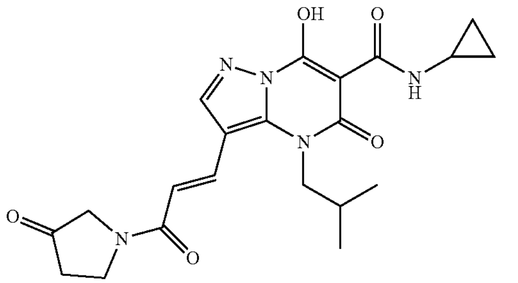

-continued
Ex 517
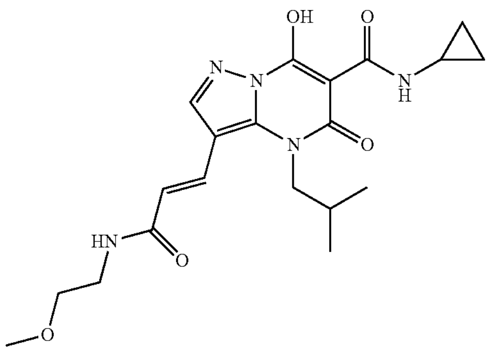
Ex 518
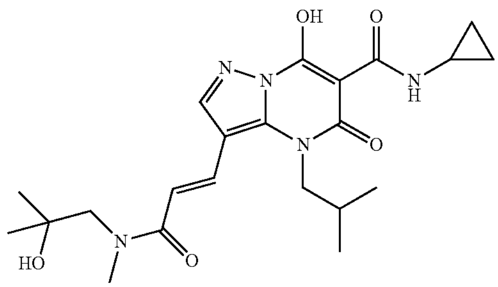
Ex 519
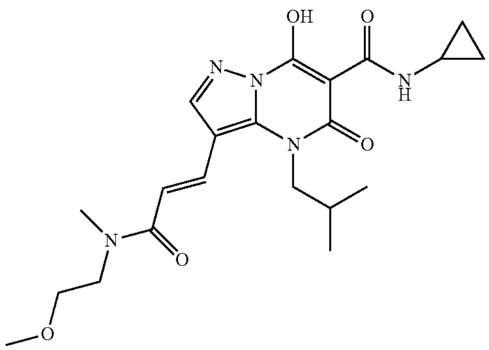
Ex 520
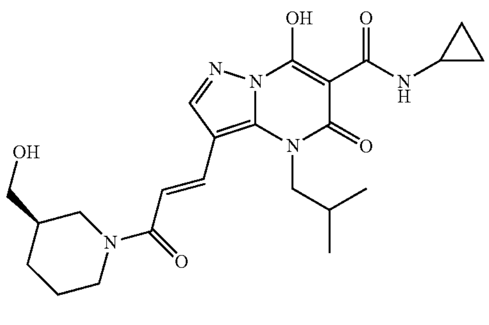
-continued
Ex 521
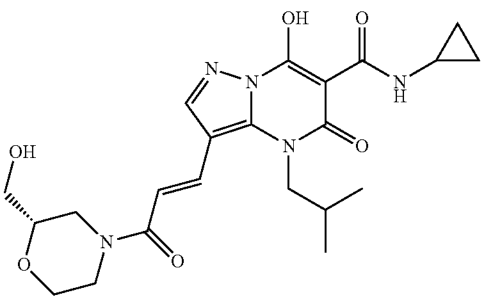
Ex 522
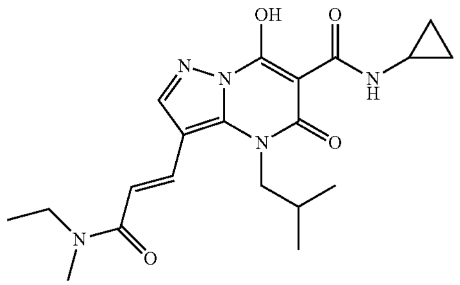
Ex 523
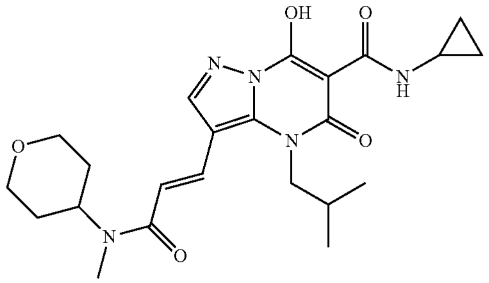
Ex 524
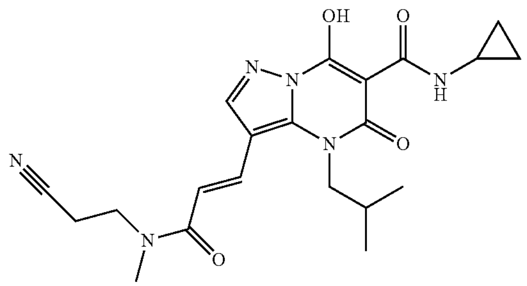
Ex 525
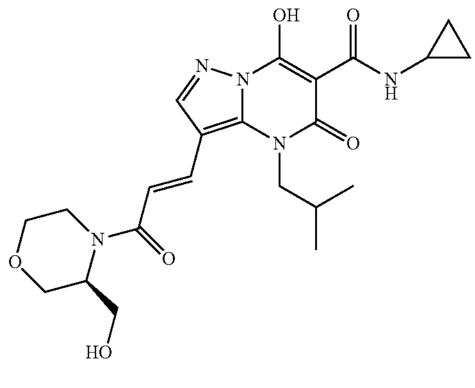

-continued
Ex 526
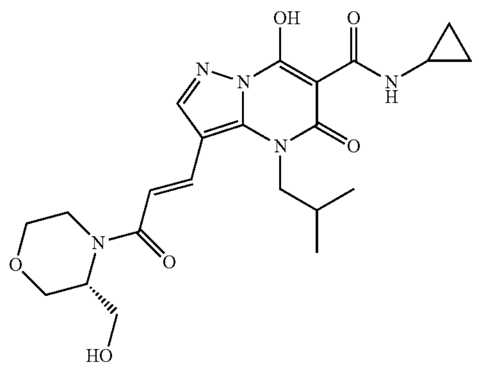
Ex 527
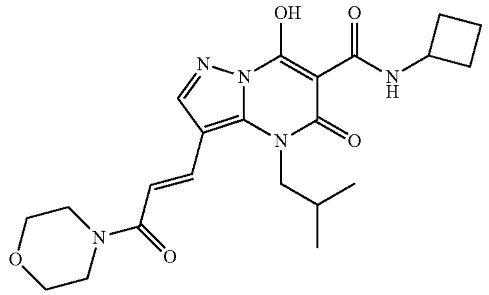
Ex 528
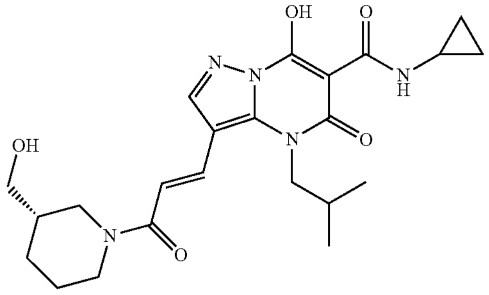
Ex 529
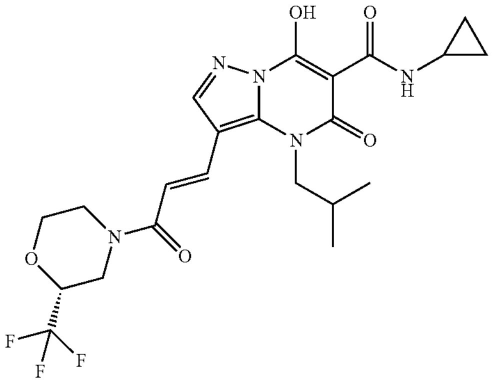
-continued
Ex 530
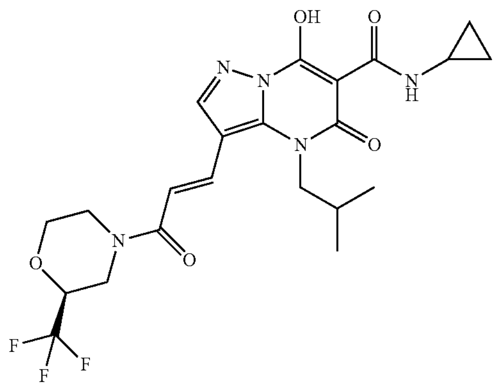
Ex 531
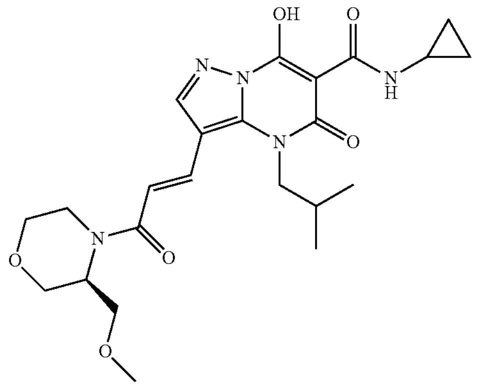
Ex 532
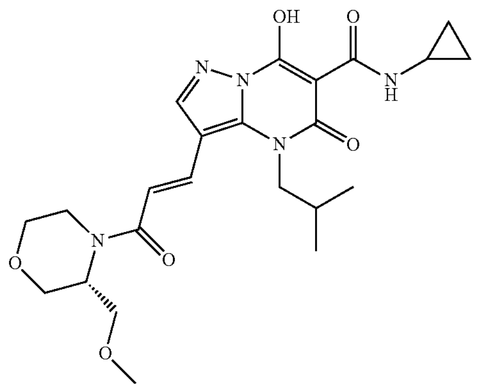
Ex 533
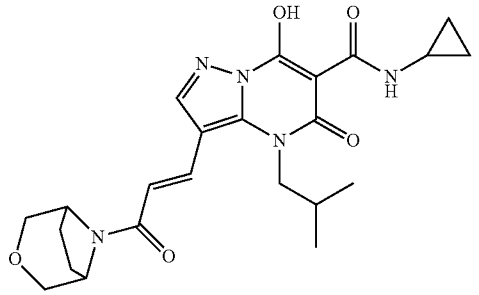

Ex 534
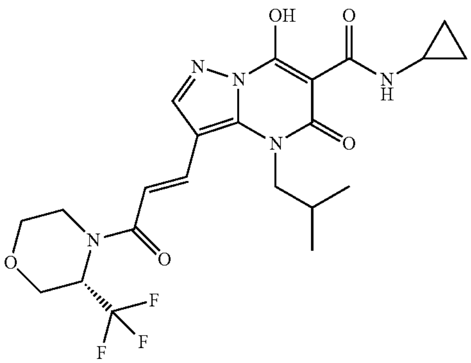
Ex 535
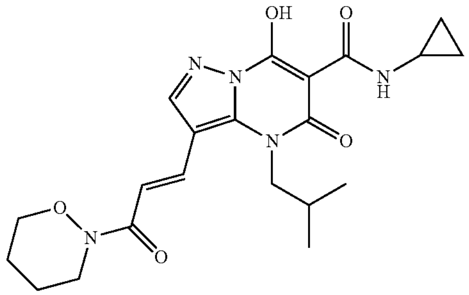
Ex 536
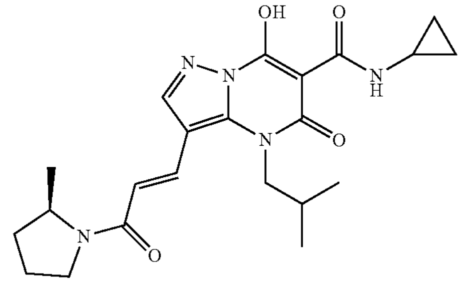
Ex 537
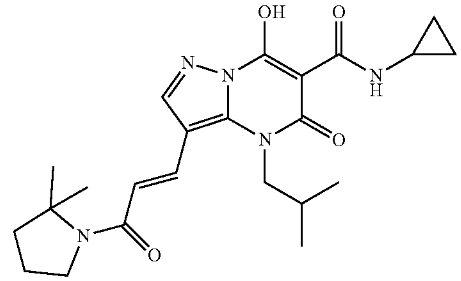
Ex 538
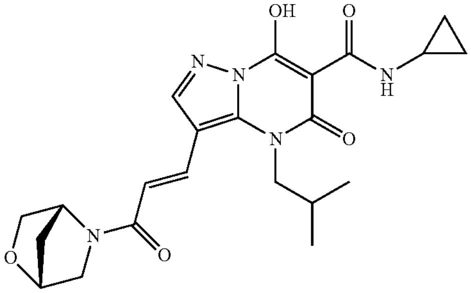
Ex 539
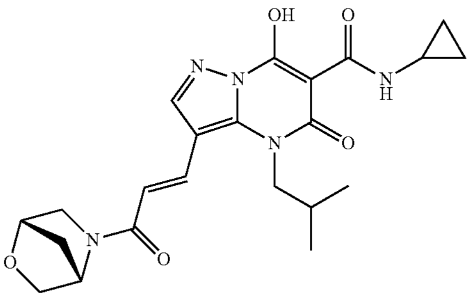
Ex 540
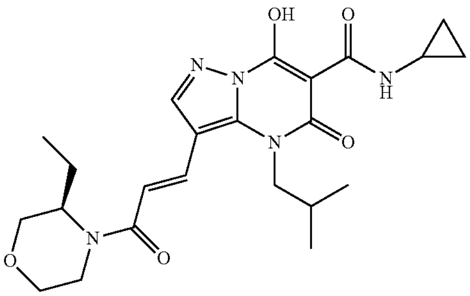
Ex 541
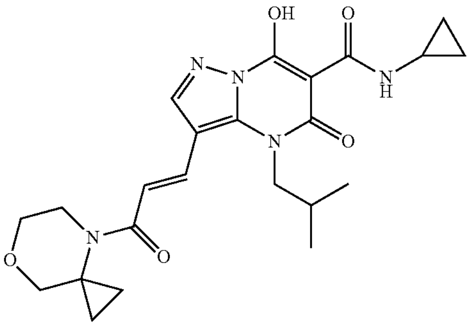
Ex 542
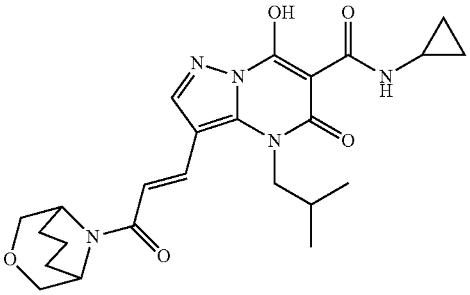
Ex 543
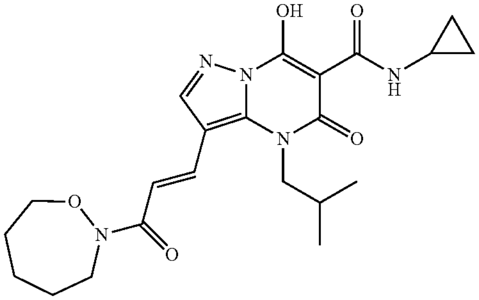

-continued
Ex 544
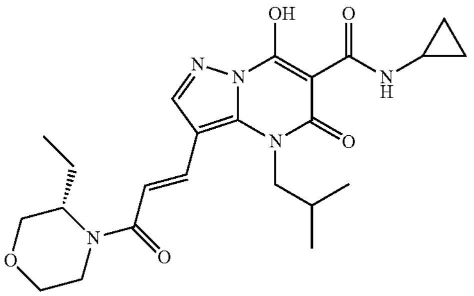
Ex 545
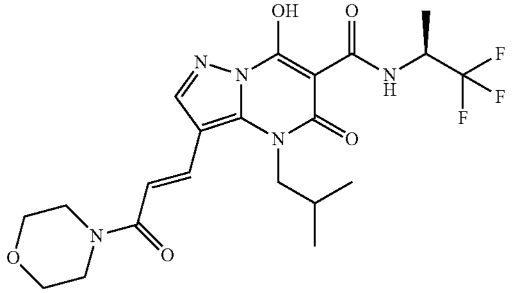
Ex 546
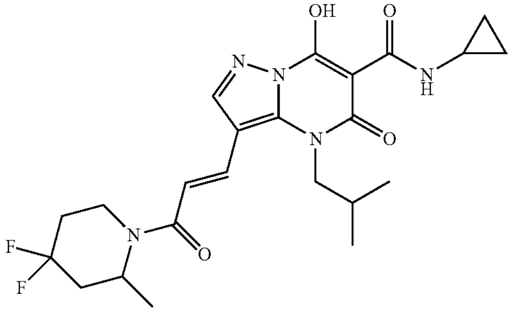
Ex 547
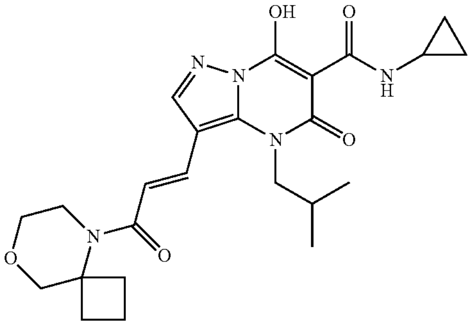
Ex 548
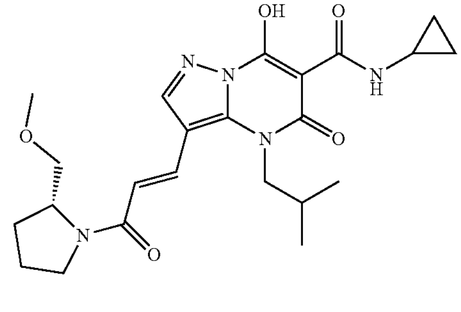
-continued
Ex 549
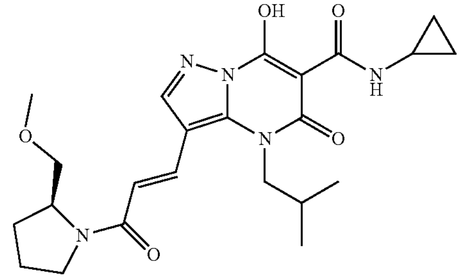
Ex 550
Isomer A
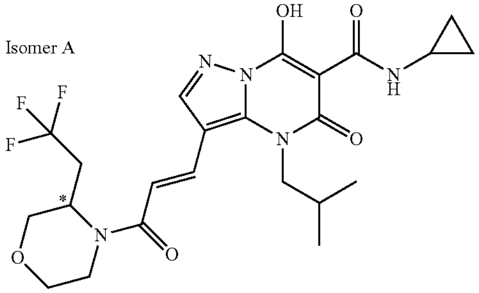
Ex 551
Isomer B
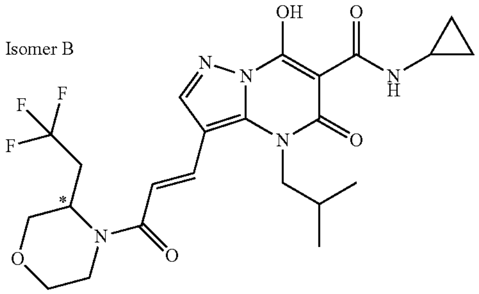
Ex 552
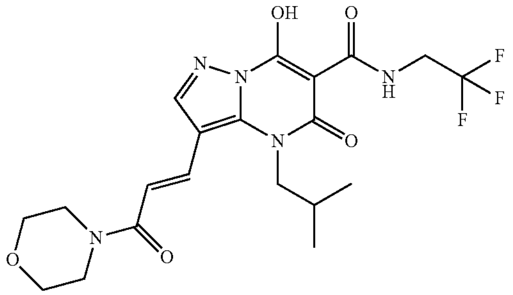
Ex 553
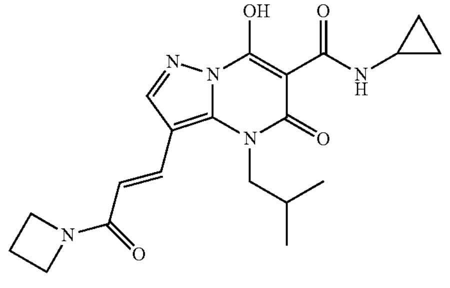

-continued
Ex 554
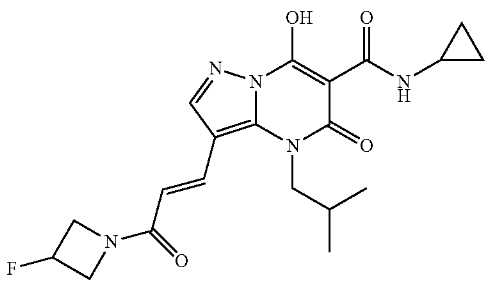
Ex 555
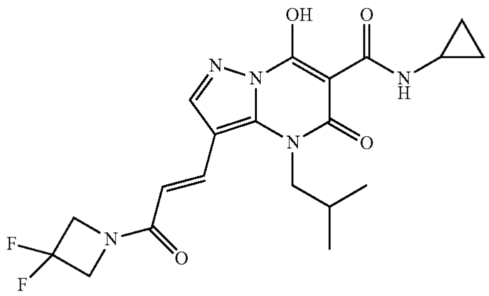
Ex 556
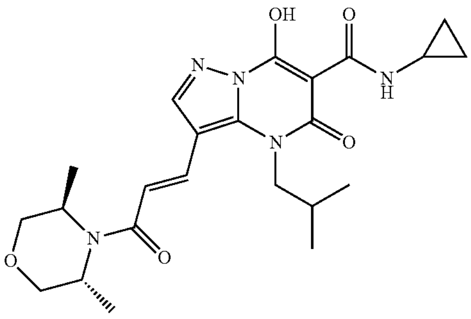
Ex 557
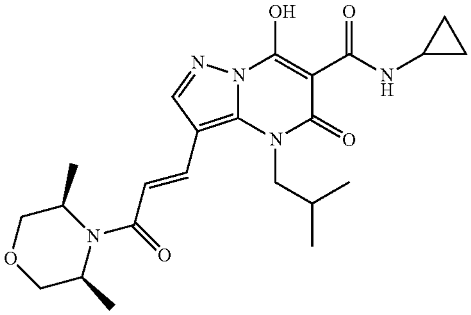
Ex 558
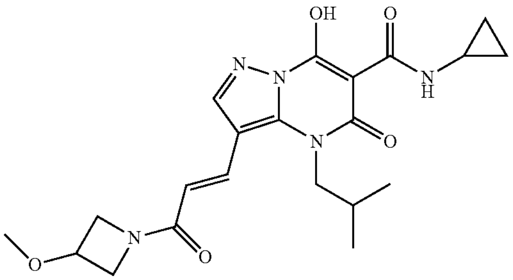
-continued
Ex 559
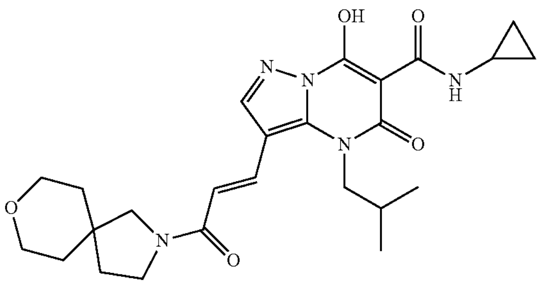
Ex 560
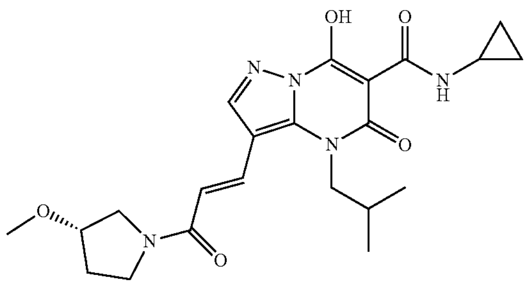
Ex 561
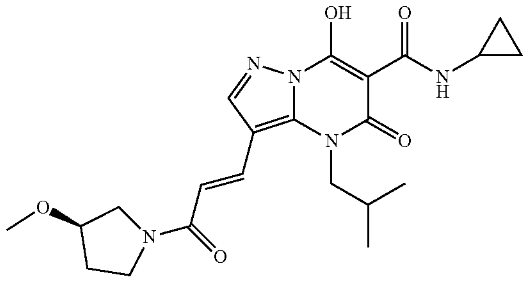
Ex 562
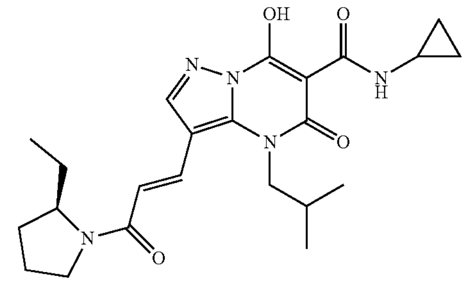
Ex 563
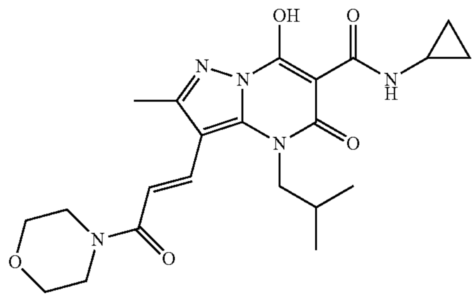

-continued
Ex 564
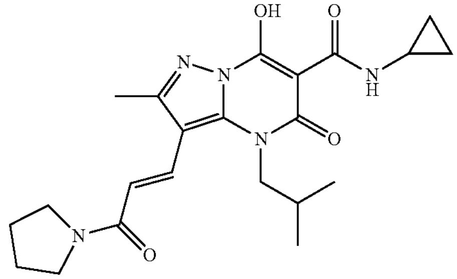
Ex 565
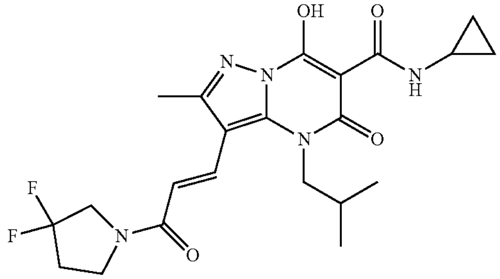
Ex 566
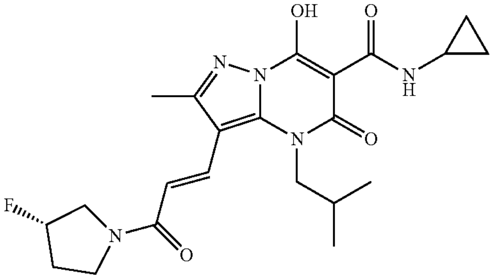
Ex 567
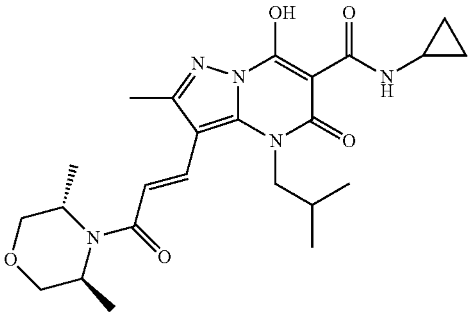
Ex 568
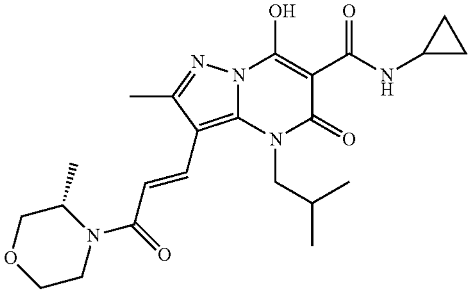
-continued
Ex 569
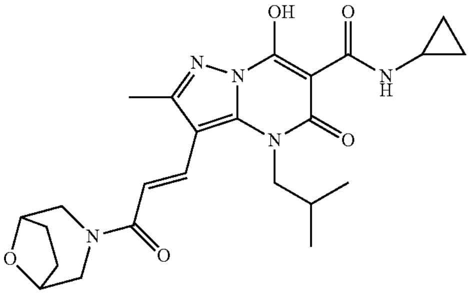
Ex 570
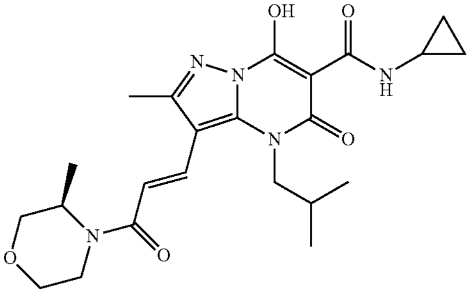
Ex 571
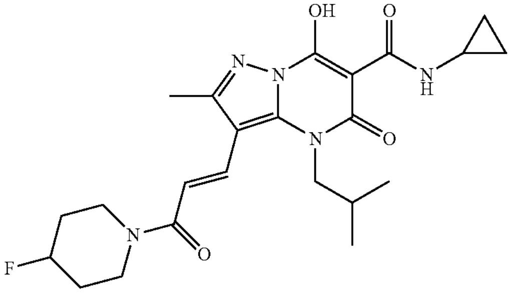
Ex 572
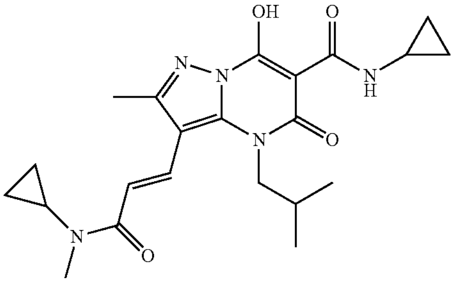
Ex 573
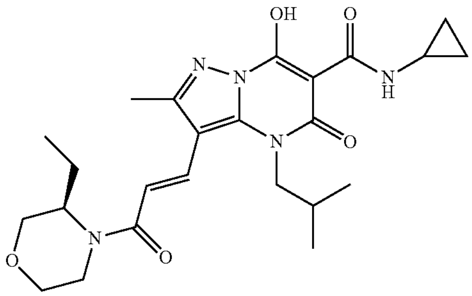

-continued
Ex 574
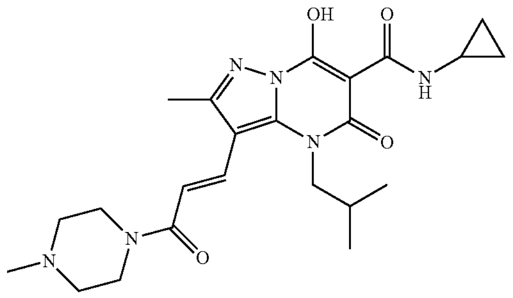
Ex 575
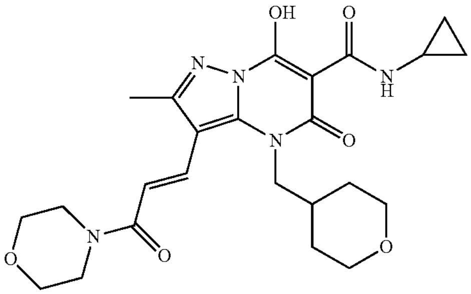
Ex 576
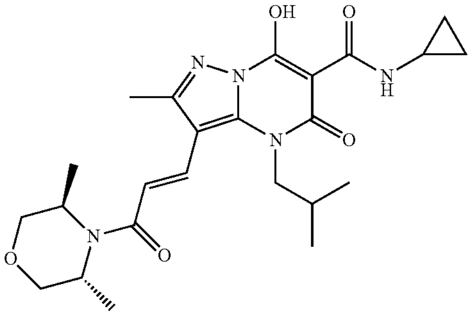
Ex 577
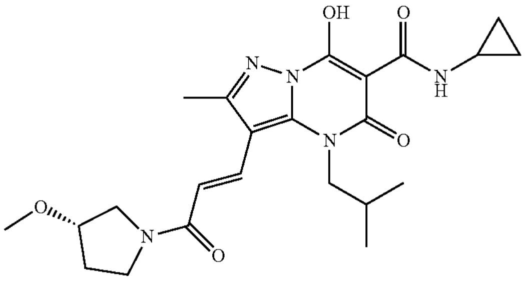
Ex 578
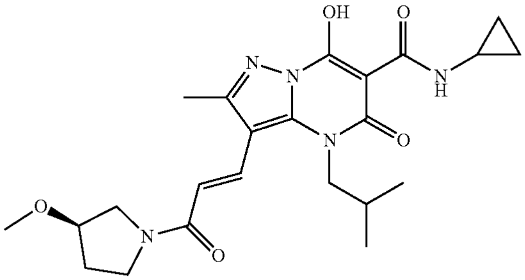
-continued
Ex 579
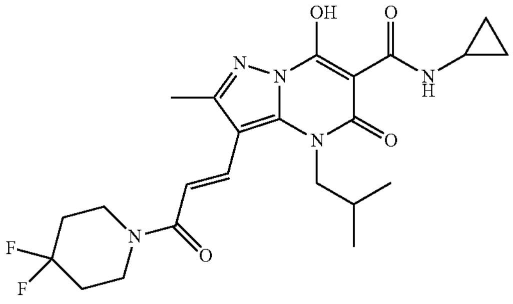
Ex 580
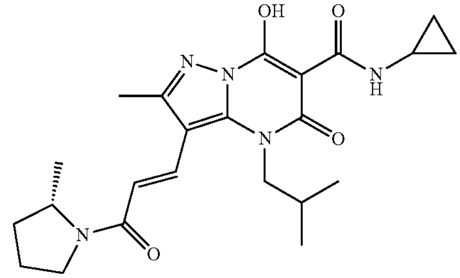
Ex 581
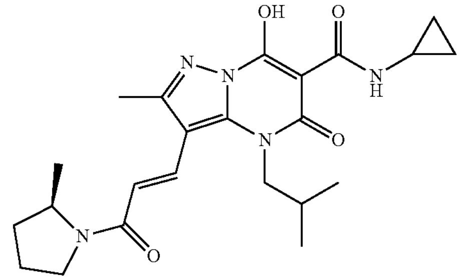
Ex 582
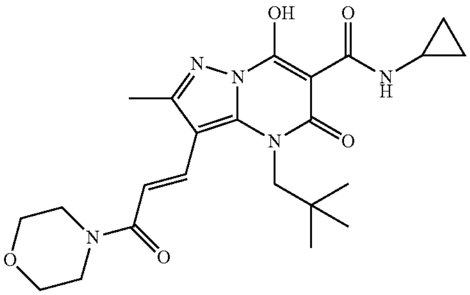
Ex 583
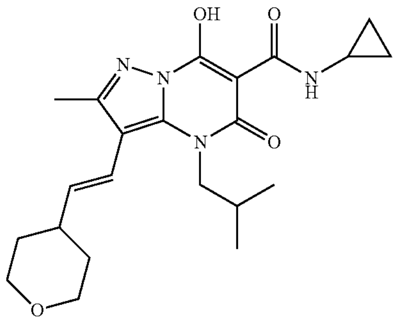

-continued
Ex 584
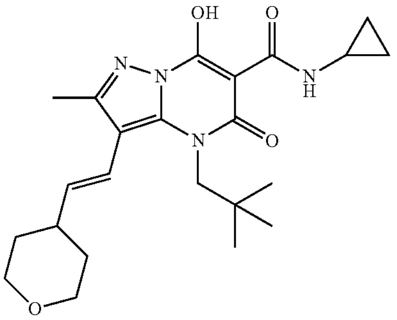
Ex 585
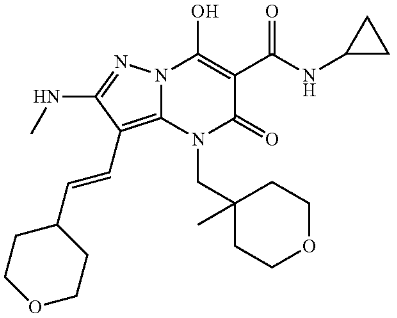
Ex 586
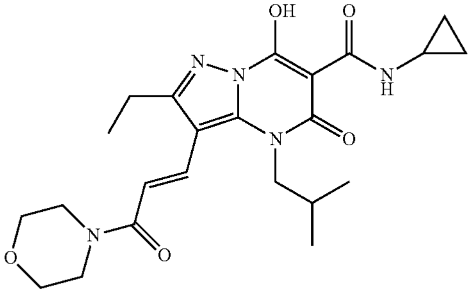
Ex 587
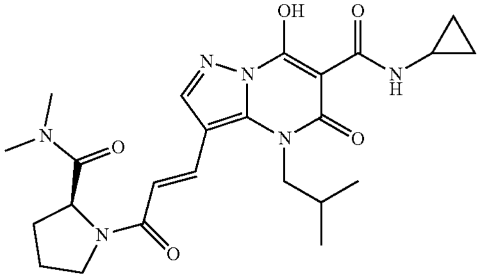
Ex 588
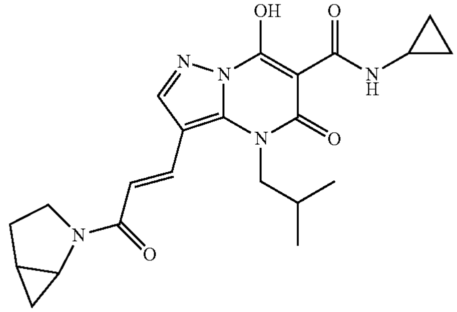
-continued
Ex 589
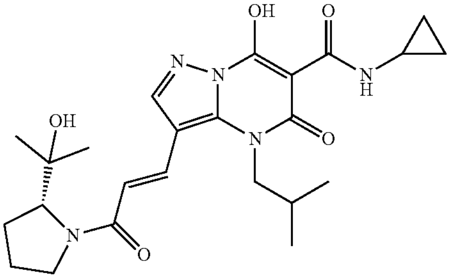
Ex 590
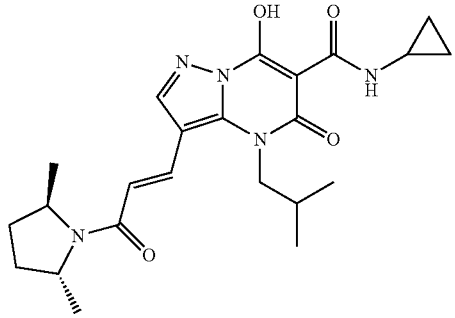
Ex 591
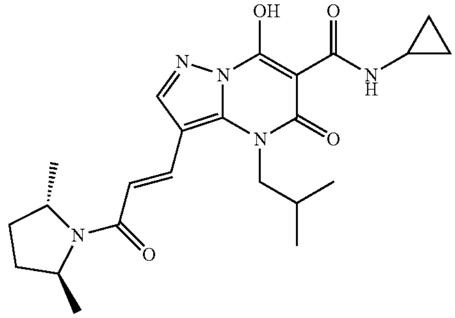
Ex 592
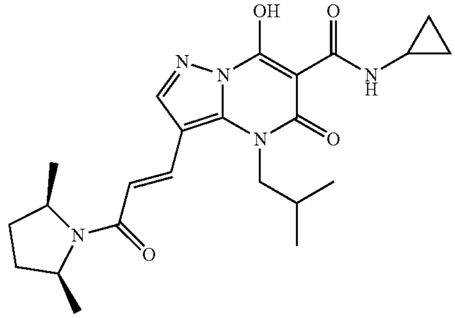
Ex 593
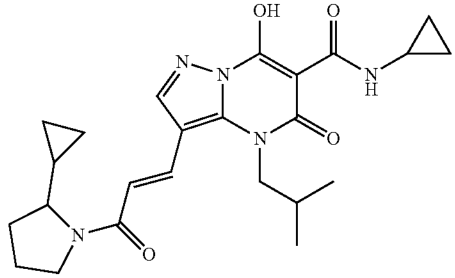

-continued
Ex 594
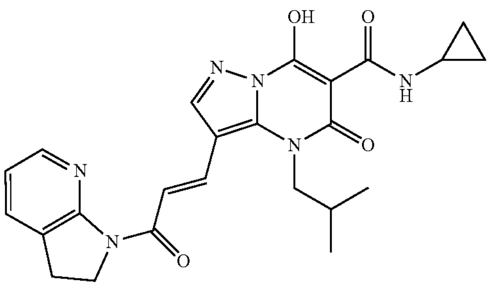
Ex 595
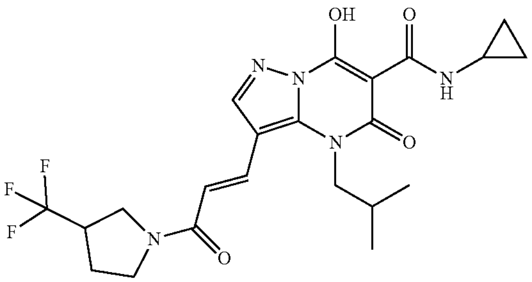
Ex 596
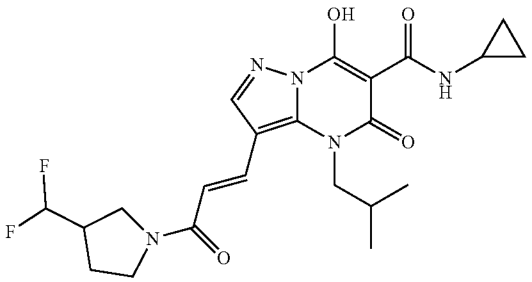
Ex 597
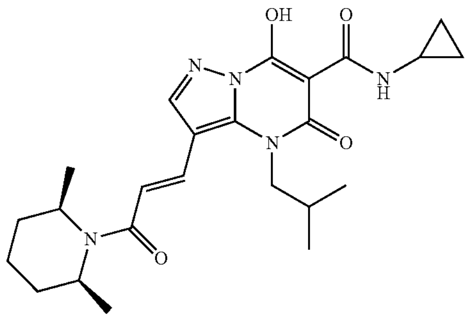
Ex 598
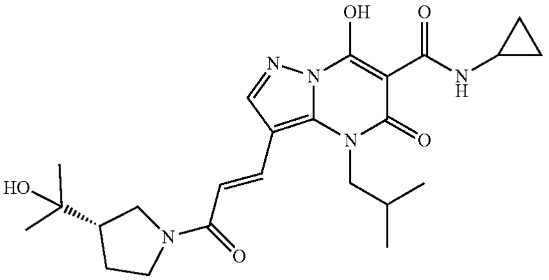
-continued
Ex 599
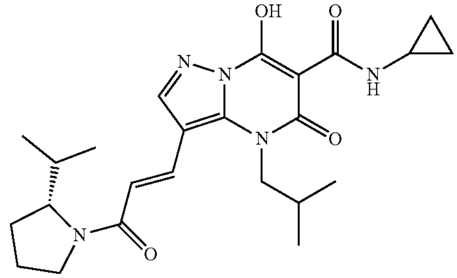
Ex 600
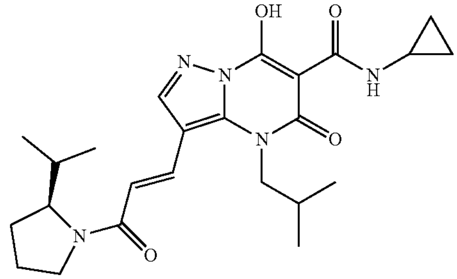
Ex 601
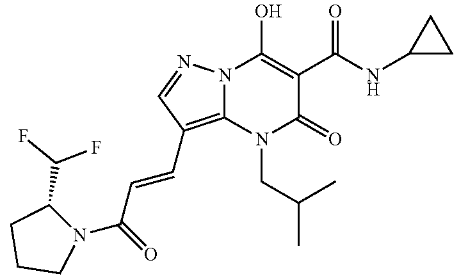
Ex 602
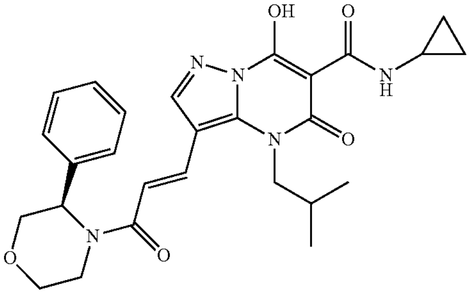
Ex 603
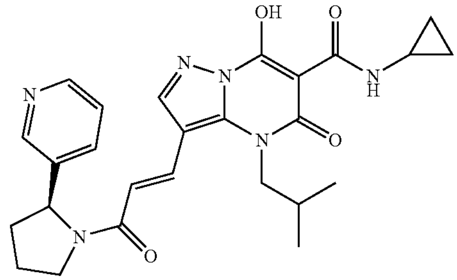

-continued
Ex 604
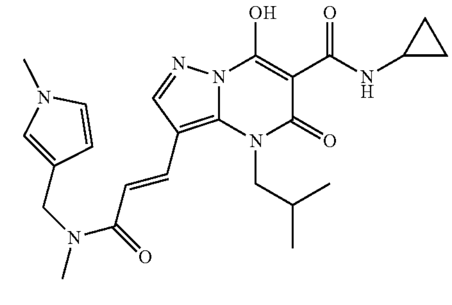
Ex 605
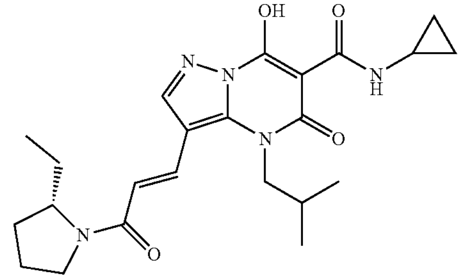
Ex 606
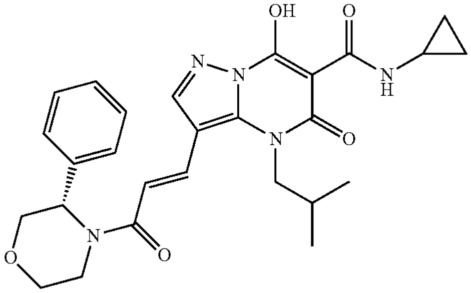
Ex 607
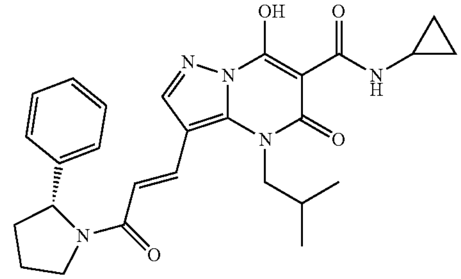
Ex 608
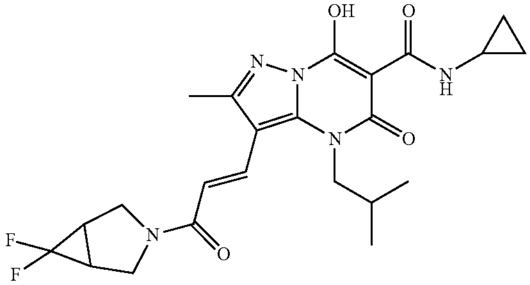
-continued
Ex 609
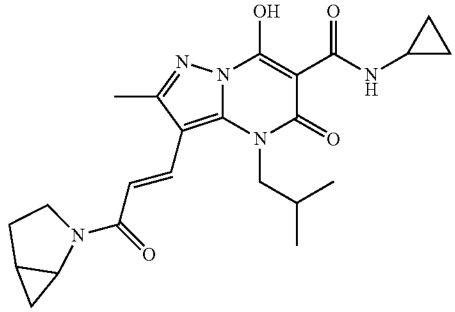
Ex 610
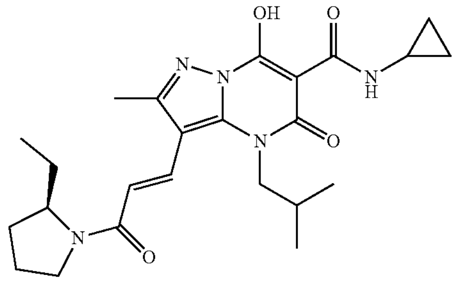
Ex 611
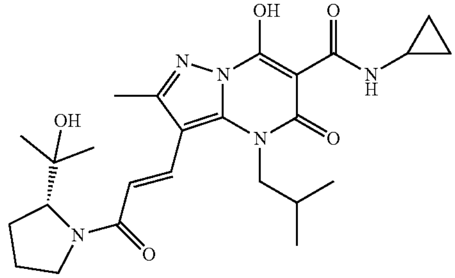
Ex 612
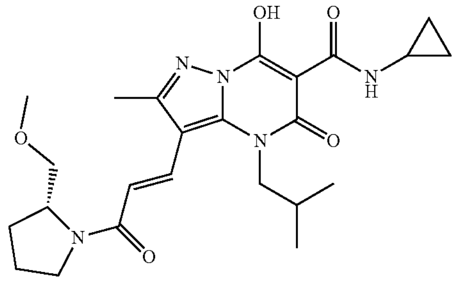
Ex 613
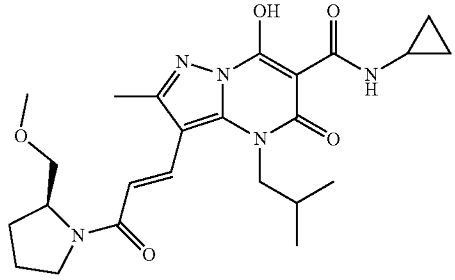

-continued
Ex 614
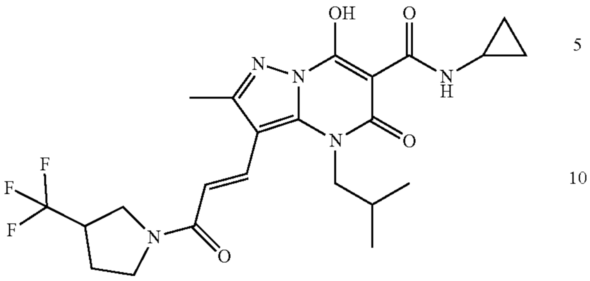
Ex 615
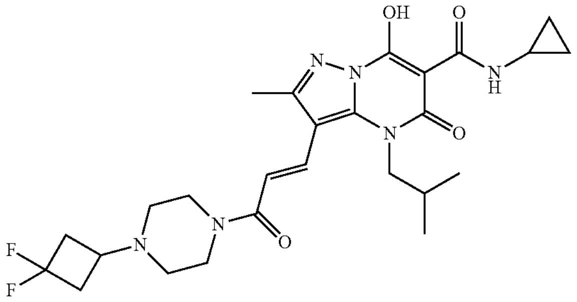
Ex 616
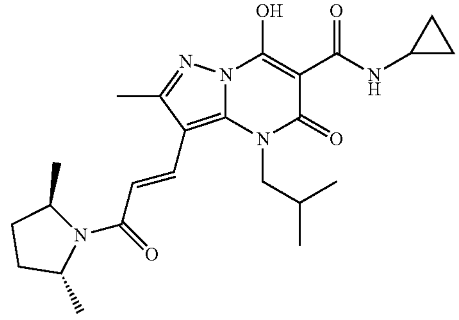
Ex 617
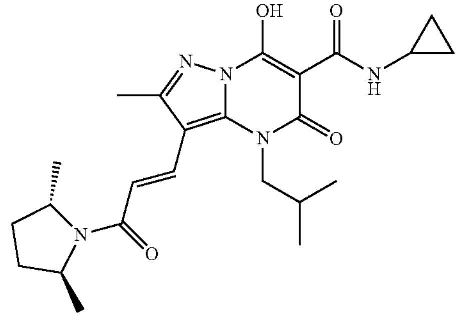
Ex 618
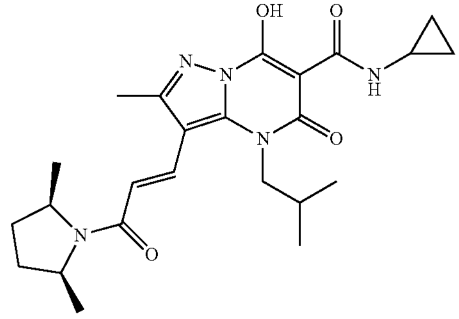
-continued
Ex 619
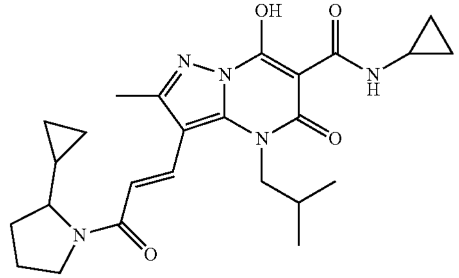
Ex 620
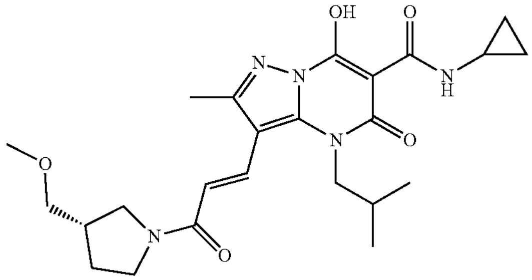
Ex 621
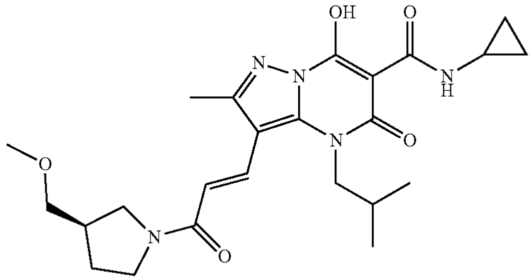
Ex 622
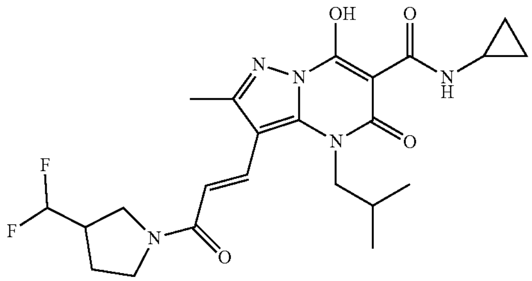
Ex 623
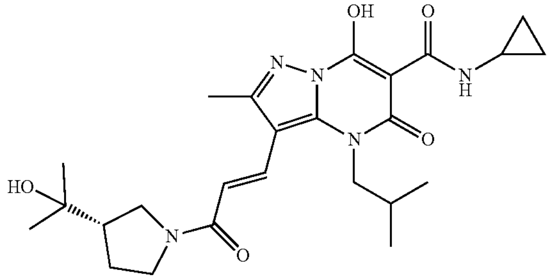

-continued
Ex 624
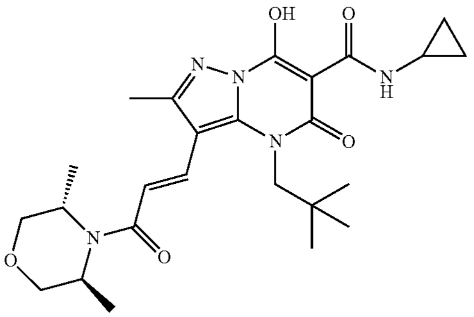
Ex 625
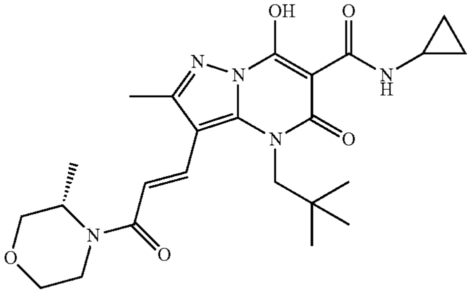
Ex 626
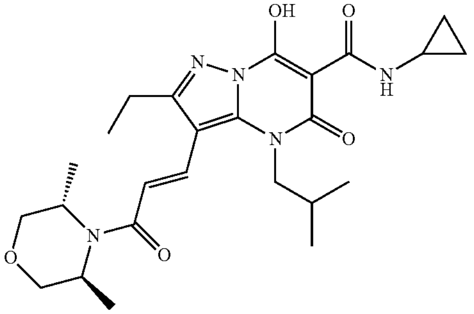
Ex 627
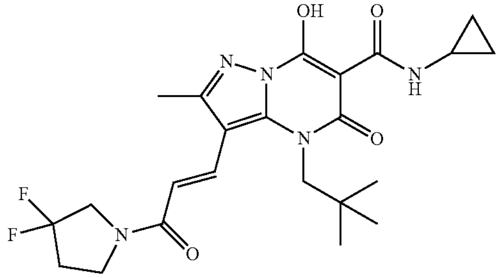
Ex 628
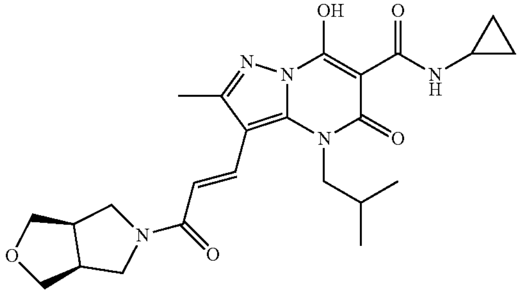
-continued
Ex 629
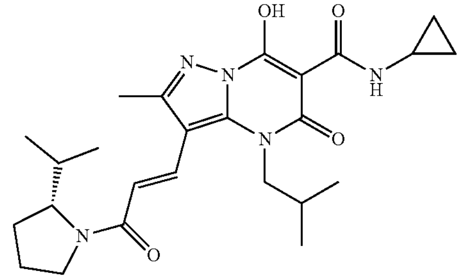
Ex 630
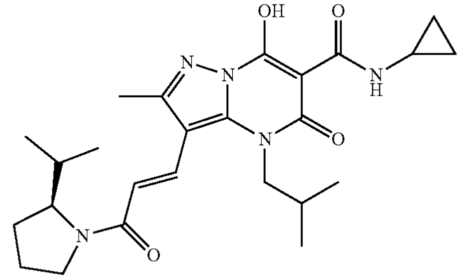
Ex 631
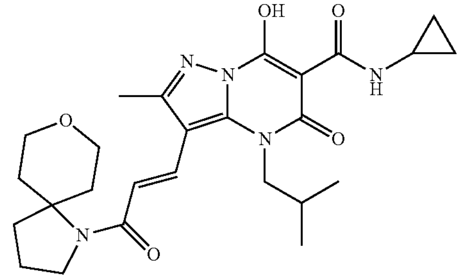
Ex 632
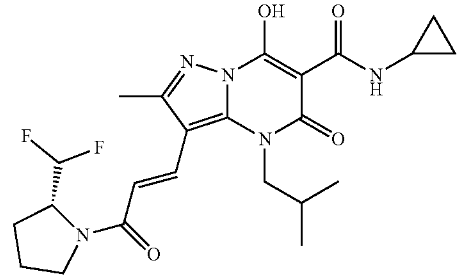
Ex 633
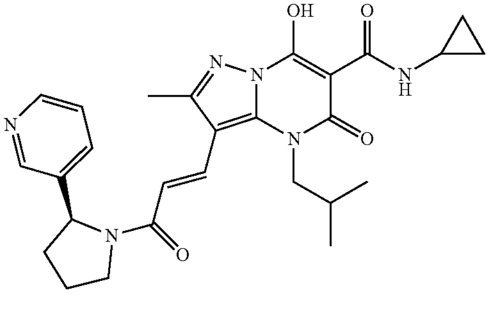

-continued
Ex 634
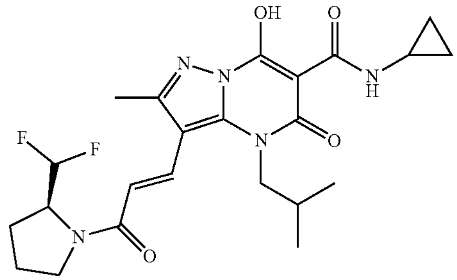
Ex 635
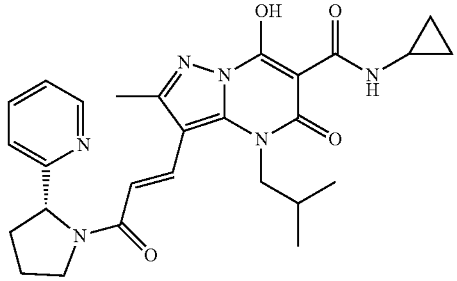
Ex 636
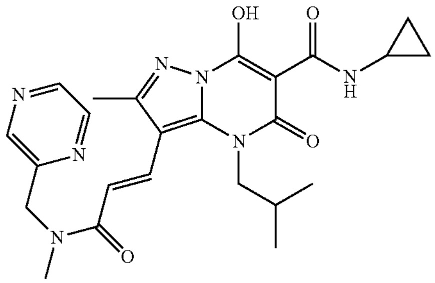
Ex 637
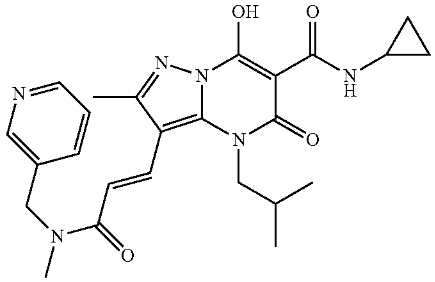
Ex 638
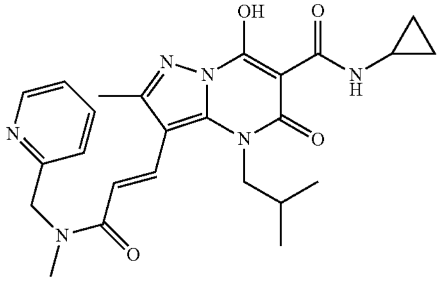
-continued
Ex 639
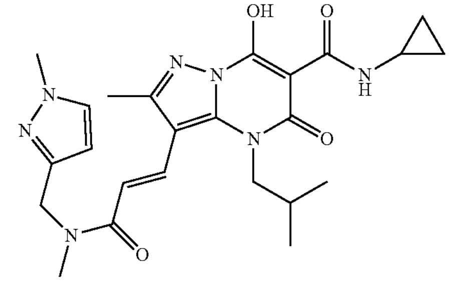
Ex 640
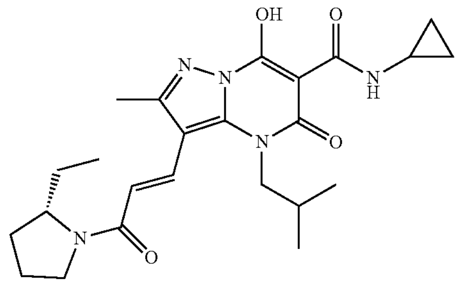
Ex 641
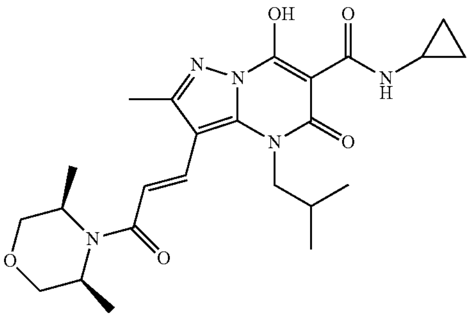
Ex 642
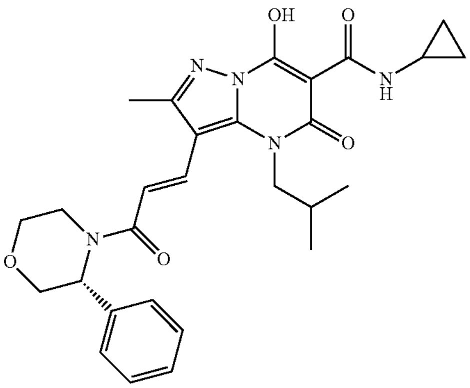

-continued
Ex 643
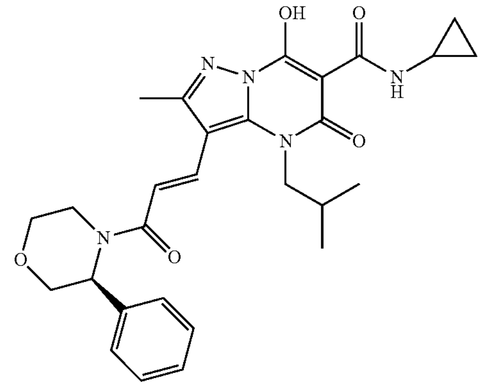
Ex 644
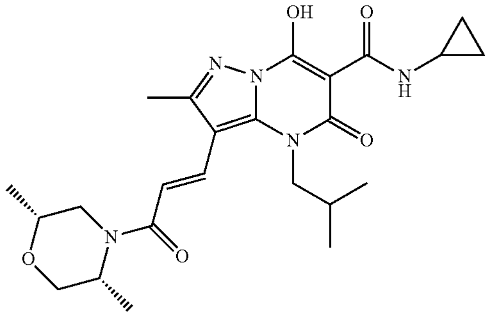
Ex 645
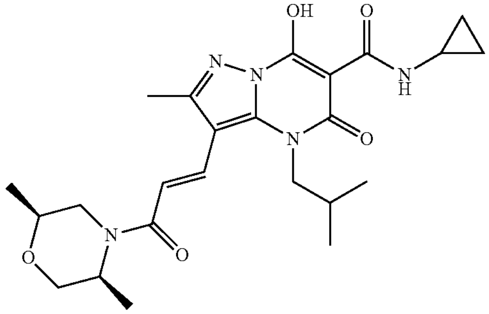
Ex 646
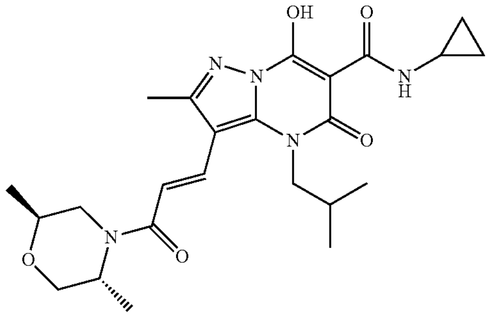
-continued
Ex 647
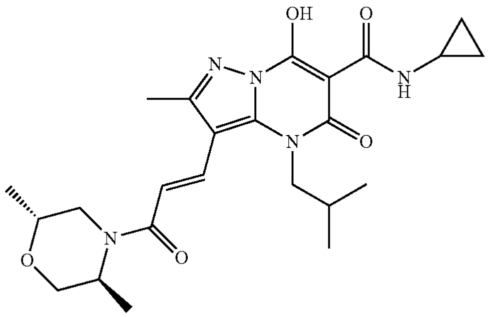
Ex 648
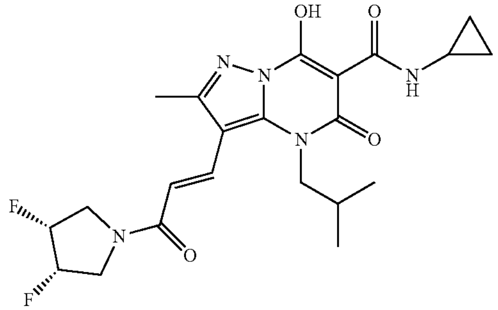
Ex 649
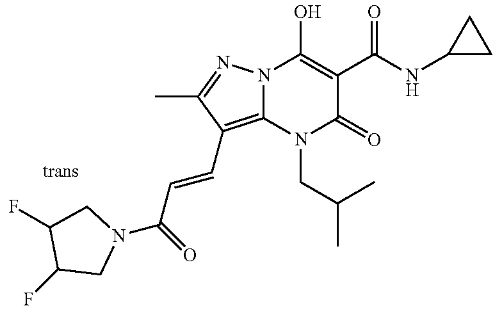
Ex 650
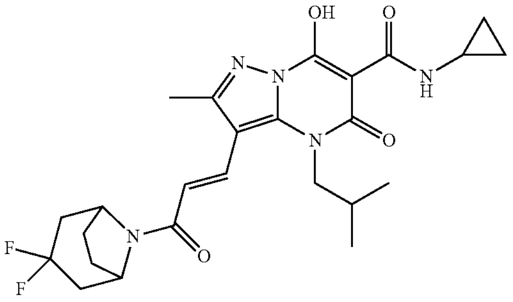
Ex 651
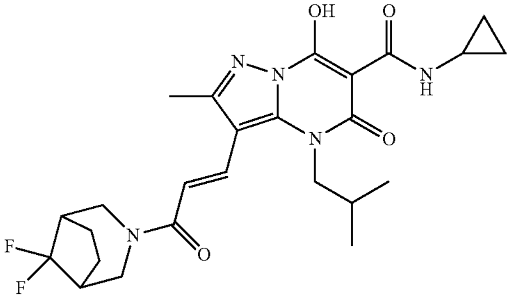

-continued
Ex 652
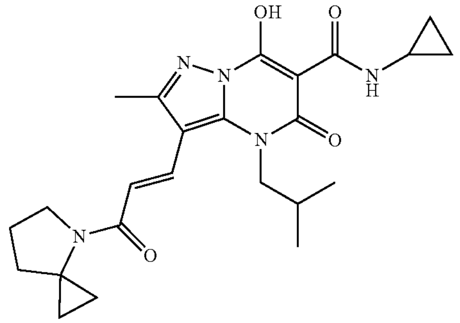
Ex 653
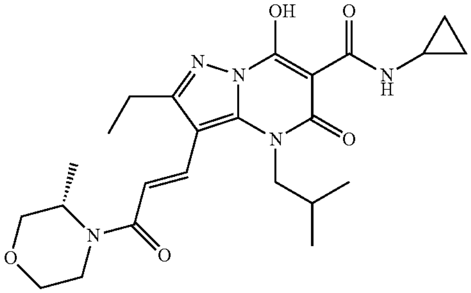
Ex 654
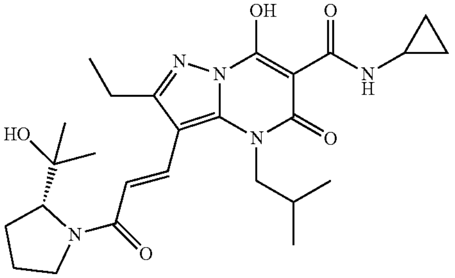
Ex 655
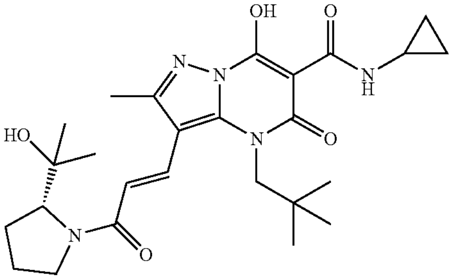
Ex 656
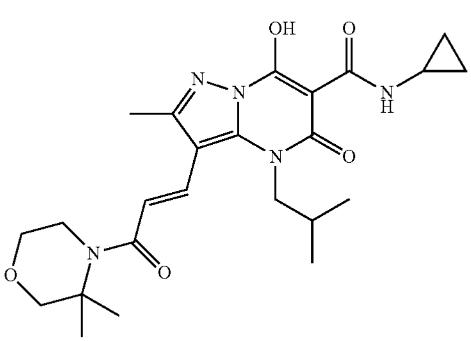
-continued
Ex 657
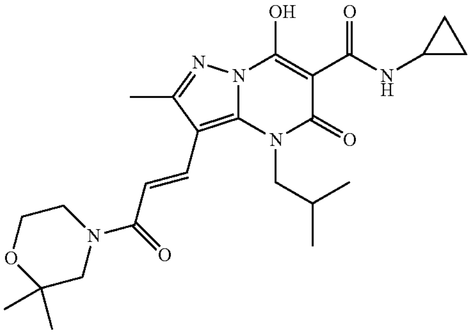
Ex 658
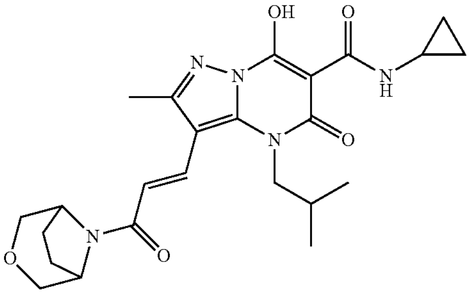
Ex 659
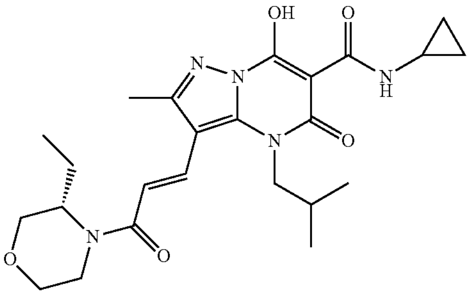
Ex 660
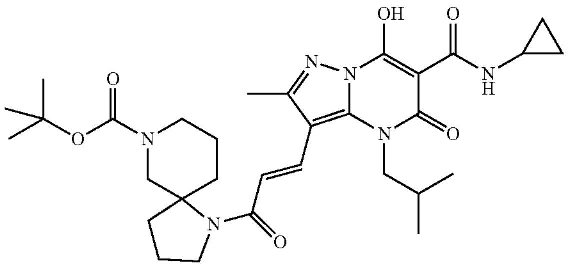
Ex 661
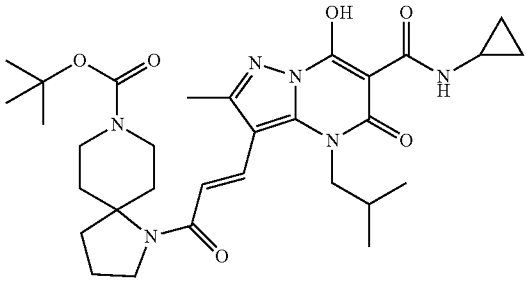

-continued
Ex 662
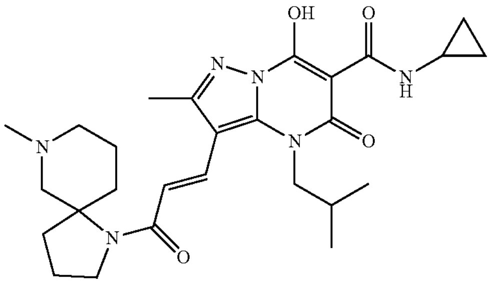
Ex 663
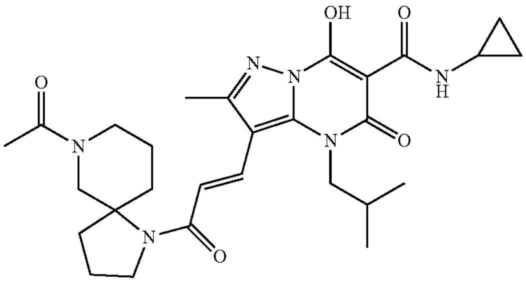
Ex 664
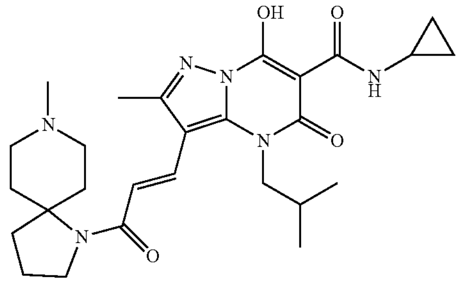
Ex 665
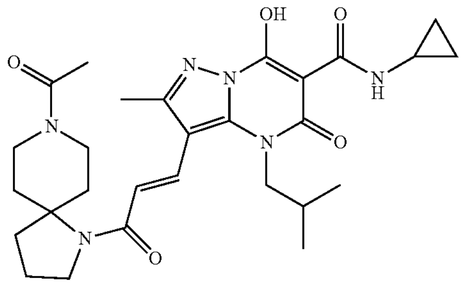
Ex 666
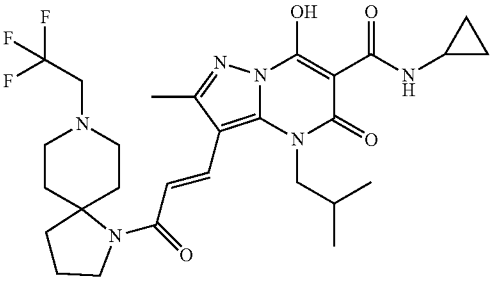
-continued
Ex 667
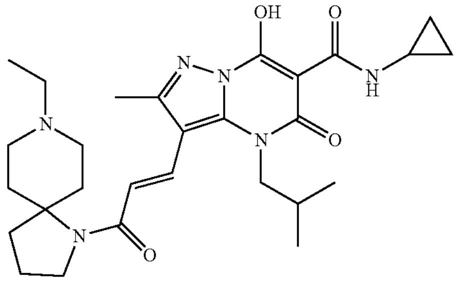
Ex 668
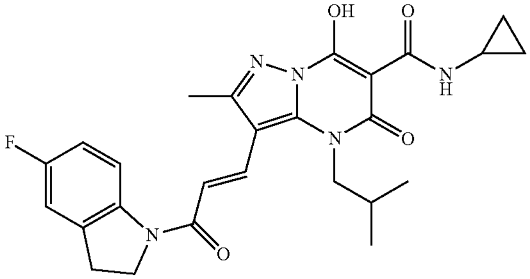
Ex 669
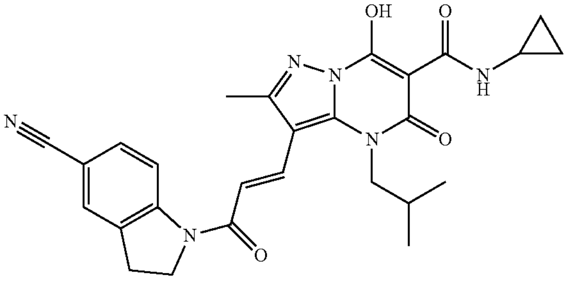
Ex 670
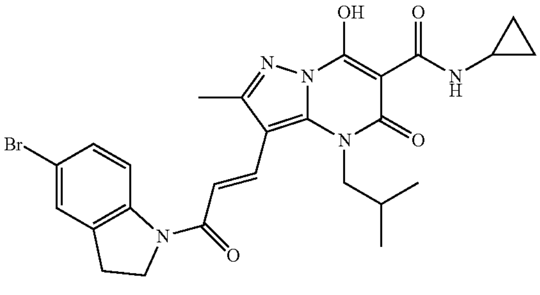
Ex 671
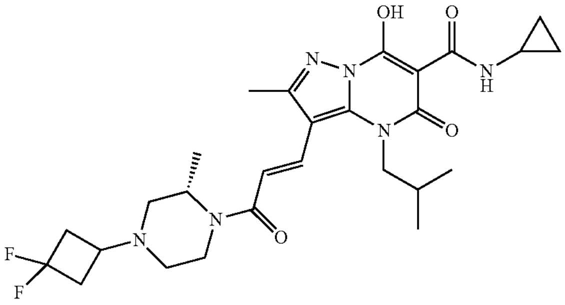

-continued
Ex 672
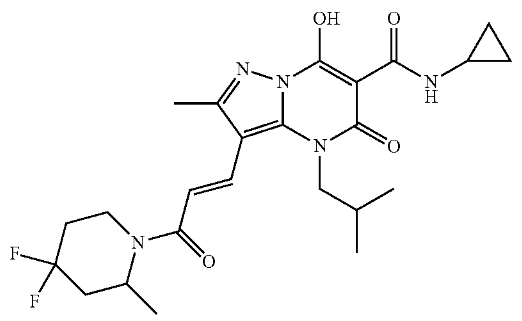
Ex 673
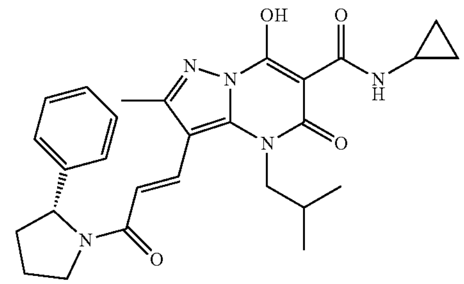
Ex 674
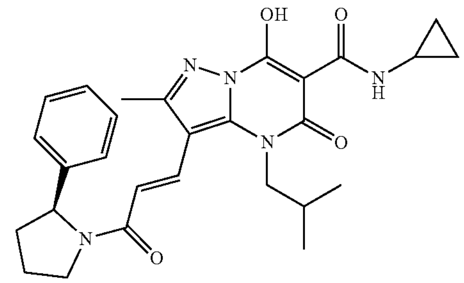
Ex 675
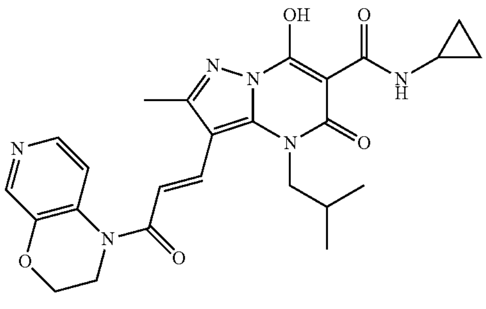
Ex 676
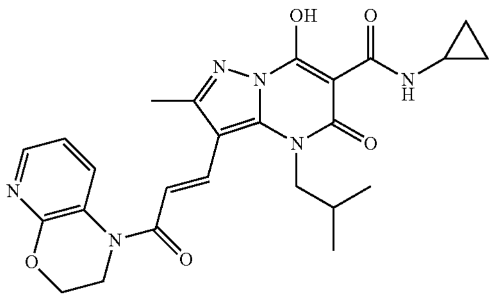
-continued
Ex 677
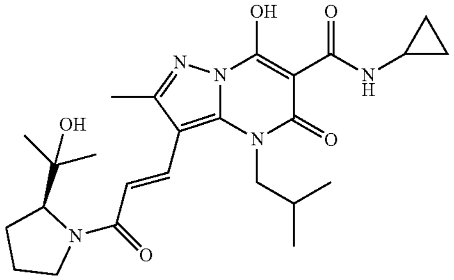
Ex 678
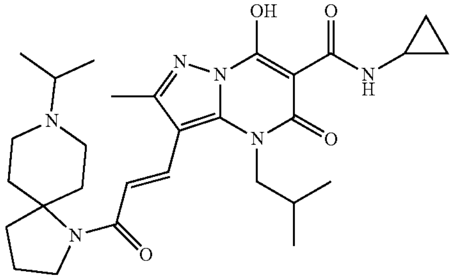
Ex 679
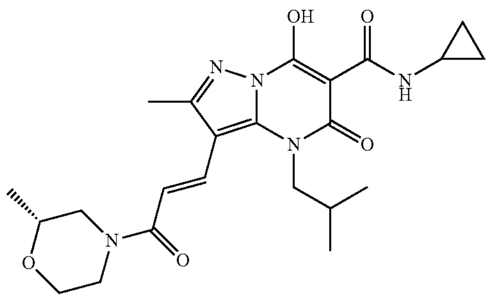
Ex 680
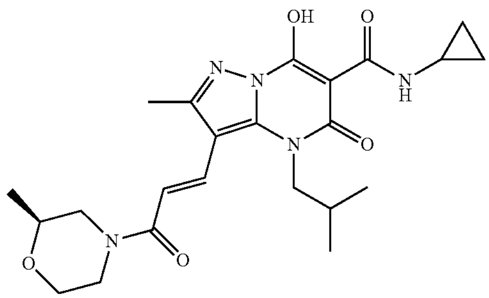
Ex 681
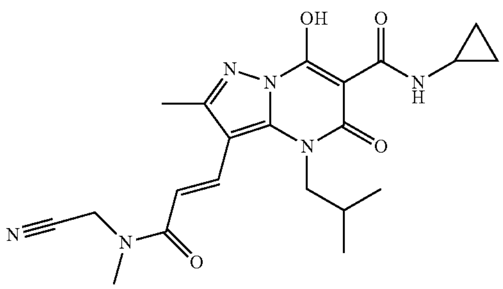

-continued
Ex 682
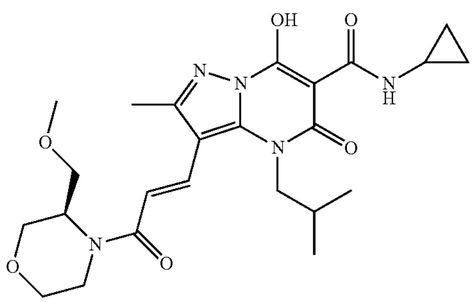
Ex 683
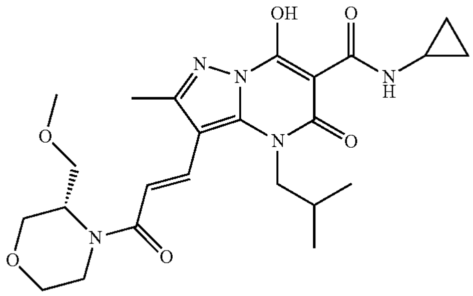
Ex 684
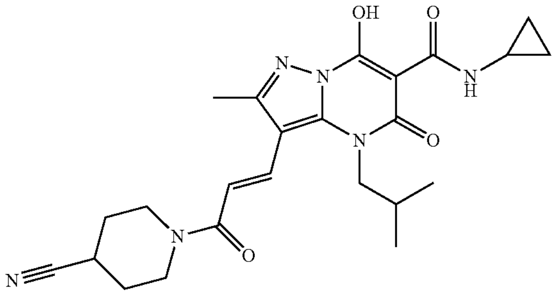
Ex 685
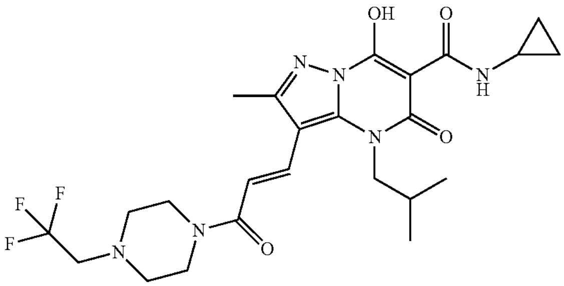
Ex 686
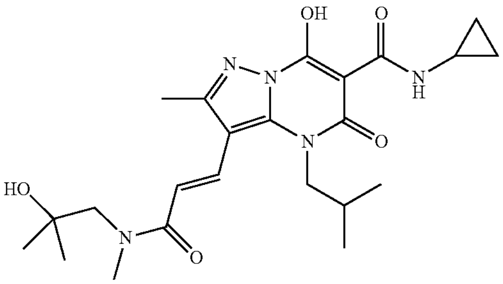
-continued
Ex 687
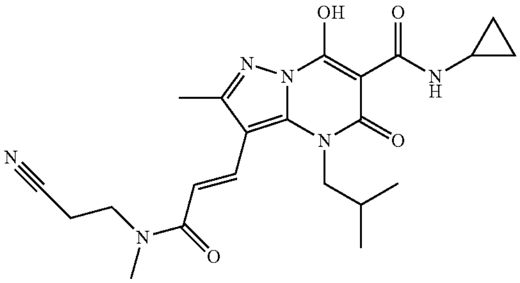
Ex 688
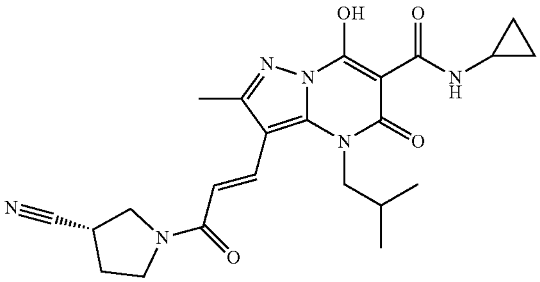
Ex 689
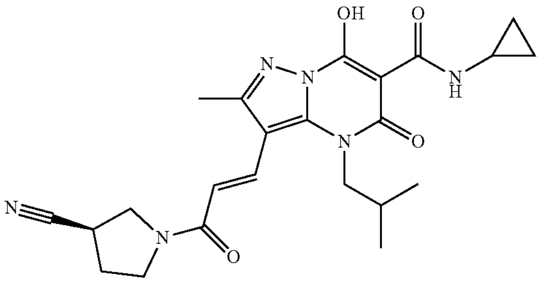
Ex 690
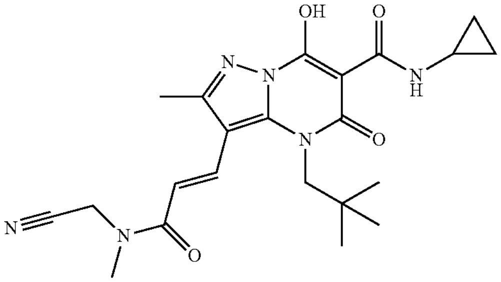
Ex 691
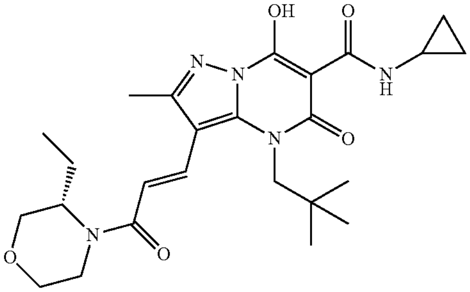

-continued
Ex 692
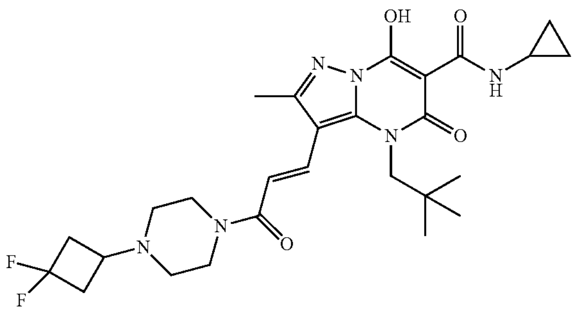
Ex 693
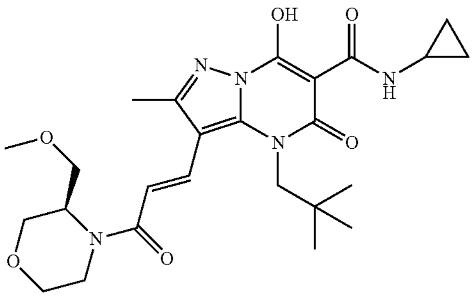
Ex 694
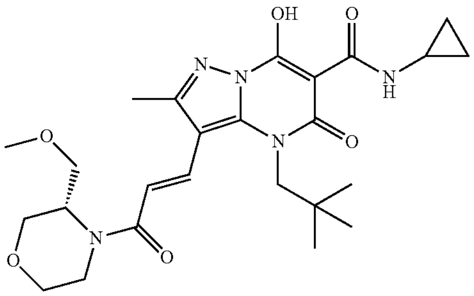
Ex 695
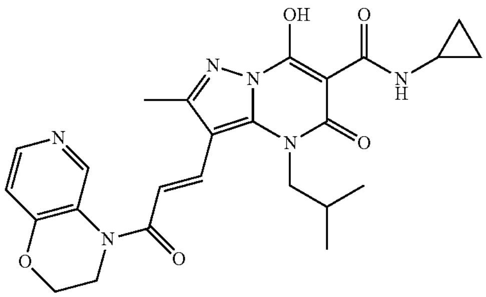
Ex 696
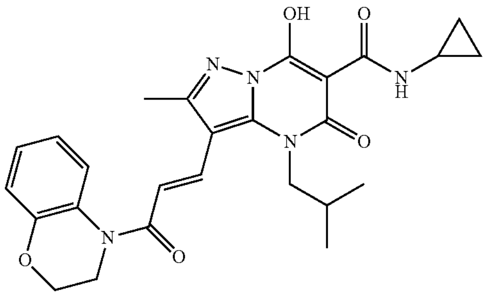
-continued
Ex 697
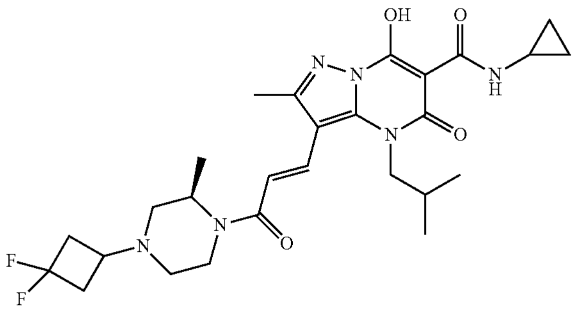
Ex 698
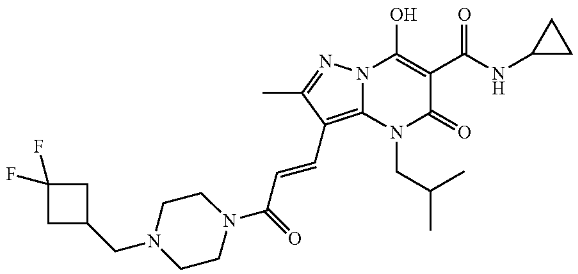
Ex 699
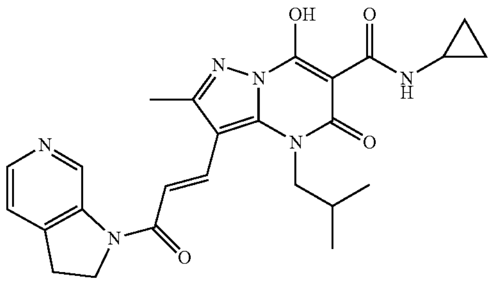
Ex 700
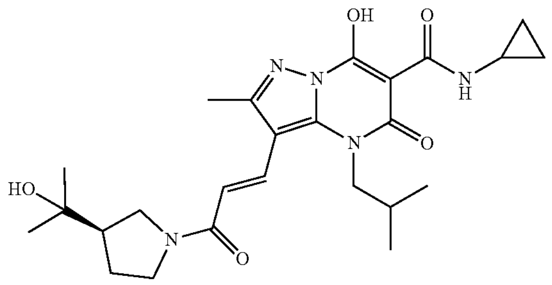
Ex 701
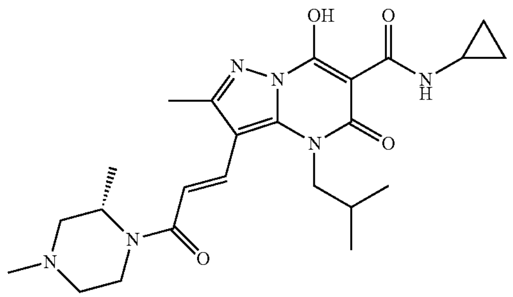

Ex 702
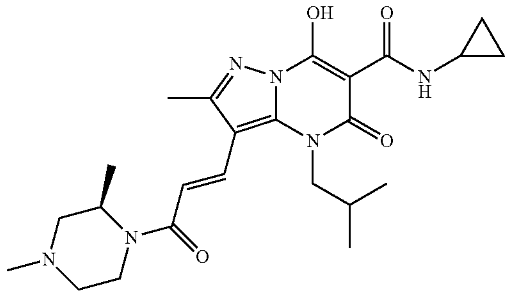
Ex 703
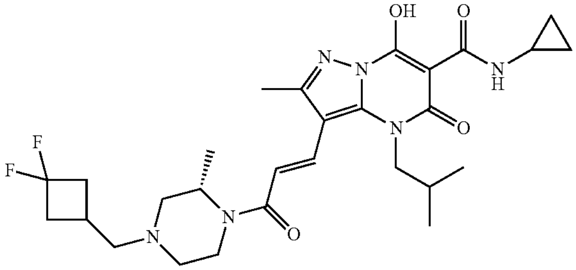
Ex 704
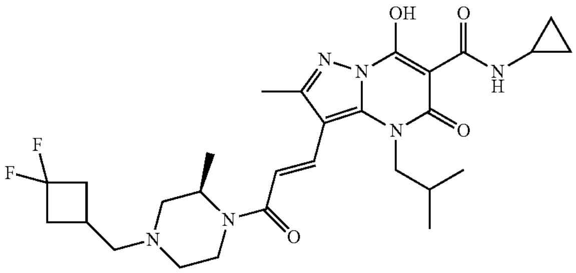
Ex 705
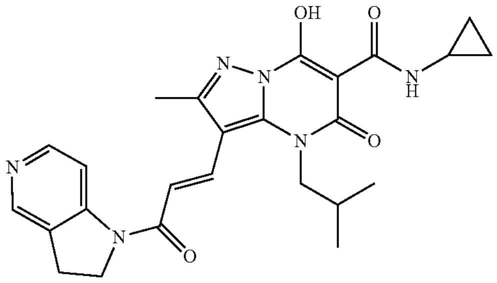
Ex 706
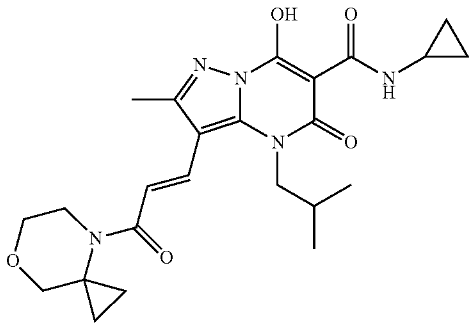
Ex 707
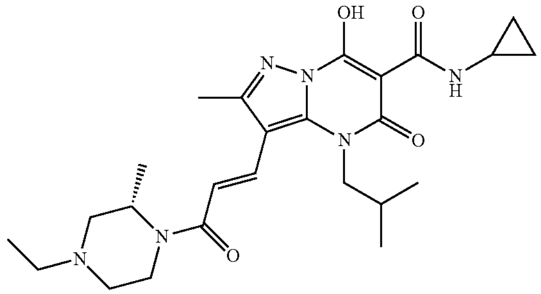
Ex 708
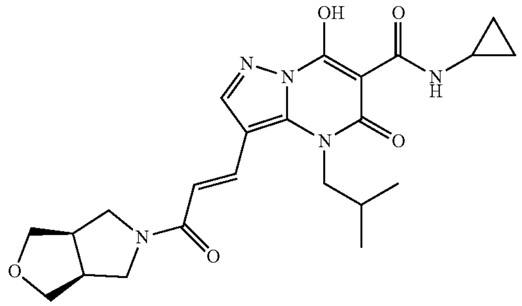
Ex 709
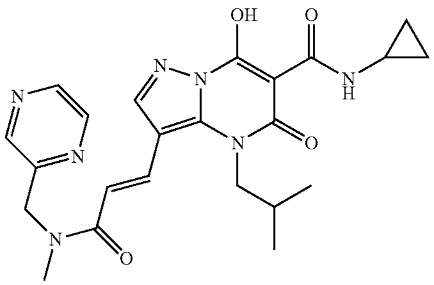
Ex 710
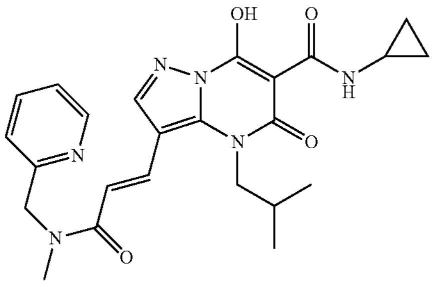
Ex 711
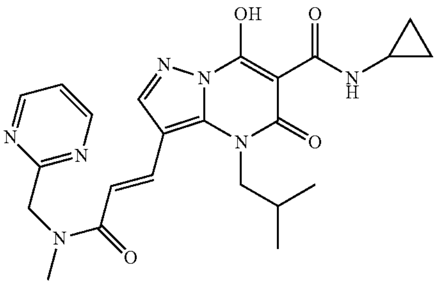

-continued
Ex 712
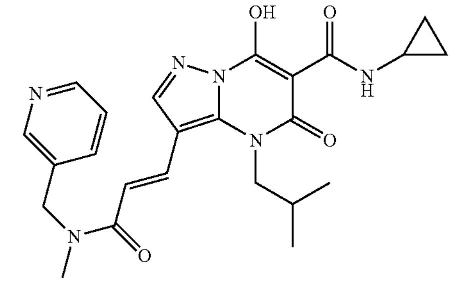
Ex 713
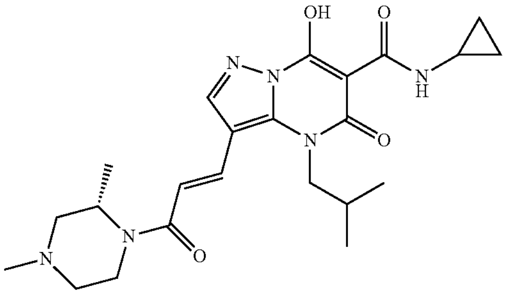
Ex 714
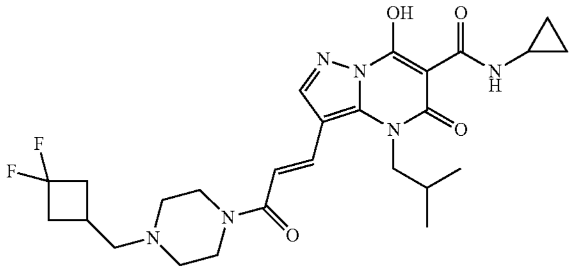
Ex 715
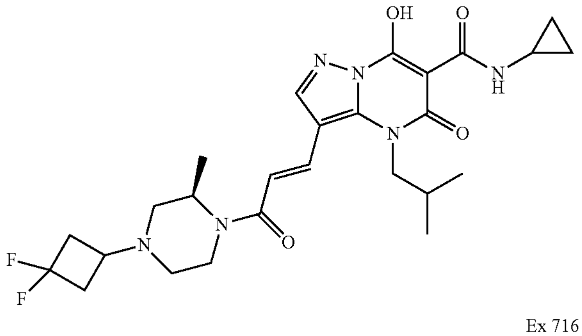
Ex 716
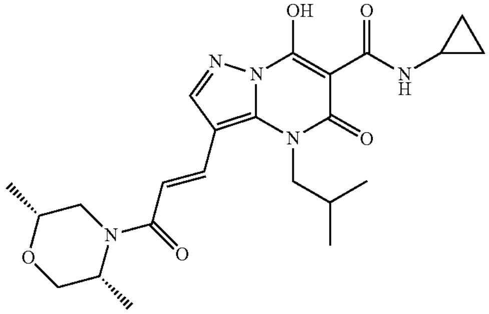
-continued
Ex 717
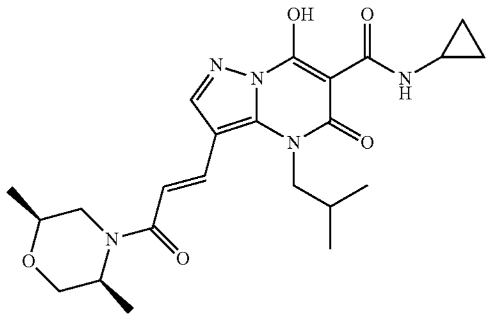
Ex 718
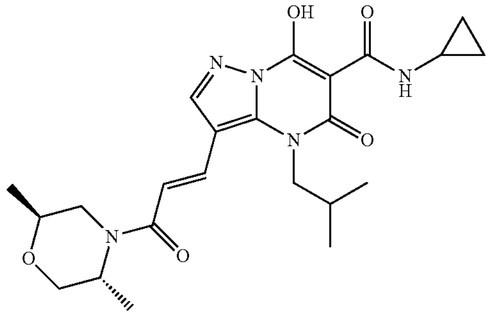
Ex 719
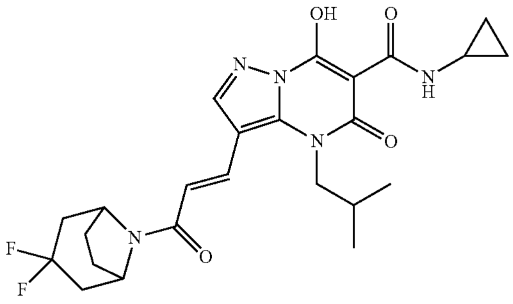
Ex 720
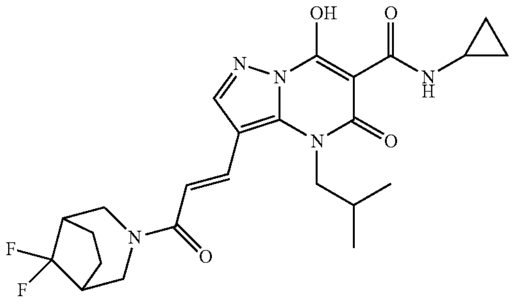
Ex 721
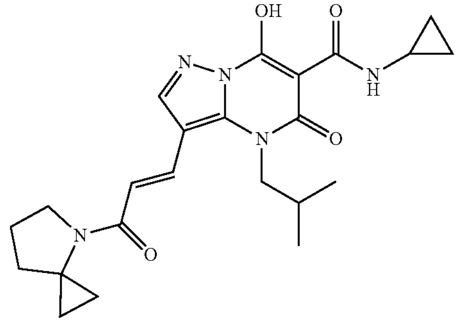

-continued
Ex 722
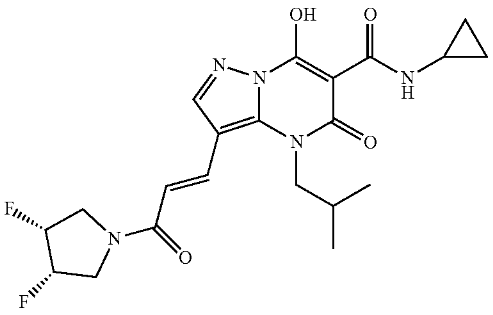
Ex 723
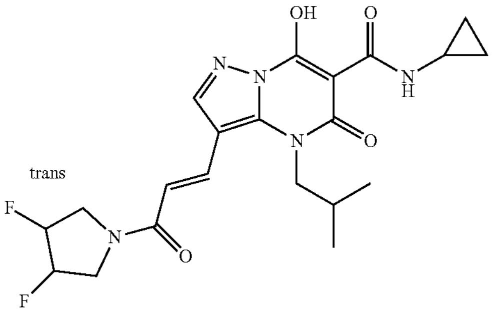
Ex 724
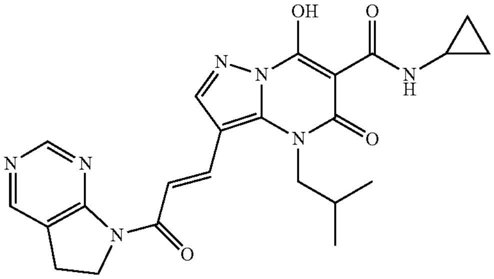
Ex 725
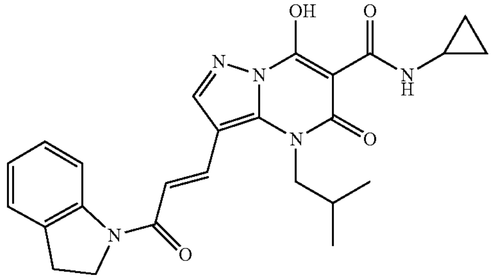
Ex 726
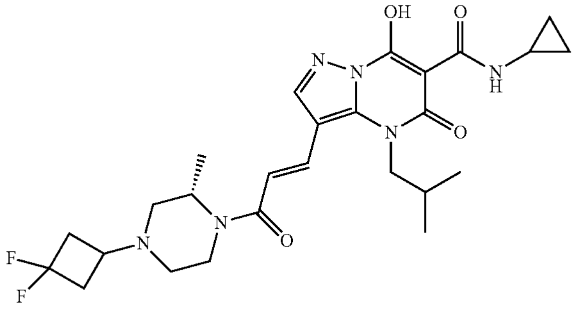
-continued
Ex 727
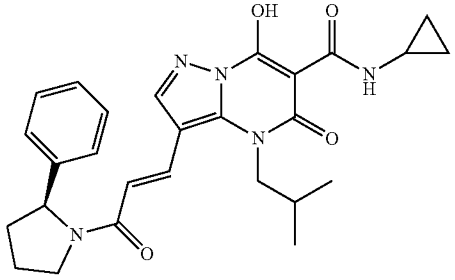
Ex 728
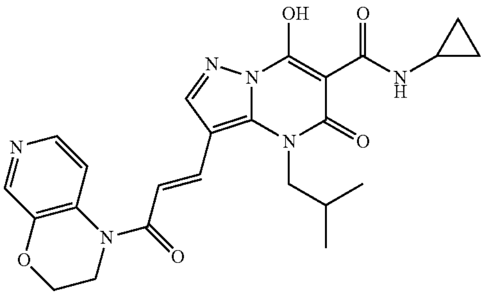
Ex 729
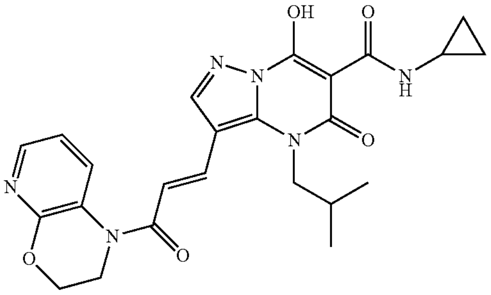
Ex 730
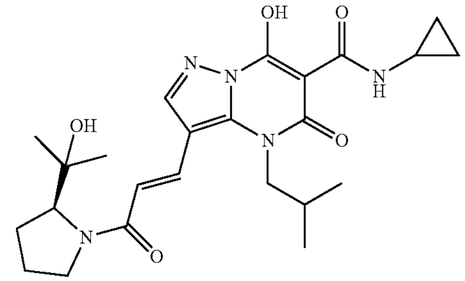
Ex 731
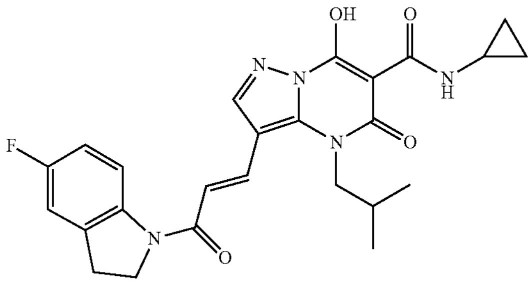

-continued
Ex 732
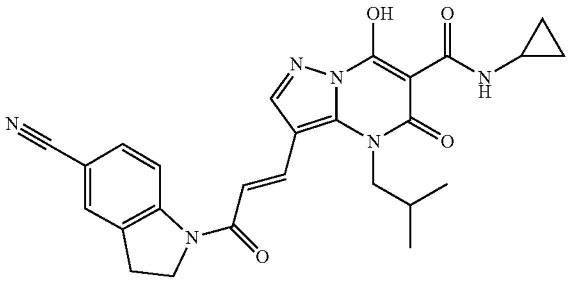
Ex 733
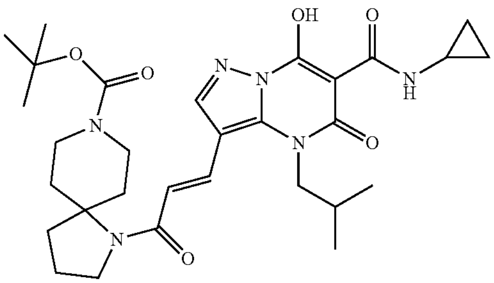
Ex 734
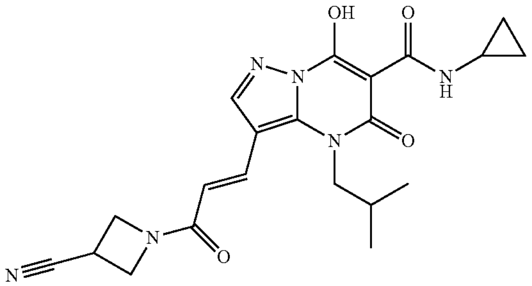
Ex 735
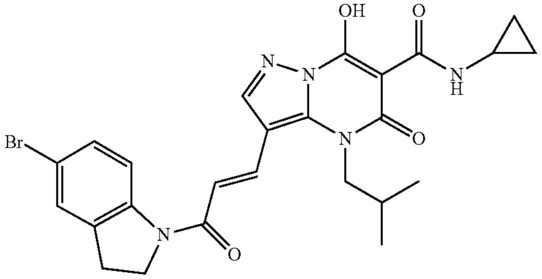
Ex 736
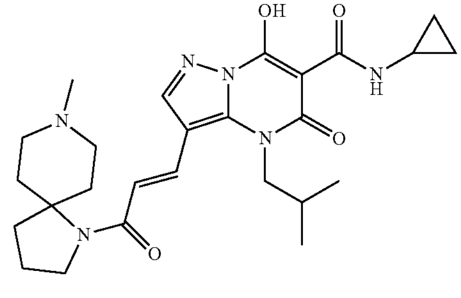
-continued
Ex 737
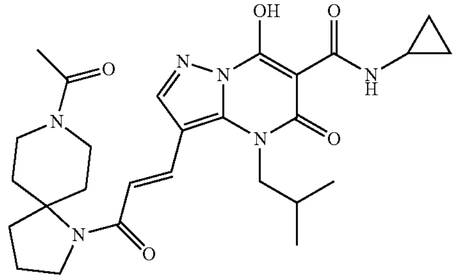
Ex 738
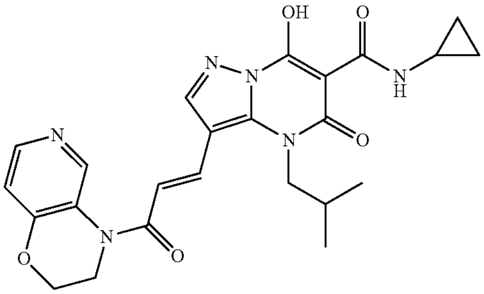
Ex 739
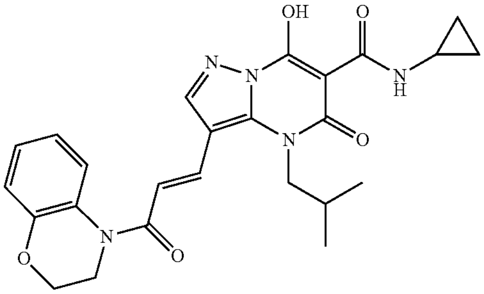
Ex 740
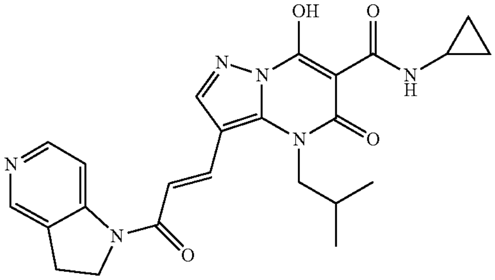
Ex 741
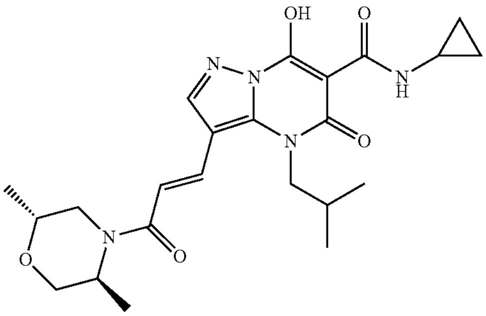

-continued
Ex 742
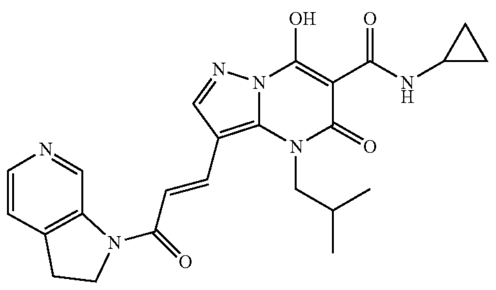
Ex 743
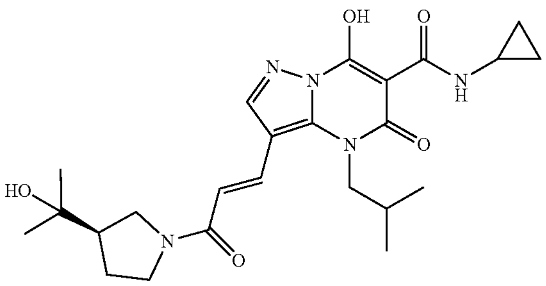
Ex 744
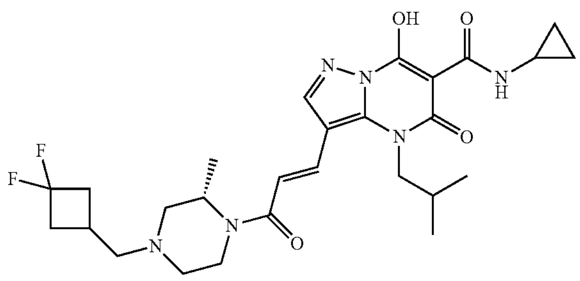
Ex 745
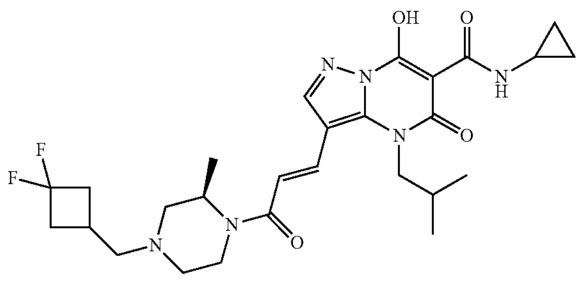
Ex 746
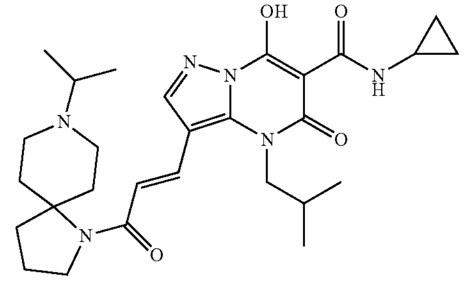
-continued
Ex 747
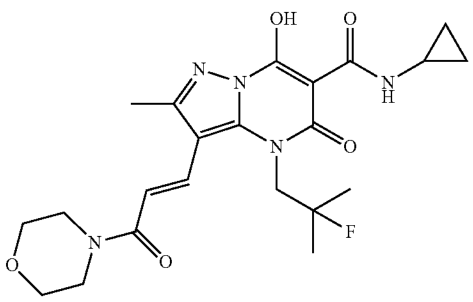
Ex 748
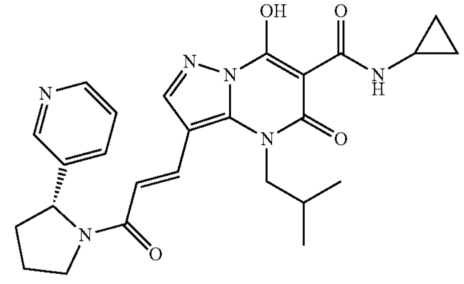
Ex 749
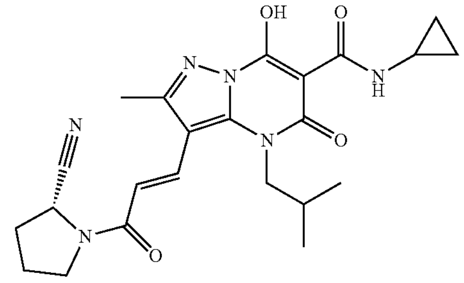
Ex 750
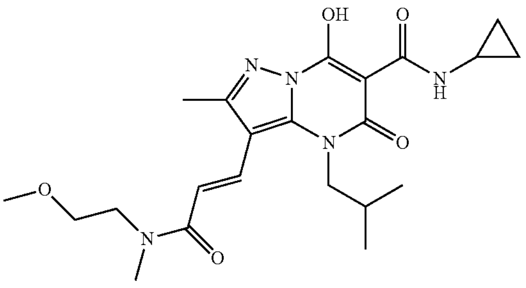
Ex 751
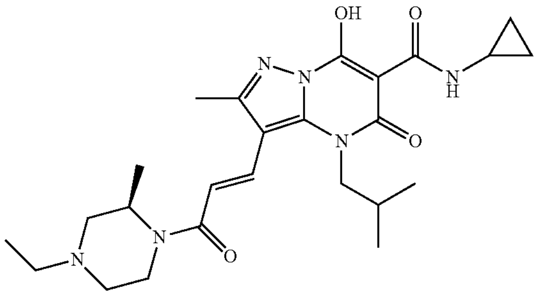

-continued

Ex 752

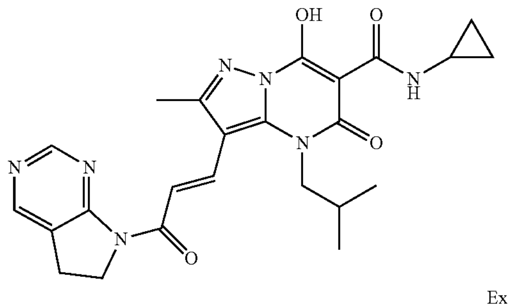

Ex 753

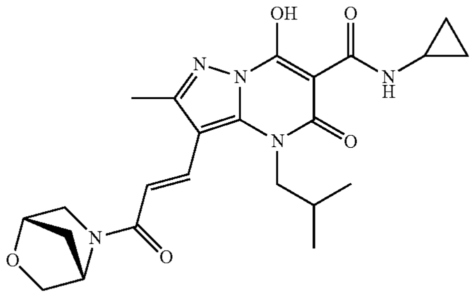

Ex 754

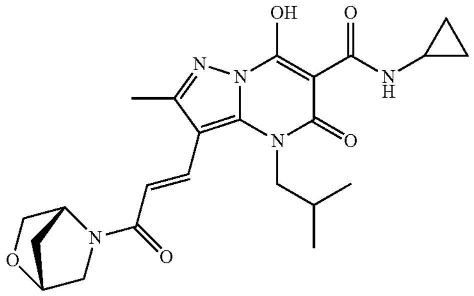

-continued

Ex 755

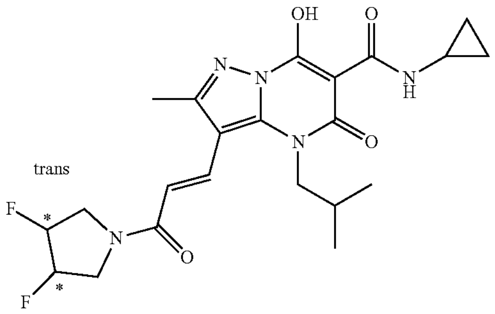

Isomer A

Ex 756

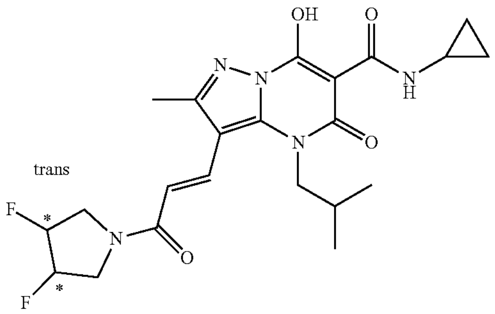

Isomer B

The NMR spectral data of the compounds produced in the aforementioned Synthesis Examples are shown in Tables 1 to 15.

TABLE 1

| Ex. | Data |
|---|---|
| 4 | $^1$H-NMR (DMSO-$D_6$) δ: 9.93-9.87 (1H, m), 7.00-6.00 (3H, br m), 5.61 (1H, s), 3.80-3.69 (2H, m), 2.97-2.86 (1H, m), 0.95 (9H, s), 0.88-0.78 (2H, m), 0.76-0.66 (2H, m). |
| 10 | $^1$H-NMR (DMSO-$D_6$) δ: 9.91 (1H, d, J = 4.5 Hz), 8.50 (1H, s), 7.60 (1H, d, J = 14.7 Hz), 7.10 (1H, d, J = 14.7 Hz), 4.01 (2H, d, J = 7.4 Hz), 3.80-3.46 (8H, br m), 3.03-2.89 (1H, m), 2.06-1.88 (1H, m), 0.96 (6H, d, J = 6.5 Hz), 0.91-0.80 (2H, m), 0.79-0.72 (2H, m). |
| 12 | $^1$H-NMR (DMSO-$D_6$) δ: 10.49 (1H, br s), 9.94 (1H, d, J = 4.5 Hz), 8.70-8.67 (1H, m), 8.43-8.38 (1H, m), 7.42-7.34 (1H, m), 7.38 (1H, d, J = 5.7 Hz), 6.50 (1H, br s), 3.84 (2H, s), 3.01-2.90 (1H, m), 0.99 (9H, s), 0.89-0.79 (2H, m), 0.78-0.67 (2H, m). |
| 13 | $^1$H-NMR (DMSO-$D_6$) δ: 10.51-10.20 (1H, m), 9.99-9.83 (1H, m), 8.73-8.69 (1H, m), 8.23-8.18 (1H, m), 8.06-8.01 (1H, m), 6.50-6.44 (1H, m), 3.82 (2H, br s), 3.00-2.88 (1H, m), 0.97 (9H, s), 0.89-0.78 (2H, m), 0.76-0.66 (2H, m). |
| 14 | $^1$H-NMR (DMSO-$D_6$) δ: 9.93 (1H, d, J = 4.1 Hz), 8.09 (1H, dd, J = 7.6, 1.8 Hz), 8.04 (1H, dd, J = 4.9, 1.6 Hz), 7.35 (2H, br s), 7.06 (1H, s), 6.70 (1H, dd, J = 7.6, 4.7 Hz), 3.88 (2H, br s), 3.03-2.92 (1H, m), 1.01 (9H, s), 0.91-0.83 (2H, m), 0.78-0.70 (2H, m). |
| 15 | $^1$H-NMR (DMSO-$D_6$) δ: 11.07-10.97 (1H, m), 9.92-9.83 (1H, m), 8.69-8.65 (2H, m), 6.63-6.48 (1H, m), 3.82 (2H, s), 2.98-2.85 (1H, m), 0.99 (9H, s), 0.87-0.76 (2H, m), 0.74-0.63 (2H, m). |
| 16 | $^1$H-NMR (DMSO-$D_6$) δ: 9.99-9.93 (1H, m), 9.83-9.79 (1H, m), 8.61-8.56 (1H, m), 8.01-7.96 (1H, m), 6.19-6.13 (1H, m), 3.86 (3H, s), 3.80 (2H, s), 2.99-2.88 (1H, m), 0.98 (9H, s), 0.89-0.81 (2H, m), 0.75-0.68 (2H, m). |

TABLE 1-continued

| Ex. | Data |
|---|---|
| 17 | $^1$H-NMR (DMSO-$D_6$) δ: 10.36-10.31 (1H, m), 9.97-9.90 (1H, m), 8.18-8.13 (1H, m), 7.71-7.66 (1H, m), 6.57-6.53 (1H, m), 3.94 (3H, s), 3.83 (2H, s), 3.00-2.89 (1H, m), 0.98 (9H, s), 0.90-0.79 (2H, m), 0.78-0.70 (2H, m). |
| 18 | $^1$H-NMR (DMSO-$D_6$) δ: 9.98-9.91 (1H, m), 5.61-5.52 (1H, m), 3.77-3.70 (2H, m), 2.95-2.86 (1H, m), 1.29-1.21 (2H, m), 1.02-0.90 (9H, m), 0.90-0.78 (2H, m), 0.76-0.65 (2H, m). |
| 19 | $^1$H-NMR (DMSO-$D_6$) δ: 11.04 (1H, s), 9.92 (1H, d, J = 3.7 Hz), 8.81 (1H, d, J = 1,2 Hz), 8.62 (1H, d, J = 1.2 Hz), 6.66 (1H, s), 3.87-3.84 (5H, m), 3.00-2.90 (1H, m), 1.00 (9H, s), 0.90-0.80 (2H, m), 0.78-0.70 (2H, m). |
| 20 | $^1$H-NMR (DMSO-$D_6$) δ: 10.96 (1H, s), 9.96-9.90 (1H, m), 8.80 (1H, d, J = 1.2 Hz), 8.64 (1H, d, J = 1.6 Hz), 6.65 (1H, s), 3.86 (2H, s), 3.00-2.91 (1H, m), 1.00 (9H, s), 0.91-0.81 (2H, m), 0.79-0.70 (2H, m). |
| 21 | $^1$H-NMR (DMSO-$D_6$) δ: 10.79 (1H, s), 10.00-9.87 (1H, m), 8.76 (1H, s), 8.66 (1H, s), 7.90 (1H, d, J = 0.8 Hz), 7.51 (1H, d, J = 0.8 Hz), 6.58 (1H, s), 3.86 (2H, s), 3.02-2.90 (1H, m), 1.00 (9H, s), 0.91-0.81 (2H, m), 0.79-0.70 (2H, m). |
| 23 | $^1$H-NMR (DMSO-$D_6$) δ: 10.39-10.31 (1H, m), 9.98-9.90 (1H, m), 8.75-8.70 (1H, m), 8.25-8.19 (1H, m), 8.09-8.02 (1H, m), 6.44-6.39 (1H, m), 3.80 (2H, d, J = 7.4 Hz), 3.01-2.88 (1H, m), 2.25-2.07 (1H, m), 0.99-0.90 (6H, m), 0.89-0.78 (2H, m), 0.78-0.69 (2H, m). |
| 24 | $^1$H-NMR (DMSO-$D_6$) δ: 9.93 (1H, d, J = 4.5 Hz), 8.12 (1H, dd, J = 7.8, 1.6 Hz), 8.04 (1H, dd, J = 4.7, 1.8 Hz), 7.40 (2H, br s), 7.03 (1H, s), 6.71 (1H, dd, J = 7.8, 4.9 Hz), 3.84 (2H, d, J = 7.8 Hz), 3.04-2.91 (1H, m), 2.32-2.17 (1H, m), 0.94 (6H, d, J = 7.0 Hz), 0.90-0.82 (2H, m), 0.79-0.71 (2H, m). |

TABLE 2

| Ex | Data |
|---|---|
| 26 | $^1$H-NMR ($CDCl_3$) δ: 10.11 (1H, br s), 8.98 (1H, br s), 8.54 (1H, br s), 8.14 (1H, br s), 8.03 (1H, br s), 6.58 (1H, br s), 4.57-4.36 (1H, m), 3.86 (2H, s), 2.53-2.33 (2H, m), 2.29-1.98 (3H, m), 1.93-1.70 (2H, m), 1.05 (9H, s). |
| 28 | $^1$H-NMR (DMSO-$D_6$) δ: 10.37-10.28 (1H, m), 10.00-9.91 (1H, m), 8.77-8.71 (1H, m), 8.25-8.17 (1H, m), 8.08-8.02 (1H, m), 6.53-6.45 (1H, m), 3.95-3.84 (2H, m), 3.71-3.61 (2H, m), 3.57-3.43 (2H, m), 3.00-2.88 (1H, m), 1.71-1.55 (2H, m), 1.35-1.21 (2H, m), 1.04 (3H, s), 0.90-0.78 (2H, m), 0.78-0.66 (2H, m). |
| 29 | $^1$H-NMR (DMSO-$D_6$) δ: 9.94 (1H, d, J = 4.4 Hz), 8.10-8.02 (2H, m), 7.32 (2H, br s), 7.07 (1H, s), 6.73-6.65 (1H, m), 3.93 (2H, s), 3.71-3.62 (2H, m), 3.56-3.45 (2H, m), 3.02-2.93 (1H, m), 1.72-1.60 (2H, m), 1.36-1.27 (2H, m), 1.08 (3H, s), 0.91-0.82 (2H, m), 0.77-0.69 (2H, m). |
| 31 | $^1$H-NMR ($CDCl_3$) δ: 10.13-10.06 (1H, m), 9.59 (1H, s), 8.51 (1H, s), 8.14-8.09 (1H, m), 8.03-7.98 (1H, m), 6.70-6.58 (1H, m), 4.52-4.37 (1H, m), 3.98-3.72 (4H, m), 3.68-3.56 (2H, m), 3.00-2.32 (3H, m), 2.22-2.01 (2H, m), 1.92-1.65 (4H, m), 1.43-1.30 (2H, m), 1.13 (3H, s). |
| 32 | $^1$H-NMR (DMSO-$D_6$) δ: 9.96-9.86 (1H, m), 9.31 (1H, s), 6.41-6.32 (2H, m), 6.29 (1H, s), 3.80 (2H, s), 2.99-2.88 (1H, m), 0.96 (9H, s), 0.89-0.80 (2H, m), 0.76-0.68 (2H, m). |
| 33 | $^1$H-NMR (DMSO-$D_6$) δ: 9.89 (1H, d, J = 4.1 Hz), 7.81 (1H, s), 7.52 (1H, s), 6.74 (1H, s), 3.88 (2H, s), 3.02-2.90 (1H, m), 0.97 (9H, s), 0.90-0.82 (2H, m), 0.80-0.70 (2H, m). |
| 35 | $^1$H-NMR (DMSO-$D_6$) δ: 9.94-9.85 (1H, m), 7.86 (1H, s), 5.89 (1H, s), 4.18 (2H, d, J = 2.5 Hz), 4.02 (2H, d, J = 7.4 Hz), 3.84-3.75 (4H, m), 3.16 (2H, t, J = 10.6 Hz), 2.99-2.93 (1H, m), 2.38-2.30 (2H, m), 1.83-1.67 (1H, m), 1.39 (2H, d, J = 13.1 Hz), 1.29-1.12 (2H, m), 0.90-0.80 (2H, m), 0.78-0.71 (2H, m). |

TABLE 3

| Ex | Data |
|---|---|
| 259 | $^1$H-NMR ($CDCl_3$) δ: 10.02 (1H, s), 7.78 (1H, s), 7.43-7.40 (1H, m), 7.31-7.24 (2H, m), 6.98 (1H, br s), 5.29 (2H, s), 3.72 (2H, d, J = 7.4 Hz), 2.99-2.97 (1H, m), 1.98-1.95 (1H, m), 0.96-0.94 (8H, m), 0.81-0.79 (2H, m) |
| 263 | $^1$H-NMR (DMSO-$D_6$) δ: 9.90 (1H, d, J = 3.3 Hz), 8.29 (1H, t, J = 4.8 Hz), 7.82 (1H, s), 4.25 (2H, d, J = 4.8 Hz), 3.89 (2H, d, J = 7.4 Hz), 3.01-2.90 (1H, m). 2.33-2.22 (1H, m), |

TABLE 3-continued

| Ex | Data |
|---|---|
| | 2.12-1.97 (3H, m), 1.89-1.52 (6H, m), 0.89 (6H, d, J = 6.6 Hz), 0.87-0.71 (4H, m). |
| 265 | $^1$H-NMR ($CDCl_3$) δ: 9.96 (1H, s), 7.87 (1H, s), 6.57 (1H, d, J = 15.8 Hz), 6.11 (1H, d, J = 15.8 Hz), 4.02 (2H, d, J = 7.4 Hz), 2.99-2.88 (1H, m), 2.17-2.05 (1H, m), 1.42 (6H, s), 0.98 (6H, d, J = 6.6 Hz), 0.94-0.89 (2H, m), 0.78-0.73 (2H, m). |
| 364 | $^1$H-NMR (DMSO-$D_6$) δ: 9.91 (1H, d, J = 3.7 Hz), 8.46 (1H, s), 7.82 (1H, d, J = 14.7 Hz), 7.04 (1H, d, J = 15.1 Hz), 4.58 (2H, d, J = 17.6 Hz), 3.73-3.50 (8H, m), 3.02-2.91 (1H, m), 1.18-1.03 (2H, m), 1.02-0.92 (2H, m), 0.90-0.81 (2H, m), 0.80-0.70 (2H, m). |
| 390 | $^1$H-NMR (DMSO-$D_6$) δ: 9.93 (1H, d, J = 4.1 Hz), 8.43 (1H, s), 7.83 (1H, d, J = 15.1 Hz), 6.99 (1H, d, J = 14.7 Hz), 4.37 (2H, d, J = 19.2 Hz), 3.79-3.47 (8H, m), 3.05-2.91 (1H, m), 1.44 (6H, d, J = 21.7 Hz), 0.91-0.81 (2H, m), 0.80-0.72 (2H, m). |
| 391 | $^1$H-NMR (DMSO-$D_6$) δ: 9.59-9.52 (1H, m), 8.55 (1H, dd, J = 4.1, 1.7 Hz), 8.41 (1H, dd, J = 8.6, 1.5 Hz), 6.89 (1H, dd, J = 8.6, 4.0 Hz), 4.22 (2H, s), 2.77-2.70 (1H, m), 0.91 (9H, s), 0.70-0.62 (2H, m), 0.44-0.36 (2H, m). |
| 394 | $^1$H-NMR (DMSO-$D_6$) δ: 11.93-11.84 (1H, m), 9.93 (1H, d, J = 4.1 Hz), 8.03 (1H, d, J = 9.8 Hz), 6.10 (1H, dd, J = 9.8, 1.6 Hz). 4.12 (2H, s), 3.03-2.90 (1H, m), 0.96 (9H, s), 0.90-0.80 (2H, m), 0.80-0.71 (2H, m). |
| 395 | $^1$H-NMR (DMSO-$D_6$) δ: 10.51 (1H, s), 10.04 (1H, s). 7.08 (1H, s), 6.21 (1H, m), 3.99 (2H, s), 2.91-3.03 (1H, m), 0.98 (9H, s), 0.88-0.80 (2H, m), 0.76-0.69 (2H, m). |
| 400 | $^1$H-NMR (DMSO-$D_6$) δ: 10.98 (1H, s), 9.89 (1H, s), 5.49 (2H, s), 3.69 (2H, s), 2.99-2.89 (1H, m), 0.93 (9H, s), 0.89-0.79 (2H, m), 0.78-0.68 (2H, m). |
| 402 | $^1$H-NMR (DMSO-$D_6$) δ: 11.10 (1H, s), 9.94 (1H, br s), 3.72 (2H, s), 3.60 (2H, s), 2.99-2.89 (1H, m), 0.95 (9H, s), 0.88-0.78 (2H, m), 0.76-0.69 (2H, m). |

TABLE 4

| Ex | Data |
|---|---|
| 403 | $^1$H-NMR (DMSO-$D_6$) δ: 10.79 (1H, s), 9.88 (1H, br s), 3.91 (2H, s), 2.87-2.99 (3H, m), 2.59-2.50 (2H, m), 0.94 (9H, s), 0.88-0.80 (2H, m), 0.76-0.66 (2H, m). |
| 405 | $^1$H-NMR (DMSO-$D_6$) δ: 10.05 (1H, s), 9.91 (1H, s), 4.53-4.36 (3H, m), 3.96 (2H, dd, J = 11.0, 4.5 Hz), 3.81 (2H, s), 3.41 (2H, t, J = 11.4 Hz), 2.98-2.90 (1H, m), 1.96 (1H, dd, J = 12.3, 4.9 Hz), 1.89 (1H, dd, J = 11.4, 4.5 Hz), 1.53 (2H, d, J = 11.9 Hz), 0.96 (9H, s), 0.89-0.83 (2H, m), 0.77-0.72 (2H, m). |
| 411 | $^1$H-NMR (DMSO-$D_6$) δ: 9.95-9.71 (1H, m), 7.87 (1H, d, J = 15.1 Hz), 6.58 (1H, d, J = 13.9 Hz), 5.44 (2H, br s), 4.22-3.92 (2H, br m), 3.59 (8H, s), 2.89-2.70 (1H, m), 0.91 (9H, s), 0.78-0.62 (2H, m), 0.59-0.33 (2H, m). |
| 414 | $^1$H-NMR (DMSO-$D_6$) δ: 9.94 (1H, d, J = 4.1 Hz), 7.65 (1H, d, J = 15.1 Hz), 6.79 (1H, d, J = 15.1 Hz), 4.43-3.79 (4H, m), 3.76-3.62 (4H, m), 2.99-2.86 (1H, m), 2.11-1.87 (5H, m), 0.93 (6H, d, J = 6.5 Hz), 0.89-0.78 (2H, m), 0.77-0.69 (2H, m). |
| 426 | $^1$H-NMR (DMSO-$D_6$) δ: 9.96 (1H, s), 7.64 (1H, d, J = 15.3 Hz), 6.68 (1H, d, J = 15.3 Hz), 5.89 (1H, br s), 3.93 (2H, br s), 3.60 (8H, s), 2.98-2.88 (1H, m), 2.80 (3H, d, J = 4.8 Hz), 2.04-1.94 (1H, m), 0.88 (6H, d, J = 6.0 Hz), 0.89-0.79 (2H, m), 0.75-0.65 (2H, m). |
| 433 | $^1$H-NMR (DMSO-$D_6$) δ: 9.91 (1H, d, J = 4.4 Hz), 6.25-6.15 (1H, m), 5.79-5.68 (1H, m), 5.53-4.97 (3H, m), 4.03 (2H, s), 3.94-3.83 (2H, m), 3.43-3.29 (2H, m), 2.97-2.86 (1H, m), 2.46-2.34 (1H, m), 1.76-1.63 (2H, m), 1.53-1.35 (2H, m), 0.91-0.76 (11H, m), 0.75-0.66 (2H, m). |
| 450 | $^1$H-NMR (DMSO-$D_6$) δ: 9.91-9.83 (1H, m), 7.98 (1H, s), 7.74 (1H, s), 7.55 (1H, d, J = 15.1 Hz), 6.93 (1H, d, J = 15,1 Hz), 3.99 (2H, d, J = 7,4 Hz), 3.66-3.50 (8H, m), 3.02-2.92 (1H, m), 1.97-1.84 (1H, m), 0.95-0.72 (10H, m). |
| 452 | $^1$H-NMR (DMSO-$D_6$) δ: 9.96-9.86 (1H, m), 8.46 (1H, s), 7.53 (1H, d, J = 15.3 Hz), 6.83 (1H, d, J = 15.3 Hz), 4.00 (2H, d, J = 7.8 Hz), 3.61 (2H, t, J = 6.8 Hz), 3.38 (2H, t, J = 6.8 Hz), 3.05-2.90 (1H, m), 2.05-1.74 (5H, m), 0.96 (6H, d, J = 7.2 Hz), 0.91-0.81 (2H, m), 0.80-0.72 (2H, m). |

TABLE 4-continued

| Ex | Data |
|---|---|
| 453 | $^1$H-NMR (DMSO-$D_6$) δ: 9.91 (1H, d, J = 4.1 Hz), 8.48 (1H, d, J = 7.4 Hz), 7.58 (1H, dd, J = 14.9, 3.9 Hz), 6.83 (1H, dd, J = 27.0, 15.1 Hz), 4.13 (1H, t, J = 13.1 Hz), 4.01 (2H, d, J = 7.0 Hz), 3.88-3.79 (2H, m), 3.62 (1H, t, J = 7.6 Hz), 3.02-2.92 (1H, m), 2.62-2.33 (2H, m), 2.04-1.89 (1H, m), 0.95 (6H, d, J = 10.0 Hz), 0.90-0.73 (4H, m). |
| 454 | $^1$H-NMR (DMSO-$D_6$) δ: 9.96 (1H, s), 8.05-8.02 (1H, m), 7.77 (1H, d, J = 15.0 Hz), 6.57-6.43 (1H, m), 5.32 (1H, dd, J = 52.3, 17.9 Hz), 4.13-3.53 (6H, m), 3.02-2.90 (1H, m), 2.36 (1H, t, J = 7.7 Hz), 2.27-2.06 (2H, m), 1.06 (6H, d, J = 6.8 Hz), 0.98-0.90 (2H, m), 0.80-0.73 (2H, m). |

TABLE 5

| Ex | Data |
|---|---|
| 455 | $^1$H-NMR ($CDCl_3$) δ: 9.96 (1H, d, J = 3.7 Hz), 8.03 (1H, s), 7.80 (1H, d, J = 14.7 Hz), 6.64 (1H, d, J = 14.7 Hz), 4.12-4.04 (2H, m), 3.99-3.96 (1H, m), 3.76 (1H, d, J = 11.4 Hz), 3.65 (1H, dd, J = 11.4, 3.3 Hz), 3.50 (1H, dd, J = 13.3, 10.4 Hz), 2.99-2.92 (1H, m), 2.17-2.08 (1H, m), 1.57-1.53 (3H, m), 1.38 (3H, d, J = 6.5 Hz), 1.06 (6H, d, J = 6.5 Hz), 0.97-0.91 (2H, m), 0. 79-0.72 (2H, m). |
| 456 | $^1$H-NMR (DMSO-$D_6$) δ: 9.91 (1H, d, J = 4.1 Hz), 8.49 (1H, s), 7.59 (1H, d, J = 15 Hz), 7.03 (1H, d, J = 15 Hz), 4.36-4.33 (2H, br m), 4.11-3.97 (4H, m), 2.98-2.95 (1H, m), 2.86 (1H, d, J = 11.9 Hz), 2.00-1.91 (1H, m), 1.82-1.58 (4H, m), 0.95 (6H, d, J = 6.5 Hz), 0.90-0.83 (2H, m), 0.80-0.72 (2H, m). |
| 457 | $^1$H-NMR ($CDCl_3$) δ: 9.96 (1H, s), 8.02 (1H, s), 7.76 (1H, d, J = 15.1 Hz), 6.62 (1H, d, J = 14,7 Hz), 4.18-4.08 (6H, m), 3.68 (2H, d, J = 8.2 Hz), 3.01-2.91 (1H, m), 2.18-2.06 (1H, m), 1.45 (3H, s), 1.42 (3H, s), 1.05 (6H, d, J = 5.7 Hz), 0.94 (2H, td, J = 7.3, 5.5 Hz), 0.80-0.73 (2H, m). |
| 458 | $^1$H-NMR ($CDCl_3$) δ: 9.96 (1H, s), 8.02 (1H, s), 7.74 (1H, t, J = 14.7 Hz), 6.53 (1H, d, J = 15.1 Hz), 4.37-4.17 (1H, m), 4.09 (2H, d, J = 7.4 Hz), 3.75-3.52 (2H, m), 3.00-2.91 (1H, m), 2.18-1.92 (5H, m), 1.27 (3H, dd, J = 7.6, 3.9 Hz), 1.05 (6H, d, J = 6.5 Hz), 0.94 (2H, td, J = 7.3, 5.5 Hz), 0.80-0.73 (2H, m). |
| 511 | $^1$H-NMR ($CDCl_3$) δ: 9.96 (1H, s), 8.03 (1H, s), 7.74 (1H, d, J = 14.7 Hz), 6.42 (1H, d, J = 14.7 Hz), 4.13-3.79 (6H, m), 3.03-2.92 (1H, m), 2.47-2.32 (2H, m), 2.16-2.03 (1H, m), 1.05 (6H, d, J = 7.0 Hz), 0.97-0.91 (2H, m), 0.80-0.73 (2H, m). |
| 534 | $^1$H-NMR ($CDCl_3$) δ: 9.96 (1H, s), 8.04 (1H, s), 7.84 (1H, d, J = 14.7 Hz), 6.62 (1H, d, J = 15.5 Hz), 4.31 (1H, d, J = 12.7 Hz), 4.13-4.00 (3H, m), 3.84-3.63 (2H, m), 3.58-3.47 (2H, m), 3.01-2.91 (1H, m), 2.18-2.03 (1H, m), 1.05 (6H, d, J = 6.1 Hz), 0.98-0.91 (2H, m), 0.80-0.74 (2H, m). |
| 544 | $^1$H-NMR ($CDCl_3$) δ: 9.97 (1H, s), 8.02 (1H, s), 7.79 (1H, d, J = 14.7 Hz), 6.65 (1H, d, J = 14.7 Hz), 4.62-4.28 (1H, m), 4.09 (2H, d, J = 7.4 Hz), 3.97-3.66 (3H, m), 3.65-3.43 (3H, m), 3.01-2.92 (1H, m), 2.17-2.08 (1H, m), 1.95-1.74 (2H, m), 1.05 (6H, d, J = 6.5 Hz), 0.99-0.89 (5H, m), 0.79-0.74 (2H, m). |
| 551 | $^1$H-NMR (DMSO-$D_6$) δ: 9.98-9.79 (1H, m), 8.55-8.30 (1H, m), 7.61 (1H, d, J = 14.7 Hz), 7.05 (1H, d, J = 14.3 Hz), 4.95-4.72 (1H, m), 4.13-3.96 (2H, m), 3.92-3.75 (2H, m), 3.63-3.39 (3H, m), 3.12-2.87 (2H, m), 2.83-2.64 (2H, m), 2.04-1.90 (1H, m), 0.95 (6H, d, J = 6.5 Hz), 0.90-0.80 (2H, m), 0.79-0.65 (2H, m). |
| 563 | $^1$H-NMR (DMSO-$D_6$) δ: 9.91 (1H, s), 7.65 (1H, d, J = 15.0 Hz), 6.74 (1H, d, J = 15.3 Hz), 3.97 (2H, d, J = 7.4 Hz), 3.60 (8H, s), 2.98-2.92 (1H, m), 2.40 (3H, s), 2.07-1.87 (1H, m), 0.91 (6H, d, J = 7.0 Hz), 0.89-0.79 (2H, m), 0.81-0.71 (2H, m). |

TABLE 6

| Ex | Data |
|---|---|
| 564 | $^1$H-NMR (DMSO-$D_6$) δ: 9.91 (1H, br s), 7.59 (1H, d, J = 15.3 Hz), 6.52 (1H, d, J = 15.3 Hz), 3.97 (2H, d, J = 7.4 Hz), 3.59 (2H, t, J = 6.7 Hz), 3.40 (2H, t, J = 6.7 Hz), 3.00-2.90 (1H, m), 2.39 (3H, s), 2.04-1.85 (3H, m), 1.85-1.76 (2H, m), 0.92 (6H, d, J = 6.9 Hz), 0.86-0.81 (2H, m), 0.81-0.71 (2H, m). |

TABLE 6-continued

| Ex | Data |
|---|---|
| 565 | $^1$H-NMR (DMSO-$D_6$) δ: 9.92 (1H, br s), 7.65 (1H, d, J = 15.6 Hz), 6.49 (1H, dd, J = 31.5, 15.3 Hz), 4.13 (1H, t, J = 13.0 Hz), 3.98 (2H, d, J = 7.4 Hz), 3.91-3.78 (2H, m), 3.63 (1H, t, J = 7.4 Hz), 3.01-2.91 (1H, m), 2.65-2.35 (2H, m), 2.42 (3H, s), 2.01-1.91 (1H, m), 0.93 (6H, d, J = 6.6 Hz), 0.90-0.80 (2H, m), 0.78-0.72 (2H, m). |
| 566 | $^1$H-NMR (DMSO-$D_6$) δ: 9.92 (1H, br s), 7.63 (1H, d, J = 15.3 Hz), 6.53 (1H, dd, J = 19.6, 15.6 Hz), 5.39 (1H, dd, J = 53.5, 21.3 Hz), 3.98 (2H, d, J = 7.4 Hz), 3.95-3.54 (3H, m), 3.51-3.30 (1H, m), 3.01-2.91 (1H, m), 2.41 (3H, s), 2.30-2.05 (2H, m), 2.02-1.91 (1H, m), 0.93 (6H, d, J = 6.3 Hz), 0.91-0.81 (2H, m), 0.80-0.70 (2H, m). |
| 567 | $^1$H-NMR (DMSO-$D_6$) δ: 9.91 (1H, s), 7.65 (1H, d, J = 15.3 Hz), 6.67 (1H, d, J = 15.0 Hz), 4.10 (2H, br s), 4.01-3.91 (4H, m), 3.56 (2H, d, J = 8.0 Hz), 2.99-2.89 (1H, m), 2.40 (3H, s), 2.03-1.93 (1H, m), 1.29 (6H, d, J = 6.4 Hz), 0.95-0.90 (6H, m), 0.88-0.81 (2H, m), 0.78-0.71 (2H, m). |
| 568 | $^1$H-NMR (DMSO-$D_6$) δ: 9.92 (1H, br s), 7.65 (1H, d, J = 15.3 Hz), 6.72 (1H, d, J = 15.3 Hz), 4.36 (1H, br s), 3.98 (1H, br s), 3.97 (2H, d, J = 7.4 Hz), 3.87 (1H, d, J = 8.3 Hz), 3.67 (1H, d, J = 11.6 Hz), 3.51 (1H, d, J = 11.3 Hz), 3.43-3.30 (2H, m), 2.99-2.89 (1H, m), 2.39 (3H, s), 2.05-1.88 (1H, m), 1.22 (3H, d, J = 6.1 Hz), 0.92 (6H, d, J = 6.9 Hz), 0.89-0.79 (2H, m), 0.78-0.70 (2H, m). |
| 569 | $^1$H-NMR (DMSO-$D_6$) δ: 9.91 (1H, d, J = 4.0 Hz), 7.63 (1H, d, J = 15.3 Hz), 6.67 (1H, d, J = 15.0 Hz), 4.35 (2H, s), 4.11 (1H, d, J = 13.2 Hz), 3.97 (2H, d, J = 7.0 Hz), 3.85 (1H, d, J = 12.9 Hz), 3.27-3.37 (1H, m), 3.01-2.91 (1H, m), 2.87 (1H, d, J = 11.4 Hz), 2.38 (3H, s), 2.01-1.91 (1H, m), 1.85-1.75 (2H, m), 1.73-1.53 (2H, m), 0.92 (6H, d, J = 6.6 Hz), 0.91-0.81 (2H, m), 0.80-0.70 (2H, m). |
| 570 | $^1$H-NMR (DMSO-$D_6$) δ: 9.91 (1H, br s), 7.64 (1H, d, J = 15.0 Hz), 6.71 (1H, d, J = 15.3 Hz), 4.37 (1H, br s), 3.98 (1H, br s), 3.97 (2H, d, J = 7.4 Hz), 3.87 (1H, d, J = 8.3 Hz), 3.66 (1H, d, J = 11.2 Hz), 3.52 (1H, d, J = 9.9 Hz), 3.43-3.30 (2H, m), 2.99-2.89 (1H, m), 2.39 (3H, s), 2.05-1.88 (1H, m), 1.22 (3H, d, J = 6.5 Hz), 0.92 (6H, d, J = 6.6 Hz), 0.89-0.79 (2H, m), 0.78-0.70 (2H, m). |
| 574 | $^1$H-NMR (DMSO-$D_6$) δ: 9.73 (1H, d, J = 4.1 Hz), 7.68 (1H, d, J = 15.3 Hz), 6.63 (1H, d, J = 15.3 Hz), 3.93 (2H, d, J = 6.5 Hz), 3.66 (4H, br s), 2.83-2.76 (1H, m), 2.56 (4H, br s), 2.36 (6H, s), 2.05-1.90 (1H, m), 0.90 (6H, d, J = 6.5 Hz), 0.80-0.71 (2H, m), 0.55-0.50 (2H, m). |
| 576 | $^1$H-NMR (DMSO-$D_6$) δ: 9.90 (1H, s), 7.65 (1H, d, J = 15.3 Hz), 6.67 (1H, d, J = 15.3 Hz), 4.10-3.96 (6H, m), 3.60-3.52 (2H, m), 3.00-2.90 (1H, m), 2.39 (3H, s), 2.05-1.95 (1H, m), 1.30 (6H, d, J = 6.5 Hz), 0.92 (6H, dd, J = 6.5, 2.7 Hz), 0.89-0.81 (2H, m), 0.80-0.70 (2H, m). |

TABLE 7

| Ex | Data |
|---|---|
| 579 | $^1$H-NMR (DMSO-$D_6$) δ: 9.91 (1H, d, J = 4.5 Hz), 7.64 (1H, d, J = 15.1 Hz), 6.80 (1H, d, J = 15.1 Hz), 3.97 (2H, d, J = 7.4 Hz), 3.80-3.63 (4H, m), 3.01-2.89 (1H, m), 2.41 (3H, s), 2.16-1.84 (5H, m), 0.92 (6H, d, J = 6.5 Hz), 0.89-0.79 (2H, m), 0.79-0.70 (2H, m). |
| 582 | $^1$H-NMR (DMSO-$D_6$) δ: 9.89 (1H, d, J = 4.1 Hz), 7.74 (1H, d, J = 15.1 Hz), 6.71 (1H, d, J = 15.1 Hz), 4.07 (2H, s), 3.72-3.49 (8H, m), 3.01-2.90 (1H, m), 2.36 (3H, s), 0.92 (9H, s), 0.89-0.79 (2H, m), 0.78-0.68 (2H, m). |
| 583 | $^1$H-NMR (DMSO-$D_6$) δ: 9.96-9.82 (1H, m), 6.38-6.25 (1H, m), 5.85-5.73 (1H, m), 3.94 (2H, d, J = 7.8 Hz), 3.92-3.83 (2H, m), 3.43-3.33 (2H, m), 2.99-2.87 (1H, m), 2.46-2.35 (1H, m), 2.21 (3H, s), 2.05-1.90 (1H, m), 1.72-1.63 (2H, m), 1.51-1.35 (2H, m), 0.94-0.78 (8H, m), 0.77-0.68 (2H, m). |
| 586 | $^1$H-NMR (DMSO-$D_6$) δ: 9.93 (1H, d, J = 3.7 Hz), 7.62 (1H, d, J = 15.5 Hz), 6.72 (1H, d, J = 15.1 Hz), 3.96 (2H, d, J = 7.4 Hz), 3.71-3.49 (8H, m), 3.01-2.91 (1H, m), 2.79 (2H, q, J = 7.5 Hz), 2.03-1.88 (1H, m), 1.23 (3H, t, J = 7.4 Hz), 0.91 (6H, d, J = 6.5 Hz), 0.88-0.79 (2H, m), 0.79-0.67 (2H, m). |
| 602 | $^1$H-NMR (DMSO-$D_6$) δ: 9.83 (1H, d, J = 3.3 Hz), 8.42-8.31 (1H, m), 7.70 (1H, d, J = 14.7 Hz), 7.55-7.33 (5H, m), 7.27 (1H, t d, J = 8.5, 4.2 Hz), 7.13 (1H, d, J = 14.7 Hz), 5.57 (1H, br s), 4.52-4.11 (2H, m), 4.00 (2H, br s), 3.94-3.72 (2H, m), 3.51 (1H, t, J = 10.5 Hz), 2.94-2.86 (1H, m), 1.97 |

TABLE 7-continued

| Ex | Data |
|---|---|
| | (1H, td, J = 13.6, 7.1 Hz), 0.95 (6H, d, J = 7.0 Hz), 0.86-0.76 (2H, m), 0.73-0.62 (2H, m). |
| 603 | $^1$H-NMR (DMSO-$D_6$) δ: 9.96-9.85 (1H, m), 8.59-8.00 (3H, m), 7.66-7.31 (3H, m), 7.01-6.42 (1H, m), 5.48-5.11 (1H, m), 4.04-3.91 (3H, m), 3.86-3.57 (1H, m), 2.96 (1H, br s), 2.46-2.26 (1H, m), 1.99-1.75 (4H, m), 0.97-0.80 (8H, m), 0.78-0.70 (2H, m). |
| 606 | $^1$H-NMR (DMSO-$D_6$) δ: 9.87 (1H, s), 8.46 (1H, s), 7.69 (1H, d, J = 14.7 Hz), 7.37 (4H, d, J = 4.1 Hz), 7.27 (1H, dd, J = 8.6, 3.7 Hz), 7.15 (1H, d, J = 14.7 Hz), 5.57 (1H, s), 4.46 (1H, d, J = 11.9 Hz), 4.18 (1H, s), 4.02 (2H, d, J = 6.5 Hz), 3.88 (1H, dd, J = 10.2, 3.9 Hz), 3.79 (1H, d, J = 9.4 Hz), 3.51 (1H, t, J = 10.4 Hz), 2.94 (1H, d, J = 4.1 Hz), 1.99 (1H, t, J = 6.7 Hz), 0.96 (6H, d, J = 6.5 Hz), 0.88-0.80 (2H, m), 0.77-0.69 (2H, m). |
| 608 | $^1$H-NMR (DMSO-$D_6$) δ: 9.91 (1H, d, J = 4.1 Hz), 7.59 (1H, d, J = 15.5 Hz), 6.47 (1H, d, J = 15.1 Hz), 4.00-3.87 (5H, m), 3.73-3.66 (1H, m), 2.98-2.91 (1H, m), 2.72-2.54 (2H, m), 2.41 (3H, s), 2.00-1.93 (1H, m), 0.92 (6H, d, J = 5.9 Hz), 0.87-0.80 (2H, m), 0.76-0.74 (2H, m). |
| 609 | $^1$H-NMR (DMSO-$D_6$) δ: 9.92-9.89 (1H, m), 7.59 (1H, d, J = 15.1 Hz), 6.80-6.46 (1H, m), 4.98 (2H, d, J = 7.4 Hz), 3.76-3.74 (2H, m), 3.20-3.16 (1H, m), 2.96-2.93 (1H, m), 2.42-2.38 (3H, m), 1.99-1.92 (3H, m), 1.74-1.71 (1H, m), 0.93 (6H, d, J = 6.5 Hz), 0.89-0.80 (3H, m), 0.76-0.74 (2H, m), 0.62-0.60 (1H, m). |
| 610 | $^1$H-NMR (DMSO-$D_6$) δ: 9.92 (1H, s), 7.61 (1H, dd, J = 15.3, 11.7 Hz), 6.52 (1H, d, J = 15.5 Hz), 3.99 (3H, d, J = 6.5 Hz), 3.61 (1H, s), 3.44 (1H, s), 2.97 (1H, br s), 2.41 (3H, s), 2.08-1.25 (7H, m), 0.95 (6H, d, J = 6.5 Hz), 0.89-0.84 (5H, br m), 0.77 (2H, s). |

TABLE 8

| Ex | Data |
|---|---|
| 611 | $^1$H-NMR (DMSO-$D_6$) δ: 9.91 (1H, s), 7.71-7.52 (1H, m), 6.96-6.57 (1H, m), 5.66 (1H, s), 4.16-3.80 (4H, m), 3.59-3.54 (1H, m), 3.05-2.90 (1H, m), 2.45-2.38 (3H, m), 2.09-1.67 (5H, m), 1.16-1.01 (6H, m), 0.93 (6H, d, J = 6.5 Hz), 0.90-0.82 (2H, m), 0.75 (2H, s). |
| 612 | $^1$H-NMR (DMSO-$D_6$) δ: 9.91 (1H, d, J = 3.7 Hz), 7.64-7.54 (1H, m), 6.70-6.46 (1H, m), 4.37-4.12 (1H, m), 4.04-3.91 (2H, m), 3.70-3.34 (4H, m), 3.28-3.24 (3H, m), 3.00-2.91 (1H, m), 2.40 (3H, s), 2.06-1.78 (5H, m), 0.98-0.90 (6H, m), 0.89-0.79 (2H, m), 0.78-0.67 (2H, m). |
| 613 | $^1$H-NMR (DMSO-$D_6$) δ: 9.91 (1H, d, J = 3.7 Hz), 7.60 (1H, d, J = 15.1 Hz), 6.72-6.46 (1H, m), 4.41-4.12 (1H, m), 4.09-3.91 (2H, m), 3.69-3.34 (4H, m), 3.28-3.22 (3H, m), 3.01-2.89 (1H, m), 2.40 (3H, s), 2.06-1.77 (5H, m), 1.00-0.90 (6H, m), 0.89-0.80 (2H, m), 0.79-0.63 (2H, m). |
| 614 | $^1$H-NMR (DMSO-$D_6$) δ: 9.91 (1H, d, J = 4.1 Hz), 7.62 (1H, d, J = 15.1 Hz), 6.60-6.45 (1H, m), 3.98 (2H, d, J = 7.4 Hz), 3.85-3.23 (5H, m), 3.01-2.91 (1H, m), 2.41 (3H, d, J = 3.3 Hz), 2.31-1.90 (3H, m), 0.93 (6H, d, J = 6.5 Hz), 0.89-0.80 (2H, m), 0.79-0.72 (2H, m). |
| 615 | $^1$H-NMR (DMSO-$D_6$) δ: 9.92-9.85 (1H, m), 7.62 (1H, d, J = 15.5 Hz), 6.74 (1H, d, J = 15.1 Hz), 3.96 (2H, d, J = 7.0 Hz), 3.67-3.54 (4H, m), 2.98-2.89 (1H, m), 2.77-2.60 (4H, m), 2.46-2.41 (1H, m), 2.38 (3H, s), 2.36-2.29 (4H, m), 2.02-1.90 (1H, m), 0.91 (6H, d, J = 7.0 Hz), 0.88-0.78 (2H, m), 0.77-0.65 (2H, m). |

TABLE 8-continued

| Ex | Data |
|---|---|
| 616 | $^1$H-NMR (DMSO-$D_6$) δ: 9.91 (1H, d, J = 4.1 Hz), 7.59 (1H, d, J = 15.1 Hz), 6.52 (1H, d, J = 15.5 Hz), 4.24 (2H, dt, J = 46.6, 6.7 Hz), 4.02-3.92 (2H, m), 2.98-2.92 (1H, m), 2.39 (3H, s), 2.27-1.93 (3H, m), 1.67-1.43 (2H, m), 1.13 (6H, dd, J = 8.6, 6.1 Hz), 0.92 (6H, dd, J = 6.7, 3.1 Hz), 0.88-0.81 (2H, m), 0.78-0.71 (2H, m). |
| 617 | $^1$H-NMR (DMSO-$D_6$) δ: 9.93 (1H, s), 7.61 (1H, d, J = 15.5 Hz), 6.53 (1H, d, J = 15.1 Hz), 4.25 (2H, dt, J = 46.2, 6.7 Hz), 3.99 (2H, t, J = 7.4 Hz), 3.02-2.91 (1H, m), 2.41 (3H, s), 2.19-1.97 (3H, m), 1.67-1.46 (2H, m), 1.15 (6H, dd, J = 8.4, 6.3 Hz), 0.94 (6H, dd, J = 6.7, 3.1 Hz), 0.90-0.82 (2H, m), 0.80-0.73 (2H, m). |
| 618 | $^1$H-NMR (DMSO-$D_6$) δ: 9.91 (1H, s), 7.63 (1H, d, J = 15.5 Hz), 6.52 (1H, d, J = 15.5 Hz), 4.33-3.92 (4H, br m), 3.01-2.91 (1H, m), 2.41 (3H, s), 2.09-1.92 (3H, m), 1.75-1.60 (2H, m), 1.27 (6H, d, J = 6.5 Hz), 0.95 (6H, d, J = 6.5 Hz), 0.92-0.81 (2H, m), 0.79-0.71 (2H, m). |
| 619 | $^1$H-NMR (DMSO-$D_6$) δ: 9.92 (1H, s), 7.68-7.53 (1H, m), 6.60-6.48 (1H, m), 3.97 (3H, s), 3.89-3.63 (1H, m), 3.59-3.40 (2H, m), 2.96 (1H, br s), 2.40 (3H, s), 2.13-1.65 (5H, m), 0.92 (6H, dd, J = 6.5, 2.0 Hz), 0.98 (1H, br s), 0.85 (2H, t, J = 5.9 Hz), 0.76 (2H, s), 0.64-0.15 (3H, m). |
| 620 | $^1$H-NMR (DMSO-$D_6$) δ: 9.90 (1H, d, J = 3.7 Hz), 7.63-7.53 (1H, m), 6.54-6.44 (1H, m), 3.97 (2H, d, J = 7.0 Hz), 3.80-3.48 (2H, m), 3.46-3.02 (7H, m), 2.99-2.90 (1H, m), 2.63-2.34 (4H, m), 2.08-1.88 (2H, m), 1.74-1.51 (1H, m), 0.92 (6H, d, J = 7.0 Hz), 0.89-0.79 (2H, m), 0.78-0.69 (2H, m). |

TABLE 9

| Ex | Data |
|---|---|
| 621 | $^1$H-NMR (DMSO-$D_6$) δ: 9.91 (1H, d, J = 3.3 Hz), 7.64-7.52 (1H, m), 6.50 (1H, d, J = 15.5 Hz), 3.97 (2H, d, J = 7.4 Hz), 3.80-3.48 (2H, m), 3.47-3.07 (7H, m), 3.01-2.89 (1H, m), 2.61-2.36 (4H, m), 2.10-1.53 (3H, m), 0.93 (6H, d, J = 6.5 Hz), 0.89-0.80 (2H, m), 0.79-0.69 (2H, m). |
| 622 | $^1$H-NMR (DMSO-$D_6$) δ: 9.91 (1H, d, J = 3,7 Hz), 7.61 (1H, d, J = 15.5 Hz), 6.58-6.46 (1H, m), 6.37-5.92 (1H, m), 3.98 (2H, d, |

TABLE 9-continued

| Ex | Data |
|---|---|
| | J = 7.4 Hz), 3.90-3.70 (1H, m), 3.69-3.53 (2H, m), 3.51-3.24 (2H, m), 3.00-2.90 (1H, m), 2.40 (3H, d, J = 2.6 Hz), 2.17-1.79 (3H, m), 0.93 (6H, d, J = 6.6 Hz), 0.89-0.79 (2H, m), 0.78-0.69 (2H, m). |
| 623 | $^{1}$H-NMR (DMSO-$D_6$) δ: 9.92 (1H, s), 7.58 (1H, d, J = 15.5 Hz), 6.56-6.48 (1H, m), 4.36 (1H, d, J = 6.6 Hz), 3.97 (2H, d, J = 6.6 Hz), 3.80-3.39 (4H, m), 2.96 (1H, br s), 2.40 (3H, d, J = 2.6 Hz), 2.30-1.80 (4H, m), 1.11 (6H, s), 0.92 (6H, d, J = 6.6 Hz), 0.86-0.84 (2H, m), 0.77-0.74 (2H, m). |
| 624 | $^{1}$H-NMR (DMSO-$D_6$) δ: 9.89 (1H, d, J = 3.7 Hz), 7.76 (1H, d, J = 15.5 Hz), 6.65 (1H, d, J = 15.1 Hz), 4.21-3.94 (6H, m), 3.62-3.50 (2H, m), 3.01-2.91 (1H, m), 2.36 (3H, s), 1.29 (6H, d, J = 6.3 Hz), 0.92 (9H, s), 0.89-0.79 (2H, m), 0.78-0.70 (2H, m). |
| 625 | $^{1}$H-NMR (DMSO-$D_6$) δ: 9.89 (1H, d, J = 4.5 Hz), 7.74 (1H, d, J = 15.5 Hz), 6.69 (1H, d, J = 15.1 Hz), 4.07 (2H, s), 3.91-3.25 (7H, m), 3.00-2.90 (1H, m), 2.36 (3H, s), 1.22 (3H, d, J = 6.5 Hz), 0.92 (9H, s), 0.89-0.79 (2H, m), 0.78-0.69 (2H, m). |
| 626 | $^{1}$H-NMR (DMSO-$D_6$) δ: 9.93 (1H, d, J = 3.7 Hz), 7.64 (1H, d, J = 15.5 Hz), 6.65 (1H, d, J = 15.1 Hz), 4.16-3.88 (6H, m), 3.64-3.50 (2H, m), 3.01-2.91 (1H, m), 2.79 (2H, q, J = 7.4 Hz), 2.05-1.86 (1H, m), 1.29 (6H, d, J = 6.5 Hz), 1.23 (3H, t, J = 7.4 Hz), 0.97-0.89 (6H, m), 0.88-0.80 (2H, m), 0.79-0.69 (2H, m). |
| 627 | $^{1}$H-NMR (DMSO-$D_6$) δ: 9.90 (1H, d, J = 4.1 Hz), 7.79 (1H, d, J = 15.5 Hz), 6.57-6.35 (1H, m), 4.22-3.57 (6H, m), 3.01-2.91 (1H, m), 2.61-2.42 (2H, m), 2.39 (3H, s), 0.93 (9H, s), 0.90-0.79 (2H, m), 0.79-0.70 (2H, m). |
| 628 | $^{1}$H-NMR (DMSO-$D_6$) δ: 9.90 (1H, d, J = 4.1 Hz), 7.59 (1H, d, J = 15.1 Hz), 6.52 (1H, d, J = 15.1 Hz), 3.97 (2H, d, J = 7.4 Hz), 3.90-3.24 (8H, m), 3.06-2.84 (3H, m), 2.40 (3H, s), 2.04-1.89 (1H, m), 0.93 (6H, d, J = 6.5 Hz), 0.89-0.79 (2H, m), 0.78-0.69 (2H, m). |
| 629 | $^{1}$H-NMR ($CDCl_3$) δ: 16.79 (1H, s), 9.96 (1H, s), 7.76 (1H, dd, J = 21.3, 15.1 Hz), 6.42 (1H, dd, J = 15.3, 4.7 Hz), 4.22-4.01 (1H, m), 4.07 (2H, d, J = 7.4 Hz), 3.91-3.84 (1H, m), 3.67-3.42 (2H, m), 3.00-2.90 (1H, m), 2.47 (3H, s), 2.16-1.79 (5H, m), 1.03 (6H, td, J = 6.7, 2.9 Hz), 0.98-0.88 (6H, m), 0.83 (2H, d, J = 7.0 Hz), 0.79-0.72 (2H, m). |
| 630 | $^{1}$H-NMR ($CDCl_3$) δ: 16.79 (1H, s), 9.97 (1H, s), 7.76 (1H, dd, J = 21.1, 15.3 Hz), 6.42 (1H, dd, J = 15.3, 4.7 Hz), 4.22-4.01 (1H, m), 4.07 (2H, d, J = 7.4 Hz), 3.91-3.82 (1H, m), 3.67-3.44 (2H, m), 2.99-2.90 (1H, m), 2.47 (3H, s), 2.14-1.79 (5H, m), 1.03 (6H, td, J = 7.0, 2.9 Hz), 0.98-0.88 (6H, m), 0.83 (2H, d, J = 7.0 Hz), 0.79-0.73 (2H, m). |
| 632 | $^{1}$H-NMR (DMSO-$D_6$) δ: 9.93 (1H, s), 7.69 (1H, d, J = 16.4 Hz), 6.66-6.04 (2H, m), 4.38 (1H, d, J = 23.3 Hz), 3.98 (2H, s), 3.70 (2H, s), 2.95 (1H, s), 2.42 (3H, s), 2.16-1.86 (5H, br m), 1.00-0.67 (10H, m). |

TABLE 10

| Ex | Data |
|---|---|
| 633 | $^{1}$H-NMR (DMSO-$D_6$) δ: 9.88 (1H, s), 8.55-8.39 (2H, m), 7.70-7.28 (3H, m), 6.72-6.03 (1H, m), 5.43-5.14 (1H, m), 4.09-3.60 (4H, m), 2.93 (1H, s), 2.48-1.72 (3H, m), 2.05-1.80 (5H, m), 1.01-0.62 (10H, m). |
| 634 | $^{1}$H-NMR (DMSO-$D_6$) δ: 9.79 (1H, d, J = 10.2 Hz), 7.70 (1H, d, J = 13.9 Hz), 6.54-5.97 (2H, m), 4.46-4.29 (1H, m), 4.04-3.56 (3H, m), 3.10-2.84 (1H, m), 2.43-1.89 (8H, m), 1.84-1.69 (1H, m), 0.97-0.48 (10H, m). |
| 635 | $^{1}$H-NMR (DMSO-$D_6$) δ: 9.89 (1H, d, J = 13.5 Hz), 8.61-8.47 (1H, m), 7.86-7.21 (4H, m), 6.72-6.06 (1H, m), 5.36-5.12 (1H, m), 4.11-3.87 (2H, m), 3.85-3.61 (2H, m), 2.94 (1H, br s), 2.47-1.78 (3H, m), 2.05-1.83 (5H, m), 1.04-0.78 (8H, m), 0.78-0.66 (2H, m), |
| 638 | $^{1}$H-NMR (DMSO-$D_6$) δ: 9.92 (1H, s), 8.54 (1H, s), 7.87-7.17 (5H, m), 6.88-6.32 (1H, m), 4.95-4.65 (2H, m), 3.96 (1H, s), 3.23-2.86 (4H, m), 2.46-2.06 (3H, m), 2.03-1.62 (1H, m), 1.03-0.38 (10H, m). |
| 639 | $^{1}$H-NMR (DMSO-$D_6$) δ: 9.93-9.87 (1H, m), 7.71-7.54 (2H, m), 6.91-6.66 (1H, m), 6.17-6.03 (1H, m), 4.63-4.48 (2H, m), 4.04-3.91 (2H, m), 3.78 (3H, s), 3.09-2.96 (3H, m), 2.98-2.91 (1H, m), 2.42-2.31 (3H, m), 2.02-1.90 (1H, m), 0.92 (6H, d, J = 6.5 Hz), 0.89-0.81 (2H, m), 0.78-0.71 (2H, m). |

TABLE 10-continued

| Ex | Data |
|---|---|
| 640 | $^{1}$H-NMR (DMSO-$D_6$) δ: 9.91 (1H, s), 7.59 (1H, dd, J = 15.1, 11.4 Hz), 6.50 (1H, d, J = 15.1 Hz), 4.07-3.87 (3H, m), 3.59 (1H, dd, J = 15.3, 8.0 Hz), 3.42 (1H, s), 2.99-2.88 (1H, m), 2.39 (3H, s), 1.97-1.68 (6H, m), 1.62-1.22 (1H, m), 0.98-0.68 (13H, m). |
| 641 | $^{1}$H-NMR (DMSO-$D_6$) δ: 9.82 (1H, s), 7.70 (1H, d, J = 15.3 Hz), 6.64 (1H, d, J = 15.3 Hz), 4.25 (2H, s), 4.02-3.90 (2H, m), 3.72 (2H, d, J = 11.3 Hz), 3.51 (2H, dd, J = 11.3, 3.7 Hz), 2.99-2.84 (1H, m), 2.37 (3H, s), 2.05-1.94 (1H, m), 1.30-1.24 (6H, m), 0.92-0.63 (10H, m). |
| 642 | $^{1}$H-NMR (DMSO-$D_6$) δ: 9.91 (1H, s), 7.71 (1H, d, J = 15.1 Hz), 7.36 (4H, d, J = 5.2 Hz), 7.30-7.25 (1H, m), 6.76 (1H, d, J = 14.7 Hz), 4.40 (1H, d, J = 11.8 Hz), 3.97 (2H, d, J = 6.3 Hz), 3.92-3.78 (2H, m), 3.53 (1H, td, J = 11.7, 3.1 Hz), 2.99-2.90 (1H, m), 2.50 (3H, s), 2.45-2.10 (2H, m), 2.06-1.88 (1H, m), 0.92 (6H, d, J = 6.3 Hz), 0.88-0.82 (2H, m), 0.77-0.70 (2H, m). |
| 644 | $^{1}$H-NMR (DMSO-$D_6$) δ: 9.91 (1H, d, J = 3.7 Hz), 7.63 (1H, dd, J = 15.1, 9.4 Hz), 6.72 (1H, d, J = 15.1 Hz), 4.40-4.23 (2H, br m), 3.99-3.92 (2H, m), 3.61-3.47 (3H, m), 3.00-2.92 (1H, m), 2.62-2.55 |

TABLE 10-continued

| Ex | Data |
|---|---|
| | (1H, m), 2.39 (3H, s), 1.98-1.96 (1H, m), 1.24 (2H, d, J = 6.5 Hz), 1.16-1.15 (4H, m), 0.92 (6H, d, J = 6.5 Hz), 0.86-0.83 (2H, m), 0.76-0.75 (2H, m). |
| 645 | $^1$H-NMR (DMSO-$D_6$) δ: 9.91 (1H, d, J = 4.1 Hz), 7.63 (1H, dd, J = 15.3, 9.6 Hz), 6.72 (1H, d, J = 15.1 Hz), 4.46-4.17 (2H, br m), 4.02-3.85 (2H, m), 3.72-3.35 (3H, m), 3.02-2.88 (2H, m), 2.67-2.53 (1H, m), 2.39 (3H, s), 1.25-1.08 (6H, m), 0.92 (6H, d, J = 7.0 Hz), 0.88-0.79 (2H, m), 0.79-0.68 (2H, m). |

TABLE 11

| Ex | Data |
|---|---|
| 646 | $^1$H-NMR (DMSO-$D_6$) δ: 9.91 (1H, d, J = 3.7 Hz), 7.65 (1H, d, J = 15.1 Hz), 6.68 (1H, d, J = 15.1 Hz), 4.36-4.33 (1H, m), 4.05-3.95 (3H, m), 3.87-3.77 (2H, m), 3.47-3.34 (2H, m), 2.98-2.93 (1H, m), 2.39 (3H, s), 1.99-1.91 (1H, m), 1.22 (3H, d, J = 6.5 Hz), 1.14 (3H, d, J = 6.5 Hz), 0.92 (6H, dd, J = 6.5, 1.2 Hz), 0.85-0.83 (2H, m), 0.76-0.75 (2H, m). |
| 647 | $^1$H-NMR (DMSO-$D_6$) δ: 9.91 (1H, d, J = 4.1 Hz), 7.65 (1H, d, J = 15.1 Hz), 6.69 (1H, d, J = 15.1 Hz), 4.37-4.34 (1H, m), 4.03-3.97 (3H, m), 3.87-3.77 (2H, m), 3.45-3.34 (2H, m), 2.97-2.92 (1H, m), 2.39 (3H, s), 2.02-1.90 (1H, m), 1.22 (3H, d, J = 6.5 Hz), 1.14 (3H, d, J = 6.5 Hz), 0.92 (6H, dd, J = 7.0, 1.2 Hz), 0.85-0.83 (2H, m), 0.77-0.74 (2H, m). |
| 648 | $^1$H-NMR (DMSO-$D_6$) δ: 9.92 (1H, d, J = 3.7 Hz), 7.64 (1H, d, J = 15.5 Hz), 6.50 (1H, d, J = 15.1 Hz), 5.46-5.29 (2H, m), 4.11-4.07 (2H, m), 3.98 (2H, d, J = 7.0 Hz), 3.80-3.60 (4H, m), 2.97-2.94 (1H, m), 1.98-1.96 (2H, m), 0.93 (6H, d, J = 6.6 Hz), 0.89-0.83 (2H, m), 0.77-0.75 (2H, m). |
| 649 | $^1$H-NMR (DMSO-$D_6$) δ: 9.90 (1H, s), 7.65 (1H, d, J = 15.1 Hz), 6.52 (1H, d, J = 15.1 Hz), 5.52-5.34 (2H, m), 4.04-3.87 (6H, m), 2.96-2.93 (1H, m), 2.43 (3H, s), 2.02-1.93 (1H, m), 0.93 (6H, d, J = 6.5 Hz), 0.87-0.83 (2H, m), 0.75-0.73 (2H, m). |
| 650 | $^1$H-NMR (DMSO-$D_6$) δ: 9.90 (1H, s), 7.68 (1H, d, J = 15.1 Hz), 6.67 (1H, d, J = 15.5 Hz), 4.77-4.68 (2H, m), 4.04-3.93 (2H, m), 3.01-2.89 (1H, m), 2.41 (3H, s), 2.17-1.98 (9H, m), 0.91 (6H, d, J = 6.5 Hz), 0.86-0.84 (2H, m), 0.79-0.76 (2H, m). |
| 651 | $^1$H-NMR (DMSO-$D_6$) δ: 9.91 (1H, d, J = 3.7 Hz), 7.64 (1H, d, J = 15.5 Hz), 6.78 (1H, d, J = 15.1 Hz), 4.43 (1H, d, J = 12.7 Hz), 4.08 (1H, d, J = 13.5 Hz), 3.97 (2H, d, J = 7.4 Hz), 3.45- 3.40 (1H, m), 2.98-2.94 (2H, m), 2.39-2.35 (5H, m), 1.99-1.96 (1H, m), 1.81-1.78 (2H, m), 1.50-1.45 (2H, m), 0.92 (6H, d, J = 6.5 Hz), 0.85-0.83 (2H, m), 0.75-0.74 (2H, m). |
| 653 | $^1$H-NMR (DMSO-$D_6$) δ: 9.93 (1H, d, J = 4.1 Hz), 7.62 (1H, d, J = 15.1 Hz), 6.70 (1H, d, J = 15.1 Hz), 4.49-3.23 (9H, m), 3.01-2.91 (1H, m), 2.79 (2H, q, J = 7.4 Hz), 2.04-1.88 (1H, m), 1.30-1.16 (6H, m), 0.97-0.64 (10H, m). |
| 654 | $^1$H-NMR (DMSO-$D_6$) δ: 10.00-9.88 (1H, m), 7.69-7.49 (1H, m), 6.91-6.56 (1H, m), 5.67-4.53 (1H, m), 4.17-3.49 (5H, m), 3.03-2.92 (1H, m), 2.85-2.71 (2H, m), 2.04-1.68 (5H, m), 1.31-1.19 (3H, m), 1.17-0.98 (6H, m), 0.97-0.80 (8H, m), 0.79-0.66 (2H, m). |
| 656 | $^1$H-NMR (DMSO-$D_6$) δ: 9.90 (1H, d, J = 3.7 Hz), 7.49 (1H, d, J = 15.3 Hz), 6.67 (1H, d, J = 15.3 Hz), 3.96 (2H, d, J = 7.5 H z), 3.71 (2H, t, J = 5.1 Hz), 3.53 (2H, t, J = 5.1 Hz), 3.60-3.30 (2H, m), 2.96-2.93 (1H, m), 2.36 (3H, s), 1.99-1.91 (1H, m), 1.37 (6H, s), 0.91 (6H, d, J = 6.8 Hz), 0.86-0.79 (2H, m), 0.75-0.73 (2H, m). |
| 657 | $^1$H-NMR (DMSO-$D_6$) δ: 9.92 (1H, d, J = 4.1 Hz), 7.65 (1H, d, J = 15.0 Hz), 6.76-6.71 (1H, m), 3.99-3.95 (2H, m), 3.61-3.57 (4H, m), 3.45 (2H, d, J = 20.1 Hz), 2.97-2.94 (1H, m), 2.38 (3H, br s), 1.98-1.95 (1H, m), 1.13 (6H, s), 0.90-0.84 (8H, m), 0.76-0.75 (2H, m). |

TABLE 12

| Ex | Data |
|---|---|
| 658 | $^1$H-NMR (DMSO-$D_6$) δ: 9.91 (1H, d, J = 3.7 Hz), 7.66 (1H, d, J = 15.3 Hz), 6.64 (1H, d, J = 15.3 Hz), 4.55-4.46 (2H, m), 3.98 (2H, d, J = 7.4 Hz), 3.65-3.45 (4H, m), 2.98-2.92 (1H, m), 2.39 (3H, s), 2.05-1.75 (5H, m), 0.93 (6H, d, J = 6.4 Hz), 0.89-0.80 (2H, m), 0.78-0.70 (2H, m). |
| 659 | $^1$H-NMR (DMSO-$D_6$) δ: 9.91 (1H, d, J = 3.7 Hz), 7.65 (1H, d, J = 15.8 Hz), 6.73 (1H, d, J = 15.5 Hz), 4.39-3.24 (9H, m), 3.02-2.85 (1H, m), 2.39 (3H, s), 2.05-1.90 (1H, m), 1.89-1.62 (2H, m), 0.98-0.88 (6H, m), 0.88-0.79 (5H, m) 0.78-0.64 (2H, m). |
| 662 | $^1$H-NMR ($CDCl_3$) δ: 9.98 (1H, s), 7.71 (1H, d, J = 15.5 Hz), 6.35 (1H, d, J = 15.1 Hz), 4.17 (1H, t, J = 11.4 Hz), 4.07 (2H, d, J = 7.4 Hz), 3.72-3.63 (2H, m), 3.50 (1H, d, J = 9.2 Hz), 3.07-2.91 (4H, m), 2.81 (3H, d, J = 3.7 Hz), 2.47 (3H, s), 2.28-1.92 (8H, m), 1.01 (6H, d, J = 6.3 Hz), 0.98-0.91 (2H, m), 0.79-0.73 (2H, m). |
| 663 | $^1$H-NMR ($CDCl_3$) δ: 9.97 (1H, s), 7.74-7.65 (1H, m), 6.39-6.33 (1H, m), 4.34 (1H, t, J = 13.6 Hz), 4.07 (2H, d, J = 7.4 Hz), 3.78-3.59 (3H, m), 3.22-3.07 (2H, m), 3.03-2.90 (1H, m), 2.46 (3H, s), 2.12 (3H, s), 2.03-1.50 (9H, m), 1.00 (6H, d, J = 5.2 MHz), 0.95-0.88 (2H, m) 0.80-0.72 (2H, m). |
| 664 | $^1$H-NMR ($CDCl_3$) δ: 9.98 (1H, s), 7.73 (1H, d, J = 15.5 Hz), 6.36 (1H, d, J = 15.1 Hz), 4.06 (2H, d, J = 7.0 Hz), 3.72 (2H, t, J = 6.1 Hz), 3.39-3.23 (5H, m), 3.01-2.91 (4H, m), 2.47 (3H, s), 2.10-1.95 (2H, m), 2.03 (3H, s), 1.68-1.62 (3H, m), 1.01 (6H, d, J = 6.6 Hz), 0.94 (2H, td, J = 7.4, 5.4 Hz), 0.79-0.73 (2H, m). |
| 665 | $^1$H-NMR ($CDCl_3$) δ: 16.78 (1H, s), 9.96 (1H, s), 7.68 (1H, d, J = 15.1 Hz), 6.39-6.32 (1H, m), 4.64 (1H, d, J = 11.4 Hz), 4.06 (2H, d, J = 7.4 Hz), 3.84 (1H, d, J = 8.5 Hz), 3.68 (2H, t, J = 6.3 Hz), 3.12 (2H, d, J = 9.6 Hz), 3.01-2.91 (2H, m), 2.66-2.56 (1H, m), 2.46 (3H, s), 2.11 (3H, s), 2.09-1.92 (5H, m), 1.45-1.34 (2H, m), 1.02-0.97 (6H, m), 0.95-0.90 (2H, m), 0.79-0.72 (2H, m). |
| 667 | $^1$H-NMR ($CDCl_3$) δ: 12.17 (1H, s), 9.97 (1H, d, J = 3.3 Hz), 7.71 (1H, d, J = 15.1 Hz), 6.38-6.31 (1H, m), 4.07 (2H, d, J = 7.4 Hz), 3.72 (2H, t, J = 6.4 Hz), 3.44-3.17 (8H, m), 3.01-2.90 (1H, m), 2.47 (3H, s), 2.12-1.98 (5H, m), 1.58 (2H, d, J = 11.1 Hz), 1.49 (3H, t, J = 7.2 Hz), 1.00 (6H, d, J = 6.6 Hz), 0.97-0.91 (2H, m), 0.80-0.73 (2H, m). |
| 671 | $^1$H-NMR (DMSO-$D_6$) δ: 9.90 (1H, s), 7.61 (1H, d, J = 15.5 Hz), 6.73 (1H, d, J = 15.5 Hz), 4.52-4.17 (2H, m), 3.96 (2H, d, J = 6.5 Hz), 2.90-2.71 (7H, m), 2.39-2.31 (4H, m), 2.04-1.96 (2H, m), 1.82-1.78 (1H, m), 1.23 (3H, s), 0.91 (6H, d, J = 6.5 Hz), 0.84-0.82 (2H, m), 0.76-0.72 (2H, m). |
| 672 | $^1$H-NMR (DMSO-$D_6$) δ: 9.90 (1H, d, J = 4.1 Hz), 7.63 (1H, d, J = 15.1 Hz), 6.78 (1H, d, J = 15.5 Hz), 4.86-4.82 (1H, m), 4.38-4.35 (1H, m), 3.96 (2H, d, J = 7.4 Hz), 3.10-3.07 (1H, m), 2.96-2.94 (1H, m), 2.40 (3H, s), 2.18-2.00 (5H, m), 1.20 (3H, d, J = 5.7 Hz), 0.92 (6H, d, J = 7.0 Hz), 0.85-0.81 (2H, m), 0.75-0.73 (2H, m). |
| 673 | $^1$H-NMR (DMSO-$D_6$) δ: 9.87 (1H, s), 7.62-7.11 (6H, m), 6.70-6.03 (1H, m), 5.31-5.10 (1H, m), 4.05-3.55 (4H, m), 2.92 (1H, s), 2.45-1.59 (8H, m), 0.97-0.57 (10H, m). |

TABLE 13

| Ex | Data |
|---|---|
| 674 | $^1$H-NMR (DMSO-$D_6$) δ: 9.88 (1H, s), 7.60-7.18 (6H, m), 6.73-6.05 (1H, m), 5.34-5.13 (1H, m), 4.05-3.58 (4H, m), 2.94 (1H, s), 1.70-2.46 (8H, m), 1.00-0.62 (10H, m). |
| 675 | $^1$H-NMR (DMSO-$D_6$) δ: 9.91 (1H, d, J = 4.1 Hz), 8.24-7.75 (4H, m), 6.78 (1H, d, J = 15.5 Hz), 4.40-4.31 (2H, m), 4.09-4.00 (4H, m), 2.97-2.94 (1H, m), 2.42 (3H, s), 2.07-1.96 (1H, m), 0.97 (6H, d, J = 6.5 Hz), 0.89-0.83 (2H, m) 0.78-0.72 (2H, m). |
| 676 | $^1$H-NMR (DMSO-$D_6$) δ: 9.91 (1H, d, J = 4.1 Hz), 8.08 (1H, s), 7.95 (1H, dd, J = 4.9, 1.6 Hz), 7.76 (1H, d, J = 15.5 Hz), 7.02 (1H, dd, J = 8.0, 4.7 Hz), 6.74 (1H, d, J = 15.1 Hz), 4.42 (2H, dd, J = 4.1, 5.3 Hz), 4.05-3.98 (4H, m), 3.00-2.91 (1H, m), 2.39 (3H, s), 2.06-1.95 (1H, m), 0.96 (6H, d, J = 6.3 Hz), 0.89-0.82 (2H, m) 0.80-0.73 (2H, m). |

TABLE 13-continued

| Ex | Data |
|---|---|
| 677 | $^1$H-NMR (DMSO-$D_6$) δ: 9.90 (1H, s), 7.71-7.50 (1H, m), 6.95-6.55 (1H, m), 5.68-4.54 (1H, m), 4.15-3.80 (4H, m), 3.57-3.52 (1H, m), 3.03-2.89 (1H, m), 2.46-2.34 (3H, m), 2.08-1.68 (5H, m), 1.27-1.00 (6H, m), 0.98-0.68 (10H, m). |
| 679 | $^1$H-NMR (DMSO-$D_6$) δ: 9.90 (1H, s), 7.65 (1H, d, J = 15.3 Hz), 6.75 (1H, d, J = 14.7 Hz), 4.85-4.72 (0H, m), 4.39-4.18 (1H, m), 4.13-3.91 (3H, m), 3.90-3.82 (1H, m), 3.49-2.71 (5H, m), 2.40 (3H, s), 2.05-1.92 (1H, m), 1.12 (3H, d, J = 6.1 Hz), 0.92 (6H, d, J = 6.4 Hz), 0.88-0.80 (2H, m), 0.78-0.70 (2H, m). |
| 680 | $^1$H-NMR (DMSO-$D_6$) δ: 9.91 (1H, s), 7.65 (1H, d, J = 15.3 Hz), 6.75 (1H, d, J = 14.3 Hz), 4.40-4.18 (1H, m), 4.15-3.91 (3H, m), 3.90-3.81 (1H, m), 3.47-2.74 (5H, m), 2.40 (3H, s), 2.04-1.91 (1H, m), 1.12 (3H, d, J = 6.5 Hz), 0.92 (6H, d, J = 6.5 Hz), 0.88-0.81 (2H, m), 0.78-0.71 (2H, m). |
| 681 | $^1$H-NMR (DMSO-$D_6$) δ: 9.95-9.86 (1H, m), 7.70 (1H. d, J = 15.5 Hz), 6.71 (1H, t, J = 16.6 Hz), 4.50 (2H, s), 3.98 (2H, d, J = 7.4 Hz), 3.21 (3H, s), 3.00-2.92 (1H, m), 2.43 (3H, s), 2.06-1.87 (1H, m), 0.93 (6H, d, J = 6.6 Hz), 0.89-0.80 (2H, m), 0.79-0.70 (2H, m). |
| 682 | $^1$H-NMR (DMSO-$D_6$) δ: 9.91 (1H, d, J = 4.1 Hz), 7.62 (1H, d, J = 15.8 Hz), 6.73 (1H, d, J = 15.5 Hz), 4.58-3.30 (10H, m), 3.27 (3H, s), 3.08-2.88 (2H, m), 2.38 (3H, s), 2.04-1.87 (1H, m), 0.93 (6H, d, J = 6.6 Hz), 0.89-0.79 (2H, m), 0.78-0.69 (2H, m). |
| 683 | $^1$H-NMR (DMSO-$D_6$) δ: 9.95-9.86 (1H, m), 7.62 (1H, d, J = 14.7 Hz), 6.73 (1H, d, J = 14.7 Hz), 4.57-3.30 (10H, m), 3.27 (3H, s), 3.05-2.90 (2H, m), 2.38 (3H, s), 2.03-1.90 (1H, m), 0.93 (6H, d, J = 6.6 Hz), 0.89-0.80 (2H, m) 0.79-0.70 (2H, m). |
| 685 | $^1$H-NMR (DMSO-$D_6$) δ: 9.96-9.85 (1H, m), 7.62 (1H, d, J = 15.1 Hz), 6.74 (1H, d, J = 15.1 Hz), 3.96 (2H, d, J = 7.0 Hz), 3.68-3.54 (4H, m), 3.27-3.17 (2H, m), 3.00-2.90 (1H, m), 2.69-2.59 (4H, m), 2.39 (3H, s), 2.04-1.87 (1H, m), 0.92 (6H, d, J = 6.5 Hz), 0.88-0.79 (2H, m), 0.77-0.69 (2H, m). |

TABLE 14

| Ex | Data |
|---|---|
| 697 | $^1$H-NMR (DMSO-$D_6$) δ: 9.89 (1H, s), 7.61 (1H, d, J = 15.5 Hz), 6.73 (1H, d, J = 15.1 Hz), 4.52-4.15 (2H, m), 3.96 (2H, d, J = 7.0 Hz), 2.95-2.66 (7H, m), 2.39-2.31 (4H, m), 2.03-1.94 (2H, m), 1.81-1.78 (1H, m), 1.23 (3H, s), 0.91 (6H, d, J = 6.5 Hz), 0.85-0.83 (2H, m), 0.78-0.71 (2H, m). |
| 701 | $^1$H-NMR (DMSO-$D_6$) δ: 9.83 (1H, s), 7.64 (1H, d, J = 15.1 Hz), 6.67 (1H, d, J = 15.1 Hz), 4.55 (1H, br ), 4.15 (1H, br s), 3.95 (2H, d, J = 7.4 Hz), 2.91-2.88 (2H, m), 2.81-2.78 (1H, m), 2.37 (3H, s), 2.28 (3H, s), 2.23-1.92 (4H, m), 1.23 (3H, s), 0.90 (6H, d, J = 6.5 Hz), 0.82-0.79 (2H, m) 0.67-0.64 (2H, m). |
| 702 | $^1$H-NMR (DMSO-$D_6$) δ: 9.83 (1H, d, J = 4.1 Hz), 7.64 (1H, d, J = 15.5 Hz), 6.68 (1H, d, J = 15.1 Hz), 4.56-4.16 (2H, m), 3.94 (2H, d, J = 7.4 Hz), 2.89-2.83 (3H, m), 2.38 (3H, s), 2.31 (3H, s), 2.12-1.99 (4H, m), 1.23 (3H, s), 0.90 (6H, d, J = 6.5 Hz), 0.83-0.77 (2H, m), 0.67-0.66 (2H, m). |
| 706 | $^1$H-NMR ($CDCl_3$) δ: 9.97 (1H, s), 7.81 (1H, d. J = 15.5 Hz), 6.78-6.75 (1H, m), 4.08 (2H, d, J = 7.4 Hz), 3.92-3.88 (1H, m), 3.77-3.73 (2H, m), 3.55-3.52 (3H, m), 2.99-2.91 (1H, m), 2.49 (3H, s), 2.15-2.04 (1H, m), 1.03 (6H, br s), 0.95-0.88 (6H, m), 0.77-0.75 (2H, m). |
| 708 | $^1$H-NMR (DMSO-$D_6$) δ: 9.91 (1H, d, J = 4.1 Hz), 8.46 (1H, s), 7.53 (1H, d, J = 15.1 Hz), 6.85 (1H, d, J = 14.7 Hz), 4.01 (2H, d, J = 7.4 Hz), 3.92-3.22 (8H, m), 3.08-2.83 (3H, m), 2.06-1.90 (1H, m), 0.95 (6H, d, J = 6.5 Hz), 0.90-0.80 (2H, m), 0.79-0.68 (2H, m). |
| 713 | $^1$H-NMR (DMSO-$D_6$) δ: 9.79 (1H, d, J = 4.1 Hz), 8.41 (1H, s), 7.62 (1H, d, J = 14.7 Hz), 7.03 (1H, d, J = 14.7 Hz), 4.67 (1 H, br s), 4.29-4.24 (1H, m), 3.99-3.97 (2H, m), 3.00-2.96 (1H, m), 2.90-2.87 (2H, m), 2.36 (3H, s), 2.17-2.11 (2H, m), 1.98-1.93 (2H, m), 1.25-1.23 (3H, m), 0.94 (6H, d, J = 6.6 Hz), 0.79-0.77 (2H, m), 0.64-0.63 (2H, m). |
| 716 | $^1$H-NMR (DMSO-$D_6$) δ: 9.92 (1H, d, J = 4.1 Hz), 8.51 (1H, d, J = 5.5 Hz), 7.62 (1H, dd, J = 14.9, 8.3 Hz), 7.07 (1H, d, J = 14.7 Hz), 4.47-4.35 (1H, m), 4.17-4.04 (3H, |

TABLE 14-continued

| Ex | Data |
|---|---|
| | m), 3.68-3.55 (2H, m), 3.00-2.91 (2H, m), 2.61-2.57 (1H, m), 2.03-1.91 (1H, m), 1.26-1.14 (6H, m), 0.96 (6H, d, J = 6.6 Hz), 0.88-0.83 (2H, m), 0.77-0.73 (2H, m). |
| 717 | $^1$H-NMR (DMSO-$D_6$ δ: 9.91 (1H, d, J = 4.1 Hz), 8.50 (1H, d, J = 5.3 Hz), 7.61 (1H, dd, J = 14.7, 8.2 Hz), 7.07 (1H, d, J = 15.1 Hz), 4.47-4.35 (1H, m), 4.21-4.00 (3H, m), 3.68-3.55 (2H, m), 3.00-2.92 (2H, m), 2.62-2.55 (1H, m), 2.03-1.94 (1H, m), 1.26-1.14 (6H, m), 0.96 (6H, d, J = 6.5 Hz), 0.88-0.83 (2H, m), 0.76-0.74 (2H, m). |
| 718 | $^1$H-NMR (DMSO-$D_6$) δ: 9.92 (1H, d, J = 4.1 Hz), 8.51 (1H, s), 7.63 (1H, d, J = 14.7 Hz), 7.04 (1H, d, J = 15.1 Hz), 4.41-4.40 (1H, m), 4.05-4.01 (3H, m), 3.91-3.82 (2H, m), 3.43-3.40 (2H, m), 2.98-2.95 (1H, m), 2.03-1.94 (1H, m), 1.22 (3H, d, J = 6.6 Hz), 1.14 (3H, d, J = 6.3 Hz), 0.96 (6H, d, J = 6.6 Hz), 0.88-0.84 (2H, m), 0.78-0.74 (2H, m). |

TABLE 15

| Ex | Data |
|---|---|
| 722 | $^1$H-NMR ($CDCl_3$) δ: 9.96 (1M, s), 8.07-8.05 (1H, m), 7.79 (1H, d, J = 15.1 Hz), 6.46-6.41 (1H, m), 5.30-5.06 (2H, m), 4.11-3.85 (6H, m), 3.01-2.93 (1H, m), 2.13-2.08 (1H, m), 1.06 (6H, d, J = 6.6 Hz), 0.98-0.91 (2H, m), 0.80-0.74 (2H, m). |
| 723 | $^1$H-NMR (DMSO-$D_6$) δ: 9.92 (1H, d, J = 3.7 Hz), 8.48 (1H, s), 7.59 (1H, d, J = 14.7 Hz), 6.86 (1H, d. J = 14.7 Hz), 5.61-5.28 (2H, m), 4.23-3.56 (6H, m), 3.00-2.94 (1H, m), 2.03-1.91 (1H, m), 0.96 (6H, d, J = 6.6 Hz), 0.90-0.82 (2H, m), 0.80-0.72 (2H, m). |
| 741 | $^1$H-NMR (DMSO-$D_6$) δ: 9.92 (1H, d, J = 3.7 Hz), 8.51 (1H, s), 7.63 (1H, d, J = 15.1 Hz), 7.04 (1H, d, J = 14.7 Hz), 4.41-4.39 (1H, m), 4.05-4.01 (3H, m), 3.91-3.82 (2H, m), 3.43-3.40 (2H, m), 2.98-2.96 (1H, m), 2.02-1.98 (1H, m), 1.22 (3H, d, J = 6.6 Hz), 1.14 (3H, d, J = 6.3 Hz), 0.94 (6H, t, J = 8.8 Hz), 0.88-0.84 (2H, m), 0.77-0.76 (2H, m). |
| 749 | $^1$H-NMR (DMSO-$D_6$) δ: 9.93 (1H, d, J = 4.1 Hz), 7.70 (1H, d, J = 15.5 Hz), 6.67-6.45 (1H, m), 5.46-4.78 (1H, m), 4.25-3.70 (3H, m), 3.67-3.57 (1H, m), 3.02-2.91 (1H, m), 2.47-2.38 (3H, m), 2.35-1.89 (5H, m), 1.01-0.91 (6H, m), 0.90-0.80 (2H, m), 0.80-0.70 (2H, m). |
| 750 | $^1$H-NMR (DMSO-$D_6$) δ: 9.97-9.86 (1H, m), 7.65-7.52 (1H, m), 6.81-6.64 (1H, m), 3.97 (2H, d, J = 7.0 Hz), 3.68-3.43 (4H, m), 3.26 (3H, s), 3.18-2.88 (4H, m), 2.42-2.33 (3H, m), 2.04-1.90 (1H, m), 0.92 (6H, d. J = 6.6 Hz), 0.89-0.79 (2H, m), 0.79-0.71 (2H, m). |
| 751 | $^1$H-NMR ($CDCl_3$) δ: 9.97 (1H, br s), 7.77 (1H, d, J = 15.1 Hz), 6.52 (1H, d, J = 15.5 Hz), 4.05 (2H, d, J = 7.4 Hz), 2.97-2.90 (2H, m), 2.79 (1H, d, J = 11.0 Hz), 2.47 (3H, s), 2.40-2.33 (2H, m), 2.21-1.99 (3H, m), 1.67-1.64 (2H, m), 1.38-1.36 (4H, m), 1.09 (3H, t, J = 7.2 Hz), 1.02 (6H, d, J = 7.0 Hz), 0.96-0.86 (2H, m), 0.77-0.74 (2H, m). |
| 752 | $^1$H-NMR ($CDCl_3$) δ: 10.00 (1H, s), 8.73 (1H, s), 8.39 (1H, s), 8.26-8.22 (1H, m), 7.98 (1H, d, J = 15.5 Hz), 4.24 (2H, t, J = 8.6 Hz), 4.13 (2H, d, J = 7.4 Hz), 3.14 (2H, t, J = 8.6 Hz), 2.99-2.92 (1H, m), 2.64 (3H, s), 2.19-2.10 (1H, m), 1.05 (6H, d, J = 6.5 Hz) 0.95-0.91 (2H, m), 0.78-0.76 (2H, m). |
| 753 | $^1$H-NMR (DMSO-$D_6$) δ: 9.90 (1H, s), 7.63 (1H, d, J = 15.3 Hz), 6.68-6.33 (1H, m), 6.01-4.62 (2H, m), 4.01-3.94 (2H, m), 3.78-3.50 (3H, m), 3.40-3.32 (1H, m), 3.02-2.89 (1H, m), 2.41-2.38 (3H, m), 2.04-1.89 (1H, m), 1.89-1.79 (2H, m), 0.96-0.78 (8H, m), 0.78-0.69 (2H, m). |
| 754 | $^1$H-NMR (DMSO-$D_6$) δ: 9.90 (1H, s), 7.63 (1H, d, J = 15.3 Hz), 6.69-6.34 (1H, m), 5.00-4.62 (2H, m), 4.01- |

TABLE 15-continued

| Ex | Data |
|---|---|
| | 3.94 (2H, m), 3.78-3.51 (3H, m), 3.41-3.34 (1H, m), 3.00-2.90 (1H, m), 2.41-2.38 (3H, m), 2.04-1.90 (1H, m), 1.89-1.79 (2H, m), 0.96-0.78 (8H, m), 0.78-0.69 (2H, m). |

The LC/MS spectral data of the compounds produced in the aforementioned Synthesis Examples are shown in Tables 16 to 35. Unless otherwise specified, ESI+ data in the Tables correspond to $[M+H]^+$, and ESI− data in the Tables correspond to $[M-H]^-$.

TABLE 16

| Ex | condition | R.time (min) | ESI+ | ESI− |
|---|---|---|---|---|
| 1 | 2 | 2.81 | 377.3 | — |
| 2 | 2 | 2.33 | 349.3 | — |
| 3 | 4 | 3.00 | 420.2 | — |
| 4 | 4 | 2.27 | 320.0 | — |
| 5 | 4 | 2.82 | 363.1 | — |
| 6 | 4 | 2.06 | 321.0 | — |
| 7 | 4 | 2.36 | 319.0 | — |
| 8 | 4 | 2.64 | 375.0 | — |
| 9 | 4 | 2.28 | 361.4 | — |
| 10 | 4 | 2.23 | 430.1 | — |
| 11 | 2 | 2.88 | 383.1 | — |
| 12 | 4 | 2.12 | 398.6 | — |
| 13 | 2 | 2.69 | 398.6 | — |
| 14 | 4 | 2.12 | 397.6 | — |
| 15 | 4 | 3.22 | 466.4 | — |
| 16 | 4 | 2.95 | 428.6 | — |
| 17 | 4 | 2.89 | 428.5 | — |
| 18 | 1 | 1.74 | 320.0 | — |
| 19 | 4 | 2.77 | 456.5 | — |
| 20 | 4 | 2.49 | 442.4 | — |
| 21 | 4 | 2.46 | 441.6 | — |
| 22 | 3 | 2.61 | 369.10 | — |
| 23 | 1 | 1.84 | 384.2 | — |
| 24 | 4 | 2.02 | 383.6 | — |
| 25 | 2 | 3.19 | 397.2 | — |
| 26 | 2 | 2.99 | 412.4 | — |
| 27 | 2 | 2.44 | 425.28 | — |
| 28 | 4 | 2.26 | 440.2 | — |
| 29 | 4 | 2.05 | 439.5 | — |
| 30 | 2 | 2.68 | 441.3 | — |
| 31 | 1 | 1.83 | 454.3 | — |
| 32 | 4 | 2.29 | 363.4 | — |
| 33 | 4 | 2.37 | 348.4 | — |
| 34 | 2 | 2.15 | 411.4 | — |
| 35 | 1 | 1.64 | 415.2 | — |
| 36 | 1 | 1.80 | 378.2 | — |
| 37 | 1 | 1.92 | 420.3 | — |
| 38 | 1 | 1.91 | 376.2 | — |
| 39 | 1 | 1.80 | 440.3 | — |
| 40 | 1 | 1.49 | 461.4 | — |

TABLE 17

| Ex | condition | R.time (min) | ESI+ | ESI− |
|---|---|---|---|---|
| 41 | 1 | 2.05 | 425.2 | — |
| 42 | 1 | 1.81 | 420.3 | — |
| 43 | 1 | 2.02 | 430.3 | — |
| 44 | 1 | 1.50 | 475.4 | — |
| 45 | 1 | 2.08 | 460.3 | — |
| 46 | 1 | 2.04 | 448.3 | — |
| 47 | 1 | 1.86 | 376.2 | — |
| 48 | 1 | 1.83 | 454.3 | — |
| 49 | 1 | 1.72 | 439.3 | — |
| 50 | 1 | 1.97 | 426.2 | — |
| 51 | 2 | 2.07 | 335.17 | — |
| 52 | 1 | 1.80 | 376.0 | — |
| 53 | 1 | 1.86 | 424.0 | — |

TABLE 17-continued

| Ex | condition | R.time (min) | ESI+ | ESI− |
|---|---|---|---|---|
| 54 | 1 | 1.32 | 417.1 | — |
| 55 | 2 | 2.52 | 362.3 | — |
| 56 | 2 | 2.50 | 334.3 | — |
| 57 | 2 | 2.63 | 413.3 | — |
| 58 | 1 | 1.74 | 335.1 | — |
| 59 | 2 | 3.03 | 333.48 | — |
| 60 | 1 | 2.18 | 376.1 | — |
| 61 | 2 | 2.72 | 347.30 | — |
| 62 | 1 | 2.30 | 390.3 | — |
| 63 | 1 | 1.86 | 348.2 | — |
| 64 | 2 | 2.81 | 406.4 | — |
| 65 | 1 | 1.84 | 406.2 | — |
| 66 | 2 | 2.29 | 405.4 | — |
| 67 | 1 | 2.31 | 438.3 | — |
| 68 | 1 | 2.08 | 362.2 | — |
| 69 | 3 | 2.04 | 306.11 | — |
| 70 | 1 | 1.35 | 401.1 | — |
| 71 | 1 | 1.75 | 388.0 | — |
| 72 | 2 | 2.62 | 398.24 | — |
| 73 | 1 | 2.14 | 446.3 | — |
| 74 | 2 | 2.96 | 395.3 | — |
| 75 | 2 | 2.31 | 366.3 | — |
| 76 | 2 | 2.56 | 338.3 | — |
| 77 | 4 | 2.39 | 381.3 | — |
| 78 | 2 | 1.53 | 387.3 | — |
| 79 | 1 | 1.81 | 402.0 | — |
| 80 | 1 | 2.22 | 472.1 | — |

TABLE 18

| Ex | condition | R.time (min) | ESI+ | ESI− |
|---|---|---|---|---|
| 81 | 2 | 1.81 | 372.3 | — |
| 82 | 2 | 2.98 | — | 472.3 |
| 83 | 2 | 1.79 | 374.3 | — |
| 84 | 1 | 2.25 | 472.1 | — |
| 85 | 2 | 1.89 | 372.3 | — |
| 86 | 2 | 1.84 | 374.3 | — |
| 87 | 1 | 1.79 | 390.1 | — |
| 88 | 2 | 2.47 | 440.4 | — |
| 89 | 2 | 2.82 | 391.3 | — |
| 90 | 1 | 1.66 | 362.1 | — |
| 91 | 1 | 1.76 | 349.1 | — |
| 92 | 1 | 1.96 | 514.2 | — |
| 93 | 2 | 1.31 | 414.5 | — |
| 94 | 1 | 1.29 | 428.2 | — |
| 95 | 2 | 3.03 | 531.4 | — |
| 96 | 2 | 2.51 | 503.4 | — |
| 97 | 1 | 1.54 | 515.2 | — |
| 98 | 1 | 1.73 | 348.0 | — |
| 99 | 1 | 1.77 | 389.1 | — |
| 100 | 1 | 1.88 | 436.1 | — |
| 101 | 2 | 2.34 | 362.6 | — |
| 102 | 2 | 1.82 | 362.6 | — |
| 103 | 1 | 1.57 | 431.2 | — |
| 104 | 2 | 2.86 | 369.15 | — |
| 105 | 1 | 1.97 | 387.0 | — |
| 106 | 1 | 2.02 | 371.1 | — |
| 107 | 1 | 1.72 | 429.0 | — |
| 108 | 1 | 1.97 | 471.1 | — |
| 109 | 1 | 1.94 | 387.1 | — |
| 110 | 1 | 1.92 | 449.0 | — |
| 111 | 1 | 1.97 | 475.0 | — |
| 112 | 1 | 1.91 | 461.0 | — |
| 113 | 1 | 1.85 | 425.1 | — |
| 114 | 1 | 2.08 | 401.1 | — |
| 115 | 1 | 2.22 | 486.1 | — |
| 116 | 2 | 1.69 | 386.3 | — |
| 117 | 1 | 1.78 | 390.0 | — |
| 118 | 6 | 1.92 | 514.3 | — |
| 119 | 2 | 2.06 | 362.1 | — |
| 120 | 1 | 2.00 | 413.1 | — |

TABLE 19

| Ex | condition | R.time (min) | ESI+ | ESI− |
|---|---|---|---|---|
| 121 | 1 | 1.90 | 373.1 | — |
| 122 | 3 | 1.62 | 372.2 | — |
| 123 | 1 | 1.40 | 400.1 | — |
| 124 | 1 | 2.11 | 413.1 | — |
| 125 | 1 | 1.83 | 368.1 | — |
| 126 | 1 | 2.07 | 401.1 | — |
| 127 | 1 | 1.60 | 410.0 | — |
| 128 | 1 | 2.03 | 436.2 | — |
| 129 | 3 | 1.61 | 386.2 | — |
| 130 | 1 | 1.86 | 386.4 | — |
| 131 | 1 | 1.88 | 409.2 | — |
| 132 | 1 | 1.70 | 461.3 | — |
| 133 | 1 | 2.26 | 371.2 | — |
| 134 | 1 | 1.28 | 428.3 | — |
| 135 | 1 | 1.74 | 373.1 | — |
| 136 | 1 | 2.05 | 425.2 | — |
| 137 | 1 | 2.15 | 472.4 | — |
| 138 | 1 | 1.47 | 488.0 | — |
| 139 | 1 | 1.42 | 438.1 | — |
| 140 | 2 | 1.39 | 414.6 | — |
| 141 | 5 | 1.53 | 425.2 | — |
| 142 | 2 | 1.88 | 388.4 | — |
| 143 | 1 | 1.89 | 375.0 | — |
| 144 | 1 | 1.81 | 403.0 | — |
| 145 | 1 | 2.04 | 437.0 | — |
| 146 | 1 | 2.24 | 486.1 | — |
| 147 | 1 | 1.48 | 414.1 | — |
| 148 | 1 | 1.44 | 474.1 | — |
| 149 | 1 | 2.17 | 482.3 | — |
| 150 | 1 | 2.30 | 473.3 | — |
| 151 | 1 | 2.29 | 473.3 | — |
| 152 | 2 | 2.57 | 331.4 | — |
| 153 | 1 | 1.88 | 428.2 | — |
| 154 | 1 | 1.79 | 402.1 | — |
| 155 | 1 | 2.20 | 417.3 | — |
| 156 | 1 | 1.40 | 443.1 | — |
| 157 | 1 | 1.69 | 388.1 | — |
| 158 | 1 | 1.84 | 450.0 | — |
| 159 | 5 | 1.91 | 472.3 | — |
| 160 | 1 | 1.56 | 360.1 | — |

TABLE 20

| Ex | condition | R.time (min) | ESI+ | ESI− |
|---|---|---|---|---|
| 161 | 1 | 1.63 | 390.0 | — |
| 162 | 5 | 2.09 | 554.3 | — |
| 163 | 2 | 2.11 | 500.7 | — |
| 164 | 2 | 1.99 | 432.3 | — |
| 165 | 2 | 1.80 | 443.4 | — |
| 166 | 1 | 1.73 | 404.0 | — |
| 167 | 2 | 2.22 | 452.4 | — |
| 168 | 1 | 1.93 | 472.2 | — |
| 169 | 4 | 2.41 | 444.6 | — |
| 170 | 1 | 1.74 | 458.2 | — |
| 171 | 1 | 1.54 | 383.0 | — |
| 172 | 1 | 1.61 | 368.0 | — |
| 173 | 1 | 1.55 | 383.1 | — |
| 174 | 1 | 1.53 | 383.0 | — |
| 175 | 1 | 1.67 | 334.0 | — |
| 176 | 2 | 2.13 | 368.5 | — |
| 177 | 1 | 1.73 | 368.0 | — |
| 178 | 1 | 1.52 | 383.0 | — |
| 179 | 1 | 1.53 | 383.0 | — |
| 180 | 1 | 2.66 | 317.4 | — |
| 181 | 1 | 2.12 | 345.2 | — |
| 182 | 1 | 1.58 | 348.1 | — |
| 183 | 1 | 1.82 | 371.0 | — |
| 184 | 2 | 1.94 | 414.4 | — |
| 185 | 1 | 1.41 | 413.3 | — |
| 186 | 2 | 2.46 | 398.3 | — |
| 187 | 1 | 1.51 | 405.1 | — |
| 188 | 4 | 2.47 | 412.5 | — |
| 189 | 2 | 2.05 | 398.3 | — |
| 190 | 1 | 1.51 | 447.3 | — |

TABLE 20-continued

| Ex | condition | R.time (min) | ESI+ | ESI− |
|---|---|---|---|---|
| 191 | 2 | 2.23 | 398.3 | — |
| 192 | 1 | 1.54 | 433.3 | — |
| 193 | 1 | 2.16 | 396.1 | — |
| 194 | 2 | 2.77 | 398.3 | — |
| 195 | 1 | 1.90 | 427.3 | — |
| 196 | 1 | 1.91 | 388.1 | — |
| 197 | 1 | 1.63 | 425.3 | — |
| 198 | 2 | 2.20 | 398.4 | — |
| 199 | 1 | 1.67 | 439.3 | — |
| 200 | 2 | 2.23 | 398.3 | — |

TABLE 21

| Ex | condition | R.time (min) | ESI+ | ESI− |
|---|---|---|---|---|
| 201 | 2 | 2.37 | 398.3 | — |
| 202 | 2 | 2.41 | 398.3 | — |
| 203 | 2 | 2.48 | 397.3 | — |
| 204 | 1 | 1.65 | 411.3 | — |
| 205 | 1 | 1.70 | 386.2 | — |
| 206 | 1 | 1.62 | 397.3 | — |
| 207 | 1 | 1.61 | 466.2 | — |
| 208 | 1 | 1.58 | 508.2 | — |
| 209 | 1 | 2.02 | 331.1 | — |
| 210 | 1 | 1.66 | 411.2 | — |
| 211 | 2 | 2.41 | 482.4 | — |
| 212 | 1 | 2.24 | 414.1 | — |
| 213 | 1 | 1.76 | 398.1 | — |
| 214 | 1 | 1.81 | 386.1 | — |

TABLE 22

| Ex | condition | R.time (min) | ESI+ | ESI− |
|---|---|---|---|---|
| 215 | 2 | 1.97 | 425.4 | — |
| 216 | 2 | 1.80 | 425.4 | — |
| 217 | 2 | 1.76 | 425.4 | — |
| 218 | 4 | 2.14 | 439.5 | — |
| 219 | 4 | 2.15 | 439.5 | — |
| 220 | 2 | 1.97 | 426.4 | — |
| 221 | 2 | 2.11 | 432.5 | — |
| 222 | 2 | 2.43 | 438.4 | — |
| 223 | 2 | 2.01 | 456.5 | — |
| 224 | 4 | 2.35 | 440.5 | — |
| 225 | 4 | 2.68 | 411.5 | — |
| 226 | 4 | 2.88 | 493.6 | — |
| 227 | 2 | 2.07 | 404.4 | — |
| 228 | 4 | 2.09 | 439.5 | — |
| 229 | 4 | 2.41 | 442.6 | — |
| 230 | 4 | 2.05 | 439.7 | — |
| 231 | 2 | 1.96 | 426.3 | — |
| 232 | 2 | 2.58 | 449.6 | — |
| 233 | 2 | 2.53 | 442.4 | — |
| 234 | 2 | 2.57 | 460.3 | — |
| 235 | 2 | 2.22 | 443.3 | — |
| 236 | 2 | 2.44 | 395.4 | — |
| 237 | 2 | 2.55 | 401.5 | — |
| 238 | 2 | 2.61 | 412.3 | — |
| 239 | 2 | 1.64 | 372.3 | — |
| 240 | 2 | 2.60 | 400.2 | — |
| 241 | 2 | 1.83 | 400.3 | — |
| 242 | 4 | 2.98 | 415.6 | — |
| 243 | 2 | 2.97 | 373.3 | — |
| 244 | 2 | 2.34 | 442.4 | — |
| 245 | 2 | 2.44 | 456.4 | — |
| 246 | 4 | 3.13 | 357.5 | — |
| 247 | 2 | 2.03 | 394.3 | — |
| 248 | 2 | 2.84 | 462.3 | — |
| 249 | 4 | 2.93 | 482.5 | — |
| 250 | 2 | 1.89 | 396.4 | — |
| 251 | 2 | 2.72 | 464.4 | — |
| 252 | 2 | 2.18 | 375.4 | — |

TABLE 22-continued

| Ex | condition | R.time (min) | ESI+ | ESI− |
|---|---|---|---|---|
| 253 | 2 | 2.48 | 478.5 | — |
| 254 | 4 | 2.50 | 444.5 | — |

TABLE 23

| Ex | condition | R.time (min) | ESI+ | ESI− |
|---|---|---|---|---|
| 255 | 4 | 2.27 | 533.7 | — |
| 256 | 2 | 2.40 | 464.5 | — |
| 257 | 2 | 2.32 | 416.5 | — |
| 258 | 2 | 2.26 | 427.3 | — |
| 259 | 4 | 1.90 | 398.5 | — |
| 260 | 4 | 3.37 | 397.5 | — |
| 261 | 4 | 2.95 | 316.4 | — |
| 262 | 4 | 2.45 | 432.6 | — |
| 263 | 2 | 2.39 | 466.4 | — |
| 264 | 2 | 2.03 | 418.3 | — |
| 265 | 4 | 2.50 | 375.5 | — |
| 266 | 4 | 2.17 | 414.5 | — |
| 267 | 2 | 2.24 | 401.3 | — |
| 268 | 2 | 2.36 | 415.2 | — |
| 269 | 2 | 2.27 | 399.2 | — |
| 270 | 2 | 2.26 | 399, 401 | — |
| 271 | 4 | 1.90 | 413.3 | — |
| 272 | 2 | 2.72 | 425, 427 | — |
| 273 | 2 | 2.63 | 411, 413 | — |
| 274 | 4 | 2.00 | 402.5 | — |
| 275 | 4 | 2.17 | 364.4 | — |
| 276 | 4 | 2.50 | 410.4 | — |
| 277 | 2 | 2.24 | 402.3 | — |
| 278 | 4 | 2.62 | 363.5 | — |
| 279 | 4 | 2.95 | 330.3 | — |
| 280 | 4 | 1.95 | 362.5 | — |
| 281 | 2 | 2.71 | 412.3 | — |
| 282 | 2 | 2.17 | 412.4 | — |
| 283 | 2 | 2.65 | 400.3 | — |
| 284 | 4 | 3.12 | 450.5 | — |
| 285 | 2 | 2.60 | 415.4 | — |
| 286 | 4 | 2.49 | 371.4 | — |
| 287 | 2 | 2.48 | 385.3 | — |
| 288 | 2 | 2.38 | 383.2 | — |
| 289 | 2 | 2.27 | 398.3 | — |
| 290 | 2 | 1.79 | 425.2 | — |
| 291 | 2 | 2.70 | 422.3 | — |
| 292 | 2 | 2.46 | 396.3 | — |
| 293 | 2 | 2.63 | 407.3 | — |
| 294 | 2 | 2.62 | 407.3 | — |

TABLE 24

| Ex | condition | R.time (min) | ESI+ | ESI− |
|---|---|---|---|---|
| 295 | 2 | 2.54 | 400.3 | — |
| 296 | 2 | 2.59 | 396.3 | — |
| 297 | 2 | 2.69 | 432.3 | — |
| 298 | 2 | 2.70 | 439.3 | — |
| 299 | 4 | 2.82 | 382.5 | — |
| 300 | 2 | 3.08 | 413.5 | — |
| 301 | 2 | 2.51 | 396.3 | — |
| 302 | 4 | 2.77 | 383.4 | — |
| 303 | 4 | 2.87 | 397.4 | — |
| 304 | 4 | 3.03 | 401.3 | — |
| 305 | 2 | 2.60 | 405.3, 407.3 | — |
| 306 | 2 | 2.35 | 422.3 | — |
| 307 | 2 | 2.23 | 422.2 | — |
| 308 | 4 | 2.08 | 411.5 | — |
| 309 | 4 | 2.14 | 411.4 | — |
| 310 | 2 | 2.26 | 428.4 | — |
| 311 | 2 | 2.21 | 484.3 | — |
| 312 | 4 | 2.48 | 414.4 | — |
| 313 | 4 | 2.69 | 518.5 | — |
| 314 | 4 | 2.36 | 442.5 | — |
| 315 | 2 | 2.45 | 512.2 | — |

TABLE 24-continued

| Ex | condition | R.time (min) | ESI+ | ESI− |
|---|---|---|---|---|
| 316 | 7 | 2.52 | 504.2 | — |
| 317 | 4 | 2.36 | 386.4 | — |
| 318 | 4 | 2.21 | 307.3 | — |
| 319 | 2 | 2.26 | 305.3 | — |
| 320 | 2 | 2.38 | 319.3 | — |
| 321 | 4 | 2.44 | 414.4 | — |
| 322 | 4 | 3.01 | 416.4 | — |
| 323 | 4 | 2.95 | 423.4 | — |
| 324 | 4 | 2.94 | 423.4 | — |
| 325 | 4 | 2.94 | 423.4 | — |
| 326 | 4 | 2.20 | 425.7 | — |
| 327 | 4 | 2.20 | 425.8 | — |
| 328 | 4 | 2.85 | 412.5 | — |
| 329 | 4 | 2.94 | 423.4 | — |
| 330 | 4 | 2.92 | 412.4 | — |
| 331 | 4 | 3.30 | 466.5 | — |
| 332 | 4 | 2.59 | 428.5 | — |
| 333 | 4 | 2.88 | 412.5 | — |
| 334 | 4 | 2.09 | 412.5 | — |

TABLE 25

| Ex | condition | R.time (min) | ESI+ | ESI− |
|---|---|---|---|---|
| 335 | 4 | 2.73 | 511.6 | — |
| 336 | 2 | 2.75 | 440.5 | — |
| 337 | 4 | 3.11 | 448.5 | — |
| 338 | 4 | 3.24 | 442.6 | — |
| 339 | 4 | 2.16 | 412.5 | — |
| 340 | 4 | 2.20 | 412.5 | — |
| 341 | 2 | 1.81 | 389.4 | — |
| 342 | 2 | 1.82 | 389.4 | — |
| 343 | 4 | 3.33 | 402.6 | — |
| 344 | 4 | 3.28 | 462.6 | — |
| 345 | 2 | 2.17 | 441.5 | — |
| 346 | 2 | 2.35 | 400.5 | — |
| 347 | 4 | 2.95 | 440.5 | — |
| 348 | 4 | 2.81 | 426.5 | — |
| 349 | 4 | 2.87 | 456.6 | — |
| 350 | 4 | 2.32 | 426.5 | — |
| 351 | 4 | 2.49 | 441.5 | — |
| 352 | 4 | 3.17 | 523.6 | — |
| 353 | 4 | 3.03 | 505.6 | — |
| 354 | 4 | 2.81 | 513.7 | — |
| 355 | 4 | 3.13 | 545.7 | — |
| 356 | 4 | 3.18 | 416.5 | — |
| 357 | 4 | 2.18 | 400.5 | — |
| 358 | 4 | 2.95 | 494.6 | — |
| 359 | 4 | 2.92 | 534.7 | — |
| 360 | 4 | 2.39 | 511.7 | — |
| 361 | 4 | 2.65 | 387.4 | — |
| 362 | 2 | 2.10 | 375.5 | — |
| 363 | 2 | 1.92 | 361.5 | — |
| 364 | 4 | 2.36 | 446.5 | — |
| 365 | 4 | 2.44 | 460.6 | — |
| 366 | 2 | 2.14 | 442.4 | — |
| 367 | 2 | 2.22 | 468.4 | — |
| 368 | 2 | 2.22 | 468.4 | — |
| 369 | 4 | 2.39 | 456.5 | — |
| 370 | 4 | 2.39 | 456.5 | — |
| 371 | 4 | 2.37 | 486.6 | — |
| 372 | 4 | 2.37 | 486.6 | — |
| 373 | 4 | 2.17 | 454.6 | — |
| 374 | 4 | 2.17 | 454.6 | — |

TABLE 26

| Ex | condition | R.time (min) | ESI+ | ESI− |
|---|---|---|---|---|
| 375 | 4 | 2.02 | 458.6 | — |
| 376 | 4 | 2.19 | 472.5 | — |
| 377 | 4 | 1.99 | 458.5 | — |
| 378 | 4 | 2.19 | 472.5 | — |

TABLE 26-continued

| Ex | condition | R.time (min) | ESI+ | ESI− |
|---|---|---|---|---|
| 379 | 2 | 2.14 | 460.3 | — |
| 380 | 4 | 2.22 | 460.4 | — |
| 381 | 2 | 2.24 | 442.3 | — |
| 382 | 4 | 2.20 | 490.4 | — |
| 383 | 4 | 2.20 | 490.4 | — |
| 384 | 2 | 1.93 | 446.2 | — |
| 385 | 2 | 1.92 | 446.2 | — |
| 386 | 2 | 1.97 | 486.2 | — |
| 387 | 2 | 2.08 | 428.2 | — |
| 388 | 2 | 2.18 | 484.2 | — |
| 389 | 2 | 2.18 | 484.2 | — |
| 390 | 2 | 1.99 | 448.1 | — |
| 391 | 2 | 2.21 | 356.4 | — |
| 392 | 4 | 2.93 | 357.4 | — |
| 393 | 4 | 3.03 | 386.5 | — |
| 394 | 2 | 2.16 | 372.3 | — |
| 395 | 4 | 2.70 | 344.4 | — |
| 396 | 4 | 2.77 | 346.4 | — |
| 397 | 2 | 2.29 | 389.4 | — |
| 398 | 4 | 3.00 | 428.5 | — |
| 399 | 2 | 2.21 | 330.1 | — |
| 400 | 2 | 2.16 | 376.3 | — |
| 401 | 4 | 2.45 | 390.5 | — |
| 402 | 2 | 2.14 | 360.2 | — |
| 403 | 4 | 2.48 | 374.4 | — |
| 404 | 2 | 2.12 | 360.4 | — |
| 405 | 4 | 2.40 | 459.5 | — |
| 406 | 4 | 2.35 | 389.4 | — |
| 407 | 2 | 2.63 | 493.3 | — |
| 408 | 4 | 2.51 | 415.4 | — |
| 409 | 2 | 2.28 | 473.2 | — |
| 410 | 4 | 2.71 | 465.4 | — |
| 411 | 2 | 2.22 | 459.5 | — |
| 412 | 2 | 2.80 | 504.5 | — |
| 413 | 4 | 3.03 | 579.7 | — |
| 414 | 2 | 2.36 | 479.5 | — |

TABLE 27

| Ex | condition | R. time (min) | ESI+ | ESI− |
|---|---|---|---|---|
| 415 | 4 | 2.70 | 545.7 | — |
| 416 | 4 | 2.35 | 445.6 | — |
| 417 | 2 | 2.13 | 459.4 | — |
| 418 | 2 | 2.13 | 459.4 | — |
| 419 | 2 | 1.96 | 443.3 | — |
| 420 | 2 | 2.30 | 477.4 | — |
| 421 | 4 | 2.73 | 535.5 | — |
| 422 | 4 | 2.39 | 473.5 | — |
| 423 | 4 | 2.42 | 485.5 | — |
| 424 | 4 | 2.37 | 502.6 | — |
| 425 | 2 | 2.05 | 503.4 | — |
| 426 | 2 | 2.09 | 459.4 | — |
| 427 | 2 | 2.18 | 443.2 | — |
| 428 | 2 | 2.33 | 479.2 | — |
| 429 | 2 | 2.16 | 461.2 | — |
| 430 | 2 | 2.18 | 473.2 | — |
| 431 | 2 | 2.16 | 485.2 | — |
| 432 | 2 | 2.28 | 487.2 | — |
| 433 | 2 | 2.45 | 430.4 | — |
| 434 | 2 | 2.37 | 416.4 | — |
| 435 | 2 | 2.24 | 332.2 | — |
| 436 | 4 | 2.67 | 348.5 | — |
| 437 | 4 | 2.62 | 334.4 | — |
| 438 | 2 | 2.44 | 360.3 | — |
| 439 | 2 | 2.77 | 388.4 | — |
| 440 | 2 | 2.66 | 386.4 | — |
| 441 | 4 | 3.41 | 414.5 | — |
| 442 | 2 | 2.74 | 388.3 | — |
| 443 | 2 | 2.04 | 458.3 | — |
| 444 | 2 | 2.36 | 416.2 | — |
| 445 | 2 | 2.12 | 472.2 | — |
| 446 | 2 | 2.46 | 430.2 | — |
| 447 | 4 | 2.78 | 354.4 | — |
| 448 | 2 | 2.22 | 475, 477 | — |

TABLE 27-continued

| Ex | condition | R. time (min) | ESI+ | ESI− |
|---|---|---|---|---|
| 449 | 2 | 1.92 | 522.4 | — |
| 450 | 2 | 2.00 | 473.4 | — |
| 451 | 2 | 2.32 | 444.3 | — |
| 452 | 2 | 2.31 | 414.4 | — |
| 453 | 2 | 2.53 | 450.4 | — |
| 454 | 2 | 2.33 | 432.4 | — |

TABLE 28

| Ex | condition | R. time (min) | ESI+ | ESI− |
|---|---|---|---|---|
| 455 | 4 | 2.55 | 444.5 | — |
| 456 | 2 | 2.21 | 456.4 | — |
| 457 | 4 | 2.56 | 458.6 | — |
| 458 | 2 | 2.36 | 428.4 | — |
| 459 | 2 | 2.47 | 458.4 | — |
| 460 | 2 | 2.12 | 519.5 | — |
| 461 | 2 | 2.22 | 444.4 | — |
| 462 | 4 | 1.73 | 471.7 | — |
| 463 | 2 | 2.45 | 446.5 | — |
| 464 | 2 | 2.60 | 464.4 | — |
| 465 | 2 | 2.85 | 512.4 | — |
| 466 | 2 | 2.61 | 478.4 | — |
| 467 | 4 | 2.31 | 458.5 | — |
| 468 | 2 | 2.34 | 453.4 | — |
| 469 | 2 | 2.71 | 492.4 | — |
| 470 | 2 | 2.51 | 472.4 | — |
| 471 | 2 | 1.93 | 469.5 | — |
| 472 | 2 | 1.95 | 483.5 | — |
| 473 | 2 | 3.10 | 470.5 | — |
| 474 | 4 | 2.43 | 486.6 | — |
| 475 | 4 | 2.63 | 472.5 | — |
| 476 | 2 | 2.07 | 444.5 | — |
| 477 | 2 | 2.00 | 471.4 | — |
| 478 | 2 | 2.46 | 528.5 | — |
| 479 | 4 | 2.82 | 442.5 | — |
| 480 | 4 | 2.93 | 496.5 | — |
| 481 | 2 | 2.32 | 432.4 | — |
| 482 | 2 | 2.25 | 439.5 | — |
| 483 | 2 | 2.25 | 439.5 | — |
| 484 | 2 | 2.61 | 482.4 | — |
| 485 | 4 | 2.92 | 482.5 | — |
| 486 | 2 | 1.91 | 457.5 | — |
| 487 | 2 | 1.91 | 457.5 | — |
| 488 | 2 | 2.11 | 506.4 | — |
| 489 | 4 | 2.62 | 458.6 | — |
| 490 | 4 | 2.62 | 458.6 | — |
| 491 | 4 | 2.62 | 458.6 | — |
| 492 | 4 | 2.57 | 458.5 | — |
| 493 | 4 | 3.02 | 442.6 | — |
| 494 | 4 | 2.55 | 444.6 | — |

TABLE 29

| Ex | condition | R. time (min) | ESI+ | ESI− |
|---|---|---|---|---|
| 495 | 2 | 2.33 | 439.4 | — |
| 496 | 2 | 2.33 | 439.4 | — |
| 497 | 2 | 2.34 | 414.5 | — |
| 498 | 2 | 2.26 | 413.4 | — |
| 499 | 2 | 2.24 | 472.5 | — |
| 500 | 4 | 2.23 | 444.5 | — |
| 501 | 2 | 1.92 | 430.5 | — |
| 502 | 2 | 1.92 | 430.5 | — |
| 503 | 4 | 2.76 | 416.5 | — |
| 504 | 4 | 2.77 | 416.5 | — |
| 505 | 2 | 2.72 | 561.5 | — |
| 506 | 2 | 2.51 | 511.5 | — |
| 507 | 2 | 2.03 | 432.5 | — |
| 508 | 2 | 1.60 | 429.5 | — |
| 509 | 2 | 2.52 | 456.3 | — |
| 510 | 2 | 2.07 | 444.3 | — |
| 511 | 2 | 2.38 | 462.3 | — |

TABLE 29-continued

| Ex | condition | R. time (min) | ESI+ | ESI− |
|---|---|---|---|---|
| 512 | 2 | 1.88 | 457.3 | — |
| 513 | 2 | 1.88 | 457.3 | — |
| 514 | 2 | 2.16 | 478.4 | — |
| 515 | 4 | 2.93 | 440.5 | — |
| 516 | 4 | 2.46 | 428.5 | — |
| 517 | 2 | 2.09 | 418.3 | — |
| 518 | 2 | 2.11 | 446.6 | — |
| 519 | 4 | 2.70 | 432.6 | — |
| 520 | 4 | 2.56 | 458.6 | — |
| 521 | 4 | 2.40 | 460.6 | — |
| 522 | 2 | 2.25 | 402.3 | — |
| 523 | 4 | 2.39 | 458.6 | — |
| 524 | 2 | 2.18 | 427.3 | — |
| 525 | 2 | 1.99 | 460.4 | — |
| 526 | 2 | 1.99 | 460.4 | — |
| 527 | 2 | 2.37 | 444.3 | — |
| 528 | 4 | 2.25 | 458.6 | — |
| 529 | 2 | 2.57 | 498.4 | — |
| 530 | 2 | 2.57 | 498.3 | — |
| 531 | 4 | 2.39 | 474.7 | — |
| 532 | 4 | 2.39 | 474.7 | — |
| 533 | 2 | 2.21 | 456.4 | — |
| 534 | 4 | 2.74 | 498.6 | — |

TABLE 30

| Ex | condition | R. time (min) | ESI+ | ESI− |
|---|---|---|---|---|
| 535 | 2 | 2.38 | 430.4 | — |
| 536 | 2 | 2.37 | 428.4 | — |
| 537 | 2 | 2.57 | 442.4 | — |
| 538 | 2 | 2.05 | 442.4 | — |
| 539 | 2 | 2.05 | 442.4 | — |
| 540 | 2 | 2.35 | 458.4 | — |
| 541 | 4 | 2.47 | 456.6 | — |
| 542 | 2 | 2.38 | 470.4 | — |
| 543 | 4 | 2.74 | 444.5 | — |
| 544 | 4 | 2.55 | 458.6 | — |
| 545 | 4 | 2.53 | 486.6 | — |
| 546 | 2 | 2.59 | 478.4 | — |
| 547 | 2 | 2.46 | 470.4 | — |
| 548 | 4 | 2.52 | 458.6 | — |
| 549 | 4 | 2.52 | 458.6 | — |
| 550 | 4 | 2.67 | 512.5 | — |
| 551 | 4 | 2.67 | 512.5 | — |
| 552 | 2 | 2.21 | 472.3 | — |
| 553 | 2 | 2.10 | 400.2 | — |
| 554 | 2 | 2.18 | 418.2 | — |
| 555 | 2 | 2.32 | 436.2 | — |
| 556 | 2 | 2.34 | 458.1 | — |
| 557 | 2 | 2.34 | 458.1 | — |
| 558 | 2 | 2.11 | 430.2 | — |
| 559 | 7 | 2.30 | 484.3 | — |
| 560 | 7 | 2.22 | 444.2 | — |
| 561 | 7 | 2.22 | 444.2 | — |
| 562 | 2 | 2.51 | 442.4 | — |
| 563 | 4 | 2.29 | 444.5 | — |
| 564 | 2 | 2.23 | 428.2 | — |
| 565 | 2 | 2.37 | 464.2 | — |
| 566 | 2 | 2.20 | 446.2 | — |
| 567 | 2 | 2.32 | 472.2 | — |
| 568 | 2 | 2.21 | 458.2 | — |
| 569 | 2 | 2.19 | 470.3 | — |
| 570 | 2 | 2.22 | 458.2 | — |
| 571 | 2 | 2.34 | 460.2 | — |
| 572 | 2 | 2.35 | 428.2 | — |
| 573 | 2 | 2.33 | 472.2 | — |
| 574 | 2 | 1.76 | 457.2 | — |

TABLE 31

| Ex | condition | R. time (min) | ESI+ | ESI− |
|---|---|---|---|---|
| 575 | 2 | 1.91 | 486.2 | — |
| 576 | 2 | 2.33 | 472.2 | — |
| 577 | 2 | 2.14 | 458.2 | — |
| 578 | 2 | 2.16 | 458.2 | — |
| 579 | 2 | 2.53 | 478.4 | — |
| 580 | 2 | 2.43 | 442.5 | — |
| 581 | 2 | 2.42 | 442.4 | — |
| 582 | 2 | 2.25 | 458.4 | — |
| 583 | 2 | 2.58 | 415.2 | — |
| 584 | 2 | 2.66 | 429.4 | — |
| 585 | 4 | 2.43 | 486.4 | — |
| 586 | 2 | 2.30 | 458.4 | — |
| 587 | 2 | 2.08 | 485.4 | — |
| 588 | 2 | 2.33 | 426.5 | — |
| 589 | 7 | 2.45 | 472.3 | — |
| 590 | 7 | 2.66 | 442.3 | — |
| 591 | 2 | 2.49 | 442.3 | — |
| 592 | 2 | 2.51 | 442.3 | — |
| 593 | 2 | 2.55 | 454.4 | — |
| 594 | 2 | 2.36 | 463.3 | — |
| 595 | 2 | 2.49 | 482.4 | — |
| 596 | 2 | 2.36 | 464.4 | — |
| 597 | 2 | 2.64 | 456.4 | — |
| 598 | 2 | 2.14 | 472.5 | — |
| 599 | 2 | 2.60 | 456.4 | — |
| 600 | 2 | 2.60 | 456.4 | — |
| 601 | 7 | 2.70 | 464.2 | — |
| 602 | 7 | 2.75 | 506.2 | — |
| 603 | 7 | 1.80 | 491.3 | — |
| 604 | 7 | 2.23 | 468.3 | — |
| 605 | 7 | 2.68 | 442.3 | — |
| 606 | 7 | 2.74 | 506.2 | — |
| 607 | 7 | 2.79 | 490.3 | — |
| 608 | 2 | 2.45 | 476.5 | — |
| 609 | 2 | 2.37 | 440.5 | — |
| 610 | 2 | 2.55 | 456.4 | — |
| 611 | 2 | 2.38 | 486.4 | — |
| 612 | 2 | 2.38 | 472.5 | — |
| 613 | 2 | 2.38 | 472.5 | — |
| 614 | 2 | 2.53 | 496.5 | — |

TABLE 32

| Ex | condition | R. time (min) | ESI+ | ESI− |
|---|---|---|---|---|
| 615 | 2 | 2.09 | 533.4 | — |
| 616 | 7 | 2.76 | 456.3 | — |
| 617 | 7 | 2.75 | 456.3 | — |
| 618 | 7 | 2.78 | 456.3 | — |
| 619 | 7 | 2.79 | 468.3 | — |
| 620 | 2 | 2.28 | 472.4 | — |
| 621 | 2 | 2.28 | 472.4 | — |
| 622 | 2 | 2.40 | 478.4 | — |
| 623 | 2 | 2.16 | 486.5 | — |
| 624 | 2 | 2.46 | 486.5 | — |
| 625 | 2 | 2.35 | 472.4 | — |
| 626 | 2 | 2.69 | 486.3 | — |
| 627 | 2 | 2.52 | 478.5 | — |
| 628 | 2 | 2.15 | 470.5 | — |
| 629 | 2 | 2.67 | 470.6 | — |
| 630 | 2 | 2.66 | 470.5 | — |
| 631 | 7 | 2.57 | 498.3 | — |
| 632 | 7 | 2.72 | 478.3 | — |
| 633 | 7 | 1.87 | 505.3 | — |
| 634 | 7 | 2.73 | 478.2 | — |
| 635 | 2 | 2.13 | 505.5 | — |
| 636 | 7 | 2.20 | 480.3 | — |
| 637 | 7 | 1.83 | 479.3 | — |
| 638 | 7 | 2.09 | 479.3 | — |
| 639 | 2 | 2.21 | 482.5 | — |
| 640 | 2 | 2.56 | 456.5 | — |
| 641 | 2 | 2.34 | 472.4 | — |
| 642 | 7 | 2.77 | 520.3 | — |
| 643 | 2 | 2.63 | 520.5 | — |
| 644 | 2 | 2.39 | 472.5 | — |

TABLE 32-continued

| Ex | condition | R. time (min) | ESI+ | ESI− |
|---|---|---|---|---|
| 645 | 2 | 2.39 | 472.5 | — |
| 646 | 2 | 2.33 | 472.5 | — |
| 647 | 2 | 2.34 | 472.5 | — |
| 648 | 2 | 2.34 | 464.5 | — |
| 649 | 2 | 2.35 | 464.5 | — |
| 650 | 2 | 2.60 | 504.5 | — |
| 651 | 2 | 2.66 | 504.5 | — |
| 652 | 2 | 2.66 | 454.5 | — |
| 653 | 7 | 2.54 | 472.3 | — |
| 654 | 7 | 2.66 | 500.3 | — |

TABLE 33

| Ex | condition | R. time (min) | ESI+ | ESI− |
|---|---|---|---|---|
| 655 | 7 | 2.59 | 500.3 | — |
| 656 | 2 | 2.45 | 472.5 | — |
| 657 | 2 | 2.28 | 472.5 | — |
| 658 | 2 | 2.21 | 470.5 | — |
| 659 | 7 | 2.51 | 472.3 | — |
| 660 | 7 | 3.21 | 597.4 | — |
| 661 | 7 | 3.15 | 597.4 | — |
| 662 | 7 | 1.89 | 511.3 | — |
| 663 | 7 | 2.40 | 539.3 | — |
| 664 | 2 | 1.96 | 511.5 | — |
| 665 | 7 | 2.31 | 539.3 | — |
| 666 | 7 | 2.72 | 579.3 | — |
| 667 | 7 | 1.85 | 525.3 | — |
| 668 | 7 | 3.07 | 494.2 | — |
| 669 | 7 | 2.95 | 501.2 | — |
| 670 | 7 | 3.38 | 554, 556 | — |
| 671 | 2 | 2.29 | 547.5 | — |
| 672 | 2 | 2.62 | 492.5 | — |
| 673 | 7 | 2.85 | 504.3 | — |
| 674 | 7 | 2.85 | 504.3 | — |
| 675 | 7 | 1.96 | 493.3 | — |
| 676 | 7 | 2.45 | 493.3 | — |
| 677 | 2 | 2.39 | 486.5 | — |
| 678 | 2 | 2.12 | 539.6 | — |
| 679 | 7 | 2.40 | 458.3 | — |
| 680 | 7 | 2.40 | 458.3 | — |
| 681 | 2 | 2.30 | 427.5 | — |
| 682 | 2 | 2.28 | 488.5 | — |
| 683 | 2 | 2.28 | 488.5 | — |
| 684 | 2 | 2.31 | 467.5 | — |
| 685 | 2 | 2.55 | 525.5 | — |
| 686 | 2 | 2.17 | 460.5 | — |
| 687 | 2 | 2.22 | 441.5 | — |
| 688 | 2 | 2.23 | 453.5 | — |
| 689 | 2 | 2.23 | 453.5 | — |
| 690 | 2 | 2.36 | 441.4 | — |
| 691 | 2 | 2.45 | 486.5 | — |
| 692 | 2 | 2.15 | 547.5 | — |
| 693 | 2 | 2.35 | 502.5 | — |
| 694 | 2 | 2.35 | 502.5 | — |

TABLE 34

| Ex | condition | R. time (min) | ESI+ | ESI− |
|---|---|---|---|---|
| 695 | 4 | 1.89 | 493.3 | — |
| 696 | 2 | 2.75 | 492.4 | — |
| 697 | 2 | 2.29 | 547.5 | — |
| 698 | 2 | 2.09 | 547.5 | — |
| 699 | 2 | 2.00 | 477.5 | — |
| 700 | 2 | 2.17 | 486.5 | — |
| 701 | 2 | 1.85 | 471.5 | — |
| 702 | 2 | 1.84 | 471.5 | — |
| 703 | 2 | 2.11 | 561.5 | — |
| 704 | 2 | 2.13 | 561.5 | — |
| 705 | 2 | 2.05 | 477.5 | — |
| 706 | 7 | 2.45 | 470.3 | — |
| 707 | 2 | 1.90 | 485.5 | — |

TABLE 34-continued

| Ex | condition | R. time (min) | ESI+ | ESI− |
|---|---|---|---|---|
| 708 | 2 | 2.11 | 456.4 | — |
| 709 | 7 | 2.16 | 466.3 | — |
| 710 | 7 | 2.01 | 465.3 | — |
| 711 | 2 | 2.09 | 466.5 | — |
| 712 | 2 | 1.86 | 465.5 | — |
| 713 | 2 | 1.83 | 457.5 | — |
| 714 | 2 | 2.09 | 533.5 | — |
| 715 | 2 | 2.22 | 533.5 | — |
| 716 | 2 | 2.36 | 458.5 | — |
| 717 | 2 | 2.36 | 458.5 | — |
| 718 | 2 | 2.30 | 458.5 | — |
| 719 | 2 | 2.56 | 490.4 | — |
| 720 | 2 | 2.62 | 490.5 | — |
| 721 | 2 | 2.61 | 440.5 | — |
| 722 | 2 | 2.30 | 450.4 | — |
| 723 | 2 | 2.30 | 450.5 | — |
| 724 | 2 | 2.36 | 464.5 | — |
| 725 | 2 | 2.78 | 462.4 | — |
| 726 | 2 | 2.23 | 533.5 | — |
| 727 | 7 | 2.78 | 490.3 | — |
| 728 | 7 | 1.94 | 479.2 | — |
| 729 | 7 | 2.42 | 479.2 | — |
| 730 | 7 | 2.45 | 472.3 | — |
| 731 | 2 | 2.90 | 480.5 | — |
| 732 | 2 | 2.86 | 487.2 | — |
| 733 | 2 | 2.84 | 583.6 | — |
| 734 | 2 | 2.13 | 425.2 | — |

TABLE 35

| Ex | condition | R. time (min) | ESI+ | ESI− |
|---|---|---|---|---|
| 735 | 2 | 3.06 | 540.2, 542.3 | — |
| 736 | 7 | 1.78 | 497.3 | — |
| 737 | 2 | 2.23 | 525.5 | — |
| 738 | 4 | 1.87 | 479.3 | — |
| 739 | 2 | 2.70 | 478.4 | — |
| 740 | 2 | 2.03 | 463.4 | — |
| 741 | 7 | 2.41 | 458.3 | — |
| 742 | 2 | 1.96 | 463.5 | — |
| 743 | 2 | 2.14 | 472.5 | — |
| 744 | 2 | 2.11 | 547.5 | — |
| 745 | 2 | 2.08 | 547.5 | — |
| 746 | 7 | 1.90 | 525.5 | — |
| 747 | 2 | 2.05 | 462.5 | — |
| 748 | 4 | 1.86 | 491.6 | — |
| 749 | 2 | 2.37 | 453.5 | — |
| 750 | 2 | 2.24 | 446.5 | — |
| 751 | 4 | 1.80 | 485.4 | — |
| 752 | 7 | 2.54 | 478.2 | — |
| 753 | 7 | 2.18 | 456.3 | — |
| 754 | 7 | 2.18 | 456.3 | — |
| 755 | 2 | 2.34 | 464.5 | — |
| 756 | 2 | 2.34 | 464.5 | — |

Pharmacological Analysis

Evaluation Examples of the compound of the present invention will next be described.

In the Evaluation Examples, "cDNA" denotes complementary deoxyribonucleic acid; "UniprotKB" denotes The Universal Protein Resource Knowledgebase; "PCR" denotes polymerase chain reaction; "IPTG" is isopropyl-β-thiogalactopyranoside; "PBS" denotes phosphate buffered saline; "MES" denotes 2-morpholinoethanesulfonic acid; "Tris-HCl" denotes trishydroxymethylaminomethane hydrochloride; "DTT" denotes dithiothreitol; "NADPH" denotes nicotinamide adenine dinucleotide phosphate; and "DMSO" denotes dimethyl sulfoxide.

Preparation of Human SPR Protein

Human SPR was prepared as described below. The full-length human SPR (1-261) cDNA was purchased from Eurofins Genomics as an artificially synthesized plasmid containing a DNA sequence optimized for the *E. coli* expression system so that the sequence of the expressed protein after transcription and translation matches the sequence described in UniprotKB (P35270).

Linearized insert and vector were prepared by PCR using primers designed for amplification of human SPR cDNA and primers designed to contain the thrombin recognition sequence of pET28a (Novagen) and a polyhistidine tag. Cloning was performed using In-Fusion (registered trademark) HD Cloning Kit (TaKaRa) to thereby construct a human SPR expression plasmid. The resultant human SPR expression plasmid was transformed into BL21 (DE3) competent cells (INVITROGEN).

The cells were inoculated into LB medium (1% triptone, 0.5% yeast extract, 1% sodium chloride) containing 50 mg/mL of kanamycin, and then precultured at 37° C. overnight. The precultured cells were inoculated into TB medium (1.2% triptone, 2.4% yeast extract, 9.4% dipotassium hydrogen phosphate, 2.2% potassium dihydrogen phosphate, 0.8% glycerin) containing 50 mg/mL of kanamycin, and the cultured at 37° C., to thereby induce SPR expression with 0.5 mM IPTG for four hours. After the induction, the cells were collected by centrifugation at 6,000 G for 30 minutes and washed with PBS, and the washing was discarded. The washed cells were suspended in buffer solution A (20 mM MES, pH 6.5, 100 mM sodium chloride, 1 mM DTT, 5 mM imidazole). Subsequently, the cell suspension was subjected to ultrasonic treatment to thereby homogenize the cells. The cell homogenate was clarified by centrifugation at 30,000 G for 60 minutes and then filtered with a 0.45 μm. The filtrate was allowed to pass through HisTrapFF 5 mL column (GE Healthcare). The resin was washed with buffer A, and then gradient elution was performed with buffer B (20 mM MES, pH 6.5, 100 mM sodium chloride, 1 mM DTT, 500 mM imidazole). Thrombin was added to a fraction containing the SPR protein, and the mixture was dialyzed in buffer A overnight, to thereby cleave the tag. After removal of the thrombin by with Benzamidine Sepharose 4 FF (GE Healthcare), the resultant product was allowed to pass through the HisTrapFF 5 mL column, to thereby remove the tag, followed by concentration with Amicon Ultra 10,000 NMWL (Merck Millipore). The concentrate was purified by gel filtration using HiLoad 16/60 Superdex 75 μg (GE Healthcare) equilibrated with buffer C (20 mM MES, pH 6.5, 100 mM sodium chloride, 1 mM DTT). The fraction containing SPR protein was concentrated and then cryopreserved at −80° C.

Evaluation Example 1: Measurement of Human SPR Inhibitory Activity

Human SPR inhibitory activity was measured by using a 384-well low adsorption clear plate (Greiner) with buffer D containing 100 mM Tris-HCl (pH 7.5) (Thermo Fisher Scientific) and 0.01% bovine serum albumin (Sigma). A compound was diluted. with DMSO to a concentration of 1 mM, and a 1 μL aliquot of the preparation was diluted with 250 μL of buffer D. The thus-diluted compound was dispensed into the 384-well plate at 20 μL/well. Thereafter, human SPR was diluted with buffer D to 200 ng/ml and then dispensed into the 384-well plate at 20 μL/well. Subsequently, 40 μL of ultrapure water containing 120 μM Sepiapterin (WuXi AppTec) and 120 μM NADPH (Nacalai) was added to each well, and mixed with a vortex mixer, to thereby initiate the reaction. The reaction mixture was incubated at room temperature for 240 minutes, and the reaction was terminated by addition of 10 μL of ultrapure water containing 2% formic acid (Nacalai). In order to determine the amount of sepiapterin after termination of the reaction, the absorbance at 420 nm was measured by applying the 384-well plate to EnSpire multimode plate reader (Perkin Elmer). The percent inhibition (%) of human SPR by the test compound was calculated by the following formula.

Percent inhibition (%)=(the absorbance of the test compound−the absorbance of the substrate only)÷(the absorbance of the control−the absorbance of the substrate only)×100

The absorbance of a solution reacted without addition of a test compound was used as "control", and the absorbance of a solution without addition of the compound and human SPR was used as "substrate only."

The concentration at 50% inhibition of human SPR ($IC_{50}$) is determined as follows. A linear formula Y=m×log(x)+b (wherein x is the concentration at each of two points between which 50% inhibition is achieved, and Y is the percent inhibition (%) at the concentration), and the value x was calculated when Y was 50. The results are shown in Table 36. In the linear equation, m represents the slope of the straight line, and b represents the Y-intercept.

TABLE 36

| Synthesis Example No. | Human SPR $IC_{50}$ (μM) |
|---|---|
| 1 | <1 μM |
| 2 | <1 μM |
| 3 | <1 μM |
| 4 | <1 μM |
| 5 | <1 μM |
| 7 | <1 μM |
| 9 | <1 μM |
| 10 | <1 μM |
| 11 | <1 μM |
| 12 | <1 μM |
| 13 | <1 μM |
| 14 | <1 μM |
| 15 | <1 μM |
| 16 | <1 μM |
| 17 | <1 μM |
| 18 | <1 μM |
| 19 | <1 μM |
| 20 | <1 μM |
| 21 | <1 μM |
| 22 | <1 μM |
| 23 | <1 μM |
| 24 | <1 μM |
| 25 | <1 μM |
| 26 | <1 μM |
| 27 | <1 μM |
| 28 | <1 μM |
| 29 | <1 μM |
| 30 | <1 μM |
| 31 | <1 μM |
| 32 | <1 μM |
| 33 | <1 μM |
| 35 | <1 μM |
| 41 | <1 μM |
| 104 | <1 μM |
| 135 | <1 μM |
| 169 | <1 μM |
| 195 | <1 μM |

Evaluation Example 2: Measurement of Human SPR Inhibitory Activity Human SPR inhibitory activity was measured by using a 384-well low adsorption clear plate (Greiner) with buffer D containing 100 mM Tris-HCl (pH 7.5) (Thermo Fisher Scientific) and 0.01% bovine serum albumin (Sigma). A compound was diluted with DMSO to achieve seven different final concentrations; i.e., 0.14 nM, 0.41 nM, 1.23 nM, 3.7 nM, 11.1 nM, 33 nM, and 100 nM. A 1.5 μL aliquot of the compound solution prepared with DMSO was diluted with 250 μL of buffer D, and the thus-diluted solution was dispensed into the 384-well plate at 20 μL/well. Thereafter, human SPR was diluted with buffer D to 150 ng/ml and then dispensed into the 384-well plate at 20 μL/well. Subsequently, 40 μL of ultrapure water containing 120 UM sepiapterin (produced by the method described in L-Sepiapterin, Heterocycles, 2008, 76, 1329-1335 and WO 2013/168693) and 160 μM NADPH(Nacalai) was added to each well, and then reaction was initiated. The reaction mixture was incubated at room temperature for 240 minutes. Thereafter, in order to determine the amount of sepiapterin, the absorbance at 420 nm was measured by applying the 384-well plate to EnSpire multimode plate reader (Perkin Elmer). The percent inhibition (%) of human SPR by the test compound was calculated by the following formula.

Percent inhibition (%)=(the absorbance of the test compound−the absorbance of the substrate only)÷(the absorbance of the control−the absorbance of the substrate only)×100

The absorbance of a solution reacted without addition of a test compound was used as "control", and the absorbance of a solution without addition of the compound and human SPR was used as "substrate only."

The concentration at 50% inhibition of human SPR ($IC_{50}$) is determined as follows. A linear formula Y=m×log(x)+b (wherein x is the concentration at two points between which 50% inhibition is achieved, and Y is the percent inhibition (%) at the concentration), and the value x was calculated when Y was 50. In the linear equation, m represents the slope of the straight line, and b represents the Y-intercept.

The results of the concentration at 50% inhibition of human SPR ($IC_{50}$) are shown in Tables 37 to 41 below. In the tables, "Ex" corresponds to Synthesis Example No.

TABLE 37

| Ex | $IC_{50}$ (nM) |
|---|---|
| 4 | 0.90 |
| 10 | 0.68 |
| 12 | 1.41 |
| 13 | 1.43 |
| 14 | 1.19 |
| 15 | 1.61 |
| 16 | 1.96 |
| 17 | 0.76 |
| 18 | 0.89 |
| 21 | 0.96 |
| 23 | 1.91 |
| 32 | 3.08 |
| 33 | 0.65 |
| 215 | 1.04 |
| 216 | 0.78 |
| 217 | 0.69 |
| 218 | 0.89 |
| 219 | 0.98 |
| 220 | 0.79 |
| 221 | 0.64 |
| 222 | 0.79 |
| 223 | 1.12 |
| 224 | 0.78 |
| 225 | 1.84 |
| 226 | 1.07 |
| 227 | 0.65 |
| 228 | 1.02 |
| 229 | 0.85 |
| 230 | 0.93 |
| 231 | 0.65 |
| 232 | 1.25 |
| 233 | 1.03 |
| 234 | 1.41 |
| 235 | 0.90 |

TABLE 37-continued

| Ex | $IC_{50}$ (nM) |
|---|---|
| 236 | 0.97 |
| 237 | 0.91 |
| 238 | 0.89 |
| 239 | 0.72 |
| 240 | 1.84 |
| 241 | 1.98 |
| 242 | 1.39 |
| 243 | 1.58 |
| 244 | 0.99 |
| 245 | 1.08 |
| 246 | 1.19 |
| 247 | 0.94 |
| 248 | 1.89 |
| 249 | 2.69 |
| 250 | 0.88 |
| 251 | 1.74 |
| 252 | 7.11 |
| 253 | 0.85 |
| 254 | 0.84 |
| 255 | 1.02 |
| 256 | 0.97 |
| 257 | 1.01 |
| 258 | 0.74 |
| 259 | 0.18 |
| 260 | 1.27 |
| 261 | 2.27 |
| 262 | 1.01 |
| 263 | 1.22 |
| 264 | 0.95 |
| 265 | 0.68 |
| 266 | 1.58 |
| 267 | 14.31 |
| 268 | 1.04 |
| 269 | 1.17 |
| 270 | 1.16 |
| 271 | 1.08 |
| 272 | 3.78 |
| 273 | 11.63 |
| 274 | 9.46 |
| 275 | 0.68 |
| 276 | 0.68 |
| 277 | 0.82 |
| 278 | 1.87 |
| 279 | 1.76 |
| 280 | 5.64 |
| 281 | 3.08 |
| 282 | 4.73 |
| 283 | 2.35 |
| 284 | 3.93 |
| 285 | 3.28 |
| 286 | 1.54 |
| 287 | 2.53 |
| 288 | 1.37 |
| 289 | 2.05 |
| 290 | 0.93 |
| 291 | 6.42 |
| 292 | 1.32 |
| 293 | 2.24 |
| 294 | 2.26 |
| 295 | 2.48 |
| 296 | 2.93 |
| 297 | 3.32 |
| 298 | 3.11 |
| 299 | 6.43 |
| 300 | 9.44 |
| 301 | 1.22 |
| 302 | 2.69 |
| 303 | 2.58 |
| 304 | 3.00 |
| 305 | 2.24 |
| 306 | 9.43 |
| 307 | 3.03 |
| 308 | 3.60 |
| 309 | 22.85 |
| 310 | 2.47 |
| 311 | 1.21 |
| 312 | 1.30 |
| 313 | 1.15 |

TABLE 37-continued

| Ex | $IC_{50}$ (nM) |
|---|---|
| 314 | 0.93 |
| 315 | 1.11 |
| 316 | 0.90 |
| 317 | 1.34 |
| 318 | 1.43 |
| 319 | 3.16 |
| 320 | 1.69 |
| 321 | 0.72 |

TABLE 38

| Ex | $IC_{50}$ (nM) |
|---|---|
| 322 | 0.98 |
| 323 | 1.20 |
| 324 | 1.61 |
| 325 | 1.45 |
| 326 | 1.96 |
| 327 | 2.39 |
| 328 | 1.56 |
| 329 | 1.69 |
| 330 | 1.83 |
| 331 | 1.71 |
| 332 | 2.06 |
| 333 | 1.86 |
| 334 | 1.00 |
| 335 | 0.73 |
| 336 | 7.13 |
| 337 | 1.48 |
| 338 | 2.73 |
| 339 | 4.57 |
| 340 | 1.92 |
| 341 | 2.60 |
| 342 | 2.31 |
| 343 | 4.71 |
| 344 | 1.69 |
| 345 | 0.92 |
| 346 | 1.77 |
| 347 | 1.87 |
| 348 | 2.84 |
| 349 | 1.36 |
| 350 | 0.75 |
| 351 | 0.90 |
| 352 | 1.04 |
| 353 | 0.82 |
| 354 | 0.86 |
| 355 | 1.10 |
| 356 | 1.16 |
| 357 | 1.50 |
| 358 | 0.87 |
| 359 | 0.88 |
| 360 | 0.76 |
| 361 | 1.42 |
| 362 | 1.48 |
| 363 | 1.61 |
| 364 | 0.63 |
| 365 | 0.65 |
| 366 | 0.75 |
| 367 | 0.62 |
| 368 | 0.61 |
| 369 | 0.58 |
| 370 | 0.54 |
| 371 | 0.61 |
| 372 | 0.55 |
| 373 | 0.74 |
| 374 | 0.65 |
| 375 | 0.65 |
| 376 | 0.72 |
| 377 | 0.78 |
| 378 | 0.79 |
| 379 | 0.70 |
| 380 | 0.76 |
| 381 | 0.71 |
| 382 | 0.87 |
| 383 | 0.82 |

TABLE 38-continued

| Ex | $IC_{50}$ (nM) |
|---|---|
| 384 | 0.82 |
| 385 | 0.83 |
| 386 | 0.60 |
| 387 | 0.86 |
| 388 | 1.53 |
| 389 | 0.95 |
| 390 | 0.71 |
| 391 | 0.92 |
| 392 | 1.50 |
| 393 | 1.38 |
| 394 | 0.39 |
| 395 | 0.89 |
| 396 | 1.35 |
| 397 | 1.75 |
| 398 | 6.08 |
| 399 | 1.56 |
| 400 | 0.70 |
| 401 | 0.56 |
| 402 | 0.63 |
| 403 | 0.61 |
| 404 | 0.63 |
| 405 | 0.77 |
| 406 | 0.93 |
| 407 | 1.23 |
| 408 | 0.83 |
| 409 | 0.75 |
| 410 | 1.50 |
| 411 | 0.65 |
| 412 | 1.85 |
| 413 | 1.32 |
| 414 | 0.70 |
| 415 | 0.74 |
| 416 | 0.59 |
| 417 | 0.59 |
| 418 | 0.61 |
| 419 | 0.83 |
| 420 | 0.75 |
| 421 | 0.77 |
| 422 | 0.75 |
| 423 | 0.71 |
| 424 | 0.67 |
| 425 | 0.77 |
| 426 | 0.70 |
| 427 | 0.95 |
| 428 | 0.84 |
| 429 | 0.80 |
| 430 | 0.92 |
| 431 | 0.81 |
| 432 | 0.66 |
| 433 | 0.97 |
| 434 | 1.40 |
| 435 | 1.46 |
| 436 | 1.20 |
| 437 | 1.38 |
| 438 | 0.98 |
| 439 | 1.61 |
| 440 | 1.20 |
| 441 | 4.74 |

TABLE 39

| Ex | $IC_{50}$ (nM) |
|---|---|
| 442 | 1.53 |
| 443 | 0.65 |
| 444 | 0.98 |
| 445 | 0.66 |
| 446 | 0.82 |
| 447 | 2.16 |
| 448 | 8.22 |
| 449 | 0.84 |
| 450 | 0.60 |
| 451 | 0.69 |
| 452 | 0.83 |
| 453 | 0.82 |

TABLE 39-continued

| Ex | $IC_{50}$ (nM) |
|---|---|
| 454 | 0.75 |
| 455 | 0.72 |
| 456 | 0.58 |
| 457 | 0.81 |
| 458 | 0.79 |
| 459 | 0.74 |
| 460 | 1.24 |
| 461 | 0.75 |
| 462 | 0.96 |
| 463 | 0.97 |
| 464 | 0.80 |
| 465 | 1.76 |
| 466 | 1.27 |
| 467 | 0.79 |
| 468 | 0.84 |
| 469 | 0.89 |
| 470 | 0.88 |
| 471 | 1.18 |
| 472 | 1.12 |
| 473 | 2.11 |
| 474 | 0.88 |
| 475 | 0.85 |
| 476 | 0.75 |
| 477 | 0.64 |
| 478 | 0.95 |
| 479 | 1.05 |
| 480 | 1.12 |
| 481 | 0.75 |
| 482 | 0.71 |
| 483 | 0.69 |
| 484 | 1.20 |
| 485 | 1.10 |
| 486 | 0.92 |
| 487 | 0.97 |
| 488 | 0.87 |
| 489 | 0.93 |
| 490 | 0.88 |
| 491 | 0.82 |
| 492 | 0.89 |
| 493 | 0.94 |
| 494 | 0.73 |
| 495 | 0.91 |
| 496 | 0.75 |
| 497 | 0.59 |
| 498 | 0.72 |
| 499 | 0.74 |
| 500 | 0.88 |
| 501 | 0.71 |
| 502 | 0.70 |
| 503 | 0.80 |
| 504 | 0.84 |
| 505 | 1.89 |
| 506 | 0.80 |
| 507 | 1.13 |
| 508 | 0.77 |
| 509 | 0.92 |
| 510 | 0.85 |
| 511 | 1.07 |
| 512 | 0.69 |
| 513 | 0.75 |
| 514 | 0.58 |
| 515 | 0.84 |
| 516 | 0.61 |
| 517 | 0.57 |
| 518 | 0.66 |
| 519 | 0.68 |
| 520 | 0.77 |
| 521 | 0.59 |
| 522 | 0.78 |
| 523 | 0.71 |
| 524 | 0.72 |
| 525 | 0.65 |
| 526 | 0.67 |
| 527 | 0.74 |
| 528 | 0.85 |
| 529 | 1.03 |
| 530 | 1.14 |
| 531 | 0.73 |

TABLE 39-continued

| Ex | $IC_{50}$ (nM) |
|---|---|
| 532 | 0.55 |
| 533 | 0.64 |
| 534 | 0.87 |
| 535 | 0.92 |
| 536 | 0.92 |
| 537 | 0.86 |
| 538 | 0.69 |
| 539 | 0.64 |
| 540 | 0.66 |
| 541 | 0.82 |
| 542 | 0.78 |
| 543 | 0.97 |
| 544 | 0.95 |
| 545 | 0.66 |
| 546 | 0.77 |
| 547 | 0.74 |
| 548 | 0.79 |
| 549 | 0.73 |
| 550 | 0.79 |
| 551 | 0.84 |
| 552 | 0.88 |
| 553 | 0.99 |
| 554 | 0.77 |
| 555 | 0.82 |
| 556 | 0.62 |
| 557 | 0.81 |
| 558 | 1.14 |
| 559 | 1.00 |
| 560 | 0.99 |
| 561 | 0.92 |

TABLE 40

| Ex | $IC_{50}$ (nM) |
|---|---|
| 562 | 1.31 |
| 563 | 0.70 |
| 564 | 0.95 |
| 565 | 0.93 |
| 566 | 0.94 |
| 567 | 0.69 |
| 568 | 0.68 |
| 569 | 0.67 |
| 570 | 0.75 |
| 571 | 0.88 |
| 572 | 1.10 |
| 573 | 0.88 |
| 574 | 0.79 |
| 575 | 0.81 |
| 576 | 0.86 |
| 577 | 1.10 |
| 578 | 0.90 |
| 579 | 0.87 |
| 580 | 0.96 |
| 581 | 1.09 |
| 582 | 0.63 |
| 583 | 0.79 |
| 584 | 1.20 |
| 585 | 1.23 |
| 586 | 0.99 |
| 587 | 1.37 |
| 588 | 1.59 |
| 589 | 1.34 |
| 590 | 1.09 |
| 591 | 1.29 |
| 592 | 1.46 |
| 593 | 1.48 |
| 594 | 2.01 |
| 595 | 1.54 |
| 596 | 0.96 |
| 597 | 1.62 |
| 598 | 1.20 |
| 599 | 1.27 |
| 600 | 1.47 |
| 601 | 1.08 |

TABLE 40-continued

| Ex | $IC_{50}$ (nM) |
|---|---|
| 602 | 1.14 |
| 603 | 1.10 |
| 604 | 0.92 |
| 605 | 1.20 |
| 606 | 1.32 |
| 607 | 1.67 |
| 608 | 1.07 |
| 609 | 1.23 |
| 610 | 1.64 |
| 611 | 1.22 |
| 612 | 1.23 |
| 613 | 1.04 |
| 614 | 1.49 |
| 615 | 1.40 |
| 616 | 1.12 |
| 617 | 1.04 |
| 618 | 1.80 |
| 619 | 1.58 |
| 620 | 1.17 |
| 621 | 1.42 |
| 622 | 1.03 |
| 623 | 1.27 |
| 624 | 0.98 |
| 625 | 1.05 |
| 626 | 0.87 |
| 627 | 0.94 |
| 628 | 0.84 |
| 629 | 1.14 |
| 630 | 1.24 |
| 631 | 0.66 |
| 632 | 1.51 |
| 633 | 0.91 |
| 634 | 1.21 |
| 635 | 1.08 |
| 636 | 1.47 |
| 637 | 0.89 |
| 638 | 1.05 |
| 639 | 1.06 |
| 640 | 1.16 |
| 641 | 0.89 |
| 642 | 0.94 |
| 643 | 1.37 |
| 644 | 0.91 |
| 645 | 0.80 |
| 646 | 0.87 |
| 647 | 0.81 |
| 648 | 0.74 |
| 649 | 0.73 |
| 650 | 0.95 |
| 651 | 1.19 |
| 652 | 2.18 |
| 653 | 0.74 |
| 654 | 0.95 |
| 655 | 1.05 |
| 656 | 1.15 |
| 657 | 0.92 |
| 658 | 0.78 |
| 659 | 0.83 |
| 660 | 3.97 |
| 661 | 2.48 |
| 662 | 1.08 |
| 663 | 1.41 |
| 664 | 0.77 |
| 665 | 0.92 |
| 666 | 2.14 |
| 667 | 0.94 |
| 668 | 7.87 |
| 669 | 1.84 |
| 670 | 11.49 |
| 671 | 1.49 |
| 672 | 0.86 |
| 673 | 1.35 |
| 674 | 1.36 |
| 675 | 0.99 |
| 676 | 0.91 |
| 677 | 0.95 |
| 678 | 1.17 |
| 679 | 0.94 |

TABLE 40-continued

| Ex | $IC_{50}$ (nM) |
|---|---|
| 680 | 0.81 |
| 681 | 0.64 |

TABLE 41

| Ex | $IC_{50}$ (nM) |
|---|---|
| 682 | 0.85 |
| 683 | 0.82 |
| 684 | 0.89 |
| 685 | 1.23 |
| 686 | 1.00 |
| 687 | 0.77 |
| 688 | 0.91 |
| 689 | 0.95 |
| 690 | 1.46 |
| 691 | 0.82 |
| 692 | 0.80 |
| 693 | 0.71 |
| 694 | 0.85 |
| 695 | 1.30 |
| 696 | 1.71 |
| 697 | 1.22 |
| 698 | 1.52 |
| 699 | 1.47 |
| 700 | 0.96 |
| 701 | 0.98 |
| 702 | 0.87 |
| 703 | 1.44 |
| 704 | 1.52 |
| 705 | 1.58 |
| 706 | 0.82 |
| 707 | 0.84 |
| 708 | 0.74 |
| 709 | 0.85 |
| 710 | 1.01 |
| 711 | 1.20 |
| 712 | 1.19 |
| 713 | 0.96 |
| 714 | 2.54 |
| 715 | 1.28 |
| 716 | 0.88 |
| 717 | 0.78 |
| 718 | 0.74 |
| 719 | 0.77 |
| 720 | 1.03 |
| 721 | 1.05 |
| 722 | 0.81 |
| 723 | 0.69 |
| 724 | 1.03 |
| 725 | 3.61 |
| 726 | 1.35 |
| 727 | 1.34 |
| 728 | 1.07 |
| 729 | 1.05 |
| 730 | 1.26 |
| 731 | 2.89 |
| 732 | 1.70 |
| 733 | 2.16 |
| 734 | 0.73 |
| 735 | 7.30 |
| 736 | 1.07 |
| 737 | 1.90 |
| 738 | 1.39 |
| 739 | 1.54 |
| 740 | 1.81 |
| 741 | 0.98 |
| 742 | 1.59 |
| 743 | 1.33 |
| 744 | 1.57 |
| 745 | 1.85 |
| 746 | 1.54 |
| 747 | 0.74 |
| 748 | 1.01 |
| 749 | 0.93 |

TABLE 41-continued

| Ex | $IC_{50}$ (nM) |
|---|---|
| 750 | 0.96 |
| 751 | 1.34 |
| 752 | 0.88 |
| 753 | 0.48 |
| 754 | 0.83 |
| 755 | 0.61 |
| 756 | 0.71 |

Next will be described Formulation Examples of the condensed heterocyclic compound of Formula (I) of the present invention.

Formulation Example 1

A granule containing the following ingredients is produced.

| | | |
|---|---|---|
| Ingredients | Compound of Formula (I) | 10 mg |
| | Lactose | 700 mg |
| | Cornstarch | 274 mg |
| | HPC-L | 16 mg |
| | Total | 1000 mg |

A compound of Formula (I) and lactose are allowed to pass through a 60-mesh sieve. Cornstarch is allowed to pass through a 120-mesh sieve. These materials are mixed with a V-type mixer. An aqueous solution of low-viscosity hydroxypropyl cellulose (HPC-L) is added to the mixed powder, and the resultant mixture is kneaded and granulated (extrusion granulation, pore size: 0.5 to 1 mm), followed by drying. The resultant dry granules are sieved with a vibration sieve (12/60 mesh) to thereby produce a granule.

Formulation Example 2

A powder for encapsulation containing the following ingredients is produced.

| | | |
|---|---|---|
| Ingredients | Compound of Formula (I) | 10 mg |
| | Lactose | 79 mg |
| | Cornstarch | 10 mg |
| | Magnesium stearate | 1 mg |
| | Total | 100 mg |

A compound of Formula (I) and lactose are allowed to pass through a 60-mesh sieve. Cornstarch is allowed to pass through a 120-mesh sieve. These materials and magnesium stearate are mixed with a V-type mixer. A No. 5 hard gelatin capsule is filled with 100 mg of the 10% powder.

Formulation Example 3

A granule for encapsulation containing the following ingredients is produced.

| | | |
|---|---|---|
| Ingredients | Compound of Formula (I) | 15 mg |
| | Lactose | 90 mg |
| | Cornstarch | 42 mg |
| | HPC-L | 3 mg |
| | Total | 150 mg |

A compound of Formula (I) and lactose are allowed to pass through a 60-mesh sieve. Cornstarch is allowed to pass through a 120-mesh sieve. These materials are mixed with a V-type mixer. An aqueous solution of low-viscosity hydroxypropyl cellulose (HPC-L) is added to the mixed powder, and the resultant mixture is kneaded and granulated, followed by drying. The resultant dry granules are sieved with a vibration sieve (12/60 mesh) to thereby prepare a granule. A No. 4 hard gelatin capsule is filled with 150 mg of the granule.

Formulation Example 4

A tablet containing the following ingredients is produced.

| | | |
|---|---|---|
| Ingredients | Compound of Formula (I) | 10 mg |
| | Lactose | 90 mg |
| | Microcrystalline cellulose | 30 mg |
| | Magnesium stearate | 5 mg |
| | CMC-Na | 15 mg |
| | Total | 150 mg |

A compound of Formula (I), lactose, microcrystalline cellulose, and CMC-Na (carboxymethyl cellulose sodium salt) are allowed to pass through a 60-mesh sieve, and then mixed together. Magnesium stearate is added to the mixed powder to thereby prepare a mixed powder for formulation. The resultant mixed powder is directly tableted to thereby produce 150 mg of a tablet.

Formulation Example 5

A formulation for intravenous injection is produced as follows.

| | |
|---|---|
| Compound of Formula (I) | 100 mg |
| Saturated fatty acid glyceride | 1000 mL |

Generally, a solution containing the aforementioned ingredients is intravenously administered to a patient at a rate of 1 mL per minute.

INDUSTRIAL APPLICABILITY

The present invention can provide a compound having an excellent sepiapterin reductase inhibitory action and particularly useful for treatment of a pain.

The invention claimed is:

1. A compound of Formula (I):

(I)

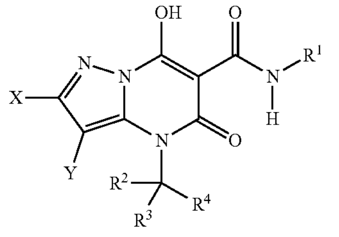

or a pharmaceutically acceptable salt, stereoisomer, or tautomer thereof, wherein $R^1$ is a substitutable hydrocarbon;

$R^2$ is a hydrogen atom or a substitutable $C_{1-6}$ alkyl;

$R^3$ is a hydrogen atom or a substitutable $C_{1-6}$ alkyl;

$R^4$ is a hydrogen atom, a substitutable hydrocarbon, or a substitutable heterocyclic group;

X is a hydrogen atom, a halogen atom, a hydroxy, a cyano, a substitutable amino, a substitutable hydrocarbon, a substitutable heterocyclic group, an acyl, or $—CR^5═NR^6$;

Y is a hydrogen atom, a halogen atom, a cyano, a substitutable hydrocarbon, a substitutable heterocyclic group, an acyl, or $—CR^7═NR^8$; or X and Y, together with the carbon atoms to which they are bonded, form a substitutable 5- to 7-membered ring;

$R^5$ is a hydrogen atom or $C_{1-6}$ alkyl;

$R^6$ is a substitutable hydroxy;

$R^7$ is a hydrogen atom or $C_{1-6}$ alkyl;

$R^8$ is a substitutable hydroxy;

with the provisos that:

if X is a hydrogen atom, Y is not a hydrogen atom; and if Y is a hydrogen atom, X is not a hydrogen atom, wherein the term "substitutable hyrocarbon" refers to a $C_{1-6}$ alkyl, a $C_{2-6}$ alkenyl, a $C_{2-6}$ alkynyl, a $C_{3-10}$ cycloalkyl, a $C_{3-10}$ cycloalkenyl, a $C_{6-14}$ aryl, or a $C_{7-16}$ aralkyl, optionally having one or more substituents independently selected from among the below-described substituent group A1 or substituent group A2;

the term "substitutable $C_{1-6}$ alkyl" refers to a $C_{1-6}$ alkyl optionally having one or more substituents independently selected from among the below-described substituent group A1 or substituent group A2;

the term "substitutable heterocyclic group" refers to a heterocyclic group having 0 to 3 substituents independently selected from substituent group A1 or substituent group A2 as defined below;

the term "substitutable 5- to 7-membered ring" refers to a 5- to 7-membered non-aromatic heterocyclic ring which may be substituted with a $C_{1-6}$ alkyl, a $C_{3-6}$ cycloalkyl or a 4- to 10-membered non-aromatic heterocyclic group, each of which may in turn be substituted with one or more substituents independently selected from the substituent group F as defined below;

the term "substitutable amino" refers to an amino optionally having one or two substituents independently selected from the group consisting of a $C_{1-6}$ alkyl, $C_{2-6}$ alkenyl, $C_{3-10}$ cycloalkyl, $C_{6-14}$ aryl, $C_{7-16}$ aralkyl, 5 to 14-membered aromatic heterocyclic group, 3- to 14-membered non-aromatic heterocyclic group, $C_{1-6}$ alkyl-carbonyl, $C_{6-14}$ aryl-carbonyl, $C_{7-16}$ aralkyl-carbonyl, 5-to 14-membered aromatic heterocyclic carbonyl, 3- to 14-membered non-aromatic heterocyclic carbonyl, $C_{1-6}$ alkoxy-carbonyl, carbamoyl, sulfamoyl, mono- or di-$C_{1-6}$ alkyl-carbamoyl, mono- or di-$C_{7-16}$ aralkyl-carbamoyl, $C_{1-6}$ alkylsulfonyl, $C_{6-14}$ arylsulfonyl, and (di-$C_{1-6}$ alkylamino)methylene, each of which may have one or more substituents independently selected from substituent group A1 or substituent group A2; and the term "substitutable hydroxy" refers to a hydroxy optionally having a substituent selected from the group consisting of a $C_{1-6}$ alkyl, $C_{2-6}$ alkenyl, $C_{3-10}$ cycloalkyl, $C_{3-10}$ cycloalkenyl, $C_{6-14}$ aryl, $C_{7-16}$ aralkyl, 5- to 14-membered aromatic heterocyclic group, 3- to 14-membered non-aromatic heterocyclic group, $C_{1-6}$ alkyl-carbonyl, $C_{6-14}$ aryl-carbonyl, $C_{7-16}$ aralkyl-carbonyl, 5- to 14-membered aromatic heterocyclic carbonyl, 3- to 14-membered non-aromatic heterocyclic carbonyl, $C_{1-6}$ alkoxy-carbonyl, carbamoyl, mono- or di-$C_{1-6}$ alkyl-carbamoyl, mono- or di-$C_{7-16}$ aralkyl-carbamoyl, $C_{1-6}$ alkylsulfonyl, and $C_{6-14}$ arylsulfonyl, each of which may have one or more substituents independently selected from substituent group A1 of substituent group A2;

wherein substituent Group A1 includes:

(1) halogen atom,
(2) nitro,
(3) cyano,
(4) oxo,
(5) hydroxy,
(6) $C_{1-6}$ alkoxy substitutable with one or more substituents independently selected from among the below-described substituent group C1,
(7) $C_{6-14}$ aryloxy,
(8) $C_{7-16}$ aralkyloxy,
(9) 5- to 14-membered aromatic heterocyclic oxy,
(10) 3- to 14-membered non-aromatic heterocyclic oxy,
(11) $C_{1-6}$ alkyl-carbonyloxy substitutable with one or more substituents independently selected from among the below-described substituent group C1,
(12) $C_{6-14}$ aryl-carbonyloxy,
(13) $C_{1-6}$ alkoxy-carbonyloxy substitutable with one or more substituents independently selected from among the below-described substituent group C1,
(14) mono- or di-$C_{1-6}$ alkyl-carbamoyloxy substitutable with one or more substituents independently selected from among the below-described substituent group C1,
(15) $C_{6-14}$ aryl-carbamoyloxy,
(16) 5- to 14-membered aromatic heterocyclic carbonyloxy,
(17) 3- to 14-membered non-aromatic heterocyclic carbonyloxy,
(18) $C_{1-6}$ alkylsulfonyloxy substitutable with one or more substituents independently selected from among the below-described substituent group C1,
(19) $C_{6-14}$ arylsulfonyloxy,
(20) $C_{1-6}$ alkylthio substitutable with one or more substituents independently selected from among the below described substituent group C1,
(21) 5- to 14-membered aromatic heterocyclic group,
(22) 3- to 14-membered non-aromatic heterocyclic group,
(23) formyl,
(24) carboxy,
(25) $C_{1-6}$ alkyl-carbonyl substitutable with one or more substituents independently selected from among the below-described substituent group C1,
(26) $C_{6-14}$ aryl-carbonyl,
(27) 5- to 14-membered aromatic heterocyclic carbonyl,
(28) 3- to 14-membered non-aromatic heterocyclic carbonyl,
(29) $C_{3-10}$ cycloalkylcarbonyl,
(30) $C_{3-10}$ cycloalkenylcarbonyl,
(31) $C_{1-6}$ alkoxy-carbonyl substitutable with one or more substituents independently selected from among the below-described substituent group C1,
(32) $C_{6-14}$ aryloxy-carbonyl,
(33) $C_{7-16}$ aralkyloxy-carbonyl,
(34) carbamoyl,
(35) thiocarbamoyl,
(36) mono- or di-$C_{1-6}$ alkyl-carbamoyl substitutable with one or more substituents independently selected from among the below-described substituent group C1,
(37) $C_{6-14}$ aryl-carbamoyl,
(38) 5- to 14-membered aromatic heterocyclic carbamoyl,
(39) 3- to 14-membered non-aromatic heterocyclic carbamoyl,
(40) (hydroxy)($C_{1-6}$ alkyl)-carbamoyl,
(41) ($C_{1-6}$ alkoxy)($C_{1-6}$ alkyl)-carbamoyl,
(42) $C_{1-6}$ alkylsulfonyl substitutable with one or more substituents independently selected from among the below-described substituent group C1,
(43) $C_{6-14}$ arylsulfonyl,
(44) 5- to 14-membered aromatic heterocyclic sulfonyl,
(45) $C_{1-6}$ alkylsulfinyl substitutable with one or more substituents independently selected from among the below-described substituent group C1,
(46) $C_{6-14}$ arylsulfinyl,
(47) 5- to 14-membered aromatic heterocyclic sulfinyl,
(48) amino,
(49) mono- or di-$C_{1-6}$ alkylamino substitutable with one or more substituents independently selected from among the below-described substituent group C1,
(50) mono- or di-$C_{6-14}$ arylamino,
(51) 5- to 14-membered aromatic heterocyclic amino,
(52) $C_{7-16}$ aralkylamino,
(53) formylamino,
(54) $C_{1-6}$ alkyl-carbonylamino substitutable with one or more substituents independently selected from among the below-described substituent group C1,
(55) ($C_{1-6}$ alkyl)($C_{1-6}$ alkyl-carbonyl)amino,
(56) $C_{6-14}$ aryl-carbonylamino,
(57) $C_{1-6}$ alkoxy-carbonylamino substitutable with one or more substituents independently selected from among the below-described substituent group C1,
(58) $C_{7-16}$ aralkyloxy-carbonylamino,
(59) $C_{1-6}$ alkylsulfonylamino substitutable with one or more substitutents independently selected from among the below-described substituent group C1,
(60) $C_{6-14}$ arylsulfonylamino,
(61) carbamoylamino,
(62) $C_{1-6}$ alkyl substitutable with one or more substituents independently selected from among the below-described substituent group C1,
(63) $C_{2-6}$ alkenyl substitutable with one or more substituents independently selected from among the below-described substituent group C1,
(64) $C_{2-6}$ alkynyl,
(65) $C_{3-10}$ cycloalkyl,
(66) $C_{3-10}$ cycloalkenyl, and
(62) $C_{6-14}$ aryl;

among (1) to (67) described above, groups having a 5- to 14-membered aromatic heterocyclic ring, a 3- to 14-membered non-aromatic heterocyclic ring, a $C_{3-10}$ cycloalkane, and a $C_{3-10}$ cycloalkene may be substituted with one or more substituents independently selected from among the below-described substituent group D1;

wherein substituent Group A2 includes:

(1) halogen atom,
(2) nitro,
(3) cyano,
(4) oxo,
(5) hydroxy, (6) $C_{1-6}$ alkoxy substitutable with one or more substituents independently selected from among the below-described substituent group C1,
(7) $C_{6-14}$ aryloxy,
(8) $C_{7-16}$ aralkyloxy,
(9) 5- to 14-membered aromatic heterocyclic oxy group,
(10) 3- to 14-membered non-aromatic heterocyclic oxy group,
(11) $C_{1-6}$ alkyl-carbonyloxy substitutable with one or more substituents independently selected from among the below-described substituent group C1,
(12) $C_{6-14}$ aryl-carbonyloxy,
(13) $C_{1-6}$ alkoxy-carbonyloxy substitutable with one or more substituents independently selected from among the below-described substituent group C1,
(14) mono- or di-$C_{1-6}$ alkyl-carbamoyloxy substitutable with one or more substituents independently selected from among the below-described substituent group C1,
(15) $C_{6-14}$ aryl-carbamoyloxy,
(16) 5- to 14-membered aromatic heterocyclic carbonyloxy,
(17) 3- to 14-membered heterocyclic carbonyloxy,
(18) $C_{1-6}$ alkylsulfonyloxy substitutable with one or more substituents independently selected from among the below-described substituent group C1,
(19) $C_{6-14}$ arylsulfonyloxy,
(20) $C_{1-6}$ alkylthio substitutable with one or more substituents independently selected from among the below-described substituent group C1,
(21) 5- to 14-membered aromatic heterocyclic group,
(22) 3- to 14-membered non-aromatic heterocyclic group,
(23) formyl,
(24) carboxy,
(25) $C_{1-6}$ alkyl-carbonyl substitutable with one or more substituents independently selected from among the below-described substituent group C1,
(26) $C_{6-14}$ aryl-carbonyl,
(27) 5 to 14-membered aromatic heterocyclic carbonyl,
(28) 3- to 14-membered non-aromatic heterocyclic carbonyl,
(29) $C_{3-10}$ cycloalkylcarbonyl,
(30) $C_{3-10}$ cycloalkenylcarbonyl,
(31) $C_{1-6}$ alkoxy-carbonyl substitutable with one or more substituents independently elected from among the below-described substituent group C1,
(32) $C_{6-14}$ aryloxy-carbonyl,
(33) $C_{7-16}$ aralkyloxy-carbonyl,
(34) carbamoyl,
(35) thiocarbamoyl,
(36) mono- or di-$C_{1-6}$ alkyl-carbamoyl substitutable with one or more substituents independently selected from among the below-described substituent group C1,
(37) $C_{6-14}$ aryl-carbamoyl,
(38) 5- to 14-membered aromatic heterocyclic carbamoyl,
(39) 3- to 14-membered non-aromatic heterocyclic carbamoyl,
(40) (hydroxy)($C_{1-6}$ alkyl)-carbamoyl,
(41) ($C_{1-6}$ alkoxy)($C_{1-6}$ alkyl)-carbamoyl,
(42) $C_{1-6}$ alkylsulfonyl substitutable with one or more substituents independently selected from among the below-described substituent group C1,
(43) $C_{6-14}$ arylsulfonyl,
(44) 5- to 14-membered aromatic heterocyclic sulfonyl,
(45) $C_{1-6}$ alkylsulfinyl substitutable with one or more substituents independently selected from among the below-described substituent group C1,
(46) $C_{6-14}$ arylsulfinyl,
(47) 5- to 14-membered aromatic heterocyclic sulfinyl,
(48) amino,
(49) mono- or di-$C_{1-6}$ alkylamino substitutable with one or more substituents independently selected from among the below-described substituent group C1,
(50) mono- or di-$C_{6-14}$ arylamino,
(51) 5- to 14-membered aromatic heterocyclic amino,
(52) $C_{7-16}$ aralkylamino,
(53) formylamino,
(54) $C_{1-6}$ alkyl-carbonylamino substitutable with one or more substituents independently selected from among the below-described substituent group C1,
(55) ($C_{1-6}$ alkyl)($C_{1-6}$ alkyl-carbonyl)amino,
(56) $C_{6-14}$ aryl-carbonylamino,
(57) $C_{1-6}$ alkoxy-carbonylamino substitutable with one or more substituents independently selected from among the below-described substituent group C1,
(58) $C_{7-16}$ aralkyloxy-carbonylamino,
(59) $C_{1-6}$ alkylsulfonylamino substitutable with one or more substituents independently selected from among the below-described substituent group C1,
(60) $C_{6-14}$ arylsulfonylamino,
(61) carbamoylamino,
(62) $C_{1-6}$ alkyl substitutable with one or more substitutents independently selected from among the below-described substituent group C1,
(63) $C_{2-6}$ alkenyl substitutable with one or more substituents independently selected from among the below-described substituent group C1,
(64) $C_{2-6}$ alkynyl,
(65) $C_{3-10}$ cycloalkyl,
(66) $C_{3-10}$ cycloalkenyl, and
(67) $C_{6-14}$ aryl,
(68) N—$C_{1-6}$ alkyl-N—$C_{3-10}$ cycloalkylcarbamoyl,
(69) N—$C_{1-6}$ alkyl-N-3- to 14-membered non-aromatic heterocyclic carbamoyl group,
(70) N,N-di-$C_{3-10}$ cycloalkylcarbamoyl,
(71) N,N-di-$C_{1-6}$ alkycarbamoyl substitutable with one or more substituents independently selected from among the below-described substituent group C2,
(72) N—$C_{1-6}$ alkylcarbamoyl substitutable with one or more substituents independently selected from among the below-described substituent group C2,
(73) $C_{6-14}$ aryl-carbonyl substituted with one or more substituents independently selected from among the below described substituent group C2,
(74) 3- to 14-membered non-aromatic heterocyclic carbonyl amino, and
(75) $C_{3-10}$ cycloalkylcarbonylamino;

in the substituent group A2, among substituents described in (1) to (75) above, groups having a 5- to 14-membered aromatic heterocyclic ring, a 3- to 14-membered non-aromatic heterocyclic ring, a $C_{3-10}$ cycloalkane, and a $C_{3-10}$ cycloalkene may be substituted with one or more substituents independently selected from among the below-described substituent group D2;

wherein substituent group B includes:

halogen atom,
nitro,
cyano, hydroxy,
formyl,
carboxy,
carbamoyl,
thiocarbamoyl,
amino,
formylamino, and
carbamoylamino;

wherein substituent group C1 includes:
substituents constituting the aforementioned substituent group B,
$C_{1-6}$ alkyl-carbonyloxy,
$C_{1-6}$ alkoxy-carbonyloxy,
mono- or di-$C_{1-6}$ alkyl-carbamoyloxy,
possibly halogenated $C_{1-6}$ alkylsulfonyloxy,
possibly halogenated $C_{1-6}$ alkyl-carbonyl,
$C_{1-6}$ alkoxy-carbonyl,
possibly halogenated $C_{1-6}$ alkylsulfonyl,
mono- or di-$C_{1-6}$ alkylamino,
$C_{1-6}$ alkyl-carbonylamino,
($C_{1-6}$ alkyl)($C_{1-6}$ alkyl-carbonyl)amino,
$C_{1-6}$ alkoxy-carbonylamino, and
$C_{1-6}$ alkylsulfonylamino;

wherein substituent group C2 includes:
substituents constituting the aforementioned substituent group C1,
$C_{7-16}$ aralkyloxy,
possibly halogenated $C_{1-6}$ alkoxy,
possibly halogenated $C_{3-10}$ cycloalkyl,
4- to 10-membered non-aromatic heterocyclic group,
4- to 10-membered non-aromatic heterocyclic oxy,
$C_{6-14}$ aryl, and
5- to 10-membered aromatic heterocyclic group substitutable with $C_{1-6}$ alkyl;

wherein substituent group D1 includes:
halogen atom,
nitro,
cyano,
hydroxy,
formyl,
carboxy,
carbamoyl,
thiocarbamoyl,
amino,
formylamino,
carbamoylamino,
$C_{1-6}$ alkyl-carbonyloxy,
$C_{1-6}$ alkoxy-carbonyloxy,
mono- or di-$C_{1-6}$ alkyl-carbamoyloxy,
possibly halogenated $C_{1-6}$ alkylsulfonyloxy,
possibly halogenated $C_{1-6}$ alkyl-carbonyl,
$C_{1-6}$ alkoxy-carbonyl,
possibly halogenated $C_{1-6}$ alkylsulfonyl,
mono- or di-$C_{1-6}$ alkylamino,
$C_{1-6}$ alkyl-carbonylamino,
($C_{1-6}$ alkyl)($C_{1-6}$ alkyl-carbonyl)amino,
$C_{1-6}$ alkoxy-carbonylamino,
$C_{1-6}$ alkylsulfonylamino,
possibly halogenated $C_{1-6}$ alkyl group, and
$C_{2-6}$ alkenyl;

wherein substituent group D2 includes:
substituents constituting the aforementioned substituent group C2,
possibly halogenated $C_{1-6}$ alkyl,
$C_{2-6}$ alkenyl,
$C_{1-6}$ alkyl substituted with $C_{1-6}$ alkoxy,
$C_{1-6}$ alkyl substituted with hydroxy,
N,N-di-$C_{1-6}$ alkylcarbamoyl, and
$C_{1-6}$ alkyl substituted with possibly halogenated $C_{3-10}$ cycloalkyl;

wherein substituent group E includes:
halogen atom,
possibly halogenated $C_{1-6}$ alkoxy,
carbamoyl,
carboxy,
hydroxy,
amino,
carbamoylamino,
$C_{1-6}$ alkyl-carbonyl,
$C_{1-6}$ alkoxy-carbonyl, and
$C_{7-16}$ aralkyloxy;

wherein substituent group F includes:
substituents constituting the aforementioned substituent group E,
4- to 7-membered non-aromatic heterocyclic group, and
possibly halogenated $C_{1-6}$ alkyl.

2. The compound, tautomer or pharmaceutically acceptable salt thereof, according to claim 1, wherein:
X is a hydrogen atom, a halogen atom, a substitutable amino, a substitutable hydrocarbon, a substitutable heterocyclic group, an acyl, or $CR^5{=}NR^6$;
Y is a hydrogen atom, a halogen atom, a substitutable hydrocarbon, a substitutable heterocyclic group, an acyl, or $—CR^7{=}NR^8$;
$R^5$, $R^6$, $R^7$, and $R^8$ have the same definition as claim 1;
when X is a hydrogen atom, Y is not a hydrogen atom; and
when Y is a hydrogen atom, X is not a hydrogen atom.

3. The compound, tautomer or pharmaceutically acceptable salt thereof, according to claim 1, wherein,
$R^2$ is a hydrogen atom, and
$R^3$ is a hydrogen atom.

4. The compound, tautomer or pharmaceutically acceptable salt thereof, according to claim 1, wherein $R^1$ is a substitutable $C_{3-10}$ cycloalkyl.

5. The compound, tautomer or pharmaceutically acceptable salt thereof according to claim 1, wherein $R^4$ is a $C_{1-6}$ alkyl substitutable with one or more substituents independently selected from the group consisting of a hydroxy, a halogen atom, and a $C_{1-6}$ alkoxy.

6. The compound, tautomer or pharmaceutically acceptable salt thereof according to claim 1, wherein $R^4$ is:
a $C_{3-10}$ cycloalkyl group, $C_{6-14}$ aryl, or 3- to 14-membered non-aromatic heterocyclic group substitutable with one or more substituents independently selected from the group consisting of:
(i) a $C_{1-6}$ alkyl substitutable with one or more substituents independently selected from the group consisting of a halogen atom and a hydroxy,
(ii) a $C_{1-6}$ alkoxy substitutable with one or more substituents independently selected from the group consisting of a halogen atom and a hydroxy,
(iii) a halogen atom,
(iv) a hydroxy, and
(v) a $C_{1-6}$ alkoxy-carbonyl.

7. The compound, tautomer or pharmaceutically acceptable salt thereof, according to claim 2, wherein:
X is a substitutable amino; and
Y is a hydrogen atom or a fluorine atom.

8. The compound, tautomer or pharmaceutically acceptable salt thereof, according to claim 2, wherein:
X is a substitutable heterocyclic group; and
Y is a hydrogen atom.

9. The compound, tautomer or pharmaceutically acceptable salt thereof, according to claim 2, wherein:

X is an acyl; and

Y is a hydrogen atom or a fluorine atom.

10. The compound, tautomer or pharmaceutically acceptable salt thereof, according to claim 2, wherein:

X is a hydrogen atom; and

Y is a substitutable hydrocarbon.

11. The compound, tautomer or pharmaceutically acceptable salt thereof, according to claim 2, wherein:

X is a hydrogen atom; and

Y is a substitutable heterocyclic group.

12. The compound, tautomer or pharmaceutically acceptable salt thereof, according to claim 2, wherein:

X is an amino or a $C_{1-6}$ alkylamino; and

Y is a substitutable hydrocarbon.

13. The compound, tautomer or pharmaceutically acceptable salt thereof, according to claim 2, wherein:

X is a $C_{1-6}$ alkyl; and

Y is a substitutable hydrocarbon.

14. The compound, tautomer or pharmaceutically acceptable salt thereof, according to claim 1, wherein:

X and Y, together with the atoms to which they are bonded, form a substitutable 5- to 7-membered ring bonded to X and Y, and the ring is a group of the following Formula (i-a), Formula (i-b), Formula (i-c), Formula (i-d), or Formula (i-e):

(I-a)

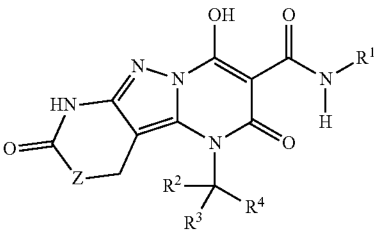

(I-b)

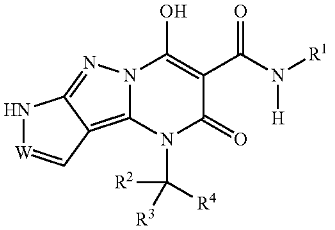

(I-c)

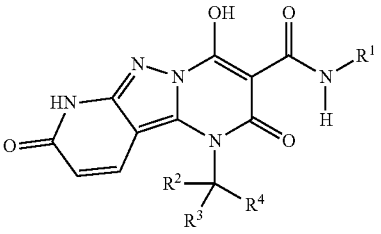

(I-d)

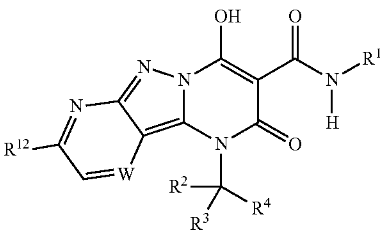

-continued (I-e)

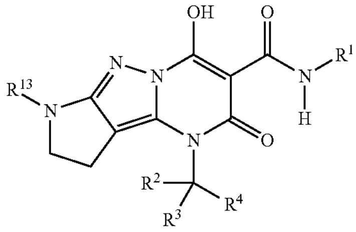

wherein;

Z is a single bond, —$CH_2$—, —O—, —$OCH_2$— (wherein O is bonded to the carbonyl, and $CH_2$ is bonded to the other carbon atom) or —$NR^{11}$—;

$R^{11}$ is a possibly halogenated $C_{1-6}$ alkyl, a possibly halogenated $C_{3-6}$ cycloalkyl, a 4- to 10-membered non-aromatic heterocyclic group, or a $C_{1-6}$ alkyl substituted with a 4- to 10-membered non-aromatic heterocyclic group;

W is CH or a nitrogen atom;

$R^{12}$ is a hydrogen atom or a $C_{1-6}$ alkoxy; and $R^{13}$ is a hydrogen atom, a possibly halogenated $C_{1-6}$ alkyl, or a carbamoyl.

15. The compound according to claim 1, wherein the compound is

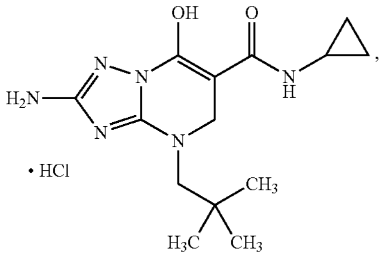 [SMILES: "· HCl" ; CC(C)(C)CN1CC(C(=O)NC2CC2)=C(O)n2nc(N)nc21]

or a tautomer thereof.

16. The compound according to claim 1, wherein the compound is

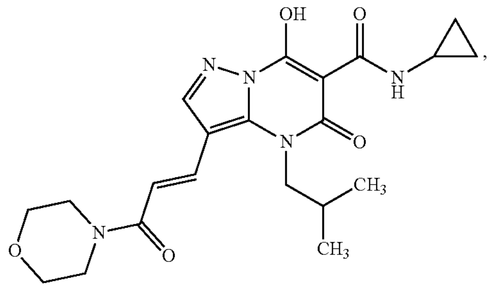 [SMILES: CC(C)Cn1c(=O)c(C(=O)NC2CC2)c(O)n2ncc(/C=C/C(=O)N3CCOCC3)c12]

or a tautomer or a pharmaceutically acceptable salt thereof.

17. The compound, tautomer or pharmaceutically acceptable salt thereof, according to claim 2, wherein:

$R^1$ is a cyclopropyl;

$R^2$ is a hydrogen atom;

$R^3$ is a hydrogen atom;

$R^4$ is a tert-butyl;

X is a (pyrimidin-4-yl)amino, a (pyrazin-2-yl)amino, a 2-aminopyridin-3-yl, a (5-(trifluoromethyl)pyrazin-2-yl)amino-grew, a (5-methoxypyrazin-2-yl)amino, a (6-methoxypyrazin-2-yl)amino, an amino, a (5-carbamoylpyrazin-2-yl)amino , a ureido, or a carbamoyl; and Y is a hydrogen atom.

18. The compound according to claim 1, wherein the compound is:

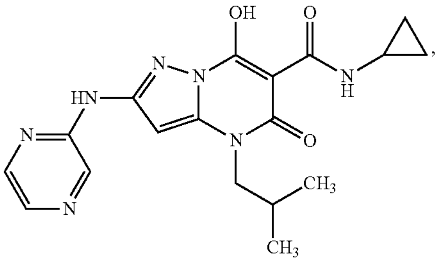 [SMILES: CC(C)Cn1c(=O)c(C(=O)NC2CC2)c(O)n2nc(Nc3cnccn3)cc12]

or a tautomer or a pharmaceutically acceptable salt thereof.

19. The compound according to claim 1, wherein the compound is:

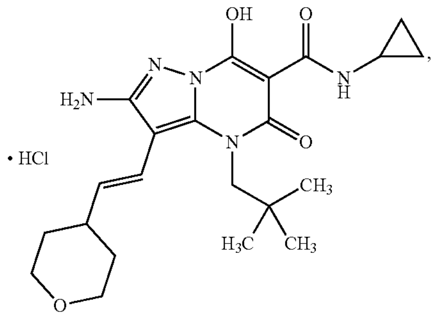 [SMILES: "· HCl" ; CC(C)(C)Cn1c(=O)c(C(=O)NC2CC2)c(O)n2nc(N)c(/C=C/C3CCOCC3)c12]

or a tautomer or a pharmaceutically acceptable salt thereof.

20. The compound according to claim 1, wherein the compound is:

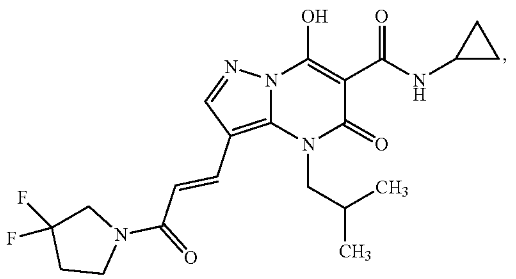 [SMILES: CC(C)Cn1c(=O)c(C(=O)NC2CC2)c(O)n2ncc(/C=C/C(=O)N3CCC(F)(F)C3)c12]

or a tautomer or a pharmaceutically acceptable salt thereof.

21. The compound according to claim 1, wherein the compound is:

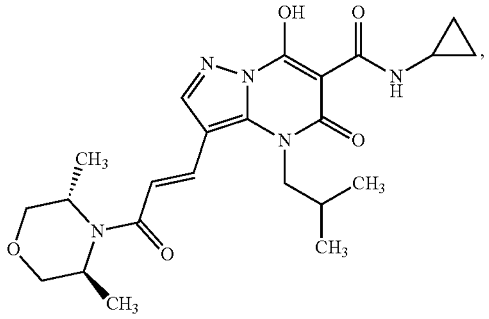 [SMILES: CC(C)Cn1c(=O)c(C(=O)NC2CC2)c(O)n2ncc(/C=C/C(=O)N3[C@@H](C)COC[C@@H]3C)c12]

or a tautomer or a pharmaceutically acceptable salt thereof.

22. The compound according to claim 1, wherein the compound is:

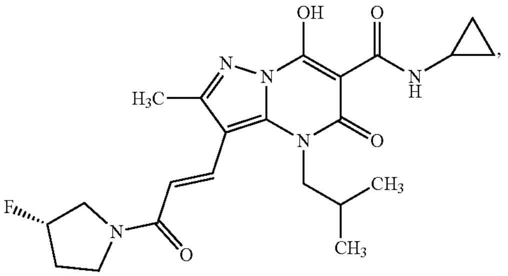 [SMILES: Cc1nn2c(O)c(C(=O)NC3CC3)c(=O)n(CC(C)C)c2c1/C=C/C(=O)N1CC[C@H](F)C1]

or a tautomer or a pharmaceutically acceptable salt thereof.

23. The compound according to claim 1, wherein the compound is:

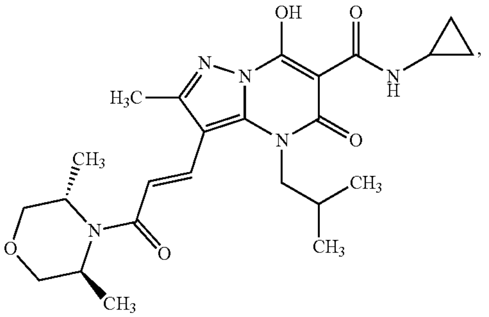 [SMILES: Cc1nn2c(O)c(C(=O)NC3CC3)c(=O)n(CC(C)C)c2c1/C=C/C(=O)N1[C@@H](C)COC[C@@H]1C]

or a tautomer or a pharmaceutically acceptable salt thereof.

24. The compound according to claim 1, wherein the compound is:

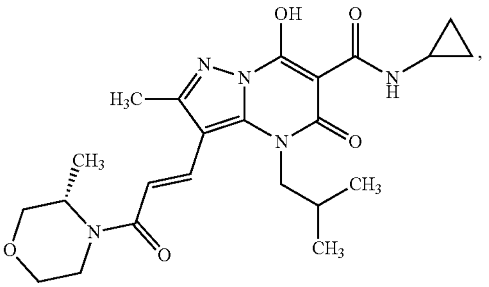 [SMILES: Cc1nn2c(O)c(C(=O)NC3CC3)c(=O)n(CC(C)C)c2c1/C=C/C(=O)N1CCOC[C@@H]1C]

or a tautomer or a pharmaceutically acceptable salt thereof.

25. The compound according to claim 1, wherein the compound is:

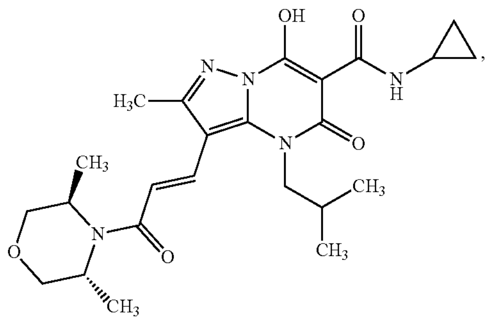 [SMILES: Cc1nn2c(O)c(C(=O)NC3CC3)c(=O)n(CC(C)C)c2c1/C=C/C(=O)N1[C@H](C)COC[C@H]1C]

or a tautomer or a pharmaceutically acceptable salt thereof.

26. The compound according to claim 1, wherein the compound is:

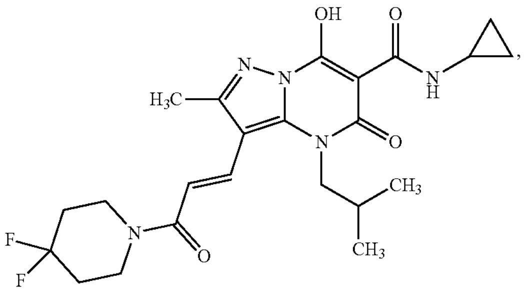 [SMILES: Cc1nn2c(O)c(C(=O)NC3CC3)c(=O)n(CC(C)C)c2c1/C=C/C(=O)N1CCC(F)(F)CC1]

or a tautomer or a pharmaceutically acceptable salt thereof.

27. The compound according to claim 1, wherein the compound is:

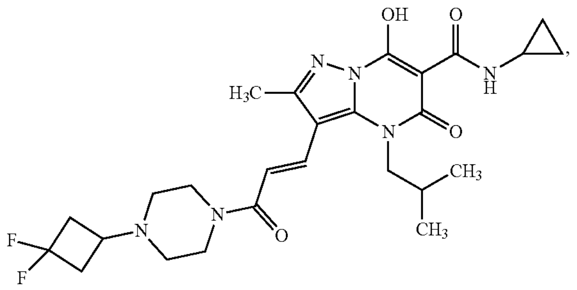 [SMILES: Cc1nn2c(O)c(C(=O)NC3CC3)c(=O)n(CC(C)C)c2c1/C=C/C(=O)N1CCN(C2CC(F)(F)C2)CC1]

on a tautomer or a pharmaceutically acceptable salt thereof.

28. A pain relief drug comprising the compound, tautomer or pharmaceutically acceptable salt of claim 1.

29. A pharmaceutical composition comprising the compound, tautomer or pharmaceutically acceptable salt of claim 1.

30. A method for inhibiting sepiapterin reductase activity in a subject in need thereof, wherein the method comprises administering to the subject a therapeutically effective amount of the compound, tautomer or pharmaceutically acceptable salt of claim 1.

31. A method for preventing, treating, and/or ameliorating pain in a subject in need thereof, the method comprising administering to the subject a therapeutically effective amount of the compound, tautomer or pharmaceutically acceptable salt of the compound according to claim 1.

* * * * *